US012485169B2

(12) United States Patent
Quibell et al.

(10) Patent No.: US 12,485,169 B2

(45) Date of Patent: Dec. 2, 2025

(54) COMPOUNDS

(71) Applicant: GREY WOLF THERAPEUTICS LIMITED, Abingdon (GB)

(72) Inventors: Martin Quibell, Oxford (GB); Anil Lallubhai Patel, Oxford (GB); Jason John Shiers, Oxford (GB); Michael Sparenberg, Oxford (GB); Peter Ian Joyce, Oxford (GB)

(73) Assignee: Grey Wolf Therapeutics Limited, Abingdon (GB)

( * ) Notice: Subject to any disclaimer, the term of this patent is extended or adjusted under 35 U.S.C. 154(b) by 1181 days.

(21) Appl. No.: 17/295,335

(22) PCT Filed: Nov. 22, 2019

(86) PCT No.: PCT/GB2019/053316

§ 371 (c)(1),
(2) Date: May 19, 2021

(87) PCT Pub. No.: WO2020/104822

PCT Pub. Date: May 28, 2020

(65) Prior Publication Data

US 2023/0064417 A1 Mar. 2, 2023

(30) Foreign Application Priority Data

Nov. 23, 2018 (GB) ..................................... 1819102
Feb. 22, 2019 (GB) ..................................... 1902440

(Continued)

(51) Int. Cl.
*C07D 211/14* (2006.01)
*A61K 31/397* (2006.01)
(Continued)

(52) U.S. Cl.
CPC ........... *A61K 39/39* (2013.01); *A61K 31/397* (2013.01); *A61K 31/402* (2013.01);
(Continued)

(58) Field of Classification Search
CPC .... A61K 39/39; A61K 31/397; A61K 31/402; A61K 31/4035; A61K 31/407;
(Continued)

(56) References Cited

U.S. PATENT DOCUMENTS

2014/0162952 A1 6/2014 Katagiri et al.
2018/0170869 A1 6/2018 Musicki et al.
2018/0230096 A1 8/2018 Larisch et al.

FOREIGN PATENT DOCUMENTS

CN 101817767 A 9/2010
CN 117881657 A 4/2024
(Continued)

OTHER PUBLICATIONS

Registry (STN) [online], Sep. 14, 2008 [Date of Search Oct. 22, 2024], CAS Registry No. 1049596-75-9. (Year: 2008).*
(Continued)

*Primary Examiner* — Clinton A Brooks
*Assistant Examiner* — Kendall Nicole Heitmeier
(74) *Attorney, Agent, or Firm* — Lathrop GPM LLP; Brian C. Trinque

(57) ABSTRACT

The present disclosure relates to a compound of formula (Ia), or a pharmaceutically acceptable salt or hydrate thereof,
(Continued)

(Ia)

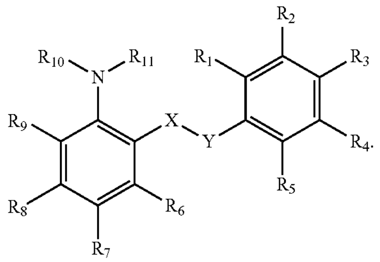

Figure 1:
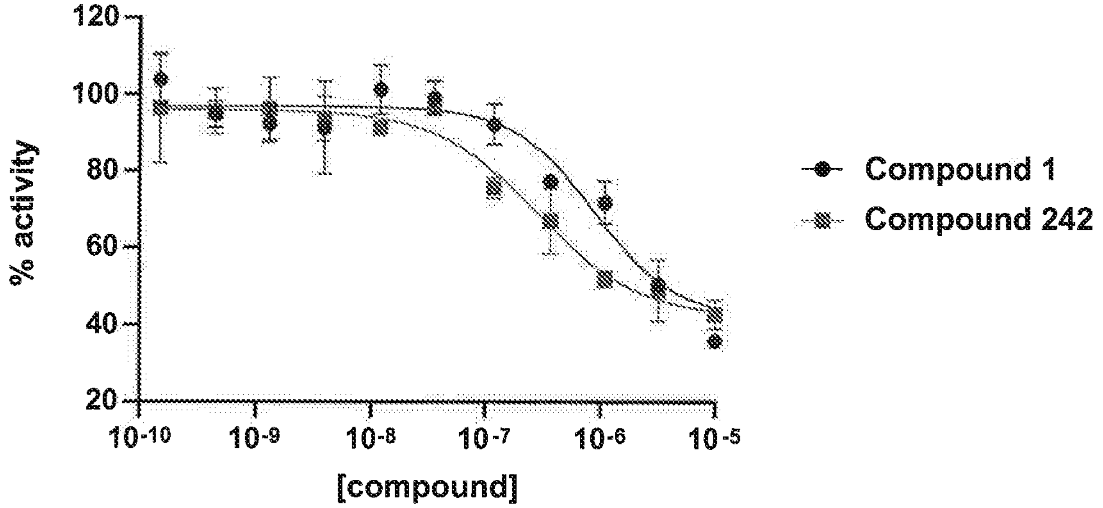

The present disclosure further relates to pharmaceutical compositions comprising a compound of formula (Ia) and methods of treating a disease or disorder (e.g., cancer) by administering a compound of formula (Ia).

11 Claims, 2 Drawing Sheets

Specification includes a Sequence Listing.

(30) Foreign Application Priority Data

May 9, 2019 (GB) ..................................... 1906571
Nov. 14, 2019 (GB) ..................................... 1916572

(51) Int. Cl.

| | |
|---|---|
| ***A61K 31/402*** | (2006.01) |
| ***A61K 31/4035*** | (2006.01) |
| ***A61K 31/407*** | (2006.01) |
| ***A61K 31/41*** | (2006.01) |
| ***A61K 31/438*** | (2006.01) |
| ***A61K 31/439*** | (2006.01) |
| ***A61K 31/451*** | (2006.01) |
| ***A61K 31/454*** | (2006.01) |
| ***A61K 31/495*** | (2006.01) |
| ***A61K 31/497*** | (2006.01) |
| ***A61K 31/4985*** | (2006.01) |
| ***A61K 31/501*** | (2006.01) |
| ***A61K 31/55*** | (2006.01) |
| ***A61K 31/553*** | (2006.01) |
| ***A61K 35/17*** | (2025.01) |
| ***A61K 39/00*** | (2006.01) |
| ***A61K 39/39*** | (2006.01) |
| ***A61K 39/395*** | (2006.01) |
| ***A61P 29/00*** | (2006.01) |
| ***A61P 31/12*** | (2006.01) |
| ***A61P 35/00*** | (2006.01) |
| ***A61P 37/00*** | (2006.01) |
| ***C07D 205/04*** | (2006.01) |
| ***C07D 207/12*** | (2006.01) |
| ***C07D 209/44*** | (2006.01) |
| ***C07D 211/10*** | (2006.01) |
| ***C07D 211/38*** | (2006.01) |
| ***C07D 211/42*** | (2006.01) |
| ***C07D 211/44*** | (2006.01) |
| ***C07D 211/46*** | (2006.01) |
| ***C07D 211/48*** | (2006.01) |
| ***C07D 223/04*** | (2006.01) |
| ***C07D 231/12*** | (2006.01) |
| ***C07D 257/04*** | (2006.01) |
| ***C07D 295/04*** | (2006.01) |
| ***C07D 295/12*** | (2006.01) |
| ***C07D 295/135*** | (2006.01) |
| ***C07D 295/185*** | (2006.01) |
| ***C07D 305/06*** | (2006.01) |
| ***C07D 471/08*** | (2006.01) |
| ***C07D 487/04*** | (2006.01) |
| ***C07D 491/107*** | (2006.01) |
| ***C07D 493/08*** | (2006.01) |
| ***C07D 493/10*** | (2006.01) |
| ***C07D 498/08*** | (2006.01) |

(52) U.S. Cl.

CPC ........ *A61K 31/4035* (2013.01); *A61K 31/407* (2013.01); *A61K 31/41* (2013.01); *A61K 31/438* (2013.01); *A61K 31/439* (2013.01); *A61K 31/451* (2013.01); *A61K 31/454* (2013.01); *A61K 31/495* (2013.01); *A61K 31/497* (2013.01); *A61K 31/4985* (2013.01); *A61K 31/501* (2013.01); *A61K 31/55* (2013.01); *A61K 31/553* (2013.01); *A61K 35/17* (2013.01); *A61K 39/00* (2013.01); *A61K 39/3955* (2013.01); *C07D 205/04* (2013.01); *C07D 207/12* (2013.01); *C07D 209/44* (2013.01); *C07D 211/14* (2013.01); *C07D 211/38* (2013.01); *C07D 211/44* (2013.01); *C07D 211/48* (2013.01); *C07D 295/135* (2013.01); *C07D 471/08* (2013.01); *C07D 487/04* (2013.01); *C07D 491/107* (2013.01); *C07D 498/08* (2013.01); *A61K 2039/5154* (2013.01); *C07B 2200/05* (2013.01)

(58) Field of Classification Search

CPC .... A61K 31/41; A61K 31/438; A61K 31/439; A61K 31/451; A61K 31/454; A61K 31/495; A61K 31/497; A61K 31/4985; A61K 31/501; A61K 31/55; A61K 31/553; A61K 35/17; A61K 39/00; A61K 39/3955; A61K 2039/5154; A61K 2039/585; C07D 205/04; C07D 207/12; C07D 209/44; C07D 211/14; C07D 211/38; C07D 211/44; C07D 211/48; C07D 295/135; C07D 471/08; C07D 487/04; C07D 491/107; C07D 498/08; C07D 211/10; C07D 211/42; C07D 211/46; C07D 231/12; C07D 257/04; C07D 295/185; C07D 305/06; C07D 413/04; C07D 493/08; C07D 493/10; C07D 295/12; C07D 223/04; C07B 2200/05; A61P 35/00; A61P 29/00; A61P 31/12; A61P 37/00

See application file for complete search history.

(56) References Cited

FOREIGN PATENT DOCUMENTS

| | | | |
|---|---|---|---|
| EP | 3146965 | A1 | 3/2017 |
| JP | 2003-057793 | A | 2/2003 |
| JP | 2018-527324 | A | 9/2018 |
| WO | WO 2004/005278 | A1 | 1/2004 |
| WO | WO 2004/046092 | A2 | 6/2004 |
| WO | WO 2005/090297 | A1 | 9/2005 |
| WO | WO 2008/008374 | A2 | 1/2008 |
| WO | WO 2008/050167 | A1 | 5/2008 |
| WO | WO 2009/064388 | A2 | 5/2009 |
| WO | WO 2016/001452 | A1 | 1/2016 |
| WO | WO 2017/017004 | A1 | 2/2017 |

(56) References Cited

FOREIGN PATENT DOCUMENTS

WO WO 2018/079855 A1 5/2018
WO WO 2023/007188 A1 2/2023

OTHER PUBLICATIONS https://web.archive.org/web/20180629160929/http:/www.ambinter.com:80/ordering-information dated Jun. 29, 2018, accessed Nov. 8, 2024. (Year: 2018).*
Registry (STN) [online], Sep. 14, 2008 [Date of Search Nov. 14, 2024], CAS Registry No. 1049596-75-9. (Year: 2008).*
American Chemical Society. Chemical Abstract Service. RN 1371458-72-8, SR Chemical Catalog Supplier; Interchim; Entered into STN Apr. 30, 2012 (Year: 2012).*
https://web.archive.org/web/20080708140342/http:/www.interchim.com:80/interchim/chemical/custom_synthesis/custom_synthesis.html (Year: 2008).*
Maben, Z. et. al. âDiscovery of Selective Inhibitors of Endoplasmic Reticulum Aminopeptidase 1â J. Med. Chem. 2020, 63, 103-121 (Year: 2020).*
International Search Report and Written Opinion corresponding to International Patent Application No. PCT/GB2019/053316, mailed Feb. 3, 2020.
Pubchem Compounds: "4-Methoxy-3-{[2-(piperidin-1-yl)-5-(trifluoromethyl)phenyl}sulfamoyl}benzioc acid", N.C.B.I., Jul. 19, 2005 (Jul. 19, 2005), XP055659781, Retrieved from the Internet: URL: https://pubchem.ncbi.nlm.nih.gov/compound/4798291-[retrieved on Jan. 21, 2020].
N.C.B.I. Bioassay Record: "MLPCN ERAP1 Measured in Biochemical System Using Plate Reader—7016-01_Inhibitor_Dose_CherryPick_Activity", PubChem AID: 743317, Mar. 17, 2014 (Mar. 17, 2014), XP55659774, Retrieved from the Internet: URL:https://pubchem.ncbi.nlm.nih.gov/bioassay/743317 [retrieved on Jan. 21, 2020].
Pubchem Bioassay N.C.B.I: "Aid 1117287—MLPCN ERAP1 Measured in Biochemical System Using Plate Reader—7016-01_", PubChem AID: 1117287, Nov. 24, 2015 (Nov. 24, 2015), XP55659786, Retrieved from the Internet: URL:https://pubchem.ncbi.nlm.nih.gov/bioassay/1117287 [retrieved on Jan. 21, 2020].
Pubchem Aid: 1117287: "AID 1117287—MLPCN ERAP1", N.C.B.I. Pubchem Bioassay Record, Nov. 15, 2015 (Nov. 15, 2015), XP55659814, [retrieved on Jan. 21, 2020].
E. Zervoudi et al: "Rationally designed inhibitor targeting antigen-trimming aminopeptidases enhances antigen presentation and cytotoxic T-cell responses", Proceedings of the National Academy of Sciences, vol. 110, No. 49, Nov. 18, 2013 (Nov. 18, 2013), pp. 19890-19895, XP055118358, ISSN: 0027-8424, DOI: 10.1073/pnas. 1309781110.
Advanced Organic Chemistry, 3rd Edition, ed. March, J., John Wiley and Sons, New York, 1985).
Bastin et al., "Salt Selection and Optimisation Procedures for Pharmaceutical New Chemical Entities", *Organic Process Research & Development* 4(5):427-435 (2000).
Berge et al., "Pharmaceutical salts", *Journal of Pharmaceutical Sciences*, 66, 1-19 (1977).
Chemical Abstracts, Database accession No. 1798782-25-8 tBuXPhos Pd(allyl)OTf.
Chen et al., "Silencing or inhibition of endoplasmic reticulum aminopeptidase 1 (ERAP1) suppresses free heavy chain expression and Th17 responses in ankylosing spondylitis", *Annals of the Rheumatic Diseases* 75:916 (2014).
Cifaldi et al., "ERAP1 Regulates Natural Killer Cell Function by Controlling the Engagement of Inhibitory Receptors", *Cancer Research* 75:824 (2015).
Conde-Jaldon et al., "Epistatic interaction of ERAP1 and HLA-B in Behçet disease: a replication study in the Spanish population", *PLoS One* 14;9(7) (2014).
Evans et al., "Interaction between ERAP1 and HLA-B27 in ankylosing spondylitis implicates peptide handling in the mechanism for HLA-B27 in disease susceptibility", *Nature Genetics* 10:43(8):761-767 (2011).
Handbook of Pharmaceutical Excipients, 2nd Edition, (1994), Edited by A Wade and PJ Weller.
James et al., "Induction of Protective Antitumor Immunity through Attenuation of ERAAP Function", *Journal of Immunology* 190:5839 (2013).
Kim et al., "Human cytomegalovirus microRNA miR-US4-1 inhibits its CD8+T cell responses by targeting the aminopeptidase ERAP1", *Nature Immunology* 12:984 (2011).
Kuiper et al., "Intraocular interleukin-17 and proinflammatory cytokines in HLA-A29-associated birdshot chorioretinopathy", *American Journal of Ophthalmology* 152(2):177-182 (2011).
Kuiper et al., "Interleukin-17 production and T helper 17 cells in peripheral blood mononuclear cells in response to ocular lysate in patients with birdshot chorioretinopathy", *Molecular Vision* 19:2606-2614 (2013).
Kuiper et al., "A genome-wide association study identifies a functional ERAP2 haplotype associated with birdshot chorioretinopathy", *Human Molecular Genetics* 23(22):6081-6087 (2014).
Kuiper et al., "Functionally distinct ERAP1 and ERAP2 are a hallmark of HLA-A29-(Birdshot) Uveitis", *Human Molecular Genetics* doi: 10.1093/hmg/ddy319 (2018).
Maben, "The Relationship Between Inhibition, Conformation, and Catalysis of the Aminopeptidase ERAP1", GSBS Dissertations and Theses. https://doi.org/10.13028/hjqm-ag71. Retrieved from https://escholarship.umassmed.edu/gsbs_diss/1003 (2018).
Nagarajan et al., "ERAAP Shapes the Peptidome Associated with Classical and Nonclassical MHC Class I Molecules"; *Journal of Immunology* 197:1035 (2016).
Pepelyayeva et al., "ERAP1 deficient mice have reduced Type 1 regulatory T cells and develop skeletal and intestinal features of Ankylosing Spondylitis", *Science Reports* 8:12464 (2018).
Reetz et al., "Proton-Transfer-Dependent Reversible Phase Changes in the 4,4'-Bipyridinium Salt of Squaric Acid", Angewandte Chemie International Edition England, 1994, vol. 33, pp. 183-186. Abstract.
Reeves et al., "The role of polymorphic ERAP1 in autoinflammatory disease", *Bioscience Reports* 29, p. 38 (2018).
Remington's Pharmaceutical Sciences, Mack Publishing Co. (A. R. Gennaro edit. 1985).
Rizvi et al., "Mutational landscape determines sensitivity to PD-1 blockade in non-small cell lung cancer". *Science* 348(6230):124-128 (2015).
Serwold et al., "ERAAP customizes peptides for MHC class I molecules in the endoplasmic reticulum" *Nature* 419:480 (2002).
Sheehan, "The ramifications of HLA-B27", *Journal of the Royal Society of Medicine* 97(1):10-14 (Jan. 2004).
Smith, "Update on ankylosing spondylitis: current concepts in pathogenesis", *Current Allergy and Asthma Reports* 15(1):489 (Jan. 2015).
Snyder et al., "Genetic Basis for Clinical Response to CTLA-4 Blockade in Melanoma", *The New England Journal of Medicine* 371:2189 (2014).
Steinbach et al., "ERAP1 overexpression in HPV-induced malignancies: A possible novel immune evasion mechanism", *Oncoimmunology* 6:e1336594 (2017).
Strange et al., "Genome-wide association study identifies new psoriasis susceptibility loci and an interaction between HLA-C and ERAP1", *Nature Genetics* 42(11):985-990 (2010).
Tenzer et al., "Antigen processing influences HIV-specific cytotoxic T lymphocyte immunodominance", *Nature Immunology* 10:636 (2009).
Uniprot ID Q9NZ08, Nov. 3, 2018.
Van Allen et al., "Genomic correlates of response to CTLA-4 blockade in metastatic melanoma", *Science* 348:124 (2015).
Registry (STN) [online] Jan. 24, 2010 [searched on Oct. 24, 2023] CAS Registry No. 1203428-33-4.
Registry (Stn) [online] Mar. 11, 2010 [searched on Oct. 28, 2023] CAS Registry No. 1208788-15-1.
Registry (STN) [online] Apr. 30, 2012 [searched on Oct. 30, 2023] CAS Registry No. 1371458-72-8.

(56) References Cited

OTHER PUBLICATIONS

Registry (STN) [online], 2010, Sep. 14, 2008 [Date of Search Apr. 19, 2024], CAS Registry No. 1049596-75-9.
CAS Registry No. 941194-12-3, Registry (STN) [online] [entered Jul. 4, 2007].
CAS Registry No. 949406-06-8, Registry (STN) [online] [entered Oct. 5, 2007].
CAS Registry No. 1013488-70-4, Registry (STN) [online] [entered Apr. 10, 2008].
CAS Registry No. 1049826-15-4, Registry (STN) [online] [entered Sep. 17, 2008].
CAS Registry No. 1049846-53-8, Registry (STN) [online] [entered Sep. 17, 2008].
CAS Registry No. 1049850-16-9, Registry (STN) [online] [entered Sep. 17, 2008].
CAS Registry No. 1050870-90-0, Registry (STN) [online] [entered Sep. 21, 2008].
CAS Registry No. 1050871-79-8, Registry (STN) [online] [entered Sep. 21, 2008].
CAS Registry No. 1050876-59-9, Registry (STN) [online] [entered Sep. 21, 2008].
CAS Registry No. 1051063-41-2, Registry (STN) [online] [entered Sep. 21, 2008].
CAS Registry No. 1051205-88-9, Registry (STN) [online] [entered Sep. 21, 2008].
CAS Registry No. 1051288-03-9, Registry (STN) [online] [entered Sep. 21, 2008].
CAS Registry No. 1053880-06-0, Registry (STN) [online] [entered Sep. 28, 2008].
CAS Registry No. 1054011-34-5, Registry (STN) [online] [entered Sep. 28, 2008].
CAS Registry No. 1054143-79-1, Registry (STN) [online] [entered Sep. 28, 2008].
CAS Registry No. 1054372-41-6, Registry (STN) [online] [entered Sep. 29, 2008].
CAS Registry No. 1054396-15-4, Registry (STN) [online] [entered Sep. 29, 2008].
CAS Registry No. 1054426-12-8, Registry (STN) [online] [entered Sep. 29, 2008].
CAS Registry No. 1054497-16-3, Registry (STN) [online] [entered Sep. 29, 2008].
CAS Registry No. 1054541-09-1, Registry (STN) [online] [entered Sep. 29, 2008].
CAS Registry No. 1057756-92-9, Registry (STN) [online] [entered Oct. 7, 2008].
CAS Registry No. 1057871-29-0, Registry (STN) [online] [entered Oct. 7, 2008].
CAS Registry No. 1057896-26-0, Registry (STN) [online] [entered Oct. 7, 2008].
CAS Registry No. 1057945-41-1, Registry (STN) [online] [entered Oct. 7, 2008].
CAS Registry No. 1057945-49-9, Registry (STN) [online] [entered Oct. 7, 2008].
CAS Registry No. 1057955-26-6, Registry (STN) [online] [entered Oct. 7, 2008].
CAS Registry No. 1289956-39-3, Registry (STN) [online] [entered May 4, 2011].
CAS Registry No. 1293893-96-5, Registry (STN) [online] [entered May 12, 2011].
CAS Registry No. 1294419-41-2, Registry (STN) [online] [entered May 13, 2011].
CAS Registry No. 1297065-47-4, Registry (STN) [online] [entered May 19, 2011].
CAS Registry No. 1316494-44-6, Registry (STN) [online] [entered Aug. 12, 2011].
CAS Registry No. 1319377-54-2, Registry (STN) [online] [entered Aug. 18, 2011].
CAS Registry No. 1423628-48-1, Registry (STN) [online] [entered Mar. 14, 2013].
CAS Registry No. 1580268-73-0, Registry (STN) [online] [entered Apr. 4, 2014].
Hilfiker (editor), "Polymorphism in the Pharmaceutical Industry", Wiley VCH ISBN 3-527-31146-7, 2006, p. 37.
Maben et al., "Discovery of Selective Inhibitors of Endoplasmic Reticulum Aminopeptidase 1", *Journal of Medicinal Chemistry* 63:103-121 (2020).
Maben et al., "Discovery of Selective Inhibitors of Endoplasmic Reticulum Aminopeptidase 1", *Journal of Medicinal Chemistry*—Supporting Information—S1-S53 (2020).
PubChem 1117287—"MLPCN ERAP1 Measured in Biochemical System Using Plate Reader—7016-01_Inhibitor_Dose_DryPowder_Activity_Set2", Broad Institute, N.C.B.I. Bioassay Record (https://pubchem.ncbi.nlm.nih.gov/bioassay/1117287, publication date: Nov. 24, 2015).
Saric et al., "An IFN-γ-induced aminopeptidase in the ER, ERAPI, trims precursors to MHC class I-presented peptides", Nature Immunology 3(12):1169-1176 (2002).
Full text of China's outstanding master's degree theses Database (Medical and Health Science and Technology), Issue 03, Mar. 15, 2017 Tang Xianshuai, Synthesis and in vitro activity study of small molecule peptidomimetic aminopeptidase N inhibitors, p. E079-34, 1-71.
Canadian Office Action for Canadian Application No. 3,117,916 dated Dec. 16, 2024, 12 pages.
Chinese First Office Action and Search Report for Chinese Application No. 201980076956.0 dated Jun. 20, 2024, with English Summary, 57 pages.
Japanese Search Report for Japanese Application No. 2021-528835 dated Nov. 16, 2023, 46 pages.
CAS Registry No. 865273-97-8, Registry (STN) [online] [entered Oct. 14, 2005].
CAS Registry No. 1057871-36-9, Registry (STN) [online] [entered Oct. 7, 2008].
"Pharmaceutical Chemistry", edited by You Qidong, published by People's Health Publishing House, p. 586, lines 4-5 and the last paragraph to p. 587, paragraph 1, published Aug. 31, 2011.
"Pharmacochemistry", edited by Peng Sixun, published by China Medical Science and Technology Press, pp. 490-492, published Aug. 31, 1999.
Wermuth, "Molecular Variations Based on Isosteric Replacements", The Practice of Medicinal Chemistry, pp. 203-217 (1996)—Japanese translation by Hiroshi Nagase (1998).

* cited by examiner

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: decapeptide substrate
<220> FEATURE:
<221> NAME/KEY: MISC_FEATURE
<222> LOCATION: (7)..(7)
<223> OTHER INFORMATION: dinitrophenyl maleimide (Dnp) residue labeling

<400> SEQUENCE: 1

Trp Arg Val Tyr Glu Lys Cys Ala Leu Lys
1               5                   10


<210> SEQ ID NO 2
<211> LENGTH: 8
<212> TYPE: PRT
<213> ORGANISM: Artificial Sequence
<220> FEATURE:
<223> OTHER INFORMATION: ovalbumin-specific peptide

<400> SEQUENCE: 2

Ser Ile Ile Asn Phe Glu Lys Leu
1               5


<210> SEQ ID NO 3
<211> LENGTH: 30
<212> TYPE: PRT
<213> ORGANISM: Artificial Sequence
<220> FEATURE:
<223> OTHER INFORMATION: ER-targeted N-terminally extended precursor
      peptide derived from ovalbumin

<400> SEQUENCE: 3

Met Arg Tyr Met Ile Leu Gly Leu Leu Ala Leu Ala Ala Val Cys Ser
1               5                   10                  15

Ala Ala Ile Val Met Lys Ser Ile Ile Asn Phe Glu His Leu
            20                  25                  30


<210> SEQ ID NO 4
<211> LENGTH: 8
<212> TYPE: PRT
```

-continued

<213> ORGANISM: Artificial Sequence
<220> FEATURE:
<223> OTHER INFORMATION: specific recognition complex peptide sequence

<400> SEQUENCE: 4

Ser Ile Ile Asn Phe Glu His Leu
1 5

COMPOUNDS

The present invention relates to compounds that are capable of modulating ERAP1. The compounds have potential therapeutic applications in the treatment of a variety of disorders, including proliferative, viral, immune and inflammatory disorders.

RELATED APPLICATIONS

This application is a 35 U.S.C. § 371 filing of International Application No. PCT/GB2019/053316, filed Nov. 22, 2019, which application claims priority to Great Britain Patent Application No. 1916572.9, filed Nov. 14, 2019, and Great Britain Patent Application No. 1906571.3, filed May 9, 2019, and Great Britain Patent Application No. 1902440.5, filed Feb. 22, 2019, and Great Britain Patent Application No. 1819102.3, filed Nov. 23, 2018. The entire contents of these applications are herein incorporated by reference in their entireties.

SEQUENCE LISTING

The present application is being filed along with a Sequence Listing in computer readable format. The Sequence Listing is provided as a file entitled 717669-DYT-030US-SEQUENCE-LISTING.txt created May 18, 2021 and is 1.49 bytes in size. The information in the computer readable format of the sequence listing is incorporated herein by reference in its entirety.

BACKGROUND TO THE INVENTION

ERAP1 (Endoplasmic Reticulum Aminopeptidase 1; also referred to as APPILS or ARTS1) is an aminopeptidase important in the generation of a proportion of antigens and neoantigens as part of the antigen presentation pathway[1]. The antigen presentation pathway starts with the breakdown of proteins by the proteasome into peptides. These peptides are transported into the endoplasmic reticulum where a proportion are processed by ERAP1 before binding to the Major Histocompatibility Complex Class I (MHC Class I)[1]. Antigens bound to MHC Class I are then transported to the surface of a cell and presented to $CD8^+$ T-cells and recognised as either self or non-self. Neoantigens are antigens that are specific to cancer and can be recognised as foreign by the immune system leading to destruction of cancer cells. Neoantigens are created either as a direct result of somatic mutations in the DNA of cancer cells, leading to the generation of mutated proteins, or through the indirect consequences of somatic mutations on protein processing and expression. Those cancers with higher rates of mutation and correspondingly higher levels of neoantigens have much greater response rates to the checkpoint inhibitor immunotherapies anti-PD-1 (e.g. pembrolizumab, nivolumab), anti-PD-L1 (e.g. atezolizumab, avelumab, durvalumab) and anti-CTLA4 antibodies (e.g. ipilimumab, tremelimuab) compared with cancers harbouring lower numbers of neoantigens[2, 3].

The role of ERAP1 in the antigen presentation pathway is to trim a proportion of peptides, via its aminopeptidase activity, to create antigens and neoantigens of the optimal length for binding to MHC Class I. ERAP1 also over-trims some neoantigens, preventing their binding to MHC Class I and presentation at the cell surface[4]. Ablation of ERAP1 activity has been shown to change the antigen and neoantigen repertoire, leading to an increase in presentation of certain antigens/neoantigens and the presentation of entirely novel antigens/neoantigens[5]. In addition, ERAP1 ablation causes $CD8^+$ T cell dependent tumour rejection in mouse cancer models[4]. Accordingly, modulators of ERAP1 activity may be useful for cancer treatment, either used alone or in combination with current cancer immunotherapy agents, including checkpoint inhibitors, because they change the antigens and neoantigens presented on the surface of cancer cells and make them more visible to the immune system, leading to tumour attack and destruction.

Knockdown of ERAP1 is also shown to reduce the levels of regulatory-like T cells and enhance the killing of cancer cells by natural killer cells[6, 7]. This suggests that modulators of ERAP1 activity might be effective cancer treatments by both modulating cancer cell visibility and creating a more anti-tumourogenic immune response. ERAP1's peptide processing role in antigen presentation is also applicable in infectious viral disease.

The present invention seeks to provide compounds that are capable of modulating ERAP1. Such compounds have potential therapeutic applications in the treatment of a variety of disorders, including proliferative disorders, immune disorders and inflammatory disorders.

STATEMENT OF INVENTION

A first aspect of the invention relates to a compound of formula (Ia), or a pharmaceutically acceptable salt or hydrate thereof, (Ia)

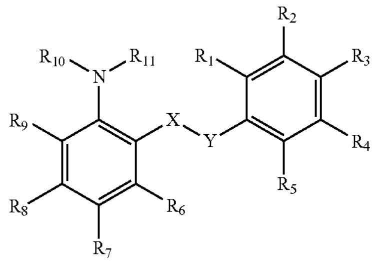

wherein:

the group X—Y is —$NHSO_2$— or —$SO_2NH$—;

$R_1$ is H or alkyl;

$R_2$ is selected from COOH and a tetrazolyl group;

$R_3$ is selected from H, Cl and alkyl;

$R_4$ is selected from H, Cl and F;

$R_5$ is selected from H, alkyl, haloalkyl, $SO_2$-alkyl, Cl, alkoxy, OH, CN, alkynyl, alkenyl, hydroxyalkyl, alkylthio, heteroaryl, cycloalkyl, heterocycloalkyl and haloalkoxy;

$R_6$ is H;

$R_7$ is selected from H, CN, haloalkyl, Cl, F, $SO_2$-alkyl, $SO_2NR_{13}R_{14}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H, $C_1$-$C_3$-alkyl, or halo;

$R_{10}$ and $R_{11}$, together with the nitrogen to which they are attached, form an azepanyl group, wherein (a) said azepanyl group is substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl, or (b) one or two carbons in said azepanyl group are replaced by a group selected from O, NH, S and CO, and said azepanyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl; or $R_{10}$ and $R_{11}$, together with the nitrogen to which they are attached, form an azetidinyl, pyrrolidinyl or piperidinyl group wherein (a) said azetidinyl, pyrrolidinyl or piperidinyl group is substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl, or (b) one or two carbons in said azetidinyl, pyrrolidinyl or piperidinyl group are replaced by a group selected from NH, S and CO; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected from alkyl, CN, cycloalkyl, OH, alkoxy, halo, haloalkyl and heteroaryl; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, cycloalkyl, OH, alkoxy, halo, haloalkyl and heteroaryl, or said bicyclic group is optionally fused to a 5 or 6-membered aryl or heteroaryl group; and $R_{13}$ and $R_{14}$ are each independently H or alkyl.

A second aspect of the invention relates to a compound of formula (Ib), or a pharmaceutically acceptable salt or hydrate thereof, (Ib)

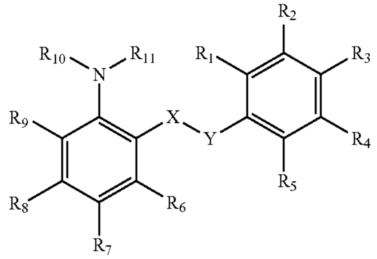

wherein:

the group X—Y is —$NHSO_2$— or —$SO_2NH$—;

$R_1$ is H or alkyl;

$R_2$ is a tetrazolyl group;

$R_3$ is selected from H, Cl and alkyl;

$R_4$ is selected from H, Cl and F;

$R_5$ is selected from H, alkyl, alkynyl, alkenyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, Cl, F, $SO_2$-alkyl, $SO_2NR_{13}R_{14}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H, $C_1$-$C_3$-alkyl or halo;

$R_{10}$ is H or alkyl;

$R_{11}$ is alkyl optionally substituted by one or more substituents selected from $NH_2$, OH, and $NHCO_2R_{12}$, wherein $R_{12}$ is alkyl; or $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected alkyl, CN, cycloalkyl, OH, alkoxy, halo, haloalkyl and heteroaryl; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, cycloalkyl, OH, alkoxy, halo, haloalkyl and heteroaryl, or said bicylic group is optionally fused to a 5 or 6-membered aryl or heteroaryl group; and $R_{13}$ and $R_{14}$ are each independently H or alkyl.

A third aspect of the invention relates to a compound of formula (Ic), or a pharmaceutically acceptable salt or hydrate thereof, (Ic)

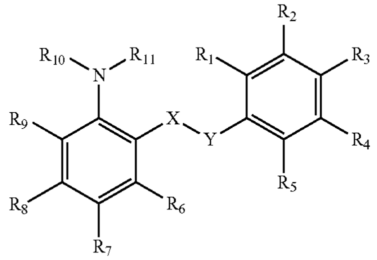

wherein:

X is $SO_2$;

Y is NH;

$R_1$ is H or alkyl;

$R_2$ is selected from COOH and a tetrazolyl group;

$R_3$ is selected from H, Cl and alkyl;

$R_4$ is selected from H, Cl and F;

$R_5$ is selected from H, alkyl, alkynyl, alkenyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, Cl, F, $SO_2$-alkyl, $SO_2NR_{13}R_{14}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H, $C_1$-$C_3$-alkyl or halo;

$R_{10}$ is H or alkyl;

$R_{11}$ is alkyl optionally substituted by one or more substituents selected from $NH_2$, OH, and $NHCO_2R_{12}$, wherein $R_{12}$ is alkyl; or $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected from alkyl, CN, cycloalkyl, OH, alkoxy, halo, haloalkyl and heteroaryl; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, cycloalkyl, OH, alkoxy, halo, haloalkyl and heteroaryl, or said bicyclic group is optionally fused to a 5 or 6-membered aryl or heteroaryl group; and $R_{13}$ and $R_{14}$ are each independently H or alkyl.

A fourth aspect of the invention relates to a compound of formula (Id), or a pharmaceutically acceptable salt or hydrate thereof, (Id)

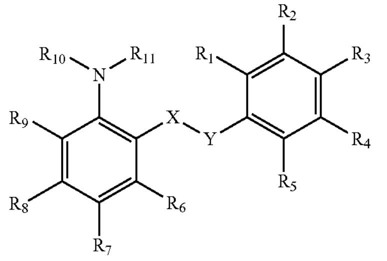

wherein:

the group X—Y is —$NHSO_2$— or —$SO_2NH$—;

$R_1$ is H or alkyl;

$R_2$ is selected from COOH and a tetrazolyl group;

$R_3$ is selected from H, Cl and alkyl;

$R_4$ is selected from H, Cl and F;

$R_5$ is selected from H, alkyl, alkynyl, alkenyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is CN, $SO_2$-alkyl, $SO_2NR_{13}R_{14}$, or a heteroaryl group, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H, $C_1$-$C_3$-alkyl, or halo;

$R_{10}$ is H or alkyl;

$R_{11}$ is alkyl optionally substituted by one or more substituents selected from $NH_2$, OH, and $NHCO_2R_{12}$, wherein $R_{12}$ is alkyl; or $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected from alkyl, CN, cycloalkyl, OH, alkoxy, halo, haloalkyl and heteroaryl; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, cycloalkyl, OH, alkoxy, halo, haloalkyl and heteroaryl, or said bicyclic group is optionally fused to a 5 or 6-membered aryl or heteroaryl group; and $R_{13}$ and $R_{14}$ are each independently H or alkyl.

Advantageously, the presently claimed compounds are capable of modulating ERAP 1, thereby rendering the compounds of therapeutic interest in the treatment of various disorders, for example, in the field of oncology and immuno-oncology.

A fifth aspect of the invention relates to a pharmaceutical composition comprising at least one compound as described above and a pharmaceutically acceptable carrier, diluent or excipient.

A sixth aspect of the invention relates to a compound as described above for use in medicine.

A seventh aspect of the invention relates to a compound as described above for use in treating or preventing a disorder selected from a proliferative disorder, an immune disorder, a viral disorder and an inflammatory disorder.

An eighth aspect of the invention relates to the use of a compound as described above in the preparation of a medicament for treating or preventing a disorder selected from a proliferative disorder, an immune disorder, a viral disorder and an inflammatory disorder.

A ninth aspect of the invention relates to a compound as described above for use in the prevention or treatment of a disorder caused by, associated with or accompanied by any abnormal ERAP1 activity.

A tenth aspect of the invention relates to the use of a compound as described above in the preparation of a medicament for the prevention or treatment of a disorder caused by, associated with or accompanied by abnormal ERAP1 activity.

An eleventh aspect of the invention relates to a method of treating a mammal having a disease state alleviated by modulation of ERAP1, wherein the method comprises administering to a mammal a therapeutically effective amount of a compound as described above.

A twelfth aspect of the invention relates to a compound as described above for use in treating or preventing a disease state alleviated by modulation of ERAP1.

A thirteenth aspect of the invention relates to the use of a compound as described above in the preparation of a medicament for treating or preventing a disease state alleviated by modulation of ERAP1.

A fourteenth aspect of the invention relates to a method of treating or preventing a disorder selected from a proliferative disorder, an immune disorder, a viral disorder and an inflammatory disorder in a subject, wherein the method comprises administering to the subject a therapeutically effective amount of a compound as described above.

A fifteenth aspect of the invention relates to a compound of formula (I), or a pharmaceutically acceptable salt or hydrate thereof, (I)

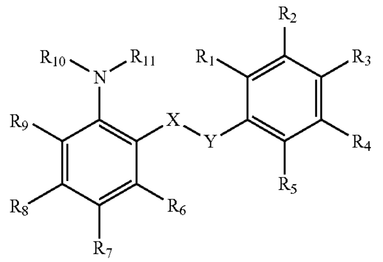

wherein:

the group X—Y is —$NHSO_2$— or —$SO_2NH$—;

$R_1$ is H or alkyl;

$R_2$ is selected from COOH and a tetrazolyl group;

$R_3$ is selected from H, Cl and alkyl;

$R_4$ is selected from H, Cl and F;

$R_5$ is selected from H, alkyl, alkynyl, alkenyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, Cl, F, $SO_2$-alkyl, $SO_2NR_{13}R_{14}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H, $C_1$-$C_3$-alkyl, or halo;

$R_{10}$ is H or alkyl;

$R_{11}$ is alkyl optionally substituted by one or more substituents selected from $NH_2$, OH, and $NHCO_2R_{12}$, wherein $R_{12}$ is alkyl; or $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected from alkyl, CN, cycloalkyl, OH, alkoxy, halo, haloalkyl and heteroaryl; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, cycloalkyl, OH, alkoxy, halo, haloalkyl and heteroaryl, or said bicyclic group is optionally fused to a 5 or 6-membered aryl or heteroaryl group; and $R_{13}$ and $R_{14}$ are each independently H or alkyl;

for use in treating or preventing a disorder selected from a proliferative disorder, an immune disorder, a viral disorder and an inflammatory disorder.

DETAILED DESCRIPTION

The present invention relates to bis-aryl sulfonamide compounds that are capable of modulating ERAP1. Preferably, the compounds selectively modulate ERAP1.

"Alkyl" is defined herein as a straight-chain or branched alkyl radical, preferably $C_{1-20}$ alkyl, more preferably $C_{1-12}$ alkyl, even more preferably $C_{1-10}$ alkyl or $C_{16}$ alkyl, or $C_{1-3}$-alkyl. Examples of suitable alkyl groups include, but are not limited to, methyl, ethyl, propyl, isopropyl, butyl, isobutyl, tert-butyl, pentyl, hexyl.

"Cycloalkyl" is defined herein as a monocyclic alkyl ring, preferably, $C_{3-7}$-cycloalkyl, more preferably $C_{3-6}$-cycloalkyl. Preferred examples include cyclopropyl, cyclobutyl, cyclopentyl, cyclohexyl or cycloheptyl, or a fused bicyclic ring system such as norbornane.

"Halogen" is defined herein as chloro, fluoro, bromo or iodo.

As used herein, the term "aryl" refers to a $C_{6-12}$ aromatic group, which may be benzocondensed, for example, phenyl or naphthyl.

"Heteroaryl" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, tetrazolyl, thiadiazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc. Particularly preferred heteroaryl groups include 1H-imidazol-5-yl, 1H-imidazol-4-yl, 1H-imidazol-2-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, thiazol-5-yl, thiazol-4-yl, thiazol-2-yl, 1H-1,2,3,4-tetrazol-4-yl, 2H-1,2,3,4-tetrazol-5-yl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, pyradizin-3-yl, pyradizin-4-yl, pyrazinyl, 1,3,4-oxadizol-2-yl, 1,3,4-oxadizol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, isoxazol-5-yl, isoxazol-4-yl and isoxazol-3-yl.

"Heterocycloalkyl" refers to a cyclic aliphatic group containing one or more heteroatoms selected from nitrogen, oxygen and sulphur, which is optionally interrupted by one or more —(CO)— groups in the ring and/or which optionally contains one or more double bonds in the ring. Preferably, the heterocycloalkyl group is monocyclic or bicyclic. Preferably, the heterocycloalkyl group is a $C_{3-7}$-heterocycloalkyl, more preferably a $C_{3-6}$-heterocycloalkyl. Alternatively, the heterocycloalkyl group is a $C_{4-7}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl. Preferably, the the heterocycloalkyl group is fully saturated.

"Azepanyl" refers to a 7-membered saturated heterocyclic ring containing six carbon atoms and one nitrogen atom. "Piperidinyl" refers to a 6-membered saturated heterocyclic ring containing five carbon atoms and one nitrogen atom. "Pyrrolidinyl" refers to a 5-membered saturated heterocyclic ring containing four carbons and one nitrogen atom. "Azetidinyl" refers to a 4-membered saturated heterocyclic ring containing three carbon atoms and one nitrogen atom.

Compounds of Formula (Ia)

One aspect of the invention relates to compounds of formula (Ia) as described above.

In one preferred embodiment, $R^1$ is H or Me, more preferably H.

In one preferred embodiment, $R_2$ is COOH.

In one preferred embodiment, X—Y is NH—SO.

In one preferred embodiment, $R_5$ is selected from alkyl, alkenyl, alkynyl, haloalkyl, $SO_2$-alkyl, Cl, alkoxy, OH, CN, hydroxyalkyl, alkylthio, heteroaryl, cycloalkyl, heterocycloalkyl and haloalkoxy.

In one preferred embodiment, $R_5$ is selected from H, Me, $CF_3$, $CHF_2$, $SO_2$—Me, Cl, ethynyl, MeO, OH, $CH_2OH$, SMe, cyclopropyl, triazolyl, oxetanyl and CN. More preferably, $R_5$ is selected from H, CN, Me, $SO_2$—Me, $CF_3$ and $CHF_2$, $CH_2OH$, SMe, cyclopropyl, 3,4-triazol-1-yl, oxetan-3-yl. More preferably, $R_5$ is selected from H, CN, Me, $SO_2$—Me, $CF_3$ and $CHF_2$.

In another preferred embodiment, $R_5$ is selected from OMe, Me, Et, Pr, ethynyl and Cl, more preferably OMe, Me, Et, Pr and Cl, and is more preferably OMe or Et.

In one preferred embodiment, $R_7$ is selected from H, CN, haloalkyl, Cl, F, $SO_2$-alkyl, $SO_2NR_{13}R_{14}$, heteroaryl and alkyl.

In one preferred embodiment, $R_7$ is selected from H, CN, $CF_3$, $CHF_2$, Cl, F, $SO_2$—Me, $SO_2NH_2$, heteroaryl and Me. More preferably, $R_7$ is selected from H, CN, Me, $SO_2$—Me, tetrazolyl, $CF_3$ and $CHF_2$.

In one preferred embodiment, $R_7$ is $CF_3$.

In one preferred embodiment, $R_7$ is CN.

In another preferred embodiment, $R_7$ is $SO_2$-alkyl, more preferably $SO_2$—Me.

In one preferred embodiment, $R_7$ is $SO_2NR_{13}R_{14}$, more preferably $SO_2NH_2$, In one preferred embodiment, $R_7$ is a heteroaryl group optionally substituted by one or more substituents selected from alkyl, halo, alkoxy, CN, haloalkyl and OH.

In one preferred embodiment, $R_7$ is a heteroaryl group selected from pyridinyl, thienyl, imidazolyl, pyrimidinyl, pyrazolyl, pyrazinyl, pyradizinyl, thiazolyl, isothiazolyl, triazinyl, pyrrolyl, furanyl, oxazolyl, isoxazolyl, oxadiazolyl, tetrazolyl and triazolyl, each of which is optionally substituted by one or more substituents selected from alkyl, halo, alkoxy, CN, haloalkyl and OH.

In one preferred embodiment, $R_7$ is a heteroaryl group selected from imidazolyl, pyrazolyl, pyrazinyl, pyradizinyl, thiazolyl, isothiazolyl, oxazolyl, isoxazolyl, oxadiazolyl, tetrazolyl and triazolyl, each of which is optionally substituted by one or more substituents selected from alkyl, halo, alkoxy, CN, haloalkyl and OH.

In one preferred embodiment, $R_7$ is a heteroaryl group selected from 1H-imidazol-5-yl, 1H-imidazol-4-yl, 1H-imidazol-2-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, thiazol-5-yl, thiazol-4-yl, thiazol-2-yl, 1H-1,2,3,4-tetrazol-4-yl, 2H-1,2,3,4-tetrazol-5-yl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, pyradizin-3-yl, pyradizin-4-yl, pyrazinyl, 1,3,4-oxadizol-2-yl, 1,3,4-oxadizol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, isoxazol-5-yl, isoxazol-4-yl and isoxazol-3-yl, each of which is optionally substituted by one or more substituents selected from alkyl, halo, CN, alkoxy, haloalkyl and OH.

In one highly preferred embodiment, $R_7$ is a heteroaryl group selected from 1H-pyrazol-5-yl, 1H-pyrazol-3-yl, 1H-pyrazol-4-yl, oxazol-2-yl, 1H-1,2,3-triazol-4-yl, 1H-1,2,3-triazol-5-yl, thiazol-5-yl, 1H-1,2,3,4-tetrazol-4-yl, 2H-1,2,3,4-tetrazol-5-yl, isoxazol-4-yl, isoxazol-5-yl, isothiazol-5-yl, pyradizin-3-yl, pyradizin-4-yl, pyrazinyl and 1,3,4-oxadizol-2-yl, each of which is optionally substituted by one or more substituents selected from Me, F, Cl, CN and MeO.

In one preferred embodiment, $R_7$ is a heteroaryl group optionally substituted by one or more alkyl groups, preferably one or more Me groups.

In one preferred embodiment, $R_7$ is haloalkyl or heteroaryl, more preferably tetrazolyl.

In one preferred embodiment, $R_7$ is haloalkyl, more preferably, $CF_3$.

In one preferred embodiment, $R_8$ is H or haloalkyl, more preferably H or $CF_3$, even more preferably H.

In one preferred embodiment, $R_8$ is selected from H, Me, $CF_3$, Cl, Br and F.

In another preferred embodiment, $R_8$ is selected from H, haloalkyl and Cl.

In one preferred embodiment, $R_9$ is H, Me or F, more preferably, H or F, more preferably H.

In one preferred embodiment, $R_1$, $R_3$, $R_4$, $R_6$, $R_8$ and $R_9$ are all H.

In one preferred embodiment:

$R_2$ is COOH;

X-Y is NH—$SO_2$;

$R_5$ is selected from OMe, Me, Et, Pr and Cl, and is more preferably OMe;

$R_1$, $R_3$, $R_4$, $R_6$, $R_8$ and $R_9$ are all H; and $R_7$ is haloalkyl, more preferably, $CF_3$.

In one preferred embodiment, $R_{10}$ and $R_{11}$, together with the nitrogen to which they are attached, form an azepanyl group, wherein (a) said azepanyl group is substituted by one or more groups (more preferably one or two groups) selected from alkyl, CN, halo and heteroaryl, wherein said heteroaryl group is in turn optionally further substituted with one or more groups (more preferably one or two groups) selected from halo and alkyl, or (b) one or two carbons in said azepanyl group are replaced by a group selected from O, NH, S and CO, and said azepanyl group is optionally substituted by one or more groups (more preferably one or two groups) selected from alkyl, CN, halo and heteroaryl, wherein said heteroaryl group is in turn optionally further substituted with one or more groups (more preferably one or two groups) selected from halo and alkyl.

In one preferred embodiment, $R_{10}$ and $R_{11}$, together with the nitrogen to which they are attached, form an azetidinyl, pyrrolidinyl or piperidinyl group wherein (a) said azetidinyl, pyrrolidinyl or piperidinyl group is substituted by one or more groups (more preferably one or two groups) selected from alkyl, CN, cycloalkyl, OH, alkoxy, halo, haloalkyl and heteroaryl, wherein said heteroaryl group is in turn optionally further substituted with one or more groups (more preferably one or two groups) selected from halo and alkyl, or (b) one or two carbons in said azetidinyl, pyrrolidinyl or piperidinyl group are replaced by a group selected from NH, S and CO.

In one preferred embodiment, $R_{10}$ and $R_{11}$, together with the nitrogen to which they are attached, form an azetidinyl, pyrrolidinyl or piperidinyl group wherein said azetidinyl, pyrrolidinyl or piperidinyl group is substituted by one or more groups (more preferably one or two groups) selected from alkyl, CN, cycloalkyl, OH, alkoxy, halo, haloalkyl and heteroaryl, wherein said heteroaryl group is in turn optionally further substituted with one or more groups (more preferably one or two groups) selected from halo and alkyl.

In one preferred embodiment, $R_{10}$ and $R_{11}$, together with the nitrogen to which they are attached, form an azetidinyl group which is substituted by one or more groups (more preferably one or two groups) selected from $C_{1-3}$-alkyl, CN, $C_{3-6}$-cycloalkyl, OH, $C_{1-3}$-alkoxy, halo and $CF_3$.

In one preferred embodiment, $R_{10}$ and $R_{11}$, together with the nitrogen to which they are attached, form a pyrrolidinyl group which is substituted by one or more groups (more preferably one or two groups) selected from $C_{1-3}$-alkyl, CN, $C_{3-6}$-cycloalkyl, OH, $C_{1-3}$-alkoxy, halo and $CF_3$.

In one preferred embodiment, $R_{10}$ and $R_{11}$, together with the nitrogen to which they are attached, form a piperidinyl group which is substituted by one or more groups (more preferably one or two groups) selected from $C_{1-3}$-alkyl, CN, $C_{3-6}$-cycloalkyl, OH, $C_{1-3}$-alkoxy, halo and $CF_3$.

In one preferred embodiment, $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups (more preferably one or two groups) selected from alkyl, CN, OH and halo.

In one preferred embodiment, $R_{10}$ and $R_{11}$, together with the nitrogen to which they are attached, form an 8, 9 or 10-membered bridged bicyclic heterocycloalkyl group, wherein one or two carbons in the bridged bicyclic heterocycloalkyl ring are optionally replaced by a group selected from O, NH, S and CO, and said bicyclic heterocycloalkyl group is optionally substituted by one or more groups (more preferably one or two groups) selected from alkyl, CN, OH and halo.

In one preferred embodiment, $R_{10}$ and $R_{11}$, together with the nitrogen to which they are attached, form a piperidinyl group which is optionally substituted by one or more groups (more preferably one or two groups) selected from alkyl, CN, OH and halo, and wherein two non-adjacent ring carbons in said piperidinyl group are linked to one another via a 2-carbon or 3-carbon alkylene bridge.

In one preferred embodiment, $R_{10}$ and $R_{11}$, together with the nitrogen to which they are attached, form a 6 to 12-membered bicyclic group containing a spirocyclic carbon atom, wherein one carbon in the bicyclic group is optionally replaced by an O, and said bicyclic group is optionally substituted by one or more groups (more preferably one or two groups) selected from alkyl, CN, halo and heteroaryl, or said bicyclic group is optionally fused to a 5 or 6-membered aryl or heteroaryl group. Preferably, $R_{10}$ and $R_{11}$, together with the nitrogen to which they are attached, form a 7 to 12-membered bicyclic group containing a spirocyclic carbon atom.

In one preferred embodiment, $R_{10}$ and $R_{11}$, together with the nitrogen to which they are attached, form a bicyclic group containing a spirocyclic carbon atom, which group is of the following formula (Z)

(Z)

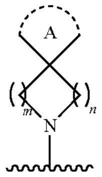

wherein:

m is 1 or 2;

n is 1, 2 or 3; and ring A is a 3, 4, 5 or 6 membered cycloalkyl or heterocycloalkyl group.

In one preferred embodiment, ring A is a 3-membered cycloalkyl or heterocycloalkyl group.

In one preferred embodiment, ring A is a 4-membered cycloalkyl or heterocycloalkyl group.

In one preferred embodiment, ring A is a 5-membered cycloalkyl or heterocycloalkyl group.

In one preferred embodiment, ring A is a 6-membered cycloalkyl or heterocycloalkyl group.

In one preferred embodiment, m is 1 and n is 1.

In one preferred embodiment, m is 1 and n is 2.

In one preferred embodiment, m is 2 and n is 2.

In one preferred embodiment, m is 2 and n is 3.

In one preferred embodiment, $R_{10}$ and $R_{11}$, together with the nitrogen to which they are attached, form a 7-membered bicyclic group containing a spirocyclic carbon atom, wherein one carbon in the bicyclic group is replaced by an O, and said bicyclic group is optionally substituted by one or more groups (more preferably one or two groups) selected from alkyl, halo and heteroaryl.

In one preferred embodiment, $R_{10}$ and $R_{11}$, together with the nitrogen to which they are attached, form an 8-membered bicyclic group containing a spirocyclic carbon atom, wherein one carbon in the bicyclic group is replaced by an O, and said bicyclic group is optionally substituted by one or more groups selected from alkyl, halo and heteroaryl.

In one preferred embodiment, $R_{10}$ and $R_{11}$, together with the nitrogen to which they are attached, form a 9-membered bicyclic group containing a spirocyclic carbon atom, wherein one carbon in the bicyclic group is replaced by an O, and said bicyclic group is optionally substituted by one or more groups (more preferably one or two groups) selected from alkyl, halo and heteroaryl.

In one preferred embodiment, $R_{10}$ and $R_{11}$, together with the nitrogen to which they are attached, form a 10-membered bicyclic group containing a spirocyclic carbon atom, wherein one carbon in the bicyclic group is replaced by an O, and said bicyclic group is optionally substituted by one or more groups (more preferably one or two groups) selected from alkyl, halo and heteroaryl.

In one preferred embodiment, $R_{10}$ and $R_{11}$, together with the nitrogen to which they are attached, form a 11-membered bicyclic group containing a spirocyclic carbon atom, wherein one carbon in the bicyclic group is replaced by an O, and said bicyclic group is optionally substituted by one or more groups (more preferably one or two groups) selected from alkyl, halo and heteroaryl.

In one preferred embodiment, $R_{10}$ and $R_{11}$, together with the nitrogen to which they are attached, form a 12-membered bicyclic group containing a spirocyclic carbon atom, wherein one carbon in the bicyclic group is replaced by an O, and said bicyclic group is optionally substituted by one or more groups (more preferably one or two groups) selected from alkyl, halo and heteroaryl.

In one preferred embodiment, $R_{10}$ and $R_{11}$, together with the nitrogen to which they are attached, form a bicyclic group comprising a ring system selected from a spiro[3.3]heptane, spiro[3.4]octane, spiro[3.5]nonane, spiro[4.4]nonane, spiro[4,5]decane, spiro[3.6]decane, spiro[5.5]undecane and spiro[5,6]dodecane arrangement, where in each of aforementioned bicyclic groups, the nitrogen of the $NR_{10}R_{11}$ group forms one member of the ring system, and another carbon in the ring system is optionally replaced by an O, and said bicyclic group is optionally substituted by one or more groups (more preferably one or two groups) selected from alkyl, halo and heteroaryl.

In one preferred embodiment. $NR_1R_{11}$ is selected from the following:

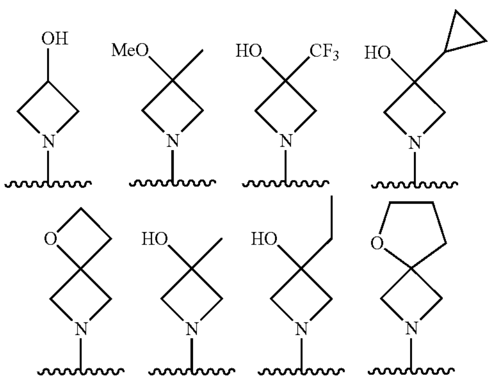

In one preferred embodiment, $NR_{10}R_{11}$ is selected from the following:

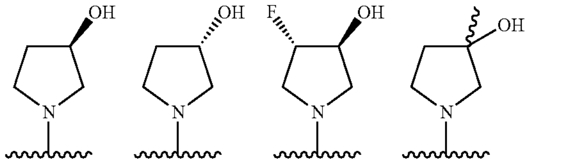

In one preferred embodiment, $NR_{10}R_{11}$ is selected from the following:

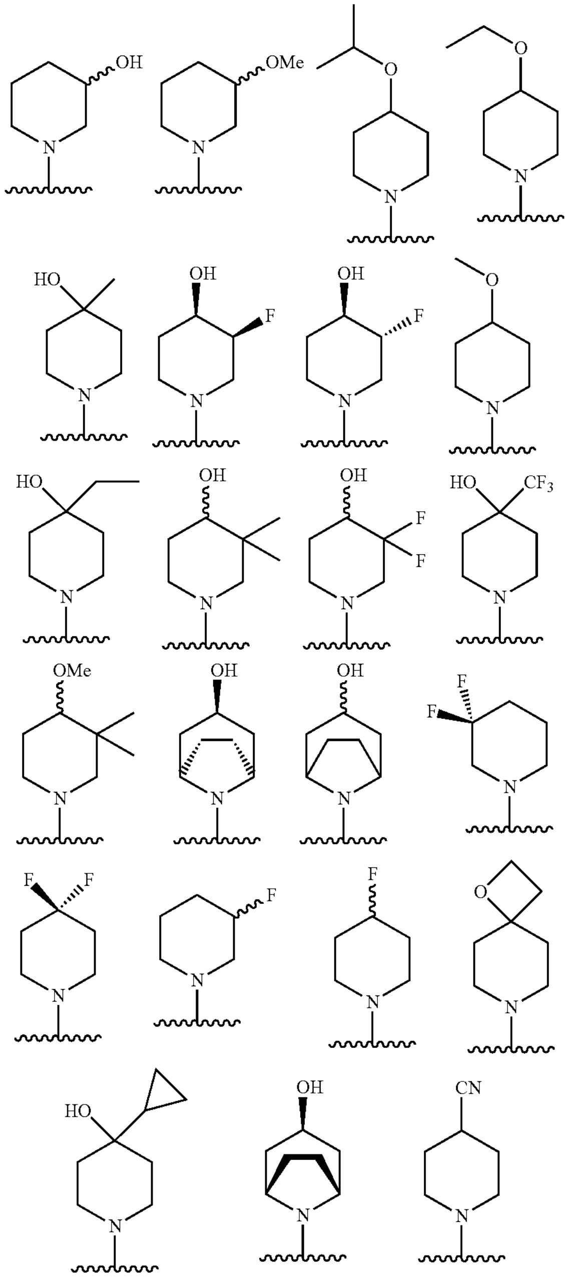

In one preferred embodiment:

$R_2$ is COOH;

X—Y is NH—$SO_2$;

$R_5$ is cyclopropyl;

$R_1$, $R_3$, $R_4$, $R_6$, $R_8$ and $R_9$ are all H; and $R_7$ is selected from CN, haloalkyl, heteroaryl and $SO_2$-alkyl; and $NR_{10}R_{11}$ is selected from the following:

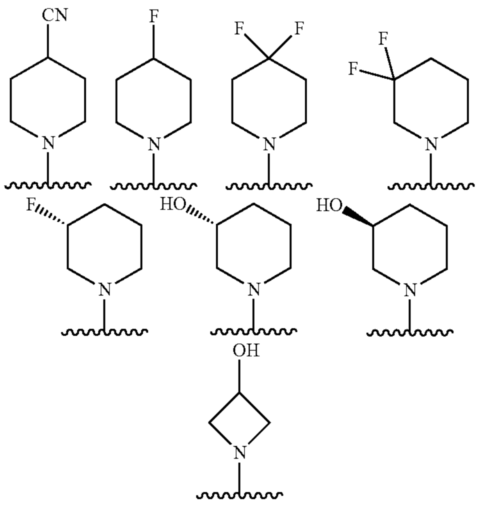

-continued

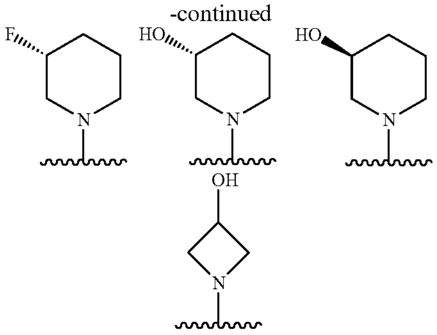

In one preferred embodiment:

$R_2$ is COOH;

X—Y is NH—$SO_2$;

$R_5$ is cyclopropyl;

$R_1$, $R_3$, $R_4$, $R_6$, $R_8$ and $R_9$ are all H; and $R_7$ is selected from CN, $CF_3$, tetrazoyl and $SO_2$—Me, more preferably CN and $SO_2$—Me;

$NR_{10}R_{11}$ is selected from the following:

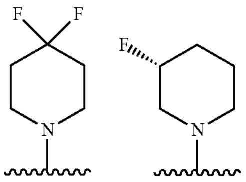

In one preferred embodiment:

$R_2$ is COOH;

X—Y is NH—$SO_2$;

$R_5$ is ethyl;

$R_1$, $R_3$, $R_4$, $R_6$, $R_8$ and $R_9$ are all H; and $R_7$ is selected from CN, haloalkyl, heteroaryl and $SO_2$-alkyl; and $NR_{10}R_{11}$ is selected from the following:

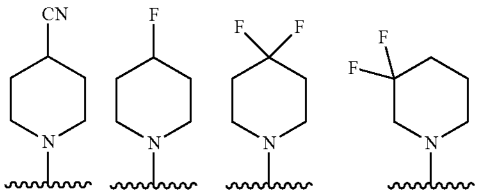

In one preferred embodiment:

$R_2$ is COOH;

X—Y is NH—$SO_2$;

$R_5$ is ethyl;

$R_1$, $R_3$, $R_4$, $R_6$, $R_8$ and $R_9$ are all H; and $R_7$ is selected from CN and $CF_3$; and $NR_{10}R_{11}$ is:

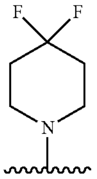

In one preferred embodiment:

$R_2$ is COOH;

X-Y is NH—$SO_2$;

$R_5$ is OMe;

$R_1$, $R_3$, $R_4$, $R_6$, $R_8$ and $R_9$ are all H; and $R_7$ is selected from CN, haloalkyl, heteroaryl and $SO_2$-alkyl; and $NR_{10}R_{11}$ is selected from the following:

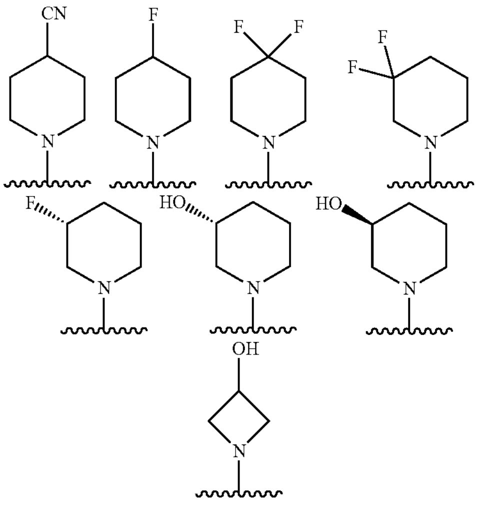

In one preferred embodiment:
$R_2$ is COOH;
X—Y is NH—$SO_2$;
$R_5$ is OMe;
$R_1$, $R_3$, $R_4$, $R_6$, $R_8$ and $R_9$ are all H; and
$R_7$ is selected from $CF_3$ and $SO_2$—Me; and
$NR_{10}R_{11}$ is selected from the following:
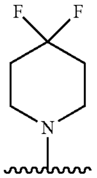 [SMILES: *N1CCC(F)(F)CC1]
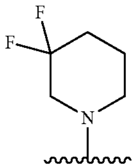
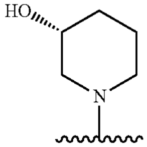
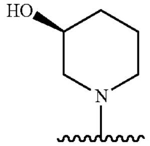
In one preferred embodiment, the compound of formula (Ia) is selected from the following:
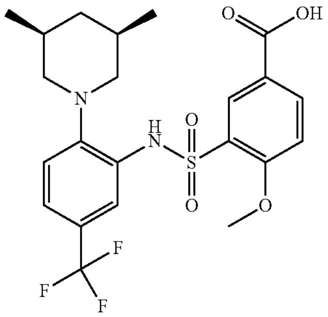 [SMILES: COc1ccc(C(=O)O)cc1S(=O)(=O)Nc1cc(C(F)(F)F)ccc1N1C[C@H](C)C[C@H](C)C1]
(6)
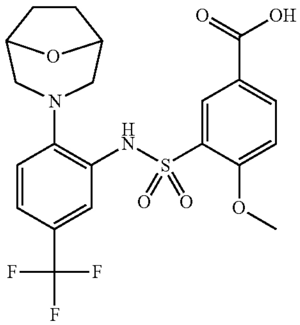 [SMILES: COc1ccc(C(=O)O)cc1S(=O)(=O)Nc1cc(C(F)(F)F)ccc1N1CC2CCC(C1)O2]
(7)
-continued
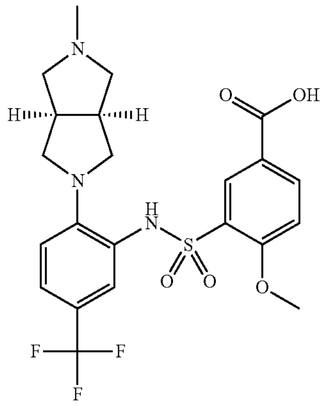 [SMILES: COc1ccc(C(=O)O)cc1S(=O)(=O)Nc1cc(C(F)(F)F)ccc1N1C[C@H]2CN(C)C[C@H]2C1]
(8)
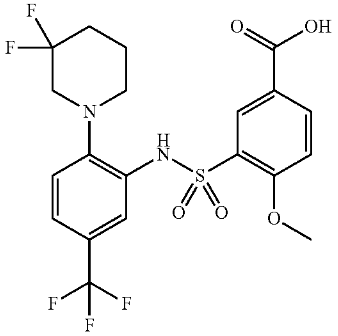 [SMILES: COc1ccc(C(=O)O)cc1S(=O)(=O)Nc1cc(C(F)(F)F)ccc1N1CCCC(F)(F)C1]
(9)
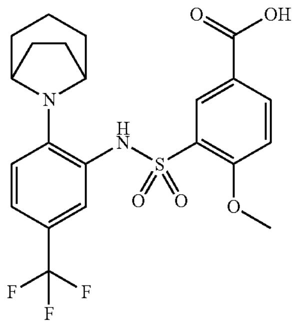 [SMILES: COc1ccc(C(=O)O)cc1S(=O)(=O)Nc1cc(C(F)(F)F)ccc1N1C2CCCC1CC2]
(10)
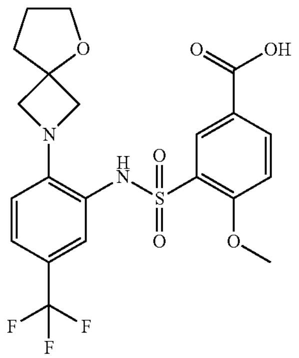 [SMILES: COc1ccc(C(=O)O)cc1S(=O)(=O)Nc1cc(C(F)(F)F)ccc1N1CC2(CCCO2)C1]
(11)

-continued
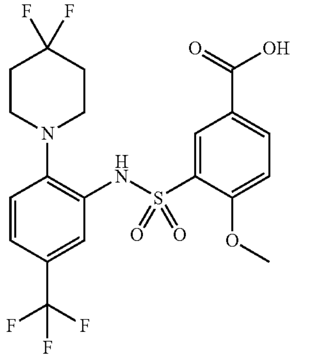
(12)
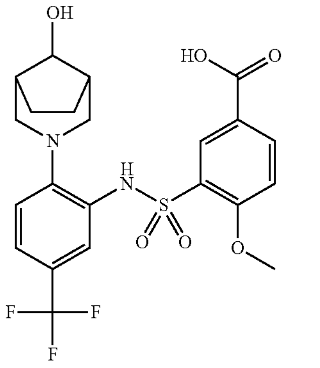 [SMILES: COc1ccc(C(=O)O)cc1S(=O)(=O)Nc1cc(C(F)(F)F)ccc1N1CC2CCC(C1)C2O]
(13)
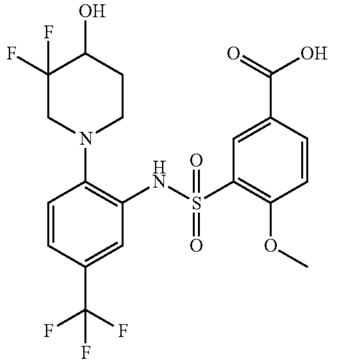 [SMILES: COc1ccc(C(=O)O)cc1S(=O)(=O)Nc1cc(C(F)(F)F)ccc1N1CCC(O)C(F)(F)C1]
(14)
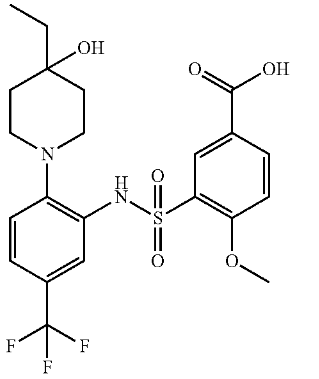 [SMILES: CCC1(O)CCN(c2ccc(C(F)(F)F)cc2NS(=O)(=O)c2cc(C(=O)O)ccc2OC)CC1]
(15)
-continued
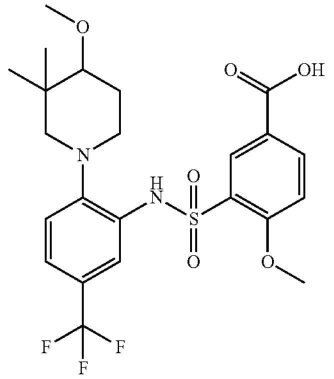
(16)
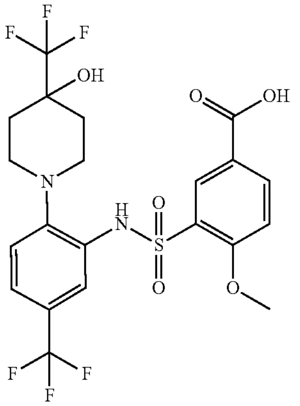 [SMILES: COc1ccc(C(=O)O)cc1S(=O)(=O)Nc1cc(C(F)(F)F)ccc1N1CCC(O)(C(F)(F)F)CC1]
(17)
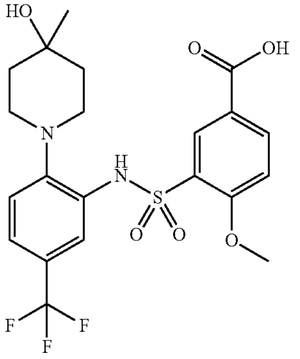
(18)
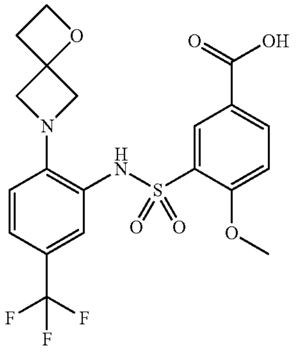 [SMILES: COc1ccc(C(=O)O)cc1S(=O)(=O)Nc1cc(C(F)(F)F)ccc1N1CC2(CCO2)C1]
(19)

-continued
(20)
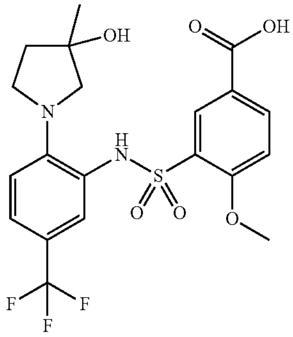 [SMILES: COc1ccc(C(=O)O)cc1S(=O)(=O)Nc1cc(C(F)(F)F)ccc1N1CCC(C)(O)C1]
(21)
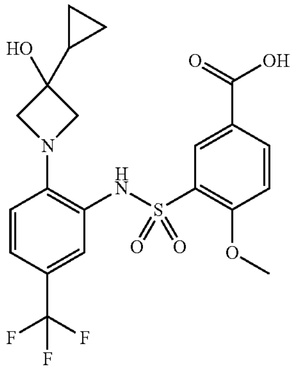 [SMILES: COc1ccc(C(=O)O)cc1S(=O)(=O)Nc1cc(C(F)(F)F)ccc1N1CC(O)(C2CC2)C1]
(22)
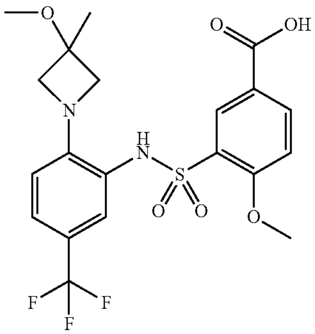
(23)
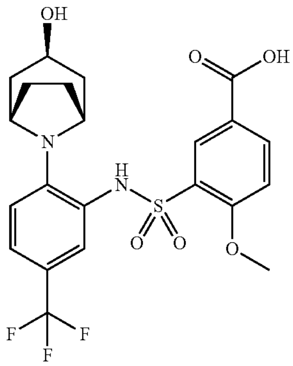 [SMILES: COc1ccc(C(=O)O)cc1S(=O)(=O)Nc1cc(C(F)(F)F)ccc1N1[C@@H]2CC[C@H]1C[C@@H](O)C2]
-continued
(24)
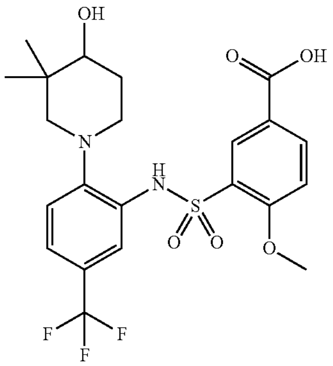 [SMILES: COc1ccc(C(=O)O)cc1S(=O)(=O)Nc1cc(C(F)(F)F)ccc1N1CCC(O)C(C)(C)C1]
(25)
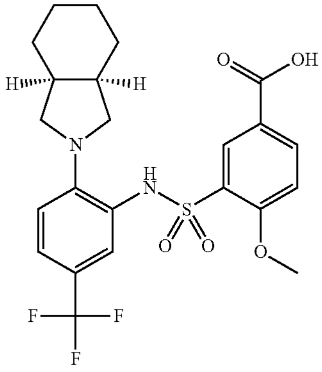 [SMILES: COc1ccc(C(=O)O)cc1S(=O)(=O)Nc1cc(C(F)(F)F)ccc1N1C[C@H]2CCCC[C@H]2C1]
(26)
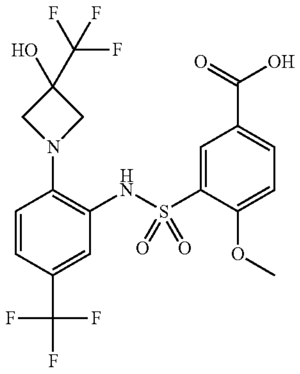 [SMILES: COc1ccc(C(=O)O)cc1S(=O)(=O)Nc1cc(C(F)(F)F)ccc1N1CC(O)(C(F)(F)F)C1]
(27)
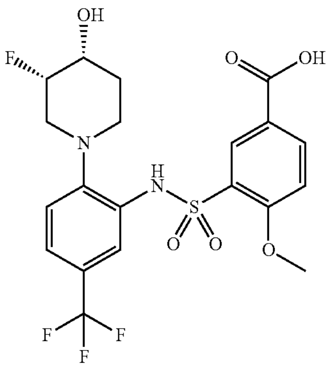 [SMILES: COc1ccc(C(=O)O)cc1S(=O)(=O)Nc1cc(C(F)(F)F)ccc1N1CC[C@@H](O)[C@@H](F)C1]

-continued
(28)
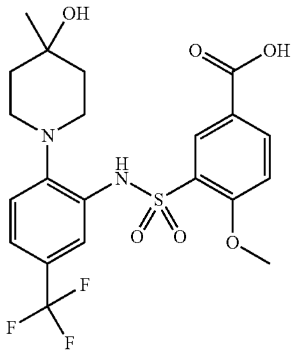 [SMILES: COc1ccc(C(=O)O)cc1S(=O)(=O)Nc1cc(C(F)(F)F)ccc1N1CCC(C)(O)CC1]
(29)
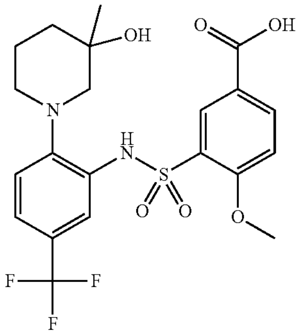 [SMILES: COc1ccc(C(=O)O)cc1S(=O)(=O)Nc1cc(C(F)(F)F)ccc1N1CCCC(C)(O)C1]
(30)
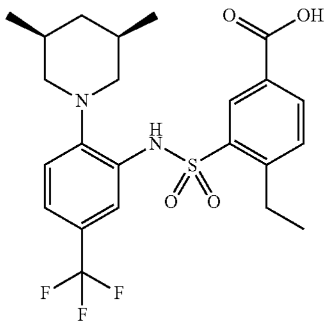 [SMILES: CCc1ccc(C(=O)O)cc1S(=O)(=O)Nc1cc(C(F)(F)F)ccc1N1C[C@H](C)C[C@H](C)C1]
(31)
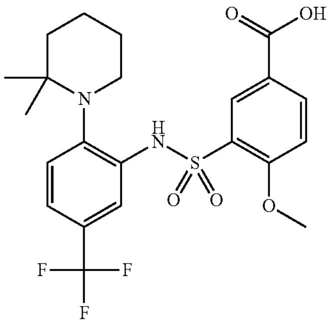
-continued
(32)
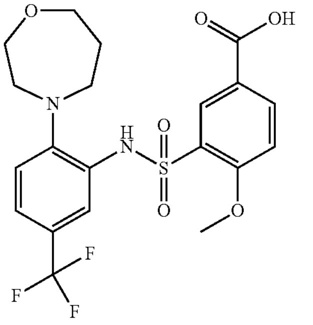 [SMILES: COc1ccc(C(=O)O)cc1S(=O)(=O)Nc1cc(C(F)(F)F)ccc1N1CCCOCC1]
(33)
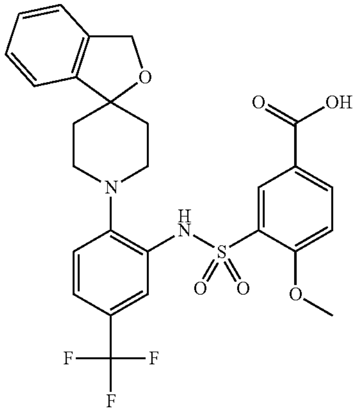 [SMILES: COc1ccc(C(=O)O)cc1S(=O)(=O)Nc1cc(C(F)(F)F)ccc1N1CCC2(CC1)OCc1ccccc12]
(35)
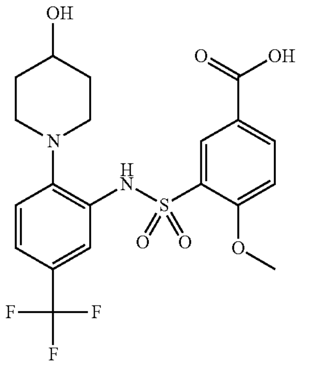 [SMILES: COc1ccc(C(=O)O)cc1S(=O)(=O)Nc1cc(C(F)(F)F)ccc1N1CCC(O)CC1]
(36)
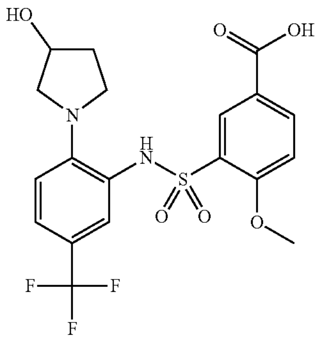

-continued
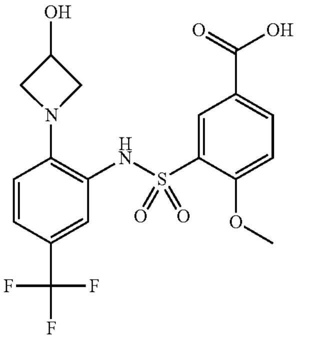
(37)
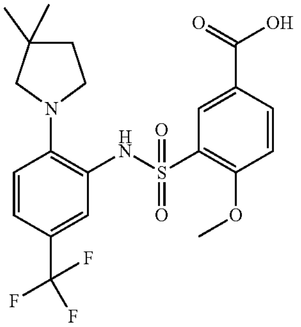 [SMILES: COc1ccc(C(=O)O)cc1S(=O)(=O)Nc1cc(C(F)(F)F)ccc1N1CCC(C)(C)C1]
(39)
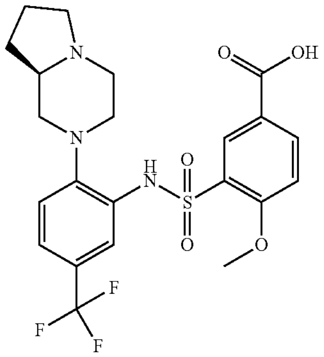 [SMILES: COc1ccc(C(=O)O)cc1S(=O)(=O)Nc1cc(C(F)(F)F)ccc1N1CCN2CCC[C@@H]2C1]
(40)
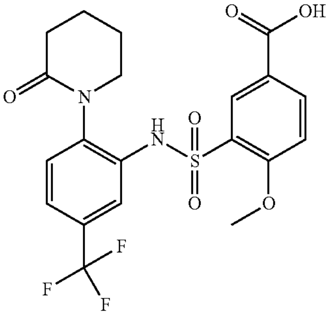 [SMILES: COc1ccc(C(=O)O)cc1S(=O)(=O)Nc1cc(C(F)(F)F)ccc1N1CCCCC1=O]
(41)
-continued
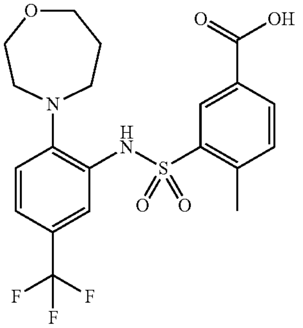 [SMILES: Cc1ccc(C(=O)O)cc1S(=O)(=O)Nc1cc(C(F)(F)F)ccc1N1CCCOCC1]
(42)
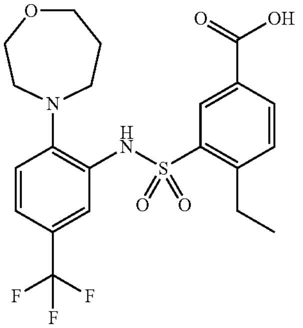 [SMILES: CCc1ccc(C(=O)O)cc1S(=O)(=O)Nc1cc(C(F)(F)F)ccc1N1CCCOCC1]
(43)
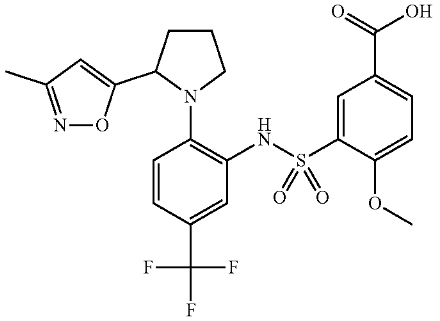
(46)
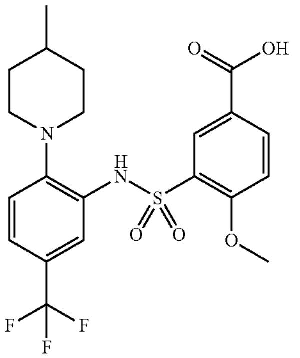 [SMILES: COc1ccc(C(=O)O)cc1S(=O)(=O)Nc1cc(C(F)(F)F)ccc1N1CCC(C)CC1]
(84)

-continued
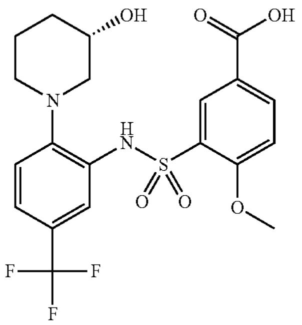
(177)
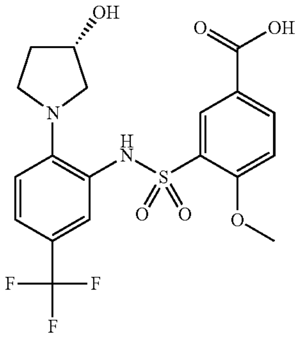 [SMILES: COc1ccc(C(=O)O)cc1S(=O)(=O)Nc1cc(C(F)(F)F)ccc1N1CC[C@H](O)C1]
(178)
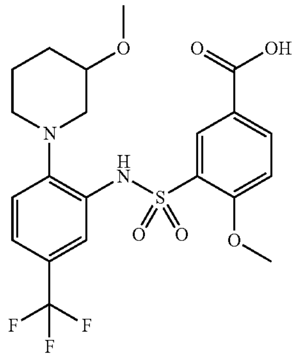
(179)
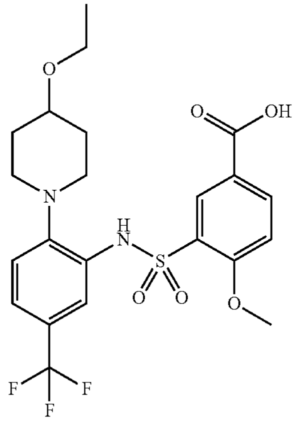
(180)
-continued
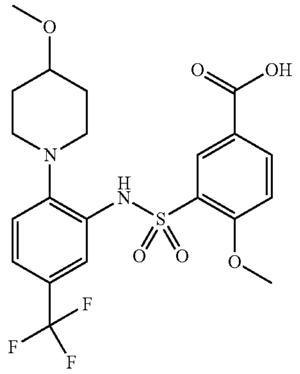 [SMILES: COc1ccc(C(=O)O)cc1S(=O)(=O)Nc1cc(C(F)(F)F)ccc1N1CCC(OC)CC1]
(181)
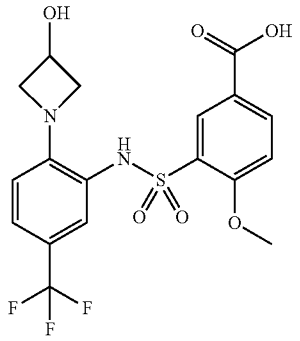
(183)
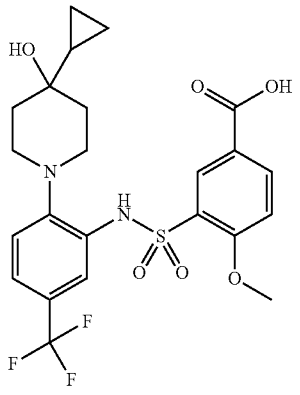 [SMILES: COc1ccc(C(=O)O)cc1S(=O)(=O)Nc1cc(C(F)(F)F)ccc1N1CCC(O)(C2CC2)CC1]
(185)
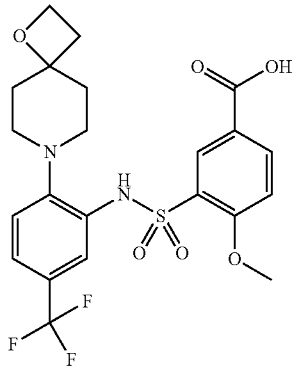 [SMILES: COc1ccc(C(=O)O)cc1S(=O)(=O)Nc1cc(C(F)(F)F)ccc1N1CCC2(CCO2)CC1]
(186)

-continued
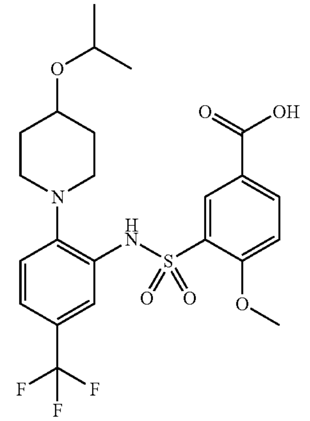 [SMILES: COc1ccc(C(=O)O)cc1S(=O)(=O)Nc1cc(C(F)(F)F)ccc1N1CCC(OC(C)C)CC1]
(187)
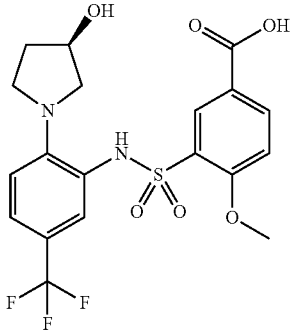 [SMILES: COc1ccc(C(=O)O)cc1S(=O)(=O)Nc1cc(C(F)(F)F)ccc1N1CC[C@@H](O)C1]
(188)
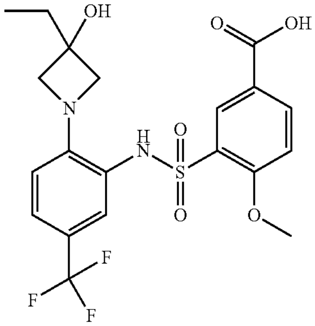 [SMILES: CCC1(O)CN(c2ccc(C(F)(F)F)cc2NS(=O)(=O)c2cc(C(=O)O)ccc2OC)C1]
(189)
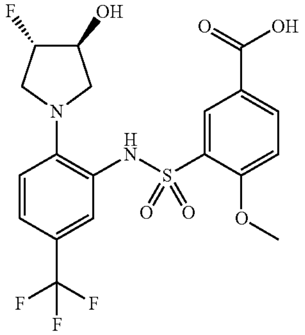 [SMILES: COc1ccc(C(=O)O)cc1S(=O)(=O)Nc1cc(C(F)(F)F)ccc1N1C[C@H](O)[C@@H](F)C1]
(190)
-continued
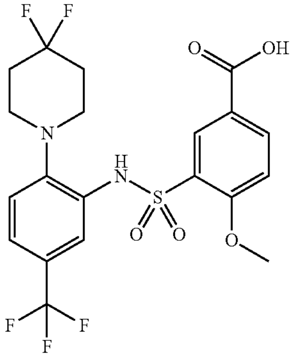
(203)
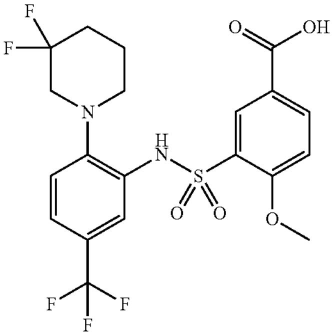 [SMILES: COc1ccc(C(=O)O)cc1S(=O)(=O)Nc1cc(C(F)(F)F)ccc1N1CCCC(F)(F)C1]
(204)
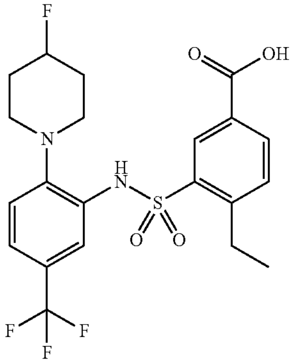
(205)
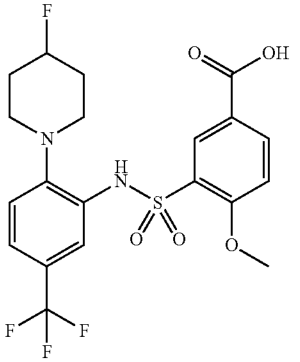
(206)

-continued
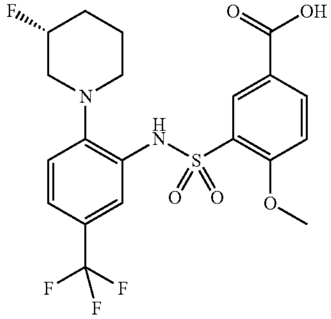
(208)
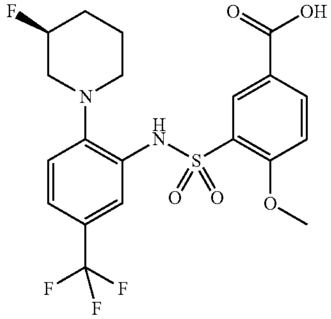 [SMILES: COc1ccc(C(=O)O)cc1S(=O)(=O)Nc1cc(C(F)(F)F)ccc1N1CCC[C@H](F)C1]
(209)
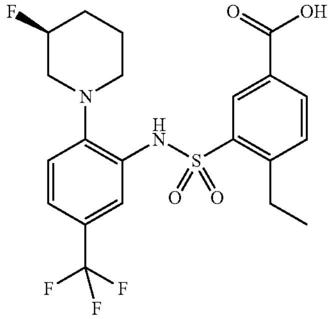 [SMILES: CCc1ccc(C(=O)O)cc1S(=O)(=O)Nc1cc(C(F)(F)F)ccc1N1CCC[C@H](F)C1]
(210)
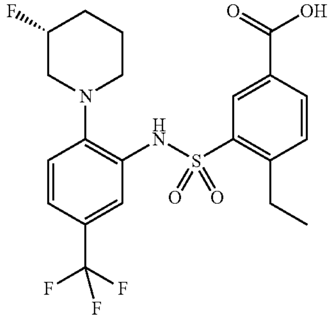 [SMILES: CCc1ccc(C(=O)O)cc1S(=O)(=O)Nc1cc(C(F)(F)F)ccc1N1CCC[C@@H](F)C1]
(211)
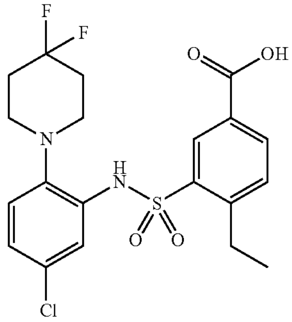 [SMILES: CCc1ccc(C(=O)O)cc1S(=O)(=O)Nc1cc(Cl)ccc1N1CCC(F)(F)CC1]
(217)
-continued
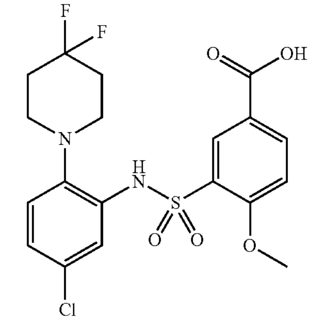 [SMILES: COc1ccc(C(=O)O)cc1S(=O)(=O)Nc1cc(Cl)ccc1N1CCC(F)(F)CC1]
(218)
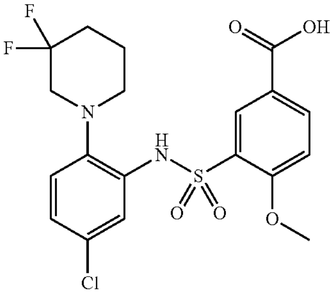 [SMILES: COc1ccc(C(=O)O)cc1S(=O)(=O)Nc1cc(Cl)ccc1N1CCCC(F)(F)C1]
(219)
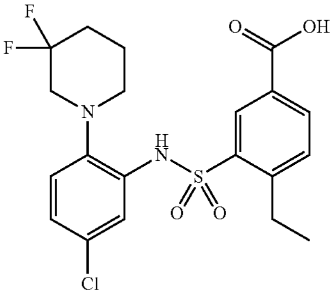
(220)
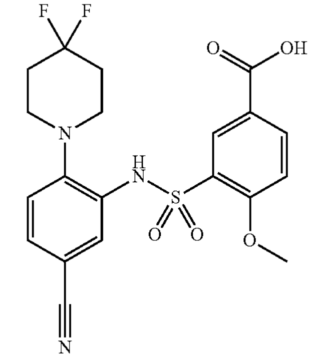
(221)
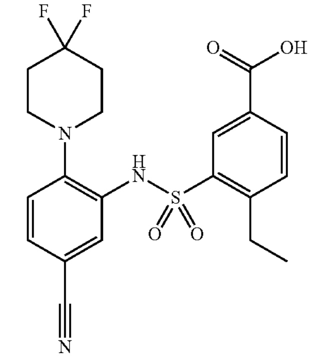
(222)

-continued
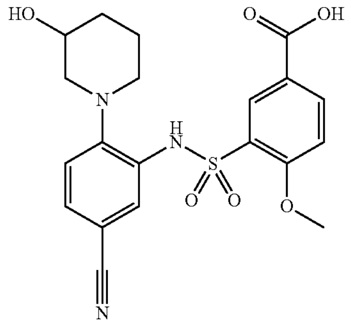
(223)
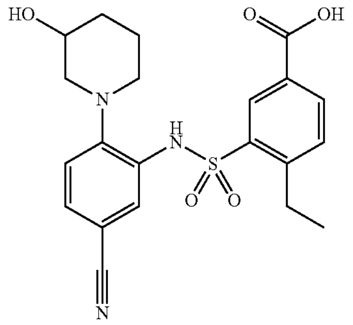
(224)
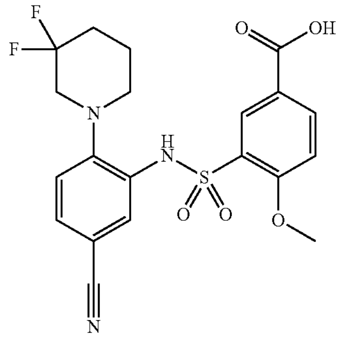 [SMILES: COc1ccc(C(=O)O)cc1S(=O)(=O)Nc1cc(C#N)ccc1N1CCCC(F)(F)C1]
(233)
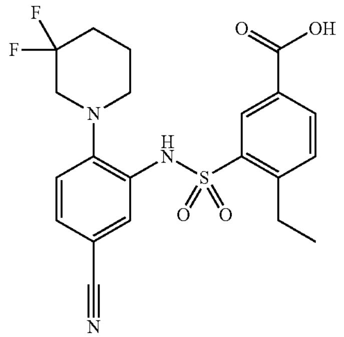 [SMILES: CCc1ccc(C(=O)O)cc1S(=O)(=O)Nc1cc(C#N)ccc1N1CCCC(F)(F)C1]
(234)
-continued
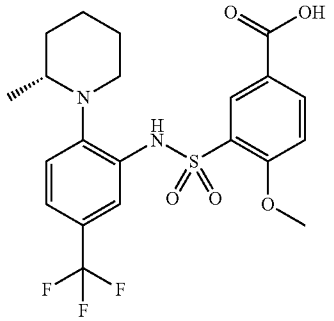
(235)
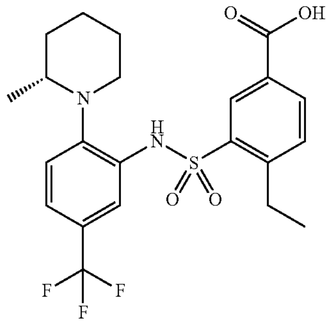
(236)
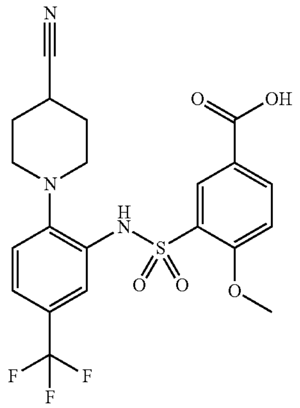
(237)
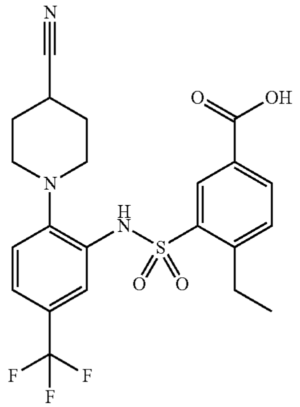
(238)

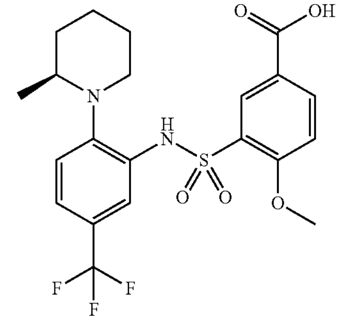
(239)
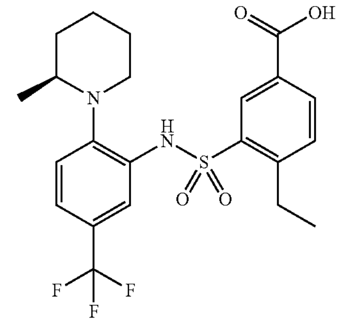
(240)
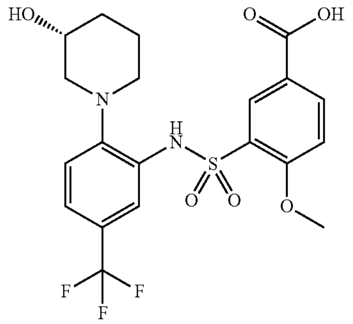 [SMILES: COc1ccc(C(=O)O)cc1S(=O)(=O)Nc1cc(C(F)(F)F)ccc1N1CCC[C@@H](O)C1]
(243)
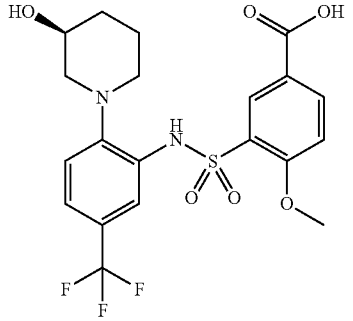 [SMILES: COc1ccc(C(=O)O)cc1S(=O)(=O)Nc1cc(C(F)(F)F)ccc1N1CCC[C@H](O)C1]
(244)
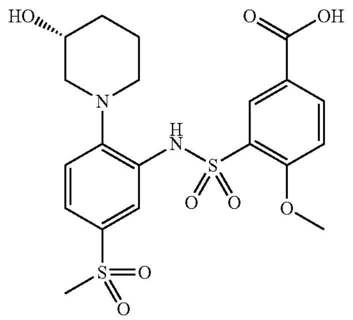 [SMILES: COc1ccc(C(=O)O)cc1S(=O)(=O)Nc1cc(S(C)(=O)=O)ccc1N1CCC[C@@H](O)C1]
(245)
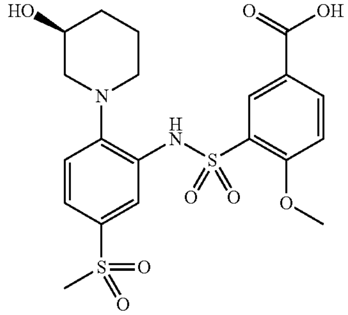 [SMILES: COc1ccc(C(=O)O)cc1S(=O)(=O)Nc1cc(S(C)(=O)=O)ccc1N1CCC[C@H](O)C1]
(246)
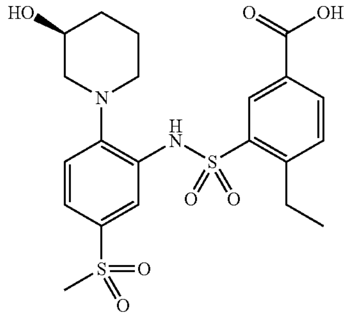 [SMILES: CCc1ccc(C(=O)O)cc1S(=O)(=O)Nc1cc(S(C)(=O)=O)ccc1N1CCC[C@H](O)C1]
(247)
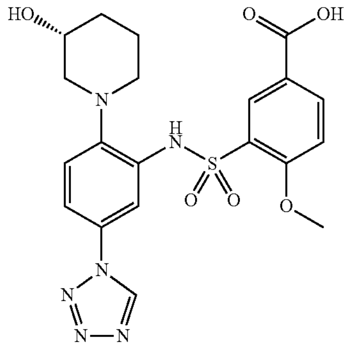 [SMILES: COc1ccc(C(=O)O)cc1S(=O)(=O)Nc1cc(-n2cnnn2)ccc1N1CCC[C@@H](O)C1]
(248)
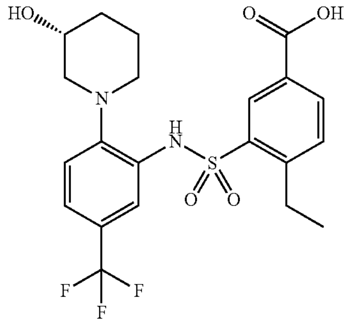 [SMILES: CCc1ccc(C(=O)O)cc1S(=O)(=O)Nc1cc(C(F)(F)F)ccc1N1CCC[C@@H](O)C1]
(249)
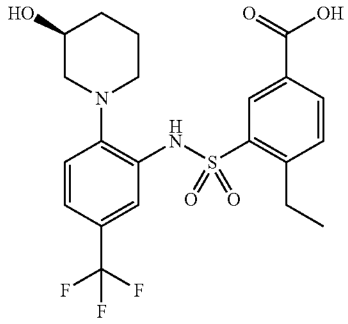 [SMILES: CCc1ccc(C(=O)O)cc1S(=O)(=O)Nc1cc(C(F)(F)F)ccc1N1CCC[C@H](O)C1]
(250)

-continued
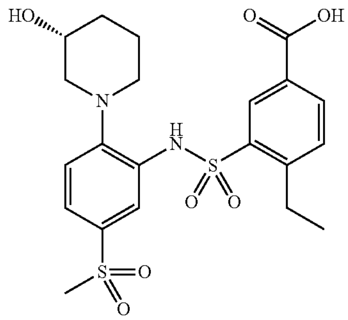 [SMILES: CCc1ccc(C(=O)O)cc1S(=O)(=O)Nc1cc(S(C)(=O)=O)ccc1N1CCC[C@@H](O)C1]
(251)
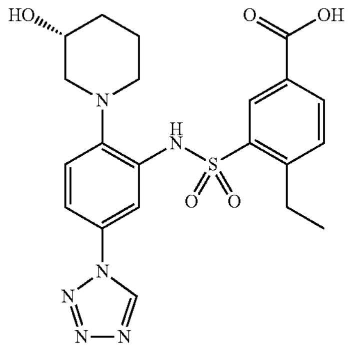 [SMILES: CCc1ccc(C(=O)O)cc1S(=O)(=O)Nc1cc(-n2cnnn2)ccc1N1CCC[C@@H](O)C1]
(252)
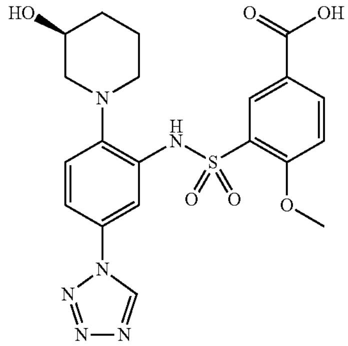 [SMILES: COc1ccc(C(=O)O)cc1S(=O)(=O)Nc1cc(-n2cnnn2)ccc1N1CCC[C@H](O)C1]
(253)
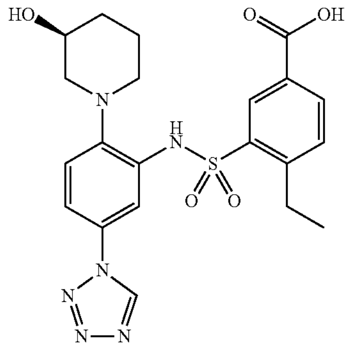 [SMILES: CCc1ccc(C(=O)O)cc1S(=O)(=O)Nc1cc(-n2cnnn2)ccc1N1CCC[C@H](O)C1]
(254)
-continued
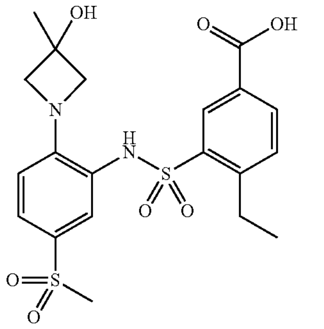 [SMILES: CCc1ccc(C(=O)O)cc1S(=O)(=O)Nc1cc(S(C)(=O)=O)ccc1N1CC(C)(O)C1]
(255)
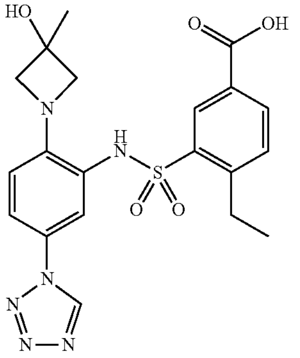 [SMILES: CCc1ccc(C(=O)O)cc1S(=O)(=O)Nc1cc(-n2cnnn2)ccc1N1CC(C)(O)C1]
(257)
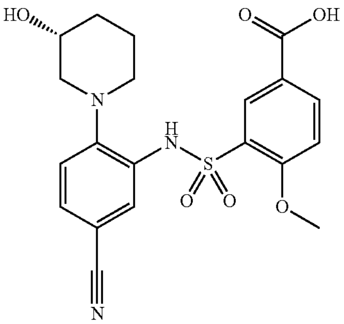
(258)
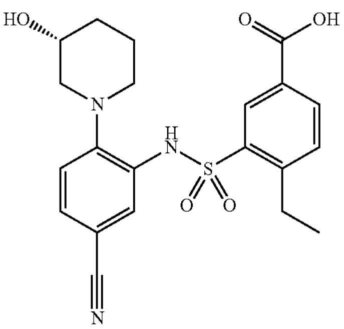
(260)

-continued
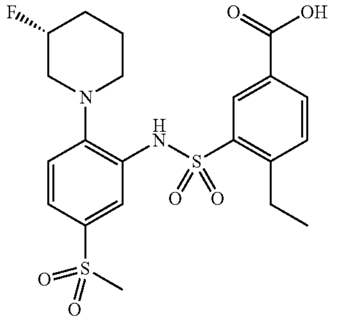
(262)
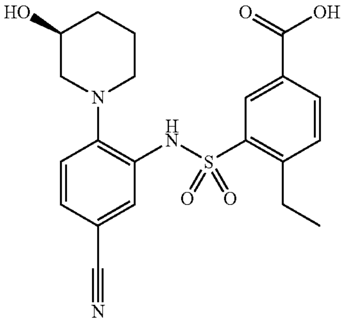
(263)
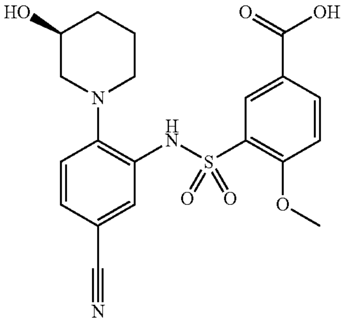
(264)
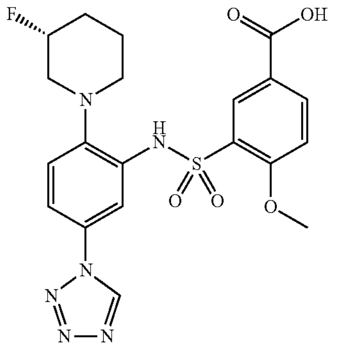
(265)
-continued
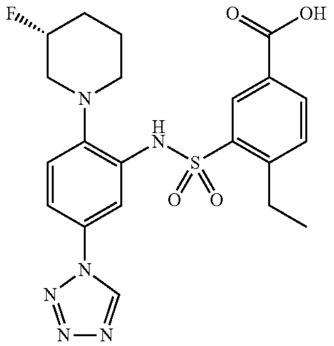
(266)
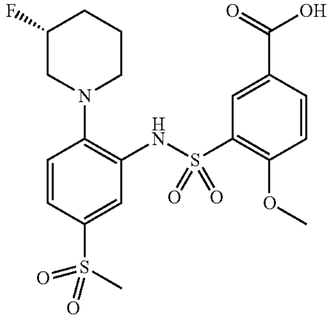
(269)
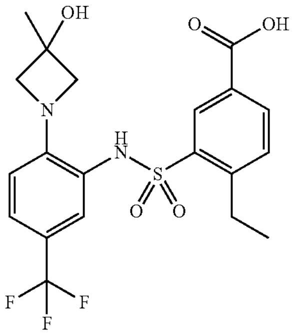 [SMILES: CCc1ccc(C(=O)O)cc1S(=O)(=O)Nc1cc(C(F)(F)F)ccc1N1CC(C)(O)C1]
(270)
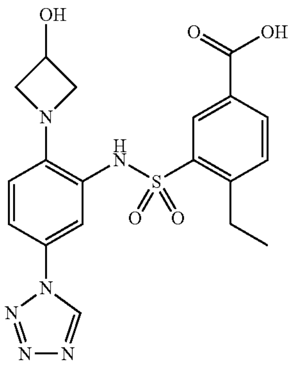 [SMILES: CCc1ccc(C(=O)O)cc1S(=O)(=O)Nc1cc(-n2cnnn2)ccc1N1CC(O)C1]
(283)

-continued
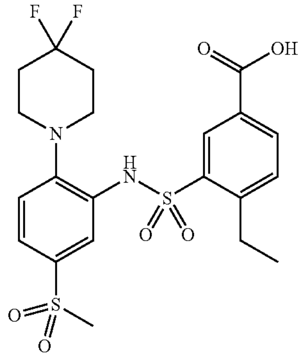 [SMILES: CCc1ccc(C(=O)O)cc1S(=O)(=O)Nc1cc(S(C)(=O)=O)ccc1N1CCC(F)(F)CC1]
(308)
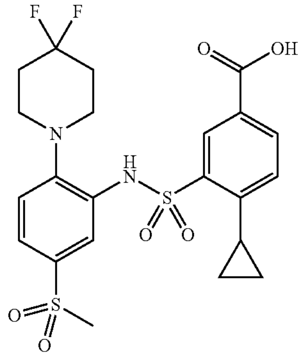 [SMILES: CS(=O)(=O)c1ccc(N2CCC(F)(F)CC2)c(NS(=O)(=O)c2cc(C(=O)O)ccc2C2CC2)c1]
(309)
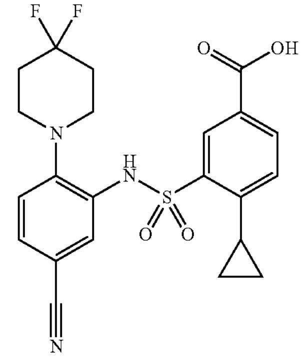 [SMILES: N#Cc1ccc(N2CCC(F)(F)CC2)c(NS(=O)(=O)c2cc(C(=O)O)ccc2C2CC2)c1]
(310)
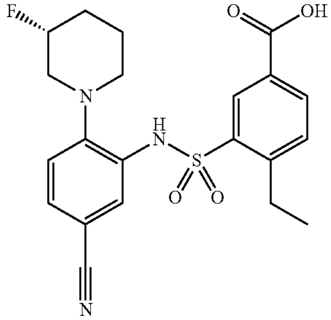 [SMILES: CCc1ccc(C(=O)O)cc1S(=O)(=O)Nc1cc(C#N)ccc1N1CCC[C@@H](F)C1]
(311)
-continued
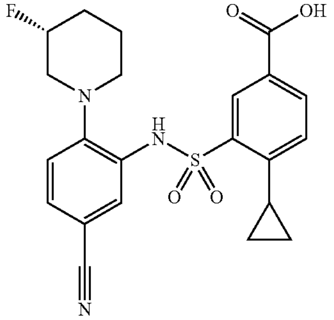 [SMILES: N#Cc1ccc(N2CCC[C@@H](F)C2)c(NS(=O)(=O)c2cc(C(=O)O)ccc2C2CC2)c1]
(312)
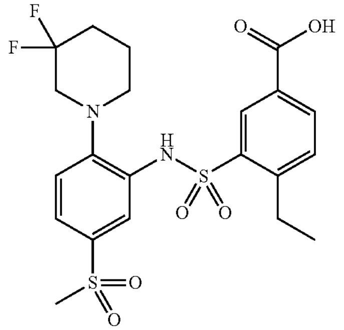 [SMILES: CCc1ccc(C(=O)O)cc1S(=O)(=O)Nc1cc(S(C)(=O)=O)ccc1N1CCCC(F)(F)C1]
(313)
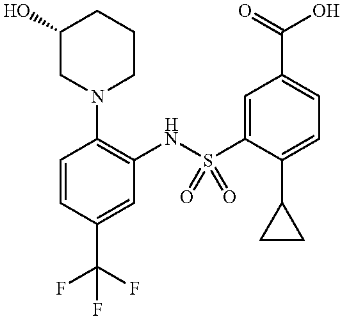 [SMILES: O=C(O)c1ccc(C2CC2)c(S(=O)(=O)Nc2cc(C(F)(F)F)ccc2N2CCC[C@@H](O)C2)c1]
(314)
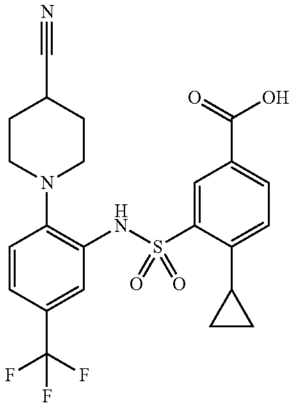
(315)

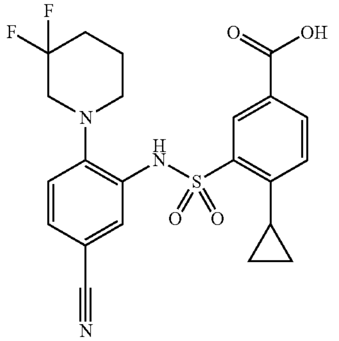 [SMILES: N#Cc1ccc(N2CCCC(F)(F)C2)c(NS(=O)(=O)c2cc(C(=O)O)ccc2C2CC2)c1]
(316)
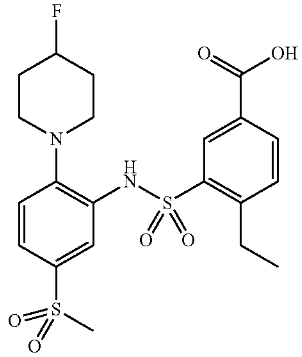 [SMILES: CCc1ccc(C(=O)O)cc1S(=O)(=O)Nc1cc(S(C)(=O)=O)ccc1N1CCC(F)CC1]
(317)
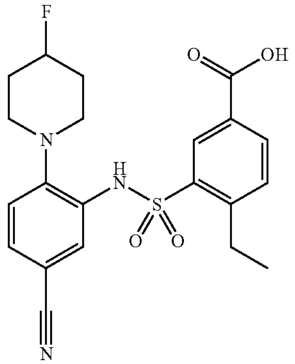 [SMILES: CCc1ccc(C(=O)O)cc1S(=O)(=O)Nc1cc(C#N)ccc1N1CCC(F)CC1]
(318)
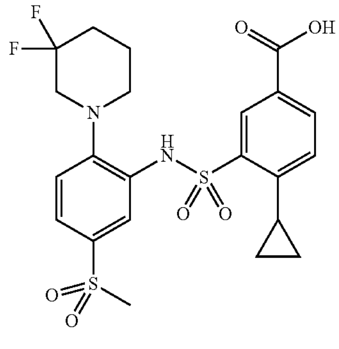 [SMILES: CS(=O)(=O)c1ccc(N2CCCC(F)(F)C2)c(NS(=O)(=O)c2cc(C(=O)O)ccc2C2CC2)c1]
(319)
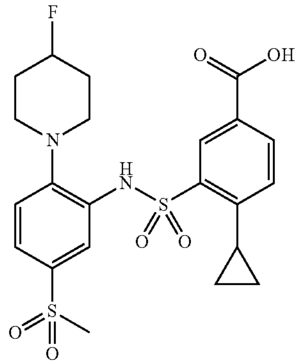 [SMILES: CS(=O)(=O)c1ccc(N2CCC(F)CC2)c(NS(=O)(=O)c2cc(C(=O)O)ccc2C2CC2)c1]
(320)
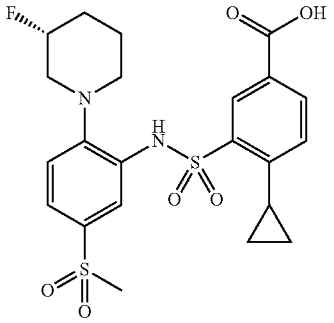 [SMILES: CS(=O)(=O)c1ccc(N2CCC[C@@H](F)C2)c(NS(=O)(=O)c2cc(C(=O)O)ccc2C2CC2)c1]
(321)
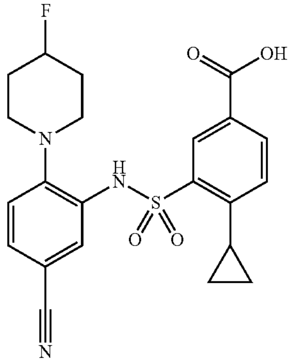 [SMILES: N#Cc1ccc(N2CCC(F)CC2)c(NS(=O)(=O)c2cc(C(=O)O)ccc2C2CC2)c1]
(322)
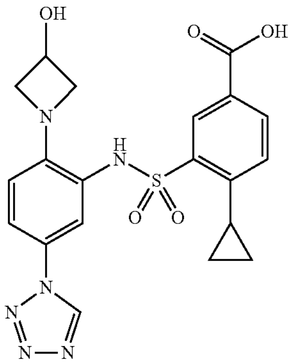 [SMILES: O=C(O)c1ccc(C2CC2)c(S(=O)(=O)Nc2cc(-n3cnnn3)ccc2N2CC(O)C2)c1]
(325)

-continued

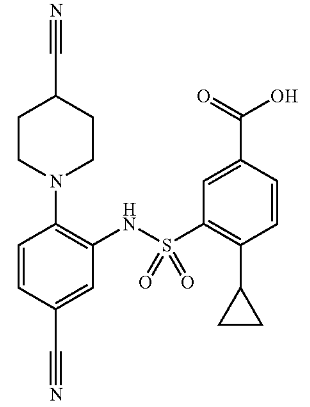 [SMILES: N#Cc1ccc(N2CCC(C#N)CC2)c(NS(=O)(=O)c2cc(C(=O)O)ccc2C2CC2)c1]

(326)

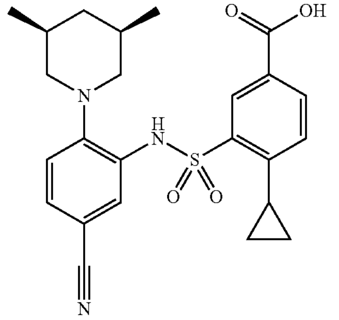 [SMILES: C[C@@H]1C[C@H](C)CN(c2ccc(C#N)cc2NS(=O)(=O)c2cc(C(=O)O)ccc2C2CC2)C1]

(328)

and pharmaceutically acceptable salts and hydrates thereof.

Compounds of Formula (Ib)

Another aspect of the invention relates to compounds of formula (Ib), or a pharmaceutically acceptable salt or hydrate thereof,

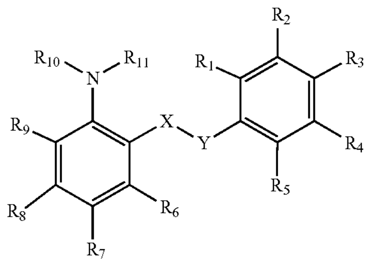

(Ib)

wherein:

the group X—Y is —$NHSO_2$— or —$SO_2NH$—;

$R_1$ is H or alkyl;

$R_2$ is a tetrazolyl group;

$R_3$ is selected from H, Cl and alkyl;

$R_4$ is selected from H, Cl and F;

$R_5$ is selected from H, alkyl, alkynyl, alkenyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, Cl, F, $SO_2$-alkyl, $SO_2NR_{13}R_{14}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H;

$R_9$ is H, $C_1$-$C_3$-alkyl or halo;

$R_{11}$ is alkyl optionally substituted by one or more substituents selected from $NH_2$, OH, and $NHCO_2R_{12}$, wherein $R_{12}$ is alkyl; or $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected from alkyl, CN, cycloalkyl, OH, alkoxy, halo, haloalkyl and heteroaryl; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, cycloalkyl, OH, alkoxy, halo, haloalkyl and heteroaryl, or said bicylic group is optionally fused to a 5 or 6-membered aryl or heteroaryl group; and $R_{13}$ and $R_{14}$ are each independently H or alkyl.

In one preferred embodiment, $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl. More preferably, $R_{10}$ and $R_{11}$, together with the nitrogen to which they are attached, form a piperidinyl, pyrrolidinyl, azepanyl or azetidinyl group, each of which is optionally substituted by one or more groups selected from alkyl, CN, cycloalkyl, OH, alkoxy, halo and haloalkyl.

In one preferred embodiment, $R_{10}$ and $R_{11}$, together with the nitrogen to which they are attached, form a 6-membered monocyclic heterocycloalkyl group selected from piperidinyl, morpholinyl, thiomorpholinyl and piperazinyl, each of which is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl. More preferably, $R_{10}$ and $R_{11}$, together with the nitrogen to which they are attached, form a 6-membered monocyclic heterocycloalkyl group selected from piperidinyl, morpholinyl, thiomorpholinyl and piperazinyl, each of which is optionally substituted by one or more groups selected from alkyl, CN, cycloalkyl, OH, alkoxy, halo and haloalkyl.

In one preferred embodiment, $R_{10}$ and $R_{11}$, together with the nitrogen to which they are attached, form a piperidinyl group, wherein one or two carbons in the monocyclic heterocycloalkyl group are optionally replaced by a group selected from O, NH, S and CO, and said piperidinyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl. In one highly preferred embodiment, $R_{10}$ and $R_{11}$, together with the nitrogen to which they are attached, form an unsubstituted piperidinyl or pyrrolidinyl group, more preferably, an unsubstituted piperidinyl.

Other preferred definitions for groups $R_1$, $R_{3-11}$, X and Y are as set out above for compounds of formula (Ia) and apply mutatis mutandis to compounds of formula (Ib).

In one preferred embodiment, the compound of formula (Ib) is:

(171)

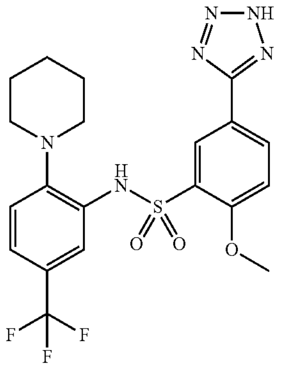 [SMILES: COc1ccc(-c2nn[nH]n2)cc1S(=O)(=O)Nc1cc(C(F)(F)F)ccc1N1CCCCC1]

or a pharmaceutically acceptable salt or hydrate thereof.

Compounds of Formula (Ic)

Another aspect of the invention relates to compounds of formula (Ic), or a pharmaceutically acceptable salt or hydrate thereof, (Ic)

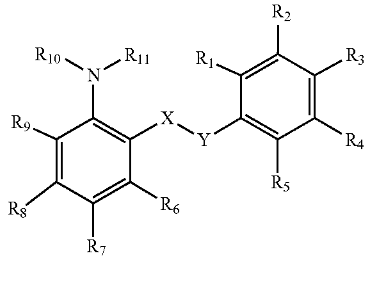

wherein:

X is $SO_2$;

Y is NH;

$R_1$ is H or alkyl;

$R_2$ is selected from COOH and a tetrazolyl group;

$R_3$ is selected from H, Cl and alkyl;

$R_4$ is selected from H, Cl and F;

$R_5$ is selected from H, alkyl, alkynyl, alkenyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, Cl, F, $SO_2$-alkyl, $SO_2NR_{13}R_{14}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H, $C_1$-$C_3$-alkyl or halo;

$R_{10}$ is H or alkyl;

$R_{11}$ is alkyl optionally substituted by one or more substituents selected from $NH_2$, OH, and $NHCO_2R_{12}$, wherein $R_{12}$ is alkyl; or $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected from alkyl, CN, cycloalkyl, OH, alkoxy, halo, haloalkyl and heteroaryl; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, cycloalkyl, OH, alkoxy, halo, haloalkyl and heteroaryl, or said bicyclic group is optionally fused to a 5 or 6-membered aryl or heteroaryl group; and $R_{13}$ and $R_{14}$ are each independently H or alkyl.

In one preferred embodiment, $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl. More preferably, $R_{10}$ and $R_{11}$, together with the nitrogen to which they are attached, form a piperidinyl, pyrrolidinyl, azepanyl or azetidinyl group, each of which is optionally substituted by one or more groups selected from alkyl, CN, cycloalkyl, OH, alkoxy, halo and haloalkyl.

In one preferred embodiment, $R_{10}$ and $R_{11}$, together with the nitrogen to which they are attached, form a 6-membered monocyclic heterocycloalkyl group selected from piperidinyl, morpholinyl, thiomorpholinyl and piperazinyl, each of which is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl. More preferably, $R_{10}$ and $R_{11}$, together with the nitrogen to which they are attached, form a 6-membered monocyclic heterocycloalkyl group selected from piperidinyl, morpholinyl, thiomorpholinyl and piperazinyl, each of which is optionally substituted by one or more groups selected from alkyl, CN, cycloalkyl, OH, alkoxy, halo and haloalkyl.

In one preferred embodiment, $R_{10}$ and $R_{11}$, together with the nitrogen to which they are attached, form a piperidinyl group, wherein one or two carbons in the monocyclic heterocycloalkyl group are optionally replaced by a group selected from O, NH, S and CO, and said piperidinyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl. In one highly preferred embodiment, $R_{10}$ and $R_{11}$, together with the nitrogen to which they are attached, form an unsubstituted piperidinyl or pyrrolidinyl group, more preferably, an unsubstituted piperidinyl.

Other preferred definitions for groups $R_{1-11}$ are as set out above for compounds of formula (Ia) and apply mutatis mutandis to compounds of formula (Ic).

In one embodiment, the compound of formula (Ic) is selected from the following:

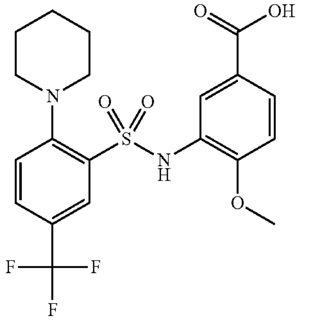 [SMILES: COc1ccc(C(=O)O)cc1NS(=O)(=O)c1cc(C(F)(F)F)ccc1N1CCCCC1]

(49)

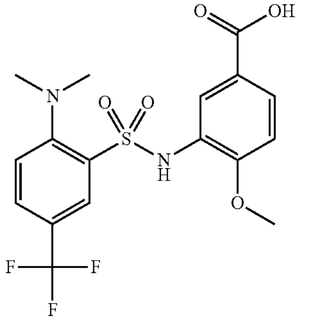

(51)

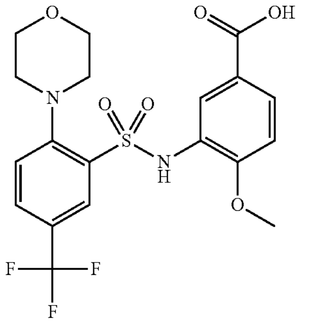

(52)

-continued

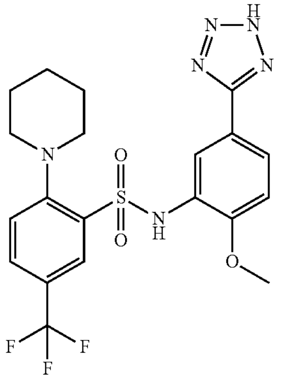 [SMILES: COc1ccc(-c2nn[nH]n2)cc1NS(=O)(=O)c1cc(C(F)(F)F)ccc1N1CCCCC1]

(63)

and pharmaceutically acceptable salts and hydrates thereof.

Compounds of Formula (Id)

A further aspect of the invention relates to compounds of formula (Id), or pharmaceutically acceptable salts or hydrates thereof,

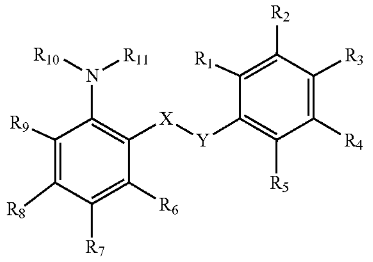

(Id)

wherein:

the group X—Y is —$NHSO_2$— or —$SO_2NH$—;

$R_1$ is H or alkyl;

$R_2$ is selected from COOH and a tetrazolyl group;

$R_3$ is selected from H, Cl and alkyl;

$R_4$ is selected from H, Cl and F;

$R_5$ is selected from H, alkyl, alkynyl, alkenyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is CN, $SO_2$-alkyl, $SO_2NR_{13}R_{14}$, or a heteroaryl group, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H, $C_1$-$C_3$-alkyl or halo;

$R_{10}$ is H or alkyl;

$R_{11}$ is alkyl optionally substituted by one or more substituents selected from $NH_2$, OH, and $NHCO_2R_{12}$, wherein $R_{12}$ is alkyl; or $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected from alkyl, CN, cycloalkyl, OH, alkoxy, halo, haloalkyl and heteroaryl; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, cycloalkyl, OH, alkoxy, halo, haloalkyl and heteroaryl, or said bicyclic group is optionally fused to a 5 or 6-membered aryl or heteroaryl group; and $R_{13}$ and $R_{14}$ are each independently H or alkyl.

Preferred definitions for substituents X, Y, $R_{1-6}$ and $R_8$-11 are as set forth above for compounds of formula (Ia) and apply mutatis mutandis to compounds of formula (Id).

In one preferred embodiment, $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl. More preferably, $R_{10}$ and $R_{11}$, together with the nitrogen to which they are attached, form a piperidinyl, pyrrolidinyl, azepanyl or azetidinyl group, each of which is optionally substituted by one or more groups selected from alkyl, CN, cycloalkyl, OH, alkoxy, halo and haloalkyl.

In one preferred embodiment, $R_{10}$ and $R_{11}$, together with the nitrogen to which they are attached, form a 6-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl.

In one preferred embodiment, $R_{10}$ and $R_{11}$, together with the nitrogen to which they are attached, form a 6-membered monocyclic heterocycloalkyl group selected from piperidinyl, morpholinyl, thiomorpholinyl and piperazinyl, each of which is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl. More preferably, $R_{10}$ and $R_{11}$, together with the nitrogen to which they are attached, form a 6-membered monocyclic heterocycloalkyl group selected from piperidinyl, morpholinyl, thiomorpholinyl and piperazinyl, each of which is optionally substituted by one or more groups selected from alkyl, CN, cycloalkyl, OH, alkoxy, halo and haloalkyl.

In one preferred embodiment, $R_{10}$ and $R_{11}$, together with the nitrogen to which they are attached, form a piperidinyl group which is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl. More preferably, $R_{10}$ and $R_{11}$, together with the nitrogen to which they are attached, form an unsubstituted piperidinyl group.

In one preferred embodiment, $R_7$ is CN.

In another preferred embodiment, $R_7$ is $SO_2$-alkyl, more preferably $SO_2$—Me.

In one preferred embodiment, $R_7$ is $SO_2NR_{13}R_{14}$, more preferably $SO_2NH_2$.

In one preferred embodiment, $R_7$ is a heteroaryl group optionally substituted by one or more substituents selected from alkyl, halo, alkoxy, CN, haloalkyl and OH.

In one preferred embodiment, $R_7$ is a heteroaryl group selected from pyridinyl, thienyl, imidazolyl, pyrimidinyl, pyrazolyl, pyrazinyl, pyradizinyl, thiazolyl, isothiazolyl, triazinyl, pyrrolyl, furanyl, oxazolyl, isoxazolyl, oxadiazolyl, tetrazolyl and triazolyl, each of which is optionally substituted by one or more substituents selected from alkyl, halo, alkoxy, CN, haloalkyl and OH.

In one preferred embodiment, $R_7$ is a heteroaryl group selected from imidazolyl, pyrazolyl, pyrazinyl, pyradizinyl, thiazolyl, isothiazolyl, oxazolyl, isoxazolyl, oxadiazolyl, tetrazolyl and triazolyl, each of which is optionally substituted by one or more substituents selected from alkyl, halo, alkoxy, CN, haloalkyl and OH.

In one preferred embodiment, $R_7$ is a heteroaryl group selected from 1H-imidazol-5-yl, 1H-imidazol-4-yl, 1H-imidazol-2-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, thiazol-5-yl, thiazol-4-yl, thiazol-2-yl, 1H-1,2,3,4-tetrazol-4-yl, 2H-1,2,3,4-tetrazol-5-yl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, pyradizin-3-yl, pyradizin-4-yl, pyrazinyl, 1,3,4-oxadizol-2-yl, 1,3,4-oxadizol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, isoxazol-5-yl, isoxazol-4-yl and isoxazol-3-yl, each of which is optionally substituted by one or more substituents selected from alkyl, halo, CN, alkoxy, haloalkyl and OH.

In one highly preferred embodiment, $R_7$ is a heteroaryl group selected from 1H-pyrazol-5-yl, 1H-pyrazol-3-yl, 1H-pyrazol-4-yl, oxazol-2-yl, 1H-1,2,3-triazol-4-yl, 1H-1,2,3-triazol-5-yl, thiazol-5-yl, 1H-1,2,3,4-tetrazol-4-yl, 2H-1,2,3,4-tetrazol-5-yl, isoxazol-4-yl, isoxazol-5-yl, isothiazol-5-yl, pyradizin-3-yl, pyradizin-4-yl, pyrazinyl and 1,3,4-oxadizol-2-yl, each of which is optionally substituted by one or more substituents selected from Me, F, Cl, CN and MeO.

In one preferred embodiment, $R_7$ is a heteroaryl group optionally substituted by one or more alkyl groups, preferably one or more Me groups.

In one highly preferred embodiment, the compound of formula (Id) is selected from the following:
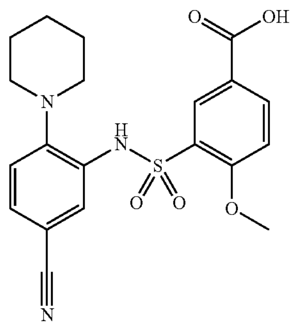 [SMILES: COc1ccc(C(=O)O)cc1S(=O)(=O)Nc1cc(C#N)ccc1N1CCCCC1]
(182)
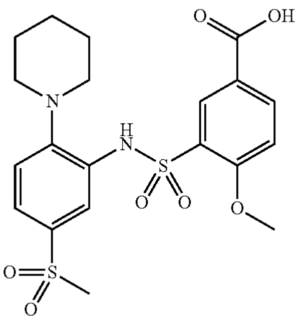 [SMILES: COc1ccc(C(=O)O)cc1S(=O)(=O)Nc1cc(S(C)(=O)=O)ccc1N1CCCCC1]
(207)
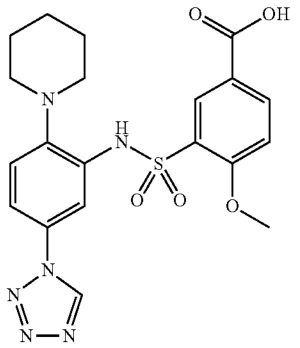 [SMILES: COc1ccc(C(=O)O)cc1S(=O)(=O)Nc1cc(-n2cnnn2)ccc1N1CCCCC1]
(214)
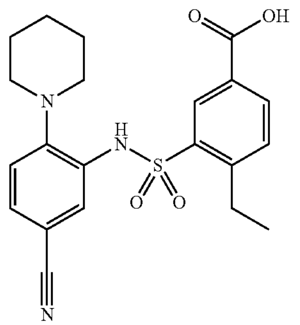 [SMILES: CCc1ccc(C(=O)O)cc1S(=O)(=O)Nc1cc(C#N)ccc1N1CCCCC1]
(215)
-continued
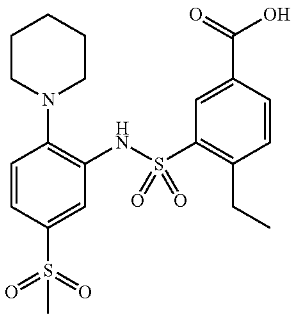 [SMILES: CCc1ccc(C(=O)O)cc1S(=O)(=O)Nc1cc(S(C)(=O)=O)ccc1N1CCCCC1]
(241)
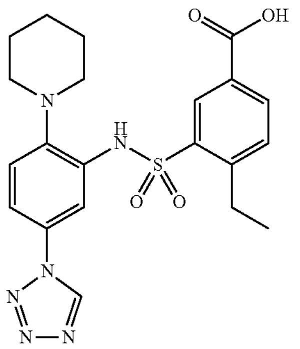 [SMILES: CCc1ccc(C(=O)O)cc1S(=O)(=O)Nc1cc(-n2cnnn2)ccc1N1CCCCC1]
(242)
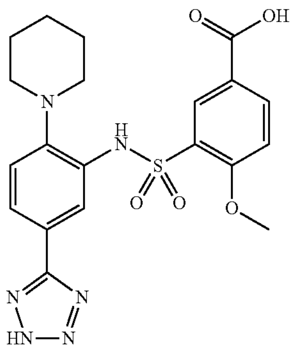 [SMILES: COc1ccc(C(=O)O)cc1S(=O)(=O)Nc1cc(-c2nn[nH]n2)ccc1N1CCCCC1]
(259)
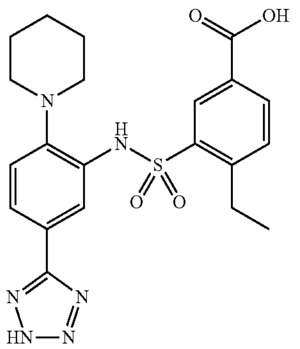 [SMILES: CCc1ccc(C(=O)O)cc1S(=O)(=O)Nc1cc(-c2nn[nH]n2)ccc1N1CCCCC1]
(261)

-continued
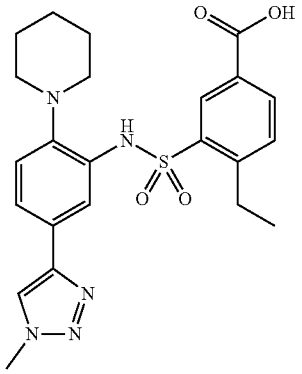 [SMILES: CCc1ccc(C(=O)O)cc1S(=O)(=O)Nc1cc(-c2cn(C)nn2)ccc1N1CCCCC1]
(273)
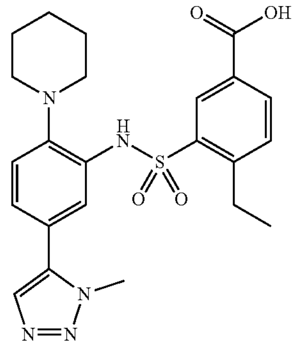 [SMILES: CCc1ccc(C(=O)O)cc1S(=O)(=O)Nc1cc(-c2cnnn2C)ccc1N1CCCCC1]
(274)
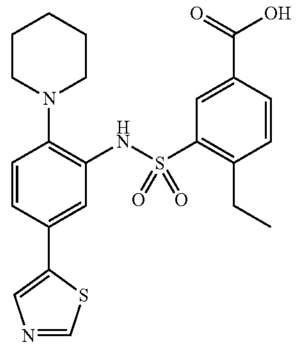 [SMILES: CCc1ccc(C(=O)O)cc1S(=O)(=O)Nc1cc(-c2cncs2)ccc1N1CCCCC1]
(275)
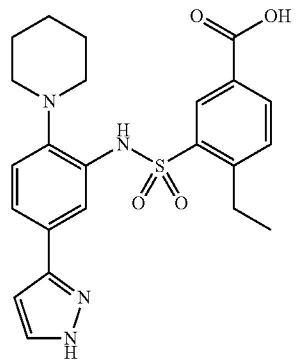 [SMILES: CCc1ccc(C(=O)O)cc1S(=O)(=O)Nc1cc(-c2cc[nH]n2)ccc1N1CCCCC1]
(276)
-continued
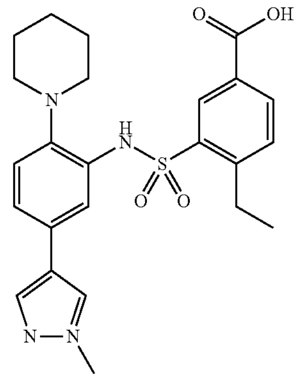
(277)
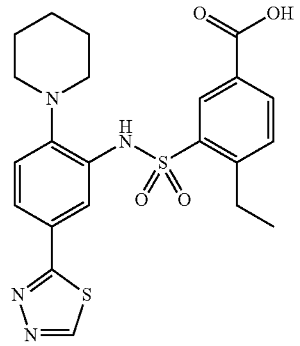
(278)
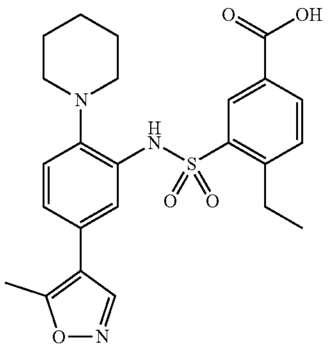 [SMILES: CCc1ccc(C(=O)O)cc1S(=O)(=O)Nc1cc(-c2cnoc2C)ccc1N1CCCCC1]
(279)
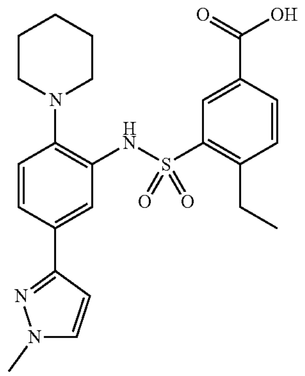 [SMILES: CCc1ccc(C(=O)O)cc1S(=O)(=O)Nc1cc(-c2ccn(C)n2)ccc1N1CCCCC1]
(280)

-continued
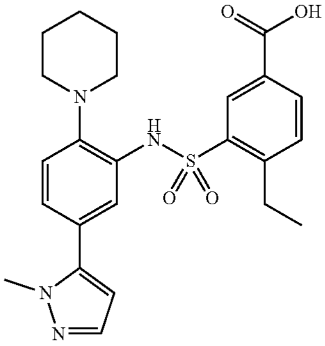 [SMILES: CCc1ccc(C(=O)O)cc1S(=O)(=O)Nc1cc(-c2ccnn2C)ccc1N1CCCCC1]
(281)
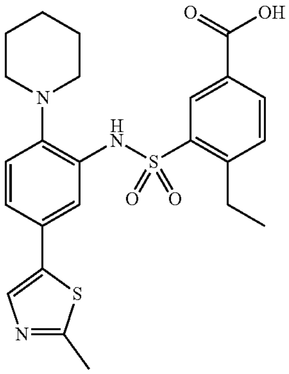 [SMILES: CCc1ccc(C(=O)O)cc1S(=O)(=O)Nc1cc(-c2cnc(C)s2)ccc1N1CCCCC1]
(282)
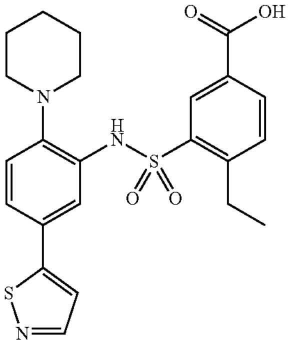 [SMILES: CCc1ccc(C(=O)O)cc1S(=O)(=O)Nc1cc(-c2ccns2)ccc1N1CCCCC1]
(286)
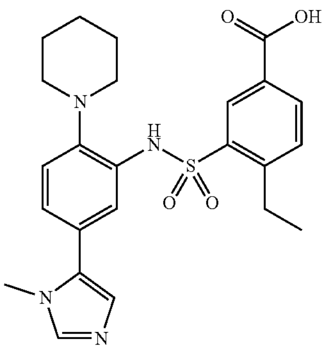 [SMILES: CCc1ccc(C(=O)O)cc1S(=O)(=O)Nc1cc(-c2cncn2C)ccc1N1CCCCC1]
(287)
-continued
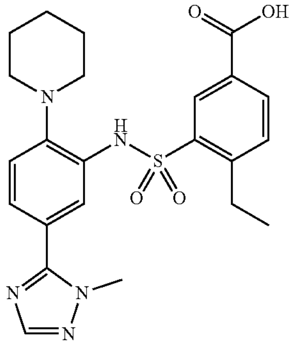 [SMILES: CCc1ccc(C(=O)O)cc1S(=O)(=O)Nc1cc(-c2ncnn2C)ccc1N1CCCCC1]
(288)
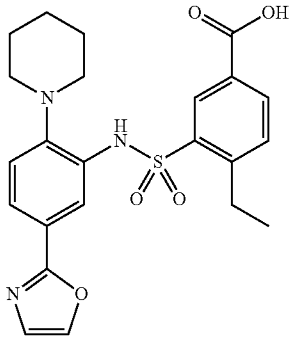 [SMILES: CCc1ccc(C(=O)O)cc1S(=O)(=O)Nc1cc(-c2ncco2)ccc1N1CCCCC1]
(289)
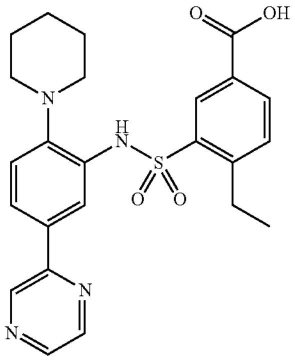
(290)
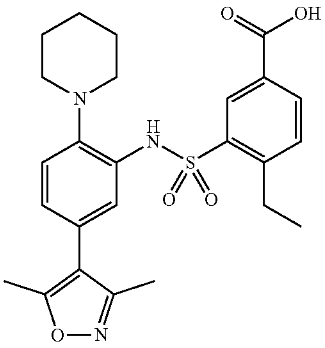 [SMILES: CCc1ccc(C(=O)O)cc1S(=O)(=O)Nc1cc(-c2c(C)noc2C)ccc1N1CCCCC1]
(291)

-continued
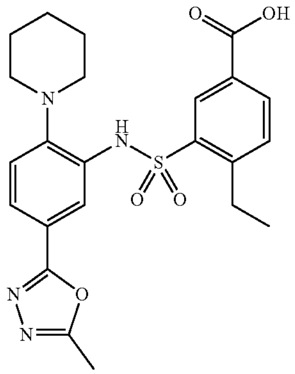 [SMILES: CCc1ccc(C(=O)O)cc1S(=O)(=O)Nc1cc(-c2nnc(C)o2)ccc1N1CCCCC1]
(292)
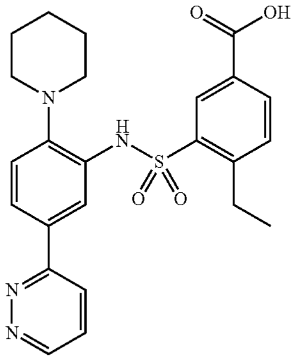
(293)
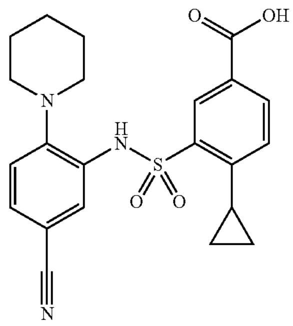 [SMILES: N#Cc1ccc(N2CCCCC2)c(NS(=O)(=O)c2cc(C(=O)O)ccc2C2CC2)c1]
(295)
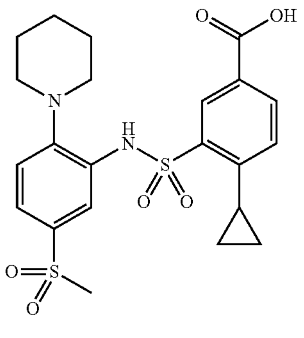
(296)
-continued
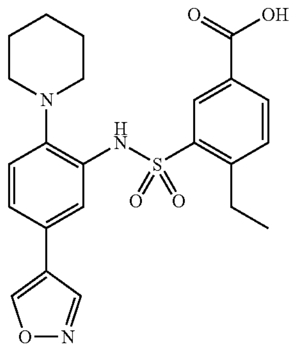 [SMILES: CCc1ccc(C(=O)O)cc1S(=O)(=O)Nc1cc(-c2cnoc2)ccc1N1CCCCC1]
(297)
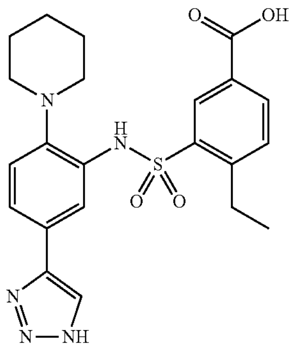 [SMILES: CCc1ccc(C(=O)O)cc1S(=O)(=O)Nc1cc(-c2c[nH]nn2)ccc1N1CCCCC1]
(298)
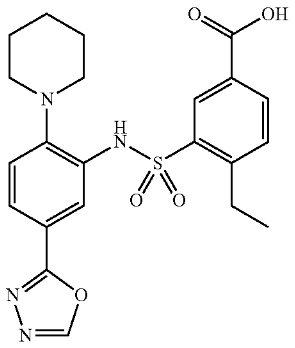
(299)
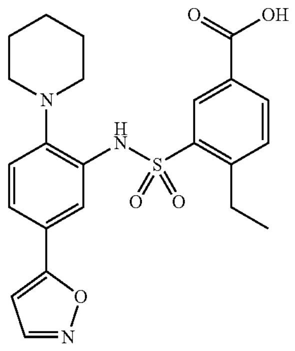 [SMILES: CCc1ccc(C(=O)O)cc1S(=O)(=O)Nc1cc(-c2ccno2)ccc1N1CCCCC1]
(300)

-continued
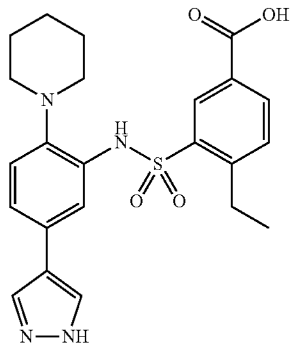
(301)
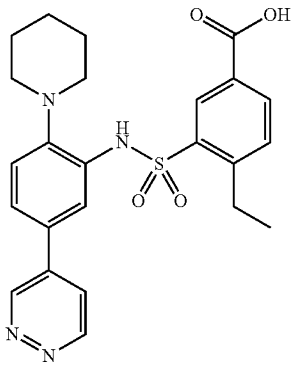 [SMILES: CCc1ccc(C(=O)O)cc1S(=O)(=O)Nc1cc(-c2ccnnc2)ccc1N1CCCCC1]
(302)
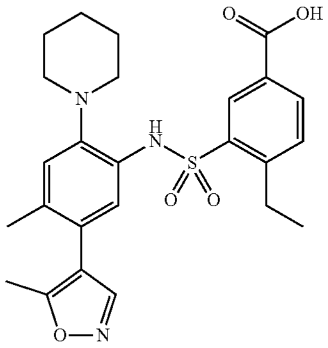 [SMILES: CCc1ccc(C(=O)O)cc1S(=O)(=O)Nc1cc(-c2cnoc2C)c(C)cc1N1CCCCC1]
(303)
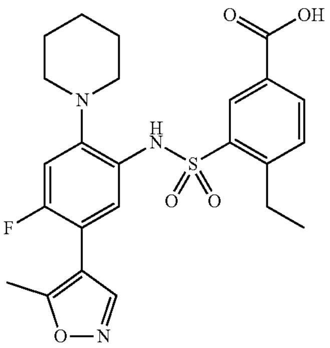
(304)
-continued
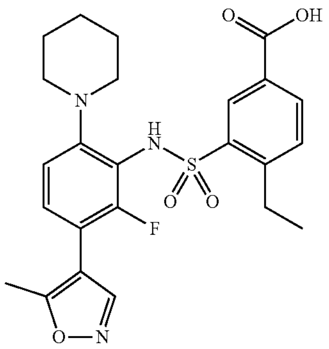 [SMILES: CCc1ccc(C(=O)O)cc1S(=O)(=O)Nc1c(N2CCCCC2)ccc(-c2cnoc2C)c1F]
(305)
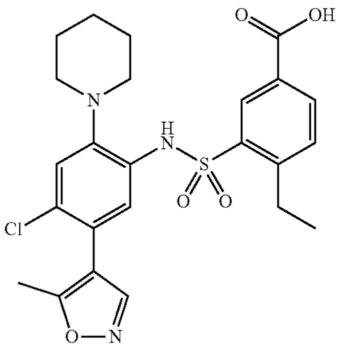 [SMILES: CCc1ccc(C(=O)O)cc1S(=O)(=O)Nc1cc(-c2cnoc2C)c(Cl)cc1N1CCCCC1]
(306)
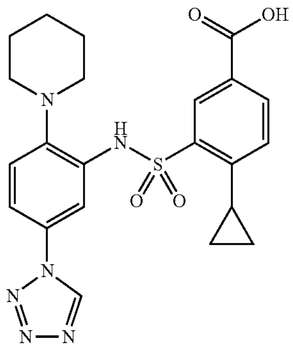 [SMILES: O=C(O)c1ccc(C2CC2)c(S(=O)(=O)Nc2cc(-n3cnnn3)ccc2N2CCCCC2)c1]
(323)
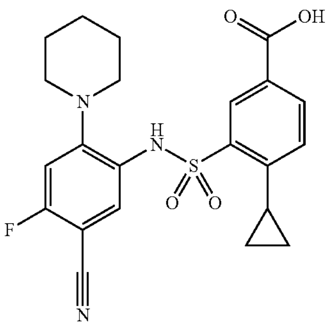 [SMILES: N#Cc1cc(NS(=O)(=O)c2cc(C(=O)O)ccc2C2CC2)c(N2CCCCC2)cc1F]
(324)

-continued
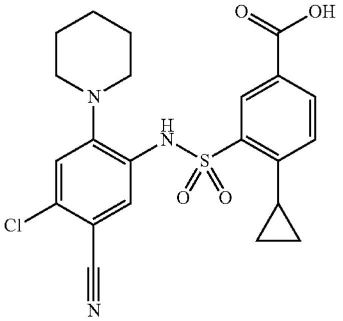 [SMILES: N#Cc1cc(NS(=O)(=O)c2cc(C(=O)O)ccc2C2CC2)c(N2CCCCC2)cc1Cl]
(327)
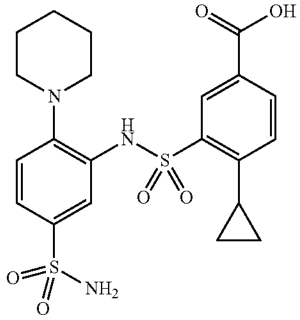 [SMILES: NS(=O)(=O)c1ccc(N2CCCCC2)c(NS(=O)(=O)c2cc(C(=O)O)ccc2C2CC2)c1]
(329)
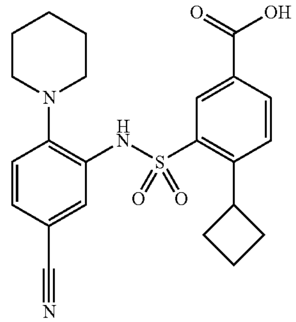 [SMILES: N#Cc1ccc(N2CCCCC2)c(NS(=O)(=O)c2cc(C(=O)O)ccc2C2CCC2)c1]
(330)
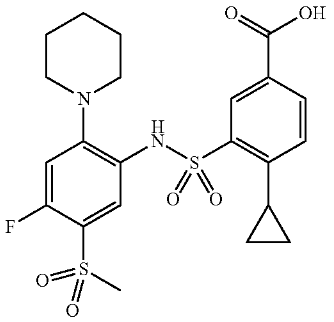 [SMILES: CS(=O)(=O)c1cc(NS(=O)(=O)c2cc(C(=O)O)ccc2C2CC2)c(N2CCCCC2)cc1F]
(331)
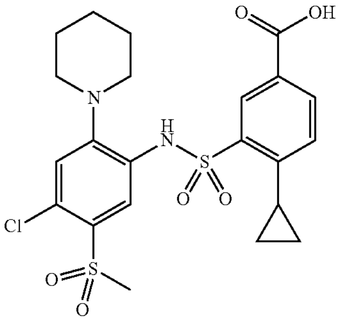 [SMILES: CS(=O)(=O)c1cc(NS(=O)(=O)c2cc(C(=O)O)ccc2C2CC2)c(N2CCCCC2)cc1Cl]
(332)
-continued
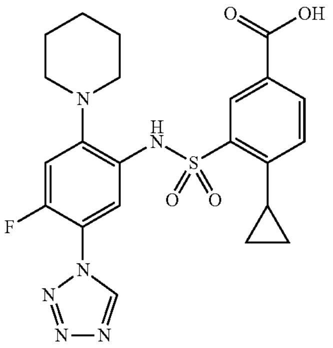 [SMILES: O=C(O)c1ccc(C2CC2)c(S(=O)(=O)Nc2cc(-n3cnnn3)c(F)cc2N2CCCCC2)c1]
(333)
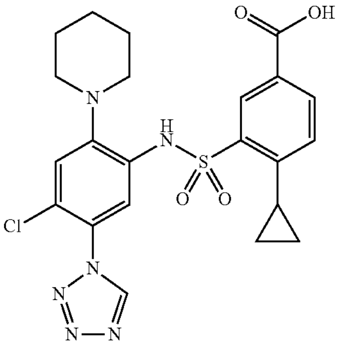 [SMILES: O=C(O)c1ccc(C2CC2)c(S(=O)(=O)Nc2cc(-n3cnnn3)c(Cl)cc2N2CCCCC2)c1]
(334)
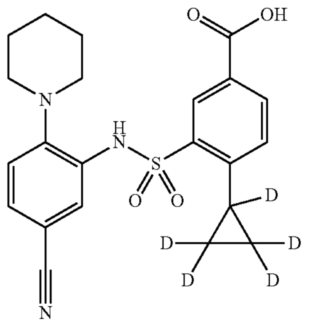 [SMILES: [2H]C1([2H])C([2H])([2H])C1([2H])c1ccc(C(=O)O)cc1S(=O)(=O)Nc1cc(C#N)ccc1N1CCCCC1]
(335)
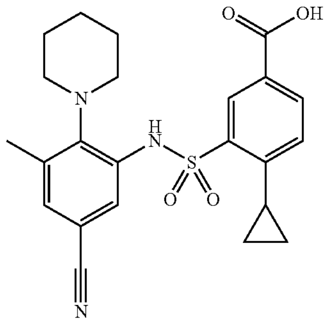 [SMILES: Cc1cc(C#N)cc(NS(=O)(=O)c2cc(C(=O)O)ccc2C2CC2)c1N1CCCCC1]
(336)

-continued
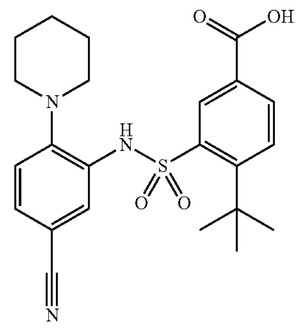 [SMILES: CC(C)(C)c1ccc(C(=O)O)cc1S(=O)(=O)Nc1cc(C#N)ccc1N1CCCCC1]
(337)
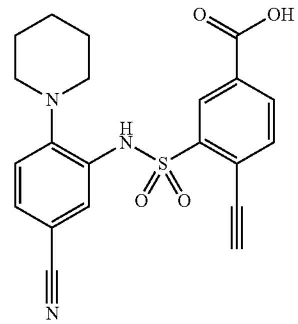 [SMILES: C#Cc1ccc(C(=O)O)cc1S(=O)(=O)Nc1cc(C#N)ccc1N1CCCCC1]
(338)
and pharmaceutically acceptable salts and hydrates thereof.
A further aspect of the invention relates to a compound selected from the following:
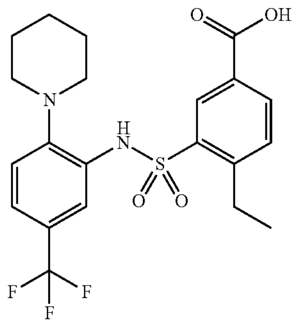
(1)
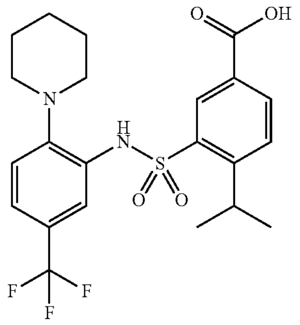
(3)
-continued
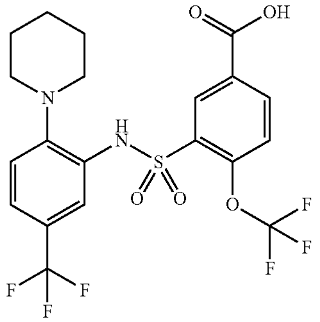 [SMILES: O=C(O)c1ccc(OC(F)(F)F)c(S(=O)(=O)Nc2cc(C(F)(F)F)ccc2N2CCCCC2)c1]
(4)
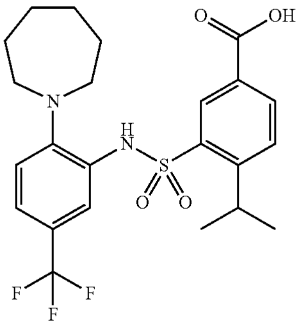 [SMILES: CC(C)c1ccc(C(=O)O)cc1S(=O)(=O)Nc1cc(C(F)(F)F)ccc1N1CCCCCC1]
(55)
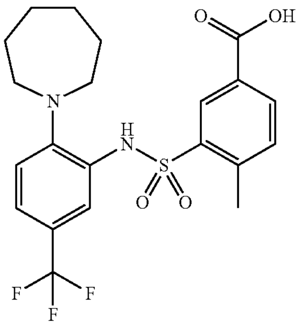 [SMILES: Cc1ccc(C(=O)O)cc1S(=O)(=O)Nc1cc(C(F)(F)F)ccc1N1CCCCCC1]
(62)
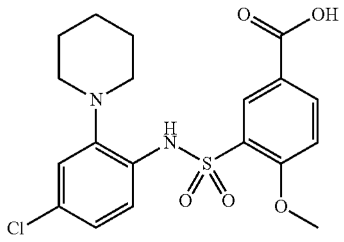 [SMILES: COc1ccc(C(=O)O)cc1S(=O)(=O)Nc1ccc(Cl)cc1N1CCCCC1]
(65)
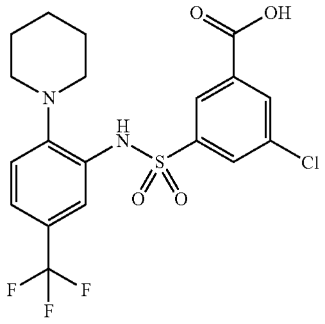 [SMILES: O=C(O)c1cc(Cl)cc(S(=O)(=O)Nc2cc(C(F)(F)F)ccc2N2CCCCC2)c1]
(80)

-continued
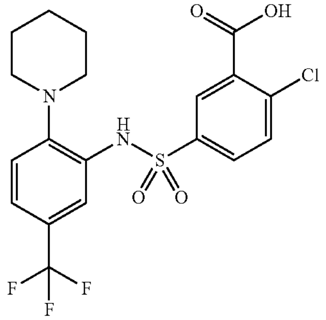 [SMILES: O=C(O)c1cc(S(=O)(=O)Nc2cc(C(F)(F)F)ccc2N2CCCCC2)ccc1Cl]
(83)
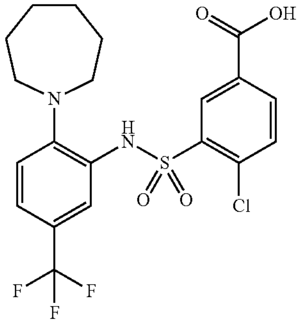 [SMILES: O=C(O)c1ccc(Cl)c(S(=O)(=O)Nc2cc(C(F)(F)F)ccc2N2CCCCCC2)c1]
(86)
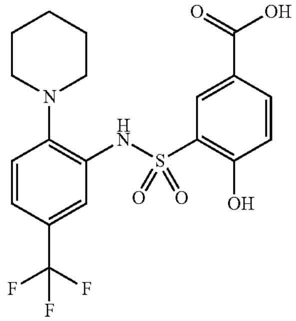
(161)
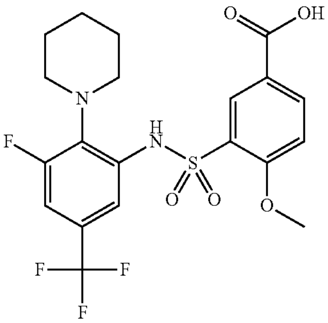 [SMILES: COc1ccc(C(=O)O)cc1S(=O)(=O)Nc1cc(C(F)(F)F)cc(F)c1N1CCCCC1]
(184)
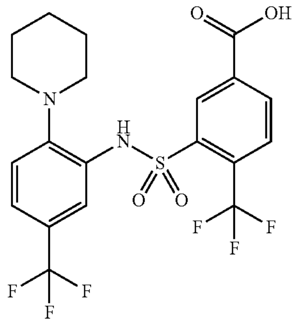
(200)
-continued
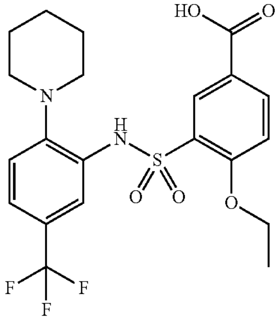
(201)
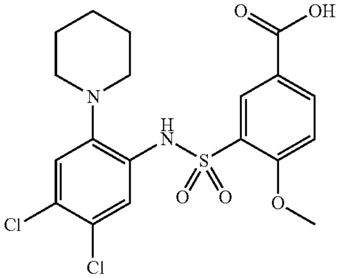 [SMILES: COc1ccc(C(=O)O)cc1S(=O)(=O)Nc1cc(Cl)c(Cl)cc1N1CCCCC1]
(202)
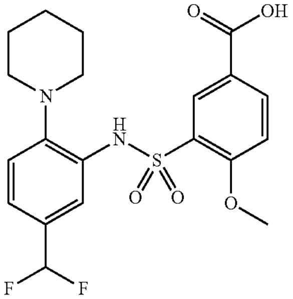
(212)
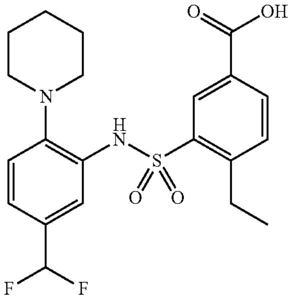
(213)
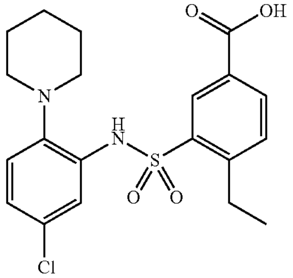 [SMILES: CCc1ccc(C(=O)O)cc1S(=O)(=O)Nc1cc(Cl)ccc1N1CCCCC1]
(216)

-continued
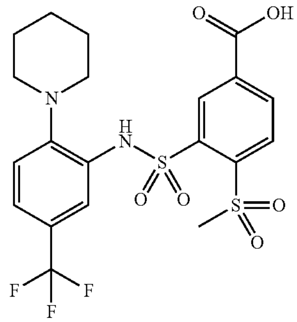 [SMILES: CS(=O)(=O)c1ccc(C(=O)O)cc1S(=O)(=O)Nc1cc(C(F)(F)F)ccc1N1CCCCC1]
(225)
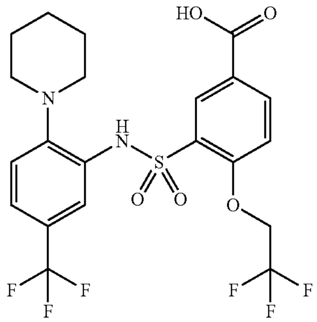
(227)
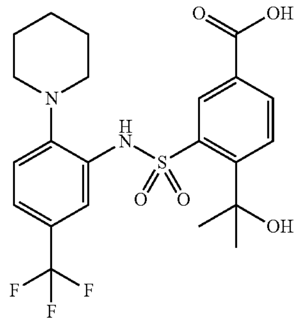
(228)
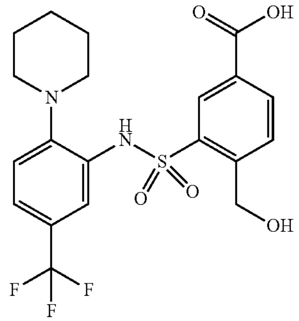
(229)
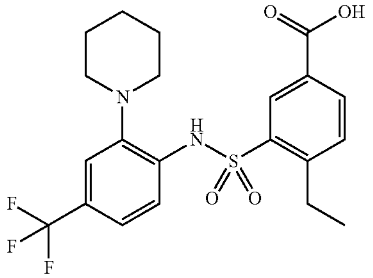 [SMILES: CCc1ccc(C(=O)O)cc1S(=O)(=O)Nc1ccc(C(F)(F)F)cc1N1CCCCC1]
(230)
-continued
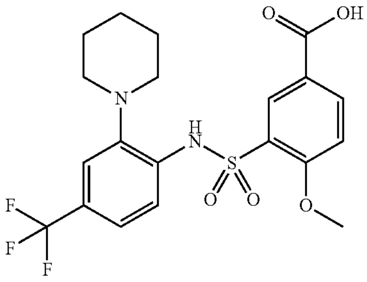 [SMILES: COc1ccc(C(=O)O)cc1S(=O)(=O)Nc1ccc(C(F)(F)F)cc1N1CCCCC1]
(231)
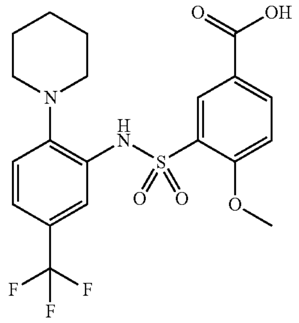
(232)
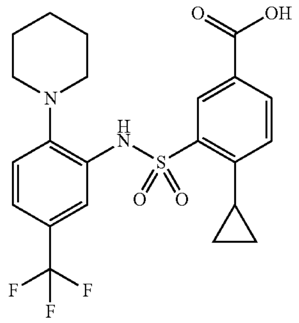 [SMILES: O=C(O)c1ccc(C2CC2)c(S(=O)(=O)Nc2cc(C(F)(F)F)ccc2N2CCCCC2)c1]
(267)
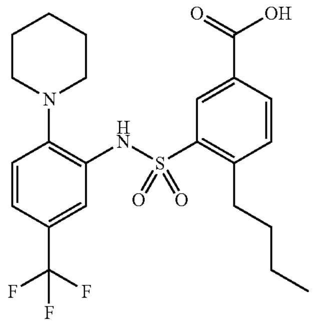 [SMILES: CCCCc1ccc(C(=O)O)cc1S(=O)(=O)Nc1cc(C(F)(F)F)ccc1N1CCCCC1]
(268)
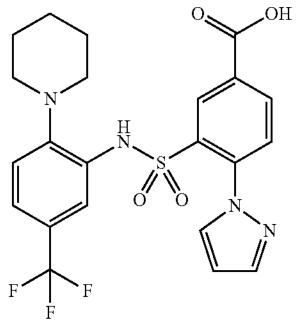 [SMILES: O=C(O)c1ccc(-n2cccn2)c(S(=O)(=O)Nc2cc(C(F)(F)F)ccc2N2CCCCC2)c1]
(271)

-continued

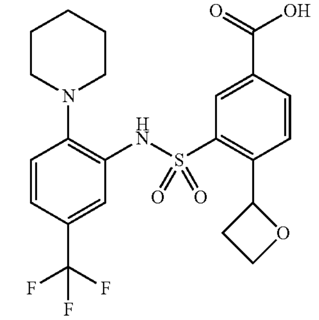

(272)

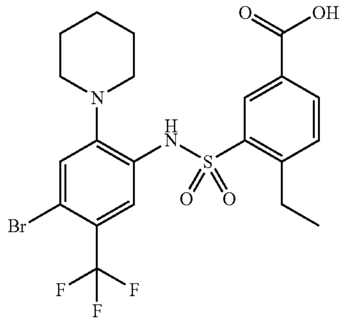 [SMILES: CCc1ccc(C(=O)O)cc1S(=O)(=O)Nc1cc(C(F)(F)F)c(Br)cc1N1CCCCC1]

(294)

and pharmaceutically acceptable salts and hydrates thereof.

Therapeutic Applications

A further aspect of the invention relates to compounds as described herein for use in medicine. The compounds have particular use in the field of oncology and immunoncology, as described in more detail below.

Yet another aspect of the invention relates to compounds as described herein for use in treating or preventing a disorder selected from a proliferative disorder, an immune disorder, an inflammatory disorder and a viral disorder.

In a preferred embodiment, the compound of the invention modulates ERAP1. More preferably, the compound modulates ERAP1's cellular antigen processing activity.

In one embodiment the compound inhibits the activity of ERAP1. More preferably, the compound inhibits ERAP1's cellular antigen processing activity.

In an alternative embodiment the compound increases the activity of ERAP1.

In one embodiment the compound of the invention may change the repertoire of presented antigens.

One aspect of the invention relates to a compound as described herein for use in treating a proliferative disorder. Preferably, the proliferative disorder is a cancer or leukemia.

A cancer may be selected from: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

Without wishing to be bound by theory, it is understood that ERAP1 modulators are capable of changing at least 10% of the antigen and neoantigen repertoire of cancer cells, as measured using immunopeptidomics and mass spectrometry analysis. Approximately 50% of this change is an upregulation in the presentation of certain antigens and neoantigens, whilst the other 50% is the presentation of entirely novel antigens and neoantigens. Both changes lead to an increase in the visibility of the tumour to the immune system, leading to measurable changes in the $CD8^+$ T cell repertoire and $CD8^+$ T cell activation status. This change in $CD8^+$ T cell response leads to immune-mediated tumour clearance and can be potentially enhanced by combining with cancer therapeutics such as antibody checkpoint inhibitors (e.g. anti-PD-1).

Without wishing to be bound by theory, it is understood that modulators of ERAP1 cause killing of cancer cells by natural killer (NK) cells due to disruption of the interaction between killer cell Ig-like receptors (KIR) or lectin-like receptor CD94-NKG2A on NK cells with classical or non-classical MHC-I-peptide (pMHC-I) complexes on cancer cells.

In one preferred embodiment, the disorder is cancer, and the compound increases the visibility of cancer cells to the immune system by altering the repertoire of antigens and neoantigens presented to the immune system.

A further aspect of the invention relates to a method of increasing the visibility of cancer cells to the immune system in a subject by altering the repertoire of antigens and neoantigens presented to the immune system, said method comprising administering to the subject a compound of formula (I), (Ia), (Ib), (Ic) or (Id).

In one preferred embodiment, the compound increases the $CD8^+$ T cell response to the cancer cell.

In one preferred embodiment, the compound of the invention is for use in the treatment of a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is modulated by the ERAP1 pathway.

In one preferred embodiment, the disease of uncontrolled cell growth, proliferation and/or survival, inappropriate cellular immune response, or inappropriate cellular inflammatory response is selected from a haematological tumour, a solid tumour and/or metastases thereof.

More preferably, the compound is for use in treating a disorder selected from leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The compound may kill cancer cells, reduce the number of proliferating cells in the cancer and/or reduce the volume or size of a tumour comprising the cancer cells. The compound may reduce the number of metastasising cancer cells.

In one embodiment the compound may be used in treating cancer in a subject who has previously had cancer. The compound may be used to reduce the likelihood of the cancer recurring, or the likelihood of further cancer developing. The compound may induce a neoantigen in the recurring or further cancer to which the subject already possesses an existing immune response. As such, the compound may increase or boost an immune response against the cancer.

In one embodiment the compound is for use in preventing cancer. The compound may be used for prophylaxis against the development of cancer. That is to say, the compound may stimulate an immune response, such as a vaccine response, against a future cancer. The compound may stimulate in a subject an immune response directed to a neoantigen. Once a cancer develops in the subject, they may be treated again with the compound (or a different compound) to stimulate development of the same neoantigen, thereby eliciting the subject's pre-existing immune response to said neoantigen to treat or prevent the cancer.

The same or a different compound may be used before and after the cancer develops in a subject.

In one embodiment the compound may be used for the prevention of cancer.

In one embodiment the subject may previously have had cancer, may have a familial history of cancer, may have a high risk for developing cancer, may have a genetic predisposition to developing cancer, or may have been exposed to a carcinogenic agent. In one embodiment the subject may be in remission from cancer.

One embodiment provides ex vivo generated antigen-presenting cells, such as dendritic cells (DCs). The antigen-presenting cells may be produced ex vivo to present neo-antigens, such as those generated by a compound according to the present invention. The compound may be used in a method for producing ex vivo an antigen-presenting cell which presents a neo-antigen, and wherein the cell may be used as a vaccine against cancer.

The antigen presenting cell such as a dendritic cell may be pulsed or loaded with the neo-antigen or genetically modified (via DNA or RNA transfer) to express one, two or more neo-antigens. Methods of preparing dendritic cell vaccines are known in the art.

The neo-antigen may be generated from the subject's normal tissue in which ERAP1 is modulated with a compound according to the invention. Sources of normal tissue may be fibroblasts or B cells, for example, that can be readily expanded in vitro. Alternatively, RNA from the cancer, total or mRNA enriched poly A+ RNA may be used. Poly A+ RNA can be also amplified to generate sufficient antigen for DC loading and thereby limit the ex vivo culture step.

In one embodiment a dendritic cell which has been treated with the compound as described above may be used to treat a subject. The dendritic cell may be contacted with the compound ex vivo, and then the dendritic cell may be administered to the subject. The compound may therefore be used in vitro or in vivo, for example either for in situ treatment or for ex vivo treatment followed by the administration of the treated cells to the subject.

Another aspect of the invention relates to a compound as described above for use in treating an immune disorder, or for modulating the immune response. In one preferred embodiment, the immune disorder is an autoimmune disorder, such as a T cell-mediated autoimmune disorder.

Examples of the autoimmune disorders include, but are not limited to: rheumatoid arthritis (RA), myasthenia gravis (MG), multiple sclerosis (MS), systemic lupus erythematosus (SLE), autoimmune thyroiditis (Hashimoto's thyroiditis), Graves' disease, inflammatory bowel disease, autoimmune uveoretinitis, polymyositis and certain types of diabetes, systemic vasculitis, polymyositis-dermatomyositis, systemic sclerosis (scleroderma), Sjogren's Syndrome, ankylosing spondylitis and related spondyloarthropathies, rheumatic fever, hypersensitivity pneumonitis, allergic bronchopulmonary aspergillosis, inorganic dust pneumoconioses, sarcoidosis, autoimmune hemolytic anemia, immunological platelet disorders, cryopathies such as cryofibrinogenemia, psoriasis, Behçet's disease, birdshot chorioretinopathy and autoimmune polyendocrinopathies.

Polymorphisms in the ERAP1 gene that impact ERAP1 enzymatic activity are strongly associated with an increased risk of autoimmunity, including the diseases ankylosing spondylitis, psoriasis, Behçet's disease and birdshot chorioretinopathyl[11]. Variants of ERAP1 that reduce ERAP1 enzymatic activity are protective against disease, whilst those that reportedly elevate activity are associated with increased disease risk[12]. This suggests that modulation of ERAP1 activity could be an effective treatment for autoimmune diseases.

Thus, in one preferred embodiment, the immune disorder is selected from ankylosing spondylitis, psoriasis, Behcet's disease and birdshot chorioretinopathy.

In one preferred embodiment, the immune disorder is ankylosing spondylitis. Ankylosing spondylitis (AS) is a type of arthritis in which there is long term inflammation of the joints of the spine. Typically the joints where the spine joins the pelvis are also affected. Occasionally other joints such as the shoulders or hips are involved. Between 0.1% and 1.8% of people are affected and onset is typically in young adults. Although the cause of ankylosing spondylitis is unknown, it involves a combination of genetic and environmental factors. More than 90% of those affected have a specific human leukocyte antigen known as the HLA-B27 antigen.[13] In addition, certain variants of ERAP1, in conjunction with HLA-B27, are clearly associated with either an elevated or reduced risk of disease, providing evidence of a clear role for modulated antigen presentation in disease.[18] There is no cure for ankylosing spondylitis and current treatments serve only to improve symptoms and prevent worsening. Medications used to date include NSAIDs, steroids, DMARDs such as sulfasalazine, and biologic agents such as infliximab.

In one preferred embodiment, the immune disorder is Behçet's disease (BD). Behçet's disease (BD) is a type of inflammatory disorder which affects multiple parts of the body. The most common symptoms include painful mouth sores, genital sores, inflammation of parts of the eye, and arthritis. The cause is not well-defined, and whilst environmental factors play a role, genetic studies have shown an increased risk of disease in patients carrying HLA-B51 in conjunction with specific variants of ERAP1.[19] The disease is primarily characterized by auto-inflammation of the blood vessels, hence it is sometimes characterised as an auto-inflammatory disease. There is currently no cure for Behcet's disease, but the symptoms can be controlled with medicines that reduce inflammation in the affected parts of the body, for example, with corticosteroids, immunosuppressants or biological therapies that target the biological processes involved in the process of inflammation. In one preferred embodiment, the immune disorder is birdshot chorioretinopathy. Birdshot chorioretinopathy, also known as Birdshot Uveitis or HLA-A29 Uveitis, is a rare form of bilateral posterior uveitis affecting the eye. It causes severe, progressive inflammation of both the choroid and retina. Symptoms include floaters, blurred vision, photopsia (flashing lights in eyes), loss of color vision and nyctalopia. Birdshot chorioretinopathy is thought to be an autoimmune disease. The disease has strong association with the Human leukocyte antigen haplotype (HLA)-A29. This indicates a role for T-lymphocytes in the pathogenesis. Birdshot chorioretinopathy is associated with IL-17, a hallmark cytokine of TH17 cells that play an important role in autoimmunity.[15, 16] A genome-wide association study has ascertained HLA-A29:02 as the primary risk factor and identified that both ERAP1 and ERAP2 are associated with birdshot chorioretinopathy.[17, 20] Genetic variants within the ERAP1 and ERAP2 loci modulate enzyme activity and also mRNA and protein expression. ERAP2 is an aminopeptidase that, together with ERAP1, trims peptides in the endoplasmic reticulum and loads these peptides on HLA molecules for presentation to T cells of the immune system.

In one preferred embodiment, the immune disorder is psoriasis. Psoriasis is a chronic skin disease in which skin cells rapidly build up on the surface of the skin forming scales and red patches that are itchy and sometimes painful. The cause is not well-defined but includes both environmental and genetic factors. HLA-C06 strongly associates with risk of disease and variants in ERAP1, possibly in conjunction with HLA-C06, are also strongly associated with disease.[21] There is no cure for psoriasis and current treatments serve only to improve symptoms and prevent worsening. Medications used in therapy include steroids, methotrexate, sulfasalazine, and biologic agents such as etanercept.

Another aspect of the invention relates to a compound as described above for use in treating or preventing a viral disorder. Modulators of ERAP1 such as the compounds described herein are capable of changing the antigen repertoire of multiple viruses, which leads to the recognition and destruction of viral infected cells. Accordingly, ERAP1 modulators have potential therapeutic applications in the treatment of viral infection and diseases. ERAP1 modulates certain viral antigens, including those from human papilloma virus (HPV), human cytomegalovirus (CMV) hepatitis C (HCV) and human immunodeficiency virus (HIV)[8, 9, 10]. In addition, knockdown of ERAP1 in HPV infected cells changes the repertoire of presented HPV antigens leading to greater recognition by $CD8^+$ T cells[8].

In one preferred embodiment, the viral disorder is a viral disease or viral infection selected from HIV, HPV, CMV and HCV.

In one preferred embodiment, the viral disorder is HIV.

In one preferred embodiment, the viral disorder is HPV.

In one preferred embodiment, the viral disorder is CMV.

In one preferred embodiment, the viral disorder is HCV.

Another aspect of the invention relates to a compound as described above for use in treating or preventing hypertension.

Another aspect relates to a compound as described herein for use in the prevention or treatment of a disorder caused by, associated with or accompanied by abnormal activity against ERAP1.

Another aspect relates to a compound as described herein for use in the the prevention or treatment of an ERAP1-associated disease or disorder.

Yet another aspect relates to the use of a compound as described herein in the preparation of a medicament for the prevention or treatment of a disorder caused by, associated with or accompanied by any abnormal activity against ERAP1.

As used herein the phrase "preparation of a medicament" includes the use of the components of the invention directly as the medicament in addition to their use in any stage of the preparation of such a medicament.

Another aspect relates to the use of a compound as described above in the preparation of a medicament for treating or preventing a disorder selected from a proliferative disorder, an immune disorder, a viral disorder and an inflammatory disorder.

Yet another aspect relates to the use of a compound as described herein in the preparation of a medicament for the prevention or treatment of an ERAP1-associated disease or disorder.

Another aspect of the invention relates to a method of treating an ERAP1-associated disease or disorder in a subject. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a subject having a disease state alleviated by modulation of ERAP1 wherein the method comprises administering to the subject a therapeutically effective amount of a compound according to the invention.

Another aspect relates to a method of treating a disease state alleviated by modulation of ERAP1, wherein the method comprises administering to a subject a therapeutically effective amount of a compound according to the invention.

Preferably, the subject is a mammal, more preferably a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$.

Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al, 1975, The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation. As used herein, "ERAP1-related disease or disorder" refers to a disease or disorder characterized by inappropriate ERAP1 activity. Inappropriate activity refers to either an increase or decrease in ERAP1 activity relative to wildtype ERAP1 (Uniprot ID Q9NZ08), caused by variation in the ERAP1 protein sequence, as measured by enzyme or cellular assays. Inappropriate activity could also be due to overexpression of ERAP1 in diseased tissue compared with healthy adjacent tissue.

Preferred diseases or disorders that the compounds described herein may be useful in preventing include proliferative disorders, viral disorders, immune disorders and inflammatory disorders as described hereinbefore.

Thus, the present invention further provides use of compounds as defined herein for the manufacture of medicaments for the treatment of diseases where it is desirable to modulate ERAP1. Such diseases include proliferative disorders, viral disorders, immune disorders and inflammatory disorders as described hereinbefore.

In one preferred embodiment, the compound activates ERAP1's conversion of (L)-leucine-7-amido-4-methylcoumarin (L-AMC) to (L)-leucine and the fluorescent molecule 7-amino-4-methylcoumarin. While the same assay can also identify inhibitors of ERAP1's cleavage of the amide bond in L-AMC, for the purposes of this application this assay is referred to as the "L-AMC activator assay". The potency of any activator is calculated and expressed as the concentration of the activator required to increase the enzyme activity of ERAP1 by 50% over its baseline level (i.e. an $EC_{50}$).

In one preferred embodiment, the compound exhibits an $EC_{50}$ value in an L-AMC activator assay of less than about 25 μM. More preferably, the compound exhibits an $EC_{50}$ value in the L-AMC activator assay assay of less than about 10 UM, more preferably, less than about 5 μM, even more preferably, less than about 1 μM, even more preferably, less than about 0.1 μM, even more preferably, less than about 0.01 μM.

In one preferred embodiment, the compound inhibits ERAP1's ability to hydrolyse the decapeptide substrate WRVYEKCdnpALK. This peptide has minimal fluorescence as the N-terminal tryptophan residue's fluorescence is quenched by the dinitrophenol (DNP) residue within the peptide. However, as ERAP1 hydrolyses the N-terminal amide bond and tryptophan is released this internal quenching is lost and the reaction is monitored by the increase in tryptophan fluorescence over the course of the assay. For the purposes of this application this assay is referred to as the "10mer inhibition assay" and compound potencies are calculated and expressed as $IC_{50}$ as would be familiar to a person skilled in the art.

In one preferred embodiment, the compound exhibits an $IC_{50}$ value in the 10mer assay of less than about 25 μM. More preferably, the compound exhibits an $IC_{50}$ value in the 10mer assay of less than about 10 UM, more preferably, less than about 5 μM, even more preferably, less than about 1 μM, even more preferably, less than about 0.1 μM, even more preferably, less than about 0.01 μM.

Therapeutic Use of Compounds of Formula I

A further aspect of the invention relates to a compound of formula (I), or a pharmaceutically acceptable salt or hydrate thereof, (I)

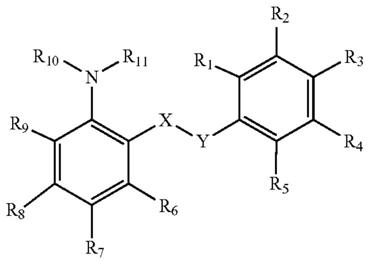

wherein:

the group X—Y is —$NHSO_2$— or —$SO_2NH$—;

$R_1$ is H or alkyl;

$R_2$ is selected from COOH and a tetrazolyl group;

$R_3$ is selected from H, Cl and alkyl;

$R_4$ is selected from H, Cl and F;

$R_5$ is selected from H, alkyl, alkynyl, alkenyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is selected from H, CN, haloalkyl, Cl, F, $SO_2$-alkyl, $SO_2NR_{13}R_{14}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H, $C_1$-$C_3$-alkyl or halo;

$R_{10}$ is H or alkyl;

$R_{11}$ is alkyl optionally substituted by one or more substituents selected from $NH_2$, OH, and $NHCO_2R_{12}$, wherein $R_{12}$ is alkyl; or $R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, OH, halo and heteroaryl, wherein said heteroaryl group is in turn optionally further substituted with one or more groups selected from halo and alkyl; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected from alkyl, CN, and halo; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, halo and heteroaryl, or said bicyclic group is optionally fused to a 5 or 6-membered aryl or heteroaryl group; and $R_{13}$ and $R_{14}$ are each independently H or alkyl;

for use in treating or preventing a disorder selected from a proliferative disorder, an autoimmune disorder, a viral disorder and an inflammatory disorder.

Preferred definitions for groups X, Y and $R_{1-11}$ are as set out above for compounds of formula (Ia) and apply mutatis mutandis to compounds of formula (I). Details of suitable proliferative disorders, autoimmune disorders, viral disorders and inflammatory disorders, are the same as those set forth above under the heading "Therapeutic Applications".

In one preferred embodiment, the compound of formula (I) for use as described above is selected from the following:

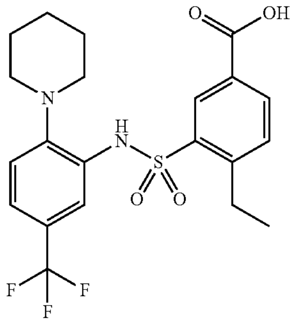
(1)

-continued

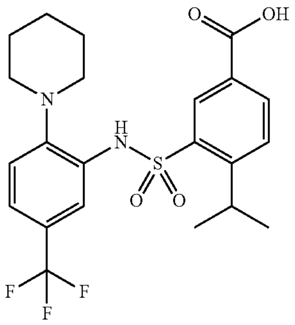
(3)

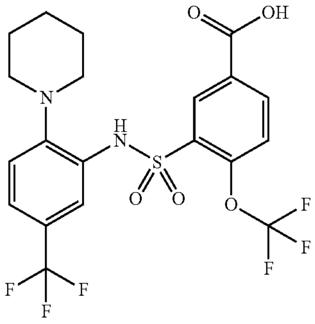 [SMILES: O=C(O)c1ccc(OC(F)(F)F)c(S(=O)(=O)Nc2cc(C(F)(F)F)ccc2N2CCCCC2)c1]
(4)

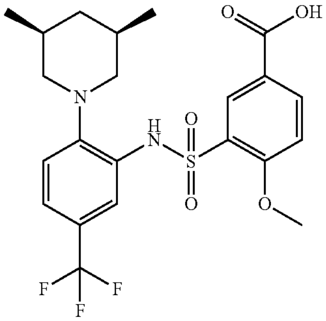 [SMILES: COc1ccc(C(=O)O)cc1S(=O)(=O)Nc1cc(C(F)(F)F)ccc1N1C[C@H](C)C[C@H](C)C1]
(6)

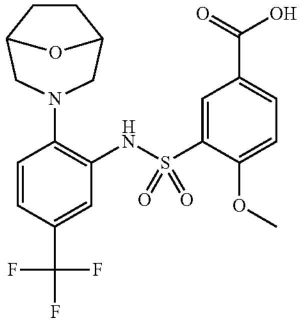 [SMILES: COc1ccc(C(=O)O)cc1S(=O)(=O)Nc1cc(C(F)(F)F)ccc1N1CC2CCC(C1)O2]
(7)

-continued
(8)
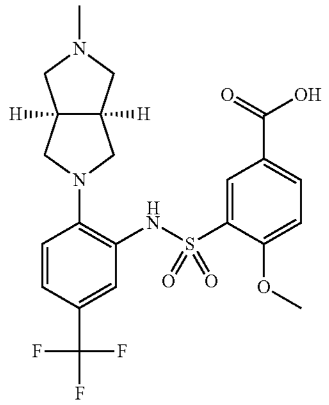 [SMILES: COc1ccc(C(=O)O)cc1S(=O)(=O)Nc1cc(C(F)(F)F)ccc1N1C[C@H]2CN(C)C[C@H]2C1]
(9)
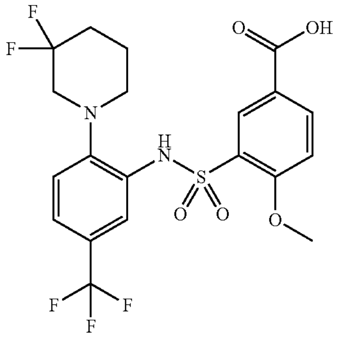 [SMILES: COc1ccc(C(=O)O)cc1S(=O)(=O)Nc1cc(C(F)(F)F)ccc1N1CCCC(F)(F)C1]
(10)
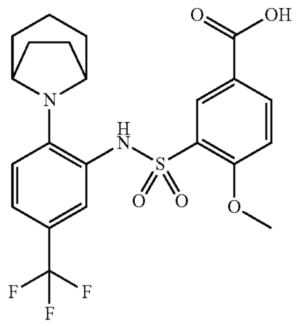
(11)
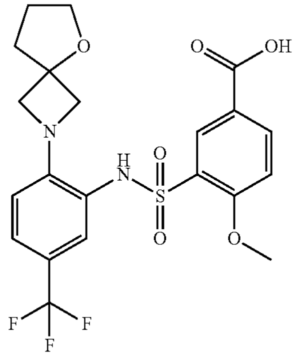
-continued
(12)
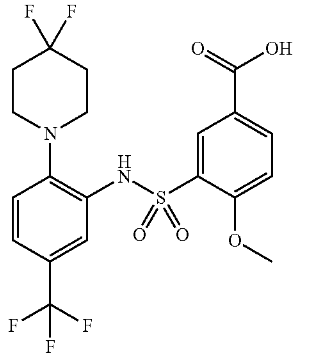
(13)
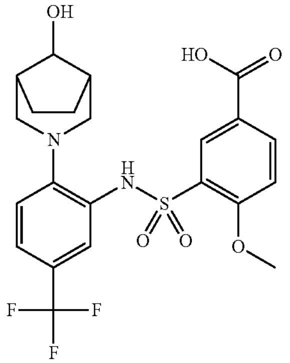 [SMILES: COc1ccc(C(=O)O)cc1S(=O)(=O)Nc1cc(C(F)(F)F)ccc1N1CC2CCC(C1)C2O]
(14)
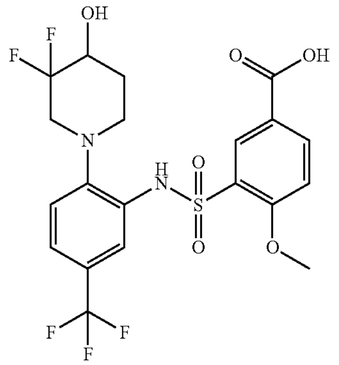 [SMILES: COc1ccc(C(=O)O)cc1S(=O)(=O)Nc1cc(C(F)(F)F)ccc1N1CCC(O)C(F)(F)C1]
(15)
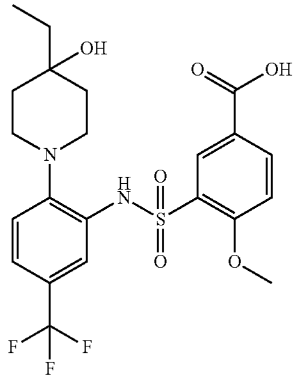 [SMILES: CCC1(O)CCN(c2ccc(C(F)(F)F)cc2NS(=O)(=O)c2cc(C(=O)O)ccc2OC)CC1]

-continued
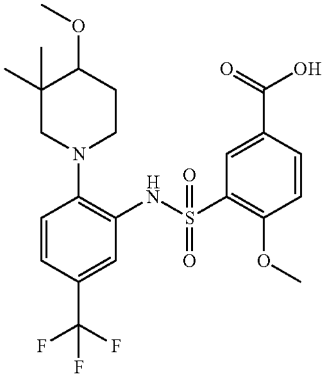 [SMILES: COc1ccc(C(=O)O)cc1S(=O)(=O)Nc1cc(C(F)(F)F)ccc1N1CCC(OC)C(C)(C)C1]
(16)
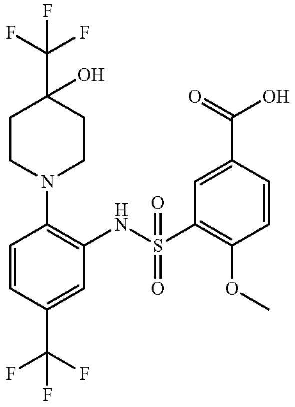
(17)
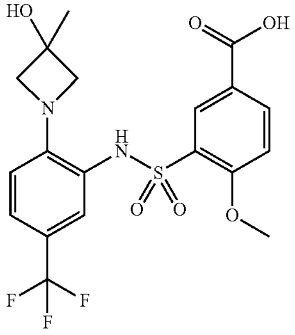 [SMILES: COc1ccc(C(=O)O)cc1S(=O)(=O)Nc1cc(C(F)(F)F)ccc1N1CC(C)(O)C1]
(18)
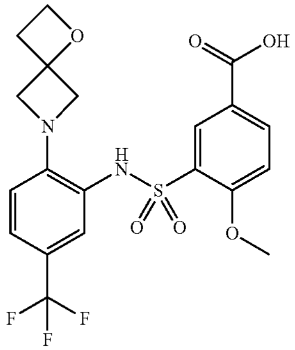 [SMILES: COc1ccc(C(=O)O)cc1S(=O)(=O)Nc1cc(C(F)(F)F)ccc1N1CC2(CCO2)C1]
(19)
-continued
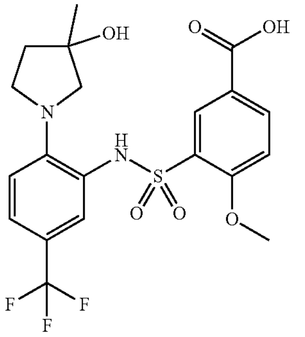 [SMILES: COc1ccc(C(=O)O)cc1S(=O)(=O)Nc1cc(C(F)(F)F)ccc1N1CCC(C)(O)C1]
(20)
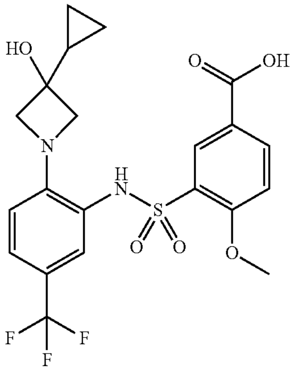 [SMILES: COc1ccc(C(=O)O)cc1S(=O)(=O)Nc1cc(C(F)(F)F)ccc1N1CC(O)(C2CC2)C1]
(21)
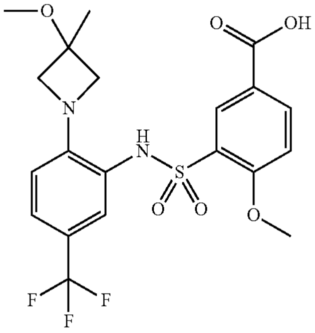
(22)
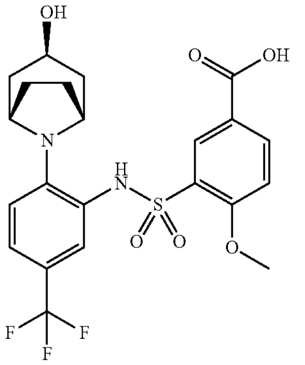 [SMILES: COc1ccc(C(=O)O)cc1S(=O)(=O)Nc1cc(C(F)(F)F)ccc1N1[C@@H]2CC[C@H]1C[C@@H](O)C2]
(23)

-continued
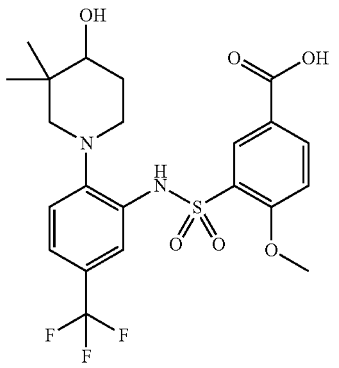
(24)
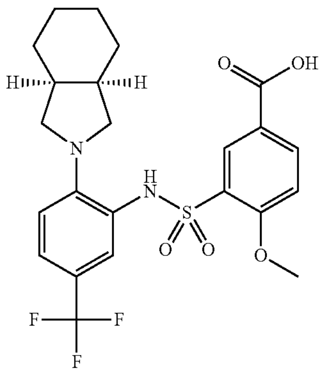 [SMILES: COc1ccc(C(=O)O)cc1S(=O)(=O)Nc1cc(C(F)(F)F)ccc1N1C[C@H]2CCCC[C@H]2C1]
(25)
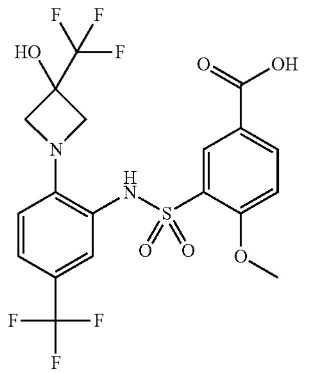 [SMILES: COc1ccc(C(=O)O)cc1S(=O)(=O)Nc1cc(C(F)(F)F)ccc1N1CC(O)(C(F)(F)F)C1]
(26)
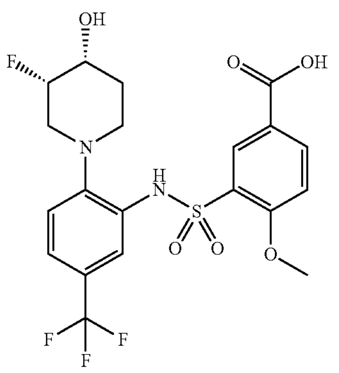 [SMILES: COc1ccc(C(=O)O)cc1S(=O)(=O)Nc1cc(C(F)(F)F)ccc1N1CC[C@@H](O)[C@@H](F)C1]
(27)
-continued
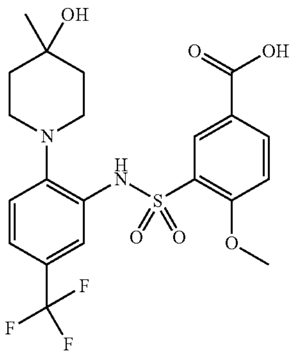 [SMILES: COc1ccc(C(=O)O)cc1S(=O)(=O)Nc1cc(C(F)(F)F)ccc1N1CCC(C)(O)CC1]
(28)
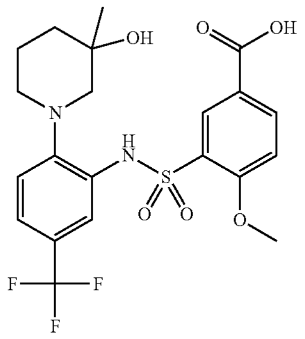 [SMILES: COc1ccc(C(=O)O)cc1S(=O)(=O)Nc1cc(C(F)(F)F)ccc1N1CCCC(C)(O)C1]
(29)
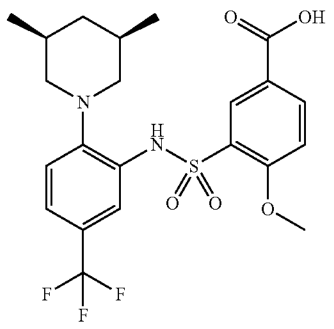
(30)
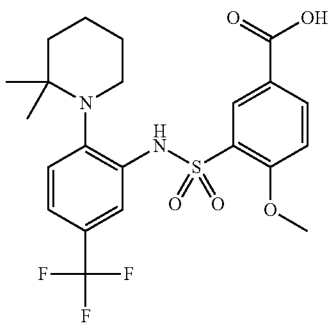
(31)

-continued
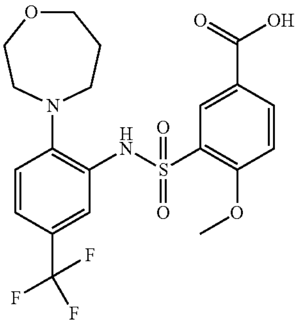 [SMILES: COc1ccc(C(=O)O)cc1S(=O)(=O)Nc1cc(C(F)(F)F)ccc1N1CCCOCC1]
(32)
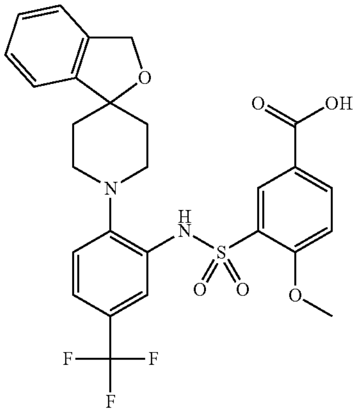 [SMILES: COc1ccc(C(=O)O)cc1S(=O)(=O)Nc1cc(C(F)(F)F)ccc1N1CCC2(CC1)OCc1ccccc12]
(33)
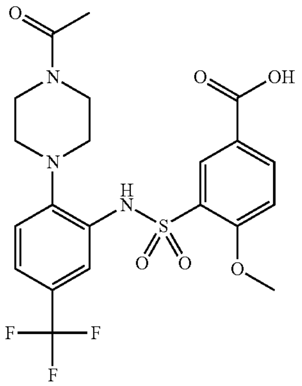 [SMILES: COc1ccc(C(=O)O)cc1S(=O)(=O)Nc1cc(C(F)(F)F)ccc1N1CCN(C(C)=O)CC1]
(34)
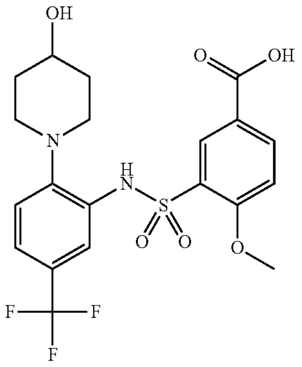
(35)
-continued
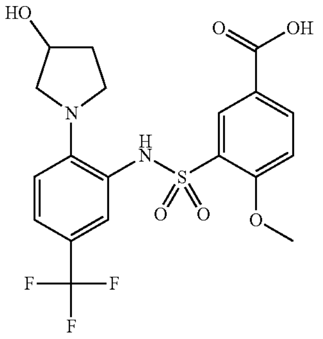
(36)
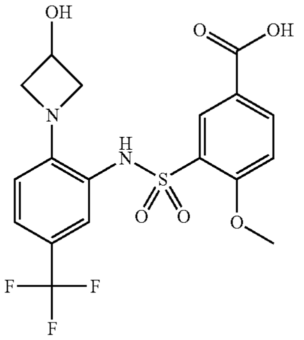 [SMILES: COc1ccc(C(=O)O)cc1S(=O)(=O)Nc1cc(C(F)(F)F)ccc1N1CC(O)C1]
(37)
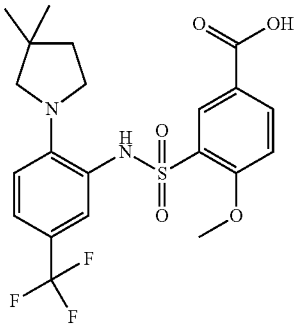 [SMILES: COc1ccc(C(=O)O)cc1S(=O)(=O)Nc1cc(C(F)(F)F)ccc1N1CCC(C)(C)C1]
(39)
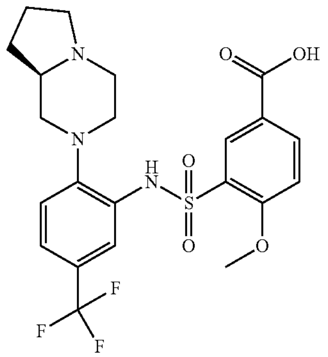 [SMILES: COc1ccc(C(=O)O)cc1S(=O)(=O)Nc1cc(C(F)(F)F)ccc1N1CCN2CCC[C@@H]2C1]
(40)

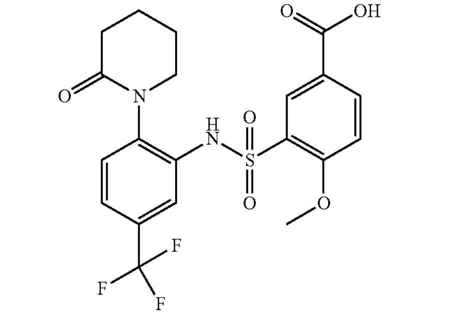 [SMILES: COc1ccc(C(=O)O)cc1S(=O)(=O)Nc1cc(C(F)(F)F)ccc1N1CCCCC1=O]
(41)
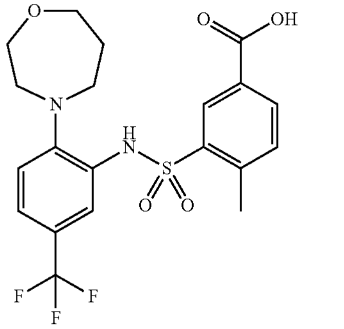 [SMILES: Cc1ccc(C(=O)O)cc1S(=O)(=O)Nc1cc(C(F)(F)F)ccc1N1CCCOCC1]
(42)
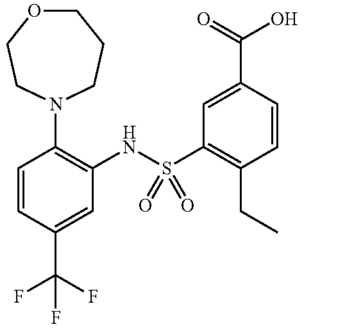 [SMILES: CCc1ccc(C(=O)O)cc1S(=O)(=O)Nc1cc(C(F)(F)F)ccc1N1CCCOCC1]
(43)
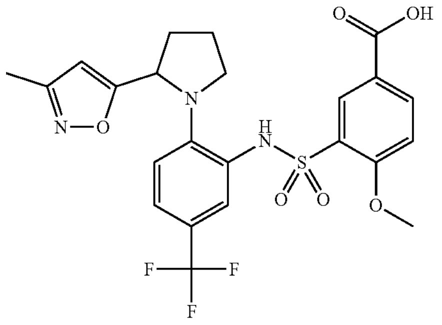 [SMILES: COc1ccc(C(=O)O)cc1S(=O)(=O)Nc1cc(C(F)(F)F)ccc1N1CCCC1c1cc(C)no1]
(46)
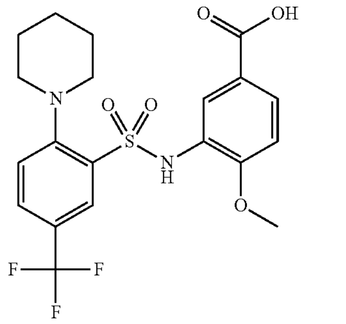 [SMILES: COc1ccc(C(=O)O)cc1NS(=O)(=O)c1cc(C(F)(F)F)ccc1N1CCCCC1]
(49)
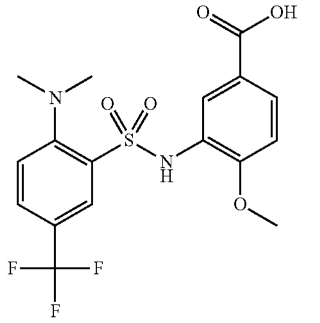 [SMILES: COc1ccc(C(=O)O)cc1NS(=O)(=O)c1cc(C(F)(F)F)ccc1N(C)C]
(51)
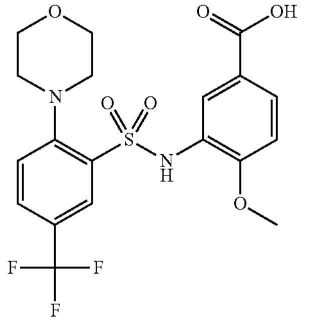
(52)
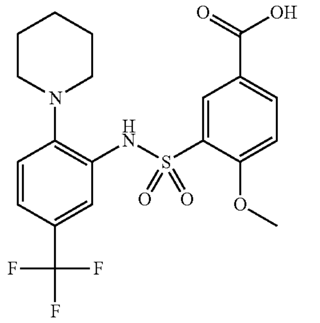 [SMILES: COc1ccc(C(=O)O)cc1S(=O)(=O)Nc1cc(C(F)(F)F)ccc1N1CCCCC1]
(54)
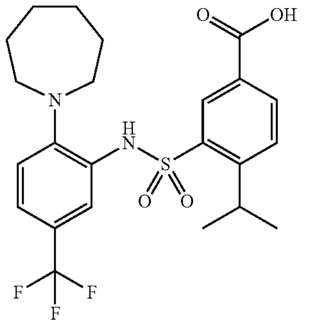 [SMILES: CC(C)c1ccc(C(=O)O)cc1S(=O)(=O)Nc1cc(C(F)(F)F)ccc1N1CCCCCC1]
(55)

-continued
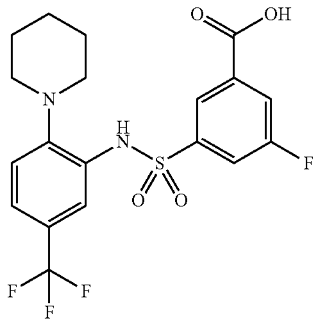 [SMILES: O=C(O)c1cc(F)cc(S(=O)(=O)Nc2cc(C(F)(F)F)ccc2N2CCCCC2)c1]
(59)
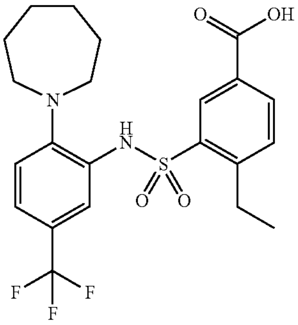
(61)
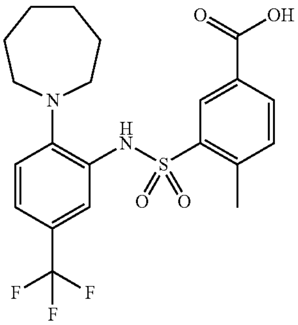 [SMILES: Cc1ccc(C(=O)O)cc1S(=O)(=O)Nc1cc(C(F)(F)F)ccc1N1CCCCCC1]
(62)
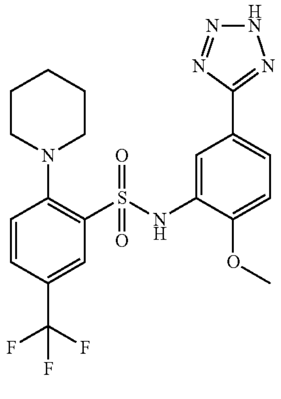 [SMILES: COc1ccc(-c2nn[nH]n2)cc1NS(=O)(=O)c1cc(C(F)(F)F)ccc1N1CCCCC1]
(63)
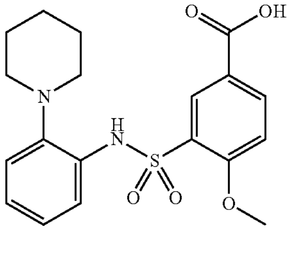 [SMILES: COc1ccc(C(=O)O)cc1S(=O)(=O)Nc1ccccc1N1CCCCC1]
(64)
-continued
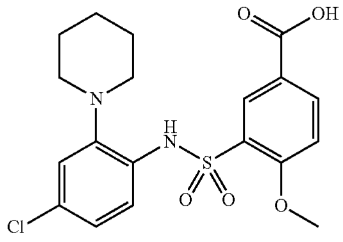 [SMILES: COc1ccc(C(=O)O)cc1S(=O)(=O)Nc1ccc(Cl)cc1N1CCCCC1]
(65)
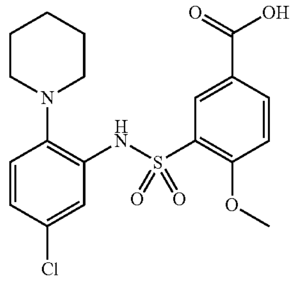 [SMILES: COc1ccc(C(=O)O)cc1S(=O)(=O)Nc1cc(Cl)ccc1N1CCCCC1]
(66)
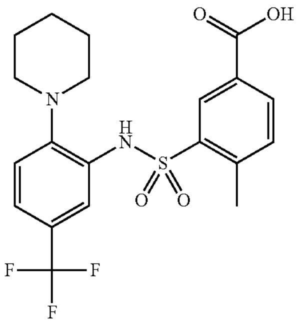 [SMILES: Cc1ccc(C(=O)O)cc1S(=O)(=O)Nc1cc(C(F)(F)F)ccc1N1CCCCC1]
(67)
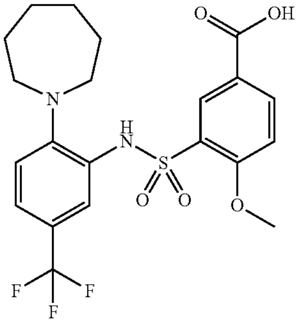
(68)
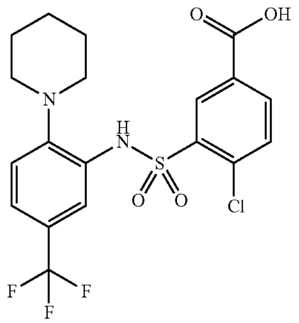
(69)

-continued
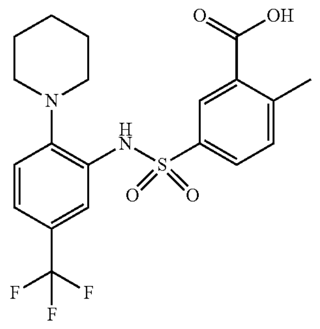 [SMILES: Cc1ccc(S(=O)(=O)Nc2cc(C(F)(F)F)ccc2N2CCCCC2)cc1C(=O)O]
(70)
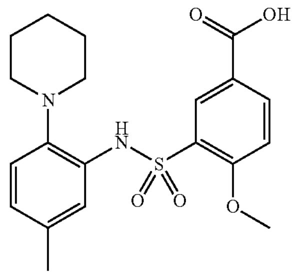 [SMILES: COc1ccc(C(=O)O)cc1S(=O)(=O)Nc1cc(C)ccc1N1CCCCC1]
(71)
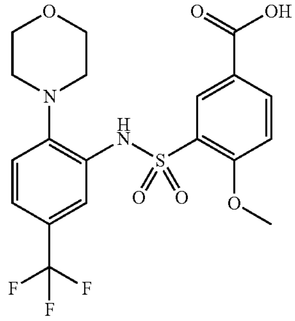
(72)
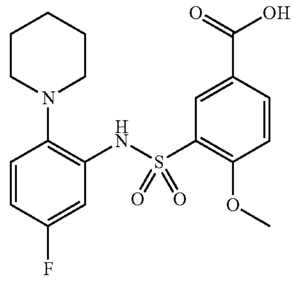 [SMILES: COc1ccc(C(=O)O)cc1S(=O)(=O)Nc1cc(F)ccc1N1CCCCC1]
(73)
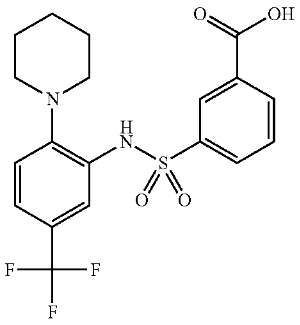 [SMILES: O=C(O)c1cccc(S(=O)(=O)Nc2cc(C(F)(F)F)ccc2N2CCCCC2)c1]
(74)
-continued
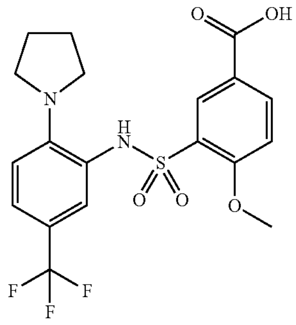 [SMILES: COc1ccc(C(=O)O)cc1S(=O)(=O)Nc1cc(C(F)(F)F)ccc1N1CCCC1]
(75)
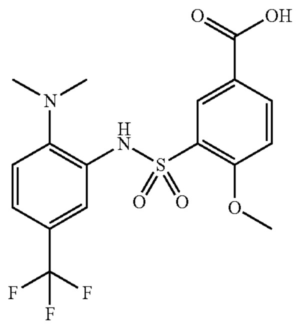 [SMILES: COc1ccc(C(=O)O)cc1S(=O)(=O)Nc1cc(C(F)(F)F)ccc1N(C)C]
(77)
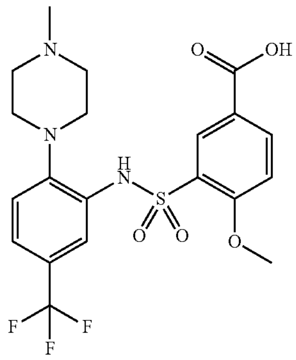 [SMILES: COc1ccc(C(=O)O)cc1S(=O)(=O)Nc1cc(C(F)(F)F)ccc1N1CCN(C)CC1]
(78)
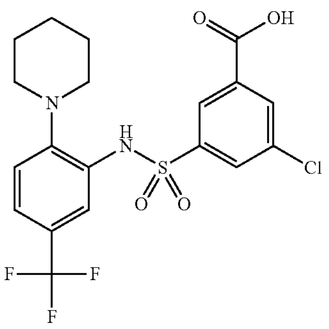 [SMILES: O=C(O)c1cc(Cl)cc(S(=O)(=O)Nc2cc(C(F)(F)F)ccc2N2CCCCC2)c1]
(80)

-continued
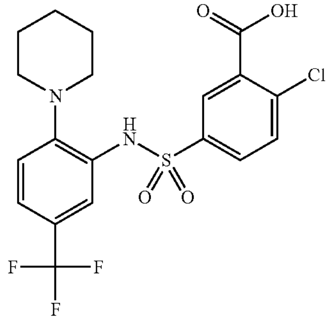 [SMILES: O=C(O)c1cc(S(=O)(=O)Nc2cc(C(F)(F)F)ccc2N2CCCCC2)ccc1Cl]
(83)
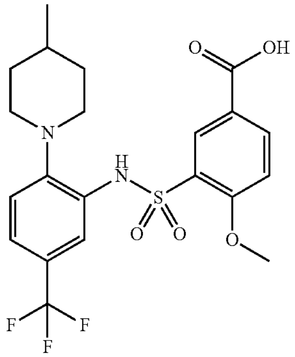 [SMILES: COc1ccc(C(=O)O)cc1S(=O)(=O)Nc1cc(C(F)(F)F)ccc1N1CCC(C)CC1]
(84)
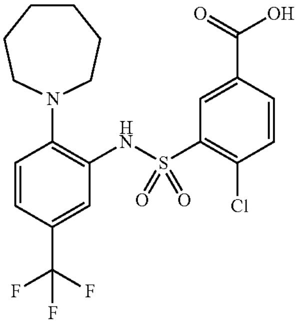 [SMILES: O=C(O)c1ccc(Cl)c(S(=O)(=O)Nc2cc(C(F)(F)F)ccc2N2CCCCCC2)c1]
(86)
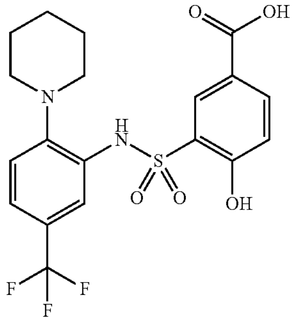
(161)
-continued
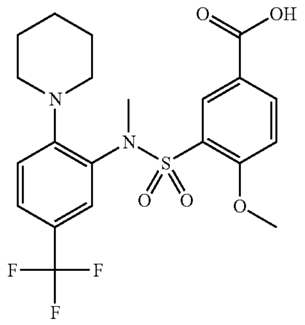 [SMILES: COc1ccc(C(=O)O)cc1S(=O)(=O)N(C)c1cc(C(F)(F)F)ccc1N1CCCCC1]
(165)
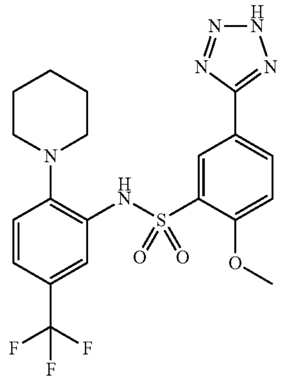 [SMILES: COc1ccc(-c2nn[nH]n2)cc1S(=O)(=O)Nc1cc(C(F)(F)F)ccc1N1CCCCC1]
(171)
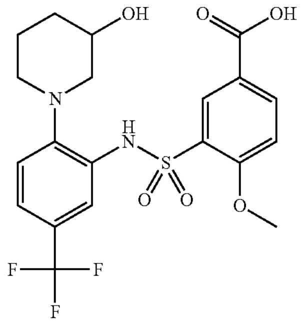
(177)
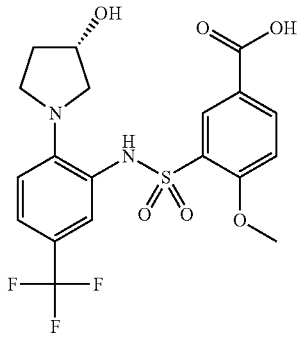 [SMILES: COc1ccc(C(=O)O)cc1S(=O)(=O)Nc1cc(C(F)(F)F)ccc1N1CC[C@H](O)C1]
(178)

-continued
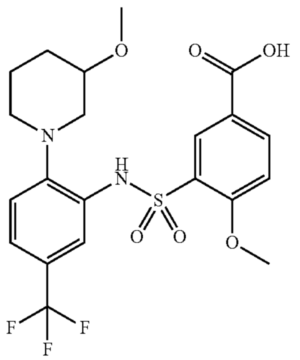
(179)
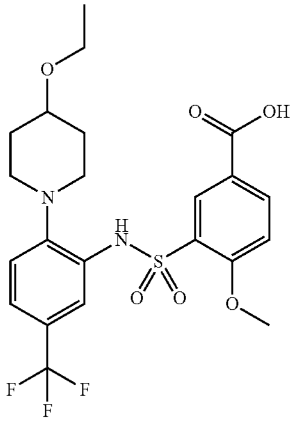
(180)
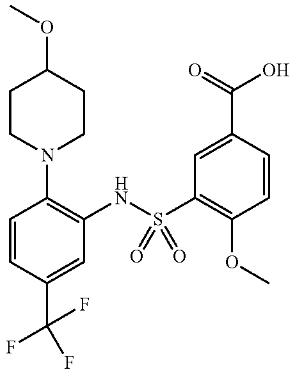
(181)
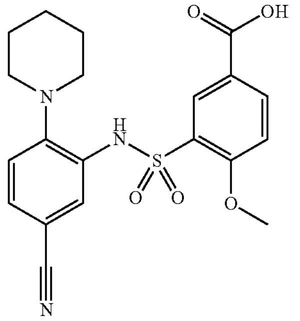 [SMILES: COc1ccc(C(=O)O)cc1S(=O)(=O)Nc1cc(C#N)ccc1N1CCCCC1]
(182)
-continued
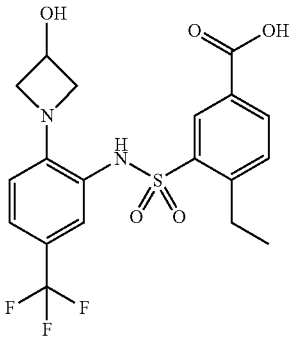 [SMILES: CCc1ccc(C(=O)O)cc1S(=O)(=O)Nc1cc(C(F)(F)F)ccc1N1CC(O)C1]
(183)
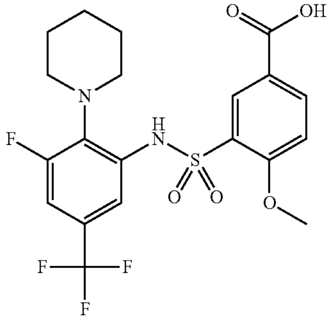 [SMILES: COc1ccc(C(=O)O)cc1S(=O)(=O)Nc1cc(C(F)(F)F)cc(F)c1N1CCCCC1]
(184)
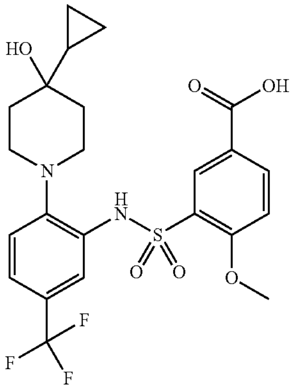 [SMILES: COc1ccc(C(=O)O)cc1S(=O)(=O)Nc1cc(C(F)(F)F)ccc1N1CCC(O)(C2CC2)CC1]
(185)
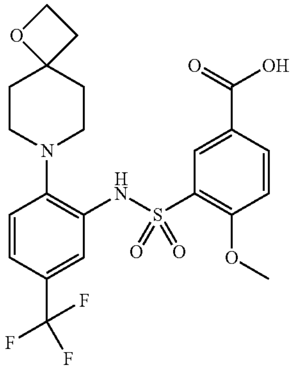 [SMILES: COc1ccc(C(=O)O)cc1S(=O)(=O)Nc1cc(C(F)(F)F)ccc1N1CCC2(CCO2)CC1]
(186)

-continued
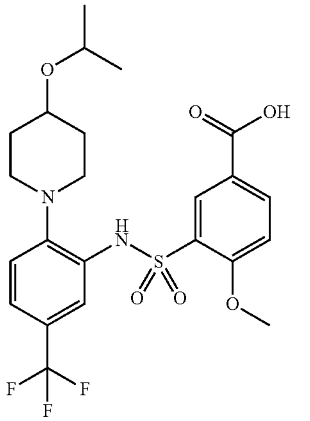 [SMILES: COc1ccc(C(=O)O)cc1S(=O)(=O)Nc1cc(C(F)(F)F)ccc1N1CCC(OC(C)C)CC1]
(187)
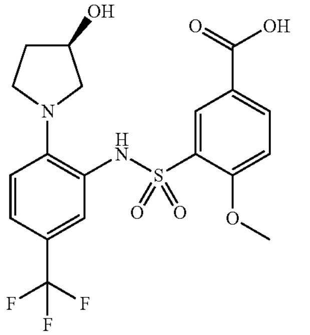 [SMILES: COc1ccc(C(=O)O)cc1S(=O)(=O)Nc1cc(C(F)(F)F)ccc1N1CC[C@@H](O)C1]
(188)
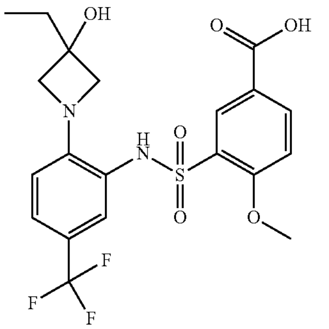 [SMILES: CCC1(O)CN(c2ccc(C(F)(F)F)cc2NS(=O)(=O)c2cc(C(=O)O)ccc2OC)C1]
(189)
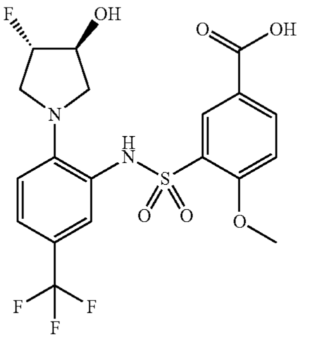 [SMILES: COc1ccc(C(=O)O)cc1S(=O)(=O)Nc1cc(C(F)(F)F)ccc1N1C[C@H](O)[C@@H](F)C1]
(190)
-continued
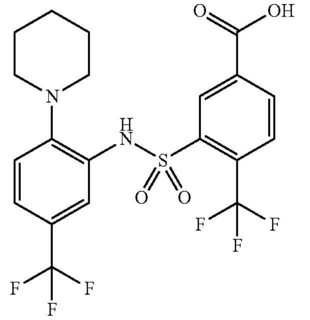
(200)
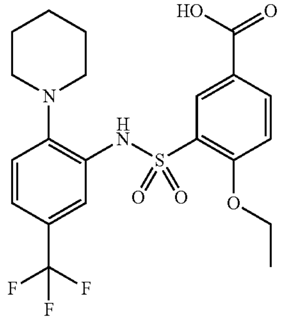
(201)
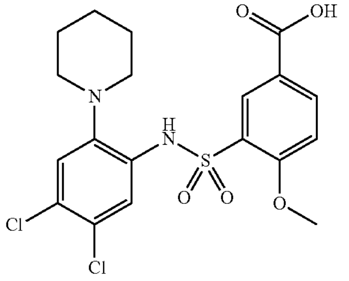 [SMILES: COc1ccc(C(=O)O)cc1S(=O)(=O)Nc1cc(Cl)c(Cl)cc1N1CCCCC1]
(202)
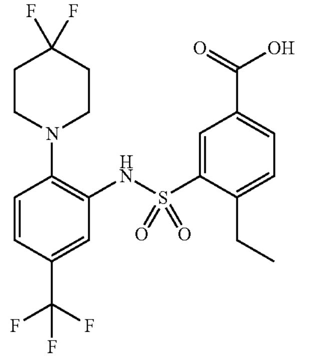
(203)
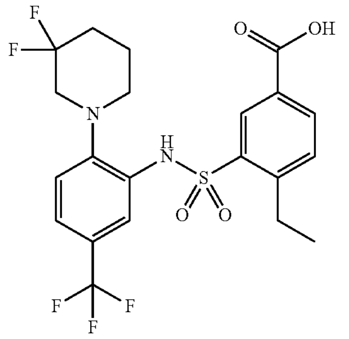 [SMILES: CCc1ccc(C(=O)O)cc1S(=O)(=O)Nc1cc(C(F)(F)F)ccc1N1CCCC(F)(F)C1]
(204)

-continued
(205)
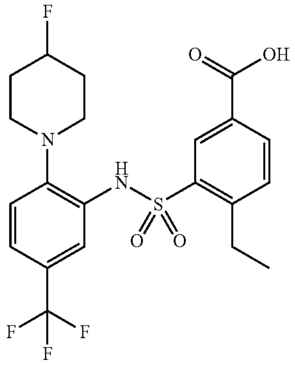
(206)
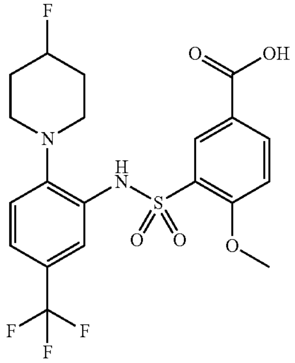
(207)
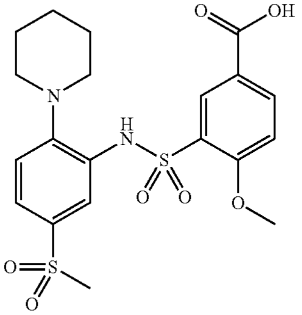 [SMILES: COc1ccc(C(=O)O)cc1S(=O)(=O)Nc1cc(S(C)(=O)=O)ccc1N1CCCCC1]
(208)
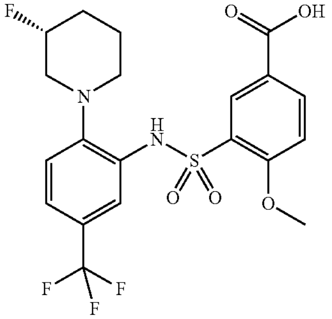
-continued
(209)
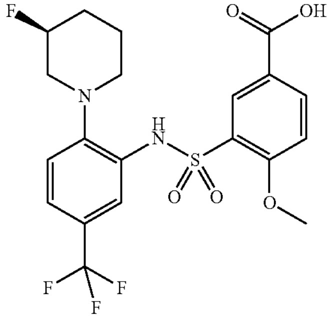 [SMILES: COc1ccc(C(=O)O)cc1S(=O)(=O)Nc1cc(C(F)(F)F)ccc1N1CCC[C@H](F)C1]
(210)
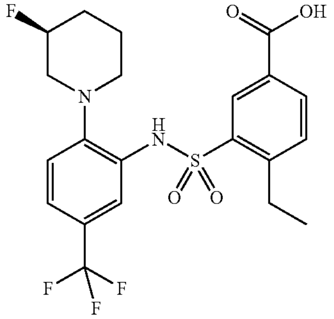
(211)
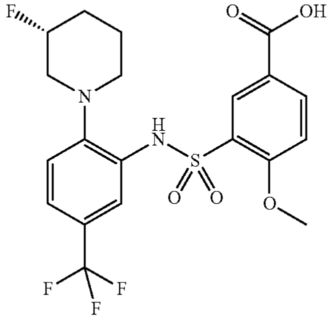
(212)
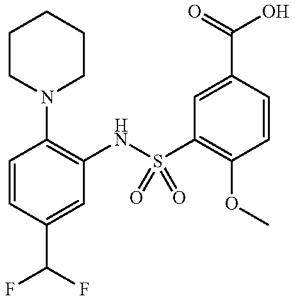
(213)
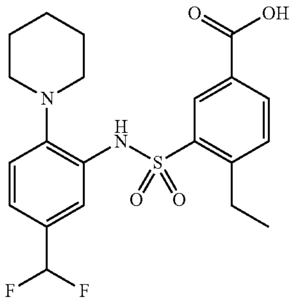

-continued
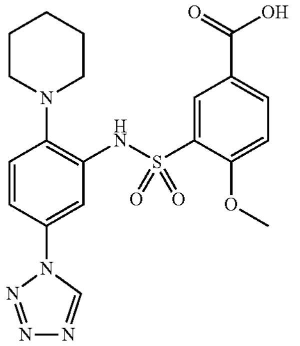 [SMILES: COc1ccc(C(=O)O)cc1S(=O)(=O)Nc1cc(-n2cnnn2)ccc1N1CCCCC1]
(214)
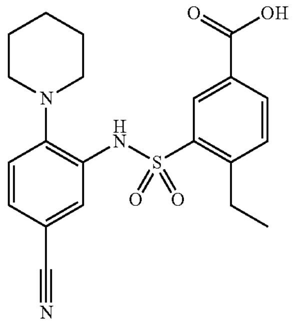 [SMILES: CCc1ccc(C(=O)O)cc1S(=O)(=O)Nc1cc(C#N)ccc1N1CCCCC1]
(215)
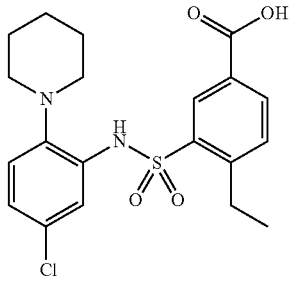 [SMILES: CCc1ccc(C(=O)O)cc1S(=O)(=O)Nc1cc(Cl)ccc1N1CCCCC1]
(216)
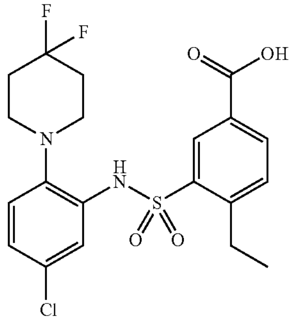 [SMILES: CCc1ccc(C(=O)O)cc1S(=O)(=O)Nc1cc(Cl)ccc1N1CCC(F)(F)CC1]
(217)
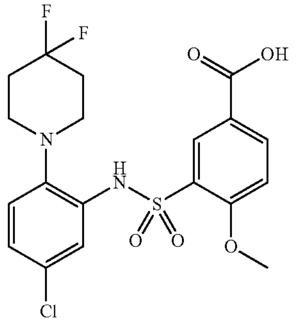 [SMILES: COc1ccc(C(=O)O)cc1S(=O)(=O)Nc1cc(Cl)ccc1N1CCC(F)(F)CC1]
(218)
-continued
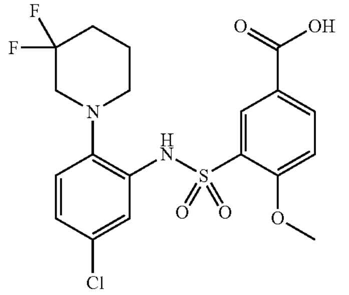 [SMILES: COc1ccc(C(=O)O)cc1S(=O)(=O)Nc1cc(Cl)ccc1N1CCCC(F)(F)C1]
(219)
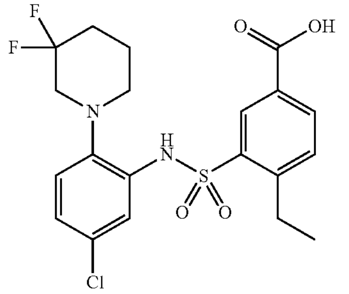 [SMILES: CCc1ccc(C(=O)O)cc1S(=O)(=O)Nc1cc(Cl)ccc1N1CCCC(F)(F)C1]
(220)
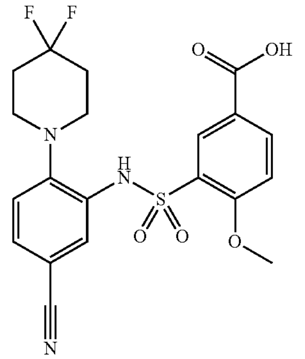
(221)
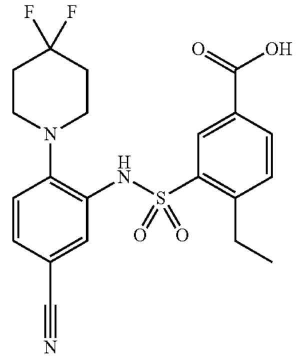
(222)

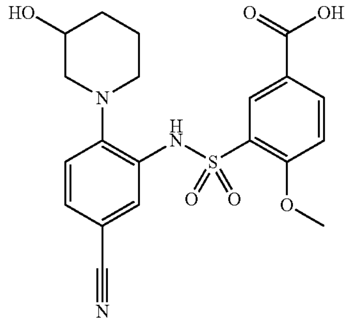
(223)
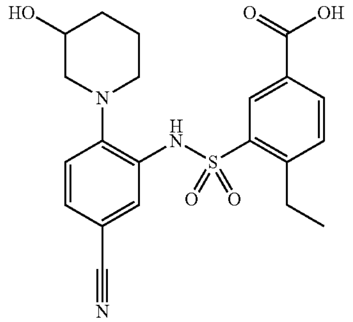
(224)
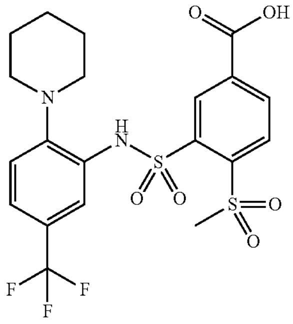
(225)
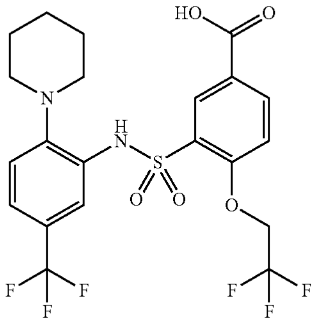 [SMILES: O=C(O)c1ccc(OCC(F)(F)F)c(S(=O)(=O)Nc2cc(C(F)(F)F)ccc2N2CCCCC2)c1]
(227)
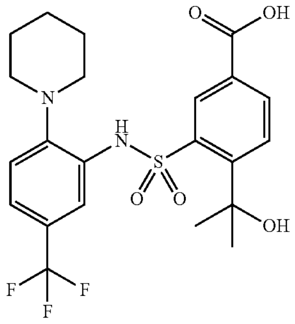
(228)
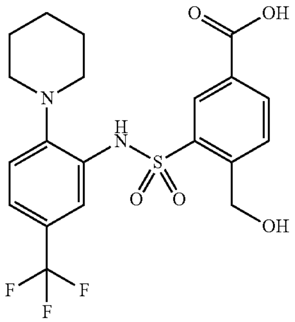
(229)
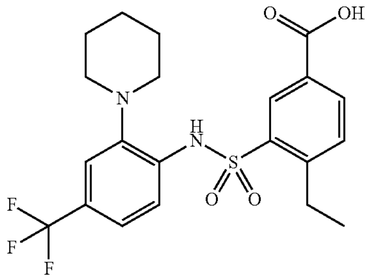 [SMILES: CCc1ccc(C(=O)O)cc1S(=O)(=O)Nc1ccc(C(F)(F)F)cc1N1CCCCC1]
(230)
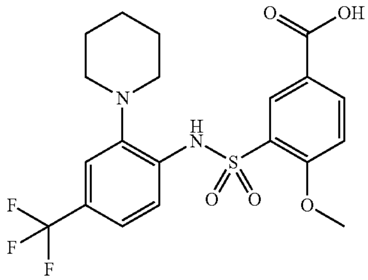 [SMILES: COc1ccc(C(=O)O)cc1S(=O)(=O)Nc1ccc(C(F)(F)F)cc1N1CCCCC1]
(231)
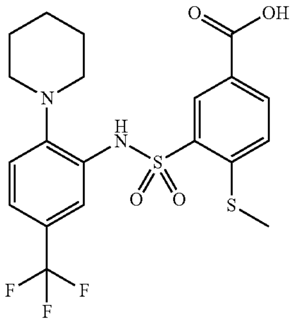 [SMILES: CSc1ccc(C(=O)O)cc1S(=O)(=O)Nc1cc(C(F)(F)F)ccc1N1CCCCC1]
(232)
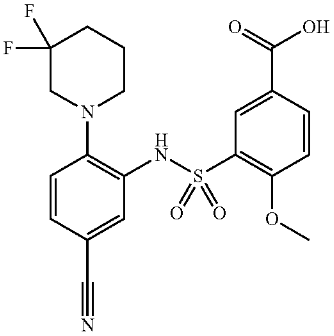 [SMILES: COc1ccc(C(=O)O)cc1S(=O)(=O)Nc1cc(C#N)ccc1N1CCCC(F)(F)C1]
(233)

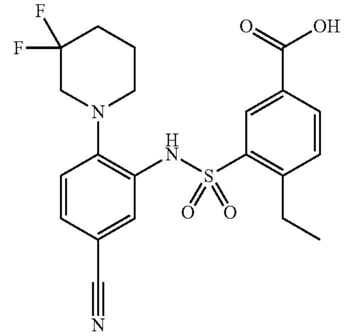 [SMILES: CCc1ccc(C(=O)O)cc1S(=O)(=O)Nc1cc(C#N)ccc1N1CCCC(F)(F)C1]
(234)
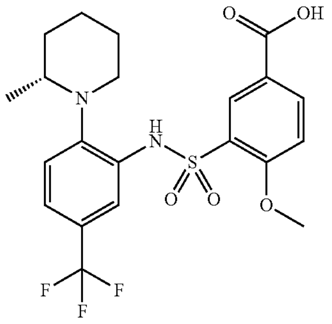
(235)
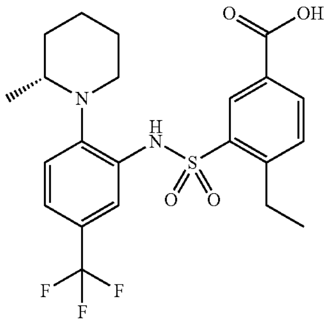
(236)
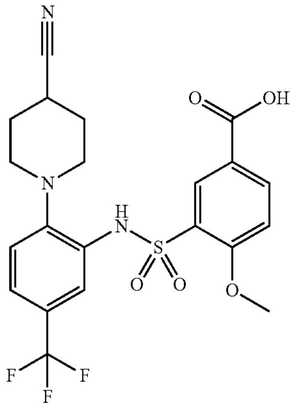
(237)
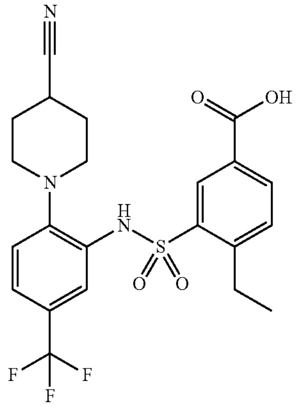
(238)
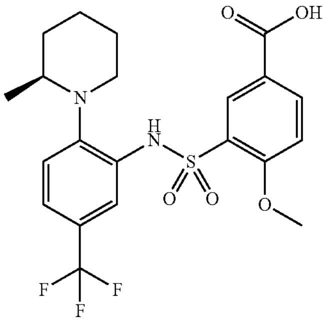
(239)
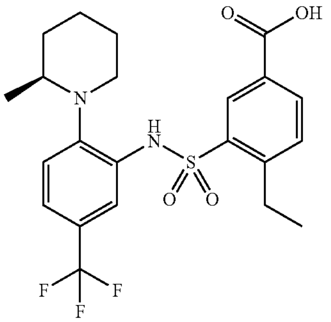
(240)
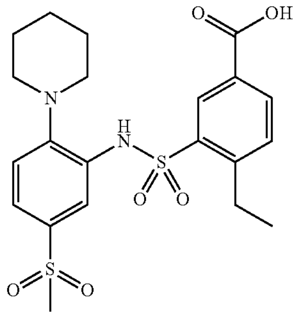 [SMILES: CCc1ccc(C(=O)O)cc1S(=O)(=O)Nc1cc(S(C)(=O)=O)ccc1N1CCCCC1]
(241)

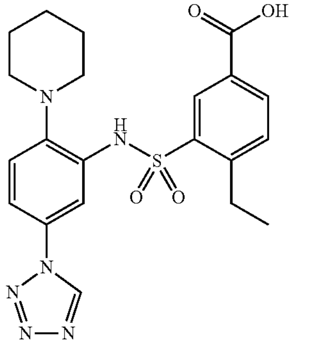 [SMILES: CCc1ccc(C(=O)O)cc1S(=O)(=O)Nc1cc(-n2cnnn2)ccc1N1CCCCC1]
(242)
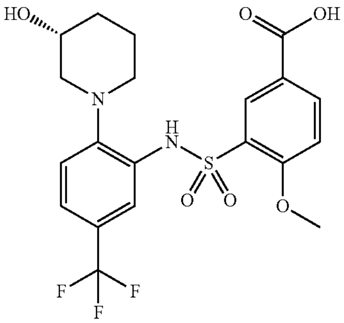 [SMILES: COc1ccc(C(=O)O)cc1S(=O)(=O)Nc1cc(C(F)(F)F)ccc1N1CCC[C@@H](O)C1]
(243)
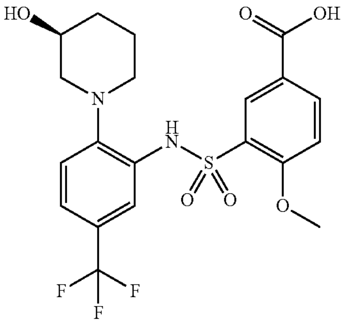
(244)
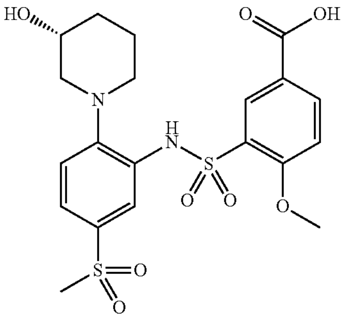
(245)
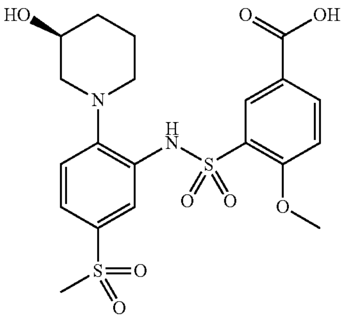
(246)
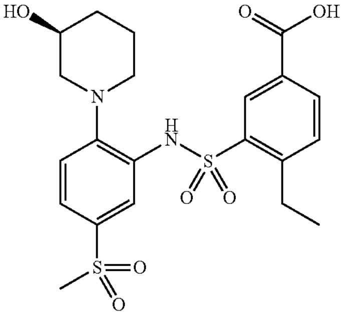
(247)
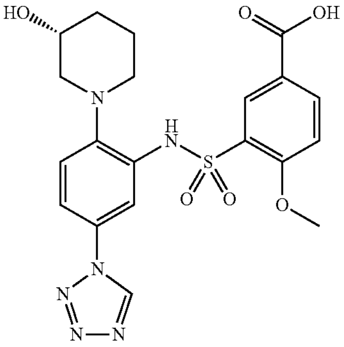 [SMILES: COc1ccc(C(=O)O)cc1S(=O)(=O)Nc1cc(-n2cnnn2)ccc1N1CCC[C@@H](O)C1]
(248)
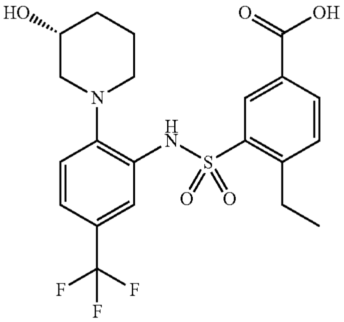
(249)
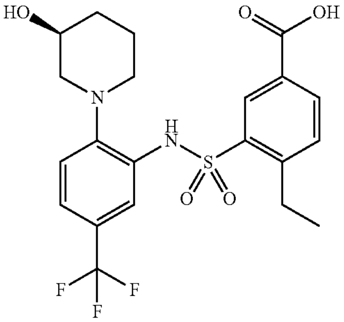
(250)

-continued
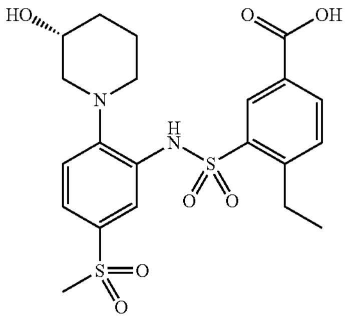
(251)
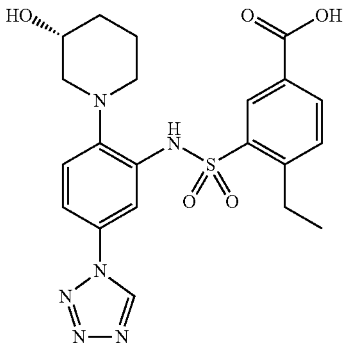 [SMILES: CCc1ccc(C(=O)O)cc1S(=O)(=O)Nc1cc(-n2cnnn2)ccc1N1CCC[C@@H](O)C1]
(252)
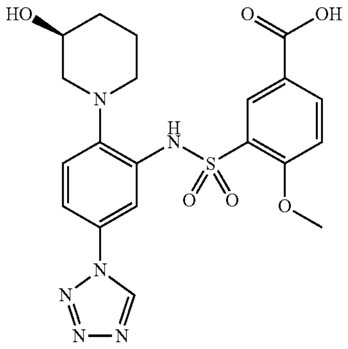 [SMILES: COc1ccc(C(=O)O)cc1S(=O)(=O)Nc1cc(-n2cnnn2)ccc1N1CCC[C@H](O)C1]
(253)
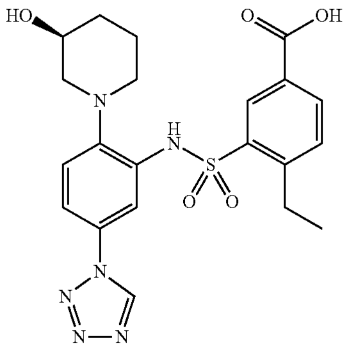 [SMILES: CCc1ccc(C(=O)O)cc1S(=O)(=O)Nc1cc(-n2cnnn2)ccc1N1CCC[C@H](O)C1]
(254)
-continued
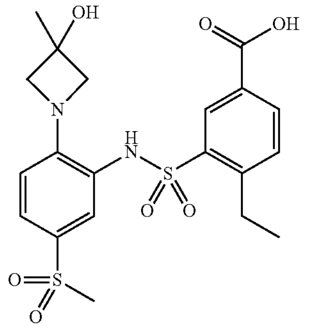 [SMILES: CCc1ccc(C(=O)O)cc1S(=O)(=O)Nc1cc(S(C)(=O)=O)ccc1N1CC(C)(O)C1]
(255)
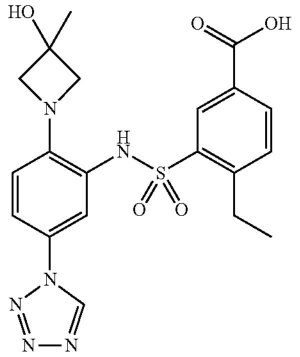 [SMILES: CCc1ccc(C(=O)O)cc1S(=O)(=O)Nc1cc(-n2cnnn2)ccc1N1CC(C)(O)C1]
(257)
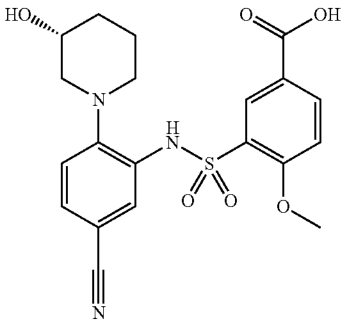
(258)
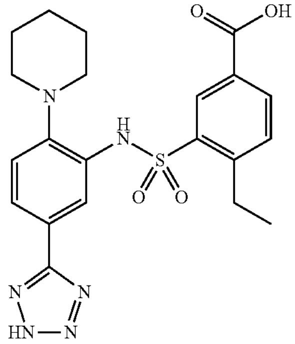 [SMILES: CCc1ccc(C(=O)O)cc1S(=O)(=O)Nc1cc(-c2nn[nH]n2)ccc1N1CCCCC1]
(259)

-continued
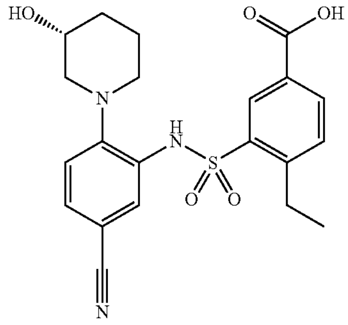
(260)
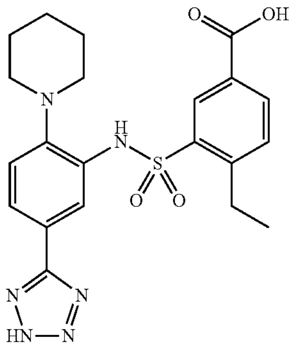 [SMILES: CCc1ccc(C(=O)O)cc1S(=O)(=O)Nc1cc(-c2nn[nH]n2)ccc1N1CCCCC1]
(261)
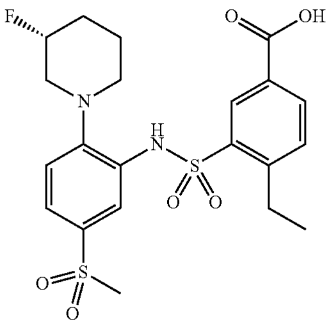
(262)
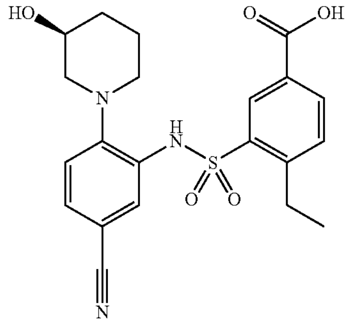
(263)
-continued
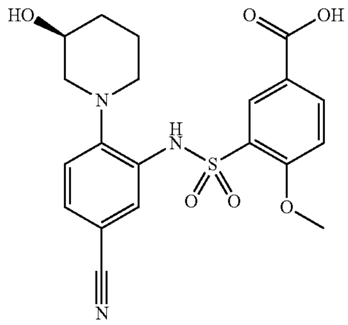
(264)
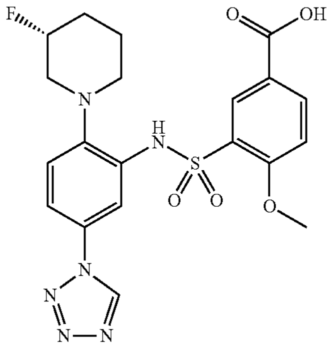
(265)
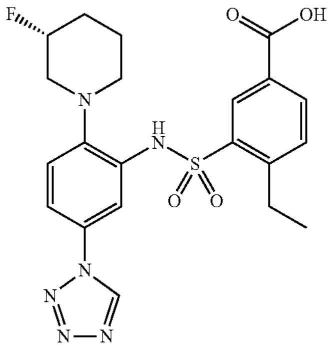
(266)
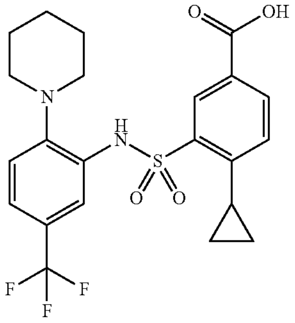 [SMILES: O=C(O)c1ccc(C2CC2)c(S(=O)(=O)Nc2cc(C(F)(F)F)ccc2N2CCCCC2)c1]
(267)

-continued
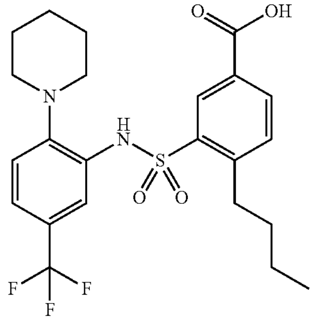 [SMILES: CCCCc1ccc(C(=O)O)cc1S(=O)(=O)Nc1cc(C(F)(F)F)ccc1N1CCCCC1]
(268)
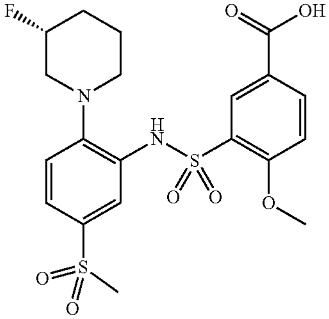
(269)
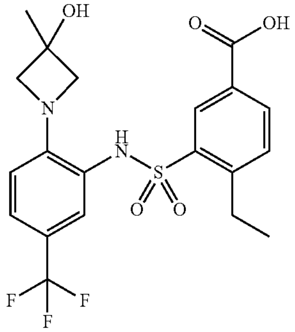
(270)
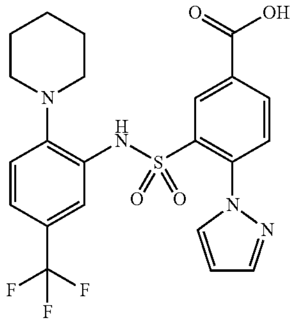
(271)
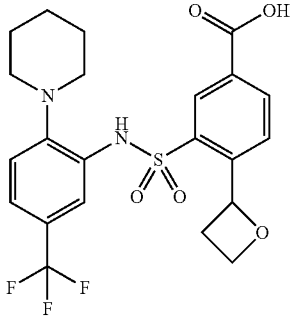
(272)
-continued
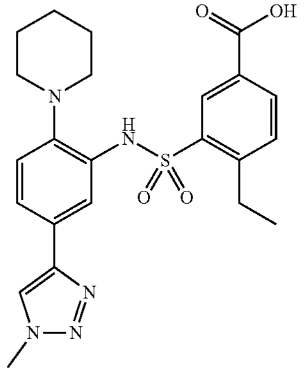 [SMILES: CCc1ccc(C(=O)O)cc1S(=O)(=O)Nc1cc(-c2cn(C)nn2)ccc1N1CCCCC1]
(273)
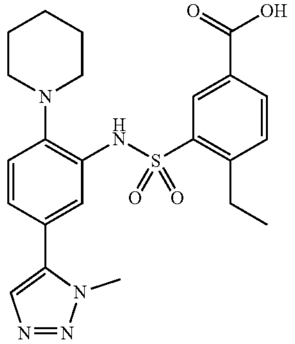 [SMILES: CCc1ccc(C(=O)O)cc1S(=O)(=O)Nc1cc(-c2cnnn2C)ccc1N1CCCCC1]
(274)
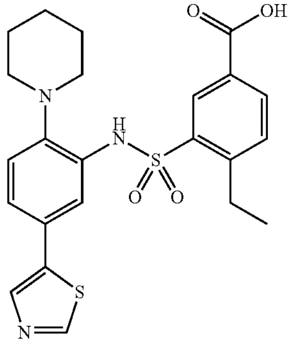 [SMILES: CCc1ccc(C(=O)O)cc1S(=O)(=O)Nc1cc(-c2cncs2)ccc1N1CCCCC1]
(275)
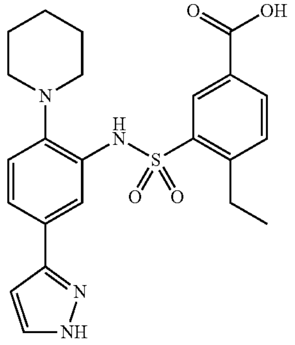 [SMILES: CCc1ccc(C(=O)O)cc1S(=O)(=O)Nc1cc(-c2cc[nH]n2)ccc1N1CCCCC1]
(276)

-continued
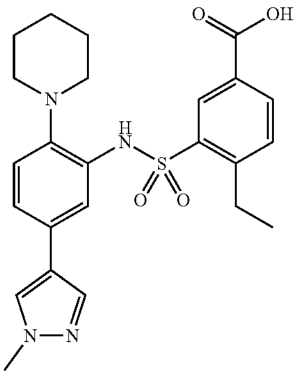 [SMILES: CCc1ccc(C(=O)O)cc1S(=O)(=O)Nc1cc(-c2cnn(C)c2)ccc1N1CCCCC1]
(277)
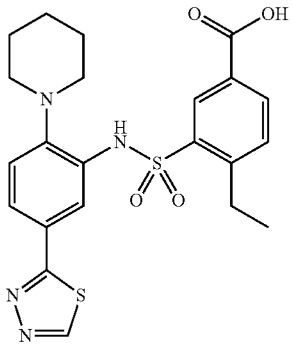 [SMILES: CCc1ccc(C(=O)O)cc1S(=O)(=O)Nc1cc(-c2nncs2)ccc1N1CCCCC1]
(278)
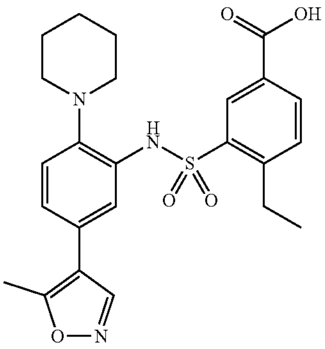 [SMILES: CCc1ccc(C(=O)O)cc1S(=O)(=O)Nc1cc(-c2cnoc2C)ccc1N1CCCCC1]
(279)
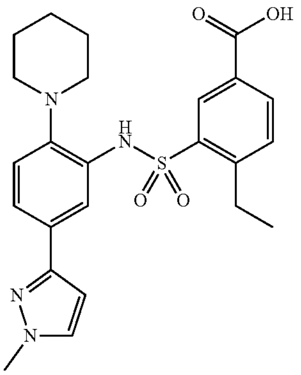 [SMILES: CCc1ccc(C(=O)O)cc1S(=O)(=O)Nc1cc(-c2ccn(C)n2)ccc1N1CCCCC1]
(280)
-continued
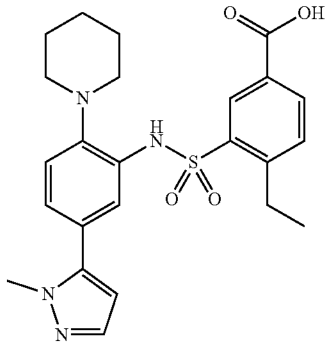 [SMILES: CCc1ccc(C(=O)O)cc1S(=O)(=O)Nc1cc(-c2ccnn2C)ccc1N1CCCCC1]
(281)
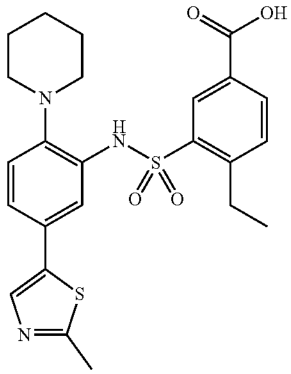 [SMILES: CCc1ccc(C(=O)O)cc1S(=O)(=O)Nc1cc(-c2cnc(C)s2)ccc1N1CCCCC1]
(282)
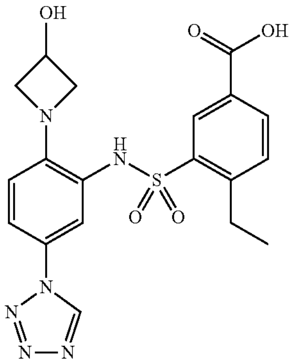 [SMILES: CCc1ccc(C(=O)O)cc1S(=O)(=O)Nc1cc(-n2cnnn2)ccc1N1CC(O)C1]
(283)
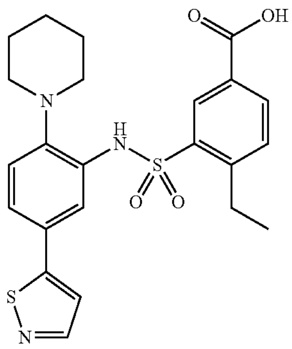 [SMILES: CCc1ccc(C(=O)O)cc1S(=O)(=O)Nc1cc(-c2ccns2)ccc1N1CCCCC1]
(286)

-continued
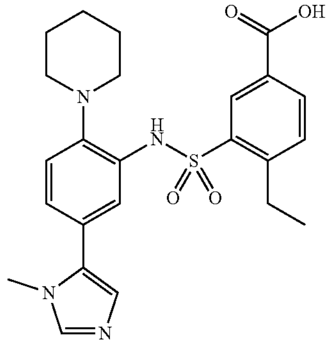 [SMILES: CCc1ccc(C(=O)O)cc1S(=O)(=O)Nc1cc(-c2cncn2C)ccc1N1CCCCC1]
(287)
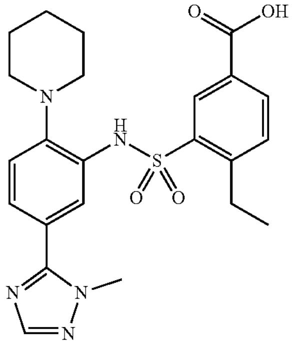 [SMILES: CCc1ccc(C(=O)O)cc1S(=O)(=O)Nc1cc(-c2ncnn2C)ccc1N1CCCCC1]
(288)
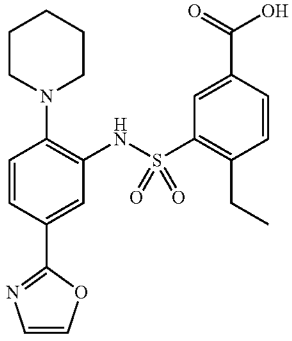 [SMILES: CCc1ccc(C(=O)O)cc1S(=O)(=O)Nc1cc(-c2ncco2)ccc1N1CCCCC1]
(289)
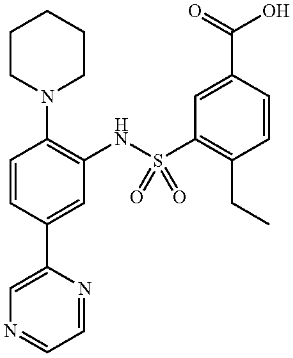 [SMILES: CCc1ccc(C(=O)O)cc1S(=O)(=O)Nc1cc(-c2cnccn2)ccc1N1CCCCC1]
(290)
-continued
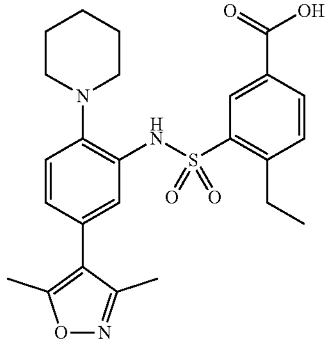 [SMILES: CCc1ccc(C(=O)O)cc1S(=O)(=O)Nc1cc(-c2c(C)noc2C)ccc1N1CCCCC1]
(291)
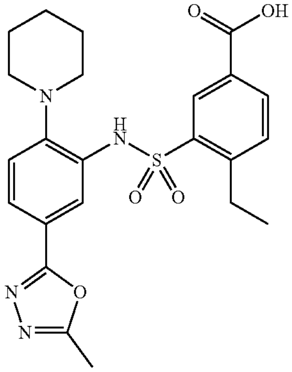 [SMILES: CCc1ccc(C(=O)O)cc1S(=O)(=O)Nc1cc(-c2nnc(C)o2)ccc1N1CCCCC1]
(292)
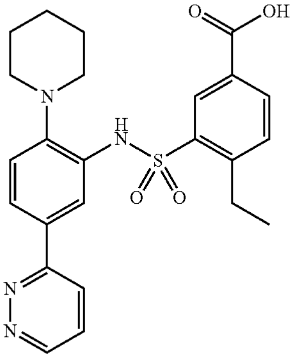 [SMILES: CCc1ccc(C(=O)O)cc1S(=O)(=O)Nc1cc(-c2cccnn2)ccc1N1CCCCC1]
(293)
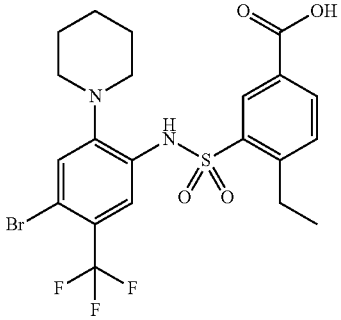
(294)

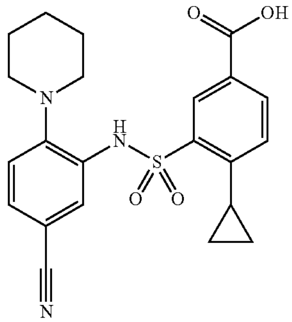 [SMILES: N#Cc1ccc(N2CCCCC2)c(NS(=O)(=O)c2cc(C(=O)O)ccc2C2CC2)c1]
(295)
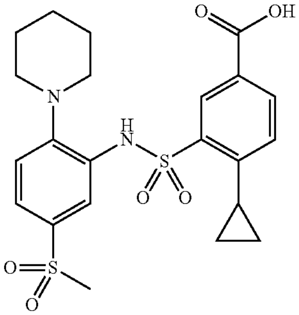 [SMILES: CS(=O)(=O)c1ccc(N2CCCCC2)c(NS(=O)(=O)c2cc(C(=O)O)ccc2C2CC2)c1]
(296)
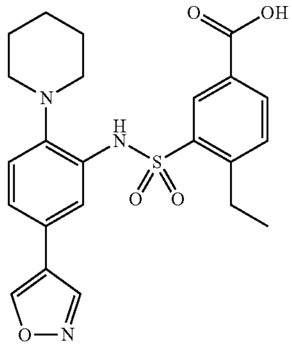 [SMILES: CCc1ccc(C(=O)O)cc1S(=O)(=O)Nc1cc(-c2cnoc2)ccc1N1CCCCC1]
(297)
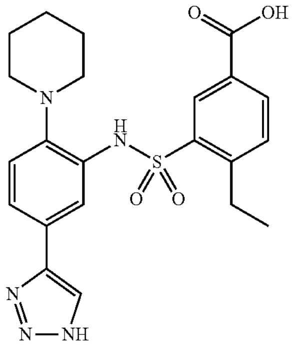 [SMILES: CCc1ccc(C(=O)O)cc1S(=O)(=O)Nc1cc(-c2c[nH]nn2)ccc1N1CCCCC1]
(298)
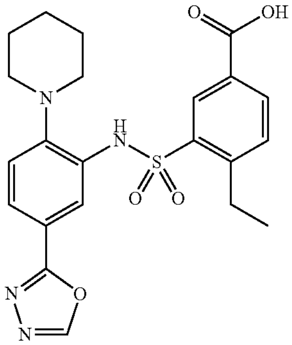 [SMILES: CCc1ccc(C(=O)O)cc1S(=O)(=O)Nc1cc(-c2nnco2)ccc1N1CCCCC1]
(299)
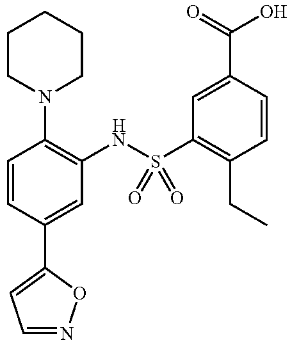 [SMILES: CCc1ccc(C(=O)O)cc1S(=O)(=O)Nc1cc(-c2ccno2)ccc1N1CCCCC1]
(300)
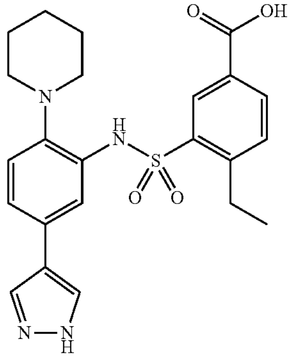 [SMILES: CCc1ccc(C(=O)O)cc1S(=O)(=O)Nc1cc(-c2cn[nH]c2)ccc1N1CCCCC1]
(301)
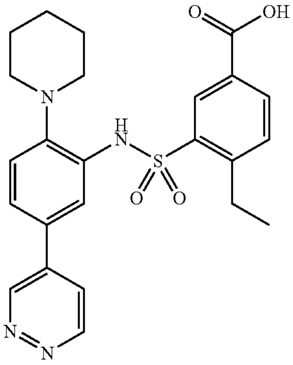 [SMILES: CCc1ccc(C(=O)O)cc1S(=O)(=O)Nc1cc(-c2ccnnc2)ccc1N1CCCCC1]
(302)

-continued
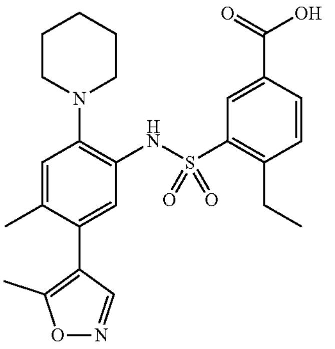 [SMILES: CCc1ccc(C(=O)O)cc1S(=O)(=O)Nc1cc(-c2cnoc2C)c(C)cc1N1CCCCC1]
(303)
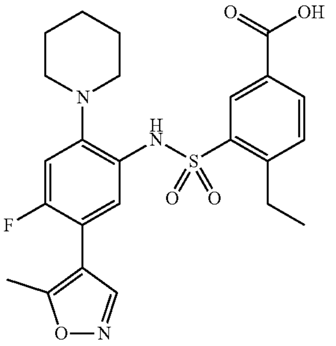 [SMILES: CCc1ccc(C(=O)O)cc1S(=O)(=O)Nc1cc(-c2cnoc2C)c(F)cc1N1CCCCC1]
(304)
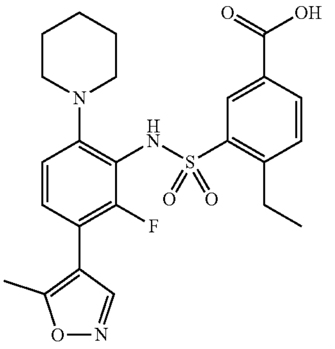 [SMILES: CCc1ccc(C(=O)O)cc1S(=O)(=O)Nc1c(N2CCCCC2)ccc(-c2cnoc2C)c1F]
(305)
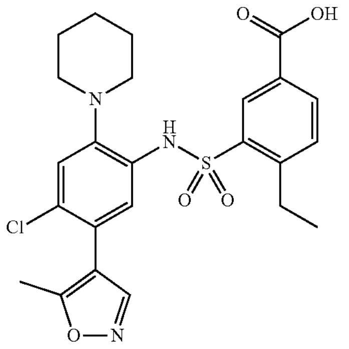 [SMILES: CCc1ccc(C(=O)O)cc1S(=O)(=O)Nc1cc(-c2cnoc2C)c(Cl)cc1N1CCCCC1]
(306)
-continued
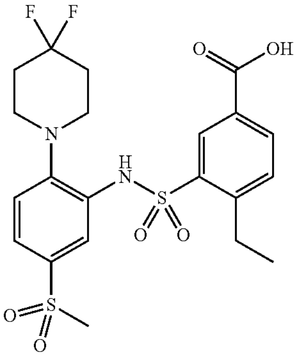 [SMILES: CCc1ccc(C(=O)O)cc1S(=O)(=O)Nc1cc(S(C)(=O)=O)ccc1N1CCC(F)(F)CC1]
(307)
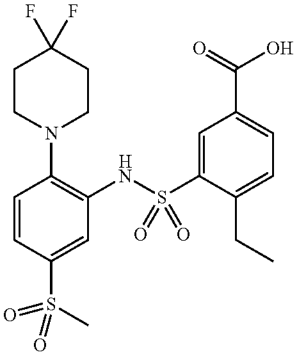 [SMILES: CCc1ccc(C(=O)O)cc1S(=O)(=O)Nc1cc(S(C)(=O)=O)ccc1N1CCC(F)(F)CC1]
(308)
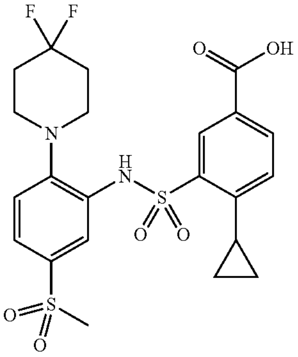 [SMILES: CS(=O)(=O)c1ccc(N2CCC(F)(F)CC2)c(NS(=O)(=O)c2cc(C(=O)O)ccc2C2CC2)c1]
(309)
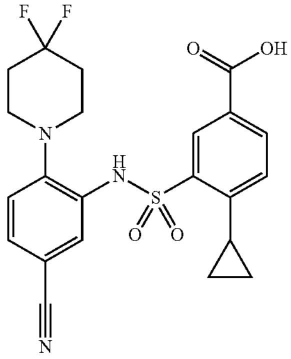 [SMILES: N#Cc1ccc(N2CCC(F)(F)CC2)c(NS(=O)(=O)c2cc(C(=O)O)ccc2C2CC2)c1]
(310)

-continued
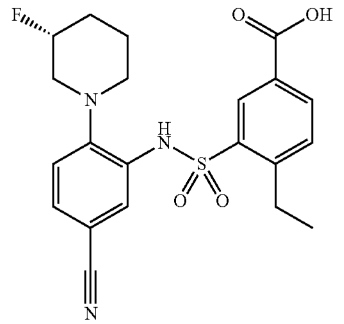 [SMILES: CCc1ccc(C(=O)O)cc1S(=O)(=O)Nc1cc(C#N)ccc1N1CCC[C@@H](F)C1]
(311)
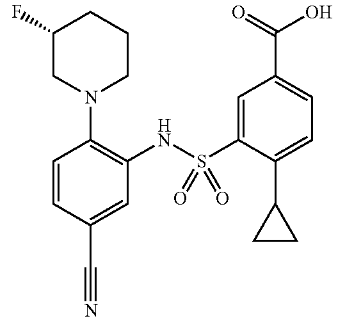 [SMILES: N#Cc1ccc(N2CCC[C@@H](F)C2)c(NS(=O)(=O)c2cc(C(=O)O)ccc2C2CC2)c1]
(312)
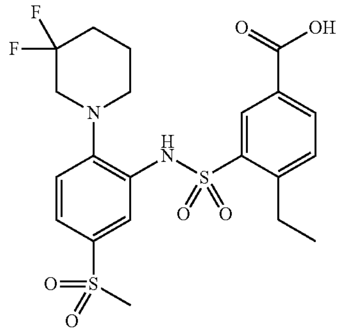 [SMILES: CCc1ccc(C(=O)O)cc1S(=O)(=O)Nc1cc(S(C)(=O)=O)ccc1N1CCCC(F)(F)C1]
(313)
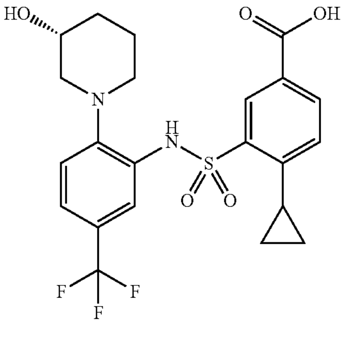 [SMILES: O=C(O)c1ccc(C2CC2)c(S(=O)(=O)Nc2cc(C(F)(F)F)ccc2N2CCC[C@@H](O)C2)c1]
(314)
-continued
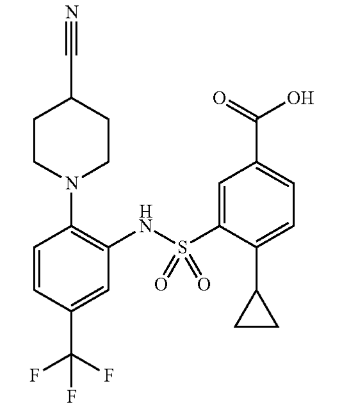
(315)
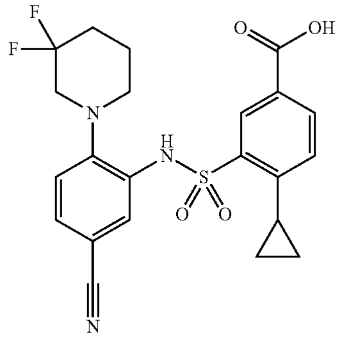 [SMILES: N#Cc1ccc(N2CCCC(F)(F)C2)c(NS(=O)(=O)c2cc(C(=O)O)ccc2C2CC2)c1]
(316)
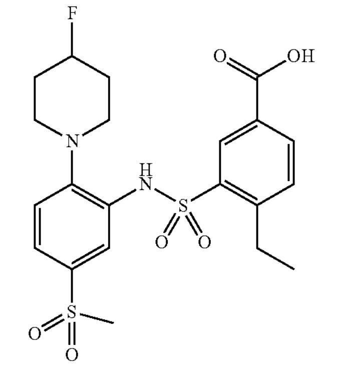 [SMILES: CCc1ccc(C(=O)O)cc1S(=O)(=O)Nc1cc(S(C)(=O)=O)ccc1N1CCC(F)CC1]
(317)
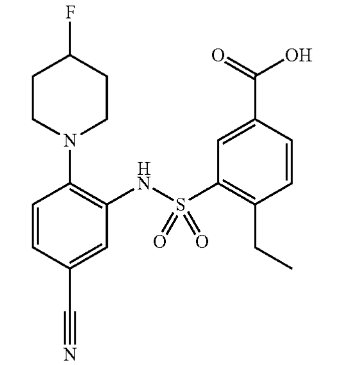 [SMILES: CCc1ccc(C(=O)O)cc1S(=O)(=O)Nc1cc(C#N)ccc1N1CCC(F)CC1]
(318)

-continued
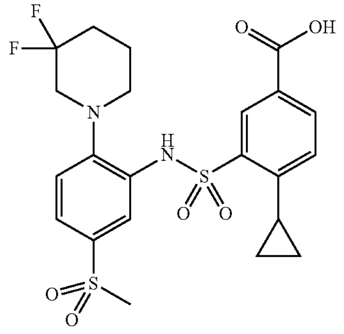 [SMILES: CS(=O)(=O)c1ccc(N2CCCC(F)(F)C2)c(NS(=O)(=O)c2cc(C(=O)O)ccc2C2CC2)c1]
(319)
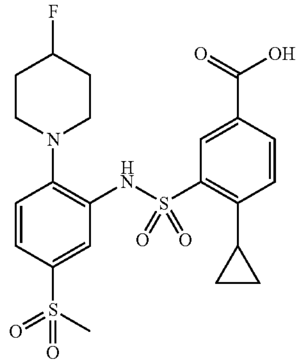 [SMILES: CS(=O)(=O)c1ccc(N2CCC(F)CC2)c(NS(=O)(=O)c2cc(C(=O)O)ccc2C2CC2)c1]
(320)
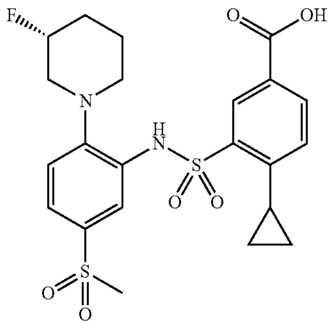 [SMILES: CS(=O)(=O)c1ccc(N2CCC[C@@H](F)C2)c(NS(=O)(=O)c2cc(C(=O)O)ccc2C2CC2)c1]
(321)
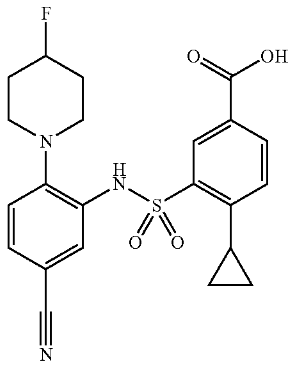 [SMILES: N#Cc1ccc(N2CCC(F)CC2)c(NS(=O)(=O)c2cc(C(=O)O)ccc2C2CC2)c1]
(322)
-continued
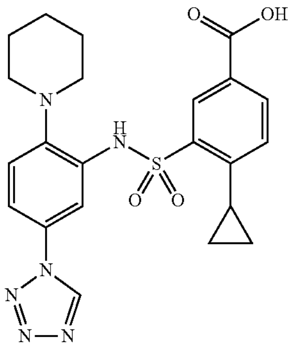 [SMILES: O=C(O)c1ccc(C2CC2)c(S(=O)(=O)Nc2cc(-n3cnnn3)ccc2N2CCCCC2)c1]
(323)
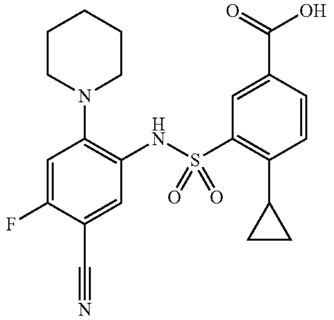 [SMILES: N#Cc1cc(NS(=O)(=O)c2cc(C(=O)O)ccc2C2CC2)c(N2CCCCC2)cc1F]
(324)
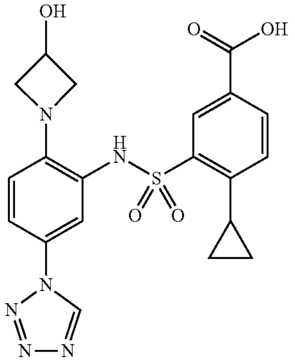 [SMILES: O=C(O)c1ccc(C2CC2)c(S(=O)(=O)Nc2cc(-n3cnnn3)ccc2N2CC(O)C2)c1]
(325)
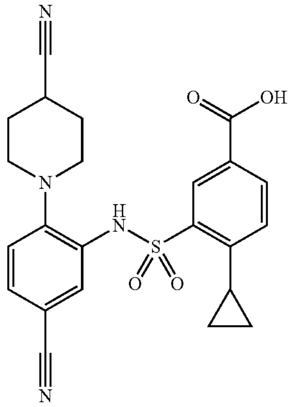 [SMILES: N#Cc1ccc(N2CCC(C#N)CC2)c(NS(=O)(=O)c2cc(C(=O)O)ccc2C2CC2)c1]
(326)

-continued
(327)
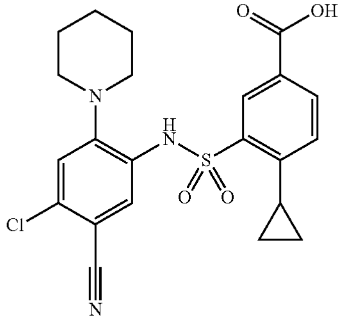 [SMILES: N#Cc1cc(NS(=O)(=O)c2cc(C(=O)O)ccc2C2CC2)c(N2CCCCC2)cc1Cl]
(328)
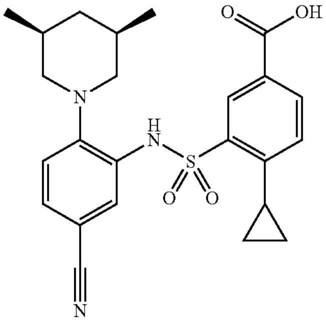 [SMILES: C[C@@H]1C[C@H](C)CN(c2ccc(C#N)cc2NS(=O)(=O)c2cc(C(=O)O)ccc2C2CC2)C1]
(329)
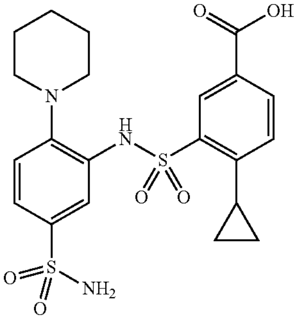 [SMILES: NS(=O)(=O)c1ccc(N2CCCCC2)c(NS(=O)(=O)c2cc(C(=O)O)ccc2C2CC2)c1]
(330)
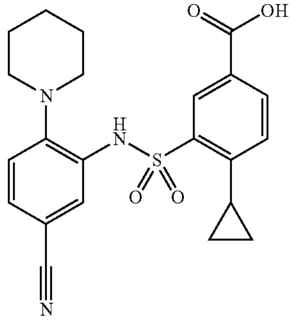 [SMILES: N#Cc1ccc(N2CCCCC2)c(NS(=O)(=O)c2cc(C(=O)O)ccc2C2CC2)c1]
(331)
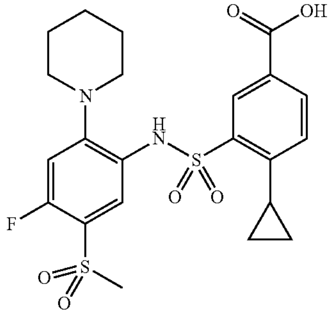 [SMILES: CS(=O)(=O)c1cc(NS(=O)(=O)c2cc(C(=O)O)ccc2C2CC2)c(N2CCCCC2)cc1F]
-continued
(332)
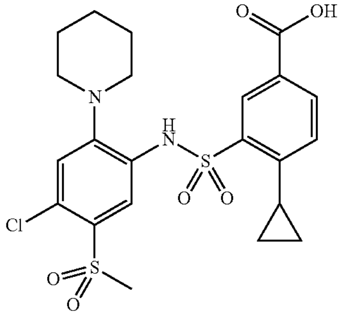 [SMILES: CS(=O)(=O)c1cc(NS(=O)(=O)c2cc(C(=O)O)ccc2C2CC2)c(N2CCCCC2)cc1Cl]
(333)
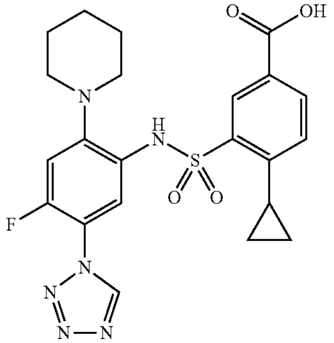 [SMILES: O=C(O)c1ccc(C2CC2)c(S(=O)(=O)Nc2cc(-n3cnnn3)c(F)cc2N2CCCCC2)c1]
(334)
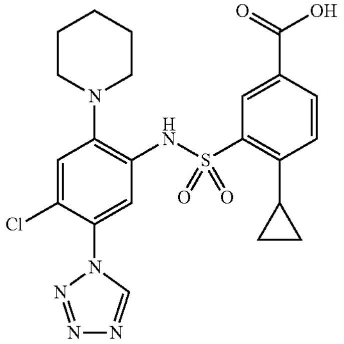 [SMILES: O=C(O)c1ccc(C2CC2)c(S(=O)(=O)Nc2cc(-n3cnnn3)c(Cl)cc2N2CCCCC2)c1]
(335)
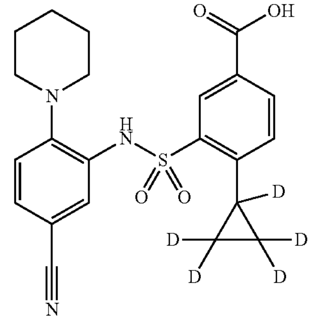 [SMILES: [2H]C1([2H])C([2H])([2H])C1([2H])c1ccc(C(=O)O)cc1S(=O)(=O)Nc1cc(C#N)ccc1N1CCCCC1]

-continued

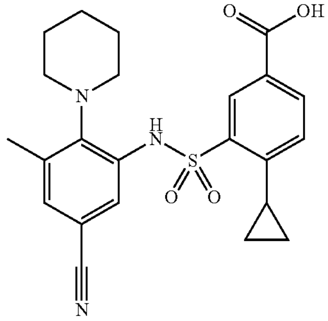 [SMILES: Cc1cc(C#N)cc(NS(=O)(=O)c2cc(C(=O)O)ccc2C2CC2)c1N1CCCCC1]
(336)

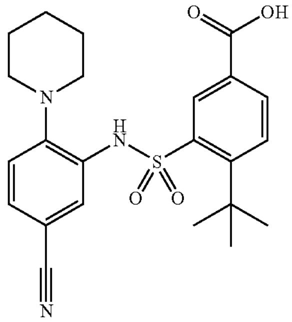 [SMILES: CC(C)(C)c1ccc(C(=O)O)cc1S(=O)(=O)Nc1cc(C#N)ccc1N1CCCCC1]
(337)

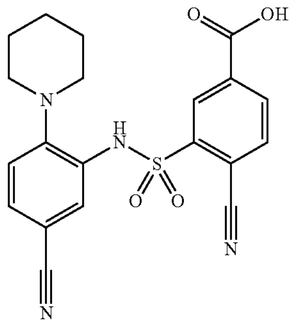 [SMILES: N#Cc1ccc(N2CCCCC2)c(NS(=O)(=O)c2cc(C(=O)O)ccc2C#N)c1]
(338)

and pharmaceutically acceptable salts and hydrates thereof.

A further aspect of the invention relates to a compound of formula (I) as defined above, other than compounds (54), (64), (69), (71), (72), (73), (74), (78) and (165).

Another aspect relates to a compound of formula (I) as defined above, other than compounds (54), (64), (69), (71), (72), (73), (74), (78) and (165) for use as defined above.

Pharmaceutical Compostions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2nd Edition, (1994), Edited by A Wade and PJ Weller. The carrier, or, if more than one be present, each of the carriers, must be acceptable in the sense of being compatible with the other ingredients of the formulation and not deleterious to the recipient.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation Isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound as described herein into conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3rd edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those compounds, and mixtures thereof. The terms used in the claims encompass these forms, provided said forms retain the appropriate functional activity (though not necessarily to the same degree).

The present invention also includes all suitable isotopic variations of the compound or a pharmaceutically acceptable salt thereof. An isotopic variation of a compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-$^{14}$, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Atropisomers

Some of the compounds of the invention may exist as atropisomers. Atropisomers are stereoisomers arising because of hindered rotation about a single bond, where energy differences due to steric strain or other contributors create a barrier to rotation that is high enough to allow for isolation of individual conformers. The invention encompasses all such atropisomers.

Prodrugs

The invention further includes the compounds of the present invention in prodrug form, i.e. covalently bonded compounds which release the active parent drug in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an) hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The dosage amount will further be modified according to the mode of administration of the compound. For example, to achieve an "effective amount" for acute therapy, parenteral administration of a compound is typically preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to modulate ERAP1. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more additional active agents, for example, existing drugs available on the market. A further aspect of the invention therefore relates to a combination comprising a compound as described herein and one or more additional active agents. In one preferred embodiment, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

In one preferred embodiment, the additional active agent is an immunotherapy agent, more preferably a cancer immunotherapy agent. An "immunotherapy agent" refers to a treatment that uses the subject's own immune system to fight diseases such as cancer.

In one preferred embodiment the compound of the invention inhibits the activity of ERAP1, and the compound is administered in combination with an immunotherapy.

The compound may increase the sensitivity of cancer cells to an immunotherapy. The immunotherapy may be mediated by T cells. In one embodiment the compound may increase the number of $CD8^+$ T cells in a tumour.

In one embodiment the compound may be used to treat cancers which are weakly responsive or not responsive to immunotherapies.

In one preferred embodiment, the additional active agent is a molecule capable of immune checkpoint intervention, a co-stimulatory antibody, a chemotherapy agent, a radiotherapy agent, a targeted therapy agent or an antibody, particularly a monoclonal antibody.

In one preferred embodiment the additional active agent is a molecule capable of immune checkpoint intervention.

Immune checkpoint molecules include CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4, B7.1, B7.2, ILT-2, ILT-4, TIGIT, HHLA2, IDO, CD39, CD73, A2aR and butyrophilins.

Immune checkpoint molecules include both inhibitory and activatory molecules, and interventions may apply to either or both types of molecule.

Immune checkpoint inhibitors include, but are not limited to, PD-1 inhibitors, PD-L1 inhibitors, LAG-3 inhibitors, TIM-3 inhibitors, TIGIT inhibitors, BTLA inhibitors and CTLA-4 inhibitors, for example. Co-stimulatory antibodies deliver positive signals through immune-regulatory receptors including but not limited to ICOS, CD137, CD27 OX-40 and GITR.

In one highly preferred embodiment, the the additional active agent is an antibody checkpoint inhibitor. Suitable examples of antibody checkpoint inhibitors, include, but are not limited to, anti-PD-1 antibodies, anti-PD-L1 antibodies and anti-CTLA4 antibodies.

In one preferred embodiment, the antibody checkpoint inhibitor is an anti-PD-1 antibody, more preferably selected from pembrolizumab, cemiplimab and nivolumab.

In one preferred embodiment, the antibody checkpoint inhibitor is an anti-PD-L1 antibody, more preferably selected from atezolizumab, avelumab and durvalumab.

In one preferred embodiment, the antibody checkpoint inhibitor is an anti-CTLA4 antibody, more preferably selected from ipilimumab and tremelimumab.

In one preferred embodiment the immunotherapy is an anti-cancer vaccine or virus, such as an oncolytic virus.

In one preferred embodiment the immunotherapy is a cell-based therapy. In one embodiment the cell-based therapy may be a T cell therapy, such as adoptive T cell therapy, or therapy with CAR-T cells.

Adoptive cell-based immunotherapy may include the following: Irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, for example expressing cytokines such as GM-CSF, and/or to express tumor-associated antigen (TAA) antigens, such as Mage-1, gp-100, patient-specific neoantigen vaccines, and the like.

In a further embodiment, the immunotherapy may comprise non-cell-based immunotherapies. In one embodiment, compositions comprising antigens with or without vaccine-enhancing adjuvants may be used. Such compositions exist in many well-known forms, such as peptide compositions, oncolytic viruses, and recombinant antigen comprising fusion proteins.

In an alternative embodiment, immunomodulatory interleukins, such as IL-2, IL-6, IL-7, IL-12, IL-17, IL-23, as well as modulators thereof (e.g., blocking antibodies or more potent or longer lasting forms) may be used. Immunomodulatory cytokines, such as interferons, G-CSF, imiquimod, T F alpha, and the like, as well as modulators thereof (e.g., blocking antibodies or more potent or longer lasting forms) may also be used. In another embodiment, immunomodulatory chemokines, such as CCL3, CCL26, and CXCL7, and the like, as well as modulators thereof (e.g., blocking antibodies or more potent or longer lasting forms) may be used. In a further embodiment, immunomodulatory molecules targeting immunosuppression, such as STAT3 signaling modulators, FkappaB signaling modulators, and immune checkpoint modulators, may be used.

In another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (Cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an EVIPDH inhibitor, mycophenolic acid, myriocin, fingolimod, an NF-xB inhibitor, raloxifene, drotrecogin alfa, denosumab, an F-xB signaling cascade inhibitor, disulfiram, olmesartan, dithiocarbamate, a proteasome inhibitor, bortezomib, MG132, Prol, PI-0052, curcumin, genistein, resveratrol, parthenolide, thalidomide, lenalidomide, flavopiridol, non-steroidal anti-inflammatory drugs (NSAIDs), arsenic tri oxide, dehydroxymethylepoxyquinomycin (DHMEQ), 13C (indole-3-carbinol)/DIM (di-indolmethane) (13C/DIM), Bay 1 1-7082, luteolin, cell permeable peptide SN-50, IKBa-super repressor overexpression, FKB decoy oligodeoxynucleotide (ODN), or a derivative or analog of any thereto, may be used.

In yet another embodiment, immunomodulatory antibodies or protein may be used. For example, antibodies that bind to CD40, Toll-like receptor (TLR), OX40, GITR, CD27, or to 4-IBB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CDI I a antibody, efalizumab, an anti-CD 18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BlyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-α4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab.

In one embodiment, the subject may be undergoing or have previously undergone treatment with a chemotherapeutic agent. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. Vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-a, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

The present invention is further described by way of the following non-limiting examples, and with reference to the following figures wherein:

FIG. 1 shows the cellular effect of representative compounds 1 and 242 according to the invention on antigen presentation as measured by assessing their effect on the presentation of an ovalbumin-specific peptide (SIINFEKL). More specifically, FIG. 1 shows representative $IC_{50}$ curve for exemplar compounds according to the invention. Data was normalized to the signal obtained in the absence of compound (high) and absence of antigen (low) and presented as the mean±STD (n=2).

Figure 2:
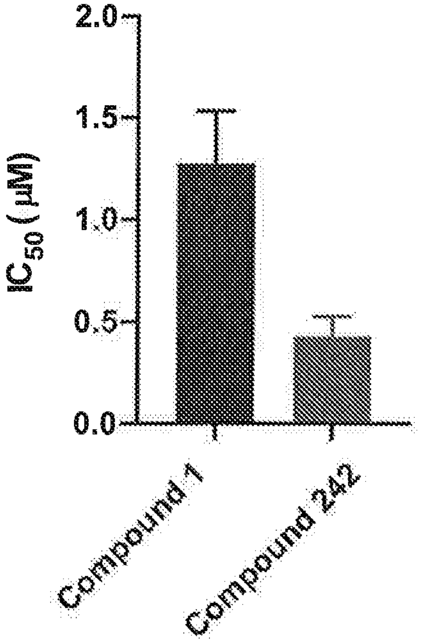

FIG. 2 shows a summary of the $IC_{50}$ data generated for exemplar compounds 1 and 242 according to the invention, as determined by the above OVA antigen presentation assay. The data is presented as the mean±SEM (n=6).

Figure 3:
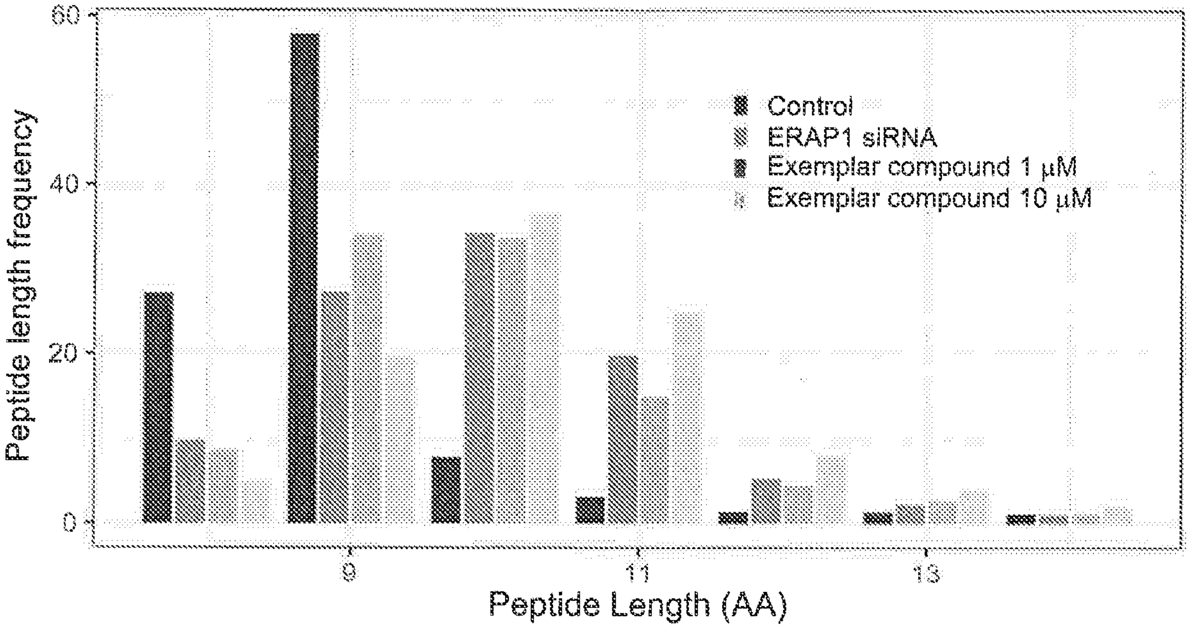

FIG. 3 shows the effect of compound 1 according to the invention on global antigen processing as determined using an unbiased proteomics pipeline. More specifically, FIG. 3 shows the effects of ERAP1 siRNA and compound inhibition (at 1 and 10 μM) compared to a control on the immunopeptidome of SiHa cells as measured by the effect on the total proportion of 8, 9, 10, 11, 12 and 13 amino acid peptides.

EXAMPLES

Where the preparation of starting materials is not described, these are commercially available, known in the literature, or readily obtainable by those skilled in the art using standard procedures. Where it is indicated that compounds were prepared analogously to earlier examples or intermediates, it will be appreciated by the skilled person that the reaction time, number of equivalents of reagents, solvent, concentration and temperature can be modified for each specific reaction and that it may be necessary or desirable to employ different work-up or purification techniques.

General Schemes

Abbreviations

A list of some common abbreviations is shown below—where other abbreviations are used which are not listed, these will be understood by the person skilled in the art.

Aq: aqueous; br: broad; ca.: circa; d: doublet; DCM: dichloromethane; dioxane: 1,4-dioxane; DMAP: 4-dimethylaminopyridine; DMF: dimethylformamide; EDC: 1-ethyl-3-(3-dimethylaminopropyl) carbodiimide hydrochloride; $Et_3N$: triethylamine; EtOAc: ethyl acetate; EtOH: ethanol; h: hours; HPLC: high performance liquid chromatography; IPA, isopropanol; LC: liquid chromatography; m: multiplet; M: molar, molecular ion; MeCN: actetonitrile; MeOH: methanol; min: minutes; MS: mass spectrometry; NMR: nuclear magnetic resonance; PDA: photodiode array; q: quartet; RT: room temperature (ca. 20° C.); RT: retention time; s: singlet, solid; t: triplet; TBME: tert-butyl methyl ether; TFA: trifluoroacetic acid; THF: tetrahydrofuran; UPLC: ultra performance liquid chromatography; UV: ultraviolet; quant.: quantitative; SEM: [2-(trimethylsilyl) ethoxy] methyl acetal; dppf: 1,1'-ferrocenediyl-bis(diphenylphosphine); NBS: n-bromosuccinimide; XantPhos-Pd-G3: [(4,5-Bis(diphenylphosphino)-9,9-dimethylxanthene)-2-(2'-amino-1,1'-biphenyl)]palladium (II) methanesulfonate (CAS: 1445085-97-1); Xphos Pd G3: (2-Dicyclohexylphosphino-2',4',6'-triisopropyl-1, 1'-biphenyl) [2-(2'-amino-1,1'-biphenyl)]palladium (II) methanesulfonate (CAS: 1445085-55-1); Pd-174: allyl(2-di-tert-butylphosphino-2',4',6'-triisopropyl-1,1'-biphenyl) palladium (II) triflate (CAS: 1798782-25-8); TBAF: tetra-n-butylammonium fluoride.

Other abbreviations are intended to convey their generally accepted meaning.

Scheme 1

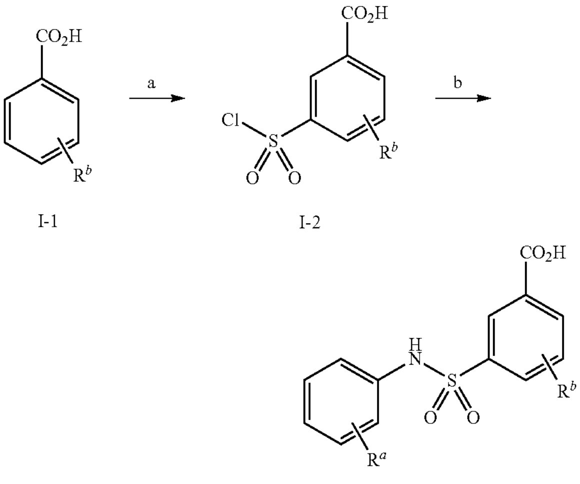

I-1 I-2 I-3 wherein $R^a$=$R_6$, $R_7$, $R_8$, $R_9$, $NR_{10}R_{11}$ and $R^b$=$R_1$, $R_3$, $R_4$, $R_5$ of formulae (I)

Reagents: (a) $ClSO_3H$, 100° C.; (b) Amine, pyridine, DCM, RT Chlorosulfonylation of I-1 using chlorosulfonic acid provided sulfonyl chloride I-2. This was reacted with the appropriate amine in the presence of pyridine to afford sulfonamide I-3.

Scheme 2

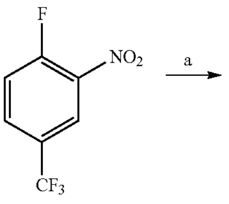

I-4

-continued

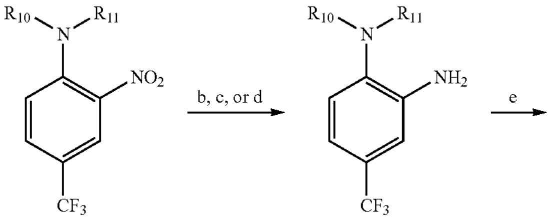

I-5

I-6

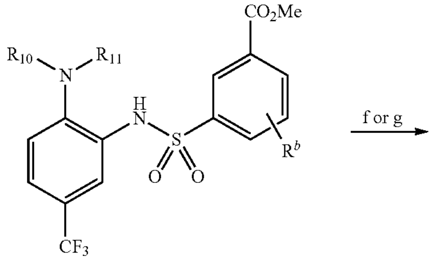

I-7

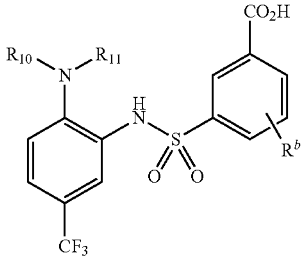

I-8 wherein $R^b$=$R_1$, $R_3$, $R_4$, $R_5$ of formulae (I)

Reagents: (a) Amine, DCM; (b) $H_2$, 10% Pd/C, EtOH; (c) Fe, $NH_4Cl$, IPA, water; (d) $NH_4OH$ (aq), $Na_2S_2O_4$, THF, $H_2O$, RT; I sulfonyl chloride, pyridine, DCM, RT; (f) LiOH (aq), THF, MeOH; (g) LiOH (aq), dioxane.

Fluoro-2-nitro-4-(trifluoromethyl)benzene (1-4) was reacted with the appropriate amine in a nucleophilic substitution reaction, followed by reduction of the resultant nitro-compound I-5 to aniline 1-6. This was reacted with the appropriate sulfonyl chloride to afford sulfonamide I-7. Ester hydrolysis provided the corresponding carboxylic acid I-8.

Scheme 3

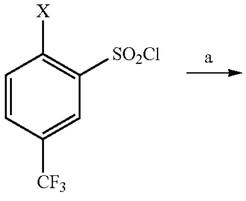

X = Br, F

I-9

-continued

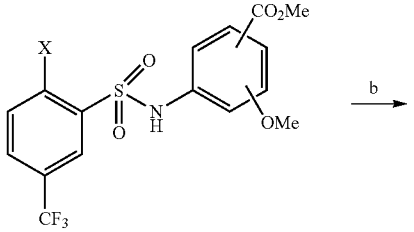

I-10

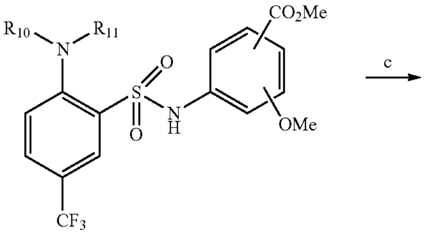

I-11

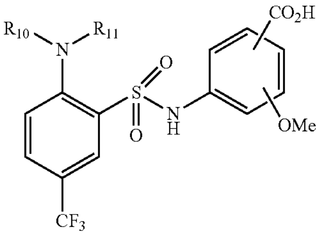

I-12

Reagents: (a) Aniline, pyridine, DCM, RT; (b) amine, THF, 60° C.; (c) LiOH(aq), THF, 50° C. Sulfonyl chloride 1-9 was reacted with the appropriate aniline to provide sulfonamide I-10. Nucleophilic substitution with the appropriate amine gave I-11, which was hydrolysed to provide the corresponding carboxylic acid I-12.

Scheme 4

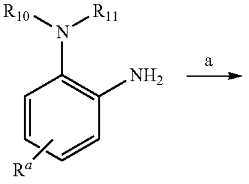

I-13

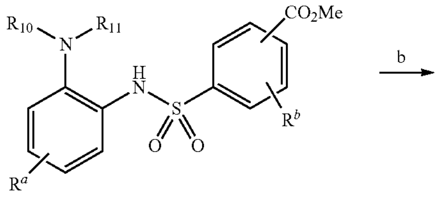

I-14

-continued

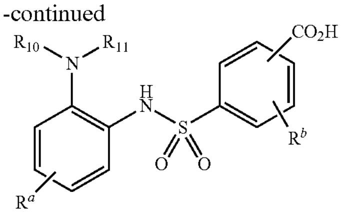

I-15 wherein $R^a$=$R_6$, $R_7$, $R_8$, $R_9$ and $R^b$=$R_1$, $R_2$, $R_3$, $R_4$, $R_5$ of formulae (I)

Reagents: (a) Sulfonyl chloride, pyridine, DCM, RT; (b) LiOH(aq), dioxane or THF, RT. Sulfonamide I-14 was prepared by the reaction of aniline I-13 with the appropriate sulfonyl chloride. Ester hydrolysis afforded the corresponding carboxylic acid I-15.

Scheme 5

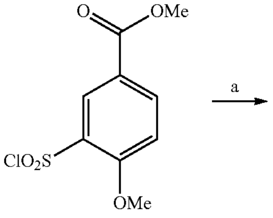

1-16

-continued

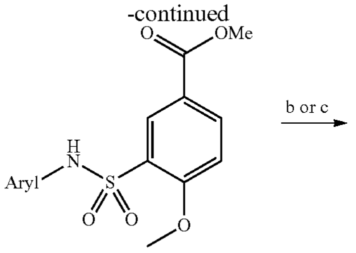

1-17

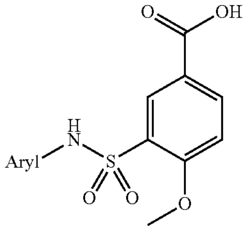

1-18

Reagents: (a) Aniline, pyridine, DCM, RT; (b) NaOH (aq), MeOH, $H_2O$, RT; (c) LiOH(aq), THF, RT.

Sulfonamide I-17 was prepared by the reaction of sulfonyl chloride I-16 with the appropriate aniline. Ester hydrolysis provided the corresponding carboxylic acid I-18.

Scheme 6

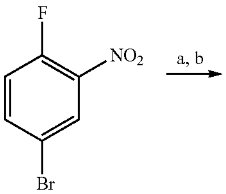

I-19

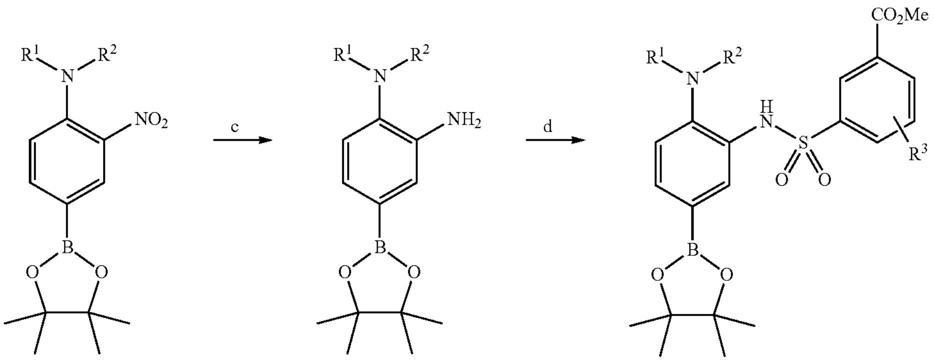

I-20 I-21 I-22

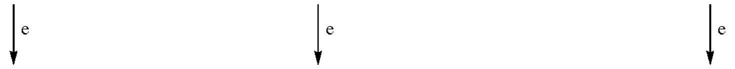

-continued

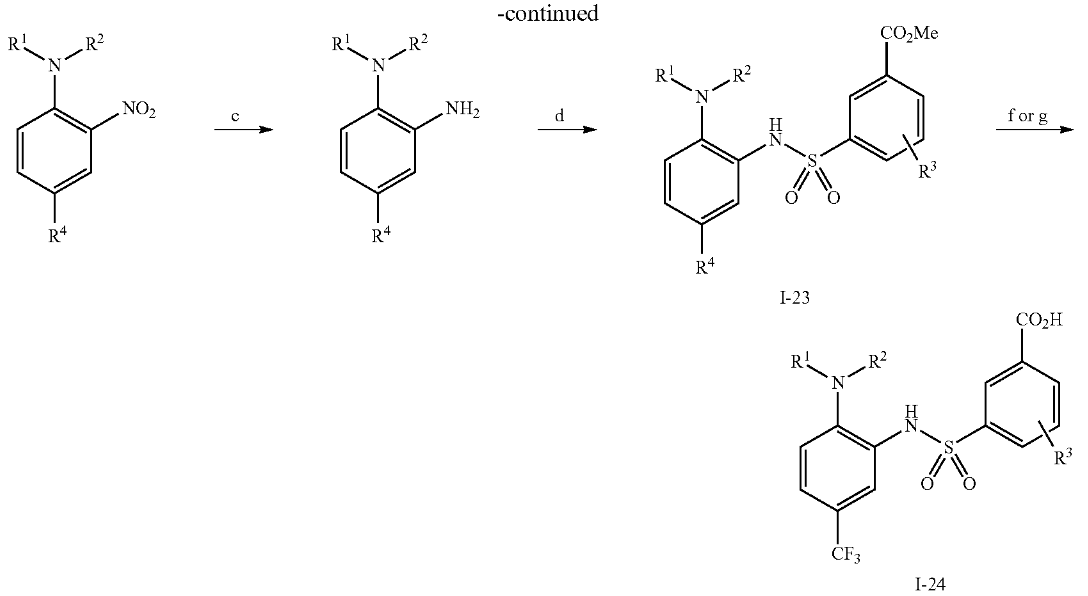

I-23

I-24

Reagents: (a) Amine, MeCN; (b) Bis(pinacolato)diboron, $PdCl_2$(dppf)·DCM, KOAc, dioxane; (c) H2, Pd/C, MeOH; (d) sulfonyl chloride, pyridine, DCM, RT; I Aryl halide, Xphos Pd G3, $K_3PO_4$, dioxane, water; (f) LiOH(aq), THF, MeOH; (g) HCl, dioxane.

4-Bromo-1-fluoro-2-nitrobenzene (I-19) was reacted with the appropriate amine in a nucleophilic substitution reaction, followed by conversion of the resultant aryl bromide to boronate ester I-20. The nitro group was then reduced to afford the corresponding aniline I-21. This was reacted with the appropriate sulfonyl chloride to afford sulfonamide I-22. The remaining substituent was introduced by Suzuki coupling prior to ester hydrolysis to provide the corresponding carboxylic acid I-24. Alternatively, the steps may be carried out in an alternative sequence as indicated.

General Experimental Conditions

All starting materials and solvents were obtained either from commercial sources or prepared according to the literature citation. Reaction mixtures were magnetically stirred and reactions performed at room temperature (ca. 20° C.) unless otherwise indicated. Column chromatography was performed on an automated flash chromatography system, such as a CombiFlash Rf system, using pre-packed silica (40 μm) cartridges, unless otherwise indicated. $^1$H NMR spectra were recorded using a Bruker Avance III HD spectrometer at 500 MHz, equipped with a Bruker 5 mm SmartProbe™. Chemical shifts are expressed in parts per million using either the central peaks of the residual protic solvent or an internal standard of tetramethylsilane as references. The spectra were recorded at 298 K unless otherwise indicated. Analytical UPLC-MS experiments to determine retention times and associated mass ions were performed using a Waters ACQUITY UPLC® H-Class system, equipped with ACQUITY PDA Detector and ACQUITY Qda Mass Detector, running one of the analytical methods described below. Analytical LC-MS experiments to determine retention times and associated mass ions were performed using an Agilent 1200 series HPLC system coupled to an Agilent 1956, 6100 or 6120 series single quadrupole mass spectrometer running one of the analytical methods described below. Preparative HPLC purifications were performed either using a Waters X-Select CSH C18, 5 μm, 19×50 mm column using a gradient of MeCN and water, both modified with 0.1% v/v formic acid, or on a Waters X-Bridge BEH C18, 5 μm, 19×50 mm column using a gradient of MeCN and 10 mM ammonium bicarbonate (aq). Fractions were collected following detection by UV at a single wavelength measured by a variable wavelength detector. Nomenclature of structures was generated using 'Structure to Name' conversion from ChemDraw® Professional 17 (PerkinElmer).

Analytical Methods

Method 1—Acidic 3 Min Method

Column: Waters ACQUITY UPLC® CSH C18, 1.7 μm, 2.1×30 mm at 40° C.

Detection: UV at 254 nm unless otherwise indicated, MS by electrospray ionisation Solvents: A: 0.1% v/v Formic acid in water, B: 0.1% v/v Formic acid in MeCN Gradient:

| Time | % A | % B | Flow rate (ml/min) |
|---|---|---|---|
| 0.00 | 95 | 5 | 0.77 |
| 0.11 | 95 | 5 | 0.77 |
| 2.15 | 5 | 95 | 0.77 |
| 2.56 | 5 | 95 | 0.77 |
| 2.83 | 95 | 5 | 0.77 |
| 3.00 | 95 | 5 | 0.77 |

Method 2—Basic 3 Min Method

Column: Waters ACQUITY UPLC® BEH C18, 1.7 μm, 2.1×30 mm at 40° C.

Solvents: A: 10 mM ammonium bicarbonate (aq), B: MeCN (other parameters the same as Method 1)

Method 3—Acidic 4 Min Method

Column: Waters X-Select CSH C18, 2.5 μm, 4.6×30 mm at 40° C.

Detection: UV at 254 nm unless otherwise indicated, MS by electrospray ionisation Solvents: A: 0.1% v/v Formic acid in water, B: 0.1% v/v Formic acid in MeCN Gradient:

| Time | % A | % B | Flow rate (ml/min) |
|---|---|---|---|
| 0.0 | 95.0 | 5.0 | 2.5 |
| 3.0 | 5.0 | 95.0 | 2.5 |
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 4—Basic 4 Min Method

Column: Waters X-Bridge BEH C18, 2.5 μm, 4.6×30 mm at 40° C.

Solvents: A: 10 mM ammonium bicarbonate (aq), B: MeCN (other parameters the same as Method 3)

Example 1:4-Ethyl-3-(N-(2-(piperidin-1-yl)-5-(trifluoromethyl)phenyl)sulfamoyl)benzoic acid

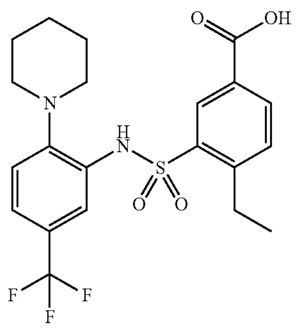 [SMILES: CCc1ccc(C(=O)O)cc1S(=O)(=O)Nc1cc(C(F)(F)F)ccc1N1CCCCC1]

Step 1: 3-(chlorosulfonyl)-4-ethylbenzoic acid: 4-ethylbenzoic acid (1 g, 6.66 mmol) in chlorosulfonic acid (10 ml, 149 mmol) was heated at 100° C. overnight. The mixture was cooled and carefully added to stirred ice. The resultant precipitate was collected by filtration to afford the title compound (1.58 g, 6.04 mmol, 91% yield, 95% purity) as a white solid. $^{1}H$ NMR (500 MHz, DMSO-$d_6$) δ 8.34 (d, J=1.9 Hz, 1H), 7.82 (dd, J=7.9, 2.0 Hz, 1H), 7.32 (d, J=7.9 Hz, 1H), 3.08 (q, J=7.5 Hz, 2H), 1.19 (t, J=7.5 Hz, 3H). One exchangeable proton not observed.

Step 2: 4-Ethyl-3-(N-(2-(piperidin-1-yl)-5-(trifluoromethyl)phenyl)sulfamoyl)benzoic acid: A solution of 2-(piperidin-1-yl)-5-(trifluoromethyl)aniline (0.200 g, 0.819 mmol) in pyridine (3 ml, 37.1 mmol) was treated with the product from step 1 above (0.244 g, 0.983 mmol) and the solution was stirred at RT for 24 h. The solvent was removed in vacuo and the crude product was purified by chromatography on silica gel (24 g cartridge, 0-100% EtOAc/isohexanes followed by 0-50% EtOAc/DCM) to afford the title compound (36.3 mg, 0.076 mmol, 9.23% yield, 97% purity) as a tan solid. UPLC-MS (Method 1) m/z 457.4 $(M+H)^+$, 455.2 $(M-H)^-$ at 1.87 min. $^{1}H$ NMR (500 MHz, DMSO-$d_6$) δ 13.28 (bs, 1H), 9.44 (bs, 1H), 8.36 (d, J=1.8 Hz, 1H), 8.09 (dd, J=8.0, 1.8 Hz, 1H), 7.60 (d, J=8.0 Hz, 1H), 7.42 (dd, J=8.4, 2.2 Hz, 1H), 7.29 (d, J=2.1 Hz, 1H), 7.25 (d, J=8.4 Hz, 1H), 3.04 (q, J=7.4 Hz, 2H), 2.72 (t, J=4.9 Hz, 4H), 1.57 (p, J=5.0 Hz, 4H), 1.50-1.45 (m, 2H), 1.21 (t, J=7.4 Hz, 3H).

Example 3:4-isopropyl-3-(N-(2-(piperidin-1-yl)-5-(trifluoromethyl)phenyl) sulfamoyl)benzoic acid

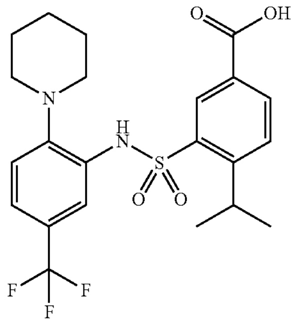 [SMILES: CC(C)c1ccc(C(=O)O)cc1S(=O)(=O)Nc1cc(C(F)(F)F)ccc1N1CCCCC1]

Step 1: 3-(chlorosulfonyl)-4-isopropylbenzoic acid: 4-isopropylbenzoic acid (1 g, 6.09 mmol) in chlorosulfonic acid (5 ml, 74.7 mmol) was heated at 100° C. overnight. The mixture was cooled and carefully added to stirred ice. The resultant precipitate was collected by filtration and dried under vacuum to give the title compound (1.28 g, 4.63 mmol, 76% yield, 95% purity) as a tan solid. $^{1}H$ NMR (500 MHz, DMSO-$d_6$) δ 12.50 (bs, 1H), 8.36 (d, J=1.9 Hz, 1H), 7.83 (dd, J=8.1, 1.9 Hz, 1H), 7.44 (d, J=8.1 Hz, 1H), 4.20 (septet, J=6.8 Hz, 1H), 1.16 (d, J=6.9 Hz, 6H).

Step 2: 4-isopropyl-3-(N-(2-(piperidin-1-yl)-5-(trifluoromethyl)phenyl)sulfamoyl)benzoic acid: A solution of 2-(piperidin-1-yl)-5-(trifluoromethyl)aniline (0.070 g, 0.287 mmol) in DCM (1 ml) and pyridine (0.139 ml, 1.720 mmol) were added to a solution of the product from step 1 above (0.090 g, 0.344 mmol) in DCM (1 ml) and the solution was stirred at RT for 16 h. The solvent was removed in vacuo and the residue purified by chromatography on silica gel (24 g cartridge, 0-50% EtOAc/DCM) to afford the title compound (14.3 mg, 0.029 mmol, 10% yield, 95% purity) as a light tan solid. UPLC-MS (Method 1) m/z 471.4 $(M+H)^+$, 469.3 $(M-H)^-$ at 1.93 min. $^{1}H$ NMR (500 MHz, DMSO-$d_6$) δ 13.29 (bs, 1H), 9.40 (bs, 1H), 8.45 (d, J=1.9 Hz, 1H), 8.13 (dd, J=8.3, 1.9 Hz, 1H), 7.76 (d, J=8.2 Hz, 1H), 7.42 (dd, J=8.2, 1.9 Hz, 1H), 7.27 (d, J=8.3 Hz, 1H), 7.19 (d, J=1.9 Hz, 1H), 3.86 (septet, J=6.8 Hz, 1H), 2.78 (t, J=5.2 Hz, 4H), 1.58 (p, J=5.5 Hz, 4H), 1.51-1.45 (m, 2H), 1.24-1.10 (m, 6H).

Example 4: 3-(N-(2-(piperidin-1-yl)-5-(trifluoromethyl)phenyl)sulfamoyl)-4-(trifluoromethoxy)benzoic acid

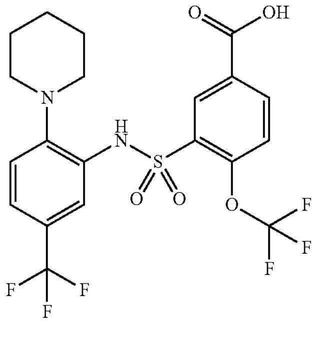 [SMILES: O=C(O)c1ccc(OC(F)(F)F)c(S(=O)(=O)Nc2cc(C(F)(F)F)ccc2N2CCCCC2)c1]

Step 1: 3-(chlorosulfonyl)-4-(trifluoromethoxy)benzoic acid: 4-(trifluoromethoxy)benzoic acid (1 g, 4.85 mmol) in chlorosulfonic acid (5 ml, 74.7 mmol) was heated at 100° C. overnight. The mixture was cooled and carefully added to stirred ice. The resultant precipitate was collected by filtration and dried under vacuum to give the title compound (0.770 g, 2.28 mmol, 46.9% yield, 90% purity) as a cream solid. $^1$H NMR (500 MHz, DMSO-$d_6$) δ 12.50 (bs, 1H), 8.40 (d, J=2.2 Hz, 1H), 8.00 (dd, J=8.5, 2.2 Hz, 1H), 7.41 (dq, J=8.5, 1.8 Hz, 1H).

Step 2: 3-(N-(2-(piperidin-1-yl)-5-(trifluoromethyl)phenyl)sulfamoyl)-4-(trifluoromethoxy)benzoic acid: A solution of 2-(piperidin-1-yl)-5-(trifluoromethyl)aniline (0.070 g, 0.287 mmol) in DCM (1 ml) and pyridine (0.139 ml, 1.72 mmol) were added to a solution of the product from step 1 above (0.105 g, 0.344 mmol) in DCM (1 ml) and the solution was stirred at RT for 16 h. The solvent was removed in vacuo and the residue purified by chromatography on silica gel (24 g cartridge, 0-50% EtOAc/DCM) to afford the title compound (5.6 mg, 10.4 μmol, 3.6% yield, 95% purity) as a cream solid. UPLC-MS (Method 1) m/z 513.3 (M+H)$^+$, 511.1 (M−H)$^-$ at 1.94 min. $^1$H NMR (500 MHz, DMSO-$d_6$) δ 13.68 (bs, 1H), 9.50 (bs, 1H), 8.45 (d, J=1.7 Hz, 1H), 8.27 (dd, J=8.2, 1.5 Hz, 1H), 7.68 (d, J=8.7 Hz, 1H), 7.46-7.44 (m, 2H), 7.27 (d, J=8.2 Hz, 1H), 2.71 (t, J=5.0 Hz, 4H), 1.62-1.34 (m, 6H).

Example 6:3-(N-(2-(cis-3,5-dimethylpiperidin-1-yl)-5-(trifluoromethyl)phenyl)sulfamoyl)-4-methoxybenzoic acid

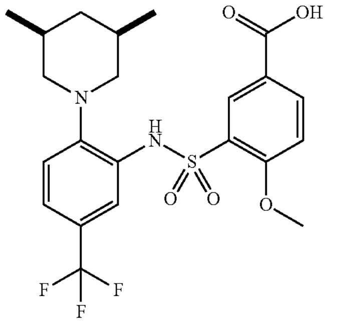

Step 1: cis-3,5-dimethyl-1-(2-nitro-4-(trifluoromethyl)phenyl)piperidine: $Et_3N$ (0.5 ml, 3.59 mmol) was added to a solution of 1-fluoro-2-nitro-4-(trifluoromethyl)benzene (201 μl, 1.44 mmol) and cis-3,5-dimethylpiperidine (211 mg, 1.87 mmol) in DCM (6 ml) and the resultant solution was stirred at RT for 20 h. The crude product was purified by chromatography on silica gel (12 g cartridge, 0-100% EtOAc in isohexanes then 0-10% MeOH/DCM) to afford the title compound (356 mg, 1.12 mmol, 78% yield, 95% purity) as a light orange solid. UPLC-MS (Method 1) m/z 303.4 (M+H)$^+$ at 2.01 min.

Step 2: 2-(cis-3,5-dimethylpiperidin-1-yl)-5-(trifluoromethyl)aniline: The product from Step 1 above (150 mg, 0.496 mmol) was dissolved in EtOH (9.9 ml) and the reaction mixture was hydrogenated in a ThalesNano H-cube® flow reactor (10% Pd/C, 30×4 mm cartridge, full hydrogen mode, 40° C., 1 ml/min flow rate, 2 passes). The reaction mixture was concentrated in vacuo and azeotroped with MeOH (6 ml) to afford the title compound (133 mg, 0.479 mmol, 96% yield, 98% purity) as a pale brown oil. UPLC-MS (Method 2) m/z 273.3 (M+H)$^+$, 271.1 (M−H)$^-$ at 2.00 min.

Step 3: methyl 3-(N-(2-(cis-3,5-dimethylpiperidin-1-yl)-5-(trifluoromethyl)phenyl)sulfamoyl)-4-methoxybenzoate: The product from Step 2 above (51.4 mg, 0.189 mmol) was dissolved in a mixture of DCM (1 ml) and pyridine (50 μl, 0.618 mmol) and treated with a solution of methyl 3-(chlorosulfonyl)-4-methoxybenzoate (60 mg, 0.227 mmol) in DCM (1 ml). The resultant solution was stirred at RT for 3 days. The reaction mixture was loaded directly and purified by chromatography on silica gel (12 g cartridge, 0-100% EtOAc/isohexanes) to afford the title compound (63 mg, 0.120 mmol, 63.3% yield, 95% purity) as a cream solid. UPLC-MS (Method 1) m/z 501.4 (M+H)$^+$, 498.9 (M−H)$^-$ at 2.05 min.

Step 4: 3-(N-(2-(cis-3,5-dimethylpiperidin-1-yl)-5-(trifluoromethyl)phenyl)sulfamoyl)-4-methoxybenzoic acid: The product from Step 3 above (61 mg, 0.122 mmol) was dissolved in THF (2 ml) and treated with 1.1 M LiOH(aq) (443 μl, 0.487 mmol). MeOH was added dropwise until a clear solution formed. The reaction mixture was heated at 40° C. for 24 h, then cooled to RT overnight. The reaction mixture was diluted with water (3 ml), concentrated in vacuo and the resultant aqueous solution diluted with water (5 ml). 1 M HCl(aq) was added dropwise to ca. pH 6. The resultant white precipitate was collected by filtration, washing with water. The solid was suspended in MeCN (4 ml), concentrated in vacuo and dried at 45° C. to afford the title compound (55 mg, 0.113 mmol, 88% yield, 95% purity) as a pale yellow solid. UPLC-MS (Method 1) m/z 487.4 (M+H)$^+$, 485.2 (M−H)$^-$ at 1.89 min. $^1$H NMR (500 MHz, DMSO-$d_6$) δ 13.16 (s, 1H), 8.82 (s, 1H), 8.34 (d, J=2.3 Hz, 1H), 8.15 (dd, J=8.7, 2.3 Hz, 1H), 7.47 (d, J=2.1 Hz, 1H), 7.36 (dd, J=8.5, 2.1 Hz, 1H), 7.30 (d, J=8.7 Hz, 1H), 7.29 (d, J=8.5 Hz, 1H), 3.84 (s, 3H), 2.89-2.80 (m, 2H), 2.14 (t, J=11.0 Hz, 2H), 1.82-1.65 (m, 3H), 0.81 (d, J=6.4 Hz, 6H), 0.67-0.59 (m, 1H).

Example 7: 3-(N-(2-(8-oxa-3-azabicyclo[3.2.1]octan-3-yl)-5-(trifluoromethyl)phenyl) sulfamoyl)-4-methoxybenzoic acid

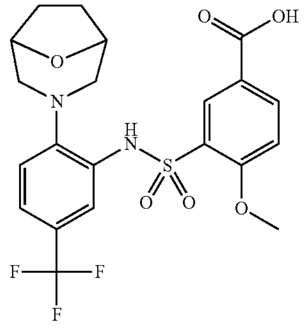 [SMILES: COc1ccc(C(=O)O)cc1S(=O)(=O)Nc1cc(C(F)(F)F)ccc1N1CC2CCC(C1)O2]

Step 1: 3-(2-nitro-4-(trifluoromethyl)phenyl)-8-oxa-3-azabicyclo[3.2.1]octane: $Et_3N$ (0.583 ml, 4.18 mmol) was added to a solution of 1-fluoro-2-nitro-4-(trifluoromethyl) benzene (0.167 ml, 1.20 mmol) and 8-oxa-3-azabicyclo [3.2.1]octane hydrochloride (221 mg, 1.44 mmol) in DCM (5 ml) and the resultant solution stirred at RT for 2 h. 1 M HCl(aq) (2 ml) was added, the organic phase separated by passage through a phase separator and concentrated in vacuo to afford the title compound (384 mg, 1.08 mmol) as a yellow solid. UPLC-MS (Method 2) m/z 303.2 $(M+H)^+$ at 1.54 min. $^1H$ NMR (500 MHz, DMSO-$d_6$) δ 8.13-8.08 (m, 1H), 7.84 (dd, J=8.9, 2.3 Hz, 1H), 7.46 (d, J=8.9 Hz, 1H), 4.39-4.32 (m, 2H), 3.16-3.11 (m, 2H), 3.02-2.97 (m, 2H), 1.89-1.77 (m, 4H).

Step 2: 2-(8-oxa-3-azabicyclo[3.2.1]octan-3-yl)-5-(trifluoromethyl)aniline: The product from Step 1 above (323 mg, 1.07 mmol) was dissolved in EtOH (21.2 ml) and the reaction mixture was hydrogenated in a ThalesNano H-cube® flow reactor (10% Pd/C, 30×4 mm cartridge, full hydrogen mode, 40° C., 1 ml/min flow rate, 4 passes). The reaction mixture was concentrated in vacuo and azeotroped with MeOH (8 ml) to afford the title compound (310 mg, 1.059 mmol, 100% yield, 93% purity) as an off-white solid. UPLC-MS (Method 2) m/z 273.3 $(M+H)^+$ at 1.43 min. $^1H$ NMR (500 MHz, DMSO-$d_6$) δ 7.05 (d, J=8.2 Hz, 1H), 7.02 (d, J=2.2 Hz, 1H), 6.86 (dd, J=8.2, 2.2 Hz, 1H), 5.01 (br s, 2H), 4.36-4.31 (m, 2H), 2.88-2.82 (m, 2H), 2.79 (dd, J=11.5, 2.0 Hz, 2H), 2.09-2.03 (m, 2H), 1.88-1.80 (m, 2H).

Step 3: methyl 3-(N-(2-(8-oxa-3-azabicyclo[3.2.1]octan-3-yl)-5-(trifluoromethyl) phenyl)sulfamoyl)-4-methoxybenzoate: Pyridine (58 μl, 0.72 mmol) was added to a solution of the product from step 2 above (66.5 mg, 0.239 mmol) and methyl 3-(chlorosulfonyl)-4-methoxybenzoate (80 mg, 0.287 mmol) in DCM (2 ml) at RT. The resultant solution was stirred at 40° C. for 4 h before additional methyl 3-(chlorosulfonyl)-4-methoxybenzoate (80 mg, 0.287 mmol) and pyridine (58 μl, 0.718 mmol) were added and the mixture stirred at 40° C. for a further 19 h. The reaction mixture was concentrated in vacuo. The crude product was purified by chromatography on silica gel (25 g cartridge, 0-80% EtOAc/isohexanes) to afford the title compound (88.3 mg, 0.173 mmol, 72.3% yield, 98% purity) as an off-white solid. UPLC-MS (Method 2) m/z 501.3 $(M+H)^+$, 499.2 $(M-H)^-$ at 1.59 min.

Step 4: 3-(N-(2-(8-oxa-3-azabicyclo[3.2.1]octan-3-yl)-5-(trifluoromethyl)phenyl)sulfamoyl)-4-methoxybenzoic acid: 1 M LiOH (aq) (0.699 ml, 0.699 mmol) was added to a solution of the product from step 3 above (87.4 mg, 0.175 mmol) in THF (1.4 ml) at RT and the resultant solution was stirred at RT for 24 h. The reaction mixture was concentrated in vacuo and the residue was redissolved in water (3 ml) and acidified using 1 M HCl(aq) until pH 4-5. The precipitate was isolated by filtration and then dried to afford the title compound (74 mg, 0.152 mmol, 87% yield, 100% purity) as a white solid. UPLC-MS (Method 1) m/z 487.3 $(M+H)^+$, 485.1 $(M-H)^-$ at 1.45 min. $^1H$ NMR (500 MHz, DMSO-$d_6$) δ 13.13 (br s, 1H), 8.88 (br s, 1H), 8.24 (d, J=2.2 Hz, 1H), 8.18 (dd, J=8.7, 2.2 Hz, 1H), 7.46-7.34 (m, 2H), 7.27 (d, J=8.5 Hz, 1H), 6.98 (d, J=2.1 Hz, 1H), 4.40-4.33 (m, 2H), 3.95 (s, 3H), 3.01 (d, J=11.2 Hz, 2H), 2.95 (dd, J=11.6, 2.0 Hz, 2H), 2.13-2.05 (m, 2H), 1.92-1.84 (m, 2H).

Example 8: 4-methoxy-3-(N-(2-(cis-5-methylhexahydropyrrolo[3,4-c]pyrrol-2 (1H)-yl)-5-(trifluoromethyl)phenyl)sulfamoyl)benzoic acid

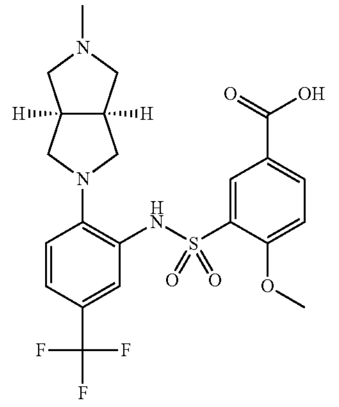 [SMILES: COc1ccc(C(=O)O)cc1S(=O)(=O)Nc1cc(C(F)(F)F)ccc1N1C[C@H]2CN(C)C[C@H]2C1]

Step 1: cis-2-methyl-5-(2-nitro-4-(trifluoromethyl)phenyl) octahydropyrrolo[3,4-c]pyrrole: $Et_3N$ (0.417 ml, 2.99 mmol) was added to a solution of 1-fluoro-2-nitro-4-(trifluoromethyl)benzene (0.167 ml, 1.20 mmol) and cis-2-methyloctahydropyrrolo[3,4-c]pyrrole (187 mg, 1.44 mmol) in DCM (5 ml) at RT and the resultant solution was stirred at RT for 2 h. 1 M HCl(aq) (2 ml) was added, the organic phase was dried by passage through a phase separator and concentrated in vacuo to afford the title compound (402 mg, 1.20 mmol, quant. Yield, 93% purity) as an orange solid. UPLC-MS (Method 2) m/z 316.3 $(M+H)^+$ at 1.40 min. $^1H$ NMR (500 MHz, DMSO-$d_6$) δ 8.04-8.01 (m, 1H), 7.72 (dd, J=9.1, 2.4 Hz, 1H), 7.22 (d, J=9.0 Hz, 1H), 3.49-3.42 (m, 2H), 3.13 (dd, J=10.8, 3.4 Hz, 2H), 2.94-2.85 (m, 2H), 2.53-2.44 (m, 4H), 2.24 (s, 3H). Signal at 2.49 ppm is obscured by DMSO signal.

Step 2: 2-(cis-5-methylhexahydropyrrolo[3,4-c]pyrrol-2 (1H)-yl)-5-(trifluoromethyl)aniline: The product from step 1 above (376 mg, 1.19 mmol) was dissolved in EtOH (23.9 ml) and the reaction mixture was hydrogenated in a ThalesNano H-cube® flow reactor (10% Pd/C, 30×4 mm cartridge, full hydrogen mode, 40° C., 1 ml/min flow rate, 2 passes). The reaction mixture was concentrated in vacuo and azeotroped with MeOH (12 ml) to afford the title compound (355 mg, 1.17 mmol, 98% yield, 94% purity) as an off-white solid. UPLC-MS (Method 2) 286.3 $(M+H)^+$ at 1.24 min.

Step 3: methyl 4-methoxy-3-(N-(2-(cis-5-methylhexahydropyrrolo[3,4-c]pyrrol-2 (1H)-yl)-5-(trifluoromethyl)phenyl)sulfamoyl)benzoate: Pyridine (58 μl, 0.72 mmol) was added to a slurry of the product from step 2 above (72.6 mg, 0.239 mmol) and methyl 3-(chlorosulfonyl)-4-methoxybenzoate (80 mg, 0.287 mmol) in DCM (2 ml) at RT. The resultant solution was stirred at 40° C. for 4 h before additional methyl 3-(chlorosulfonyl)-4-methoxybenzoate (80 mg, 0.287 mmol) and pyridine (0.058 ml, 0.718 mmol) were added and the mixture stirred at 40° C. for a further 19 h. The reaction mixture was concentrated in vacuo and the crude product was purified by chromatography on silica gel (25 g cartridge, 0-10% MeOH/DCM) to afford the title compound (158 mg, 0.193 mmol, 81% yield, 63% purity) as an off-white solid. UPLC-MS (Method 2) m/z 514.4 $(M+H)^+$, 512.2 $(M-H)^-$ at 1.26 min.

Step 4: 4-methoxy-3-(N-(2-(cis-5-methylhexahydropyrrolo[3,4-c]pyrrol-2 (1H)-yl)-5-(trifluoromethyl)phenyl)sulfamoyl)benzoic acid: 1 M LiOH(aq) (1.23 ml, 1.23 mmol) was added to a solution of the product from step 3 above (158 mg, 0.308 mmol) in THF (2.5 ml) at RT and the solution was stirred at RT for 26 h. The reaction mixture was concentrated in vacuo, the residue was redissolved in water (3 ml) and acidified using 1 M HCl(aq) until pH 4-5. The precipitate was isolated by filtration and then dried in vacuo to afford the title compound (63.5 mg, 0.127 mmol, 41.3% yield, 98% purity) as an off-white solid. UPLC-MS (Method 2) m/z 500.3 $(M+H)^+$, 498.3 $(M-H)^-$ at 0.83 min. $^1H$ NMR (500 MHz, DMSO-$d_6$) δ 8.22 (d, J=2.2 Hz, 1H), 8.13 (dd, J=8.7, 2.2 Hz, 1H), 7.31 (d, J=8.7 Hz, 1H), 7.28-7.24 (m, 1H), 6.97-6.91 (m, 2H), 3.90 (s, 3H), 3.36 (dd, J=9.8, 6.5 Hz, 2H), 3.22 (dd, J=10.0, 2.7 Hz, 2H), 2.86-2.80 (m, 2H), 2.75-2.69 (m, 2H), 2.64-2.59 (m, 2H), 2.38 (s, 3H). Two exchangeable protons not seen.

Example 9: 3-(N-(2-(3,3-difluoropiperidin-1-yl)-5-(trifluoromethyl)phenyl)sulfamoyl)-4-methoxybenzoic acid

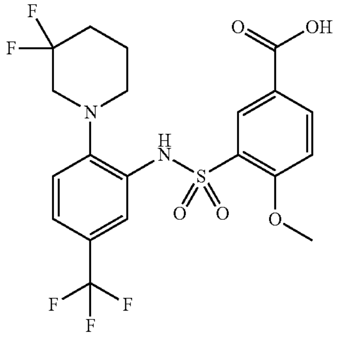 [SMILES: COc1ccc(C(=O)O)cc1S(=O)(=O)Nc1cc(C(F)(F)F)ccc1N1CCCC(F)(F)C1]

Step 1: 3,3-difluoro-1-(2-nitro-4-(trifluoromethyl)phenyl) piperidine: $Et_3N$ (0.500 ml, 3.59 mmol) was added to a solution of 1-fluoro-2-nitro-4-(trifluoromethyl)benzene (0.201 ml, 1.44 mmol) and 3,3-difluoropiperidine hydrochloride (271 mg, 1.72 mmol) in DCM (6 ml) and the resultant solution was stirred at RT for 20 h. Water (3 ml) was added and the phases were separated using a phase separator. The aqueous phase was extracted with DCM (2×3 ml) and the organic phases were combined, dried by passage through a phase separator and concentrated in vacuo. The crude product was purified by chromatography on silica gel (12 g cartridge, 0-100% EtOAc/isohexanes) to afford the title compound (399 mg, 1.26 mmol, 87.8% yield, >98% purity) as a bright yellow solid. UPLC-MS (Method 2) m/z 309.0 $(M-H)^-$ at 1.64 min.

Step 2: 2-(3, 3-difluoropiperidin-1-yl)-5-(trifluoromethyl) aniline: The product from step 1 above (156 mg, 0.503 mmol) was dissolved in EtOH (10.1 ml) and the reaction mixture was hydrogenated in a ThalesNano H-cube® flow reactor (10% Pd/C, 30×4 mm, full hydrogen mode, 40° C., 1 ml/min flow rate, 2 passes). The reaction mixture was concentrated in vacuo and azeotroped with MeOH (6 ml) to afford the title compound (119 mg, 0.408 mmol, 81% yield, 96% purity) as a colourless oil. UPLC-MS (Method 2) m/z 280.8 $(M+H)^+$ at 1.64 min.

Step 3: methyl 3-(N-(2-(3,3-difluoropiperidin-1-yl)-5-(trifluoromethyl)phenyl)sulfamoyl)-4-methoxybenzoate: The product from step 2 above (53.0 mg, 0.189 mmol) was dissolved in a mixture of DCM (1 ml) and pyridine (0.05 ml, 0.618 mmol) and treated with a solution of methyl 3-(chlorosulfonyl)-4-methoxybenzoate (60.0 mg, 0.227 mmol) in DCM (1 ml). The resultant solution was stirred at RT for 4 days. The crude product was purified by chromatography on silica gel (12 g cartridge, 0-10% MeOH/DCM) to afford the title compound (39.9 mg, 0.075 mmol, 39.4% yield, 95% purity) as a white solid. UPLC-MS (Method 1) m/z 509.4 $(M+H)^+$, 507.2 $(M-H)^-$ at 1.75 min.

Step 4: 3-(N-(2-(3,3-difluoropiperidin-1-yl)-5-(trifluoromethyl)phenyl)sulfamoyl)-4-methoxybenzoic acid: The product from step 3 above (38 mg, 0.075 mmol) was dissolved in THF (2 ml) and treated with 1.1 M LiOH(aq) (272 μl, 0.299 mmol) and MeOH was added dropwise until the mixture was a solution. The reaction mixture was stirred at 30° C. for 4 days. The reaction mixture was diluted with water (3 ml), concentrated in vacuo and the resultant aqueous solution diluted with water (to ca. 5 ml) and neutralised to ca. pH 6 with 1 M HCl. The resultant lumpy suspension was sonicated to afford a cloudy solution. The white precipitate was collected by filtration, washing with water and the solid was suspended in MeCN (4 ml), concentrated in vacuo and dried at 45° C. to afford the title compound (34 mg, 0.065 mmol, 87% yield, 95% purity) as a white solid. UPLC-MS (Method 1) m/z 495.1 $(M+H)^+$, 493.1 $(M-H)^-$ at 1.59 min, 98% purity (254 nm). $^1H$ NMR (500 MHz, DMSO-$d_6$) δ 13.18 (br s, 1H), 8.60 (br s, 1H), 8.37 (d, J=2.2 Hz, 1H), 8.16 (dd, J=8.7, 2.2 Hz, 1H), 7.41-7.36 (m, 3H), 7.32 (d, J=8.8 Hz, 1H), 3.91 (s, 3H), 3.17 (t, J=11.1 Hz, 2H), 2.95 (t, J=5.3 Hz, 2H), 2.13-2.00 (m, 2H), 1.88-1.84 (m, 2H).

Example 10:3-(N-(2-(8-azabicyclo[3.2.1]octan-8-yl)-5-(trifluoromethyl)phenyl) sulfamoyl)-4-methoxybenzoic acid

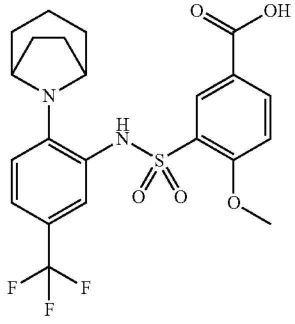 [SMILES: COc1ccc(C(=O)O)cc1S(=O)(=O)Nc1cc(C(F)(F)F)ccc1N1C2CCCC1CC2]

Step 1: 8-(2-nitro-4-(trifluoromethyl)phenyl)-8-azabicyclo[3.2.1]octane: $Et_3N$ (0.236 ml, 1.69 mmol) was added to a solution of 1-fluoro-2-nitro-4-(trifluoromethyl)benzene (0.095 ml, 0.677 mmol) and 8-azabicyclo[3.2.1]octane hydrochloride (100 mg, 0.677 mmol) in DCM (2 ml) and the resultant solution was stirred at RT for 20 h. Water (3 ml) was added and the phases were separated using a phase separator. The aqueous phase was extracted with DCM (2×3 ml) and the organic phases were combined, dried by passage through a phase separator and concentrated in vacuo. The crude product was purified by chromatography on silica gel (12 g cartridge, 0-100% EtOAc/isohexanes) to afford the title compound (183 mg, 0.597 mmol, 88.2% yield, 98% purity). UPLC-MS (Method 2) m/z 301.3 $(M+H)^+$ at 1.85 min.

Step 2: 2-(8-azabicyclo[3.2.1]octan-8-yl)-5-(trifluoromethyl)aniline: The product from step 1 above (134 mg, 0.446 mmol) was dissolved in EtOH (8.9 ml) and the reaction mixture was hydrogenated in a ThalesNano H-cube® flow reactor (10% Pd/C, 30×4 mm, full hydrogen mode, 40° C., 1 ml/min flow rate, 2 passes). The reaction mixture was concentrated in vacuo and azeotroped with MeOH (6 ml) to afford the title compound (104 mg, 0.366 mmol, 82% yield, 95% purity) as a colourless oil. UPLC-MS (Method 2) m/z 271.3 $(M+H)^+$ at 1.83 min.

Step 3: methyl 3-(N-(2-(-8-azabicyclo[3.2.1]octan-8-yl)-5-(trifluoromethyl)phenyl)sulfamoyl)-4-methoxybenzoate: The product from step 2 above (51.1 mg, 0.189 mmol) was dissolved in a mixture of DCM (1 ml) and pyridine (0.05 ml, 0.618 mmol) and treated with a solution methyl 3-(chlorosulfonyl)-4-methoxybenzoate (60.0 mg, 0.227 mmol) in DCM (1 ml). The resultant solution was stirred at RT for 4 days. The crude product was purified by chromatography on silica gel (12 g cartridge, 0-10% MeOH/DCM) to afford the title compound (32.1 mg, 0.061 mmol, 32.4% yield, 95% purity) as a white solid. UPLC-MS (Method 1) m/z 499.3 $(M+H)^+$, 497.2 $(M-H)^-$ at 1.90 min.

Step 4: 3-(N-(2-(-8-azabicyclo[3.2.1]octan-8-yl)-5-(trifluoromethyl)phenyl)sulfamoyl)-4-methoxybenzoic acid: The product from step 3 above (30 mg, 0.060 mmol) was dissolved in THF (2 ml) and treated with 1.1 M LiOH(aq) (219 µl, 0.241 mmol). MeOH was added dropwise until the mixture was a solution and the reaction was stirred at 30° C. for 4 days. The reaction mixture was diluted with water (3 ml), concentrated in vacuo and the resultant aqueous solution diluted with water (to ca. 5 ml) and neutralised to ca. pH 6 with 1 M HCl. The resultant lumpy suspension was sonicated to afford a cloudy solution and the precipitate was collected by filtration, washing with water. The solid was suspended in MeCN (4 ml), concentrated in vacuo and dried at 45° C. The crude product was purified by preparative HPLC (Waters, Acidic (0.1% Formic acid), Acidic, Waters X-Select Prep-C18, 5 µm, 19×50 mm column, 50-80% MeCN in Water) to afford the title compound (9.0 mg, 0.018 mmol, 29.3% yield, 95% purity) as a white solid. UPLC-MS (Method 1) m/z 485.2 $(M+H)^+$, 483.3 $(M-H)^-$ at 1.74 min. 1H NMR (500 MHz, DMSO-$d_6$) δ 13.12 (br s, 1H), 8.96 (br s, 1H), 8.21 (d, J=2.2 Hz, 1H), 8.16 (dd, J=8.8, 2.2 Hz, 1H), 7.34 (d, J=8.7 Hz, 1H), 7.27 (dd, J=8.7, 2.3 Hz, 1H), 7.01 (d, J=8.7 Hz, 1H), 6.95-6.92 (m, 1H), 4.29 (s, 2H), 3.93 (s, 3H), 1.91-1.86 (m, 2H), 1.79-1.68 (m, 6H), 1.55-1.46 (m, 1H), 1.45-1.37 (m, 1H).

Example 11: 3-(N-(2-(5-oxa-2-azaspiro[3.4]octan-2-yl)-5-(trifluoromethyl)phenyl) sulfamoyl)-4-methoxybenzoic acid

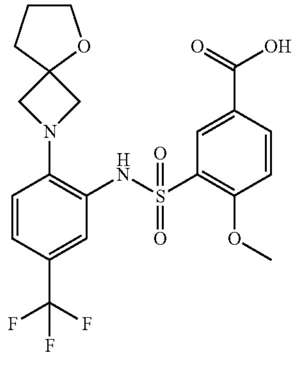 [SMILES: COc1ccc(C(=O)O)cc1S(=O)(=O)Nc1cc(C(F)(F)F)ccc1N1CC2(CCCO2)C1]

Step 1: 2-(2-nitro-4-(trifluoromethyl)phenyl)-5-oxa-2-azaspiro[3.4]octane: $Et_3N$ (500 µl, 3.59 mmol) was added to a solution of 1-fluoro-2-nitro-4-(trifluoromethyl)benzene (201 µl, 1.44 mmol) and 5-oxa-2-azaspiro[3.4]octane hemioxalate (349 mg, 2.21 mmol) in DCM (6 ml) and the resultant solution was stirred at RT for 20 h. 1 M HCl(aq) (2 ml) was added and the organic phase was dried by passage through a phase separator. The organic phase was concentrated in vacuo to afford the title compound (438 mg, 1.44 mmol, 100% yield, 99% purity) as a light yellow sticky oil. UPLC-MS (Method 2) m/z 303.3 $(M+H)^+$ at 1.59 min.

Step 2: 2-(5-oxa-2-azaspiro[3.4]octan-2-yl)-5-(trifluoromethyl)aniline: The product from step 1 above (217 mg, 0.718 mmol) was dissolved in EtOH (14.4 ml) and the reaction mixture was hydrogenated in a ThalesNano H-cube® flow reactor (10% Pd/C, 30×4 mm, full hydrogen mode, 40° C., 1 ml/min flow rate, 2 passes). The reaction mixture was concentrated in vacuo and azeotroped with MeOH (6 ml) to give the title compound (198 mg, 0.691 mmol, 96% yield, 95% purity) as a white solid. UPLC-MS (Method 2) m/z 273.3 $(M+H)^+$ at 1.37 min.

Step 3: methyl 3-(N-(2-(5-oxa-2-azaspiro[3.4]octan-2-yl)-5-(trifluoromethyl)phenyl)sulfamoyl)-4-methoxybenzoate: The product from step 2 above (0.073 g, 0.268 mmol) was dissolved in a mixture of DCM (1 ml) and pyridine (0.087 ml, 1.07 mmol) and treated with a solution methyl 3-(chlorosulfonyl)-4-methoxybenzoate (0.085 g, 0.321 mmol) in DCM (1 ml). The resultant solution was stirred at RT for 20 h. The crude product was purified directly by chromatography on silica gel (12 g cartridge, 0-100% EtOAc/isohexanes) to afford the title compound (93.7 mg, 0.178 mmol, 70.0% yield, 95% purity) as an off white solid. UPLC-MS (Method 1) m/z 501.4 $(M+H)^+$, 498.8 $(M-H)^-$ at 1.54 min.

Step 4: 3-(N-(2-(5-oxa-2-azaspiro[3.4]octan-2-yl)-5-(trifluoromethyl)phenyl)sulfamoyl)-4-methoxybenzoic acid: The product from step 3 above (92 mg, 0.184 mmol) was dissolved in THF (2 ml) and treated with 1.1 M LiOH(aq) (668 µl, 0.735 mmol). MeOH was added dropwise until the mixture was a solution and the reaction was stirred at 30° C. for 3 days. The reaction mixture was diluted with water (3 ml), concentrated in vacuo and the resultant aqueous solution diluted with water (to ca. 5 ml) and neutralised to ca. pH 6 with 1 M HCl. The resultant lumpy suspension was sonicated to afford a cloudy solution. The white precipitate was collected by filtration, washing with water and the solid was suspended in MeCN (4 ml), concentrated in vacuo and dried at 45° C. The crude product was purified by preparative HPLC (Waters, Acidic (0.1% Formic acid), Acidic, Waters X-Select Prep-C18, 5 µm, 19×50 mm column, 35-65% MeCN in Water) to afford the title compound (3 mg, 5.98 µmol, 3.25% yield, 97% purity) as a fluffy white solid. UPLC-MS (Method 1) m/z 487.0 $(M+H)^+$, 485.2 $(M-H)^-$ at 1.37 min. $^1$H NMR (500 MHz, Methanol-$d_4$) δ 8.33 (d, J=2.2 Hz, 1H), 8.29 (dd, J=8.7, 2.2 Hz, 1H), 7.35 (d, J=8.7 Hz, 1H), 7.30 (dd, J=8.6, 2.2 Hz, 1H), 6.70 (d, J=2.1 Hz, 1H), 6.55 (d, J=8.6 Hz, 1H), 4.21 (d, J=9.0 Hz, 2H), 4.08 (d, J=9.0 Hz, 2H), 4.02 (s, 3H), 3.88 (t, J=7.0 Hz, 2H), 2.20 (t, J=7.0 Hz, 2H), 2.00 (p, J=7.0 Hz, 2H). Two exchangeable protons not observed.

Example 12: 3-(N-(2-(4,4-difluoropiperidin-1-yl)-5-(trifluoromethyl)phenyl)sulfamoyl)-4-methoxybenzoic acid

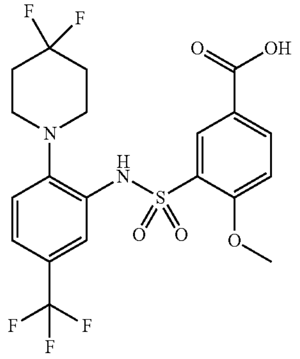 [SMILES: COc1ccc(C(=O)O)cc1S(=O)(=O)Nc1cc(C(F)(F)F)ccc1N1CCC(F)(F)CC1]

Step 1: 4,4-difluoro-1-(2-nitro-4-(trifluoromethyl)phenyl) piperidine: $Et_3N$ (0.47 ml, 3.37 mmol) was added to a solution of 1-fluoro-2-nitro-4-(trifluoromethyl)benzene (0.188 ml, 1.34 mmol) and 4,4-difluoropiperidine (196 mg, 1.62 mmol) in DCM (5 ml) and the resultant solution was stirred at RT for 19 h. Water (2.5 ml) was added, the organic phase was isolated using a phase separator and concentrated in vacuo to afford the title compound (434 mg, 1.04 mmol, 77% yield, 74% purity) as an orange oil. UPLC (Method 2) 1.67 min. $^1$H NMR (500 MHz, DMSO-$d_6$) δ 8.20 (d, J=2.3 Hz, 1H), 7.89 (dd, J=8.9, 2.4 Hz, 1H), 7.53 (d, J=8.8 Hz, 1H), 3.28-3.23 (m, 4H), 2.16-2.06 (m, 4H).

Step 2: 2-(4,4-difluoropiperidin-1-yl)-5-(trifluoromethyl) aniline: The product from step 1 above (180 mg, 0.580 mmol) was dissolved in EtOH (23.2 ml) and the reaction mixture was hydrogenated in a ThalesNano H-cube® flow reactor (10% Pd/C, 30×4 mm, full hydrogen mode, 21° C., 1 ml/min flow rate, 1 pass). The reaction mixture was concentrated in vacuo and azeotroped with MeOH (8 ml) to afford the title compound (159 mg, 0.545 mmol, 94% yield, 96% purity) as an off-white solid. UPLC-MS (Method 2) m/z 281.3 $(M+H)^+$ at 1.63 min. 1H NMR (500 MHz, DMSO-$d_6$) δ 7.04 (d, J=8.1 Hz, 1H), 6.97 (d, J=2.2 Hz, 1H), 6.82 (dd, J=8.2, 2.1 Hz, 1H), 5.27 (s, 2H), 2.93 (br t, J=5.5 Hz, 4H), 2.24-2.09 (m, 4H).

Step 3: methyl 3-(N-(2-(4,4-difluoropiperidin-1-yl)-5-(trifluoromethyl)phenyl)sulfamoyl)-4-methoxybenzoate: Pyridine (0.058 ml, 0.718 mmol) was added to a solution of the product from step 2 above (69.8 mg, 0.239 mmol) and methyl 3-(chlorosulfonyl)-4-methoxybenzoate (80 mg, 0.287 mmol) in DCM (2.0 ml) at RT. The reaction mixture was stirred and heated at 40° C. for 18 h. Additional methyl 3-(chlorosulfonyl)-4-methoxybenzoate (33 mg, 0.120 mmol) was added and the resultant solution was stirred at 40° C. for a further 3 h. The reaction mixture was concentrated in vacuo and the crude product was purified by chromatography on silica gel (10 g cartridge, 0-30% EtOAc/isohexanes) to afford the title compound (107 mg, 0.196 mmol, 82% yield, 93% purity) as an off-white solid. UPLC-MS (Method 2) m/z 509.3 $(M+H)^+$, 507.2 $(M-H)^-$ at 1.72 min.

Step 4: 3-(N-(2-(4,4-difluoropiperidin-1-yl)-5-(trifluoromethyl)phenyl)sulfamoyl)-4-methoxybenzoic acid: 1 M LiOH(aq) (0.632 ml, 0.632 mmol) was added to a solution of the product from step 3 above (107 mg, 0.210 mmol) in THF (1.26 ml) at RT. The resultant clear solution was stirred at RT for 20 h. Additional 1 M LiOH(aq) (0.211 ml, 0.211 mmol) was added and the solution was stirred for a further 1 h. The reaction mixture was concentrated in vacuo and the residue was redissolved in water (3 ml) and acidified using 1 M HCl(aq) until pH 4-5. The precipitate was dissolved in DCM (10 ml) and the phases were separated. The aqueous phase was extracted with DCM (2×3 ml). The combined organic phases were dried by passage through a phase separator and concentrated in vacuo. The crude product was purified by chromatography on silica gel (10 g cartridge, 0-3.5% MeOH/DCM) to afford an off-white solid (40.1 mg). The product was purified by preparative HPLC (Waters, Acidic (0.1% Formic acid), Acidic, Waters X-Select Prep-C18, 5 μm, 19×50 mm column, 50-80% MeCN in Water) to afford the title compound (19 mg, 0.038 mmol, 18.3% yield, 100% purity) as a white solid. UPLC-MS (Method 1) m/z 495.3 $(M+H)^+$, 493.2 $(M-H)^-$ at 1.61 min. $^1$H NMR (500 MHz, DMSO-$d_6$) δ 13.15 (br s, 1H), 9.30 (br s, 1H), 8.36 (d, J=2.2 Hz, 1H), 8.16 (dd, J=8.7, 2.3 Hz, 1H), 7.48-7.44 (m, 1H), 7.41-7.35 (m, 1H), 7.35 (d, J=8.5 Hz, 1H), 7.32 (d, J=8.8 Hz, 1H), 3.87 (s, 3H), 2.96-2.86 (m, 4H), 2.18-2.08 (m, 4H).

Example 13: 3-(N-(2-(8-hydroxy-3-azabicyclo[3.2.1]octan-3-yl)-5-(trifluoromethyl)phenyl) sulfamoyl)-4-methoxybenzoic acid

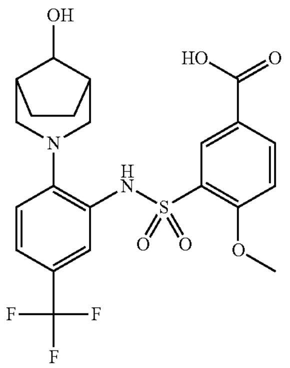 [SMILES: COc1ccc(C(=O)O)cc1S(=O)(=O)Nc1cc(C(F)(F)F)ccc1N1CC2CCC(C1)C2O]

Step 1: 3-(2-nitro-4-(trifluoromethyl)phenyl)-3-azabicyclo[3.2.1]octan-8-ol: $Et_3N$ (500 μl, 3.59 mmol) was added to a solution of 1-fluoro-2-nitro-4-(trifluoromethyl)benzene (201 μl, 1.44 mmol) and 3-azabicyclo[3.2.1]octan-8-ol hydrochloride (250 mg, 1.53 mmol) in DCM (6 ml) and the resultant solution was stirred at RT for 20 h. 1 M HCl(aq) (2 ml) was added and the organic phase was dried by passage through a phase separator and concentrated in vacuo to afford the title compound (468 mg, 1.44 mmol, 100% yield, 97% purity) as a light orange solid. UPLC-MS (Method 2) m/z 315.1 $(M-H)^-$ at 1.53 min.

Step 2: 3-(2-amino-4-(trifluoromethyl)phenyl)-3-azabicyclo[3.2.1]octan-8-ol: The product from step 1 above (227 mg, 0.718 mmol) was dissolved in EtOH (14.4 ml) and the reaction mixture was hydrogenated in a ThalesNano H-cube® flow reactor (10% Pd/C, 30×4 mm, full hydrogen, 40° C., 1 ml/min flow rate, 2 passes). The reaction mixture was concentrated in vacuo and azeotroped with MeOH (6 ml) to afford the title compound (186 mg, 0.585 mmol, 81% yield, 90% purity) as a light pink solid. UPLC-MS (Method 2) m/z 287.3 $(M+H)^+$, 285.2 $(M-H)^-$ at 1.38 min.

Step 3: methyl 3-(N-(2-(8-hydroxy-3-azabicyclo[3.2.1]octan-3-yl)-5-(trifluoromethyl)phenyl) sulfamoyl)-4-methoxybenzoate: The product from step 2 above (63.1 mg, 0.220 mmol) was dissolved in a mixture of DCM (1 ml) and pyridine (71.3 µl, 0.882 mmol) and treated with a solution methyl 3-(chlorosulfonyl)-4-methoxybenzoate (70 mg, 0.264 mmol) in DCM (1 ml). The resultant solution was stirred at RT for 20 h. The crude product was purified by chromatography on silica gel (12 g cartridge, 0-100% EtOAc/isohexanes) to afford the title compound (51 mg, 0.087 mmol, 39.6% yield, 88% purity) as a white solid. UPLC-MS (Method 1) m/z 515.4 $(M+H)^+$, 513.2 $(M-H)^-$ at 1.60 min.

Step 4: 3-(N-(2-(8-hydroxy-3-azabicyclo[3.2.1]octan-3-yl)-5-(trifluoromethyl)phenyl)sulfamoyl)-4-methoxybenzoic acid: The product from step 3 above (49 mg, 0.095 mmol) was dissolved in THF (2 ml) and treated with 1.1 M LiOH(aq) (346 µl, 0.381 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ca. 5 ml). The aqueous phase was washed with EtOAc (2×5 ml) and neutralised to ca. pH 6 with 1 M HCl. The resultant lumpy suspension was sonicated to afford a cloudy solution which was concentrated in vacuo to ca. 2 ml. The precipitate was collected by filtration, washing with water (2×2 ml). The solid was suspended in MeCN (4 ml) and concentrated in vacuo and dried at 45° C. to afford the title compound (21.9 mg, 0.042 mmol, 44.6% yield, 97% purity) as a white solid. UPLC-MS (Method 1) m/z 501.3 $(M+H)^+$, 499.2 $(M-H)^-$ at 1.42 min. $^1H$ NMR (500 MHz, DMSO-$d_6$) δ 13.17 (s, 1H), 8.69 (s, 1H), 8.34 (d, J=2.2 Hz, 1H), 8.17 (dd, J=8.7, 2.2 Hz, 1H), 7.40-7.32 (m, 3H), 7.17 (d, J=1.6 Hz, 1H), 5.07 (s, 1H), 3.93 (s, 3H), 3.90-3.82 (m, 1H), 3.33-3.31 (m, 2H), 2.61 (dd, J=10.7, 3.6 Hz, 2H), 2.01-1.97 (m, 2H), 1.86-1.73 (m, 4H).

The following examples were prepared by methods analogous to Example 13, substituting appropriate starting materials and intermediates where necessary:

| Example | Structure | Name/Analytical Data |
|---|---|---|
| 14 | 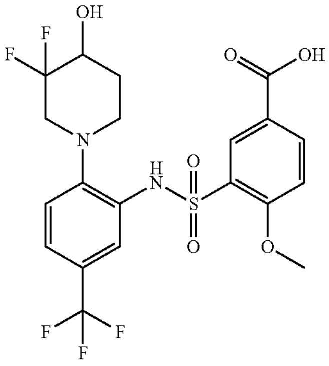 | 3-(N-(2-(3,3-difluoro-4-hydroxypiperidin-1-yl)-5-(trifluoromethyl)phenyl)sulfamoyl)-4-methoxybenzoic acid<br>UPLC-MS (Method 1) m/z 511.3 $(M + H)^+$, 509.1 $(M - H)^-$ at 1.37 min. $^1H$ NMR (500 MHz, DMSO-$d_6$) δ 13.18 (br s, 1H), 8.62 (br s, 1H), 8.36 (d, J = 2.2 Hz, 1H), 8.15 (dd, J = 8.7, 2.2 Hz, 1H), 7.44-7.23 (m, 4H), 5.74 (d, J = 5.5 Hz, 1H), 3.93-3.83 (m, 4H), 3.15-3.01 (m, 2H), 2.92 (t, J = 9.8 Hz, 1H), 2.04-1.94 (m, 1H), 1.87-1.77 (m, 1H). One proton obscured by solvent. |
| 15 | 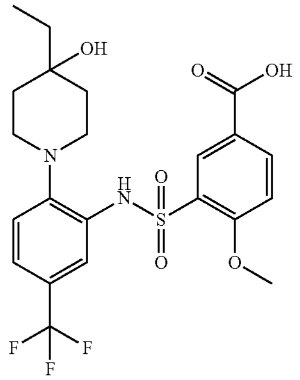 [SMILES: CCC1(O)CCN(c2ccc(C(F)(F)F)cc2NS(=O)(=O)c2cc(C(=O)O)ccc2OC)CC1] | 3-(N-(2-(4-ethyl-4-hydroxypiperidin-1-yl)-5-(trifluoromethyl)phenyl)sulfamoyl)-4-methoxybenzoic acid<br>UPLC-MS (Method 1) m/z 503.4 $(M + H)^+$, 501.2 $(M - H)^-$ at 1.46 min. $^1H$ NMR (500 MHz, DMSO-$d_6$) δ 13.27 (s, 1H), 8.74 (s, 1H), 8.36 (d, J = 2.2 Hz, 1H), 8.12 (dd, J = 8.7, 2.2 Hz, 1H), 7.46 (s, 1H), 7.33 (s, 2H), 7.26 (d, J = 8.7 Hz, 1H), 4.09 (s, 1H), 3.88 (s, 3H), 2.92 (td, J = 11.1, 3.4 Hz, 2H), 2.72 (d, J = 10.9 Hz, 2H), 1.65-1.50 (m, 4H), 1.45 (q, J = 7.4 Hz, 2H), 0.88 (t, J = 7.4 Hz, 3H). |
| 16 | 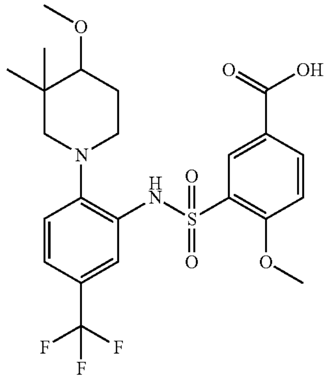 | 4-methoxy-3-(N-(2-(4-methoxy-3,3-dimethylpiperidin-1-yl)-5-(trifluoromethyl)phenyl)sulfamoyl)benzoic acid<br>UPLC-MS (Method 1) m/z 515.2 $(M - H)^-$ at 1.75 min. $^1H$ NMR (500 MHz, DMSO-$d_6$) δ 13.18 (br s, 1H), 8.57 (br s, 1H), 8.36 (d, J = 2.2 Hz, 1H), 8.16 (dd, J = 8.7, 2.2 Hz, 1H), 7.42-7.26 (m, 4H), 3.88 (s, 3H), 3.31 (s, 3H), 3.08-2.99 (m, 1H), 2.94 (dd, J = 9.1, 3.9 Hz, 1H), 2.85-2.76 (m, 1H), 2.67-2.60 (m, 1H), 2.37 (d, J = 11.7 Hz, 1H), 2.05-1.96 (m, 1H), 1.73-1.61 (m, 1H), 1.02 (s, 3H), 0.96 (s, 3H). |

-continued

| Example | Structure | Name/Analytical Data |
| --- | --- | --- |
| 17 | 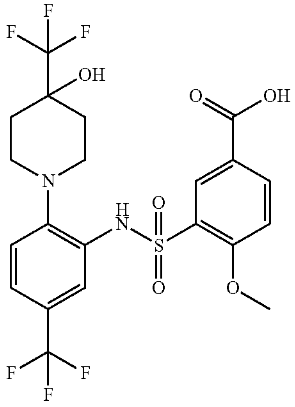 [SMILES: COc1ccc(C(=O)O)cc1S(=O)(=O)Nc1cc(C(F)(F)F)ccc1N1CCC(O)(C(F)(F)F)CC1] | 3-(N-(2-(4-hydroxy-4-(trifluoromethyl) piperidin-1-yl)-5-(trifluoromethyl) phenyl)sulfamoyl)-4-methoxybenzoic acid UPLC-MS (Method 1) m/z 543.4 $(M + H)^+$, 541.1 $(M - H)^-$ at 1.50 min. $^1H$ NMR (500 MHz, DMSO-$d_6$) δ 13.14 (br s, 1H), 9.18 (br s, 1H), 8.34 (d, J = 2.2 Hz, 1H), 8.15 (dd, J = 8.7, 2.2 Hz, 1H), 7.46 (d, J = 2.1 Hz, 1H), 7.39 (d, J = 8.7 Hz, 1H), 7.33-7.31 (m, 2H), 5.94 (s, 1H), 3.85 (s, 3H), 2.94-2.83 (m, 4H), 1.94-1.84 (m, 2H), 1.66 (d, J = 12.7 Hz, 2H). |
| 18 | 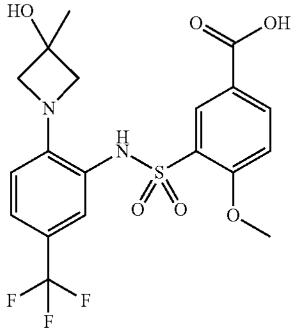 [SMILES: COc1ccc(C(=O)O)cc1S(=O)(=O)Nc1cc(C(F)(F)F)ccc1N1CC(C)(O)C1] | 3-(N-(2-(3-hydroxy-3-methylazetidin-1-yl)-5-(trifluoromethyl)phenyl)sulfamoyl)-4-methoxybenzoic acid UPLC-MS (Method 1) m/z 461.3 $(M + H)^+$, 459.1 $(M - H)^-$ at 1.19 min. $^1H$ NMR (500 MHz, DMSO-$d_6$) δ 13.06 (br s, 1H), 9.27 (s, 1H), 8.19 (dd, J = 8.7, 2.3 Hz, 1H), 8.12 (d, J = 2.2 Hz, 1H), 7.40 (d, J = 8.8 Hz, 1H), 7.31 (dd, J = 8.6, 1.6 Hz, 1H), 6.52-6.46 (m, 2H), 5.51 (s, 1H), 4.00 (d, J = 8.2 Hz, 2H), 3.94 (s, 3H), 3.88 (d, J = 8.2 Hz, 2H), 1.41 (s, 3H). |
| 19 | 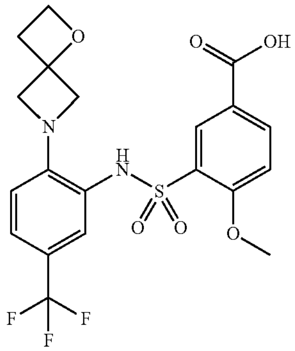 [SMILES: COc1ccc(C(=O)O)cc1S(=O)(=O)Nc1cc(C(F)(F)F)ccc1N1CC2(CCO2)C1] | 3-(N-(2-(1-oxa-6-azaspiro[3.3]heptan-6-yl)-5-(trifluoromethyl)phenyl)sulfamoyl)-4-methoxybenzoic acid UPLC-MS (Method 1) m/z 473.3 $(M + H)^+$, 471.1 $(M - H)^-$ at 1.27 min. $^1H$ NMR (500 MHz, DMSO-$d_6$) δ 13.07 (br s, 1H), 9.29 (br s, 1H), 8.19 (dd, J = 8.7, 2.3 Hz, 1H), 8.11 (d, J = 2.2 Hz, 1H), 7.40 (d, J = 8.8 Hz, 1H), 7.35-7.29 (m, 1H), 6.53-6.47 (m, 2H), 4.44 (t, J = 7.5 Hz, 2H), 4.36 (d, J = 9.8 Hz, 2H), 4.16 (d, J = 9.8 Hz, 2H), 3.95 (s, 3H), 2.85 (t, J = 7.5 Hz, 2H). |
| 20 | 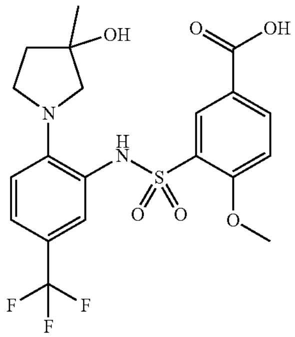 [SMILES: COc1ccc(C(=O)O)cc1S(=O)(=O)Nc1cc(C(F)(F)F)ccc1N1CCC(C)(O)C1] | 3-(N-(2-(3-hydroxy-3-methylpyrrolidin-1-yl)-5-(trifluoromethyl)phenyl)sulfamoyl)-4-methoxybenzoic acid UPLC-MS (Method 1) m/z 475.4 $(M + H)^+$, 473.2 $(M - H)^-$ at 1.24 min. $^1H$ NMR (500 MHz, DMSO-$d_6$) δ 13.03 (br s, 1H), 9.29 (br s, 1H), 8.17 (dd, J = 8.7, 2.2 Hz, 1H), 8.06 (d, J = 2.2 Hz, 1H), 7.39 (d, J = 8.8 Hz, 1H), 7.28 (dd, J = 8.8, 1.9 Hz, 1H), 6.72 (d, J = 8.9 Hz, 1H), 6.52 (d, J = 1.9 Hz, 1H), 4.77 (br s, 1H), 3.97 (s, 3H), 3.63-3.56 (m, 1H), 3.53 (d, J = 10.5 Hz, 1H), 3.50-3.44 (m, 1H), 3.39 (d, J = 10.5 Hz, 1H), 1.91-1.84 (m, 1H), 1.81-1.73 (m, 1H), 1.31 (s, 3H). |

-continued

| Example | Structure | Name/Analytical Data |
|---|---|---|
| 21 | 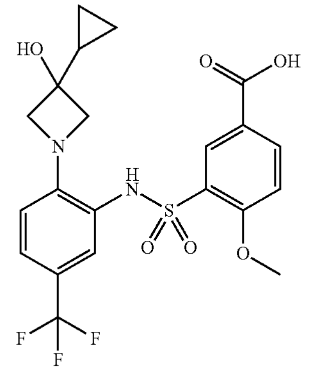 [SMILES: COc1ccc(C(=O)O)cc1S(=O)(=O)Nc1cc(C(F)(F)F)ccc1N1CC(O)(C2CC2)C1] | 3-(N-(2-(3-cyclopropyl-3-hydroxyazetidin-1-yl)-5-(trifluoromethyl)phenyl)sulfamoyl)-4-methoxybenzoic acid UPLC-MS (Method 1) m/z 487.0 $(M + H)^+$, 485.1 $(M - H)^-$ at 1.28 min. $^1H$ NMR (500 MHz, DMSO-$d_6$) δ 13.07 (br s, 1H), 9.25 (br s, 1H), 8.18 (dd, J = 8.7, 2.2 Hz, 1H), 8.11 (d, J = 2.2 Hz, 1H), 7.39 (d, J = 8.8 Hz, 1H), 7.30 (dd, J = 8.7, 2.1 Hz, 1H), 6.51-6.47 (m, 2H), 5.47 (s, 1H), 3.97 (d, J = 8.4 Hz, 2H), 3.95 (s, 3H), 3.83 (d, J = 8.5 Hz, 2H), 1.22-1.14 (m, 1H), 0.45-0.31 (m, 4H). |
| 22 | 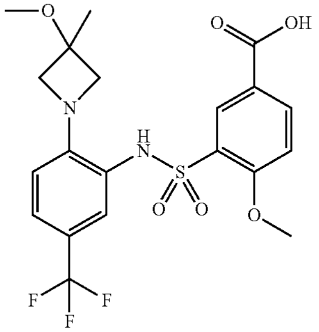 | 4-methoxy-3-(N-(2-(3-methoxy-3-methylazetidin-1-yl)-5-(trifluoromethyl)phenyl)sulfamoyl)benzoic acid UPLC-MS (Method 1) m/z 475.4 $(M + H)^+$, 473.2 $(M - H)^-$ at 1.36 min. $^1H$ NMR (500 MHz, DMSO-$d_6$) δ 13.04 (br s, 1H), 9.29 (br s, 1H), 8.19 (dd, J = 8.7, 2.3 Hz, 1H), 8.13 (d, J = 2.2 Hz, 1H), 7.40 (d, J = 8.8 Hz, 1H), 7.33 (dd, J = 8.7, 2.1 Hz, 1H), 6.55 (d, J = 2.1 Hz, 1H), 6.51 (d, J = 8.8 Hz, 1H), 3.99 (d, J = 8.6 Hz, 2H), 3.94 (s, 3H), 3.93 (d, J = 8.6 Hz, 2H), 3.18 (s, 3H), 1.44 (s, 3H). |
| 23 | 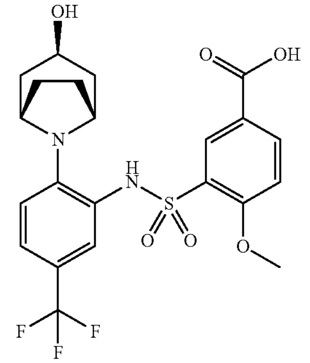 [SMILES: COc1ccc(C(=O)O)cc1S(=O)(=O)Nc1cc(C(F)(F)F)ccc1N1[C@@H]2CC[C@H]1C[C@@H](O)C2] | 3-(N-(2-(endo-3-hydroxy-8-azabicyclo[3.2.1]octan-8-yl)-5-(trifluoromethyl)phenyl)sulfamoyl)-4-methoxybenzoic acid UPLC-MS (Method 1) m/z 501.3 $(M + H)^+$, 499.1 $(M - H)^-$ at 1.40 min. $^1H$ NMR (500 MHz, DMSO-$d_6$) δ 8.98 (s, 1H), 8.20 (d, J = 2.2 Hz, 1H), 8.16 (dd, J = 8.6, 2.2 Hz, 1H), 7.34 (d, J = 8.8 Hz, 1H), 7.27 (dd, J = 8.7, 2.3 Hz, 1H), 7.00 (d, J = 8.7 Hz, 1H), 6.92 (d, J = 2.2 Hz, 1H), 4.55 (br s, 1H), 4.32-4.24 (m, 2H), 3.92 (s, 3H), 3.88 (t, J = 5.0 Hz, 1H), 2.23-2.20 (m, 2H), 2.04-1.94 (m, 2H), 1.83-1.77 (m, 2H), 1.71-1.58 (m, 2H). One exchangeable proton not observed. |
| 24 | 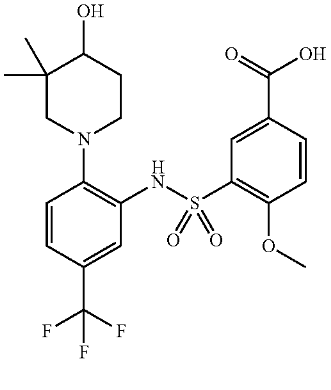 [SMILES: COc1ccc(C(=O)O)cc1S(=O)(=O)Nc1cc(C(F)(F)F)ccc1N1CCC(O)C(C)(C)C1] | 3-(N-(2-(4-hydroxy-3,3-dimethylpiperidin-1-yl)-5-(trifluoromethyl)phenyl)sulfamoyl)-4-methoxybenzoic acid UPLC-MS (Method 1) m/z 503.1 $(M + H)^+$, 501.2 $(M - H)^-$ at 1.47 min. $^1H$ NMR (500 MHz, DMSO-$d_6$) δ 13.19 (br s, 1H), 8.53 (br s, 1H), 8.37 (d, J = 2.2 Hz, 1H), 8.15 (dd, J = 8.7, 2.2 Hz, 1H), 7.37 (d, J = 1.9 Hz, 1H), 7.36-7.29 (m, 3H), 4.67 (d, J = 4.8 Hz, 1H), 3.88 (s, 3H), 3.29-3.23 (m, 1H), 3.04-2.95 (m, 1H), 2.84-2.77 (m, 1H), 2.68-2.60 (m, 1H), 2.31 (d, J = 11.8 Hz, 1H), 1.84-1.76 (m, 1H), 1.76-1.64 (m, 1H), 1.02 (s, 3H), 0.92 (s, 3H). |

-continued

| Example | Structure | Name/Analytical Data |
|---|---|---|
| 25 | 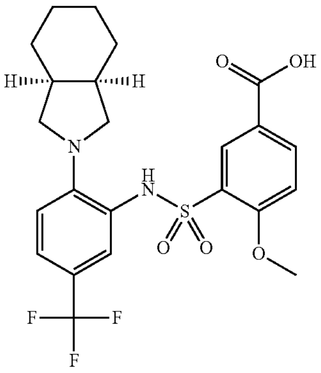 [SMILES: COc1ccc(C(=O)O)cc1S(=O)(=O)Nc1cc(C(F)(F)F)ccc1N1C[C@H]2CCCC[C@H]2C1] | 4-methoxy-3-(N-(2-(cis-octahydroisoindol-2-yl)-5-(trifluoromethyl)phenyl) sulfamoyl)benzoic acid UPLC-MS (Method 1) m/z 499.4 $(M + H)^+$, 497.2 $(M - H)^-$ at 1.72 min. $^1$H NMR (500 MHz, DMSO-$d_6$) δ 13.07 (br s, 1H), 9.28 (br s, 1H), 8.17 (dd, J = 8.7, 2.2 Hz, 1H), 8.06 (d, J = 2.2 Hz, 1H), 7.38 (d, J = 8.7 Hz, 1H), 7.28 (dd, J = 8.9, 2.0 Hz, 1H), 6.72 (d, J = 8.9 Hz, 1H), 6.55 (d, J = 1.9 Hz, 1H), 3.96 (s, 3H), 3.51-3.40 (m, 4H), 2.27-2.17 (m, 2H), 1.61-1.44 (m, 4H), 1.45-1.30 (m, 4H). |
| 26 | 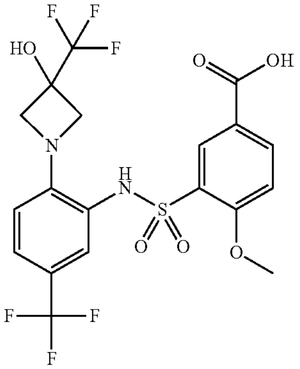 [SMILES: COc1ccc(C(=O)O)cc1S(=O)(=O)Nc1cc(C(F)(F)F)ccc1N1CC(O)(C(F)(F)F)C1] | 3-(N-(2-(3-hydroxy-3-(trifluoromethyl)azetidin-1-yl)-5-(trifluoromethyl)phenyl)sulfamoyl)-4-methoxybenzoic acid UPLC-MS (Method 1) m/z 515.2 $(M + H)^+$, 513.1 $(M - H)^-$ at 1.33 min. $^1$H NMR (500 MHz, DMSO-$d_6$) δ 13.04 (br s, 1H), 9.31 (br s, 1H), 8.16 (d, J = 8.7 Hz, 1H), 8.14-8.09 (m, 1H), 7.42-7.24 (m, 3H), 6.63-6.49 (m, 2H), 4.39 (d, J = 9.7 Hz, 2H), 4.10 (d, J = 9.7 Hz, 2H), 3.94 (s, 3H). |
| 27 | 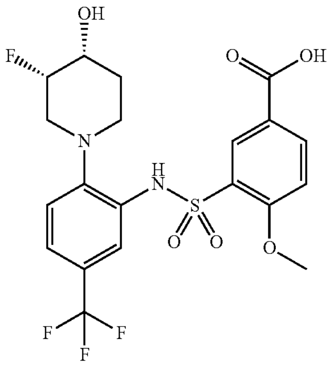 [SMILES: COc1ccc(C(=O)O)cc1S(=O)(=O)Nc1cc(C(F)(F)F)ccc1N1CC[C@@H](O)[C@@H](F)C1] | 3-(N-(2-((3S,4R)-3-fluoro-4-hydroxypiperidin-1-yl)-5-(trifluoromethyl)phenyl)sulfamoyl)-4-methoxybenzoic acid UPLC-MS (Method 1) m/z 493.1 $(M + H)^+$, 491.2 $(M - H)^-$ at 1.29 min. $^1$H NMR (500 MHz, DMSO-$d_6$) δ 13.18 (br s, 1H), 8.71 (br s, 1H), 8.38(d, J = 2.2 Hz, 1H), 8.15 (dd, J = 8.7, 2.3 Hz, 1H), 7.44 (s, 1H), 7.37-7.26 (m, 3H), 5.15 (d, J = 5.3 Hz, 1H), 4.83-4.65 (m, 1H), 3.91 (s, 3H), 3.84-3.72 (m, 1H), 3.21-3.14 (m, 1H), 3.00-2.82 (m, 3H), 1.95-1.74 (m, 2H). |
| 28 | 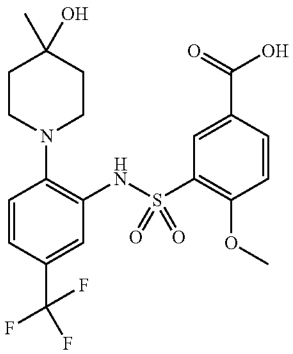 [SMILES: COc1ccc(C(=O)O)cc1S(=O)(=O)Nc1cc(C(F)(F)F)ccc1N1CCC(C)(O)CC1] | 3-(N-(2-(4-hydroxy-4-methylpiperidin-1-yl)-5-(trifluoromethyl)phenyl)sulfamoyl)-4-methoxybenzoic acid UPLC-MS (Method 1) m/z 489.3 $(M + H)^+$, 487.2 $(M - H)^-$ at 1.37 min. $^1$H NMR (500 MHz, DMSO-$d_6$) δ 13.17 (br s, 1H), 8.80 (br s, 1H), 8.36 (d, J = 2.2 Hz, 1H), 8.15 (dd, J = 8.7, 2.2 Hz, 1H), 7.44 (s, 1H), 7.37-7.33 (m, 2H), 7.31 (d, J = 8.8 Hz, 1H), 4.31 (s, 1H), 3.90 (s, 3H), 2.92 (td, J = 11.0, 3.3 Hz, 2H), 2.73-2.65 (m, 2H), 1.66-1.54 (m, 4H), 1.18 (s, 3H). |

Example 29: 3-(N-(2-(3-hydroxy-3-methylpiperidin-1-yl)-5-(trifluoromethyl)phenyl) sulfamoyl)-4-methoxybenzoic acid

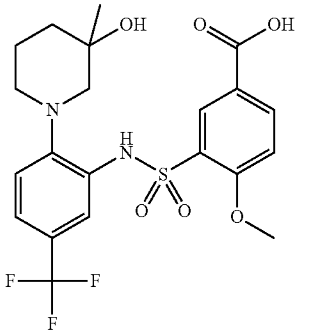 [SMILES: COc1ccc(C(=O)O)cc1S(=O)(=O)Nc1cc(C(F)(F)F)ccc1N1CCCC(C)(O)C1]

Step 1: 3-methyl-1-(2-nitro-4-(trifluoromethyl)phenyl)piperidin-3-ol: $Et_3N$ (0.500 ml, 3.59 mmol) was added to a solution of 1-fluoro-2-nitro-4-(trifluoromethyl)benzene (0.201 ml, 1.44 mmol) and 3-methylpiperidin-3-ol (198 mg, 1.72 mmol) in DCM (6 ml) at RT. The clear solution was stirred at RT for 17 h. The organic phase was washed with 1 M HCl(aq) (3 ml) and the organic phase was dried by passage through a phase separator and concentrated in vacuo to afford the title compound (452 mg, 1.35 mmol, 94% yield, 91% purity) as a red/orange oil. UPLC-MS (Method 1) m/z 305.2 $(M+H)^+$ at 1.49 min. $^1H$ NMR (500 MHz, DMSO-$d_6$) δ 8.07 (d, J=2.3 Hz, 1H), 7.76 (dd, J=9.0, 2.4 Hz, 1H), 7.44 (d, J=8.9 Hz, 1H), 4.51 (s, 1H), 3.16 (ddd, J=13.2, 6.1, 3.7 Hz, 1H), 3.08 (ddd, J=12.8, 8.3, 3.2 Hz, 1H), 3.00 (d, J=12.6 Hz, 1H), 2.90 (d, J=12.7 Hz, 1H), 1.87-1.76 (m, 1H), 1.60-1.55 (m, 2H), 1.55-1.48 (m, 1H), 1.10 (s, 3H).

Step 2: 1-(2-amino-4-(trifluoromethyl)phenyl)-3-methylpiperidin-3-ol: 5% Pd/C (50% w/w water) Type 87L (50 mg, 0.012 mmol) in EtOH (0.5 ml) was added to a solution of the product from step 1 above (224 mg, 0.670 mmol) in EtOH (3.0 ml) at RT. The reaction mixture was hydrogenated at 4 bar at RT for 19 h. The catalyst was removed by filtration through Celite® and washed with MeOH (20 ml). The organic phase was concentrated in vacuo and the residue was redissolved in EtOAc (10 ml). The organic phase was washed with water (5 ml), dried over $MgSO_4$, filtered and concentrated in vacuo to the title compound (112 mg, 0.404 mmol, 60.3% yield, 99% purity) as a pale orange solid. UPLC-MS (Method 1) m/z 275.3 $(M+H)^+$ at 1.42 min. $^1H$ NMR (500 MHz, DMSO-$d_6$) δ 6.94 (d, J=8.1 Hz, 1H), 6.92 (d, J=1.8 Hz, 1H), 6.81 (dd, J=8.1, 1.8 Hz, 1H), 5.27 (br s, 2H), 4.58 (s, 1H), 2.91-2.81 (m, 1H), 2.73-2.67 (m, 1H), 2.60-2.51 (m, 2H), 1.95-1.84 (m, 1H), 1.60-1.50 (m, 2H), 1.47-1.38 (m, 1H), 1.15 (s, 3H).

Step 3: methyl 3-(N-(2-(3-hydroxy-3-methylpiperidin-1-yl)-5-(trifluoromethyl)phenyl)sulfamoyl)-4-methoxybenzoate: Pyridine (0.075 ml, 0.933 mmol) was added to a cloudy solution of the product from step 2 above (64.6 mg, 0.233 mmol) and methyl 3-(chlorosulfonyl)-4-methoxybenzoate (78 mg, 0.280 mmol) in DCM (2.0 ml) at RT. The resultant clear solution was stirred at RT for 20 h. The reaction mixture was concentrated in vacuo and the crude product was purified by chromatography on silica gel (12 g cartridge, 30-100% EtOAc/isohexanes) to afford the title compound (98.5 mg, 0.196 mmol, 84% yield, 100% purity) as an off-white foam. UPLC-MS (Method 1) m/z 503.4 $(M+H)^+$, 501.2 $(M-H)^-$ at 1.66 min.

Step 4: 3-(N-(2-(3-hydroxy-3-methylpiperidin-1-yl)-5-(trifluoromethyl)phenyl)sulfamoyl)-4-methoxybenzoic acid: 1 M LiOH(aq) (0.784 ml, 0.784 mmol) was added to a solution of the product from step 3 above (98.5 mg, 0.196 mmol) in THF (1.57 ml) at RT. The solution was stirred at RT for 18 h and then concentrated in vacuo. The residue was redissolved in water (3 ml) and acidified using 1 M HCl(aq) until pH 4-5. The precipitate was isolated by filtration and then redissolved in EtOAc (5 ml). The organic phase was washed with water (3 ml), dried over $MgSO_4$, filtered and concentrated in vacuo to afford the title compound (64 mg, 0.130 mmol, 73.4% yield, 99% purity) as an off-white solid. UPLC-MS (Method 1) m/z 489.4 $(M+H)^+$, 487.3 $(M-H)^-$ at 1.49 min. $^1H$ NMR (500 MHz, DMSO-$d_6$) δ 13.14 (br s, 1H), 9.44 (br s, 1H), 8.41 (d, J=2.2 Hz, 1H), 8.14 (dd, J=8.7, 2.2 Hz, 1H), 7.54 (d, J=2.1 Hz, 1H), 7.30 (dd, J=8.4, 1.7 Hz, 1H), 7.27 (d, J=8.8 Hz, 1H), 7.20 (d, J=8.3 Hz, 1H), 5.02 (br s, 1H), 3.78 (s, 3H), 2.93-2.85 (m, 1H), 2.63 (td, J=11.1, 2.4 Hz, 1H), 2.56-2.52 (m, 1H), 2.52-2.48 (m, 1H), 2.03-1.90 (m, 1H), 1.62-1.55 (m, 1H), 1.54-1.46 (m, 1H), 1.37 (td, J=12.6, 4.5 Hz, 1H), 1.02 (s, 3H).

Example 30:3-(N-(2-(cis-3,5-dimethylpiperidin-1-yl)-5-(trifluoromethyl)phenyl sulfamoyl)-4-ethylbenzoic acid

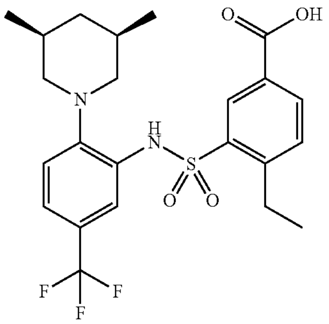 [SMILES: CCc1ccc(C(=O)O)cc1S(=O)(=O)Nc1cc(C(F)(F)F)ccc1N1C[C@H](C)C[C@H](C)C1]

A solution of the product from example 6, step 2, (72 mg, 0.264 mmol) in DCM (1 ml) and pyridine (0.128 ml, 1.59 mmol) were added to a suspension of the product from example 1, step 1, (79 mg, 0.317 mmol) in DCM (1 ml) and the solution was stirred at RT for 4 days. The crude product was purified directly by chromatography on silica gel (12 g cartridge, 0-10% MeOH/DCM). The product from chromatography was partitioned between isohexanes (3 ml) and MeCN (3 ml). The phases were separated, the MeCN phase was washed with isohexanes (2×3 ml) and concentrated in vacuo. The product was loaded onto a silica plug in the minimum amount of DCM, the column was eluted with DCM (5 ml), isohexanes (5 ml), 5% MeOH in EtOAc (5 ml) then 5% MeOH in EtOAc (5 ml) to afford the title compound (26.7 mg, 0.052 mmol, 19.80% yield, 95% purity) as a white solid. UPLC-MS (Method 1) m/z 485.4 $(M+H)^+$, 483.3 $(M-H)^-$ at 2.06 min. $^1H$ NMR (500 MHz, Methanol-$d_4$) δ 8.54 (d, J=1.8 Hz, 1H), 8.15 (dd, J=8.0, 1.8 Hz, 1H), 7.59 (d, J=2.0 Hz, 1H), 7.55 (d, J=8.0 Hz, 1H), 7.36-7.27 (m, 2H), 3.07 (q, J=7.5 Hz, 2H), 2.79-2.72 (m, 2H), 2.18 (t, J=11.1 Hz, 2H), 1.89-1.76 (m, 3H), 1.28 (t, J=7.5 Hz, 3H), 0.90 (d, J=6.5 Hz, 6H), 0.75-0.64 (m, 1H). Two exchangeable protons not observed.

Example 31: 3-(N-(2-(2,2-dimethylpiperidin-1-yl)-5-(trifluoromethyl)phenyl)sulfamoyl)-4-methoxybenzoic acid

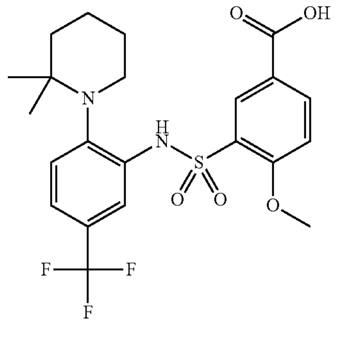

Step 1: 2,2-dimethyl-1-(2-nitro-4-(trifluoromethyl)phenyl)piperidine: $Et_3N$ (0.500 ml, 3.59 mmol) was added to a solution of 2,2-dimethylpiperidine (195 mg, 1.72 mmol) and 1-fluoro-2-nitro-4-(trifluoromethyl)benzene (0.201 ml, 1.44 mmol) in DCM (6 ml) and the resultant solution was stirred at RT for 96 h. Additional 2,2-dimethylpiperidine (75 mg, 0.663 mmol) was added and the reaction was stirred at RT for 1 day. Water (3 ml) was added and the phases were separated before the aqueous phase was extracted with DCM (2×3 ml). The organic phases were combined, dried by passage through a phase separator and concentrated in vacuo. The crude product was purified by chromatography on silica gel (12 g cartridge, 0-100% EtOAc/isohexanes) to afford the title compound (163 mg, 0.512 mmol, 35.7% yield, 95% purity) as a dark orange viscous oil. UPLC-MS (Method 2) m/z 303.3 $(M+H)^+$ at 1.96 min.

Step 2: 2-(2,2-dimethylpiperidin-1-yl)-5-(trifluoromethyl)aniline: Iron powder (297 mg, 5.33 mmol) was added to a solution of the product from step 1 above (161 mg, 0.533 mmol) and ammonium chloride (34.2 mg, 0.639 mmol) in IPA (5 ml) and water (2.5 ml) at RT. The resultant suspension was heated and stirred at 90° C. for 1 h then cooled to RT overnight. Additional iron powder (297 mg, 5.33 mmol) was added and the reaction was heated at 90° C. for a further 2 h then cooled to RT. The reaction mixture was filtered through Celite®, washed with excess MeOH (100 ml) and concentrated in vacuo. The residue was redissolved in DCM (25 ml) and washed with water (5 ml). The aqueous phase was extracted with DCM (2×5 ml) and the combined organic phases were washed with brine (10 ml), dried over $MgSO_4$, filtered and concentrated in vacuo to afford the title compound (78 mg, 0.215 mmol, 40.3% yield, 75% purity) as a pale yellow oil. UPLC-MS (Method 2) m/z 273.3 $(M+H)^+$ at 1.95 min.

Step 3: methyl 3-(N-(2-(2,2-dimethylpiperidin-1-yl)-5-(trifluoromethyl)phenyl)sulfamoyl)-4-methoxybenzoate: The product from step 2 above (51.4 mg, 0.189 mmol) was dissolved in a mixture of DCM (1 ml) and pyridine (0.05 ml, 0.618 mmol) and treated with a solution of methyl 3-(chlorosulfonyl)-4-methoxybenzoate (60 mg, 0.227 mmol) in DCM (1 ml). The resultant solution was stirred at RT for 18 h. The reaction mixture was loaded directly on to silica gel and purified by column chromatography (12 g cartridge, 0-100% EtOAc/isohexanes) to afford the title compound (64 mg, 0.121 mmol, 64.3% yield, 100% purity) as a white sticky solid. UPLC-MS (Method 1) m/z 501.4 $(M+H)^+$, 499.1 $(M-H)^-$ at 1.95 min.

Step 4: 3-(N-(2-(2,2-dimethylpiperidin-1-yl)-5-(trifluoromethyl)phenyl)sulfamoyl)-4-methoxybenzoic acid: The product from step 3 above (62 mg, 0.124 mmol) was dissolved in THF (2 ml) and treated with 1.1 M LiOH(aq) (450 μl, 0.495 mmol). The reaction was stirred at RT for 1 day. MeOH was added dropwise until the mixture was a solution, the reaction mixture was heated at 40° C. for 4 h and then cooled to RT overnight. The reaction mixture was diluted with water (3 ml), concentrated in vacuo and the resultant aqueous solution diluted with water (5 ml). 1 M HCl(aq) was added dropwise to ca. pH 6. The resultant white precipitate was collected by filtration, washing with water. The solid was suspended in MeCN (4 ml), concentrated in vacuo and dried at 45° C. to afford the title compound (57 mg, 0.111 mmol, 90% yield, 99% purity) as a white solid. UPLC-MS (Method 1) m/z 487.3 $(M+H)^+$, 485.2 $(M-H)^-$ at 1.80 min. $^1H$ NMR (500 MHz, DMSO-$d_6$) δ13.20 (br s, 1H), 8.96 (s, 1H), 8.41 (d, J=2.2 Hz, 1H), 8.14 (dd, J=8.7, 2.2 Hz, 1H), 7.59 (s, 1H), 7.47 (d, J=8.3 Hz, 1H), 7.33-7.27 (m, 2H), 3.93 (s, 3H), 1.73-1.55 (m, 6H), 1.32-0.62 (m, 8H).

Example 32: 3-(N-(2-(1,4-oxazepan-4-yl)-5-(trifluoromethyl)phenyl)sulfamoyl)-4-methoxybenzoic acid

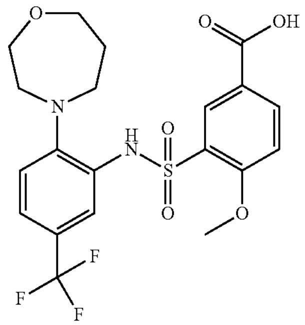 [SMILES: COc1ccc(C(=O)O)cc1S(=O)(=O)Nc1cc(C(F)(F)F)ccc1N1CCCOCC1]

Step 1: 4-(2-nitro-4-(trifluoromethyl)phenyl)-1,4-oxazepane: $Et_3N$ (0.500 ml, 3.59 mmol) was added to a solution of 1-fluoro-2-nitro-4-(trifluoromethyl)benzene (0.201 ml, 1.44 mmol) and 1,4-oxazepane hydrochloride (237 mg, 1.72 mmol) in DCM (6 ml) and the resultant solution was stirred at RT for 7 days. Water (3 ml) was added and the phases were separated using a phase separator. The aqueous phase was extracted with DCM (2×3 ml) and the organic phases were combined, dried by passage through a phase separator and concentrated in vacuo to afford the title compound as a viscous orange oil (429 mg, 1.14 mmol, 98% yield, 95% purity). UPLC-MS (Method 2) m/z 290.8 $(M+H)^+$ at 1.48 min.

Step 2: 2-(1,4-oxazepan-4-yl)-5-(trifluoromethyl)aniline: Iron powder (822 mg, 14.71 mmol) was added to a solution of the product from step 1 above (427 mg, 1.471 mmol) and ammonium chloride (94 mg, 1.765 mmol) in IPA (5 ml) and water (2.5 ml) at RT. The resultant suspension was heated and stirred at 90° C. for 1 h then cooled to RT. The reaction mixture was filtered through Celite®, washed with excess MeOH (100 ml) and concentrated in vacuo. The residue was redissolved In DCM (25 ml) and washed with water (5 ml). The aqueous phase was extracted with DCM (2×5 ml) and the combined organic phases were washed with brine (10 ml), dried over $MgSO_4$, filtered and concentrated in vacuo. The crude product was purified by chromatography on silica gel (12 g cartridge, 0-100% EtOAc/isohexanes) to afford the title compound (186 mg, 0.700 mmol, 47.6% yield, 98% purity) as a dark orange solid. UPLC-MS (Method 2) m/z 261.3 $(M+H)^+$ at 1.39 min.

Step 3: methyl 3-(N-(2-(1,4-oxazepan-4-yl)-5-(trifluoromethyl)phenyl)sulfamoyl)-4-methoxybenzoate: The product from step 2 above (54.8 mg, 0.189 mmol) was dissolved in a mixture of DCM (1 ml) and pyridine (0.05 ml, 0.618 mmol) and treated with a solution of methyl 3-(chlorosulfonyl)-4-methoxybenzoate (60 mg, 0.227 mmol) in DCM (1 ml). The resultant solution was stirred at RT for 18 h. The reaction mixture was loaded directly on silica gel and purified by column chromatography (12 g cartridge, 0-100% EtOAc/isohexanes) to afford the title compound (66 mg, 0.132 mmol, 70.1% yield, 98% purity) as a cream solid. UPLC-MS (Method 1) m/z 489.3 $(M+H)^+$, 487.2 $(M-H)^-$ at 1.59 min.

Step 4: 3-(N-(2-(1,4-oxazepan-4-yl)-5-(trifluoromethyl) phenyl)sulfamoyl)-4-methoxybenzoic acid: The product from step 3 above (64 mg, 0.131 mmol) was dissolved in THF (2 ml), treated with 1.1 M LiOH(aq) (476 µl, 0.524 mmol) and stirred at RT for 1 day. MeOH was added dropwise until the mixture was a solution, the reaction mixture was heated at 40° C. for 4 h then cooled to RT overnight. The reaction mixture was diluted with water (3 ml), concentrated in vacuo and the resultant aqueous solution diluted with water (to ca. 5 ml) and neutralised to ca. pH 6 with 1 M HCl. The resultant lumpy suspension was sonicated to afford a cloudy solution and the white precipitate was collected by filtration, washing with water. The solid was suspended in MeCN (4 ml), concentrated in vacuo and dried at 45° C. to afford the title compound (60 mg, 0.120 mmol, 92% yield, 95% purity) as a pale grey solid. UPLC-MS (Method 1) m/z 475.4 $(M+H)^+$, 473.3 $(M-H)^-$ at 1.43 min. $^1H$ NMR (500 MHz, DMSO-$d_6$) δ 13.12 (s, 1H), 9.11 (s, 1H), 8.23 (s, 1H), 8.16 (dd, J=8.7, 2.2 Hz, 1H), 7.38-7.32 (m, 2H), 7.23 (d, J=8.5 Hz, 1H), 7.10 (s, 1H), 3.93 (s, 3H), 3.76-3.70 (m, 4H), 3.29-3.20 (m, 4H), 1.91 (t, J=5.8 Hz, 2H).

Example 33: 3-(N-(2-(spiro[isobenzofuran-1,4'-piperidin]-1'-yl)-5-(trifluoromethyl)phenyl) sulfamoyl)-4-methoxybenzoic acid

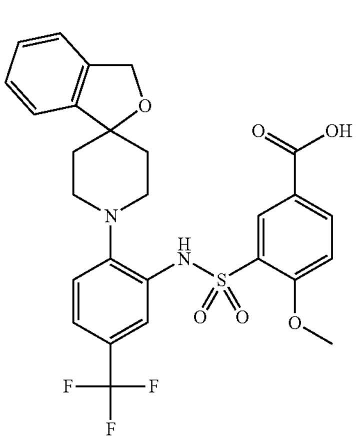 [SMILES: COc1ccc(C(=O)O)cc1S(=O)(=O)Nc1cc(C(F)(F)F)ccc1N1CCC2(CC1)OCc1ccccc12]

Step 1: 1'-(2-nitro-4-(trifluoromethyl)phenyl)spiro [isobenzofuran-1,4'-piperidine]: $Et_3N$ (0.417 ml, 2.99 mmol) was added to a solution of 1-fluoro-2-nitro-4-(trifluoromethyl)benzene (0.167 ml, 1.20 mmol) and spiro [isobenzofuran-1,4'-piperidine]hydrochloride (324 mg, 1.44 mmol) in DCM (6 ml) at RT and the reaction mixture was stirred at RT for 68 h. Water (2 ml) was added and the phases were separated. The aqueous phase was extracted with DCM (2×3 ml) and the combined organic phases were dried by passage through a phase separator and concentrated in vacuo to afford the title compound (536 mg, 0.907 mmol, 76% yield, 64% purity) as an orange oil. UPLC-MS (Method 1) m/z 379.2 $(M+H)^+$ at 1.91 min. $^1H$ NMR (500 MHz, DMSO-$d_6$) δ 8.17 (d, J=1.6 Hz, 1H), 7.86 (dd, J=8.9, 2.3 Hz, 1H), 7.53 (d, J=8.8 Hz, 1H), 7.34-7.27 (m, 4H), 5.04 (s, 2H), 3.39-3.29 (m, 4H), 2.06 (dt, J=17.4, 5.8 Hz, 2H), 1.74 (dd, J=13.9, 2.5 Hz, 2H).

Step 2: 2-(spiro[isobenzofuran-1,4'-piperidin]-1'-yl)-5-(trifluoromethyl)aniline: Iron powder (335 mg, 6.00 mmol) was added to a solution of the product from step 1 above (227 mg, 0.600 mmol) and ammonium chloride (38.5 mg, 0.720 mmol) in IPA (3.5 ml) and water (1.25 ml) and heated to 90° C. for 2 h. The reaction mixture was cooled to RT, filtered and washed with excess MeOH (100 ml). The filtrate was concentrated in vacuo, redissolved in DCM (25 ml) and washed with water (5 ml). The aqueous phase was extracted with DCM (2×5 ml) and the combined organic phases were washed with brine (10 ml), dried by passage through a phase separator and concentrated in vacuo. The crude product was purified by chromatography on silica gel (12 g cartridge, 0-35% EtOAc/isohexanes) to afford the title compound (144 mg, 0.401 mmol, 66.8% yield, 97% purity) as an orange powder. UPLC-MS (Method 1) m/z 349.2 $(M+H)^+$ at 1.83 min. $^1H$ NMR (500 MHz, DMSO-$d_6$) δ7.36-7.24 (m, 4H), 7.07 (d, J=8.1 Hz, 1H), 6.98 (d, J=2.1 Hz, 1H), 6.85 (dd, J=8.2, 2.1 Hz, 1H), 5.22 (s, 2H), 5.03 (s, 2H), 3.12-3.01 (m, 2H), 2.91 (td, J=12.0, 2.3 Hz, 2H), 2.18 (td, J=12.9, 4.5 Hz, 2H), 1.79-1.67 (m, 2H).

Step 3: methyl 3-(N-(2-(spiro[isobenzofuran-1,4'-piperidin]-1'-yl)-5-(trifluoromethyl) phenyl)sulfamoyl)-4-methoxybenzoate: Pyridine (0.058 ml, 0.718 mmol) was added to a solution of the product from step 2 above (86 mg, 0.239 mmol) and methyl 3-(chlorosulfonyl)-4-methoxybenzoate (80 mg, 0.287 mmol) in DCM (2 ml) at RT. The reaction mixture was stirred and heated at 40° C. for 18 h. Additional methyl 3-(chlorosulfonyl)-4-methoxybenzoate (33 mg, 0.120 mmol) was added and the reaction mixture was stirred at 40° C. for a further 3 h. The reaction mixture was concentrated in vacuo and the crude product was purified by chromatography on silica gel (25 g cartridge, 0-45% EtOAc/isohexanes) to afford the title compound (117 mg, 0.187 mmol, 78% yield, 92% purity) as an off-white solid. UPLC-MS (Method 2) m/z 577.4 $(M+H)^+$ 575.2, $(M-H)^-$ at 1.89 min.

Step 4: 3-(N-(2-(spiro[isobenzofuran-1,4'-piperidin]-1'-yl)-5-(trifluoromethyl)phenyl)sulfamoyl)-4-methoxybenzoic acid: 1 M LiOH(aq) (0.812 ml, 0.812 mmol) was added to a solution of the product from step 3 above (117 mg, 0.203 mmol) in THF (1.6 ml) at RT. The solution was stirred at RT for 25 h before concentrating in vacuo. The residue was redissolved in water (3 ml) and acidified using 1 M HCl(aq) until pH 4-5. The precipitate was isolated by filtration and dried in vacuo to afford the title compound (92 mg, 0.164 mmol, 81% yield, 94% purity) as an off-white solid. UPLC-MS (Method 1) m/z 563.3 $(M+H)^+$, 561.1 $(M-H)^-$ at 1.80 min. $^1H$ NMR (500 MHz, DMSO-$d_6$) δ 9.02 (br s, 1H), 8.39 (d, J=2.3 Hz, 1H), 8.15 (dd, J=8.7, 2.2 Hz, 1H), 7.51 (d, J=1.7 Hz, 1H), 7.39-7.27 (m, 7H), 5.02 (s, 2H), 3.88 (s, 3H), 3.01 (t, J=11.9 Hz, 2H), 2.96-2.90 (m, 2H), 2.19-2.08 (m, 2H), 1.73-1.65 (m, 2H). One exchangeable proton not seen.

The following examples were prepared by methods analagous to Example 33, substituting appropriate starting materials and intermediates where necessary:

| Example | Structure | Name/Analytical Data |
|---|---|---|
| 34 | 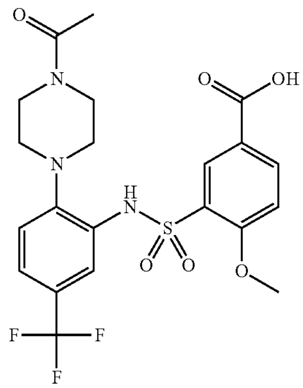 [SMILES: COc1ccc(C(=O)O)cc1S(=O)(=O)Nc1cc(C(F)(F)F)ccc1N1CCN(C(C)=O)CC1] | 3-(N-(2-(4-acetylpiperazin-1-yl)-5-(trifluoromethyl)phenyl)sulfamoyl)-4-methoxybenzoic acid<br>UPLC-MS (Method 1) m/z 502.3 $(M + H)^+$, 500.2 $(M - H)^-$ at 1.28 min. $^1H$ NMR (500 MHz, DMSO-$d_6$) δ 13.00 (s, 1H), 9.14 (s, 1H), 8.35 (d, J = 2.1 Hz, 1H), 8.16 (dd, J = 8.7, 2.2 Hz, 1H), 7.48 (d, J = 2.0 Hz, 1H), 7.38 (dd, J = 8.5, 2.0 Hz, 1H), 7.32 (m, 2H), 3.91 (s, 3H), 3.64-3.53 (m, 4H), 2.83 (t, J = 4.8 Hz, 2H), 2.74 (t, J = 5.0 Hz, 2H), 2.04 (s, 3H). |
| 35 | 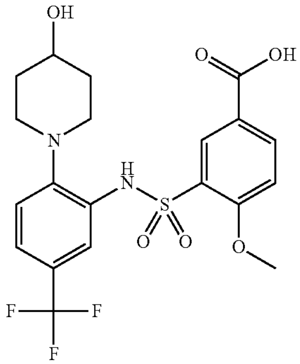 [SMILES: COc1ccc(C(=O)O)cc1S(=O)(=O)Nc1cc(C(F)(F)F)ccc1N1CCC(O)CC1] | 3-(N-(2-(4-hydroxypiperidin-1-yl)-5-(trifluoromethyl)phenyl)sulfamoyl)-4-methoxybenzoic acid<br>UPLC-MS (Method 1) m/z 475.4 $(M + H)^+$, 473.2 $(M - H)^-$ at 1.31 min. $^1H$ NMR (500 MHz, DMSO-$d_6$) δ 13.16 (br s, 1H), 8.80 (br s, 1H), 8.36 (d, J = 2.2 Hz, 1H), 8.15 (dd, J = 8.7, 2.2 Hz, 1H), 7.46-7.40 (m, 1H), 7.37-7.28 (m, 3H), 4.71 (d, J = 4.1 Hz, 1H), 3.92 (s, 3H), 3.68-3.59 (m, 1H), 2.94 (dt, J = 10.4, 4.5 Hz, 2H), 2.66 (ddd, J = 12.1, 9.6, 2.9 Hz, 2H), 1.90-1.79 (m, 2H), 1.63-1.51 (m, 2H). |
| 36 | 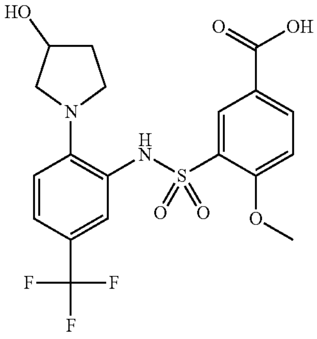 | 3-(N-(2-(3-hydroxypyrrolidin-1-yl)-5-(trifluoromethyl)phenyl)sulfamoyl)-4-methoxybenzoic acid<br>UPLC-MS (Method 1) m/z 461.3 $(M + H)^+$, 459.2 $(M - H)^-$ at 1.18 min. $^1H$ NMR (500 MHz, DMSO-$d_6$) δ 13.03 (br s, 1H), 9.28 (br s, 1H), 8.17 (dd, J = 8.7, 2.2 Hz, 1H), 8.06 (d, J = 2.2 Hz, 1H), 7.38 (d, J = 8.8 Hz, 1H), 7.29 (dd, J = 8.8, 2.3 Hz, 1H), 6.74 (d, J = 8.8 Hz, 1H), 6.51 (d, J = 2.3 Hz, 1H), 4.96 (br s, 1H), 4.34 (p, J = 4.2 Hz, 1H), 3.98 (s, 3H), 3.79 (dd, J = 10.9, 4.7 Hz, 1H), 3.59-3.52 (m, 1H), 3.49-3.44 (m, 1H), 3.38-3.33 (m, 1H), 1.97-1.83 (m, 1H), 1.84 (td, J = 7.7, 3.4 Hz, 1H). |
| 37 | 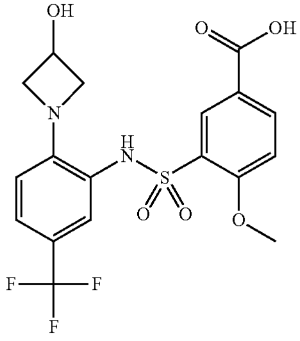 [SMILES: COc1ccc(C(=O)O)cc1S(=O)(=O)Nc1cc(C(F)(F)F)ccc1N1CC(O)C1] | 3-(N-(2-(3-hydroxyazetidin-1-yl)-5-(trifluoromethyl)phenyl)sulfamoyl)-4-methoxybenzoic acid<br>UPLC-MS (Method 1) m/z 447.3 $(M + H)^+$, 445.2 $(M - H)^-$ at 1.12 min. $^1H$ NMR (500 MHz, DMSO-$d_6$) δ 13.05 (br s, 1 H), 9.23 (br s, 1H), 8.18 (dd, J = 8.7, 2.3 Hz, 1H), 8.12 (d, J = 2.2 Hz, 1H), 7.39 (d, J = 8.8 Hz, 1H), 7.30 (dd, J = 8.6, 2.1 Hz, 1H), 6.52-6.44 (m, 2H), 5.62 (br s, 1H), 4.55-4.49 (m, 1H), 4.35 (dd, J = 8.6, 6.6 Hz, 2H), 3.95 (s, 3H), 3.80 (dd, J = 8.8, 4.8 Hz, 2H). |

-continued

| Example | Structure | Name/Analytical Data |
|---|---|---|
| 39 | 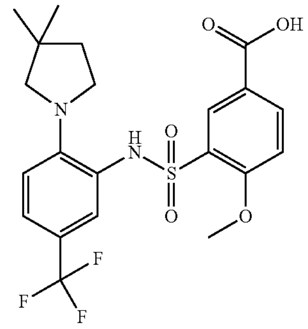 [SMILES: COc1ccc(C(=O)O)cc1S(=O)(=O)Nc1cc(C(F)(F)F)ccc1N1CCC(C)(C)C1] | 3-(N-(2-(3,3-dimethylpyrrolidin-1-yl)-5-(trifluoromethyl)phenyl)sulfamoyl)-4-methoxybenzoic acid UPLC-MS (Method 1) m/z 473.4 (M + H)$^+$, 471.2 (M − H)$^-$ at 1.63 min. $^1$H NMR (500 MHz, DMSO-$d_6$) δ 13.12 (s, 1H), 9.11 (s, 1H), 8.23 (d, J = 2.2 Hz, 1H), 8.16 (dd, J = 8.7, 2.2 Hz, 1H), 7.38-7.32 (m, 2H), 7.26-7.20 (m, 1H), 7.10 (s, 1H), 3.93 (s, 3H), 3.77-3.70 (m, 4H), 3.29-3.20 (m, 4H), 1.91 (t, J = 5.8 Hz, 2H). Two protons obscured by solvent. |
| 40 | 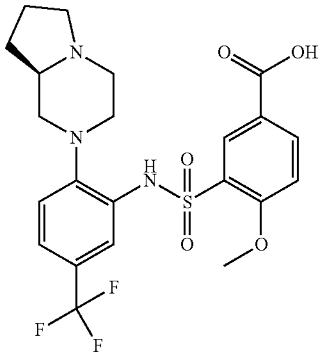 [SMILES: COc1ccc(C(=O)O)cc1S(=O)(=O)Nc1cc(C(F)(F)F)ccc1N1CCN2CCC[C@@H]2C1] | (R)-3-(N-(2-(hexahydropyrrolo[1,2-a]pyrazin-2(1H)-yl)-5-(trifluoromethyl)phenyl) sulfamoyl)-4-methoxybenzoic acid UPLC-MS (Method 1) m/z 500.3 (M + H)$^+$, 498.4 (M − H)$^-$ at 0.87 min. $^1$H NMR (500 MHz, DMSO-$d_6$) δ 13.13 (s, 1H), 9.40 (s, 1H), 8.34 (d, J = 2.2 Hz, 1H), 8.17 (dd, J = 8.7, 2.2 Hz, 1H), 7.47-7.41 (m, 2H), 7.39-7.30 (m, 2H), 3.86 (s, 3H), 3.21-2.83 (m, 6H), 2.04-1.88 (m, 3H), 1.23 (s, 2H). Two protons obscured by solvent. |

Example 41: 4-methoxy-3-(N-(2-(2-oxopiperidin-1-yl)-5-(trifluoromethyl)phenyl) sulfamoyl)benzoic acid

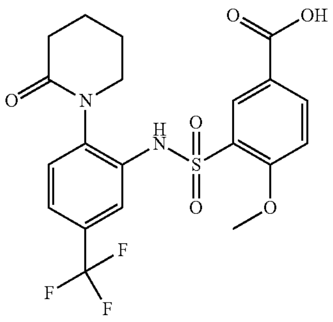 [SMILES: COc1ccc(C(=O)O)cc1S(=O)(=O)Nc1cc(C(F)(F)F)ccc1N1CCCCC1=O]

Step 1: 1-(2-nitro-4-(trifluoromethyl)phenyl)piperidin-2-one: NaH (63.1 mg, 1.58 mmol, 60% w/w in mineral oil) was added to a solution of piperidin-2-one (142 mg, 1.44 mmol) in anhydrous DMF (3 ml) at 0° C. under $N_2$. The reaction was stirred at this temperature for 10 min then a solution of 1-fluoro-2-nitro-4-(trifluoromethyl)benzene (0.201 ml, 1.44 mmol) in anhydrous DMF (3 ml) was added dropwise at 0° C. The reaction was stirred at RT overnight. The reaction mixture was diluted with EtOAc (100 ml) and washed sequentially with water (50 ml) and brine (2×50 ml). The organic phase was separated, dried over $MgSO_4$, filtered and concentrated under reduced pressure. The crude product was purified by chromatography on silica gel (12 g cartridge, 0-100% EtOAc/isohexane) to afford the title compound (245 mg, 0.808 mmol, 56.3% yield, 100% purity) as a light yellow solid. UPLC-MS (Method 2) m/z 289.5 (M+H)$^+$ at 1.23 min.

Step 2: 1-(2-amino-4-(trifluoromethyl)phenyl)piperidin-2-one: Iron powder (508 mg, 9.09 mmol) was added to a suspension of the product from step 1 above (131 mg, 0.455 mmol) and ammonium chloride (29.2 mg, 0.545 mmol) in propan-2-ol (5 ml) and water (2.5 ml) at RT. The resulting suspension was heated and stirred at 90° C. for 2 h. The reaction was filtered through Celite®, washed with excess MeOH (100 ml) and concentrated in vacuo. The residue was redissolved in DCM (25 ml) and washed sequentially with water (10 ml) and brine (10 ml), dried over $MgSO_4$, filtered and concentrated in vacuo. The crude product was purified by chromatography on silica gel (12 g cartridge, 0-100% EtOAc/isohexane) to afford the title compound (22 mg, 0.076 mmol, 16.7% yield, 89% purity) as a cream solid. UPLC-MS (Method 2) m/z 259.3 (M+H)$^+$ at 1.07 min.

Step 3: methyl 4-methoxy-3-(N-(2-(2-oxopiperidin-1-yl)-5-(trifluoromethyl)phenyl) sulfamoyl)benzoate: The product from step 2 above (22 mg, 0.085 mmol) was dissolved in a mixture of DCM (0.5 ml) and pyridine (22.5 μl, 0.279 mmol) and treated with a solution methyl 3-(chlorosulfonyl)-4-methoxybenzoate (27.1 mg, 0.102 mmol) in DCM (0.5 ml). The resultant solution was stirred at RT for 18 h. More methyl 3-(chlorosulfonyl)-4-methoxybenzoate (11.3 mg, 0.043 mmol) and pyridine (6.89 μl, 0.085 mmol) were added and the reaction mixture was stirred at RT for 1 h. The crude product was purified directly by chromatography on silica gel (12 g cartridge, 0-100% EtOAc/isohexane) to afford the title compound (18.6 mg, 0.037 mmol, 43.5% yield, 97% purity) as a white solid. UPLC-MS (Method 1) m/z 487.6 (M+H)$^+$, 484.8 (M−H)$^-$ at 1.40 min.

Step 4: 4-methoxy-3-(N-(2-(2-oxopiperidin-1-yl)-5-(trifluoromethyl)phenyl)sulfamoyl)benzoic acid: The product from step 3 above (18.6 mg, 0.038 mmol) was dissolved in THF (1 ml) and treated with 1.1 M LiOH(aq) (139 μl, 0.153 mmol). The reaction was stirred at RT for 1 day then MeOH was added dropwise until the mixture was a solution and the reaction mixture was heated at 40° C. for 20 h before cooling to RT. The reaction mixture was diluted with water (3 ml), concentrated in vacuo and the resultant aqueous solution diluted with water (to ~5 ml) and neutralised to ~pH 6 with 1 M HCl. The white precipitate was collected by filtration, washing with water. The solid was suspended in MeCN (4 ml), concentrated in vacuo and dried at 45° C. to afford the title compound (17.1 mg, 0.034 mmol, 90% yield, 95% purity) as a pale yellow solid. UPLC-MS (Method 1) m/z 473.0 $(M+H)^+$, 471.1 $(M-H)^-$ at 1.23 min. $^1H$ NMR (500 MHz, DMSO-$d_6$) δ 13.12 (s, 1H), 9.70 (s, 1H), 8.33 (d, J=2.2 Hz, 1H), 8.15 (dd, J=8.7, 2.2 Hz, 1H), 7.65 (s, 1H), 7.54-7.39 (m, 2H), 7.31 (d, J=8.8 Hz, 1H), 3.80 (s, 3H), 3.09-3.23 (m, 2H), 2.44-2.22 (m, 2H), 1.90-1.70 (m, 4H).

Example 42: 3-(N-(2-(1,4-oxazepan-4-yl)-5-(trifluoromethyl)phenyl)sulfamoyl)-4-methylbenzoic acid

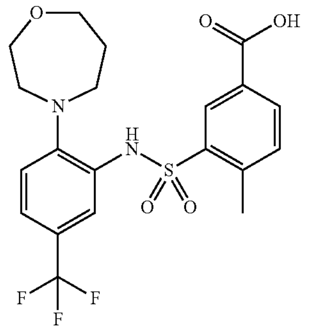 [SMILES: Cc1ccc(C(=O)O)cc1S(=O)(=O)Nc1cc(C(F)(F)F)ccc1N1CCCOCC1]

A solution of the product from example 32, step 2 above 62 mg, 0.238 mmol) in DCM (1 ml) and pyridine (0.116 ml, 1.43 mmol) were added to a solution of 3-(chlorosulfonyl)-4-methylbenzoic acid (67.1 mg, 0.286 mmol) in DCM (1 ml) and the solution was stirred at RT for 4 days. The crude product was purified directly by chromatography on silica gel (12 g cartridge, 0-10% MeOH/DCM) to afford a cream solid (23 mg). 8 mg of this crude product was loaded onto a silica plug in the minimal amount of DCM, the column was eluted with DCM (5 ml), isohexanes (5 ml), 5% MeOH in EtOAc (5 ml) then 20% MeOH in EtOAc (5 ml) to afford the title compound (7.0 mg, 0.015 mmol, 6.09% yield, 95% purity) as a white solid. UPLC-MS (Method 1) m/z 459.4 $(M+H)^+$, 457.3 $(M-H)^-$ at 1.64 min. $^1H$ NMR (500 MHz, Methanol-$d_4$) δ 8.58 (d, J=2.1 Hz, 1H), 8.48 (s, 1H), 8.00 (dd, J=7.9, 2.1 Hz, 1H), 7.52-7.42 (m, 3H), 3.97 (t, J=6.2 Hz, 2H), 3.94-3.89 (m, 2H), 3.28-3.22 (m, 4H), 2.79 (s, 3H), 2.15-2.07 (m, 2H). Two exchangeable protons not observed.

Example 43: 3-(N-(2-(1,4-oxazepan-4-yl)-5-(trifluoromethyl)phenyl)sulfamoyl)-4-ethylbenzoic acid

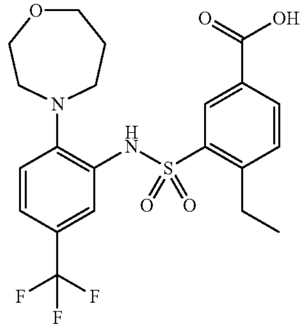 [SMILES: CCc1ccc(C(=O)O)cc1S(=O)(=O)Nc1cc(C(F)(F)F)ccc1N1CCCOCC1]

A solution of the product from example 32, step 2 above (62 mg, 0.238 mmol) in DCM (1 ml) and pyridine (0.116 ml, 1.429 mmol) were added to a solution of the product from example 1, step 1 above (71.1 mg, 0.286 mmol) in DCM (1 ml) and the solution was stirred at RT for 4 days. The crude product was purified directly by chromatography on silica gel (12 g cartridge, 0-10% MeOH/DCM) to afford a cream solid. This was loaded onto a silica plug in the minimal amount of DCM, the column was eluted sequentially with DCM (5 ml), isohexanes (5 ml), 5% MeOH in EtOAc (5 ml) then 5% MeOH in EtOAc (5 ml) to afford the title compound (11.7 mg, 0.024 mmol, 9.87% yield, 95% purity) as a white solid. UPLC-MS (Method 1) m/z 473.4 $(M+H)^+$, 471.2 $(M-H)^-$ at 1.61 min. $^1H$ NMR (500 MHz, Methanol-$d_4$) δ 8.53 (d, J=1.8 Hz, 1H), 8.17 (dd, J=8.0, 1.8 Hz, 1H), 7.57 (d, J=8.0 Hz, 1H), 7.34-7.28 (m, 3H), 3.90 (t, J=5.9 Hz, 2H), 3.86-3.81 (m, 2H), 3.23-3.16 (m, 4H), 3.08 (q, J=7.5 Hz, 2H), 2.02 (p, J=5.8 Hz, 2H), 1.29 (t, J=7.5 Hz, 3H). Two exchangeable protons not observed.

Example 46: 4-methoxy-3-(N-(2-(2-(3-methylisoxazol-5-yl) pyrrolidin-1-yl)-5-(trifluoromethyl)phenyl) sulfamoyl)benzoic acid

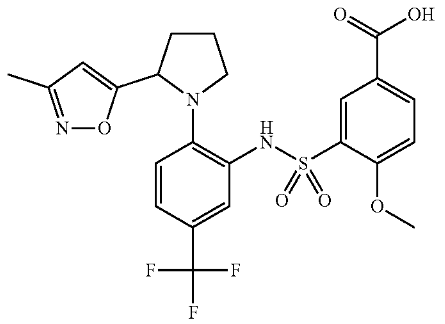

Step 1: 3-methyl-5-(1-(2-nitro-4-(trifluoromethyl)phenyl) pyrrolidin-2-yl) isoxazole: $Et_3N$ (302 mg, 2.99 mmol) was added to a solution of 1-fluoro-2-nitro-4-(trifluoromethyl) benzene (0.167 ml, 1.20 mmol) and 3-methyl-5-(pyrrolidin-2-yl) isoxazole (218 mg, 1.44 mmol) in DCM (5 ml) and the resultant solution was stirred at RT for 19 h. Water (2.5 ml) was added and the organic phase was dried by passage through a phase separator and concentrated in vacuo to give the title compound (489 mg, 1.19 mmol, 99% yield, 83% purity) as a yellow oil. UPLC-MS (Method 2) m/z 342.4 $(M+H)^+$ at 1.61 min. $^1H$ NMR (500 MHz, DMSO-$d_6$) δ 8.07 (m, 1H), 7.71 (dd, J=9.1, 2.0 Hz, 1H), 7.17 (d, J=9.1 Hz, 1H), 6.18 (s, 1H), 5.34 (t, J=7.3 Hz, 1H), 3.55-3.50 (m, 1H), 3.02-2.98 (m, 1H), 2.54-2.51 (m, 1H), 2.16 (s, 3H), 2.08-2.02 (m, 1H), 2.02-1.89 (m, 2H).

Step 2: 2-(2-(3-methylisoxazol-5-yl) pyrrolidin-1-yl)-5-(trifluoromethyl)aniline: Ammonium hydroxide (28% aq. Solution) (0.319 ml, 2.30 mmol) and sodium dithionite (1.18 g, 5.74 mmol) were added to a solution of the product from step 1 above (236 mg, 0.574 mmol) in THF (2.5 ml) and water (2.5 ml) at RT and then stirred at RT for 2 h. The reaction mixture was concentrated in vacuo and the residue was redissolved in DCM (10 ml) and washed with water (5 ml). The aqueous phase was extracted with DCM (2×5 ml) and the organic phases were combined, washed with brine (5 ml), dried by passage through a phase separator and concentrated in vacuo. The crude product was purified by chromatography on silica gel (10 g cartridge, 0-50% EtOAc/isohexanes) to afford the title compound (95 mg, 0.302 mmol, 52.6% yield, 99% purity) as a red/brown oil. UPLC-MS (Method 1) m/z 312.1 $(M+H)^+$ at 1.52 min. 1H NMR (500 MHz, DMSO-$d_6$) δ 7.03 (d, J=8.2 Hz, 1H), 6.92 (d, J=2.2 Hz, 1H), 6.74 (dd, J=8.3, 2.1 Hz, 1H), 6.05 (s, 1H), 5.17 (s, 2H), 4.98 (dd, J=7.9, 5.9 Hz, 1H), 3.72-3.65 (m, 1H), 2.76-2.68 (m, 1H), 2.45-2.37 (m, 1H), 2.10 (s, 3H), 2.08-1.99 (m, 1H), 1.98-1.87 (m, 2H).

Step 3: methyl 4-methoxy-3-(N-(2-(2-(3-methylisoxazol-5-yl) pyrrolidin-1-yl)-5-(trifluoromethyl)phenyl)sulfamoyl) benzoate: Pyridine (0.069 ml, 0.852 mmol) was added to a solution of the product from step 2 above (88 mg, 0.284 mmol) and methyl 3-(chlorosulfonyl)-4-methoxybenzoate (95 mg, 0.341 mmol) in DCM (2.5 ml) at RT. The reaction mixture was stirred at RT for 65 h and then at 40° C. for 5 h. The crude reaction mixture was filtered and the filtered product was redissolved in MeCN (10 ml) and concentrated in vacuo to afford the title compound (69 mg, 0.123 mmol, 43.2% yield, 96% purity) as an off-white solid. UPLC-MS (Method 2) m/z 540.3 $(M+H)^+$, 538.2 $(M-H)^-$ at 1.58 min.

Step 4: 4-methoxy-3-(N-(2-(2-(3-methylisoxazol-5-yl) pyrrolidin-1-yl)-5-(trifluoromethyl)phenyl)sulfamoyl)benzoic acid: 1 M LiOH(aq) (0.384 ml, 0.384 mmol) was added to a suspension of the product from step 3 above (69 mg, 0.128 mmol) in THF (0.768 ml) at RT. The resultant clear solution was stirred at RT for 20 h. Additional 1 M LiOH(aq) (0.128 ml, 0.128 mmol) was added and the solution was stirred for a further 1 h. The reaction mixture was concentrated in vacuo and the residue was redissolved in water (2 ml) and acidified using 1 M HCl(aq) until pH 4-5. The precipitate was dissolved in DCM (10 ml) and the phases were separated. The aqueous phase was extracted with DCM (2×3 ml) and the combined organic phases were dried by passage through a phase separator and concentrated in vacuo to afford the title compound (47.9 mg, 0.091 mmol, 71.3% yield, 97% purity) as a light yellow solid. UPLC-MS (Method 1) m/z 526.3 $(M+H)^+$, 524.2 $(M-H)^-$ at 1.46 min. $^1H$ NMR (500 MHz, DMSO-$d_6$) δ 13.08 (br s, 1H), 9.39 (br s, 1H), 8.17 (dd, J=8.7, 2.3 Hz, 1H), 8.10 (d, J=2.2 Hz, 1H), 7.38 (d, J=8.8 Hz, 1H), 7.27 (dd, J=8.8, 2.3 Hz, 1H), 6.78 (d, J=8.8 Hz, 1H), 6.67 (d, J=2.3 Hz, 1H), 6.02 (s, 1H), 5.35 (t, J=6.4 Hz, 1H), 4.01 (app. Dt, J=9.7, 7.0 Hz, 1H), 3.95 (s, 3H), 3.45 (ddd, J=9.9, 7.3, 5.2 Hz, 1H), 2.40-2.35 (m, 1H), 2.13 (s, 3H), 2.01-1.85 (m, 3H).

Example 49 Methyl Ester: methyl 4-methoxy-3-((2-(piperidin-1-yl)-5-(trifluoromethyl)phenyl)sulfonamido)benzoate

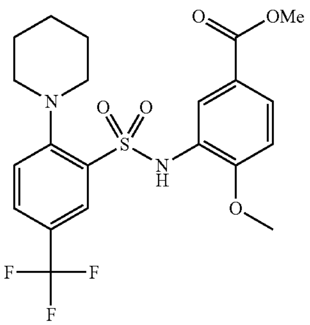 [SMILES: COC(=O)c1ccc(OC)c(NS(=O)(=O)c2cc(C(F)(F)F)ccc2N2CCCCC2)c1]

Step 1: methyl 3-(2-bromo-5-(trifluoromethyl)phenylsulfonamido)-4-methoxybenzoate: A mixture of 2-bromo-5-(trifluoromethyl)benzene-1-sulfonyl chloride (230 μl, 1.32 mmol), methyl 3-amino-4-methoxybenzoate (200 mg, 1.10 mmol) and pyridine (268 μl, 3.31 mmol) in DCM (4 ml) was stirred at RT over the weekend. The mixture was concentrated onto silica and purified by chromatography on silica gel (24 g cartridge, 0-100% EtOAc/isohexanes) to afford the title compound (510 mg, 1.07 mmol, 97% yield, 98% purity) as a pale beige solid. UPLC-MS (Method 2) m/z 468.0/470.0 $(M/M+2)^+$ at 1.43 min. $^1H$ NMR (500 MHz, DMSO-$d_6$) δ 10.26 (s, 1H), 8.12 (d, J=8.3 Hz, 1H), 8.10 (d, J=2.2 Hz, 1H), 7.92 (dd, J=8.3, 2.2 Hz, 1H), 7.83-7.77 (m, 2H), 7.08 (d, J=8.6 Hz, 1H), 3.80 (s, 3H), 3.56 (s, 3H).

Step 2: methyl 4-methoxy-3-(2-(piperidin-1-yl)-5-(trifluoromethyl)phenylsulfonamido)benzoate: A mixture of the product from step 1 above (100 mg, 0.214 mmol) and piperidine (25 μl, 0.253 mmol) in THF (1 ml) was heated to 60° C. and stirred overnight. Additional piperidine (25 μl, 0.253 mmol) was added and stirring at 60° C. was continued for 7 h. Additional piperidine (25 μl, 0.253 mmol) was added and stirring at 60° C. was continued overnight. Upon cooling to RT the mixture was concentrated in vacuo and the residue was loaded onto silica and purified by chromatography on silica gel (12 g cartridge, 0-100% EtOAc/isohexanes) to afford the title compound (82 mg, 0.165 mmol, 78% yield, 95% purity) as a white solid. UPLC-MS (Method 2) m/z 473.3 $(M+H)^+$ at 1.84 min. $^1H$ NMR (500 MHz, DMSO-$d_6$) δ 9.04 (s, 1H), 8.05 (s, 1H), 7.93 (d, J=8.4 Hz, 1H), 7.87 (s, 1H), 7.67 (d, J=8.7 Hz, 1H), 7.59 (d, J=8.4 Hz, 1H), 7.05 (d, J=8.7 Hz, 1H), 3.78 (s, 3H), 3.73 (s, 3H), 2.92 (t, J=5.3 Hz, 4H), 1.77-1.65 (m, 4H), 1.57-1.51 (m, 2H).

Example 49:4-methoxy-3-((2-(piperidin-1-yl)-5-(trifluoromethyl)phenyl) sulfonamido)benzoic acid

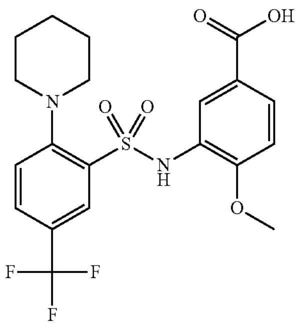

A mixture of the product from example 49 methyl ester, step 2 above 70 mg, 0.148 mmol) in THF (1.25 ml) and 2 M LiOH(aq) (0.25 ml, 0.500 mmol) was stirred at 50° C. overnight. Additional 2 M LiOH(aq) (0.25 ml, 0.500 mmol) was added and stirring at 50° C. was continued for 5 h. The mixture was diluted with $H_2O$ (5 ml), acidified to ca. pH 4 with 1 M HCl(aq) and extracted with EtOAc (3×10 ml). The combined organic extracts were washed with brine (10 ml), passed through a phase separator and the solvent was removed in vacuo. The residue was loaded onto silica and purified by chromatography on silica gel (4 g cartridge, 0-10% MeOH/DCM) and triturated with TBME to afford the title compound (44.3 mg, 0.093 mmol, 62.6% yield, 96% purity) as a white solid. UPLC-MS (Method 2) m/z 459.3 $(M+H)^+$, 457.2 $(M-H)^-$ at 1.19 min. $^1H$ NMR (500 MHz, DMSO-$d_6$) δ 12.71 (s, 1H), 8.99 (s, 1H), 8.05 (d, J=2.3 Hz, 1H), 7.93 (dd, J=8.5, 2.3 Hz, 1H), 7.89 (d, J=2.1 Hz, 1H), 7.64 (dd, J=8.7, 2.1 Hz, 1H), 7.60 (d, J=8.5 Hz, 1H), 7.02 (d, J=8.7 Hz, 1H), 3.71 (s, 3H), 2.92 (t, J=5.1 Hz, 4H), 1.76-1.65 (m, 4H), 1.59-1.48 (m, 2H).

General Compound A: 4-methoxy-2-((2-(piperidin-1-yl)-5-(trifluoromethyl)phenyl) sulfonamido)benzoic acid

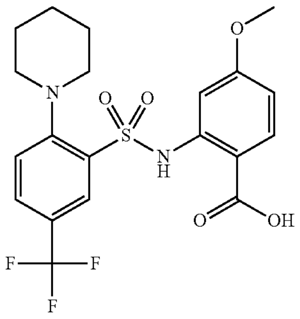

Step 1: methyl 2-(2-fluoro-5-(trifluoromethyl)phenylsulfonamido)-4-methoxybenzoate: A mixture of 2-fluoro-5-(trifluoromethyl)benzene-1-sulfonyl chloride (87 mg, 0.331 mmol), methyl 2-amino-4-methoxybenzoate (50 mg, 0.276 mmol) and pyridine (0.067 ml, 0.828 mmol) in DCM (2 ml) was stirred at RT overnight. The mixture was concentrated onto silica and purified by chromatography on silica gel (12 g cartridge, 0-100% EtOAc/isohexanes) to afford the title compound (98 mg, 0.180 mmol, 65.4% yield, 75% purity) as a white solid. UPLC-MS (Method 2) 405.5 $(M-H)^-$ at 1.67 min. $^1H$ NMR (500 MHz, DMSO-$d_6$) δ 11.13 (s, 1H), 8.24-8.12 (m, 2H), 7.87 (d, J=8.9 Hz, 1H), 7.73 (t, J=9.5 Hz, 1H), 6.94 (d, J=2.5 Hz, 1H), 6.83-6.76 (m, 1H), 3.79 (s, 3H), 3.77 (s, 3H).

Step 2: methyl 4-methoxy-2-(2-(piperidin-1-yl)-5-(trifluoromethyl)phenyl sulfonamido)benzoate: A mixture of the product from step 1 above (98 mg, 0.180 mmol) and piperidine (0.06 ml, 0.606 mmol) in THF (2 ml) was stirred at 60° C. for 6 days. The mixture was concentrated onto silica and purified by chromatography on silica gel (12 g cartridge, 0-50% EtOAc/isohexanes) to afford the title compound (52 mg, 0.109 mmol, 60.4% yield, 99% purity) as a white solid. UPLC-MS (Method 2) m/z 473.3 $(M+H)^+$ at 2.01 min. $^1H$ NMR (500 MHz, DMSO-$d_6$) δ 11.11 (s, 1H), 8.28 (d, J=2.3 Hz, 1H), 8.06-7.95 (m, 1H), 7.85 (d, J=8.9 Hz, 1H), 7.59 (d, J=8.5 Hz, 1H), 6.73 (d, J=2.5 Hz, 1H), 6.63 (dd, J=8.9, 2.5 Hz, 1H), 3.84 (s, 3H), 3.66 (s, 3H), 2.84 (t, J=5.3 Hz, 4H), 1.74-1.64 (m, 4H), 1.58-1.49 (m, 2H).

Step 3: 4-methoxy-2-(2-(piperidin-1-yl)-5-(trifluoromethyl)phenylsulfonamido)benzoic acid: A mixture of the product from step 2 above (52 mg, 0.109 mmol) and 2 M LiOH(aq) (250 µl, 0.500 mmol) in THF (1.25 ml) was stirred at 50° C. overnight. The mixture was diluted with $H_2O$ (2 ml) and acidified to ca. pH 4 with 1 M HCl. The mixture was extracted with EtOAc (3×15 ml), the combined organic extracts were washed with brine, passed through a phase separator and the solvent was removed in vacuo. The residue was loaded onto silica and purified by chromatography on silica gel (4 g cartridge, 0-5% MeOH/DCM) to afford the title compound (14.1 mg, 0.030 mmol, 27.1% yield, 96% purity) as a white solid. UPLC-MS (Method 2) m/z 459.3 $(M+H)^+$, 457.2 $(M-H)^-$ at 1.22 min. $^1H$ NMR (500 MHz, DMSO-$d_6$) δ 13.63 (s, 1H), 11.65 (s, 1H), 8.29 (d, J=2.3 Hz, 1H), 7.99 (dd, J=8.5, 2.3 Hz, 1H), 7.83 (d, J=8.9 Hz, 1H), 7.58 (d, J=8.5 Hz, 1H), 6.65 (d, J=2.4 Hz, 1H), 6.57 (dd, J=8.9, 2.4 Hz, 1H), 3.64 (s, 3H), 2.86 (t, J=5.1 Hz, 4H), 1.77-1.66 (m, 4H), 1.60-1.46 (m, 2H).

The following examples were prepared by methods analogous to General Compound A substituting appropriate starting materials and intermediates where necessary:

| Example | Structure | Name/Analytical Data |
|---|---|---|
| 51 | 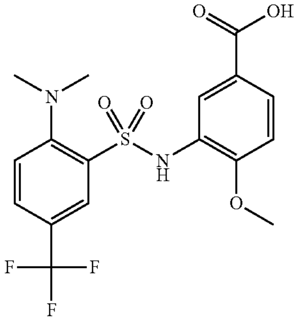 | 3-((2-(dimethylamino)-5-(trifluoromethyl) phenyl)sulfonamido)-4-methoxybenzoic acid UPLC-MS (Method 2) m/z 419.2 (M + H)$^+$, 417.1 (M − H)$^-$ at 1.02 min. $^1$H NMR (500 MHz, DMSO-$d_6$) δ 12.65 (s, 1H), 9.51 (s, 1H), 8.04 (d, J = 2.3 Hz, 1H), 7.86-7.79 (m, 2H), 7.67 (dd, J = 8.6, 2.1 Hz, 1H), 7.49 (d, J = 8.5 Hz, 1H), 7.04 (d, J = 8.6 Hz, 1H), 3.74 (s, 3H), 2.80 (s, 6H). |
| 52 | 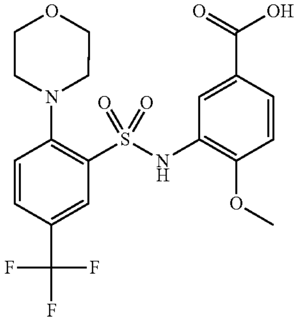 [SMILES: COc1ccc(C(=O)O)cc1NS(=O)(=O)c1cc(C(F)(F)F)ccc1N1CCCCC1] | 4-methoxy-3-((2-morpholino-5-(trifluoromethyl)phenyl)sulfonamido)benzoic acid UPLC-MS (Method 2) m/z 461.3 (M + H)$^+$, 459.1 (M − H)$^-$ at 0.90 min. $^1$H NMR (500 MHz, DMSO-$d_6$) δ 12.74 (s, 1H), 9.23 (s, 1H), 8.06 (d, J = 2.3 Hz, 1H), 7.95 (dd, J = 8.5, 2.3 Hz, 1H), 7.87 (d, J = 2.1 Hz, 1H), 7.66 (dd, J = 8.6, 2.1 Hz, 1H), 7.63 (d, J = 8.5 Hz, 1H), 7.01 (d, J = 8.6 Hz, 1H), 3.79-3.72 (m, 4H), 3.65 (s, 3H), 2.99-2.92 (m, 4H). |

Example 54 Methyl Ester: methyl 4-methoxy-3-(N-(2-(piperidin-1-yl)-5-(trifluoromethyl)phenyl)sulfamoyl)benzoate

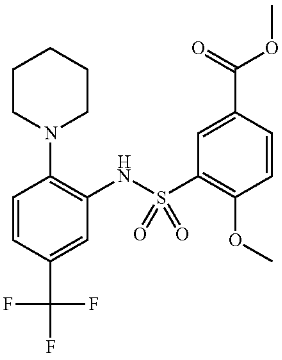 [SMILES: COC(=O)c1ccc(OC)c(S(=O)(=O)Nc2cc(C(F)(F)F)ccc2N2CCCCC2)c1]

A solution of 2-(piperidin-1-yl)-5-(trifluoromethyl)aniline (0.100 g, 0.409 mmol) in DCM (1 ml) and pyridine (0.1 ml, 1.236 mmol) were added to a solution of methyl 3-(chlorosulfonyl)-4-methoxybenzoate (0.130 g, 0.491 mmol) in DCM (1 ml) and the solution was stirred at RT for 23 h. The solvent was removed in vacuo and the crude product was purified by chromatography on silica gel (12 g cartridge, 0-50% EtOAc/isohexanes) to afford an orange oil. This was repurified by chromatography on silica gel (24 g cartridge, 0-50% EtOAc/isohexanes) to afford the title compound (0.143 g, 0.294 mmol, 71.7% yield, 97% purity) as a pale yellow slowly cystallising oil. UPLC-MS (Method 2) m/z 473.2 (M+H)$^+$, 471.1 (M−H)$^-$ at 1.83 min. $^1$H NMR (500 MHz, DMSO-$d_6$) δ 8.81 (br s, 1H), 8.37 (d, J=2.3 Hz, 1H), 8.19 (dd, J=8.7, 2.3 Hz, 1H), 7.45 (d, J=2.0 Hz, 1H), 7.40-7.30 (m, 3H), 3.94 (s, 3H), 3.86 (s, 3H), 2.78-2.75 (m, 4H), 1.68-1.64 (m, 4H), 1.56-1.52 (m, 2H).

Example 54: 4-methoxy-3-(N-(2-(piperidin-1-yl)-5-(trifluoromethyl)phenyl) sulfamoyl)benzoic acid

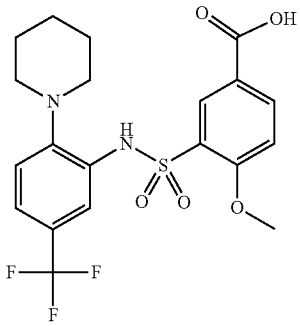 [SMILES: COc1ccc(C(=O)O)cc1S(=O)(=O)Nc1cc(C(F)(F)F)ccc1N1CCCCC1]

1 M LiOH(aq) (3 ml, 3.00 mmol) was added to a solution of the product from example 54 methyl ester (0.068 g, 0.144 mmol) in dioxane (3 ml) and the solution was stirred at RT overnight. The solvent was removed in vacuo and the residue was redissolved in water (5 ml) and extracted with EtOAc (3×5 ml). The aqueous phase was acidified with 1 M HCl(aq) and the product was extracted into EtOAc (3×10 ml). The combined organic phases were dried over $MgSO_4$, filtered and the solvent was removed in vacuo to give the title compound (0.047 g, 0.100 mmol, 69.8% yield, 98% purity) as an off-white solid. UPLC-MS (Method 2) m/z 459.2 (M+H)$^+$, 457.0 (M−H)$^-$ at 1.15 min. $^1$H NMR (500 MHz, DMSO-$d_6$) δ 13.16 (s, 1H), 8.76 (s, 1H), 8.37 (d, J=2.2 Hz, 1H), 8.16 (dd, J=8.7, 2.2 Hz, 1H), 7.45 (d, J=1.9 Hz, 1H), 7.38-7.30 (m, 3H), 3.93 (s, 3H), 2.76 (t, J=5.3 Hz, 4H), 1.67 (p, J=5.3 Hz, 4H), 1.55 (p, J=5.3 Hz, 2H).

Example 55: 3-(N-(2-(azepan-1-yl)-5-(trifluoromethyl)phenyl)sulfamoyl)-4-isopropylbenzoic acid

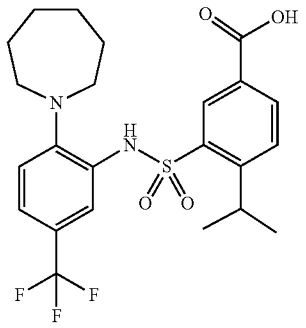 [SMILES: CC(C)c1ccc(C(=O)O)cc1S(=O)(=O)Nc1cc(C(F)(F)F)ccc1N1CCCCCC1]

A solution of 2-(azepan-1-yl)-5-(trifluoromethyl)aniline (50 mg, 0.194 mmol) in DCM (1 ml) and pyridine (0.094 ml, 1.16 mmol) were added to a solution of 3-(chlorosulfonyl)-4-isopropylbenzoic acid (61.0 mg, 0.232 mmol) in DCM (1 ml) and the solution was stirred at RT for 4 days. The crude product was purified directly by chromatography on silica gel (12 g cartridge, 0-10% MeOH/DCM) to afford a light yellow solid (11.1 mg). 9 mg of this was loaded onto a silica plug in the minimal amount of DCM, the column was eluted with DCM (5 ml), isohexanes (5 ml), 5% MeOH in EtOAc (5 ml) then 5% MeOH in EtOAc (5 ml) to afford the title compound (5.4 mg, 10.6 μmol, 5.47% yield, 95% purity) as a light yellow solid. UPLC-MS (Method 2) m/z 485.4 $(M+H)^+$, 483.1 $(M-H)^-$ at 1.99 min. $^1H$ NMR (500 MHz, Methanol-$d_4$) δ 8.58 (d, J=1.8 Hz, 1H), 8.20 (dd, J=8.2, 1.8 Hz, 1H), 7.70 (d, J=8.2 Hz, 1H), 7.33-7.21 (m, 3H), 3.90 (septet, J=6.8 Hz, 1H), 3.20-3.13 (m, 4H), 1.86-1.77 (m, 4H), 1.76-1.71 (m, 4H), 1.24 (d, J=6.7 Hz, 6H). Two exchangeable protons not observed.

The following examples were prepared by methods analogous to Example 55, substituting appropriate starting materials and intermediates where necessary:

| Example | Structure | Name/Analytical Data |
| --- | --- | --- |
| 59 | 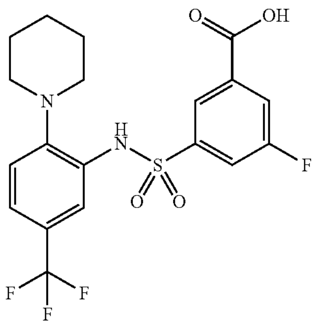 [SMILES: O=C(O)c1cc(F)cc(S(=O)(=O)Nc2cc(C(F)(F)F)ccc2N2CCCCC2)c1] | 3-fluoro-5-(N-(2-(piperidin-1-yl)-5-(trifluoromethyl)phenyl)sulfamoyl)benzoic acid<br>UPLC-MS (Method 1) m/z 447.4 $(M + H)^+$, 445.2 $(M - H)^-$ at 1.86 min. $^1H$ NMR (500 MHz, DMSO-$d_6$) δ 13.75 (br s, 1H), 9.69 (br s, 1H), 8.13 (s, 1H), 7.96 (d, J = 9.0 Hz, 1H), 7.85 (d, J = 8.3 Hz, 1H), 7.47 (d, J = 9.0 Hz, 1H), 7.32 (s, 1H), 7.23 (d, J = 8.3 Hz, 1H), 2.70 (t, J = 5.1 Hz, 4H), 1.56-1.52 (m, 4H), 1.48-1.44 (m, 2H). |
| 61 | 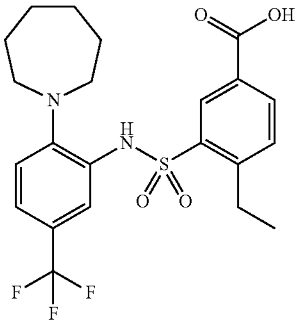 [SMILES: CCc1ccc(C(=O)O)cc1S(=O)(=O)Nc1cc(C(F)(F)F)ccc1N1CCCCCC1] | 3-(N-(2-(azepan-1-yl)-5-(trifluoromethyl)phenyl)sulfamoyl)-4-ethylbenzoic acid<br>UPLC-MS (Method 1) m/z 471.3 $(M + H)^+$, 469.3 $(M - H)^-$ at 2.27 min. $^1H$ NMR (500 MHz, Methanol-$d_4$) δ 8.59 (d, J = 2.1 Hz, 1H), 8.38 (d, J = 2.0 Hz, 1H), 8.01 (dd, J = 8.0, 2.1 Hz, 1H), 7.55 (d, J = 8.0 Hz, 1H), 7.46-7.34 (m, 2H), 3.25 (q, J = 7.5 Hz, 2H), 3.22-3.17 (m, 4H), 1.89-1.82 (m, 4H), 1.81-1.75 (m, 4H), 1.36 (t, J = 7.5 Hz, 3H). Two exchangeable protons not observed. |
| 62 | 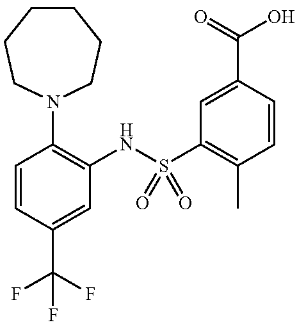 [SMILES: Cc1ccc(C(=O)O)cc1S(=O)(=O)Nc1cc(C(F)(F)F)ccc1N1CCCCCC1] | 3-(N-(2-(azepan-1-yl)-5-(trifluoromethyl)phenyl)sulfamoyl)-4-methylbenzoic acid<br>UPLC-MS (Method 1) m/z 457.4 $(M + H)^+$, 455.0 $(M - H)^-$ at 1.86 min. $^1H$ NMR (500 MHz, DMSO-$d_6$) δ 13.12 (br s, 1H), 9.46 (br s, 1H), 8.22 (d, J = 1.8 Hz, 1H), 8.03 (dd, J = 7.9, 1.9 Hz, 1H), 7.53 (d, J = 7.9 Hz, 1H), 7.32 (d, J = 8.8 Hz, 1H), 7.06 (d, J = 8.7 Hz, 1H), 6.61 (s, 1H), 3.39-3.26 (m, 4H), 2.55 (s, 3H), 1.75-1.66 (m, 4H), 1.58-1.49 (m, 4H). |

-continued

| Example | Structure | Name/Analytical Data |
|---|---|---|
| 63 | 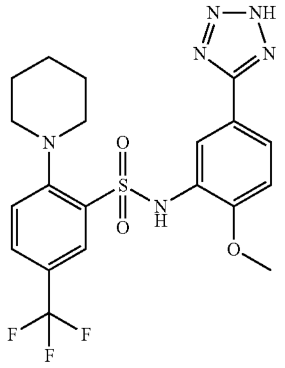 [SMILES: COc1ccc(-c2nn[nH]n2)cc1NS(=O)(=O)c1cc(C(F)(F)F)ccc1N1CCCCC1] | N-(2-methoxy-5-(tetrazol-5-yl)phenyl)-2-(piperidin-1-yl)-5-(trifluoromethyl) benzenesulfonamide UPLC-MS (Method 1) m/z 483.4 $(M + H)^+$, 481.2 $(M - H)^-$ at 1.66 min. $^1H$ NMR (500 MHz, DMSO-$d_6$) δ 9.11 (s, 1H), 8.11 (d, J = 2.2 Hz, 1H), 8.06 (d, J = 2.1 Hz, 1H), 7.93 (dd, J = 8.4, 2.2 Hz, 1H), 7.75 (dd, J = 8.6, 2.2 Hz, 1H), 7.62 (d, J = 8.4 Hz, 1H), 7.17 (d, J = 8.6 Hz, 1H), 3.72 (s, 3H), 2.94 (t, J = 5.1 Hz, 4H), 1.71 (p, J = 5.8 Hz, 4H), 1.58-1.50 (m, 2H). One exchangeable proton not observed. |

Example 64: 4-methoxy-3-(N-(2-(piperidin-1-yl)phenyl)sulfamoyl)benzoic acid

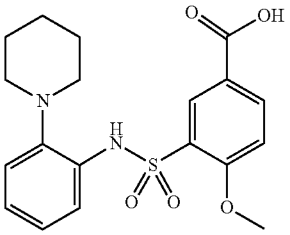 [SMILES: COc1ccc(C(=O)O)cc1S(=O)(=O)Nc1ccccc1N1CCCCC1]

Step 1: methyl 4-methoxy-3-(N-(2-(piperidin-1-yl)phenyl)sulfamoyl)benzoate: A solution of 2-(piperidin-1-yl)aniline hydrochloride (0.050 g, 0.235 mmol) in DCM (1 ml) and pyridine (0.114 ml, 1.410 mmol) was added to a solution of methyl 3-(chlorosulfonyl)-4-methoxybenzoate (0.075 g, 0.282 mmol) in DCM (1 ml) and the solution was stirred at RT for 96 h. The solvent was removed in vacuo and the crude product was purified by chromatography on silica gel (24 g cartridge, 0-50% EtOAc/isohexanes) to afford the title compound (0.095 g, 0.169 mmol, 71.9% yield, 72% purity) as a pale yellow slowly cystallising oil. UPLC-MS (Method 2) m/z 405.2 $(M+H)^+$, 403.4 $(M-H)^-$ at 1.69 min.

Step 2: 4-methoxy-3-(N-(2-(piperidin-1-yl)phenyl)sulfamoyl)benzoic acid: 1 M LiOH(aq) (0.470 ml, 0.470 mmol) was added to a solution of the product from step 1 above (0.095 g, 0.235 mmol) in dioxane (3 ml) and the solution was stirred at RT overnight. The solvent was removed in vacuo and the residue redissolved in water (5 ml) and extracted with EtOAc (3×5 ml). The aqueous phase was acidified with 1 M HCl(aq) and the product was extracted into EtOAc (3×10 ml). The combined organic phases were dried over $MgSO_4$, filtered and the solvent was removed in vacuo. The crude product was purified by chromatography on silica gel (12 g cartridge, 0-70% EtOAc/isohexanes) to afford the title compound (40 mg, 0.097 mmol, 41.4% yield, 95% purity) as a white solid. UPLC-MS (Method 1) m/z 391.3 $(M+H)^+$, 389.3 $(M-H)^-$ at 1.41 min. $^1H$ NMR (500 MHz, DMSO-$d_6$) δ 13.23 (bs, 1H), 8.60 (s, 1H), 8.39 (d, J=2.3 Hz, 1H), 8.14 (dd, J=8.7, 2.3 Hz, 1H), 7.31 (d, J=8.8 Hz, 1H), 7.25 (dd, J=7.4, 2.1 Hz, 1H), 7.22 (dd, J=7.5, 2.2 Hz, 1H), 7.12-6.85 (m, 2H), 3.96 (s, 3H), 2.75-2.63 (m, 4H), 1.69 (p, J=5.5 Hz, 4H), 1.58-1.52 (m, 2H).

Example 65: 3-(N-(4-chloro-2-(piperidin-1-yl)phenyl)sulfamoyl)-4-methoxybenzoic acid

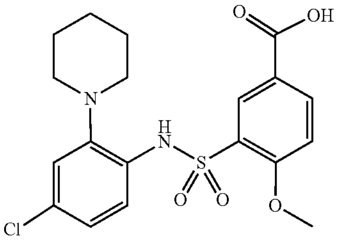 [SMILES: COc1ccc(C(=O)O)cc1S(=O)(=O)Nc1ccc(Cl)cc1N1CCCCC1]

Step 1: methyl 3-(N-(4-chloro-2-(piperidin-1-yl)phenyl)sulfamoyl)-4-methoxybenzoate: A solution of 4-chloro-2-(piperidin-1-yl)aniline (0.050 g, 0.237 mmol) in DCM (1 ml) and pyridine (0.115 ml, 1.42 mmol) were added to a solution of methyl 3-(chlorosulfonyl)-4-methoxybenzoate (0.075 g, 0.285 mmol) in DCM (1 ml) and the solution was stirred at RT for 96 h. The solvent was removed in vacuo and the crude product was purified by chromatography on silica gel (24 g cartridge, 0-50% EtOAc/isohexanes) to afford the title compound (0.093 g, 0.165 mmol, 69.6% yield) as a pale yellow slowly cystallising oil. UPLC-MS (Method 2) m/z 439.3 $(M+H)^+$, 437.2 $(M-H)^-$ at 1.81 min.

Step 2: 3-(N-(4-chloro-2-(piperidin-1-yl)phenyl)sulfamoyl)-4-methoxybenzoic acid: 1 M LiOH(aq) (0.424 ml, 0.424 mmol) was added to a solution of the product from step 1 above (0.093 g, 0.212 mmol) in dioxane (3 ml) and the solution was stirred at RT overnight. The solvent was removed in vacuo and the residue redissolved in water (5 ml) and extracted with EtOAc (3×5 ml). The aqueous phase was acidified with 1 M HCl(aq) and the product was extracted into EtOAc (3×10 ml). The combined organic phases were dried over $MgSO_4$, filtered and the solvent was removed in vacuo. The crude product was purified by chromatography on silica gel (12 g cartridge, 0-80% EtOAc/isohexanes) to afford the title compound (34 mg, 0.076 mmol, 35.9% yield, 95% purity) as a white solid. UPLC-MS (Method 1) m/z 425.3 $(M+H)^+$, 423.2 $(M-H)^-$ at 1.69 min. $^1H$ NMR (500 MHz, DMSO-$d_6$)· 13.24 (bs, 1H), 8.58 (s, 1H), 8.36 (d, J=2.3 Hz, 1H), 8.16 (dd, J=8.7, 2.2 Hz, 1H), 7.32 (d, J=8.8 Hz, 1H), 7.28-7.14 (m, 2H), 7.07 (dd, J=8.8, 2.4 Hz, 1H), 3.96 (s, 3H), 2.72-2.68 (m, 4H), 1.66 (p, J=5.5 Hz, 4H), 1.56-1.50 (m, 2H).

Example 66: 3-(N-(5-chloro-2-(piperidin-1-yl)phenyl)sulfamoyl)-4-methoxybenzoic acid

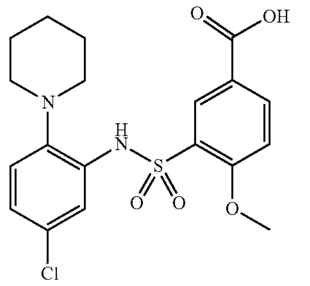 [SMILES: COc1ccc(C(=O)O)cc1S(=O)(=O)Nc1cc(Cl)ccc1N1CCCCC1]

Step 1: methyl 3-(N-(5-chloro-2-(piperidin-1-yl)phenyl) sulfamoyl)-4-methoxybenzoate: A solution of 5-chloro-2-(piperidin-1-yl)aniline hydrochloride (0.050 g, 0.202 mmol) in DCM (1 ml) and pyridine (0.098 ml, 1.21 mmol) were added to a solution of methyl 3-(chlorosulfonyl)-4-methoxybenzoate (0.064 g, 0.243 mmol) in DCM (1 ml) and the solution was stirred at RT for 96 h. The solvent was removed in vacuo the crude product was purified by chromatography on silica gel (24 g cartridge, 0-50% EtOAc/isohexanes) to afford the title compound (0.066 g, 0.143 mmol, 70.6% yield, 95% purity) as a pale yellow slowly cystallising oil. UPLC-MS (Method 2) m/z 439.3 $(M+H)^+$, 437.3 $(M-H)^-$ at 1.81 min.

Step 2: 3-(N-(5-chloro-2-(piperidin-1-yl)phenyl)sulfamoyl)-4-methoxybenzoic acid: 1 M LiOH(aq) (0.301 ml, 0.301 mmol) was added to a solution of the product from step 1 above (0.066 g, 0.150 mmol) in dioxane (3 ml) and the solution was stirred at RT overnight. The solvent was removed in vacuo and the residue redissolved in water (5 ml) and extracted with EtOAc (3×5 ml). The aqueous phase was acidified with 1 M HCl(aq) and the product was extracted into EtOAc (3×10 ml). The combined organic phases were dried over $MgSO_4$, filtered and the solvent was removed in vacuo. The crude product was purified by chromatography on silica gel (12 g cartridge, 0-70% EtOAc/isohexanes) to afford the title compound (22 mg, 0.049 mmol, 32.7% yield, 95% purity) as a white solid. UPLC-MS (Method 1) m/z 425.1 $(M+H)^+$, 423.2 $(M-H)^-$ at 1.67 min. $^1H$ NMR (500 MHz, DMSO-$d_6$)· 13.25 (br s, 1H), 8.69 (br s, 1H), 8.38 (d, J=2.2 Hz, 1H), 8.17 (dd, J=8.7, 2.2 Hz, 1H), 7.34 (d, J=8.8 Hz, 1H), 7.25 (d, J=2.5 Hz, 1H), 7.24 (d, J=8.5 Hz, 1H), 7.05 (dd, J=8.5, 2.5 Hz, 1H), 3.96 (s, 3H), 2.75-2.61 (m, 4H), 1.67 (p, J=5.5 Hz, 4H), 1.56-1.50 (m, 2H).

Example 67:4-methyl-3-(N-(2-(piperidin-1-yl)-5-(trifluoromethyl)phenyl) sulfamoyl)benzoic acid

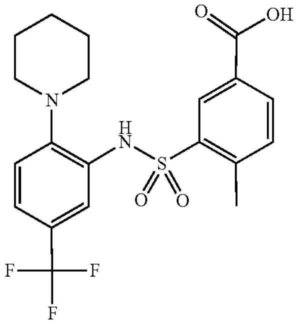 [SMILES: Cc1ccc(C(=O)O)cc1S(=O)(=O)Nc1cc(C(F)(F)F)ccc1N1CCCCC1]

Step 1: methyl 4-methyl-3-(N-(2-(piperidin-1-yl)-5-(trifluoromethyl)phenyl)sulfamoyl)benzoate: 2-(piperidin-1-yl)-5-(trifluoromethyl)aniline (50 mg, 0.205 mmol) was dissolved in a mixture of DCM (1 ml) and pyridine (0.05 ml, 0.618 mmol) and treated with a solution of methyl 3-(chlorosulfonyl)-4-methylbenzoate (52 mg, 0.209 mmol) in DCM (1 ml). The resultant solution was stirred at RT for 18 h. Additional methyl 3-(chlorosulfonyl)-4-methylbenzoate (15 mg, 0.060 mmol) was added and the reaction was stirred for a further 24 h at RT. The reaction mixture was loaded directly on to silica gel (12 g cartridge, 0-50% EtOAc/isohexanes) and purified to afford the title compound (73 mg, 0.155 mmol, 76% yield, 97% purity) as a colourless oil, which crystallised upon standing. UPLC-MS (Method 1) m/z 457.1 $(M+H)^+$, 455.3 $(M-H)^-$ at 1.95 min.

Step 2: 4-methyl-3-(N-(2-(piperidin-1-yl)-5-(trifluoromethyl)phenyl)sulfamoyl)benzoic acid: The product from step 1 above (71 mg, 0.151 mmol) was dissolved in THF (2 ml) and treated with 1.1 M LiOH(aq) (499 μl, 0.549 mmol). MeOH was added to give a clear solution, which was allowed to stand at RT. After 2 days, the solution was diluted with water (2 ml) and was allowed to stand at RT for a further 24 h. The solution was further diluted with water (2 ml) and concentrated in vacuo. The resultant aqueous suspension was diluted with water (2 ml) and filtered, washing with water (1 ml). The resultant solution was neutralised with 1 M HCl(aq) (0.4 ml) and sonicated, then adjusted to ca. pH 6 with 1 M HCl(aq) (2 drops). The resultant off-white precipitate was collected by filtration, washing with water. The solid was suspended in MeCN (4 ml), concentrated in vacuo and dried at 45° C. to afford the title compound (55 mg, 0.122 mmol, 81% yield, 98% purity) as a tan powder. UPLC-MS (Method 1) m/z 443.3 $(M+H)^+$ 441.3 $(M-H)^-$ at 1.81 min.

Example 68: 3-(N-(2-(azepan-1-yl)-5-(trifluoromethyl)phenyl)sulfamoyl)-4-methoxybenzoic acid

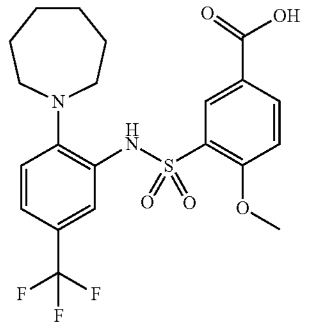 [SMILES: COc1ccc(C(=O)O)cc1S(=O)(=O)Nc1cc(C(F)(F)F)ccc1N1CCCCCC1]

Step 1: methyl 3-(N-(2-(azepan-1-yl)-5-(trifluoromethyl)phenyl)sulfamoyl)-4-methoxybenzoate: 2-(azepan-1-yl)-5-(trifluoromethyl)aniline (48.8 mg, 0.189 mmol) was dissolved in a mixture of DCM (1 ml) and pyridine (0.05 ml, 0.618 mmol) and treated with a solution methyl 3-(chlorosulfonyl)-4-methoxybenzoate (60 mg, 0.227 mmol) in DCM (1 ml). The resultant solution was stirred at RT for 18 h. The reaction mixture was loaded directly on to silica gel and purified by chromatography on silica gel (12 g cartridge, 0-70% EtOAc/isohexanes) to afford the title compound (44 mg, 0.084 mmol, 44.5% yield, 93% purity) as a sticky light yellow solid. UPLC-MS (Method 1) m/z 487.4 $(M+H)^+$, 485.2 $(M-H)^-$ at 1.91 min.

Step 2: 3-(N-(2-(azepan-1-yl)-5-(trifluoromethyl)phenyl)sulfamoyl)-4-methoxybenzoic acid: The product from step 1 above (42 mg, 0.086 mmol) was dissolved in THF (2 ml) and treated with 1.1 M LiOH(aq) (235 µl, 0.259 mmol). The reaction mixture was stirred at RT for 2 days. Additional 1.1 M LiOH(aq) (78 µl, 0.086 mmol) was added and the reaction warmed to 30° C. for 18 h. The reaction mixture was diluted with water (3 ml), concentrated in vacuo and the resultant aqueous solution diluted with water (to ca. 5 ml) and neutralised with 1 M HCl(aq) (0.4 ml). The resultant lumpy suspension was sonicated to afford a cloudy solution and neutralised to ca. pH 6 with 1 M HCl. The aqueous phase was acidified with 1 M HCl(aq) and the product was extracted into EtOAc (3×10 ml). The combined organic phases were dried over $MgSO_4$, filtered and the solvent was removed in vacuo. The crude product was purified by chromatography on silica gel (12 g cartridge, 0-70% EtOAc/isohexanes) to afford the title compound (2.2 mg, 4.42 µmol, 5.12% yield, 95% purity) as a white solid. UPLC-MS (Method 1) m/z 473.4 $(M+H)^+$, 471.1 $(M-H)^-$ at 1.79 min. $^1H$ NMR (500 MHz, DMSO-$d_6$)· 13.13 (br s, 1H), 8.76 (br s, 1H), 8.36 (d, J=2.2 Hz, 1H), 8.14 (dd, J=8.7, 2.2 Hz, 1H), 7.44 (d, J=1.9 Hz, 1H), 7.38-7.26 (m, 3H), 3.91 (s, 3H), 2.92 (d, J=11.4 Hz, 2H), 2.67-2.57 (m, 2H), 1.72-1.65 (m, 1H), 1.55-1.43 (m, 1H), 1.34-1.20 (m, 3H), 0.97 (d, J=6.5 Hz, 3H).

Example 69: 4-chloro-3-(N-(2-(piperidin-1-yl)-5-(trifluoromethyl)phenyl) sulfamoyl)benzoic acid

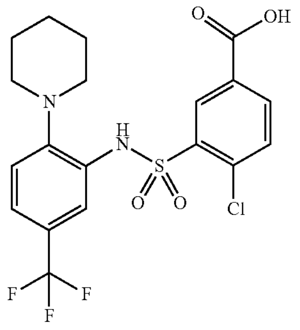 [SMILES: O=C(O)c1ccc(Cl)c(S(=O)(=O)Nc2cc(C(F)(F)F)ccc2N2CCCCC2)c1]

Step 1: methyl 4-chloro-3-(N-(2-(piperidin-1-yl)-5-(trifluoromethyl)phenyl)sulfamoyl)benzoate: 2-(piperidin-1-yl)-5-(trifluoromethyl)aniline (45.4 mg, 0.186 mmol) was dissolved in a mixture of DCM (1 ml) and pyridine (0.05 ml, 0.618 mmol) and treated with a solution methyl 4-chloro-3-(chlorosulfonyl)benzoate (60 mg, 0.223 mmol) in DCM (1 ml). The resultant solution was stirred at RT for 18 h. The reaction mixture was loaded directly on to silica and purified by chromatography on silica gel (12 g cartridge, 0-70% EtOAc/isohexanes) to afford the title compound (45.5 mg, 0.094 mmol, 50.3% yield, 98% purity) as a tan solid. UPLC-MS (Method 1) m/z 477.3 $(M+H)^+$, 475.1 $(M-H)^-$ at 2.00 min.

Step 2: 4-chloro-3-(N-(2-(piperidin-1-yl)-5-(trifluoromethyl)phenyl)sulfamoyl)benzoic acid: The product from step 1 above (43 mg, 0.090 mmol) was dissolved in THF (2 ml) and treated with 1.1 M LiOH(aq) (328 µl, 0.361 mmol). The reaction was stirred at RT for 2 days. The reaction mixture was diluted with water (3 ml), concentrated in vacuo and the resultant aqueous solution diluted with water (to ca. 5 ml) and neutralised with 1 M HCl(aq) (0.4 ml). The resultant lumpy suspension was sonicated to afford a cloudy solution and neutralised to ca. pH 6 with 1 M HCl(aq). The aqueous phase was acidified with 1 M HCl(aq) and the product was extracted into EtOAc (3×10 ml). The combined organic phases were dried over $MgSO_4$, filtered and the solvent was removed in vacuo. The crude product was purified by chromatography on silica gel (12 g cartridge, 0-10% MeOH/DCM) to afford the title compound (20.5 mg, 0.042 mmol, 46.7% yield, 95% purity) as a white solid. UPLC-MS (Method 1) m/z 463.3 $(M+H)^+$, 461.2 $(M-H)^-$ at 1.88 min. $^1H$ NMR (500 MHz, DMSO-$d_6$)· 13.48 (br s, 1H), 9.54 (br s, 1H), 8.44 (d, J=2.0 Hz, 1H), 8.12 (dd, J=8.3, 2.1 Hz, 1H), 7.80 (d, J=8.3 Hz, 1H), 7.42 (d, J=8.3 Hz, 1H), 7.34 (s, 1H), 7.29 (d, J=8.4 Hz, 1H), 2.77 (t, J=5.1 Hz, 4H), 1.58-1.51 (m, 4H), 1.50-1.43 (m, 2H).

The following examples were prepared by methods analogous to Example 69, substituting appropriate starting materials and intermediates where necessary:

| Example | Structure | Name/Analytical Data |
| --- | --- | --- |
| 70 | 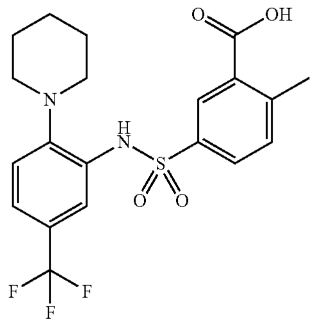 [SMILES: Cc1ccc(S(=O)(=O)Nc2cc(C(F)(F)F)ccc2N2CCCCC2)cc1C(=O)O] | 2-methyl-5-(N-(2-(piperidin-1-yl)-5-(trifluoromethyl)phenyl)sulfamoyl)benzoic acid UPLC-MS (Method 1) 443.3 $(M + H)^+$, 441.2 (M − H) at 1.81 min. $^1H$ NMR (500 MHz, DMSO-$d_6$) δ 13.34 (br s, 1H), 9.34 (br s, 1H), 8.23 (d, J = 2.2 Hz, 1H), 7.81 (dd, J = 8.0, 2.2 Hz, 1H), 7.52 (d, J = 8.2 Hz, 1H), 7.47-7.35 (m, 2H), 7.22 (d, J = 8.3 Hz, 1H), 2.67-2.63 (m, 4H), 2.57 (s, 3H), 1.57 (p, J = 5.5 Hz, 4H), 1.56-1.47 (m, 2H). |
| 71 | 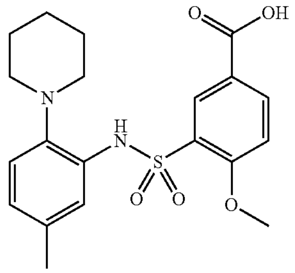 [SMILES: COc1ccc(C(=O)O)cc1S(=O)(=O)Nc1cc(C)ccc1N1CCCCC1] | 4-methoxy-3-(N-(5-methyl-2-(piperidin-1-yl)phenyl)sulfamoyl)benzoic acid UPLC-MS (Method 1) 405.4 $(M + H)^+$, 403.4 $(M - H)^-$ at 1.43 min. $^1H$ NMR (500 MHz, DMSO-$d_6$) δ 13.20 (s, 1H), 8.56 (s, 1H), 8.39 (d, J = 2.1 Hz, 1H), 8.14 (dd, J = 8.7, 2.2 Hz, 1H), 7.30 (d, J = 8.8 Hz, 1H), 7.16-7.02 (m, 2H), 6.78 (dd, J = 8.2, 1.9 Hz, 1H), 3.96 (s, 3H), 2.71-2.58 (m, 4H), 2.13 (s, 3H), 1.67 (p, J = 5.5 Hz, 4H), 1.56-1.50 (m, 2H). |
| 72 | 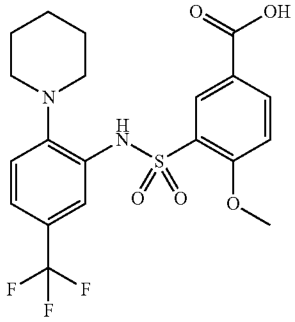 | 4-methoxy-3-(N-(2-morpholino-5-(trifluoromethyl)phenyl)sulfamoyl)benzoic acid UPLC-MS (Method 1) 461.3 $(M + H)^+$, 459.2 $(M - H)^-$ at 1.38 min. $^1H$ NMR (500 MHz, DMSO-$d_6$) δ 13.15 (br s, 1H), 9.06 (br s, 1H), 8.34 (d, J = 2.1 Hz, 1H), 8.16 (d, J = 8.8 Hz, 1H), 7.46 (s, 1H), 7.43-7.26 (m, 3H), 3.91 (s, 3H), 3.72 (t, J = 4.5 Hz, 4H), 2.83 (t, J = 4.5 Hz, 4H). |
| 73 | 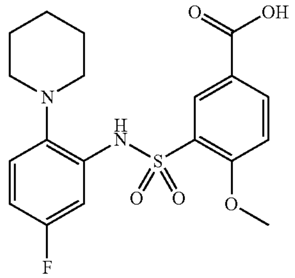 [SMILES: COc1ccc(C(=O)O)cc1S(=O)(=O)Nc1cc(F)ccc1N1CCCCC1] | 3-(N-(5-fluoro-2-(piperidin-1-yl)phenyl)sulfamoyl)-4-methoxybenzoic acid UPLC-MS (Method 1) m/z 409.4 $(M + H)^+$, 407.2 $(M - H)^-$ at 1.57 min. $^1H$ NMR (500 MHz, DMSO-$d_6$) δ 13.26 (s, 1H), 8.74 (s, 1H), 8.39 (d, J = 2.2 Hz, 1H), 8.17 (dd, J = 8.7, 2.2 Hz, 1H), 7.34 (d, J = 8.8 Hz, 1H), 7.29 (dd, J = 8.8, 5.8 Hz, 1H), 7.05 (dd, J = 10.6, 2.9 Hz, 1H), 6.82 (app. td, J = 8.6, 3.0 Hz, 1H), 3.97 (s, 3H), 2.65-2.61 (m, 4H), 1.68 (p, J = 5.5 Hz, 4H), 1.57-1.51 (m, 2H). |
| 74 | 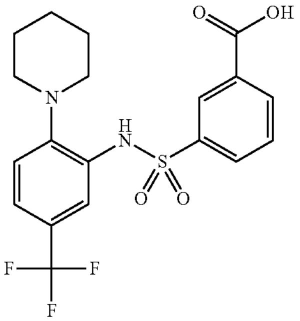 | 3-(N-(2-(piperidin-1-yl)-5-(trifluoromethyl)phenyl)sulfamoyl)benzoic acid UPLC-MS (Method 1) m/z 429.4 $(M + H)^+$, 427.2 $(M - H)^-$ at 1.77 min. |

-continued

| Example | Structure | Name/Analytical Data |
|---|---|---|
| 75 | 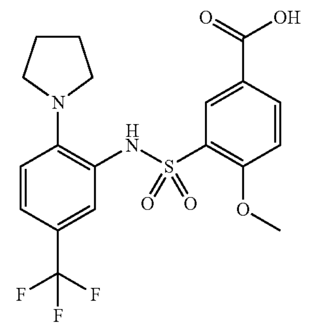 [SMILES: COc1ccc(C(=O)O)cc1S(=O)(=O)Nc1cc(C(F)(F)F)ccc1N1CCCC1] | 4-methoxy-3-(N-(2-(pyrrolidin-1-yl)-5-(trifluoromethyl)phenyl)sulfamoyl)benzoic acid<br>UPLC-MS (Method 1) 445.3 $(M + H)^+$, 443.5 $(M - H)^-$ at 1.46 min. $^1H$ NMR (500 MHz, DMSO-$d_6$) δ 8.17 (dd, J = 8.7, 2.3 Hz, 1H), 8.07 (d, J = 2.2 Hz, 1H), 7.44-7.34 (m, 1H), 7.29 (dd, J = 8.8, 2.4 Hz, 1H), 6.76 (d, J = 8.8 Hz, 1H), 6.55 (d, J = 2.3 Hz, 1H), 3.98 (s, 3H), 3.52-3.46 (m, 4H), 2.00-1.79 (m, 4H). 2 exchangeable protons not observed. |
| 77 | 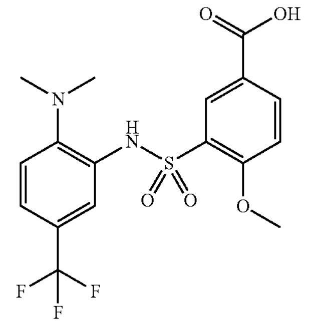 [SMILES: COc1ccc(C(=O)O)cc1S(=O)(=O)Nc1cc(C(F)(F)F)ccc1N(C)C] | 3-(N-(2-(dimethylamino)-5-(trifluoromethyl)phenyl)sulfamoyl)-4-methoxybenzoic acid<br>UPLC-MS (Method 1) m/z 419.4 $(M + H)^+$, 417.2 $(M - H)^-$ at 1.47 min. $^1H$ NMR (500 MHz, DMSO-$d_6$) δ 13.10 (br s, 1H) 9.15 (br s, 1H), 8.26 (d, J = 2.2 Hz, 1H), 8.15 (dd, J = 8.7, 2.2 Hz, 1H), 7.40-7.28 (m, 3H), 7.22 (d, J = 8.4 Hz, 1H), 3.94 (s, 3H), 2.61 (s, 6H). |
| 78 | 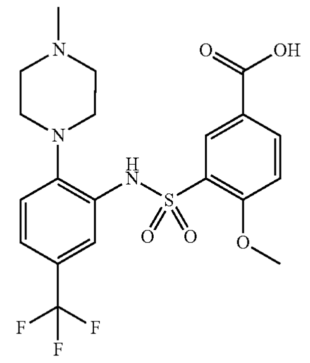 | 4-methoxy-3-(N-(2-(4-methylpiperazin-1-yl)-5-(trifluoromethyl)phenyl)sulfamoyl)benzoic acid<br>UPLC-MS (Method 1) m/z 474.4 $(M + H)^+$, 472.2 $(M - H)^-$ at 0.83 min. $^1H$ NMR (500 MHz, DMSO-$d_6$) δ 9.10 (br s, 2H), 8.35 (d, J = 2.2 Hz, 1H), 8.15 (dd, J = 8.7, 2.2 Hz, 1H), 7.44 (d, J = 2.0 Hz, 1H), 7.38 (dd, J = 8.5, 2.1 Hz, 1H), 7.34 (d, J = 8.5 Hz, 1H), 7.32 (d, J = 8.7 Hz, 1H), 3.91 (s, 3H), 2.91 (t, J = 4.9 Hz, 4H), 2.75-2.67 (m, 4H), 2.39 (s, 3H). |
| 80 | 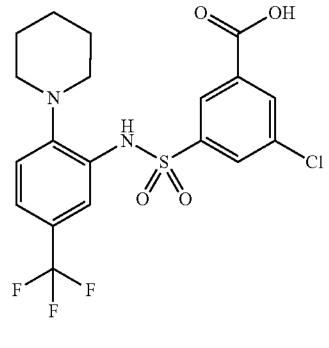 | 3-chloro-5-(N-(2-(piperidin-1-yl)-5-(trifluoromethyl)phenyl)sulfamoyl)benzoic acid<br>UPLC-MS (Method 1) m/z 463.3 $(M + H)^+$, 461.2 $(M - H)^-$ at 1.96 min. $^1H$ NMR (500 MHz, DMSO-$d_6$) δ 13.78 (br s, 1H), 9.72 (br s, 1H), 8.19 (app. t, J = 1.6 Hz, 1H), 8.13 (app. t, J = 1.7 Hz, 1H), 7.99 (app. t, J = 1.9 Hz, 1H), 7.47 (dd, J = 8.5, 2.2 Hz, 1H), 7.32 (d, J = 2.2 Hz, 1H), 7.22 (d, J = 8.4 Hz, 1H), 2.69 (t, J = 5.2 Hz, 4H), 1.56-1.49 (m, 4H), 1.48-1.41 (m, 2H). |

-continued

| Example | Structure | Name/Analytical Data |
| --- | --- | --- |
| 83 | 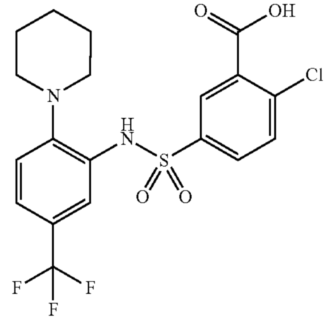 [SMILES: O=C(O)c1cc(S(=O)(=O)Nc2cc(C(F)(F)F)ccc2N2CCCCC2)ccc1Cl] | 2-chloro-5-(N-(2-(piperidin-1-yl)-5-(trifluoromethyl)phenyl)sulfamoyl)benzoic acid UPLC-MS (Method 1) m/z 463.3 $(M + H)^+$, 461.0 $(M - H)^-$ at 1.85 min. $^1H$ NMR (500 MHz, DMSO-$d_6$) δ 13.88 (br s, 1H), 9.59 (br s, 1H), 8.16 (d, J = 2.4 Hz, 1H), 7.87 (dd, J = 8.5, 2.4 Hz, 1H), 7.79 (d, J = 8.5 Hz, 1H), 7.47 (dd, J = 8.5, 2.2 Hz, 1H), 7.34 (d, J = 2.2 Hz, 1H), 7.22 (d, J = 8.4 Hz, 1H), 2.68 (t, J = 5.2 Hz, 4H), 1.56-1.50 (m, 4H), 1.48-1.38 (m, 2H). |
| 84 | 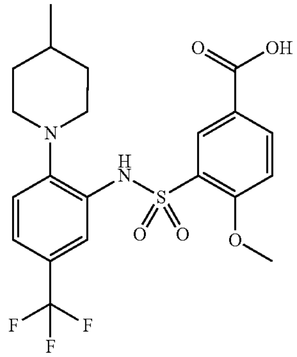 | 4-methoxy-3-(N-(2-(4-methylpiperidin-1-yl)-5-(trifluoromethyl)phenyl)sulfamoyl)benzoic acid UPLC-MS (Method 1) m/z 473.4 (M + H)+ (ES+); 471.3 (M − H)− (ES−), at 1.80 min, 100% purity (254 nm). $^1H$ NMR (500 MHz, DMSO-$d_6$) δ 13.13 (br s, 1H), 8.78 (br s, 1H), 8.37 (d, J = 2.3 Hz, 1H), 8.15 (dd, J = 8.7, 2.3 Hz, 1H), 7.45 (d, J = 1.9 Hz, 1H), 7.38-7.27 (m, 3H), 3.92 (s, 3H), 2.93 (d, J = 11.7 Hz, 2H), 2.63 (t, J = 11.8, 2.3 Hz, 2H), 1.73-1.64 (m, 2H), 1.56-1.41 (m, 1H), 1.35-1.20 (m, 2H), 0.97 (d, J = 6.5 Hz, 3H). |
| 86 | 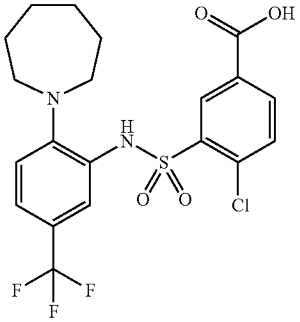 [SMILES: O=C(O)c1ccc(Cl)c(S(=O)(=O)Nc2cc(C(F)(F)F)ccc2N2CCCCCC2)c1] | 3-(N-(2-(azepan-1-yl)-5-(trifluoromethyl)phenyl)sulfamoyl)-4-chlorobenzoic acid UPLC-MS (Method 1) m/z 477.4 $(M + H)^+$, 474.9 $(M - H)^-$ at 1.93 min. $^1H$ NMR (500 MHz, DMSO-$d_6$) δ 13.59 (br s, 1H), 9.74 (br s, 1H), 8.28 (d, J = 2.1 Hz, 1H), 8.14 (dd, J = 8.3, 2.1 Hz, 1H), 7.86 (d, J = 8.3 Hz, 1H), 7.36 (dd, J = 8.8, 2.4 Hz, 1H), 7.11 (d, J = 8.7 Hz, 1H), 6.74 (d, J = 2.3 Hz, 1H), 3.36-3.29 (m, 4H), 1.75-1.67 (m, 4H), 1.58-1.50 (m, 4H). |

Example 161: 4-hydroxy-3-(N-(2-(piperidin-1-yl)-5-(trifluoromethyl)phenyl) sulfamoyl)benzoic acid

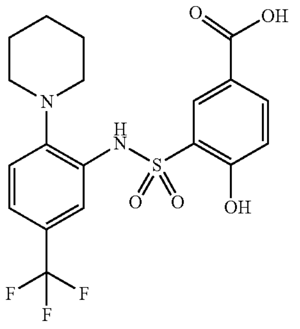 [SMILES: O=C(O)c1ccc(O)c(S(=O)(=O)Nc2cc(C(F)(F)F)ccc2N2CCCCC2)c1]

Step 1: methyl 4-methoxy-3-(N-(2-(piperidin-1-yl)-5-(trifluoromethyl)phenyl) sulfamoyl)benzoate: A solution of 2-(piperidin-1-yl)-5-(trifluoromethyl)aniline (0.130 g, 0.532 mmol) in DCM (1 ml) and pyridine (0.258 ml, 3.19 mmol) was added to a solution of methyl 3-(chlorosulfonyl)-4-methoxybenzoate (0.169 g, 0.639 mmol) in DCM (1 ml) and the solution was stirred at RT for 16 h. The solvent was removed in vacuo. The crude product was purified by chromatography on silica gel (24 g cartridge, 0-50% EtOAc/DCM) to afford the title compound (0.230 g, 0.433 mmol, 81% yield, 89% purity) as a white solid. UPLC-MS (Method 1) m/z 473.4 $(M+H)^+$, 471.3 $(M-H)^-$ at 1.86 min. $^1H$ NMR (500 MHz, DMSO-$d_6$) δ 8.81 (s, 1H), 8.37 (d, J=2.3 Hz, 1H), 8.19 (dd, J=8.7, 2.3 Hz, 1H), 7.45 (d, J=2.0 Hz, 1H), 7.41-7.28 (m, 3H), 3.94 (s, 3H), 3.86 (s, 3H), 2.84-2.69 (m, 4H), 1.66 (p, J=5.6 Hz, 4H), 1.57-1.51 (m, 2H).

Step 2: methyl 4-hydroxy-3-(N-(2-(piperidin-1-yl)-5-(trifluoromethyl)phenyl) sulfamoyl)benzoate: A solution of the product from step 1 above (0.230 g, 0.438 mmol) in DCM (10 ml) was treated with 1.0 M $BBr_3$ in DCM (0.166 ml, 1.75 mmol) and the solution was stirred at RT for 16 h. The solvent was removed in vacuo to give the title compound as a yellow oil (0.200 g, 0.393 mmol, 90% yield, 90% purity). UPLC-MS (Method 1) m/z 459 $(M+H)^+$ at 1.7 min.

Step 3: 4-hydroxy-3-(N-(2-(piperidin-1-yl)-5-(trifluoromethyl)phenyl)sulfamoyl)benzoic acid: 1 M LiOH(aq) (1.31 ml, 1.31 mmol) was added to a solution of the product from step 2 above (0.2 g, 0.436 mmol) in MeOH (10 ml) and the solution was stirred at RT overnight. The solvent was removed in vacuo and the residue redissolved in water (5 ml) and extracted with EtOAc (3×5 ml). The aqueous phase was acidified with 1 M HCl(aq) and the product was extracted into EtOAc (3×10 ml). The combined organic phases were dried over $MgSO_4$, filtered and the solvent was removed in vacuo. The crude product was purified by chromatography on silica gel (24 g cartridge, 0-50% EtOAc/DCM) to afford the title compound (60 mg, 0.128 mmol, 29.4% yield, 95% purity) as a white solid. UPLC-MS (Method 1) m/z 445.3 $(M+H)^+$, 443.2 $(M-H)^-$ at 1.56 min. $^1$H NMR (500 MHz, DMSO-$d_6$) δ 12.96 (br s, 1H), 8.29 (d, J=2.3 Hz, 1H), 7.98 (dd, J=8.6, 2.3 Hz, 1H), 7.52 (d, J=1.8 Hz, 1H), 7.37-7.33 (m, 2H), 7.04 (d, J=8.6 Hz, 1H), 2.75 (t, J=5.2 Hz, 4H), 1.68 (p, J=5.5 Hz, 4H), 1.58-1.51 (m, 2H). 2 exchangeable protons not observed.

Example 165: 4-methoxy-3-(N-methyl-N-(2-(piperidin-1-yl)-5-(trifluoromethyl)phenyl) sulfamoyl)benzoic acid

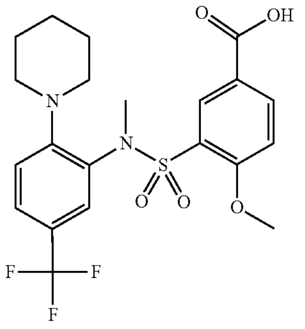 [SMILES: COc1ccc(C(=O)O)cc1S(=O)(=O)N(C)c1cc(C(F)(F)F)ccc1N1CCCCC1]

Step 1: methyl 4-methoxy-3-(N-(2-(piperidin-1-yl)-5-(trifluoromethyl)phenyl) sulfamoyl)benzoate: A mixture of 2-(piperidin-1-yl)-5-(trifluoromethyl)aniline (100 mg, 0.409 mmol), methyl 3-(chlorosulfonyl)-4-methoxybenzoate (130 mg, 0.491 mmol) and pyridine (100 μl, 1.24 mmol) in DCM (1.5 ml) was stirred at RT overnight. The mixture was concentrated onto silica and purified by chromatography on silica gel (12 g cartridge, 0-100% EtOAc/isohexane) to afford the title compound (189 mg, 0.384 mmol, 94% yield, 96% purity) as a white solid. UPLC-MS (Method 2) m/z 473.3 $(M+H)^+$ at 1.80 min. $^1$H NMR (500 MHz, DMSO-$d_6$) δ 8.80 (s, 1H), 8.36 (d, J=2.2 Hz, 1H), 8.18 (dd, J=8.8, 2.2 Hz, 1H), 7.44 (d, J=2.0 Hz, 1H), 7.40-7.29 (m, 3H), 3.93 (s, 3H), 3.85 (s, 3H), 2.76 (t, J=5.2 Hz, 4H), 1.70-1.61 (m, 4H), 1.59-1.49 (m, 2H).

Step 2: methyl 4-methoxy-3-(N-methyl-N-(2-(piperidin-1-yl)-5-(trifluoromethyl)phenyl) sulfamoyl)benzoate: To a suspension of sodium hydride (12 mg, 0.500 mmol) in THF (1 ml) at 0° C. was added the product from step 1 above (189 mg, 0.384 mmol) in THF (1 ml). The mixture was warmed to RT and stirred for 30 min before iodomethane (30 μl, 0.480 mmol) was added and mixture was stirred at RT overnight. The mixture was quenched with $H_2O$ (10 ml) and extracted with EtOAc (3×20 ml). The combined organic extracts were washed with brine (15 ml), passed through a phase separator and the solvent was removed in vacuo. The residue was loaded onto silica and purified by chromatography on silica gel (12 g cartridge, 0-50% EtOAc/isohexanes) to afford the title compound (172 mg, 0.283 mmol, 73.7% yield, 80% purity) as a clear colourless oil. UPLC-MS (Method 2) m/z 487.3 $(M+H)^+$ at 1.83 min. $^1$H NMR (500 MHz, DMSO-$d_6$) δ 8.25 (dd, J=8.7, 2.2 Hz, 1H), 8.22 (d, J=2.2 Hz, 1H), 7.54 (dd, J=8.6, 2.2 Hz, 1H), 7.48 (d, J=8.7 Hz, 1H), 7.21 (d, J=8.6 Hz, 1H), 7.02 (d, J=2.2 Hz, 1H), 4.00 (s, 3H), 3.83 (s, 3H), 3.27 (s, 3H), 3.06 (t, J=5.1 Hz, 4H), 1.64-1.57 (m, 4H), 1.57-1.50 (m, 2H).

Step 3: 4-methoxy-3-(N-methyl-N-(2-(piperidin-1-yl)-5-(trifluoromethyl)phenyl) sulfamoyl)benzoic acid: A mixture of the product from step 2 above (170 mg, 0.349 mmol) and 2 M LiOH(aq) (0.35 ml, 0.700 mmol) in THF (1.5 ml) was stirred at 50° C. overnight. The mixture was diluted with $H_2O$ (5 ml), acidified to ca. pH 4 with 1 M HCl(aq) and extracted with EtOAc (3×10 ml). The combined organic extracts were washed with brine (10 ml), passed through a phase separator and the solvent was removed in vacuo. The residue was loaded onto silica and purified by chromatography on silica gel (4 g cartridge, 0-10% MeOH/DCM) to give the title compound (66.1 mg, 0.134 mmol, 38.3% yield, 96% purity) as a white solid. UPLC-MS (Method 2) m/z 473.3 $(M+H)^+$, 471.2 $(M-H)^-$ at 1.17 min. $^1$H NMR (500 MHz, DMSO-$d_6$) δ 13.10 (s, 1H), 8.22 (m, 2H), 7.53 (dd, J=8.5, 2.3 Hz, 1H), 7.48-7.41 (m, 1H), 7.20 (d, J=8.5 Hz, 1H), 7.01 (d, J=2.2 Hz, 1H), 3.99 (s, 3H), 3.28 (s, 3H), 3.09-3.02 (m, 4H), 1.65-1.57 (m, 4H), 1.57-1.48 (m, 2H).

Example 171:2-methoxy-N-(2-(piperidin-1-yl)-5-(trifluoromethyl)phenyl)-5-(tetrazol-5-yl)benzenesulfonamide

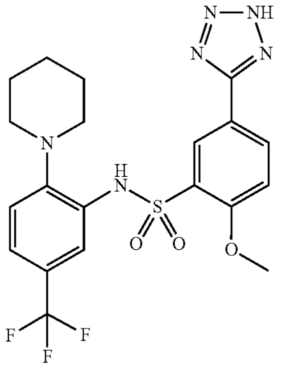 [SMILES: COc1ccc(-c2nn[nH]n2)cc1S(=O)(=O)Nc1cc(C(F)(F)F)ccc1N1CCCCC1]

Step 1: 5-cyano-2-methoxy-N-(2-(piperidin-1-yl)-5-(trifluoromethyl)phenyl)benzenesulfonamide: 2-(piperidin-1-yl)-5-(trifluoromethyl)aniline (200 mg, 0.819 mmol) was dissolved in a mixture of DCM (2 ml) and pyridine (0.15 ml, 1.86 mmol) and treated with a solution of the 5-cyano-2-methoxybenzenesulfonyl chloride (237 mg, 1.02 mmol) in DCM (1 ml). The resultant solution was allowed to stand at RT for 18 h, then diluted with water (ca. 0.1 ml) and concentrated in vacuo. The crude product was purified by chromatography on silica gel (12 g cartridge, 0-50% EtOAc/isohexanes) to afford the title compound (325 mg, 0.717 mmol, 88% yield, 99% purity) as a pale yellow solid. UPLC-MS (Method 1) m/z 440.4 $(M+H)^+$, 438.1 $(M-H)^-$ at 1.82 min.

Step 2: 2-methoxy-N-(2-(piperidin-1-yl)-5-(trifluoromethyl)phenyl)-5-(tetrazol-5-yl)benzenesulfonamide: The product from step 1 above (100 mg, 0.228 mmol) was combined with sodium azide (74.0 mg, 1.14 mmol) and zinc bromide (102 mg, 0.455 mmol) in IPA (1 ml) and water (0.3 ml). The resultant mixture was heated at 80° C. overnight then concentrated in vacuo. The crude product was purified by chromatography on silica gel (24 g cartridge, 0-100% EtOAc/isohexanes followed by 0-10% MeOH/DCM) to afford the title compound (7.9 mg, 0.016 mmol, 6.84% yield, 95% purity) as a white solid. UPLC-MS (Method 1) m/z 483.4 $(M+H)^+$, 481.2 $(M-H)^-$ at 1.67 min. $^1H$ NMR (500 MHz, DMSO-$d_6$) δ 8.79 (s, 1H), 8.55 (d, J=2.2 Hz, 1H), 8.27 (dd, J=8.7, 2.2 Hz, 1H), 7.51 (s, 1H), 7.44 (d, J=8.8 Hz, 1H), 7.37-7.33 (m, 2H), 3.94 (s, 3H), 2.78 (t, J=5.3 Hz, 4H), 1.70-1.65 (m, 4H), 1.57-1.50 (m, 2H). One exchangeable proton not observed.

Example 177: 3-(N-(2-(3-hydroxypiperidin-1-yl)-5-(trifluoromethyl)phenyl)sulfamoyl)-4-methoxybenzoic acid

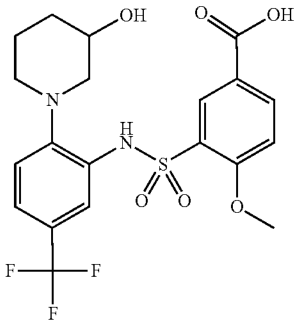 [SMILES: COc1ccc(C(=O)O)cc1S(=O)(=O)Nc1cc(C(F)(F)F)ccc1N1CCCC(O)C1]

Step 1: 1-(2-nitro-4-(trifluoromethyl)phenyl)piperidin-3-ol: $Et_3N$ (0.500 ml, 3.59 mmol) was added to a solution of 1-fluoro-2-nitro-4-(trifluoromethyl)benzene (0.201 ml, 1.44 mmol) and piperidin-3-ol (174 mg, 1.72 mmol) in DCM (6 ml) at RT. The clear solution was stirred at RT for 17 h. The organic phase was washed with 1 M HCl (3 ml) and dried by passage through a phase separator and concentrated in vacuo to afford the title compound (468 mg, 1.40 mmol, 98% yield, 87% purity) as a red/orange oil. UPLC-MS (Method 1) m/z 291.5 $(M+H)^+$ at 1.39 min. $^1H$ NMR (500 MHz, DMSO-$d_6$) δ 8.12-8.07 (m, 1H), 7.80 (dd, J=9.0, 2.4 Hz, 1H), 7.41 (d, J=8.9 Hz, 1H), 4.91 (d, J=4.3 Hz, 1H), 3.65-3.57 (m, 1H), 3.26 (dd, J=12.4, 3.9 Hz, 1H), 3.21 (dt, J=13.0, 4.5 Hz, 1H), 2.98-2.91 (m, 1H), 2.75 (dd, J=12.3, 8.5 Hz, 1H), 1.93-1.85 (m, 1H), 1.81-1.73 (m, 1H), 1.56-1.46 (m, 1H), 1.40-1.30 (m, 1H).

Step 2: 1-(2-amino-4-(trifluoromethyl)phenyl)piperidin-3-ol: 5% Pd/C (50% w/w water) Type 87L (50 mg, 0.012 mmol) in EtOH (0.5 ml) was added to a solution of the product from step 1 above (234 mg, 0.701 mmol) in EtOH (3.0 ml) at RT. The reaction mixture was hydrogenated (4 bar) at RT for 19 h. The catalyst was removed by filtration through Celite®, washing with MeOH (15 ml). The filtrate was concentrated in vacuo and the residue was dissolved in MeOH (10 ml), dried over $MgSO_4$, filtered and concentrated in vacuo to afford a white solid. MeCN (10 ml) was added and the resultant slurry was dried again with a large excess of $MgSO_4$, filtered and concentrated in vacuo to afford the title compound (153 mg, 0.576 mmol, 82% yield, 98% purity) as a yellow solid. UPLC-MS (Method 1) m/z 261.4 $(M+H)^+$ at 1.29 min. 1H NMR (500 MHz, DMSO-$d_6$) δ 6.96 (d, J=8.1 Hz, 1H), 6.94 (d, J=2.2 Hz, 1H), 6.84-6.80 (m, 1H), 5.14 (s, 2H), 4.79 (d, J=5.4 Hz, 1H), 3.74-3.66 (m, 1H), 3.04-2.96 (m, 1H), 2.92-2.85 (m, 1H), 2.58-2.50 (m, 1H), 2.49-2.41 (m, 1H), 1.86-1.75 (m, 2H), 1.65-1.55 (m, 1H), 1.37-1.28 (m, 1H).

Step 3: methyl 3-(N-(2-(3-hydroxypiperidin-1-yl)-5-(trifluoromethyl)phenyl)sulfamoyl)-4-methoxybenzoate: Pyridine (0.075 ml, 0.933 mmol) was added to a cloudy solution of the product from step 2 above (62.0 mg, 0.233 mmol) and methyl 3-(chlorosulfonyl)-4-methoxybenzoate (78 mg, 0.280 mmol) in DCM (2.0 ml) at RT. The resultant clear solution was stirred at RT for 20 h and the reaction mixture was concentrated in vacuo. The crude product was purified by chromatography on silica gel (10 g cartridge, 0-100% EtOAc/isohexane) to afford the title compound (88.1 mg, 0.177 mmol, 76% yield, 98% purity) as a yellow oil. UPLC-MS (Method 1) m/z 489.3 $(M+H)^+$, 487.2 $(M-H)^-$ at 1.59 min.

Step 4: 3-(N-(2-(3-hydroxypiperidin-1-yl)-5-(trifluoromethyl)phenyl)sulfamoyl)-4-methoxybenzoic acid: 1 M LiOH (aq) (0.707 ml, 0.707 mmol) was added to a solution of the product from step 3 above (88.1 mg, 0.177 mmol) in THF (1.4 ml) at RT. The reaction mixture was stirred at RT for 18 h and then concentrated in vacuo. The residue was dissolved in water (3 ml) and acidified using 1 M HCl until pH 4-5. The precipitate was isolated by filtration and then dissolved in EtOAc (5 ml). The organic phase was washed with water (3 ml), dried over $MgSO_4$, filtered and concentrated in vacuo to afford the title compound (50 mg, 0.104 mmol, 59% yield, 99% purity) as a pale pink solid. UPLC-MS (Method 1) m/z 475.4 $(M+H)^+$, 473.1 $(M-H)^-$ at 1.38 min. $^1H$ NMR (500 MHz, DMSO-$d_6$) δ 13.16 (br s, 1H), 9.14 (br s, 1H), 8.39 (d, J=2.2 Hz, 1H), 8.14 (dd, J=8.7, 2.2 Hz, 1H), 7.46 (d, J=1.8 Hz, 1H), 7.33-7.27 (m, 2H), 7.25 (d, J=8.3 Hz, 1H), 5.09 (br s, 1H), 3.89 (s, 3H), 3.79-3.73 (m, 1H), 2.87-2.79 (m, 2H), 2.74-2.68 (m, 1H), 2.67-2.62 (m, 1H), 1.93-1.85 (m, 1H), 1.77-1.69 (m, 1H), 1.60-1.51 (m, 1H), 1.51-1.43 (m, 1H).

Example 178: (S)-3-(N-(2-(3-hydroxypyrrolidin-1-yl)-5-(trifluoromethyl)phenyl) sulfamoyl)-4-methoxybenzoic acid

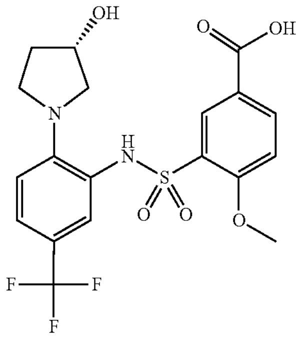 [SMILES: COc1ccc(C(=O)O)cc1S(=O)(=O)Nc1cc(C(F)(F)F)ccc1N1CC[C@H](O)C1]

Step 1: (S)-1-(2-nitro-4-(trifluoromethyl)phenyl) pyrrolidin-3-ol: $Et_3N$ (0.500 ml, 3.59 mmol) was added to a solution of 1-fluoro-2-nitro-4-(trifluoromethyl)benzene (0.201 ml, 1.44 mmol) and(S)-pyrrolidin-3-ol (0.139 ml, 1.72 mmol) in DCM (6 ml) at RT. The clear solution was stirred at RT for 17 h. The organic phase was washed with 1 M HCl (3 ml), dried by passage through a phase separator and concentrated in vacuo to afford the title compound (445 mg, 1.37 mmol, 95% yield, 85% purity) as an orange oil. UPLC-MS (Method 1) m/z 277.2 $(M+H)^+$ at 1.33 min. $^1H$ NMR (500 MHz, DMSO-$d_6$) δ 8.06-8.03 (m, 1H), 7.72 (dd, J=9.1, 2.3 Hz, 1H), 7.19 (d, J=9.1 Hz, 1H), 5.05 (d, J=3.4 Hz, 1H), 4.41-4.36 (m, 1H), 3.50 (app. Td, J=9.8, 6.8 Hz, 1H), 3.41 (dd, J=11.1, 4.3 Hz, 1H), 3.25-3.19 (m, 1H), 2.85-2.80 (m, 1H), 2.04-1.96 (m, 1H), 1.94-1.88 (m, 1H).

Step 2: (S)-1-(2-amino-4-(trifluoromethyl)phenyl) pyrrolidin-3-ol: 5% Pd/C (50% w/w water) Type 87L (50 mg, 0.012 mmol) in EtOH (0.5 ml) was added to a solution of the product from step 1 above (220 mg, 0.677 mmol) in EtOH (3.0 ml) at RT. The reaction mixture was hydrogenated (4 bar) at RT for 19 h. The catalyst was removed by filtration through Celite®, washing with MeOH (20 ml). The organic phase was concentrated in vacuo and the residue was dissolved in DCM (10 ml). The organic phase was washed with water (5 ml), dried over $MgSO_4$, filtered and concentrated in vacuo to afford the title compound (134 mg, 0.522 mmol, 77% yield, 96% purity) as a dark brown oil. UPLC-MS (Method 1) m/z 247.3 $(M+H)^+$ at 1.08 min. $^1H$ NMR (500 MHz, DMSO-$d_6$) δ 6.92 (d, J=1.8 Hz, 1H), 6.88 (d, J=8.2 Hz, 1H), 6.80 (dd, J=8.2, 1.5 Hz, 1H), 4.97 (br s, 2H), 4.86 (d, J=4.9 Hz, 1H), 4.35-4.28 (m, 1H), 3.31-3.22 (m, 2H), 2.99 (ddd, J=9.1, 7.9, 5.0 Hz, 1H), 2.90 (dd, J=10.0, 3.0 Hz, 1H), 2.12-2.04 (m, 1H), 1.79-1.71 (m, 1H).

Step 3: (S)-methyl 3-(N-(2-(3-hydroxypyrrolidin-1-yl)-5-(trifluoromethyl)phenyl)sulfamoyl)-4-methoxybenzoate: Pyridine (0.075 ml, 0.933 mmol) was added to a cloudy solution of the product from step 2 above (60.5 mg, 0.233 mmol) and methyl 3-(chlorosulfonyl)-4-methoxybenzoate (78 mg, 0.280 mmol) in DCM (2.0 ml) at RT. The resultant clear solution was stirred at RT for 20 h then concentrated in vacuo. The crude product was purified by chromatography on silica gel (10 g cartridge, 0-100% EtOAc/isohexane) to afford the title compound (96.7 mg, 0.196 mmol, 84% yield, 96% purity) as an orange oil. UPLC-MS (Method 1) m/z 475.4 $(M+H)^+$, 473.2 $(M-H)^-$ at 1.35 min.

Step 4: (S)-3-(N-(2-(3-hydroxypyrrolidin-1-yl)-5-(trifluoromethyl)phenyl)sulfamoyl)-4-methoxybenzoic acid: 1 M LiOH (aq) (0.783 ml, 0.783 mmol) was added to a solution of the product from step 3 above (96.7 mg, 0.196 mmol) in THF (1.6 ml) at RT. The reaction mixture was stirred at RT for 20 h then concentrated in vacuo. The residue was dissolved in water (3 ml) and acidified using 1 M HCl until pH 4-5. The precipitate was isolated by filtration and then dissolved in EtOAc (5 ml). The organic phase was washed with water (3 ml), dried over $MgSO_4$ and concentrated in vacuo. The crude product was purified by chromatography on silica gel (10 g cartridge, 0-5% MeOH/DCM) to afford the title compound (22.3 mg, 0.046 mmol, 26.3% yield, 96% purity) as an off-white solid. UPLC-MS (Method 1) m/z 461.3 $(M+H)^+$, 459.2 $(M-H)^-$ at 1.17 min. $^1H$ NMR (500 MHz, DMSO-$d_6$) δ 13.06 (br s, 1H), 9.30 (br s, 1H), 8.17 (dd, J=8.7, 2.2 Hz, 1H), 8.06 (d, J=2.2 Hz, 1H), 7.39 (d, J=8.8 Hz, 1H), 7.29 (dd, J=8.8, 2.4 Hz, 1H), 6.74 (d, J=8.9 Hz, 1H), 6.50 (d, J=2.3 Hz, 1H), 4.96 (br s, 1H), 4.37-4.31 (m, 1H), 3.99 (s, 3H), 3.79 (dd, J=11.0, 4.8 Hz, 1H), 3.59-3.52 (m, 1H), 3.49-3.43 (m, 1H), 3.38-3.34 (m, 1H), 1.96-1.88 (m, 1H), 1.87-1.81 (m, 1H).

Example 179:4-methoxy-3-(N-(2-(3-methoxypiperidin-1-yl)-5-(trifluoromethyl)phenyl) sulfamoyl)benzoic acid

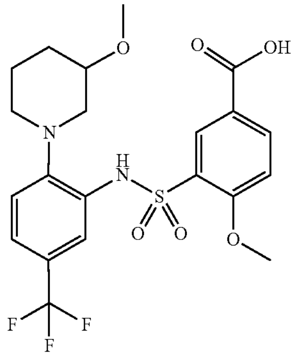 [SMILES: COc1ccc(C(=O)O)cc1S(=O)(=O)Nc1cc(C(F)(F)F)ccc1N1CCCC(OC)C1]

Step 1: 3-methoxy-1-(2-nitro-4-(trifluoromethyl)phenyl) piperidine: $Et_3N$ (0.500 ml, 3.59 mmol) was added to a solution of 1-fluoro-2-nitro-4-(trifluoromethyl)benzene (0.201 ml, 1.44 mmol) and 3-methoxypiperidine (198 mg, 1.72 mmol) in DCM (6 ml) at RT. The clear solution was stirred at RT for 16 h. The organic phase was washed with 1 M HCl (3 ml), dried by passage through a phase separator and concentrated in vacuo to afford the title compound (438 mg, 1.41 mmol, 98% yield, 98% purity) as an orange oil. $^1H$ NMR (500 MHz, DMSO-$d_6$) δ 8.13-8.10 (m, 1H), 7.81 (dd, J=8.9, 2.4 Hz, 1H), 7.43 (d, J=8.9 Hz, 1H), 3.42-3.33 (m, 2H), 3.24 (s, 3H), 3.19 (app. Dt, J=12.9, 4.7 Hz, 1H), 3.03-2.96 (m, 1H), 2.86 (dd, J=12.2, 7.5 Hz, 1H), 2.00-1.93 (m, 1H), 1.82-1.73 (m, 1H), 1.57-1.47 (m, 1H), 1.47-1.38 (m, 1H).

Step 2: 2-(3-methoxypiperidin-1-yl)-5-(trifluoromethyl) aniline: 5% Pd/C (50% w/w water) Type 87L (50 mg, 0.012 mmol) in EtOH (0.5 ml) was added to a solution of the product from step 1 above (214 mg, 0.689 mmol) in EtOH (3.0 ml) at RT. The reaction mixture was hydrogenated (4 bar) at RT for 18 h. The catalyst was removed by filtration through a pad of Celite®, washing with EtOH (15 ml). The filtrate was concentrated in vacuo and azeotroped with MeOH (6 ml) to afford the title compound (151 mg, 0.484 mmol, 70% yield, 88% purity) as an off-white solid. UPLC-MS (Method 1) m/z 275.3 (M+H)+ (ES+), at 1.58 min. $^1H$ NMR (500 MHz, DMSO-$d_6$) δ 6.99 (d, J=8.1 Hz, 1H), 6.95 (d, J=2.2 Hz, 1H), 6.83 (dd, J=8.1, 1.5 Hz, 1H), 5.12 (br s, 2H), 3.46-3.40 (m, 1H), 3.29 (s, 3H), 3.17-3.09 (m, 1H), 2.99-2.93 (m, 1H), 2.57-2.46 (m, 2H), 1.98-1.90 (m, 1H), 1.80-1.73 (m, 1H), 1.67-1.58 (m, 1H), 1.40-1.29 (m, 1H).

Step 3: methyl 4-methoxy-3-(N-(2-(3-methoxypiperidin-1-yl)-5-(trifluoromethyl)phenyl) sulfamoyl)benzoate: Pyridine (0.081 ml, 1.01 mmol) was added to a cloudy solution of the product from step 2 above (79 mg, 0.252 mmol) and methyl 3-(chlorosulfonyl)-4-methoxybenzoate (80 mg, 0.302 mmol) in DCM (2.0 ml) at RT. The resultant clear solution was stirred at RT for 18 h then concentrated in vacuo. The crude product was purified by chromatography on silica gel (10 g cartridge, 0-60% EtOAc/isohexane) to afford the title compound (84 mg, 0.167 mmol, 66% yield, 100% purity) as a cream solid. UPLC-MS (Method 1) m/z 503.4 $(M+H)^+$, 501.2 $(M-H)^-$ at 1.77 min.

Step 4: 4-methoxy-3-(N-(2-(3-methoxypiperidin-1-yl)-5-(trifluoromethyl)phenyl) sulfamoyl)benzoic acid: 1 M LiOH (aq) (0.669 ml, 0.669 mmol) was added to a solution of the product from step 3 above (84 mg, 0.167 mmol) in THF (1.3 ml) at RT. The reaction mixture was stirred at RT for 18 h then concentrated in vacuo. The residue was dissolved in water (3 ml) and washed with EtOAc (5 ml). The aqueous phase was acidified using 1 M HCl until pH 4-5 and the product was extracted into EtOAc (5 ml×3). The combined organic phases were dried over $MgSO_4$ and concentrated in vacuo to afford the title compound (63 mg, 0.128 mmol, 77% yield, 100% purity) as a white solid. UPLC-MS (Method 1) m/z 489.3 $(M+H)^+$, 487.1 $(M-H)^-$ at 1.60 min. $^1H$ NMR (500 MHz, DMSO-$d_6$) δ 13.19 (br s, 1H), 9.06 (br s, 1H), 8.39 (d, J=2.2 Hz, 1H), 8.15 (dd, J=8.7, 2.2 Hz, 1H), 7.47 (d, J=1.6 Hz, 1H), 7.35-7.23 (m, 3H), 3.89 (s, 3H), 3.47-3.41 (m, 1H), 3.35 (s, 3H), 2.98-2.88 (m, 2H), 2.78-2.71 (m, 2H), 1.85-1.70 (m, 2H), 1.69-1.55 (m, 2H).

Example 180:3-(N-(2-(4-ethoxypiperidin-1-yl)-5-(trifluoromethyl)phenyl)sulfamoyl)-4-methoxybenzoic acid

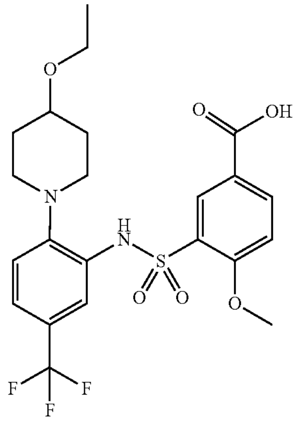

Step 1: 4-ethoxy-1-(2-nitro-4-(trifluoromethyl)phenyl)piperidine: $Et_3N$ (0.500 ml, 3.59 mmol) was added to a solution of 1-fluoro-2-nitro-4-(trifluoromethyl)benzene (0.201 ml, 1.44 mmol) and 4-ethoxypiperidine (222 mg, 1.72 mmol) in DCM (6 ml) at RT. The clear solution was stirred at RT for 16 h. The organic phase was washed with 1 M HCl (3 ml), dried by passage through a phase separator and concentrated in vacuo to afford the title compound (471 mg, 1.435 mmol, 100% yield, 97% purity) as an orange oil. $^1H$ NMR (500 MHz, DMSO-$d_6$) δ 8.13-8.10 (m, 1H), 7.81 (dd, J=8.9, 2.4 Hz, 1H), 7.42 (d, J=8.8 Hz, 1H), 3.55-3.45 (m, 3H), 3.30-3.25 (m, 2H), 3.03-2.97 (m, 2H), 1.95-1.87 (m, 2H), 1.59-1.51 (m, 2H), 1.12 (t, J=7.0 Hz, 3H).

Step 2: 2-(4-ethoxypiperidin-1-yl)-5-(trifluoromethyl) aniline: 5% Pd/C (50% w/w water) Type 87L (50 mg, 0.012 mmol) in EtOH (0.5 ml) was added to a solution of the product from step 1 above (228 mg, 0.695 mmol) in EtOH (3.0 ml) at RT. The reaction mixture was hydrogenated (4 bar) at RT for 18 h. The catalyst was removed by filtration through a pad of Celite®, washing with EtOH (15 ml). The filtrate was concentrated in vacuo and azeotroped with MeOH (6 ml) to afford the title compound (179 mg, 0.559 mmol, 80% yield, 90% purity) as an off-white solid. UPLC-MS (Method 1) m/z 289.3 $(M+H)^+$ at 1.66 min. $^1H$ NMR (500 MHz, DMSO-$d_6$) δ 6.99 (d, J=8.1 Hz, 1H), 6.95 (d, J=2.2 Hz, 1H), 6.82 (dd, J=8.2, 1.6 Hz, 1H), 5.10 (br s, 2H), 3.48 (q, J=7.0 Hz, 2H), 3.45-3.38 (m, 1H), 3.06-2.99 (m, 2H), 2.65-2.57 (m, 2H), 1.99-1.91 (m, 2H), 1.68-1.59 (m, 2H), 1.12 (t, J=7.0 Hz, 3H).

Step 3: methyl 3-(N-(2-(4-ethoxypiperidin-1-yl)-5-(trifluoromethyl)phenyl)sulfamoyl)-4-methoxybenzoate: Pyridine (0.081 ml, 1.01 mmol) was added to a cloudy solution of the product from step 2 above (81 mg, 0.252 mmol) and methyl 3-(chlorosulfonyl)-4-methoxybenzoate (80 mg, 0.302 mmol) in DCM (2.0 ml) at RT. The resultant clear solution was stirred at RT for 18 h then concentrated in vacuo. The crude product was purified by chromatography on silica gel (10 g cartridge, 0-60% EtOAc/isohexane) to afford the title compound (92.5 mg, 0.159 mmol, 63% yield, 89% purity) as a colourless oil. UPLC-MS (Method 1) m/z 517.4 $(M+H)^+$, 515.2 $(M-H)^-$ at 1.80 min.

Step 4: 3-(N-(2-(4-ethoxypiperidin-1-yl)-5-(trifluoromethyl)phenyl)sulfamoyl)-4-methoxybenzoic acid: 1 M LiOH (aq) (0.634 ml, 0.634 mmol) was added to a solution of the product from step 3 above (92 mg, 0.159 mmol) in THF (1.3 ml) at RT. The reaction mixture was stirred at RT for 18 h then concentrated in vacuo. The residue was dissolved in water (3 ml) and washed with EtOAc (2×5 ml). The aqueous phase was acidified using 1 M HCl until pH 4-5 and the product was extracted into EtOAc (3×5 ml). The combined organic phases were dried over $MgSO_4$ and concentrated in vacuo to afford the title compound (61 mg, 0.118 mmol, 74% yield, 97% purity) as an off-white solid. UPLC-MS (Method 1) m/z 503.3 $(M+H)^+$, 501.3 $(M-H)^-$ at 1.63 min. $^1H$ NMR (500 MHz, DMSO-$d_6$) δ 13.18 (br s, 1H), 8.87 (br s, 1H), 8.36 (d, J=2.2 Hz, 1H), 8.16 (dd, J=8.7, 2.2 Hz, 1H), 7.44 (d, J=1.7 Hz, 1H), 7.36 (dd, J=8.4, 1.6 Hz, 1H), 7.34-7.30 (m, 2H), 3.91 (s, 3H), 3.52-3.42 (m, 3H), 2.99-2.91 (m, 2H), 2.72-2.64 (m, 2H), 1.98-1.90 (m, 2H), 1.67-1.58 (m, 2H), 1.14 (t, J=7.0 Hz, 3H).

Example 181: 4-methoxy-3-(N-(2-(4-methoxypiperidin-1-yl)-5-(trifluoromethyl)phenyl) sulfamoyl) benzoic acid

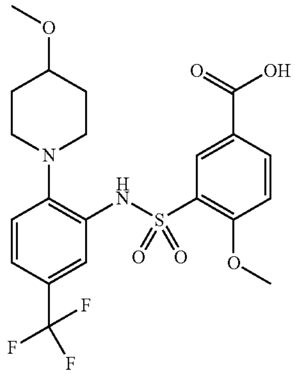 [SMILES: COc1ccc(C(=O)O)cc1S(=O)(=O)Nc1cc(C(F)(F)F)ccc1N1CCC(OC)CC1]

Step 1: 4-methoxy-1-(2-nitro-4-(trifluoromethyl)phenyl) piperidine: $Et_3N$ (318 μl, 2.28 mmol) was added to a solution of 1-fluoro-2-nitro-4-(trifluoromethyl)benzene (128 μl, 0.912 mmol) and 4-methoxypiperidine (105 mg, 0.912 mmol) in DCM (3 ml) and the resultant solution was stirred at RT for 20 h. 1 M HCl (2 ml) was added and the organic phase was dried by passage through a phase separator. The organic phase was concentrated in vacuo to afford the title compound (277 mg, 0.912 mmol, 100% yield, 100% purity) as a light orange oil. UPLC-MS (Method 1) m/z 305.6 $(M+H)^+$ at 1.60 min.

Step 2: 2-(4-methoxypiperidin-1-yl)-5-(trifluoromethyl)aniline: The product from step 1 above (277 mg, 0.912 mmol) was dissolved in EtOH (14.2 ml) and hydrogenated in a ThalesNano H-cube® flow reactor (10% Pd/C, 30×4 mm, full hydrogen mode, 40° C., 1 ml/min flow rate, 2 passes). The reaction mixture was concentrated in vacuo and azeotroped with MeOH (6 ml) to afford the title compound (239 mg, 0.854 mmol, 94% yield, 98% purity) as a cream solid. UPLC-MS (Method 2) m/z 275.3 $(M+H)^+$, 273.3 $(M-H)^-$ at 1.53 min.

Step 3: methyl 4-methoxy-3-(N-(2-(4-methoxypiperidin-1-yl)-5-(trifluoromethyl)phenyl) sulfamoyl)benzoate: The product from step 2 above (69.1 mg, 0.252 mmol) was dissolved in a mixture of DCM (1 ml) and pyridine (81 μl, 1.01 mmol) and treated with a solution methyl 3-(chlorosulfonyl)-4-methoxybenzoate (80 mg, 0.302 mmol) in DCM (1 ml). The resultant solution was stirred at RT for 4 days. The crude product was purified directly by chromatography on silica gel (12 g cartridge, 0-100% EtOAc/isohexane) to afford the title compound (52.8 mg, 0.103 mmol, 40.9% yield, 98% purity) as a white solid. UPLC-MS (Method 1) m/z 503.4 (M+H)+(ES+); 501.2 (M−H)−(ES−), at 1.71 min.

Step 4: 4-methoxy-3-(N-(2-(4-methoxypiperidin-1-yl)-5-(trifluoromethyl)phenyl) sulfamoyl)benzoic acid: The product from step 3 above (50 mg, 0.100 mmol) was dissolved in THF (2 ml) and treated with 1.1 M LiOH (aq) (362 μl, 0.398 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 with 1 M HCl. The resultant lumpy suspension was sonicated to afford a cloudy mixture. The cloudy mixture was concentrated in vacuo to ~2 ml. The resultant precipitate was collected by filtration, washing with water (2×2 ml). The solid was suspended in MeCN (4 ml), concentrated in vacuo and dried at 45° C. to afford the title compound (38.8 mg, 0.078 mmol, 78% yield, 98% purity) as a white solid. UPLC-MS (Method 1) m/z 489.2 $(M+H)^+$, 487.1 $(M-H)^-$ at 1.53 min. $^1$H NMR (500 MHz, DMSO-$d_6$) δ 13.16 (s, 1H), 8.88 (s, 1H), 8.35 (d, J=2.2 Hz, 1H), 8.15 (dd, J=8.7, 2.2 Hz, 1H), 7.43 (d, J=2.0 Hz, 1H), 7.38-7.28 (m, 3H), 3.91 (s, 3H), 3.35-3.28 (m, 1H), 3.27 (s, 3H), 2.98-2.90 (m, 2H), 2.71-2.62 (m, 2H), 1.99-1.90 (m, 2H), 1.67-1.57 (m, 2H).

Example 182: 3-(N-(5-cyano-2-(piperidin-1-yl)phenyl)sulfamoyl)-4-methoxybenzoic acid

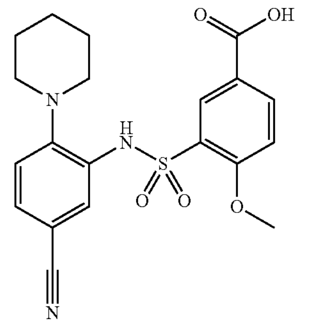 [SMILES: COc1ccc(C(=O)O)cc1S(=O)(=O)Nc1cc(C#N)ccc1N1CCCCC1]

Step 1: 3-nitro-4-(piperidin-1-yl)benzonitrile: A mixture of 4-fluoro-3-nitrobenzonitrile (300 mg, 1.81 mmol), piperidine (0.2 ml, 2.02 mmol) and $Et_3N$ (0.65 ml, 4.66 mmol) in DCM (6 ml) was stirred at RT overnight. The mixture was washed with water (10 ml), passed through a phase separator, concentrated onto silica and purified by chromatography on silica gel (12 g cartridge, 0-100% EtOAc/isohexane) to afford the title compound (400 mg, 1.73 mmol, 96% yield, 100% purity) as a pale orange solid. UPLC-MS (Method 2) m/z 232.1 $(M+H)^+$ at 1.60 min. $^1$H NMR (500 MHz, DMSO-$d_6$) δ 8.28 (d, J=2.1 Hz, 1H), 7.84 (dd, J=8.9, 2.1 Hz, 1H), 7.34 (d, J=8.9 Hz, 1H), 3.18-3.10 (m, 4H), 1.65-1.54 (m, 6H).

Step 2: 3-amino-4-(piperidin-1-yl)benzonitrile: A solution of the product from step 1 above (398 mg, 1.72 mmol) in EtOH (35 ml) was hydrogenated in a ThalesNano H-cube® flow reactor (10% Pt/C, 30×4 mm, full hydrogen mode, 25° C., 1 ml/min flow rate, 1 pass). The mixture was concentrated onto silica and purified by chromatography on silica gel (12 g cartridge, 0-50% EtOAc/isohexane) to afford the title compound (118 mg, 0.542 mmol, 32% yield, 93% purity) as a thick red oil. UPLC-MS (Method 2) m/z 202.2 $(M+H)^+$ at 1.58 min. $^1$H NMR (500 MHz, DMSO-$d_6$) δ 6.96-6.95 (m, 3H), 5.07 (s, 2H), 2.79 (t, J=5.1 Hz, 4H), 1.71-1.63 (m, 4H), 1.57-1.48 (m, 2H).

Step 3: methyl 3-(N-(5-cyano-2-(piperidin-1-yl)phenyl) sulfamoyl)-4-methoxybenzoate: A mixture of the product from step 2 above (118 mg, 0.542 mmol), methyl 3-(chlorosulfonyl)-4-methoxybenzoate (172 mg, 0.651 mmol) and pyridine (130 μl, 1.61 mmol) in DCM (5 ml) was stirred at RT over the weekend. The mixture was concentrated onto silica and purified by chromatography on silica gel (12 g cartridge, 0-100% EtOAc/isohexane) to afford the title compound (172 mg, 0.394 mmol, 73% yield, 98% purity) as a white solid. UPLC-MS (Method 2) m/z 430.2 $(M+H)^+$, 428.1 $(M-H)^-$ at 1.58 min. $^1$H NMR (500 MHz, DMSO-$d_6$) δ 8.94 (s, 1H), 8.33 (d, J=2.3 Hz, 1H), 8.20 (dd, J=8.7, 2.3 Hz, 1H), 7.50 (dd, J=8.5, 2.0 Hz, 1H), 7.41-7.35 (m, 2H), 7.24 (d, J=8.5 Hz, 1H), 3.94 (s, 3H), 3.86 (s, 3H), 2.82 (t, J=5.3 Hz, 4H), 1.65-1.57 (m, 4H), 1.55-1.46 (m, 2H).

Step 4: 3-(N-(5-cyano-2-(piperidin-1-yl)phenyl)sulfamoyl)-4-methoxybenzoic acid: A mixture of the product from step 3 above (170 mg, 0.390 mmol) and LiOH (40 mg, 1.67 mmol) in THF/$H_2O$ (4:1, 4 ml) was stirred at RT for 1 h and then at 35° C. overnight. The mixture was diluted with $H_2O$ (10 ml) and EtOAc (15 ml) and acidified to ~pH 4 with 1 M HCl. The phases were separated and the aqueous was extracted with EtOAc (2×15 ml). The combined organic extracts were washed with brine (15 ml), passed through a phase separator and the solvent was removed in vacuo. The residue was loaded onto silica and purified by chromatography on silica gel (12 g cartridge, 0-100% EtOAc/isohexane) to afford the title compound (105 mg, 0.243 mmol, 62% yield, 96% purity) as a white solid. UPLC-MS (Method 1) m/z 416.2 $(M+H)^+$, 413.7 $(M-H)^-$ at 1.47 min. $^1$H NMR (500 MHz, DMSO-$d_6$) δ 13.18 (s, 1H), 8.88 (s, 1H), 8.33 (d, J=2.2 Hz, 1H), 8.17 (dd, J=8.7, 2.2 Hz, 1H), 7.50 (dd, J=8.3, 2.0 Hz, 1H), 7.39 (d, J=2.0 Hz, 1H), 7.34 (d, J=8.7 Hz, 1H), 7.24 (d, J=8.3 Hz, 1H), 3.92 (s, 3H), 2.81 (t, J=5.2 Hz, 4H), 1.67-1.56 (m, 4H), 1.56-1.45 (m, 2H).

Example 183:4-ethyl-3-(N-(2-(3-hydroxyazetidin-1-yl)-5-(trifluoromethyl)phenyl) sulfamoyl)benzoic acid

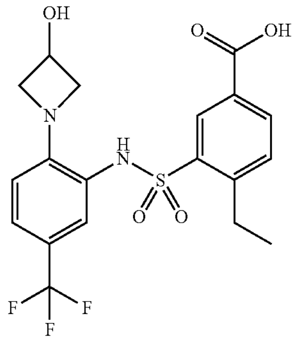 [SMILES: CCc1ccc(C(=O)O)cc1S(=O)(=O)Nc1cc(C(F)(F)F)ccc1N1CC(O)C1]

Step 1: methyl 3-(chlorosulfonyl)-4-ethylbenzoate: Thionyl chloride (5 ml, 68.5 mmol) was added portionwise to the product from example 1, step 1, 3-((chlorosulfonyl)-4-ethylbenzoic acid) (0.888 g, 3.57 mmol) at RT. The mixture was heated to 75° C. for 1 h. The solution was cooled to RT and concentrated in vacuo. The residue was dissolved in DCM (5 ml), treated with MeOH (0.144 ml, 3.57 mmol) followed by Et&N (0.536 ml, 3.93 mmol) and stirred at RT overnight. The mixture was diluted with DCM (50 ml), washed with water (50 ml), dried over $MgSO_4$, filtered and concentrated in vacuo to give the title compound (0.450 g, 1.37 mmol, 38% yield, 80% purity) as a light brown oil. $^1H$ NMR (500 MHz, DMSO-$d_6$) δ 8.73 (d, J=1.8 Hz, 1H), 8.32 (dd, J=8.1, 1.8 Hz, 1H), 7.61 (d, J=8.0 Hz, 1H), 3.99 (s, 3H), 3.28 (q, J=7.3 Hz, 2H), 1.40 (t, J=7.4 Hz, 3H).

Step 2: 1-(2-nitro-4-(trifluoromethyl)phenyl) azetidin-3-ol: $Et_3N$ (0.700 ml, 5.02 mmol) was added to a solution of 1-fluoro-2-nitro-4-(trifluoromethyl)benzene (0.201 ml, 1.44 mmol) and azetidin-3-ol hydrochloride (189 mg, 1.72 mmol) in DCM (6 ml) at RT. The clear solution was stirred at RT for 16 h. The organic phase was washed with 1 M HCl (3 ml) and the organic phase was dried via hydrophobic frit and concentrated in vacuo to afford the title compound (461 mg, 1.39 mmol, 97% yield, 79% purity) as an orange oil. $^1H$ NMR (500 MHz, DMSO-$d_6$) δ 8.09-8.05 (m, 1H), 7.73 (dd, J=9.0, 2.3 Hz, 1H), 6.90 (d, J=8.9 Hz, 1H), 5.79 (d, J=6.3 Hz, 1H), 4.55-4.49 (m, 1H), 4.19 (ddd, J=9.7, 6.7, 1.4 Hz, 2H), 3.77 (ddd, J=9.7, 4.1, 1.3 Hz, 2H).

Step 3: 1-(2-amino-4-(trifluoromethyl)phenyl) azetidin-3-ol: The product from step 2 above (455 mg, 1.37 mmol) was dissolved in EtOH (27.4 ml) and hydrogenated in a ThalesNano H-cube® flow reactor (10% Pd/C, 30×4 mm, full hydrogen mode, 40° C., 1 ml/min flow rate, 1 pass). The reaction mixture was concentrated in vacuo and azeotroped with MeOH (12 ml) to afford the title compound (395 mg, 1.37 mmol, 100% yield, 81% purity) as a pale yellow oil. UPLC-MS (Method 1) m/z 233.3 $(M+H)^+$ at 1.00 min. $^1H$ NMR (500 MHz, DMSO-$d_6$) δ 6.86 (d, J=2.1 Hz, 1H), 6.83-6.79 (m, 1H), 6.50 (d, J=8.1 Hz, 1H), 5.52 (d, J=6.5 Hz, 1H), 4.74 (br s, 2H), 4.46 (sextet, J=6.2 Hz, 1H), 4.19-4.13 (m, 2H), 3.45-3.40 (m, 2H).

Step 4: methyl 4-ethyl-3-(N-(2-(3-hydroxyazetidin-1-yl)-5-(trifluoromethyl)phenyl) sulfamoyl)benzoate: Pyridine (0.072 ml, 0.896 mmol) was added to a solution of the product from step 3 above (65 mg, 0.224 mmol) and the product from step 1 above (92 mg, 0.280 mmol) in DCM (2.0 ml) at RT. The resultant cloudy solution was stirred at RT for 21 h. The reaction mixture was concentrated in vacuo and the crude product was purified by chromatography on silica gel (10 g cartridge, 0-65% EtOAc/isohexane) to afford the title compound (51 mg, 0.102 mmol, 46% yield, 92% purity) as a red oil. UPLC-MS (Method 1) m/z 459.4 $(M+H)^+$, 457.2 $(M-H)^-$ at 0.66 min.

Step 5: 4-ethyl-3-(N-(2-(3-hydroxyazetidin-1-yl)-5-(trifluoromethyl)phenyl)sulfamoyl)benzoic acid: 1 M LiOH (aq) (0.409 ml, 0.409 mmol) was added to a solution of the product from step 4 above (51 mg, 0.102 mmol) in THF (0.82 ml) at RT. The solution was stirred at RT for 17 h then concentrated in vacuo. The residue was dissolved in water (3 ml) and washed with EtOAc (5 ml). The aqueous phase was acidified using 1 M HCl until pH 4-5 and the product was extracted into EtOAc (3×5 ml). The organic phases were combined, dried over $MgSO_4$ and concentrated in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (7.3 mg, 0.016 mmol, 16% yield, 99% purity) as a white solid. UPLC-MS (Method 1) m/z 445.3 $(M+H)^+$, 443.2 $(M-H)^-$ at 1.32 min. 1H NMR (500 MHz, DMSO-$d_6$) δ 13.24 (br s, 1H), 9.55 (br s, 1H), 8.25 (d, J=1.8 Hz, 1H), 8.11 (dd, J=8.0, 1.5 Hz, 1H), 7.62 (d, J=8.1 Hz, 1H), 7.31 (br d, J=8.7 Hz, 1H), 6.51 (d, J=8.6 Hz, 1H), 6.24 (br s, 1H), 5.63 (br d, J=5.9 Hz, 1H), 4.58-4.48 (m, 1H), 4.40-4.33 (m, 2H), 3.82 (dd, J=8.7, 4.8 Hz, 2H), 2.94 (q, J=7.4 Hz, 2H), 1.17 (t, J=7.4 Hz, 3H).

Example 184: 3-(N-(3-fluoro-2-(piperidin-1-yl)-5-(trifluoromethyl)phenyl)sulfamoyl)-4-methoxybenzoic acid

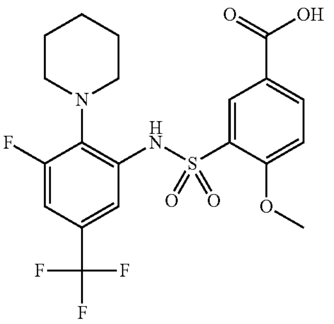 [SMILES: COc1ccc(C(=O)O)cc1S(=O)(=O)Nc1cc(C(F)(F)F)cc(F)c1N1CCCCC1]

Step 1: 1-(2-fluoro-6-nitro-4-(trifluoromethyl)phenyl)piperidine: $Et_3N$ (0.767 ml, 5.50 mmol) was added to a solution of 1,2-difluoro-3-nitro-5-(trifluoromethyl)benzene (500 mg, 2.20 mmol) and piperidine (0.261 ml, 2.64 mmol) in DCM (6 ml) at RT. The clear solution was stirred at RT for 23 h. The organic phase was washed with 1 M HCl (3 ml), dried by passage through a phase separator and concentrated in vacuo to afford the title compound (676 mg, 2.20 mmol, 100% yield, 98% purity) as a brown oil. UPLC-MS (Method 1) m/z 293.5 $(M+H)^+$ at 1.93 min.

Step 2: 3-fluoro-2-(piperidin-1-yl)-5-(trifluoromethyl) aniline: The product from step 1 above (0.642 g, 2.20 mmol) was dissolved in EtOH (44 ml) and hydrogenated in a ThalesNano H-cube® flow reactor (10% Pd/C, 30×4 mm, full hydrogen mode, RT, 1 ml/min flow rate, 1 pass). The crude product was concentrated in vacuo and azeotroped with MeOH (12 ml) to afford the title compound (0.543 g, 1.97 mmol, 90% yield, 95% purity) as a pale yellow oil. UPLC-MS (Method 1) m/z 263.3 $(M+H)^+$ at 1.89 min.

Step 3: methyl 3-(N-(3-fluoro-2-(piperidin-1-yl)-5-(trifluoromethyl)phenyl)sulfamoyl)-4-methoxybenzoate: Pyridine (0.139 ml, 1.72 mmol) was added to a solution of the product from step 2 above (0.15 g, 0.572 mmol) and methyl 3-(chlorosulfonyl)-4-methoxybenzoate (0.189 g, 0.715 mmol) in DCM (10 ml) and the solution was stirred at RT for 18 h. The solution was concentrated in vacuo and the crude product was purified by chromatography on silica gel (12 g cartridge, 0-100% EtOAc/isohexane) to afford the title compound (0.372 g, 0.546 mmol, 95% yield, 72% purity) as a white solid. UPLC-MS (Method 1) m/z 491.3 $(M+H)^+$, 489.2 $(M-H)^-$ at 1.96 min.

Step 4: 3-(N-(3-fluoro-2-(piperidin-1-yl)-5-(trifluoromethyl)phenyl)sulfamoyl)-4-methoxybenzoic acid: 1 M LiOH (aq) (3.28 ml, 3.28 mmol) was added to a solution of the product from step 3 above (0.268 g, 0.547 mmol) in THF (12 ml) and MeOH (3 ml) and the solution was stirred at RT overnight. The solvent was removed in vacuo and the residue dissolved in water (5 ml) and extracted with TBME (3×5 ml). The aqueous phase was acidified with conc. HCl and the product was extracted into TBME (3×10 ml). The organic phases were combined and dried by passage through a phase separator. The solvent was removed in vacuo to afford the title compound (0.184 g, 0.378 mmol, 69% yield, 98% purity) as an off white solid. UPLC-MS (Method 1) m/z 477.3 $(M+H)^+$, 474.9 $(M-H)^-$ at 1.81 min. $^1H$ NMR (500 MHz, DMSO-$d_6$) δ 13.19 (s, 1H), 8.99 (s, 1H), 8.38 (d, J=2.2 Hz, 1H), 8.17 (dd, J=8.7, 2.2 Hz, 1H), 7.37-7.31 (m, 3H), 3.94 (s, 3H), 2.91-2.81 (m, 4H), 1.69-1.62 (m, 4H), 1.58-1.51 (m, 2H).

The following examples were prepared by methods analogous to Example 184, substituting appropriate starting materials and intermediates where necessary:

| Example | Structure | Name/Analytical Data |
|---|---|---|
| 185 | 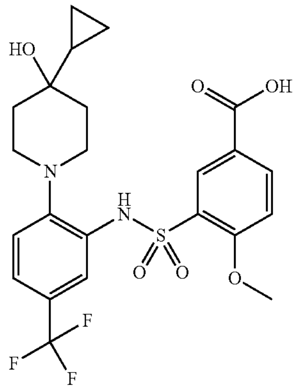 [SMILES: COc1ccc(C(=O)O)cc1S(=O)(=O)Nc1cc(C(F)(F)F)ccc1N1CCC(O)(C2CC2)CC1] | 3-(N-(2-(4-cyclopropyl-4-hydroxypiperidin-1-yl)-5-(trifluoromethyl)phenyl)sulfamoyl)-4-methoxybenzoic acid<br>UPLC-MS (Method 1) m/z 515.4 $(M + H)^+$, 512.9 $(M - H)^-$ at 1.50 min. $^1H$ NMR (500 MHz, DMSO-$d_6$) δ 13.17 (s, 1H), 8.84 (s, 1H), 8.36 (d, J = 2.2 Hz, 1H), 8.15 (dd, J = 8.7, 2.2 Hz, 1H), 7.45 (d, J = 1.9 Hz, 1H), 7.39-7.28 (m, 3H), 3.91-3.89 (m, 4H), 2.91 (td, J = 11.5, 2.6 Hz, 2H), 2.78-2.72 (m, 2H), 1.68 (td, J = 12.5, 4.2 Hz, 2H), 1.57-1.49 (m, 2H), 0.94-0.86 (m, 1H), 0.39-0.34 (m, 2H), 0.28-0.18 (m, 2H). |
| 186 | 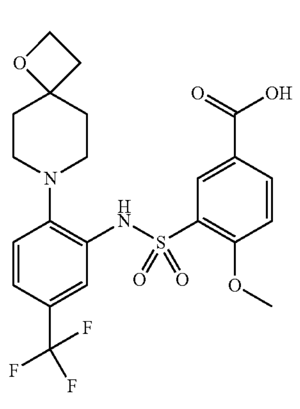 [SMILES: COc1ccc(C(=O)O)cc1S(=O)(=O)Nc1cc(C(F)(F)F)ccc1N1CCC2(CCO2)CC1] | 3-(N-(2-(1-oxa-7-azaspiro[3.5]nonan-7-yl)-5-(trifluoromethyl)phenyl)sulfamoyl)-4-methoxybenzoic acid<br>UPLC-MS (Method 1) m/z 501.3 $(M + H)^+$, 499.3 $(M - H)^-$ at 1.46 min. $^1H$ NMR (500 MHz, DMSO-$d_6$) δ 13.17 (s, 1H), 8.90 (s, 1H), 8.35 (d, J = 2.2 Hz, 1H), 8.14 (dd, J = 8.7, 2.2 Hz, 1H), 7.44 (d, J = 2.1 Hz, 1H), 7.37-7.25 (m, 3H), 4.41 (t, J = 7.7 Hz, 2H), 3.89 (s, 3H), 2.89-2.78 (m, 2H), 2.74-2.67 (m, 2H), 2.39 (t, J = 7.7 Hz, 2H), 1.92 (t, J = 5.5 Hz, 4H). |

-continued

| Example | Structure | Name/Analytical Data |
|---|---|---|
| 187 | 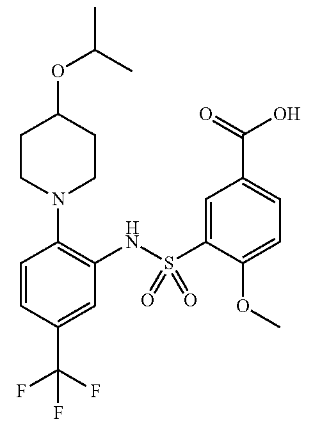 [SMILES: COc1ccc(C(=O)O)cc1S(=O)(=O)Nc1cc(C(F)(F)F)ccc1N1CCC(OC(C)C)CC1] | 3-(N-(2-(4-isopropoxypiperidin-1-yl)-5-(trifluoromethyl)phenyl)sulfamoyl)-4-methoxybenzoic acid UPLC-MS (Method 1) m/z 517.3 $(M + H)^+$, 515.2 $(M - H)^-$ at 1.72 min. $^1H$ NMR (500 MHz, DMSO-$d_6$) δ 13.15 (br s, 1H), 8.86 (br s, 1H), 8.36 (d, J = 2.2 Hz, 1H), 8.16 (dd, J = 8.7, 2.2 Hz, 1H), 7.43 (d, J = 1.7 Hz, 1H), 7.36 (dd, J = 8.5, 1.6 Hz, 1H), 7.32 (app. d, J = 8.7 Hz, 2H), 3.91 (s, 3H), 3.73 (hept, J = 6.1 Hz, 1H), 3.57-3.50 (m, 1H), 2.98-2.91 (m, 2H), 2.72-2.65 (m, 2H), 1.93-1.86 (m, 2H), 1.64-1.55 (m, 2H), 1.10 (d, J = 6.1 Hz, 6H). |
| 188 | 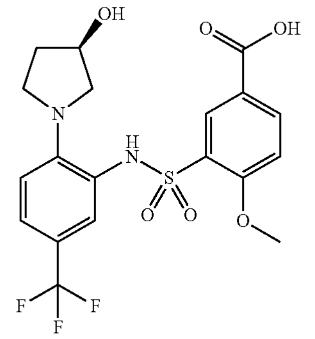 [SMILES: COc1ccc(C(=O)O)cc1S(=O)(=O)Nc1cc(C(F)(F)F)ccc1N1CC[C@@H](O)C1] | (R)-3-(N-(2-(3-hydroxypyrrolidin-1-yl)-5-(trifluoromethyl)phenyl)sulfamoyl)-4-methoxybenzoic acid UPLC-MS (Method 1) m/z 461.4 $(M + H)^+$, 459.2 $(M - H)^-$ at 1.17 min. $^1H$ NMR (500 MHz, DMSO-$d_6$) δ 8.15 (dd, J = 8.6, 2.2 Hz, 1H), 8.08 (d, J = 2.2 Hz, 1H), 7.34 (d, J = 8.7 Hz, 1H), 7.28 (dd, J = 8.9, 2.3 Hz, 1H), 6.74 (d, J = 8.8 Hz, 1H), 6.56 (d, J = 2.3 Hz, 1H), 4.96 (br s, 1H), 4.37-4.32 (m, 1H), 3.97 (s, 3H), 3.80 (dd, J = 10.9, 4.9 Hz, 1H), 3.60-3.53 (m, 1H), 3.49-3.43 (m, 1H), 3.38-3.33 (m, 1H), 1.97-1.89 (m, 1H), 1.88-1.81 (m, 1H). Two exchangeable protons not observed. |
| 189 | 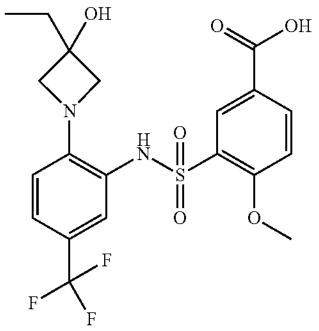 [SMILES: CCC1(O)CN(c2ccc(C(F)(F)F)cc2NS(=O)(=O)c2cc(C(=O)O)ccc2OC)C1] | 3-(N-(2-(3-ethyl-3-hydroxyazetidin-1-yl)-5-(trifluoromethyl)phenyl)sulfamoyl)-4-methoxybenzoic acid UPLC-MS (Method 1) m/z 475.4 $(M + H)^+$, 472.9 $(M - H)^-$ at 1.27 min. $^1H$ NMR (500 MHz, DMSO-$d_6$) δ 13.03 (br s, 1H), 9.26 (br s, 1H), 8.18 (dd, J = 8.7, 2.2 Hz, 1H), 8.12 (d, J = 2.2 Hz, 1H), 7.39 (d, J = 8.8 Hz, 1H), 7.31 (dd, J = 8.8, 2.2 Hz, 1H), 6.57-6.44 (m, 2H), 5.41 (br s, 1H), 4.01 (d, J = 8.4 Hz, 2H), 3.93 (s, 3H), 3.83 (d, J = 8.3 Hz, 2H), 1.66 (q, J = 7.3 Hz, 2H), 0.90 (t, J = 7.3 Hz, 3H). |
| 190 | 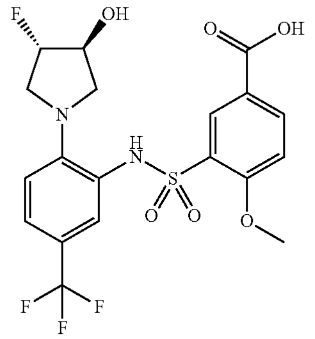 [SMILES: COc1ccc(C(=O)O)cc1S(=O)(=O)Nc1cc(C(F)(F)F)ccc1N1C[C@H](O)[C@@H](F)C1] | 3-(N-(2-(trans-3-fluoro-4-hydroxypyrrolidin-1-yl)-5-(trifluoromethyl)phenyl)sulfamoyl)-4-methoxybenzoic acid UPLC-MS (Method 1) m/z 479.4 $(M + H)^+$, 477.1 $(M - H)^-$ at 1.22 min. $^1H$ NMR (500 MHz, DMSO-$d_6$) δ 13.07 (br s, 1H), 9.31 (br s, 1H), 8.18 (dd, J = 8.7, 2.2 Hz, 1H), 8.08 (d, J = 2.2 Hz, 1H), 7.39 (d, J = 8.8 Hz, 1H), 7.32 (dd, J = 8.8, 1.6 Hz, 1H), 6.78 (d, J = 8.8 Hz, 1H), 6.57-6.52 (m, 1H), 5.56 (br s, 1H), 5.11-4.99 (m, 1H), 4.31 (dd, J = 9.1, 4.1 Hz, 1H), 4.02-3.83 (m, 5H), 3.72 (dd, J = 25.7, 12.7 Hz, 1H), 3.45 (d, J = 11.3 Hz, 1H). |

Example 200: 3-(N-(2-(piperidin-1-yl)-5-(trifluoromethyl)phenyl)sulfamoyl)-4-(trifluoromethyl)benzoic acid

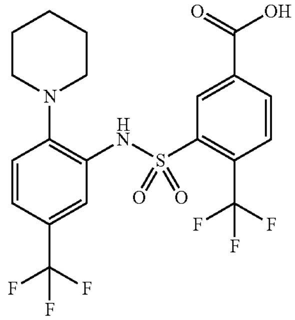 [SMILES: O=C(O)c1ccc(C(F)(F)F)c(S(=O)(=O)Nc2cc(C(F)(F)F)ccc2N2CCCCC2)c1]

Step 1: methyl 3-(N-(2-(piperidin-1-yl)-5-(trifluoromethyl)phenyl)sulfamoyl)-4-(trifluoromethyl)benzoate: A mixture of 2-(piperidin-1-yl)-5-(trifluoromethyl)aniline (75 mg, 0.307 mmol), methyl 3-(chlorosulfonyl)-4-(trifluoromethyl)benzoate (101 mg, 0.335 mmol) and pyridine (75 μl, 0.927 mmol) in DCM (4 ml) was stirred at RT overnight and then at 35° C. for 11 days. The mixture was concentrated onto silica and purified by chromatography on silica gel (12 g cartridge, 0-50% EtOAc/isohexane) to afford the title compound (91 mg, 0.178 mmol, 58.1% yield, 100% purity) as a pale yellow solid. UPLC-MS (Method 1) m/z 511.2 $(M+H)^+$, 509.0 $(M-H)^-$ at 1.99 min. $^1H$ NMR (500 MHz, DMSO-$d_6$) δ9.73 (s, 1H), 8.46 (s, 1H), 8.34 (d, J=8.2 Hz, 1H), 8.19 (d, J=8.2 Hz, 1H), 7.50 (d, J=8.4 Hz, 1H), 7.37 (d, J=2.2 Hz, 1H), 7.26 (dd, J=8.4, 2.2 Hz, 1H), 3.89 (s, 3H), 2.71-2.65 (m, 4H), 1.48-1.36 (m, 6H). Step 2: 3-(N-(2-(piperidin-1-yl)-5-(trifluoromethyl)phenyl)sulfamoyl)-4-(trifluoro-methyl)benzoic acid: A mixture of the product from step 1 above (91 mg, 0.178 mmol) and LiOH (17 mg, 0.710 mmol) in THE/MeOH/water (4:1:1, 2.4 ml) was stirred at 35° C. overnight. The mixture was diluted with water (10 ml) and EtOAc (15 ml) and acidified to ~pH 4 with 1 M HCl(aq). The phases were separated and the aqueous phase was extracted with EtOAc (2×15 ml). The organic extracts were combined and washed with brine (15 ml), dried by passage through a phase separator and the solvent was removed in vacuo. The residue was triturated with isohexane/TBME (5:1) to give the title compound (33.4 mg, 0.066 mmol, 37.0% yield, 98% purity) as a beige solid. UPLC-MS (Method 1) m/z 497.2 $(M+H)^+$, 495.1 $(M-H)^-$ at 1.92 min. $^1H$ NMR (500 MHz, DMSO-$d_6$) δ 13.89 (s, 1H), 9.69 (s, 1H), 8.48 (d, J=1.6 Hz, 1H), 8.32 (dd, J=8.2, 1.6 Hz, 1H), 8.16 (d, J=8.2 Hz, 1H), 7.49 (dd, J=8.5, 2.2 Hz, 1H), 7.35 (d, J=2.2 Hz, 1H), 7.26 (d, J=8.5 Hz, 1H), 2.73-2.64 (m, 4H), 1.49-1.35 (m, 6H).

Example 201: 4-ethoxy-3-(N-(2-(piperidin-1-yl)-5-(trifluoromethyl)phenyl) sulfamoyl)benzoic acid

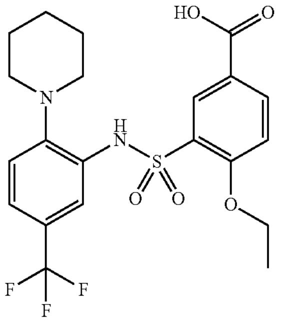 [SMILES: CCOc1ccc(C(=O)O)cc1S(=O)(=O)Nc1cc(C(F)(F)F)ccc1N1CCCCC1]

Step 1: methyl 4-ethoxy-3-(N-(2-(piperidin-1-yl)-5-(trifluoromethyl)phenyl)sulfamoyl)benzoate: A solution of 2-(piperidin-1-yl)-5-(trifluoromethyl)aniline (0.100 g, 0.409 mmol) in DCM (5 ml) and pyridine (0.199 ml, 2.46 mmol) were added to a solution of methyl 3-(chlorosulfonyl)-4-ethoxybenzoate (0.114 g, 0.409 mmol) in DCM (10 ml) and the solution was stirred at RT for 24 h. The solvent was removed in vacuo and the crude product was purified by chromatography on silica gel (40 g cartridge, 0-50% EtOAc/isohexane) to afford the title compound (0.160 g, 0.326 mmol, 80% yield, 99% purity) as a cream waxy solid. UPLC-MS (Method 1) m/z 487.4 $(M+H)^+$, 485.2 $(M-H)^-$ at 1.93 min.

Step 2: 4-ethoxy-3-(N-(2-(piperidin-1-yl)-5-(trifluoromethyl)phenyl)sulfamoyl)benzoic acid: 1 M LiOH (aq) (0.024 g, 0.987 mmol) was added to a solution of the product from step 1 (0.160 g, 0.329 mmol) in THF (5 ml) and the solution was stirred at RT overnight. The reaction mixture was concentrated in vacuo to water. The pH was adjusted to pH 6 with 1 M HCl(aq) to form a precipitate which was filtered and washed with water (10 ml) and isohexane (20 ml) to give the title compound (0.151 g, 0.304 mmol, 92% yield, 95% purity) as a white solid. UPLC-MS (Method 1) m/z 473.4 $(M+H)^+$, 471.2 $(M-H)^-$ at 1.78 min. $^1H$ NMR (500 MHz, DMSO-$d_6$) δ 13.20 (br s, 1H), 8.55 (br s, 1H), 8.40 (d, J=2.2 Hz, 1H), 8.13 (dd, J=8.7, 2.2 Hz, 1H), 7.47 (d, J=2.0 Hz, 1H), 7.39-7.34 (m, 1H), 7.32-7.30 (m, 2H), 4.22 (q, J=7.0 Hz, 2H), 2.76 (t, J=5.3 Hz, 4H), 1.62 (p, J=5.5 Hz, 4H), 1.52 (p, J=6.3 Hz, 2H), 1.27 (t, J=7.0 Hz, 3H).

Example 202: 3-(N-(4,5-dichloro-2-(piperidin-1-yl) phenyl)sulfamoyl)-4-methoxybenzoic acid

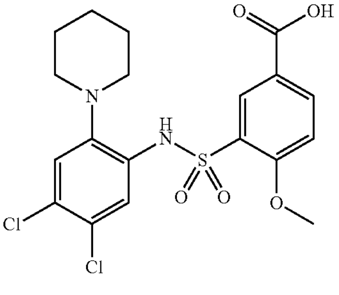 [SMILES: COc1ccc(C(=O)O)cc1S(=O)(=O)Nc1cc(Cl)c(Cl)cc1N1CCCCC1]

Step 1: methyl 3-(N-(4,5-dichloro-2-(piperidin-1-yl)phenyl)sulfamoyl)-4-methoxybenzoate: Pyridine (0.166 ml, 2.06 mmol) was added to a solution of 4,5-dichloro-2-(piperidin-1-yl)aniline (0.168 g, 0.685 mmol) and methyl 3-(chlorosulfonyl)-4-methoxybenzoate (0.227 g, 0.857 mmol) in DCM (10 ml). The solution was stirred at RT for 18 h and then concentrated in vacuo. The crude product was purified by chromatography on silica gel (12 g cartridge, 0-100% EtOAc/isohexane) to afford the title compound (0.257 g, 0.543 mmol, 79% yield, 81% purity) as a white solid. UPLC-MS (Method 1) m/z 475.4 $(M+H)^+$, 472.8 $(M-H)^-$ at 1.75 min.

Step 2: 3-(N-(4,5-dichloro-2-(piperidin-1-yl)phenyl)sulfamoyl)-4-methoxybenzoic acid: 1 M LiOH (aq) (3.26 ml, 3.26 mmol) was added to a solution of the product from step 1 above (0.257 g, 0.543 mmol) in THF (13 ml) and MeOH (3 ml) and the solution was stirred at RT overnight. The solvent was removed in vacuo and the residue dissolved in water (5 ml) and washed with TBME (3×5 ml). The aqueous phase was acidified with conc. HCl and extracted with TBME (3×10 ml). The combined organic phases were dried by passage through a phase separator and the solvent was removed in vacuo to afford the title compound (0.229 g, 0.494 mmol, 91% yield, 97% purity) as an off white solid. UPLC-MS (Method 1) m/z 459.3/461.3 $(M+H)^+$, 457.2/459.2 $(M-H)^-$ at 1.82 min. $^1H$ NMR (500 MHz, DMSO-$d_6$) δ 13.22 (s, 1H), 8.75 (s, 1H), 8.35 (d, J=2.2 Hz, 1H), 8.17 (dd, J=8.7, 2.2 Hz, 1H), 7.42 (s, 1H), 7.38 (s, 1H), 7.34 (d, J=8.8 Hz, 1H), 3.94 (s, 3H), 2.70-2.64 (m, 4H), 1.67-1.56 (m, 4H), 1.56-1.42 (m, 2H).

Example 203:3-(N-(2-(4,4-difluoropiperidin-1-yl)-5-(trifluoromethyl)phenyl)sulfamoyl)-4-ethylbenzoic acid

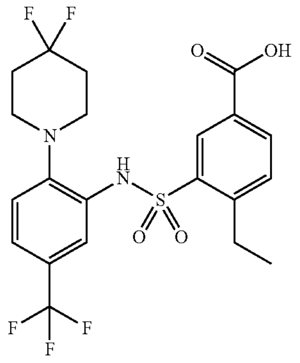 [SMILES: CCc1ccc(C(=O)O)cc1S(=O)(=O)Nc1cc(C(F)(F)F)ccc1N1CCC(F)(F)CC1]

Step 1: 3-(chlorosulfonyl)-4-ethylbenzoic acid: 4-ethylbenzoic acid (7 g, 46.6 mmol) in chlorosulfonic acid (20 ml, 299 mmol) was heated at 100° C. for 5 h. The mixture was cooled and carefully added to stirred ice-water (200 ml). The solid precipitated out was collected by filtration, washed with water (100 ml) and dried in vacuo to give the title compound (10.9 g, 41.5 mmol, 89% yield, 95% purity) as a white solid. $^1H$ NMR (500 MHz, DMSO-$d_6$) δ 13.65 (br s, 1H), 8.34 (d, J=1.9 Hz, 1H), 7.82 (dd, J=7.9, 2.0 Hz, 1H), 7.32 (d, J=7.9 Hz, 1H), 3.08 (q, J=7.5 Hz, 2H), 1.18 (t, J=7.5 Hz, 3H).

Step 2: methyl 3-(chlorosulfonyl)-4-ethylbenzoate: Thionyl Chloride (10 ml, 137 mmol) was added portionwise to the product from step 1 above (4 g, 16.1 mmol) at RT. The mixture was heated to 75° C. for 2 h, cooled to RT, concentrated in vacuo and azeotroped with toluene. The solid was dissolved in DCM (10 ml) and treated with MeOH (0.716 ml, 17.7 mmol) followed by $Et_3N$ (2.41 ml, 17.7 mmol) and stirred at RT overnight. The mixture was diluted with DCM (50 ml), washed with water (50 ml), dried ($MgSO_4$) and concentrated in vacuo. The crude product was purified by chromatography on silica gel (40 g cartridge, 0-50% EtOAc/isohexane) to afford the title compound (3.60 g, 13.02 mmol, 81% yield, 95% purity) as a white solid. $^1H$ NMR (500 MHz, DMSO-$d_6$) δ 8.74 (d, J=1.8 Hz, 1H), 8.32 (dd, J=8.0, 1.8 Hz, 1H), 7.61 (d, J=8.0 Hz, 1H), 3.99 (s, 3H), 3.28 (q, J=7.5 Hz, 2H), 1.41 (t, J=7.5 Hz, 3H).

Step 3: methyl 3-(N-(2-(4,4-difluoropiperidin-1-yl)-5-(trifluoromethyl)phenyl)sulfamoyl)-4-ethylbenzoate: Pyridine (0.069 ml, 0.856 mmol) was added to a solution of the product from Example 12 step 2 (0.08 g, 0.285 mmol) and the product from step 2 above (0.094 g, 0.357 mmol) in DCM (10 ml) and the solution was stirred at RT for 18 h. The solution was concentrated in vacuo and the crude product was purified by chromatography on silica gel (12 g cartridge, 0-100% EtOAc/isohexane) to afford the title compound (0.137 g, 0.227 mmol, 80% yield, 84% purity) as a white solid. UPLC-MS (Method 1) m/z 507.4 $(M+H)^+$, 505.2 $(M-H)^-$ at 1.90 min.

Step 4: 3-(N-(2-(4,4-difluoropiperidin-1-yl)-5-(trifluoromethyl)phenyl)sulfamoyl)-4-ethylbenzoic acid: 1 M LiOH (aq) (1.35 ml, 1.35 mmol) was added to a solution of the product from step 3 above (0.137 g, 0.225 mmol) in THF (6 ml) and MeOH (1.3 ml) and the solution was stirred at RT overnight. The solvent was removed in vacuo and the residue dissolved in water (5 ml) and washed with TBME (3×5 ml). The aqueous phase was acidified with conc. HCl and extracted with TBME (3×10 ml). The organic phases were combined and dried by passage through a phase separator and the solvent removed in vacuo to give the title compound (0.105 g, 0.209 mmol, 93% yield, 98% purity) as an off white solid. UPLC-MS (Method 1) m/z 493.3 $(M+H)^+$, 490.9 $(M-H)^-$ at 1.76 min. $^1H$ NMR (500 MHz, DMSO-$d_6$) δ 13.31 (s, 1H), 9.85 (s, 1H), 8.37 (d, J=1.8 Hz, 1H), 8.10 (dd, J=8.0, 1.8 Hz, 1H), 7.61 (d, J=8.0 Hz, 1H), 7.44 (dd, J=8.5, 2.1 Hz, 1H), 7.36-7.31 (m, 2H), 3.03 (q, J=7.4 Hz, 2H), 2.89-2.80 (m, 4H), 2.13-2.00 (m, 4H), 1.18 (t, J=7.4 Hz, 3H).

Example 204:3-(N-(2-(3,3-difluoropiperidin-1-yl)-5-(trifluoromethyl)phenyl)sulfamoyl)-4-ethylbenzoic acid

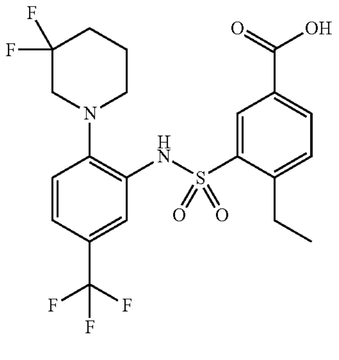

Step 1: methyl 3-(N-(2-(3,3-difluoropiperidin-1-yl)-5-(trifluoromethyl)phenyl)sulfamoyl)-4-ethylbenzoate: Pyridine (0.052 ml, 0.642 mmol) was added to a solution of the product from Example 9 step 2 (60 mg, 0.214 mmol) and the product from Example 203 step 2 (70 mg, 0.268 mmol) in DCM (10 ml). The solution was stirred at RT for 18 h then concentrated in vacuo. The crude product was purified by chromatography on silica gel (12 g cartridge, 0-100% EtOAc/isohexane) to afford the title compound (0.057 g, 0.113 mmol, 52.6% yield, 100% purity) as a white solid. UPLC-MS (Method 1) m/z 507.7 $(M+H)^+$, 505.2 $(M-H)^-$ at 1.89 min.

Step 2: 3-(N-(2-(3,3-difluoropiperidin-1-yl)-5-(trifluoromethyl)phenyl)sulfamoyl)-4-ethylbenzoic acid: 1 M LiOH (aq) (0.675 ml, 0.675 mmol) was added to a solution of the product from step 1 above (0.057 g, 0.113 mmol) in THF (8 ml) and MeOH (2 ml). The solution was stirred at RT overnight and then concentrated in vacuo. The residue was dissolved in water (5 ml) and washed with TBME (3×5 ml). The aqueous phase was acidified with conc. HCl and extracted with TBME (3×10 ml). The organic phases were combined, dried by passage through a phase separator and concentrated in vacuo to afford the title compound (0.056 g, 0.110 mmol, 98% yield, 97% purity) as an off white solid. UPLC-MS (Method 1) m/z 493.7 $(M+H)^+$, 491.1 $(M-H)^-$ at 1.74 min. $^1H$ NMR (500 MHz, DMSO-$d_6$) δ 13.30 (s, 1H), 9.30 (s, 1H), 8.35 (d, J=1.8 Hz, 1H), 8.11 (dd, J=8.0, 1.8 Hz, 1H), 7.62 (d, J=8.0 Hz, 1H), 7.45 (dd, J=8.5, 2.1 Hz, 1H), 7.33 (d, J=8.5 Hz, 1H), 7.12 (d, J=2.1 Hz, 1H), 3.21 (t, J=11.4 Hz, 2H), 3.00 (q, J=7.4 Hz, 2H), 2.98-2.94 (m, 2H), 2.08-1.96 (m, 2H), 1.84-1.75 (m, 2H), 1.19 (t, J=7.4 Hz, 3H).

Example 205:4-ethyl-3-(N-(2-(4-fluoropiperidin-1-yl)-5-(trifluoromethyl)phenyl) sulfamoyl)benzoic acid

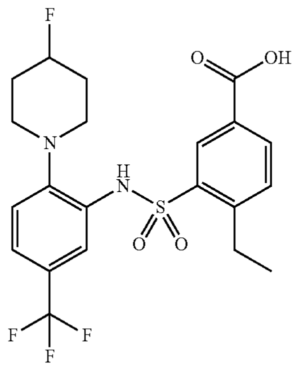 [SMILES: CCc1ccc(C(=O)O)cc1S(=O)(=O)Nc1cc(C(F)(F)F)ccc1N1CCC(F)CC1]

Step 1: 4-fluoro-1-(2-nitro-4-(trifluoromethyl)phenyl)piperidine: $Et_3N$ (500 μl, 3.59 mmol) was added to a solution of 1-fluoro-2-nitro-4-(trifluoromethyl)benzene (201 μl, 1.44 mmol) and 4-fluoropiperidine (192 mg, 1.87 mmol) in DCM (6 ml) and the resultant solution was stirred at RT for 3 days. 1 M HCl(aq) (2 ml) was added and the organic phase was separated by passage through a phase separator. The organic phase was concentrated in vacuo to afford the title compound (419 mg, 1.44 mmol, 100% yield, 100% purity) as a pale yellow viscous oil. UPLC-MS (Method 2) m/z 293.3 $(M+H)^+$ at 1.62 min.

Step 2: 2-(4-fluoropiperidin-1-yl)-5-(trifluoromethyl)aniline: The product from step 1 above (419 mg, 1.44 mmol) was dissolved in EtOH (28.8 ml) and the reaction mixture was hydrogenated in a ThalesNano H-cube® flow reactor (10% Pd/C, 30×4 mm, full hydrogen mode, 40° C., 1 ml/min flow rate, 2 passes). The reaction mixture was concentrated in vacuo and azeotroped with MeOH (6 ml) to afford the title compound (371 mg, 1.27 mmol, 89% yield, 90% purity) as a clear viscous oil. UPLC-MS (Method 2) m/z 263.3 $(M+H)^+$ at 1.59 min.

Step 3: methyl 4-ethyl-3-(N-(2-(4-fluoropiperidin-1-yl)-5-(trifluoromethyl)phenyl)sulfamoyl)benzoate: The product from step 2 above (66.5 mg, 0.254 mmol) was dissolved in a mixture of DCM (1 ml) and pyridine (82 μl, 1.02 mmol) and treated with a suspension of the product from Example 203 step 2 (80 mg, 0.305 mmol) in DCM (1 ml). The resultant solution was stirred at RT for 20 h. The reaction mixture was purified directly by chromatography on silica gel (12 g cartridge, 0-100% EtOAc/isohexane) to afford the title compound (61 mg, 0.112 mmol, 44.3% yield, 90% purity) as a cream solid. UPLC-MS (Method 1) m/z 489.3 $(M+H)^+$, 487.2 $(M-H)^-$ at 1.87 min.

Step 4: 4-ethyl-3-(N-(2-(4-fluoropiperidin-1-yl)-5-(trifluoromethyl)phenyl)sulfamoyl)benzoic acid: The product from step 3 above (59 mg, 0.121 mmol) was dissolved in THF (2 ml) and treated with 1.1 M LiOH (aq) (439 μl, 0.483 mmol). MeOH was added dropwise to afford a solution, which was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 with 1 M HCl. The lumpy suspension was sonicated to afford a cloudy solution which was concentrated in vacuo to ~2 ml. The resultant precipitate was collected by filtration and washed with water (2×2 ml). The solid was suspended in MeCN (4 ml), concentrated in vacuo and dried at 45° C. to afford the title compound (38.4 mg, 0.078 mmol, 64.3% yield, 96% purity) as a white solid. UPLC-MS (Method 1) m/z 475.4 $(M+H)^+$, 473.2 $(M-H)^-$ at 1.74 min. $^1H$ NMR (500 MHz, DMSO-$d_6$) δ 13.29 (br s, 1H), 9.68 (br s, 1H), 8.34 (d, J=1.8 Hz, 1H), 8.09 (dd, J=8.0, 1.8 Hz, 1H), 7.61 (d, J=8.0 Hz, 1H), 7.46-7.40 (m, 1H), 7.31-7.24 (m, 2H), 4.85-4.70 (m, 1H), 3.03 (q, J=7.4 Hz, 2H), 2.89 (t, J=9.9 Hz, 2H), 2.74-2.67 (m, 2H), 2.00-1.87 (m, 2H), 1.85-1.73 (m, 2H), 1.19 (t, J=7.4 Hz, 3H).

Example 206:3-(N-(2-(4-fluoropiperidin-1-yl)-5-(trifluoromethyl)phenyl)sulfamoyl)-4-methoxybenzoic acid

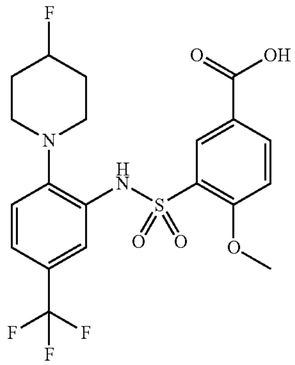 [SMILES: COc1ccc(C(=O)O)cc1S(=O)(=O)Nc1cc(C(F)(F)F)ccc1N1CCC(F)CC1]

Step 1: methyl 3-(N-(2-(4-fluoropiperidin-1-yl)-5-(trifluoromethyl)phenyl)sulfamoyl)-4-methoxybenzoate: The product from Example 205 step 2 (66.1 mg, 0.252 mmol) was dissolved in a mixture of DCM (1 ml) and pyridine (81 μl, 1.01 mmol) and treated with a solution methyl 3-(chlorosulfonyl)-4-methoxybenzoate (80 mg, 0.302 mmol) in DCM (1 ml). The resultant solution was stirred at RT for 20 h. The reaction mixture was purified directly by chromatography on silica gel (12 g cartridge, 0-100% EtOAc/isohexane) to afford the title compound (88 mg, 0.161 mmol, 64.1% yield, 90% purity) as a sticky cream solid. UPLC-MS (Method 1) m/z 491.4 $(M+H)^+$, 489.1 $(M-H)^-$ at 1.73 min.

Step 2: 3-(N-(2-(4-fluoropiperidin-1-yl)-5-(trifluoromethyl)phenyl)sulfamoyl)-4-methoxybenzoic acid: The product from step 1 above (86 mg, 0.175 mmol) was dissolved in THF (2 ml) and treated with 1.1 M LiOH (aq) (638 μl, 0.701 mmol). MeOH was added dropwise to afford a solution, which was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 with 1 M HCl. The lumpy suspension was sonicated to afford a cloudy solution which was concentrated in vacuo to ~2 ml. The resultant precipitate was collected by filtration, washing with water (2×2 ml). The solid was suspended in MeCN (4 ml), concentrated in vacuo and dried at 45° C. to afford the title compound (52.7 mg, 0.108 mmol, 61.8% yield, 98% purity) as a white solid. UPLC-MS (Method 1) m/z 477.3 $(M+H)^+$, 475.1 $(M-H)^-$ at 1.56 min. $^1H$ NMR (500 MHz, DMSO-d6) δ 13.16 (br s, 1H), 9.00 (br s, 1H), 8.35 (d, J=2.2 Hz, 1H), 8.16 (dd, J=8.7, 2.2 Hz, 1H), 7.44 (d, J=2.0 Hz, 1H), 7.40-7.29 (m, 3H), 4.93-4.75 (m, 1H), 3.90 (s, 3H), 2.94 (t, J=9.8 Hz, 2H), 2.79-2.73 (m, 2H), 2.10-1.94 (m, 2H), 1.93-1.79 (m, 2H).

Example 207:4-methoxy-3-(N-(5-(methylsulfonyl)-2-(piperidin-1-yl)phenyl)sulfamoyl)benzoic acid

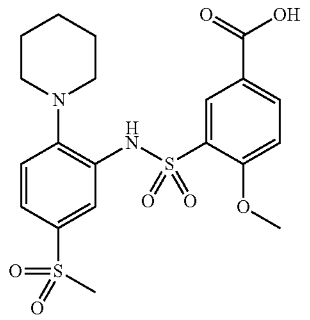 [SMILES: COc1ccc(C(=O)O)cc1S(=O)(=O)Nc1cc(S(C)(=O)=O)ccc1N1CCCCC1]

Step 1: 1-(4-(methylsulfonyl)-2-nitrophenyl)piperidine: $Et_3N$ (0.795 ml, 5.70 mmol) was added to a solution of 1-fluoro-4-(methylsulfonyl)-2-nitrobenzene (500 mg, 2.28 mmol) and piperidine (0.226 ml, 2.28 mmol) in DCM (6 ml) at RT. The clear solution was stirred at RT for 23 h. The organic phase was washed with 1 M HCl(aq) (3 ml), dried by passage through a phase separator and concentrated in vacuo to afford the title compound (0.676 g, 2.28 mmol, 100% yield, 100% purity) as a brown oil. UPLC-MS (Method 1) m/z 285.2 $(M+H)^+$ at 1.32 min.

Step 2: 5-(methylsulfonyl)-2-(piperidin-1-yl)aniline: The product from step 1 above (0.676 g, 2.38 mmol) was dissolved in EtOH (44 ml) and the reaction mixture was hydrogenated in a ThalesNano H-cube® flow reactor (10% Pd/C, 30×4 mm, full hydrogen mode, RT, 1 ml/min flow rate, 1 pass). The reaction mixture was concentrated in vacuo and then azeotroped with MeOH (12 ml) to afford the title compound (0.615 g, 2.370 mmol, 100% yield, 98% purity) as a pale yellow oil. UPLC-MS (Method 1) m/z 255.3 $(M+H)^+$ at 1.20 min.

Step 3: methyl 4-methoxy-3-(N-(5-(methylsulfonyl)-2-(piperidin-1-yl)phenyl)sulfamoyl)benzoate: Pyridine (0.143 ml, 1.77 mmol) was added to a solution of the product from step 2 above (0.15 g, 0.590 mmol) and methyl 3-(chlorosulfonyl)-4-methoxybenzoate (0.195 g, 0.737 mmol) in DCM (10 ml). The resultant solution was stirred at RT for 18 h. The solution was concentrated in vacuo and the crude product was purified by chromatography on silica gel (12 g cartridge, 0-100% EtOAc/isohexane) to afford the title compound (0.201 g, 0.412 mmol, 69.9% yield, 99% purity) as a white solid. UPLC-MS (Method 1) m/z 483.3 $(M+H)^+$, 481.0 $(M-H)^-$ at 1.49 min.

Step 4: 4-methoxy-3-(N-(5-(methylsulfonyl)-2-(piperidin-1-yl)phenyl)sulfamoyl)benzoic acid: 1 M LiOH (aq) (2.47 ml, 2.47 mmol) was added to a solution of the product from step 3 above (0.199 g, 0.412 mmol) in THF (10 ml) and MeOH (2.5 ml) and the solution was stirred at RT overnight. The solvent was removed in vacuo and the residue dissolved in water (5 ml) and washed with TBME (3×5 ml). The aqueous phase was acidified with conc. HCl and extracted with TBME (3×10 ml). The organic phases were combined and dried by passage through a phase separator. The solvent was removed in vacuo to afford the title compound (0.176 g, 0.372 mmol, 90% yield, 99% purity) as an off white solid. UPLC-MS (Method 1) m/z 469.4 $(M+H)^+$, 467.0 $(M-H)^-$ at 1.36 min. $^1H$ NMR (500 MHz, DMSO-$d_6$) δ 13.17 (s, 1H), 8.82 (s, 1H), 8.35 (d, J=2.2 Hz, 1H), 8.15 (dd, J=8.7, 2.2 Hz, 1H), 7.65 (d, J=2.2 Hz, 1H), 7.55 (dd, J=8.4, 2.2 Hz, 1H), 7.34 (d, J=8.4 Hz, 1H), 7.33 (d, J=8.7 Hz, 1H), 3.94 (s, 3H), 3.00 (s, 3H), 2.85-2.78 (m, 4H), 1.71-1.60 (m, 4H), 1.58-1.50 (m, 2H).

Example 208: I-3-(N-(2-(3-fluoropiperidin-1-yl)-5-(trifluoromethyl)phenyl)sulfamoyl)-4-methoxybenzoic acid

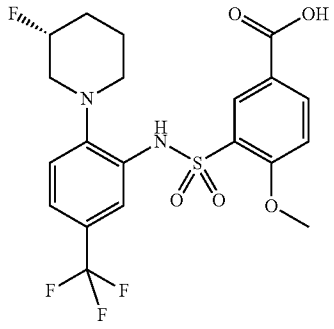 [SMILES: COc1ccc(C(=O)O)cc1S(=O)(=O)Nc1cc(C(F)(F)F)ccc1N1CCC[C@@H](F)C1]

Step 1: I-3-fluoro-1-(2-nitro-4-(trifluoromethyl)phenyl)piperidine: $Et_3N$ (500 μl, 3.59 mmol) was added to a solution of 1-fluoro-2-nitro-4-(trifluoromethyl)benzene (300 mg, 1.44 mmol) and I-3-fluoropiperidine (250 mg, 2.42 mmol) in DCM (6 ml). The resultant solution was stirred at RT for 20 h. 1 M HCl(aq) (2 ml) was added and the organic phase was separated by passage through a phase separator. The organic phase was concentrated in vacuo to afford the title compound (488 mg, 1.44 mmol, 100% yield, 86% purity) as a pale orange viscous oil. UPLC-MS (Method 2) m/z 293.0 $(M+H)^+$ at 1.59 min.

Step 2: I-2-(3-fluoropiperidin-1-yl)-5-(trifluoromethyl)aniline: The product from step 1 above (419 mg, 1.44 mmol) was dissolved in EtOH (28.8 ml) and the reaction mixture was hydrogenated in a ThalesNano H-cube® flow reactor (10% Pd/C, 30×4 mm, full hydrogen mode, 40° C., 1 ml/min flow rate, 2 passes). The reaction mixture was concentrated in vacuo and azeotroped with MeOH (6 ml) to afford the title compound (457 mg, 1.394 mmol, 97% yield, 80% purity) as a cream coloured gel. UPLC-MS (Method 2) m/z 263.3 $(M+H)^+$ at 1.59 min.

Step 3: I-methyl 3-(N-(2-(3-fluoropiperidin-1-yl)-5-(trifluoromethyl)phenyl)sulfamoyl)-4-methoxybenzoate: The product from step 3 above (66.1 mg, 0.252 mmol) was dissolved in a mixture of DCM (1 ml) and pyridine (81 µl, 1.01 mmol) and treated with a solution methyl 3-(chlorosulfonyl)-4-methoxybenzoate (80 mg, 0.302 mmol) in DCM (1 ml). The resultant solution was stirred at RT for 3 days. The reaction mixture was purified directly by chromatography on silica gel (12 g cartridge, 0-100% EtOAc/isohexane) to afford the title compound (72.4 mg, 0.118 mmol, 46.9% yield, 80% purity) as an off-white solid. UPLC-MS (Method 1) m/z 491.3 $(M+H)^+$, 489.1 $(M-H)^-$ at 1.73 min.

Step 4: I-3-(N-(2-(3-fluoropiperidin-1-yl)-5-(trifluoromethyl)phenyl)sulfamoyl)-4-methoxybenzoic acid: The product from step 3 above (69 mg, 0.141 mmol) was dissolved in THF (2 ml) and treated with 1.1 M LiOH (aq) (512 µl, 0.563 mmol). MeOH was added dropwise to afford a solution, which was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 with 1 M HCl. The lumpy suspension was sonicated to afford a cloudy solution which was concentrated in vacuo to ~2 ml. The precipitate was collected by filtration, washing with water (2×2 ml). The solid was suspended in MeCN (4 ml), concentrated in vacuo and dried at 45° C. to afford the title compound (55.2 mg, 0.110 mmol, 78% yield) as a white solid. UPLC-MS (Method 1) m/z 477.4 $(M+H)^+$, 475.1 $(M-H)^-$ at 1.57 min. $^1H$ NMR (500 MHz, DMSO-$d_6$) δ 13.19 (br s, 1H), 8.75 (br s, 1H), 8.38 (d, J=2.2 Hz, 1H), 8.16 (dd, J=8.7, 2.2 Hz, 1H), 7.44 (s, 1H), 7.38-7.33 (m, 2H), 7.31 (d, J=8.8 Hz, 1H), 4.95-4.79 (m, 1H), 3.91 (s, 3H), 3.09-2.86 (m, 3H), 2.85-2.75 (m, 1H), 1.95-1.75 (m, 3H), 1.74-1.63 (m, 1H).

Example 209: (S)-3-(N-(2-(3-fluoropiperidin-1-yl)-5-(trifluoromethyl)phenyl)sulfamoyl)-4-methoxybenzoic acid

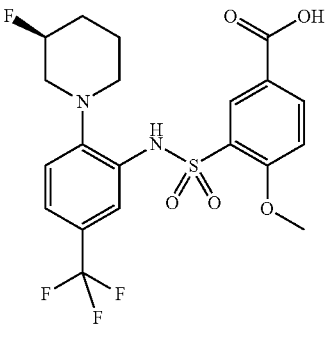 [SMILES: COc1ccc(C(=O)O)cc1S(=O)(=O)Nc1cc(C(F)(F)F)ccc1N1CCC[C@H](F)C1]

Step 1: (S)-3-fluoro-1-(2-nitro-4-(trifluoromethyl)phenyl)piperidine: $Et_3N$ (500 µl, 3.59 mmol) was added to a solution of 1-fluoro-2-nitro-4-(trifluoromethyl)benzene (300 mg, 1.44 mmol) and(S)-3-fluoropiperidine (250 mg, 2.42 mmol) in DCM (6 ml) and the resultant solution was stirred at RT for 20 h. 1 M HCl(aq) (2 ml) was added and the organic phase was separated and concentrated in vacuo to afford the title compound (461 mg, 1.44 mmol, 100% yield, 91% purity) as a pale orange viscous oil. UPLC-MS (Method 2) m/z 293.1 $(M+H)^+$ at 1.60 min.

Step 2: (S)-2-(3-fluoropiperidin-1-yl)-5-(trifluoromethyl)aniline: The product from step 1 above (419 mg, 1.44 mmol) was dissolved in EtOH (28.8 ml). The reaction mixture was hydrogenated in a ThalesNano H-cube® flow reactor (10% Pd/C, 30×4 mm, full hydrogen mode, 40° C., 1 ml/min flow rate, 2 passes). The reaction mixture was concentrated in vacuo and azeotroped with MeOH (6 ml) to afford the title compound (475 mg, 1.43 mmol, 100% yield, 79% purity) as a cream coloured gel. UPLC-MS (Method 2) m/z 263.3 $(M+H)^+$ at 1.59 min.

Step 3: (S)-methyl 3-(N-(2-(3-fluoropiperidin-1-yl)-5-(trifluoromethyl)phenyl)sulfamoyl)-4-methoxybenzoate: The product from step 2 above (66.1 mg, 0.252 mmol) was dissolved in a mixture of DCM (1 ml) and pyridine (81 µl, 1.01 mmol) and treated with a solution methyl 3-(chlorosulfonyl)-4-methoxybenzoate (80 mg, 0.302 mmol) in DCM (1 ml). The resultant solution was stirred at RT for 3 days. The reaction mixture was purified directly by chromatography on silica gel (12 g cartridge, 0-100% EtOAc/isohexane) to afford the title compound (81.4 mg, 0.133 mmol, 52.7% yield, 80% purity) as an off white solid. UPLC-MS (Method 1) m/z 491.4 $(M+H)^+$, 489.3 $(M-H)^-$ at 1.74 min.

Step 4: (S)-3-(N-(2-(3-fluoropiperidin-1-yl)-5-(trifluoromethyl)phenyl)sulfamoyl)-4-methoxybenzoic acid: The product from step 3 above (78 mg, 0.159 mmol) was dissolved in THF (2 ml) and treated with 1.1 M LiOH (aq) (578 µl, 0.636 mmol). MeOH was added dropwise to afford a solution, which was stirred at 30° C. for 20 h. The reaction mixture was diluted with water (3 ml), concentrated in vacuo and the resultant aqueous solution diluted with water (to ~5 ml). This was washed with EtOAc (2×5 ml) and neutralised to ~pH 6 with 1 M HCl. The lumpy suspension was sonicated to afford a cloudy solution which was concentrated in vacuo to ~2 ml. The precipitate was collected by filtration, washing with water (2×2 ml). The solid was suspended in MeCN (4 ml), concentrated in vacuo and dried at 45° C. to afford the title compound (55.2 mg, 0.110 mmol, 69.2% yield, 95% purity) as a white solid. UPLC-MS (Method 1) m/z 477.3 $(M+H)^+$, 475.2 $(M-H)^-$ at 1.57 min. $^1H$ NMR (500 MHz, DMSO-$d_6$)· 13.18 (br s, 1H), 8.74 (br s, 1H), 8.37 (d, J=2.2 Hz, 1H), 8.15 (dd, J=8.7, 2.2 Hz, 1H), 7.44 (s, 1H), 7.39-7.27 (m, 3H), 4.95-4.79 (m, 1H), 3.91 (s, 3H), 3.08-2.86 (m, 3H), 2.83-2.76 (m, 1H), 1.95-1.75 (m, 3H), 1.74-1.63 (m, 1H).

Example 210: (S)-4-ethyl-3-(N-(2-(3-fluoropiperidin-1-yl)-5-(trifluoromethyl)phenyl) sulfamoyl)benzoic acid

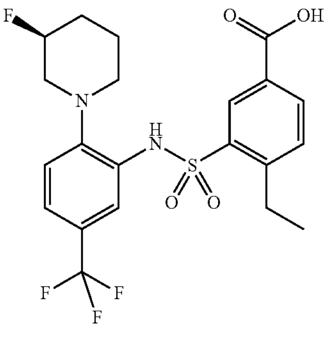 [SMILES: CCc1ccc(C(=O)O)cc1S(=O)(=O)Nc1cc(C(F)(F)F)ccc1N1CCC[C@H](F)C1]

Step 1: (S)-methyl 4-ethyl-3-(N-(2-(3-fluoropiperidin-1-yl)-5-(trifluoromethyl)phenyl)sulfamoyl)benzoate: The product from Example 209 step 2 (67 mg, 0.255 mmol) was dissolved in a mixture of DCM (1 ml) and pyridine (83 µl, 1.02 mmol) and treated with a suspension of the product from Example 203 step 2 (124 mg, 0.307 mmol) in DCM (1 ml). The resultant solution was stirred at RT for 3 days. The reaction mixture was purified directly by chromatography on silica gel (12 g cartridge, 0-100% EtOAc/isohexane) to afford the title compound (65.9 mg, 0.108 mmol, 42.2% yield, 80% purity) as an off white solid. UPLC-MS (Method 1) m/z 489.4 $(M+H)^+$, 487.2 $(M-H)^-$ at 1.89 min.

Step 2: (S)-4-ethyl-3-(N-(2-(3-fluoropiperidin-1-yl)-5-(trifluoromethyl)phenyl)sulfamoyl)benzoic acid: The product from step 1 above (63 mg, 0.129 mmol) was dissolved in THF (2 ml) and treated with 1.1 LiOH (aq) (469 µl, 0.516 mmol). MeOH was added dropwise to afford a solution, which was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 with 1 M HCl. The lumpy suspension was sonicated to afford a cloudy solution which was concentrated in vacuo to ~2 ml. The precipitate was collected by filtration, washing with water (2×2 ml). The solid was suspended in MeCN (4 ml), concentrated in vacuo and dried at 45° C. to afford the title compound (35.9 mg, 0.072 mmol, 55.7% yield) as a cream solid. UPLC-MS (Method 1) m/z 475.3 $(M+H)^+$, 473.2 $(M-H)^-$ at 1.74 min. $^1H$ NMR (500 MHz, DMSO-$d_6$) δ 13.31 (br s, 1H), 9.36 (br s, 1H), 8.36 (d, J=1.8 Hz, 1H), 8.09 (dd, J=8.0, 1.8 Hz, 1H), 7.61 (d, J=8.1 Hz, 1H), 7.42 (dd, J=8.4, 2.1 Hz, 1H), 7.33-7.24 (m, 2H), 1.98-1.85 (m, 1H), 3.13-2.97 (m, 3H), 2.89-2.79 (m, 2H), 2.71 (td, J=8.1, 4.0 Hz, 1H), 1.98-1.85 (m, 1H), 1.82-1.71 (m, 1H), 1.71-1.55 (m, 2H), 1.19 (t, J=7.4 Hz, 3H).

Example 211: I-4-ethyl-3-(N-(2-(3-fluoropiperidin-1-yl)-5-(trifluoromethyl)phenyl) sulfamoyl)benzoic acid

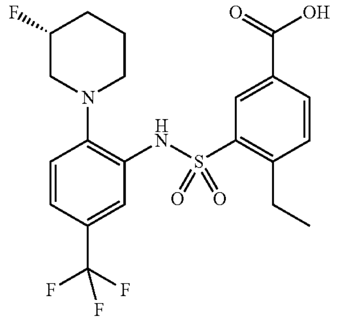 [SMILES: CCc1ccc(C(=O)O)cc1S(=O)(=O)Nc1cc(C(F)(F)F)ccc1N1CCC[C@@H](F)C1]

Step 1: I-methyl 4-ethyl-3-(N-(2-(3-fluoropiperidin-1-yl)-5-(trifluoromethyl)phenyl)sulfamoyl)benzoate: The product from Example 208 step 2 (67 mg, 0.255 mmol) was dissolved in a mixture of DCM (1 ml) and pyridine (83 µl, 1.02 mmol) and treated with a suspension of the product from Example 203 step 2 (124 mg, 0.307 mmol) in DCM (1 ml). The resultant solution was stirred at RT for 3 days. The reaction mixture was purified directly by chromatography on silica gel (12 g cartridge, 0-100% EtOAc/isohexane) to afford the title compound (76.7 mg, 0.126 mmol, 49.2% yield, 80% purity) as an off white solid. UPLC-MS (Method 1) m/z 489.3 $(M+H)^+$, 487.2 $(M-H)^-$ at 1.89 min.

Step 2: I-4-ethyl-3-(N-(2-(3-fluoropiperidin-1-yl)-5-(trifluoromethyl)phenyl)sulfamoyl)benzoic acid: The product from step 1 above (74 mg, 0.151 mmol) was dissolved in THF (2 ml) and treated with 1.1 M LiOH (aq) (551 µl, 0.606 mmol). MeOH was added dropwise to afford a solution, which was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 with 1 M HCl. The lumpy suspension was sonicated to afford a cloudy solution which was concentrated in vacuo to ~2 ml. The resultant precipitate was collected by filtration, washing with water (2×2 ml). The solid was suspended in MeCN (4 ml), concentrated in vacuo and dried at 45° C. to afford the title compound (43.5 mg, 0.087 mmol, 57.5% yield, 95% purity) as a cream solid. UPLC-MS (Method 1) m/z 475.4 $(M+H)^+$, 473.2 $(M-H)^-$ at 1.74 min. $^1H$ NMR (500 MHz, DMSO-$d_6$) δ 13.31 (br s, 1H), 9.36 (br s, 1H), 8.36 (d, J=1.8 Hz, 1H), 8.09 (dd, J=8.0, 1.8 Hz, 1H), 7.61 (d, J=8.0 Hz, 1H), 7.45-7.38 (m, 1H), 7.33-7.25 (m, 2H), 4.84-4.68 (m, 1H), 3.13-2.96 (m, 3H), 2.89-2.79 (m, 2H), 2.75-2.67 (m, 1H), 1.98-1.85 (m, 1H), 1.82-1.72 (m, 1H), 1.70-1.54 (m, 2H), 1.19 (t, J=7.4 Hz, 3H).

Example 212: 3-(N-(5-(difluoromethyl)-2-(piperidin-1-yl)phenyl)sulfamoyl)-4-methoxybenzoic acid

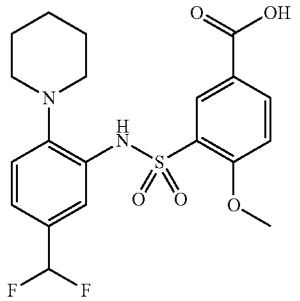 [SMILES: COc1ccc(C(=O)O)cc1S(=O)(=O)Nc1cc(C(F)F)ccc1N1CCCCC1]

Synthesis of 3-(chlorosulfonyl)-4-methoxybenzoic acid 4-methoxybenzoic acid (6.5 g, 42.7 mmol) was added portionwise to chlorosulfonic acid (30 ml, 448 mmol) at RT. The mixture was heated to 80° C. for 2 h, then cooled to RT and added cautiously to ice-water (300 ml), then stirred for 1 h. The solid was collected, washed with water (200 ml) and dried in vacuo to give the title compound (7.92 g, 30.0 mmol, 70.3% yield, 95% purity) as a white solid. $^1H$ NMR (500 MHz, DMSO-$d_6$) δ 13.31 (br s, 1H), 8.30 (d, J=2.3 Hz, 1H), 7.90 (dd, J=8.6, 2.4 Hz, 1H), 7.07 (d, J=8.6 Hz, 1H), 3.83 (s, 3H).

Synthesis of 3-(N-(5-(difluoromethyl)-2-(piperidin-1-yl)phenyl)sulfamoyl)-4-methoxybenzoic acid Step 1: 1-(4-(difluoromethyl)-2-nitrophenyl)piperidine: $Et_3N$ (547 µl, 3.92 mmol) was added to a solution of 4-(difluoromethyl)-1-fluoro-2-nitrobenzene (300 mg, 1.57 mmol) and piperidine (202 µl, 2.04 mmol) in DCM (6 ml)

and the resultant solution was stirred at RT for 20 h. 1 M HCl(aq) (2 ml) was added and the organic phase was separated by passage through a phase separator. The organic phase was concentrated in vacuo to afford the title compound (402 mg, 1.57 mmol, 100% yield, 100% purity) as a yellow viscous oil. UPLC-MS (Method 1) m/z 257.3 $(M+H)^+$ at 1.63 min.

Step 2: 5-(difluoromethyl)-2-(piperidin-1-yl)aniline: The product from step 1 above (402 mg, 1.57 mmol) was dissolved in EtOH (14.4 ml). The reaction mixture was hydrogenated in a ThalesNano H-cube® flow reactor (10% Pd/C, 30×4 mm, full hydrogen mode, 40° C., 1 ml/min flow rate, 2 passes). The reaction mixture was concentrated in vacuo and azeotroped with MeOH (6 ml) to afford the title compound (324 mg, 1.403 mmol, 89% yield, 98% purity) as a light yellow oil. UPLC-MS (Method 1) m/z 227.3 $(M+H)^+$ at 1.58 min.

Step 3: 3-(N-(5-(difluoromethyl)-2-(piperidin-1-yl)phenyl)sulfamoyl)-4-methoxybenzoic acid: The product from step 2 above (60.2 mg, 0.266 mmol) was dissolved in a mixture of DCM (1 ml) and pyridine (86 μl, 1.06 mmol) and treated with a suspension of 3-(chlorosulfonyl)-4-methoxybenzoic acid (80 mg, 0.319 mmol) in DCM (1 ml). The resultant solution was stirred at RT for 20 h. The reaction mixture was filtered and the filtrate was purified directly by chromatography on silica gel (12 g cartridge, 100% isohexane then 0-100% 10% MeOH in EtOAc/isohexane). The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (18 mg, 0.040 mmol, 14.9% yield, 97% purity) as a white solid. UPLC-MS (Method 1) m/z 441.2 $(M+H)^+$, 439.1 $(M-H)^-$ at 1.57 min. $^1$H NMR (500 MHz, DMSO-$d_6$) δ 13.15 (br s, 1H), 8.66 (br s, 1H), 8.39 (d, J=2.2 Hz, 1H), 8.14 (dd, J=8.7, 2.2 Hz, 1H), 7.42 (s, 1H), 7.30 (d, J=8.9 Hz, 1H), 7.29 (d, J=8.2 Hz, 1H), 7.18 (d, J=8.2, 1H), 6.89 (t, J=55.9 Hz, 1H), 3.93 (s, 3H), 2.71 (t, J=5.2 Hz, 4H), 1.67 (p, J=5.5 Hz, 4H), 1.57-1.50 (m, 2H).

Example 213: 3-(N-(5-(difluoromethyl)-2-(piperidin-1-yl)phenyl)sulfamoyl)-4-ethylbenzoic acid

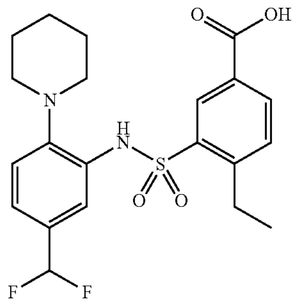 [SMILES: CCc1ccc(C(=O)O)cc1S(=O)(=O)Nc1cc(C(F)F)ccc1N1CCCCC1]

Step 1: methyl 3-(N-(5-(difluoromethyl)-2-(piperidin-1-yl)phenyl)sulfamoyl)-4-ethylbenzoate: The product of Example 212 step 2 (57.4 mg, 0.254 mmol) was dissolved in a mixture of DCM (1 ml) and pyridine (82 μl, 1.02 mmol) and treated with a suspension of the product of Example 203 step 2 (80 mg, 0.305 mmol) in DCM (1 ml). The resultant solution was stirred at RT for 20 h. The reaction mixture was purified directly by chromatography on silica gel (12 g cartridge, 0-100% EtOAc/isohexane) to afford the title compound (54 mg, 0.119 mmol, 47.0% yield, 100% purity) as a light yellow solid. UPLC-MS (Method 1) m/z 453.4 $(M+H)^+$, 451.1 $(M-H)^-$ at 1.91 min.

Step 2: 3-(N-(5-(difluoromethyl)-2-(piperidin-1-yl)phenyl)sulfamoyl)-4-ethylbenzoic acid: Conc. HCl (2.2 ml, 72.4 mmol) was added to water (0.737 ml) and this solution was added to a solution of the product from step 1 above (52 mg, 0.115 mmol) in dioxane (2.2 ml). The reaction mixture was heated at 50° C. for 2 days. The solution was concentrated in vacuo and the crude product was purified by chromatography on silica gel (24 g cartridge, 0-100% 10% MeOH in EtOAc/pentane) to afford the title compound (18 mg, 0.039 mmol, 33.9% yield, 95% purity) as a cream solid. UPLC-MS (Method 1) m/z 439.4 $(M+H)^+$, 437.3 $(M-H)^-$ at 1.75 min. 1H NMR (500 MHz, DMSO-$d_6$) δ 13.28 (br s, 1H), 9.21 (br s, 1H), 8.36 (d, J=1.8 Hz, 1H), 8.07 (dd, J=8.0, 1.8 Hz, 1H), 7.59 (d, J=8.1 Hz, 1H), 7.32-7.18 (m, 3H), 7.02-6.08 (m, 1H), 3.03 (q, J=7.4 Hz, 2H), 2.67-2.61 (m, 4H), 1.59-1.50 (m, 4H), 1.49-1.42 (m, 2H), 1.20 (t, J=7.4 Hz, 3H).

Example 214: 4-methoxy-3-(N-(2-(piperidin-1-yl)-5-(1H-tetrazol-1-yl)phenyl)sulfamoyl)benzoic acid

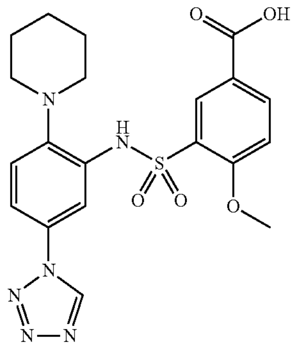

Step 1: 1-(4-fluoro-3-nitrophenyl)tetrazole: Trimethylsilyl azide (1.70 ml, 12.8 mmol) was added to 4-fluoro-3-nitroaniline (0.4 g, 2.56 mmol) and triethyl orthoformate (2.13 ml, 12.8 mmol) in acetic acid (9.97 ml) at 0° C. The resultant mixture was stirred for 30 min then heated to 80° C. over 1 h and stirred for 20 h. The solvent was removed in vacuo and the crude product was purified by chromatography on silica gel (12 g cartridge, 0-10% MeOH/DCM) to afford the title compound (0.469 g, 2.220 mmol, 87% yield, 99% purity) as a white solid. UPLC-MS (Method 1) m/z no ionisation at 1.75 min. $^1$H NMR (500 MHz, $CDCl_3$) δ 9.16 (s, 1H), 8.50 (dd, J=6.1, 2.8 Hz, 1H), 8.15-8.09 (m, 1H), 7.61 (app. T, J=9.4 Hz, 1H).

Step 2: 1-(2-nitro-4-(1H-tetrazol-1-yl)phenyl)piperidine: $Et_3N$ (0.781 ml, 5.61 mmol) was added to a solution of the product from step 1 above (0.469 g, 2.24 mmol) and piperidine (0.266 ml, 2.69 mmol) in DCM (6 ml) at RT. The clear solution was stirred at RT for 23 h. The organic phase was washed with 1 M HCl(aq) (3 ml), dried by passage through a phase separator and concentrated in vacuo to afford the title compound (0.609 g, 2.20 mmol, 98% yield, 99% purity) as a brown oil. UPLC-MS (Method 1) m/z 1.39 min. $^1$H NMR (500 MHz, $CDCl_3$) δ 8.98 (s, 1H), 8.12 (d, J=2.7 Hz, 1H), 7.78 (dd, J=9.0, 2.7 Hz, 1H), 7.27 (d, J=9.0 Hz, 1H), 3.22-3.05 (m, 4H), 1.81-1.71 (m, 4H), 1.69-1.61 (m, 2H).

Step 3: 2-(piperidin-1-yl)-5-(1H-tetrazol-1-yl)aniline: The product from step 2 above (0.609 g, 2.22 mmol) was dissolved in EtOH (48 ml) and the reaction mixture was hydrogenated in a ThalesNano H-cube® flow reactor (10% Pd/C, 30×4 mm, full hydrogen mode, RT, 1 ml/min flow rate, 1 pass). The reaction mixture was concentrated in vacuo and azeotroped with MeOH (12 ml) to afford the title compound (0.531 g, 2.15 mmol, 97% yield, 99% purity) as a pale yellow oil. UPLC-MS (Method 1) m/z no 1.18 min. $^1$H NMR (500 MHz, DMSO-$d_6$) δ 9.91 (s, 1H), 7.14 (d, J=2.5 Hz, 1H), 7.05 (d, J=8.4 Hz, 1H), 6.98 (dd, J=8.3, 2.6 Hz, 1H), 5.21 (s, 2H), 2.91-2.69 (m, 4H), 1.75-1.62 (m, 4H), 1.60-1.47 (m, 2H).

Step 4: methyl 4-methoxy-3-(N-(2-(piperidin-1-yl)-5-(1H-tetrazol-1-yl)phenyl)sulfamoyl)benzoate: Pyridine (0.199 ml, 2.46 mmol) was added to a solution of the product from step 3 above (200 mg, 0.819 mmol) and methyl 3-(chlorosulfonyl)-4-methoxybenzoate (260 mg, 0.982 mmol) in DCM (8 ml) and the solution was stirred at RT for 18 h. The solution was concentrated in vacuo and the crude product was purified by chromatography on silica gel (12 g cartridge, 0-100% EtOAc/isohexane) to afford the title compound (0.221 g, 0.468 mmol, 57.1% yield, 100% purity) as a white solid. UPLC-MS (Method 1) m/z 473.3 $(M+H)^+$, 471.3 $(M-H)^-$ at 1.52 min.

Step 5: 4-methoxy-3-(N-(2-(piperidin-1-yl)-5-(1H-tetrazol-1-yl)phenyl)sulfamoyl)benzoic acid: 1 M LiOH (aq) (2.81 ml, 2.81 mmol) was added to a solution of the product from step 4 above (0.221 g, 0.468 mmol) in THF (11 ml) and MeOH (3 ml) and the solution was stirred at RT overnight. The solvent was removed in vacuo and the residue was dissolved in water (5 ml) and washed with TBME (3×5 ml). The aqueous phase was acidified with conc. HCl and extracted with TBME (3×10 ml). The organic phases were combined and dried by passage through a phase separator and the solvent was removed in vacuo to give the title compound (0.171 g, 0.369 mmol, 79% yield, 99% purity) as an off white solid. UPLC-MS (Method 1) m/z 459.3 $(M+H)^+$, 457.2 $(M-H)^-$ at 1.40 min. $^1$H NMR (500 MHz, DMSO-$d_6$) δ 13.16 (s, 1H), 9.95 (s, 1H), 8.83 (s, 1H), 8.41 (d, J=2.2 Hz, 1H), 8.14 (dd, J=8.7, 2.2 Hz, 1H), 7.80 (d, J=2.5 Hz, 1H), 7.53 (dd, J=8.6, 2.5 Hz, 1H), 7.45 (d, J=8.6 Hz, 1H), 7.33 (d, J=8.8 Hz, 1H), 3.95 (s, 3H), 2.77-2.68 (m, 4H), 1.74-1.61 (m, 4H), 1.60-1.49 (m, 2H).

Example 215: 3-(N-(5-cyano-2-(piperidin-1-yl)phenyl)sulfamoyl)-4-ethylbenzoic acid

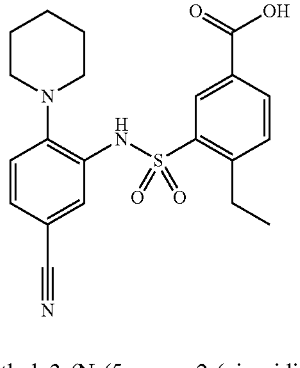

Step 1: methyl 3-(N-(5-cyano-2-(piperidin-1-yl)phenyl)sulfamoyl)-4-ethylbenzoate: A mixture of the product from Example 182 step 2 (90 mg, 0.443 mmol), the product from Example 203 step 2 (174 mg, 0.664 mmol) and pyridine (150 μl, 1.86 mmol) in DCM (3 ml) was stirred at 35° C. for 2 days. The mixture was concentrated onto silica and the crude product was purified by chromatography on silica gel (12 g cartridge, 0-25% EtOAc/isohexane) to afford the title compound (129 mg, 0.272 mmol, 61.3% yield, 90% purity) as a pale brown oil. UPLC-MS (Method 1) m/z 428.2 $(M+H)^+$, 426.2 $(M-H)^-$ at 1.80 min. $^1$H NMR (500 MHz, DMSO-$d_6$) δ 9.62 (s, 1H), 8.30 (d, J=1.9 Hz, 1H), 8.12 (dd, J=8.0, 1.9 Hz, 1H), 7.65 (d, J=8.0 Hz, 1H), 7.56 (dd, J=8.4, 2.0 Hz, 1H), 7.26 (d, J=2.0 Hz, 1H), 7.16 (d, J=8.4 Hz, 1H), 3.86 (s, 3H), 3.02 (q, J=7.4 Hz, 2H), 2.82-2.73 (m, 4H), 1.53-1.39 (m, 6H), 1.21 (t, J=7.4 Hz, 3H).

Step 2: 3-(N-(5-cyano-2-(piperidin-1-yl)phenyl)sulfamoyl)-4-ethylbenzoic acid: A mixture of the product from step 1 above (129 mg, 0.272 mmol) and LiOH (26.0 mg, 1.09 mmol) in THF/MeOH/water (4:1:1, 3.6 ml) was stirred at 40° C. overnight. The mixture was diluted with water (5 ml) and EtOAc (15 ml) and acidified to ~pH 4 with 1 M HCl(aq). The phases were separated and the aqueous extracted with EtOAc (2×15 ml). The organic extracts were combined, washed with brine (10 ml), dried by passage through a phase separator and the solvent was removed in vacuo. The residue was triturated with hexane/TBME (2:1) to give the title compound (50.3 mg, 0.121 mmol, 44.4% yield, 99% purity) as a beige solid. UPLC-MS (Method 1) m/z 414.2 $(M+H)^+$, 412.0 $(M-H)^-$ at 1.65 min. $^1$H NMR (500 MHz, DMSO-$d_6$)· 13.30 (s, 1H), 9.58 (s, 1H), 8.30 (d, J=1.9 Hz, 1H), 8.10 (dd, J=8.0, 1.9 Hz, 1H), 7.62 (d, J=8.0 Hz, 1H), 7.56 (dd, J=8.4, 2.0 Hz, 1H), 7.26 (d, J=2.0 Hz, 1H), 7.16 (d, J=8.4 Hz, 1H), 3.01 (q, J=7.4 Hz, 2H), 2.84-2.69 (m, 4H), 1.54-1.39 (m, 6H), 1.21 (t, J=7.4 Hz, 3H).

Example 216:3-(N-(5-chloro-2-(piperidin-1-yl)phenyl)sulfamoyl)-4-ethylbenzoic acid

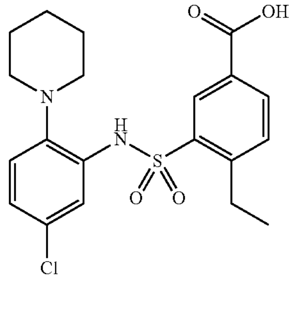 [SMILES: CCc1ccc(C(=O)O)cc1S(=O)(=O)Nc1cc(Cl)ccc1N1CCCCC1]

Step 1: methyl 3-(N-(5-chloro-2-(piperidin-1-yl)phenyl)sulfamoyl)-4-ethylbenzoate: A mixture of 5-chloro-2-(piperidin-1-yl)aniline (212 mg, 0.956 mmol), the product from Example 203 step 2 (300 mg, 1.14 mmol) and pyridine (0.34 ml, 4.20 mmol) in DCM (7 ml) was stirred at 35° C. overnight. The mixture was concentrated onto silica and purified by chromatography on silica gel (12 g cartridge, 0-20% EtOAc/isohexane) to afford the title compound (326 mg, 0.671 mmol, 70.2% yield, 90% purity) as a dark purple oil. UPLC-MS (Method 1) m/z 437.2 $(M+H)^+$, 435.2 $(M-H)^-$ at 2.01 min. $^1$H NMR (500 MHz, DMSO-$d_6$) δ 9.29 (s, 1H), 8.34 (d, J=1.9 Hz, 1H), 8.11 (dd, J=8.0, 1.9 Hz, 1H), 7.64 (d, J=8.0 Hz, 1H), 7.19-7.10 (m, 3H), 3.86 (s, 3H), 3.06 (q, J=7.4 Hz, 2H), 2.54 (t, J=5.3 Hz, 4H), 1.59-1.48 (m, 4H), 1.47-1.37 (m, 2H), 1.22 (t, J=7.4 Hz, 3H).

Step 2: 3-(N-(5-chloro-2-(piperidin-1-yl)phenyl)sulfamoyl)-4-ethylbenzoic acid: A mixture of the product from step 1 above (326 mg, 0.671 mmol) and 2 M LiOH (aq) (0.336 ml, 0.671 mmol) in THF/MeOH/water (4:1:1, 8.4 ml) was stirred at 40° C. overnight. The mixture was diluted with water (10 ml) and EtOAc (25 ml) and acidified to ~pH 4 with 1 M HCl. The phases were separated and the aqueous extracted with EtOAc (2×25 ml). The combined organic extracts were washed with brine (15 ml), dried by passage through a phase separator and the solvent was removed in vacuo. The crude product was purified by chromatography on silica gel (12 g cartridge, 0-100% EtOAc/isohexane) to afford the title compound (89.7 mg, 0.207 mmol, 30.8% yield, 98% purity) as a light grey solid. UPLC-MS (Method 1) m/z 423.3 $(M+H)^+$, 421.2 $(M-H)^-$ at 1.86 min. $^1H$ NMR (500 MHz, DMSO-$d_6$) δ 13.33 (s, 1H), 9.23 (s, 1H), 8.34 (d, J=1.8 Hz, 1H), 8.09 (dd, J=8.0, 1.8 Hz, 1H), 7.61 (d, J=8.0 Hz, 1H), 7.19-7.09 (m, 3H), 3.05 (q, J=7.4 Hz, 2H), 2.55 (t, J=5.3 Hz, 4H), 1.60-1.50 (m, 4H), 1.48-1.38 (m, 2H), 1.21 (t, J=7.4 Hz, 3H).

Example 217:3-(N-(5-chloro-2-(4,4-difluoropiperidin-1-yl)phenyl)sulfamoyl)-4-ethylbenzoic acid

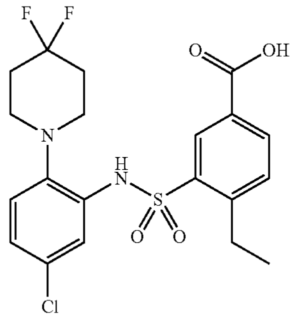 [SMILES: CCc1ccc(C(=O)O)cc1S(=O)(=O)Nc1cc(Cl)ccc1N1CCC(F)(F)CC1]

Step 1: 1-(4-chloro-2-nitrophenyl)-4,4-difluoropiperidine: $Et_3N$ (0.992 ml, 7.12 mmol) was added to a solution of 4-chloro-1-fluoro-2-nitrobenzene (500 mg, 2.85 mmol) and 4,4-difluoropiperidine (414 mg, 3.42 mmol) in DCM (6 ml) at RT. The clear solution was stirred at RT for 23 h. The organic phase was washed with 1 M HCl(aq) (3 ml), separated by passage through a phase separator and concentrated in vacuo to afford the title compound (803 mg, 2.76 mmol, 97% yield, 95% purity) as a brown oil. UPLC-MS (Method 1) m/z 277.2 $(M+H)^+$ at 1.67 min.

Step 2: 5-chloro-2-(4,4-difluoropiperidin-1-yl)aniline: Iron powder (1.62 g, 28.9 mmol) was added to a suspension of the product from step 1 above (400 mg, 1.45 mmol) and ammonium chloride (93 mg, 1.74 mmol) in IPA (10 ml) and water (5 ml) at RT. The resultant suspension was heated and stirred at 90° C. for 2 h. The reaction was filtered through Celite®, washed with MeOH (100 ml) and concentrated in vacuo. The residue was dissolved in DCM (25 ml) and washed with water (10 ml) and brine (10 ml), dried ($MgSO_4$) and concentrated in vacuo. The crude product was purified by chromatography on silica gel (12 g cartridge, 0-100% EtOAc/isohexane) to afford the title compound (0.152 g, 0.592 mmol, 40.9% yield, 96% purity) as a cream solid. UPLC-MS (Method 1) m/z 247.3 $(M+H)^+$ at 1.58 min.

Step 3: methyl 3-(N-(5-chloro-2-(4,4-difluoropiperidin-1-yl)phenyl)sulfamoyl)-4-ethylbenzoate: Pyridine (0.074 ml, 0.912 mmol) was added to a solution of the product from step 2 above (0.075 g, 0.304 mmol) and the product from Example 203 step 2 (0.100 g, 0.380 mmol) in DCM (10 ml) and the solution was stirred at RT for 18 h. The solution was concentrated in vacuo and the crude product was purified by chromatography on silica gel (12 g cartridge, 0-100% EtOAc/isohexane) to afford the title compound (0.096 g, 0.189 mmol, 62.1% yield, 93% purity) as a white solid. UPLC-MS (Method 1) m/z 473.0 $(M+H)^+$, 470.9 $(M-H)^-$ at 1.89 min.

Step 4: 3-(N-(5-chloro-2-(4,4-difluoropiperidin-1-yl)phenyl)sulfamoyl)-4-ethylbenzoic acid: 1 M LiOH (aq) (1.13 ml, 1.13 mmol) was added to a solution of the product from step 3 above (0.089 g, 0.189 mmol) in THF (4.5 ml) and MeOH (1.1 ml) and the solution was stirred at RT overnight. The solvent was removed in vacuo and the residue dissolved in water (5 ml) and washed with TBME (3×5 ml). The aqueous phase was acidified with conc. HCl and extracted with TBME (3×10 ml). The organic phases were combined and dried by passage through a phase separator and the solvent was removed in vacuo to give the title compound (0.073 g, 0.156 mmol, 82% yield, 98% purity) as an off white solid. UPLC-MS (Method 1) m/z 459.6 $(M+H)^+$, 456.9 $(M-H)^-$ at 1.76 min. $^1H$ NMR (500 MHz, DMSO-$d_6$) δ 13.34 (s, 1H), 9.70 (s, 1H), 8.36 (d, J=1.8 Hz, 1H), 8.09 (dd, J=8.0, 1.8 Hz, 1H), 7.61 (d, J=8.0 Hz, 1H), 7.26-7.19 (m, 2H), 7.14 (dd, J=8.5, 2.5 Hz, 1H), 3.04 (q, J=7.4 Hz, 2H), 2.69 (t, J=5.6 Hz, 4H), 2.10-1.97 (m, 4H), 1.19 (t, J=7.4 Hz, 3H).

Example 218:3-(N-(5-chloro-2-(4,4-difluoropiperidin-1-yl)phenyl)sulfamoyl)-4-methoxybenzoic acid

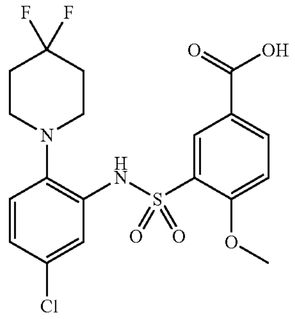 [SMILES: COc1ccc(C(=O)O)cc1S(=O)(=O)Nc1cc(Cl)ccc1N1CCC(F)(F)CC1]

Step 1: Methyl 3-(N-(5-chloro-2-(4,4-difluoropiperidin-1-yl)phenyl)sulfamoyl)-4-methoxybenzoate: Pyridine (0.074 ml, 0.912 mmol) was added to a solution of the product from Example 217 step 2 (0.075 g, 0.304 mmol) and methyl 3-(chlorosulfonyl)-4-methoxybenzoate (0.101 g, 0.380 mmol) in DCM (10 ml) and the solution was stirred at RT for 18 h. The solution was concentrated in vacuo and the crude product was purified by chromatography on silica gel (12 g cartridge, 0-100% EtOAc/isohexane) to afford the title compound (0.113 g, 0.193 mmol, 63.4% yield, 81% purity) as a white solid. UPLC-MS (Method 1) m/z 475.4 $(M+H)^+$, 472.8 $(M-H)^-$ at 1.75 min.

Step 2: 3-(N-(5-chloro-2-(4,4-difluoropiperidin-1-yl)phenyl)sulfamoyl)-4-methoxybenzoic acid: 1 M LiOH (aq) (1.16 ml, 1.16 mmol) was added to a solution of the product from step 1 above (0.092 g, 0.193 mmol) in THF (4.5 ml) and MeOH (1.1 ml) and the solution was stirred at RT overnight. The solvent was removed in vacuo and the residue dissolved in water (5 ml) and washed with TBME (3×5 ml). The aqueous phase was acidified with conc. HCl and extracted with TBME (3×10 ml). The organic phases were combined and dried by passage through a phase separator and the solvent was removed in vacuo to give the title compound (0.078 g, 0.166 mmol, 86% yield, 98% purity) as an off white solid. UPLC-MS (Method 1) m/z 461.0 $(M+H)^+$, 459.0 $(M-H)^-$ at 1.59 min. $^1$H NMR (500 MHz, DMSO-$d_6$) δ 13.19 (s, 1H), 9.13 (s, 1H), 8.37 (d, J=2.2 Hz, 1H), 8.17 (dd, J=8.7, 2.2 Hz, 1H), 7.33 (d, J=8.7 Hz, 1H), 7.29-7.23 (m, 2H), 7.07 (dd, J=8.5, 2.5 Hz, 1H), 3.90 (s, 3H), 2.78 (t, J=5.6 Hz, 4H), 2.18-2.06 (m, 4H).

Example 219:3-(N-(5-chloro-2-(3,3-difluoropiperidin-1-yl)phenyl)sulfamoyl)-4-methoxybenzoic acid

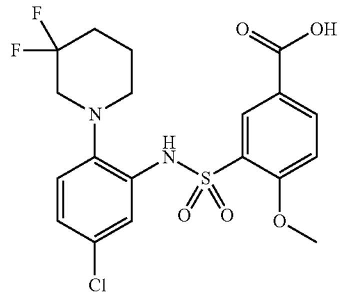

Step 1: 1-(4-chloro-2-nitrophenyl)-3,3-difluoropiperidine: $Et_3N$ (1.79 ml, 12.8 mmol) was added to a solution of 4-chloro-1-fluoro-2-nitrobenzene (0.335 ml, 2.85 mmol) and 3,3-difluoropiperidine hydrochloride (539 mg, 3.42 mmol) in DCM (6 ml) at RT. The mixture was stirred at RT for 23 h. The solvent was removed in vacuo and the residue was dissolved in THF (6 ml) and heated to 50° C. for 18 h. DMF (6 ml) was added and the mixture was heated to 90° C. for 18 h. The solvents were removed in vacuo and DCM (6 ml) and 1 M HCl(aq) (3 ml) were added. The organic phase was dried by passage through a phase separator and concentrated in vacuo to afford the title compound (0.490 g, 1.68 mmol, 59.1% yield, 95% purity) as a brown oil. UPLC-MS (Method 1) m/z 277.2 $(M+H)^+$ at 1.63 min.

Step 2: 5-chloro-2-(3,3-difluoropiperidin-1-yl)aniline: Iron powder (1.62 g, 28.9 mmol) was added to a suspension of the product from step 1 above (0.490 g, 1.77 mmol) and ammonium chloride (0.093 g, 1.74 mmol) in IPA (10 ml) and water (5 ml) at RT. The resultant suspension was heated and stirred at 90° C. for 2 h. The reaction mixture was filtered through Celite®, washed with MeOH (100 ml) and concentrated in vacuo. The residue was dissolved in DCM (25 ml) and washed sequentially with water (10 ml) and brine (10 ml), dried ($MgSO_4$) and concentrated in vacuo. The crude product was purified by chromatography on silica gel (12 g cartridge, 0-100% EtOAc/isohexane) to afford the title compound (0.252 g, 1.02 mmol, 70.6% yield, 100% purity) as a cream solid. UPLC-MS (Method 1) m/z 247.2 $(M+H)^+$ at 1.59 min.

Step 3: methyl 3-(N-(5-chloro-2-(3,3-difluoropiperidin-1-yl)phenyl)sulfamoyl)-4-methoxybenzoate: Pyridine (0.123 ml, 1.52 mmol) was added to a solution of the product from step 2 above (0.125 g, 0.507 mmol) and methyl 3-(chlorosulfonyl)-4-methoxybenzoate (0.168 g, 0.633 mmol) in DCM (10 ml) and the solution was stirred at RT for 18 h. The solution was concentrated in vacuo and the crude product was purified by chromatography on silica gel (12 g cartridge, 0-100% EtOAc/isohexane) to afford the title compound (0.241 g, 0.502 mmol, 99% yield, 99% purity) as a white solid. UPLC-MS (Method 1) m/z 475.3 $(M+H)^+$, 472.8 $(M-H)^-$ at 1.73 min.

Step 4: 3-(N-(5-chloro-2-(3,3-difluoropiperidin-1-yl)phenyl)sulfamoyl)-4-methoxybenzoic acid: 1 M LiOH (aq) (3.04 ml, 3.04 mmol) was added to a solution of the product from step 3 above (0.241 g, 0.507 mmol) in THF (12 ml) and MeOH (3 ml) and the solution was stirred at RT overnight. The solvent was removed in vacuo and the residue dissolved in water (5 ml) and washed with TBME (3×5 ml). The aqueous phase was acidified with conc. HCl and extracted with TBME (3×10 ml). The organic phases were combined and dried by passage through a phase separator and the solvent was removed in vacuo to give the title compound (0.211 g, 0.458 mmol, 90% yield, 100% purity) as an off white solid. UPLC-MS (Method 1) m/z 461.3 $(M+H)^+$, 459.1 $(M-H)^-$ at 1.57 min. $^1$H NMR (500 MHz, DMSO-$d_6$) δ 13.25 (s, 1H), 8.46 (s, 1H), 8.40 (d, J=2.2 Hz, 1H), 8.19 (dd, J=8.7, 2.2 Hz, 1H), 7.35 (d, J=8.7 Hz, 1H), 7.31 (d, J=8.6 Hz, 1H), 7.22 (d, J=2.4 Hz, 1H), 7.09 (dd, J=8.5, 2.4 Hz, 1H), 3.94 (s, 3H), 3.04 (t, J=11.1 Hz, 2H), 2.85-2.76 (m, 2H), 2.11-1.98 (m, 2H), 1.90-1.79 (m, 2H).

Example 220:3-(N-(5-chloro-2-(3,3-difluoropiperidin-1-yl)phenyl)sulfamoyl)-4-ethylbenzoic acid

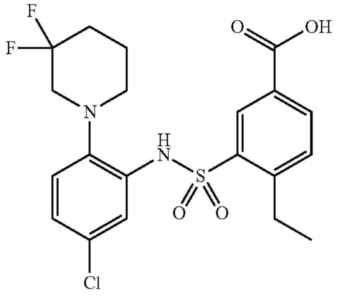

Step 1: methyl 3-(N-(5-chloro-2-(3,3-difluoropiperidin-1-yl)phenyl)sulfamoyl)-4-ethylbenzoate: Pyridine (0.123 ml, 1.52 mmol) was added to a solution of the product from Example 219 step 2 (0.125 g, 0.507 mmol) and the product from Example 203 step 2 (0.166 g, 0.633 mmol) in DCM (10 ml) and the solution was stirred at RT for 18 h. The solution was concentrated in vacuo and the crude product was purified by chromatography on silica gel (12 g cartridge, 0-100% EtOAc/isohexane) to afford the title compound (0.166 g, 0.351 mmol, 69.3% yield, 100% purity) as a white solid. UPLC-MS (Method 1) m/z 473.4 $(M+H)^+$, 471.2 $(M-H)^-$ at 1.89 min.

Step 2: 3-(N-(5-chloro-2-(3,3-difluoropiperidin-1-yl)phenyl)sulfamoyl)-4-ethylbenzoic acid: 1 M LiOH (aq) (2.11 ml, 2.11 mmol) was added to a solution of the product from step 1 above (0.166 g, 0.351 mmol) in THF (8.5 ml) and MeOH (2.1 ml) and the solution was stirred at RT overnight. The solvent was removed in vacuo and the residue dissolved in water (5 ml) and washed with TBME (3×5 ml). The aqueous phase was acidified with conc. HCl and extracted with TBME (3×10 ml). The organic phases were combined and dried by passage through a phase separator and the solvent was removed in vacuo to afford the title compound (0.143 g, 0.308 mmol, 88% yield, 99% purity) as an off white solid. UPLC-MS (Method 1) m/z 459.1 $(M+H)^+$, 457.0 (M−H)$^-$ at 1.75 min. $^1$H NMR (500 MHz, DMSO-$d_6$) δ 13.36 (s, 1H), 8.98 (s, 1H), 8.37 (d, J=1.8 Hz, 1H), 8.11 (dd, J=8.0, 1.8 Hz, 1H), 7.63 (d, J=8.0 Hz, 1H), 7.26 (d, J=8.6 Hz, 1H), 7.15 (dd, J=8.6, 2.5 Hz, 1H), 7.07 (d, J=2.4 Hz, 1H), 3.06-2.96 (m, 4H), 2.81-2.72 (m, 2H), 2.06-1.93 (m, 2H), 1.80-1.71 (m, 2H), 1.21 (t, J=7.4 Hz, 3H).

Example 221: 3-(N-(5-cyano-2-(4,4-difluoropiperidin-1-yl)phenyl)sulfamoyl)-4-methoxybenzoic acid

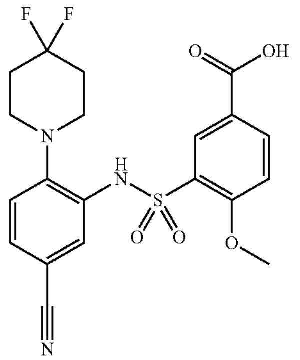 [SMILES: COc1ccc(C(=O)O)cc1S(=O)(=O)Nc1cc(C#N)ccc1N1CCC(F)(F)CC1]

Step 1: 4-(4,4-difluoropiperidin-1-yl)-3-nitrobenzonitrile: A mixture of 4-fluoro-3-nitrobenzonitrile (500 mg, 3.01 mmol), 4,4-difluoropiperidine (400 mg, 3.30 mmol) and $Et_3N$ (0.65 ml, 4.66 mmol) in DMF (5 ml) was stirred at 90° C. overnight. The mixture was diluted with water (20 ml) and extracted with EtOAc (3×35 ml). The combined organic extracts were washed with brine (2×30 ml), dried by passage through a phase separator and the solvent was removed in vacuo. The residue was loaded onto silica and purified by chromatography on silica gel (24 g cartridge, 0-10% EtOAc/isohexane) to afford the title compound (541 mg, 2.02 mmol, 67.3% yield, 100% purity) as a bright yellow solid. UPLC-MS (Method 2) m/z 1.39 min. $^1$H NMR (500 MHz, DMSO-$d_6$) δ 8.37 (d, J=2.1 Hz, 1H), 7.94 (dd, J=8.7, 2.1 Hz, 1H), 7.46 (d, J=8.7 Hz, 1H), 3.31-3.25 (m, 4H), 2.15-2.04 (m, 4H).

Step 2: 3-amino-4-(4,4-difluoropiperidin-1-yl)benzonitrile: A mixture of the product from step 1 above (541 mg, 2.02 mmol), iron powder (2.5 g, 44.8 mmol), ammonium chloride (130 mg, 2.43 mmol), IPA (16 ml) and water (8 ml) was heated at 90° C. overnight. The mixture was filtered over Celite®, rinsing with MeOH and the solvent was removed in vacuo. The residue was diluted with DCM (20 ml), dried by passage through a phase separator and concentrated onto silica. The crude product was purified by chromatography on silica gel (24 g cartridge, 100% DCM) to afford the title compound (260 mg, 1.10 mmol, 54.1% yield, 100% purity) as a light yellow solid. UPLC-MS (Method 2) m/z 238.2 (M+H)$^+$, 236.0 (M−H)$^-$ at 1.34 min. $^1$H NMR (500 MHz, DMSO-$d_6$) δ 7.04-6.90 (m, 3H), 5.29 (s, 2H), 2.94 (t, J=5.5 Hz, 4H), 2.24-2.08 (m, 4H).

Step 3: methyl 3-(N-(5-cyano-2-(4,4-difluoropiperidin-1-yl)phenyl)sulfamoyl)-4-methoxybenzoate: A mixture of the product from step 2 above (130 mg, 0.548 mmol), methyl 3-(chlorosulfonyl)-4-methoxybenzoate (0.160 g, 0.603 mmol), pyridine (140 μl, 1.73 mmol) and DCM (3.5 ml) was stirred at RT overnight. The mixture was concentrated onto silica and purified by chromatography on silica gel (12 g cartridge, 0-100% EtOAc/isohexane) to afford the title compound (148 mg, 0.312 mmol, 56.9% yield, 98% purity) as a white solid. UPLC-MS (Method 1) m/z 466.3 (M+H)$^+$, 464.1 (M−H)$^-$ at 1.54 min. $^1$H NMR (500 MHz, DMSO-$d_6$) δ 9.43 (s, 1H), 8.32 (d, J=2.3 Hz, 1H), 8.21 (dd, J=8.7, 2.3 Hz, 1H), 7.54 (dd, J=8.3, 1.9 Hz, 1H), 7.42-7.35 (m, 2H), 7.28 (d, J=8.3 Hz, 1H), 3.90 (s, 3H), 3.85 (s, 3H), 2.98 (t, J=5.6 Hz, 4H), 2.13-2.01 (m, 4H).

Step 4: 3-(N-(5-cyano-2-(4,4-difluoropiperidin-1-yl)phenyl)sulfamoyl)-4-methoxybenzoic acid: A mixture of the product from step 3 above (0.148 g, 0.312 mmol) and LiOH (30 mg, 1.253 mmol) in THF/MeOH/water (4:1:1, 3.6 ml) was stirred at 40° C. overnight. The mixture was diluted with water (5 ml) and acidified to ~pH 4 with 1 M HCl(aq). The mixture was extracted with EtOAc (3×20 ml) and the combined organic extracts were washed with brine (10 ml), dried by passage through a phase separator and the solvent was removed in vacuo. The residue was loaded onto silica and purified by chromatography on silica gel (4 g cartridge, 0-100% EtOAc/isohexane) to afford the title compound (85.6 mg, 0.185 mmol, 59.3% yield, 97% purity) as a white solid after trituration with TBME. UPLC-MS (Method 1) m/z 452.2 (M+H)$^+$, 450.2 (M−H)$^-$ at 1.40 min. $^1$H NMR (500 MHz, DMSO-$d_6$) δ 13.17 (s, 1H), 9.40 (s, 1H), 8.32 (d, J=2.3 Hz, 1H), 8.18 (dd, J=8.8, 2.3 Hz, 1H), 7.53 (dd, J=8.3, 2.0 Hz, 1H), 7.41 (d, J=2.0 Hz, 1H), 7.35 (d, J=8.8 Hz, 1H), 7.28 (d, J=8.3 Hz, 1H), 3.89 (s, 3H), 3.04-2.92 (m, 4H), 2.15-2.01 (m, 4H).

Example 222: 3-(N-(5-cyano-2-(4,4-difluoropiperidin-1-yl)phenyl)sulfamoyl)-4-ethylbenzoic acid

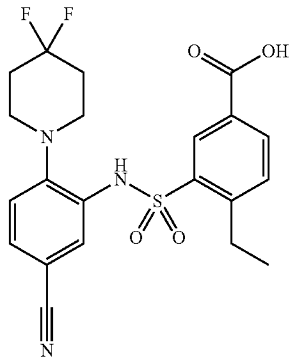 [SMILES: CCc1ccc(C(=O)O)cc1S(=O)(=O)Nc1cc(C#N)ccc1N1CCC(F)(F)CC1]

Step 1: methyl 3-(N-(5-cyano-2-(4,4-difluoropiperidin-1-yl)phenyl)sulfamoyl)-4-ethylbenzoate: A mixture of the product from Example 221 step 2 (130 mg, 0.548 mmol), the product from Example 203 step 2 (0.244 g, 0.603 mmol), pyridine (140 μl, 1.73 mmol) and DCM (3.5 ml) was stirred at RT overnight. The mixture was concentrated onto silica and purified by chromatography on silica gel (12 g cartridge, 0-100% EtOAc/isohexane) to afford the title compound (102 mg, 0.211 mmol, 38.6% yield, 96% purity) as a white solid. UPLC-MS (Method 1) m/z 464.3 (M+H)$^+$, 462.1 (M−H)$^-$ at 1.68 min. $^1$H NMR (500 MHz, DMSO-$d_6$) δ 9.91 (s, 1H), 8.33 (d, J=1.9 Hz, 1H), 8.13 (dd, J=8.0, 1.9 Hz, 1H), 7.66 (d, J=8.0 Hz, 1H), 7.59 (dd, J=8.4, 1.9 Hz, 1H), 7.33 (d, J=1.9 Hz, 1H), 7.27 (d, J=8.4 Hz, 1H), 3.86 (s, 3H), 3.01 (q, J=7.4 Hz, 2H), 2.91 (t, J=5.6 Hz, 4H), 2.05-1.94 (m, 4H), 1.20 (t, J=7.4 Hz, 3H).

Step 2: 3-(N-(5-cyano-2-(4,4-difluoropiperidin-1-yl)phenyl)sulfamoyl)-4-ethylbenzoic acid: A mixture of the product from step 3 above (0.102 g, 0.211 mmol) and LiOH (30 mg, 1.253 mmol) in THF/MeOH/water (4:1:1, 3.6 ml) was stirred at 40° C. overnight. The mixture was diluted with water (5 ml) and acidified to ~pH 4 with 1 M HCl. The mixture was extracted with EtOAc (3×20 ml) and the combined organic extracts were washed with brine (10 ml), dried by passage through a phase separator and the solvent was removed in vacuo. The residue was loaded onto silica and purified by chromatography on silica gel (4 g cartridge, 0-100% EtOAc/isohexane) to afford the title compound (32.6 mg, 0.070 mmol, 33.2% yield, 97% purity) as a white solid after trituration with TBME. UPLC-MS (Method 1) m/z 450.2 $(M+H)^+$, 448.2 $(M-H)^-$ at 1.56 min. $^1H$ NMR (500 MHz, DMSO-$d_6$) δ 13.33 (s, 1H), 9.88 (s, 1H), 8.33 (d, J=1.9 Hz, 1H), 8.11 (dd, J=8.1, 1.9 Hz, 1H), 7.63 (d, J=8.1 Hz, 1H), 7.58 (dd, J=8.4, 2.0 Hz, 1H), 7.33 (d, J=2.0 Hz, 1H), 7.27 (d, J=8.4 Hz, 1H), 3.01 (q, J=7.4 Hz, 2H), 2.94-2.88 (m, 4H), 2.06-1.97 (m, 4H), 1.20 (t, J=7.3 Hz, 3H).

Example 223:3-(N-(5-cyano-2-(3-hydroxypiperidin-1-yl)phenyl)sulfamoyl)-4-methoxybenzoic acid

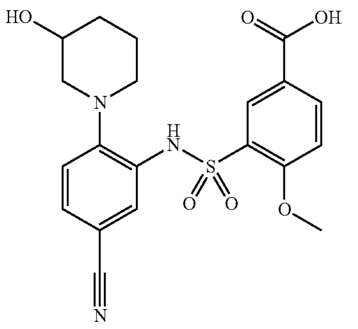 [SMILES: COc1ccc(C(=O)O)cc1S(=O)(=O)Nc1cc(C#N)ccc1N1CCCC(O)C1]

Step 1: 4-(3-hydroxypiperidin-1-yl)-3-nitrobenzonitrile: A mixture of 4-fluoro-3-nitrobenzonitrile (500 mg, 3.01 mmol), piperidin-3-ol (350 mg, 3.46 mmol) and $Et_3N$ (0.65 ml, 4.66 mmol) in DCM (10 ml) was stirred at RT overnight. The mixture was concentrated onto silica and purified by chromatography on silica gel (24 g cartridge, 0-100% EtOAc/isohexane) to afford the title compound (698 mg, 2.63 mmol, 87% yield, 93% purity) as a thick orange oil. UPLC-MS (Method 2) m/z 248.2 $(M+H)^+$, 246.4 $(M-H)^-$ at 1.02 min. $^1H$ NMR (500 MHz, DMSO-$d_6$)· 8.28 (d, J=2.1 Hz, 1H), 7.83 (dd, J=8.9, 2.1 Hz, 1H), 7.35 (d, J=8.9 Hz, 1H), 4.92 (d, J=4.2 Hz, 1H), 3.67-3.57 (m, 1H), 3.29-3.21 (m, 2H), 3.01 (ddd, J=12.8, 9.6, 3.1 Hz, 1H), 2.81 (dd, J=12.8, 8.2 Hz, 1H), 1.91-1.84 (m, 1H), 1.82-1.73 (m, 1H), 1.54-1.44 (m, 1H), 1.43-1.33 (m, 1H).

Step 2: 3-amino-4-(3-hydroxypiperidin-1-yl)benzonitrile: A mixture of the product from step 1 above (698 mg, 2.65 mmol), iron powder (3 g, 53.7 mmol), ammonium chloride (170 mg, 3.18 mmol), IPA (20 ml) and water (10 ml) was heated to 90° C. overnight. The mixture was filtered over Celite®, rinsing with MeOH and the filtrate was concentrated in vacuo. The residue was diluted with DCM (20 ml), dried by passage through a phase separator and concentrated onto silica. The crude product was purified by chromatography on silica gel (24 g cartridge, 0-5% MeOH/DCM) to afford the title compound (381 mg, 1.72 mmol, 64.8% yield, 98% purity) as a light orange solid. UPLC-MS (Method 2) m/z 218.2 $(M+H)^+$, 216.2 $(M-H)^-$ at 0.94 min. $^1H$ NMR (500 MHz, DMSO-$d_6$) δ 6.98-6.90 (m, 3H), 5.15 (s, 2H), 4.80 (d, J=5.4 Hz, 1H), 3.75-3.66 (m, 1H), 3.06-2.97 (m, 1H), 2.96-2.87 (m, 1H), 2.56 (t, J=10.3 Hz, 1H), 2.49-2.42 (m, 1H), 1.89-1.74 (m, 2H), 1.67-1.54 (m, 1H), 1.41-1.27 (m, 1H).

Step 3: methyl 3-(N-(5-cyano-2-(3-hydroxypiperidin-1-yl)phenyl)sulfamoyl)-4-methoxybenzoate: A mixture of the product from step 2 above (100 mg, 0.451 mmol), methyl 3-(chlorosulfonyl)-4-methoxybenzoate (131 mg, 0.496 mmol), pyridine (110 μl, 1.36 mmol) and DCM (3 ml) was stirred at RT overnight. The mixture was concentrated onto silica and purified by chromatography on silica gel (12 g cartridge, 0-100% EtOAc/isohexane) to afford the title compound (111 mg, 0.219 mmol, 48.6% yield, 88% purity) as a white solid. UPLC-MS (Method 1) m/z 446.3 $(M+H)^+$, 444.1 $(M-H)^-$ at 1.31 min. $^1H$ NMR (500 MHz, DMSO-$d_6$) δ 9.28 (s, 1H), 8.36 (d, J=2.3 Hz, 1H), 8.23-8.17 (m, 1H), 7.49-7.43 (m, 1H), 7.43-7.39 (m, 1H), 7.35 (d, J=8.7 Hz, 1H), 7.19 (d, J=8.3 Hz, 1H), 5.09 (d, J=5.2 Hz, 1H), 3.90 (s, 3H), 3.86 (s, 3H), 3.75-3.67 (m, 1H), 2.96-2.86 (m, 2H), 2.78-2.70 (m, 1H), 2.70-2.61 (m, 1H), 1.90-1.80 (m, 1H), 1.76-1.66 (m, 1H), 1.57-1.40 (m, 2H).

Step 4: 3-(N-(5-cyano-2-(3-hydroxypiperidin-1-yl)phenyl)sulfamoyl)-4-methoxybenzoic acid: A mixture of the product from step 3 above (111 mg, 0.219 mmol) and LiOH (21.0 mg, 0.877 mmol) in THF/MeOH/water (4:1:1, 3 ml) was stirred at 40° C. overnight. The mixture was diluted with water (5 ml), acidified to ~pH 4 with 1 M HCl(aq) and extracted with EtOAc (3×20 ml). The combined organic extracts were washed with brine (10 ml), dried by passage through a phase separator and the solvent was removed in vacuo. The residue was loaded onto silica and purified by chromatography on silica gel (4 g cartridge, 0-5% MeOH/DCM) to afford the title compound (69.3 mg, 0.157 mmol, 71.8% yield, 98% purity) as a white solid. UPLC-MS (Method 1) m/z 432.2 $(M+H)^+$, 430.2 $(M-H)^-$ at 1.14 min. $^1H$ NMR (500 MHz, DMSO-$d_6$)· 13.19 (s, 1H), 9.24 (s, 1H), 8.36 (d, J=2.3 Hz, 1H), 8.16 (dd, J=8.7, 2.3 Hz, 1H), 7.45 (dd, J=8.3, 2.0 Hz, 1H), 7.41 (d, J=2.0 Hz, 1H), 7.32 (d, J=8.7 Hz, 1H), 7.19 (d, J=8.3 Hz, 1H), 5.10 (br s, 1H), 3.89 (s, 3H), 3.72 (br s, 1H), 2.96-2.84 (m, 2H), 2.78-2.71 (m, 1H), 2.67 (dd, J=11.6, 6.3 Hz, 1H), 1.91-1.80 (m, 1H), 1.75-1.67 (m, 1H), 1.56-1.44 (m, 2H).

Example 224: 3-(N-(5-cyano-2-(3-hydroxypiperidin-1-yl)phenyl)sulfamoyl)-4-ethylbenzoic acid

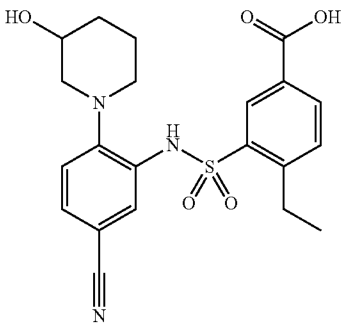 [SMILES: CCc1ccc(C(=O)O)cc1S(=O)(=O)Nc1cc(C#N)ccc1N1CCCC(O)C1]

Step 1: methyl 3-(N-(5-cyano-2-(3-hydroxypiperidin-1-yl)phenyl)sulfamoyl)-4-ethylbenzoate: A mixture of the product from Example 223 step 2 (100 mg, 0.451 mmol), the product from Example 203 step 2 (201 mg, 0.496 mmol), pyridine (110 μl, 1.36 mmol) and DCM (3 ml) was stirred at RT overnight. The mixture was concentrated onto silica and purified by chromatography on silica gel (12 g cartridge, 0-100% EtOAc/isohexane) to afford the title compound (108 mg, 0.219 mmol, 48.6% yield, 90% purity) as a white solid. UPLC-MS (Method 1) m/z 444.2 $(M+H)^+$, 442.1 $(M-H)^-$ at 1.49 min. $^1$H NMR (500 MHz, DMSO-$d_6$) δ9.79 (s, 1H), 8.35 (d, J=1.9 Hz, 1H), 8.15-8.09 (m, 1H), 7.64 (d, J=8.2 Hz, 1H), 7.50 (d, J=8.4 Hz, 1H), 7.32 (d, J=1.9 Hz, 1H), 7.15 (d, J=8.2 Hz, 1H), 5.15 (d, J=5.5 Hz, 1H), 3.87 (s, 3H), 3.71-3.66 (m, 1H), 3.11-3.00 (m, 2H), 2.98-2.93 (m, 1H), 2.93-2.87 (m, 1H), 2.67-2.59 (m, 2H), 1.84-1.74 (m, 1H), 1.71-1.62 (m, 1H), 1.52-1.40 (m, 2H), 1.20 (t, J=7.4 Hz, 3H).

Step 2: 3-(N-(5-cyano-2-(3-hydroxypiperidin-1-yl)phenyl)sulfamoyl)-4-ethylbenzoic acid: A mixture of the product from step 2 above (108 mg, 0.219 mmol) and LiOH (21.0 mg, 0.877 mmol) in THF/MeOH/water (4:1:1, 3 ml) was stirred at 40° C. overnight. The mixture was diluted with water (5 ml), acidified to ~pH 4 with 1 M HCl(aq) and extracted with EtOAc (3×20 ml). The combined organic extracts were washed with brine (10 ml), dried by passage through a phase separator and the solvent was removed in vacuo. The residue was loaded onto silica and purified by chromatography on silica gel (4 g cartridge, 0-5% MeOH/DCM) to afford the title compound (75 mg, 0.169 mmol, 77% yield, 97% purity) as a white solid. UPLC-MS (Method 1) m/z 430.3 $(M+H)^+$, 428.2 $(M-H)^-$ at 1.33 min. $^1$H NMR (500 MHz, DMSO-$d_6$) δ 13.33 (s, 1H), 9.76 (s, 1H), 8.35 (d, J=1.9 Hz, 1H), 8.10 (dd, J=8.0, 1.9 Hz, 1H), 7.61 (d, J=8.0 Hz, 1H), 7.48 (dd, J=8.4, 2.0 Hz, 1H), 7.31 (d, J=2.0 Hz, 1H), 7.15 (d, J=8.4 Hz, 1H), 5.16 (br s, 1H), 3.70 (br s, 1H), 3.13-2.98 (m, 2H), 2.98-2.93 (m, 1H), 2.93-2.85 (m, 1H), 2.70-2.61 (m, 2H), 1.85-1.75 (m, 1H), 1.72-1.62 (m, 1H), 1.52-1.41 (m, 2H), 1.20 (t, J=7.4 Hz, 3H).

Example 225:4-(methylsulfonyl)-3-(N-(2-(piperidin-1-yl)-5-(trifluoromethyl)phenyl) sulfamoyl)benzoic acid

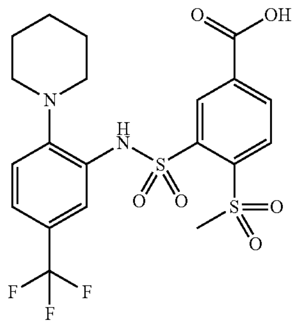 [SMILES: CS(=O)(=O)c1ccc(C(=O)O)cc1S(=O)(=O)Nc1cc(C(F)(F)F)ccc1N1CCCCC1]

Step 1: methyl 4-fluoro-3-(N-(2-(piperidin-1-yl)-5-(trifluoromethyl)phenyl)sulfamoyl)benzoate: Pyridine (0.199 ml, 2.46 mmol) was added to a solution of 2-(piperidin-1-yl)-5-(trifluoromethyl)aniline (200 mg, 0.819 mmol) and methyl 3-(chlorosulfonyl)-4-fluorobenzoate (259 mg, 1.02 mmol) in DCM (10 ml) and the solution was stirred at RT for 18 h. The solution was concentrated in vacuo and the crude product was purified by chromatography on silica gel (12 g cartridge, 0-100% EtOAc/isohexane) to afford the title compound (0.183 g, 0.389 mmol, 47.6% yield, 98% purity) as a white solid. UPLC-MS (Method 1) m/z 461.3 $(M+H)^+$, 459.2 $(M-H)^-$ at 1.91 min.

Step 2: methyl 4-(methylthio)-3-(N-(2-(piperidin-1-yl)-5-(trifluoromethyl)phenyl)sulfamoyl)benzoate: Sodium thiomethoxide (0.084 g, 1.19 mmol) was added to a solution of the product from step 1 above (0.183 g, 0.397 mmol) in DMF (4 ml) and stirred at RT for 18 h. The mixture was partitioned between DCM (10 ml) and water (10 ml) and the organic phase was separated. The aqueous phase was extracted with DCM (2×10 ml) and the combined organic phases were dried by passage through a phase separator. The solvent was removed in vacuo to give the title compound (0.095 g, 0.193 mmol, 48.4% yield, 99% purity) as an off white solid. UPLC-MS (Method 1) m/z 489.3 $(M+H)^+$, 486.8 $(M-H)^-$ at 1.95 min.

Step 3: methyl 4-(methylsulfonyl)-3-(N-(2-(piperidin-1-yl)-5-(trifluoromethyl)phenyl)sulfamoyl)benzoate and methyl 4-(methylsulfinyl)-3-(N-(2-(piperidin-1-yl)-5-(trifluoromethyl)phenyl)sulfamoyl)benzoate: 3-Chloroperoxybenzoic acid (0.044 g, 0.194 mmol, 77% w/w) was added to the product from step 2 above (0.095 g, 0.194 mmol) in DCM (4 ml) and stirred at RT for 72 h. The solvent was removed in vacuo and the crude product was purified by chromatography on silica gel (12 g cartridge, 0-100% EtOAc/isohexane) to afford methyl 4-(methylsulfonyl)-3-(N-(2-(piperidin-1-yl)-5-(trifluoromethyl)phenyl)sulfamoyl)benzoate (0.060 g, 0.112 mmol, 57.5% yield, 97% purity) as an off white solid. UPLC-MS (Method 1) m/z 521.3 $(M+H)^+$, 518.9 $(M-H)^-$ at 1.28 min. Methyl 4-(methylsulfinyl)-3-(N-(2-(piperidin-1-yl)-5-(trifluoromethyl)phenyl)sulfamoyl)benzoate (0.032 g, 0.058 mmol, 30.0% yield, 92% purity) was also isolated as an off white solid. UPLC-MS (Method 1) m/z 505.3 $(M+H)^+$, 503.1 $(M-H)^-$ at 1.69 min.

Step 4: 4-(methylsulfonyl)-3-(N-(2-(piperidin-1-yl)-5-(trifluoromethyl)phenyl)sulfamoyl)benzoic acid: 1 M LiOH (aq) (0.692 ml, 0.692 mmol) was added to a solution of methyl 4-(methylsulfonyl)-3-(N-(2-(piperidin-1-yl)-5-(trifluoromethyl)phenyl)sulfamoyl)benzoate from step 3 above (0.06 g, 0.115 mmol) in THF (3 ml) and MeOH (0.7 ml) and the solution was stirred at RT overnight. The solvent was removed in vacuo and the residue dissolved in water (5 ml) and washed with TBME (3×5 ml). The aqueous phase was acidified with conc. HCl and extracted with TBME (3×10 ml). The organic phases were combined and dried by passage through a phase separator and the solvent was removed in vacuo. The crude product was purified by chromatography on silica gel (4 g cartridge, 0-10% MeOH/DCM) to afford the title compound (0.049 g, 0.096 mmol, 83% yield, 99% purity) as an off white solid. UPLC-MS (Method 1) m/z 507.3 $(M+H)^+$, 504.8 $(M-H)^-$ at 1.13 min. $^1$H NMR (500 MHz, DMSO-$d_6$) δ15.98 (s, 1H), 13.59 (s, 1H), 8.43 (d, J=1.7 Hz, 1H), 8.30 (dd, J=8.1, 1.7 Hz, 1H), 8.24 (d, J=8.1 Hz, 1H), 7.87 (d, J=8.7 Hz, 1H), 7.76 (d, J=2.0 Hz, 1H), 7.23 (dd, J=8.9, 2.1 Hz, 1H), 4.37-4.25 (m, 2H), 3.92 (d, J=11.8 Hz, 1H), 3.72 (d, J=11.8 Hz, 1H), 2.85 (s, 3H), 2.28-2.15 (m, 2H), 1.87-1.72 (m, 3H), 1.59-1.44 (m, 1H).

Example 227: 3-(N-(2-(piperidin-1-yl)-5-(trifluoromethyl)phenyl)sulfamoyl)-4-(2,2,2-trifluoroethoxy)benzoic acid

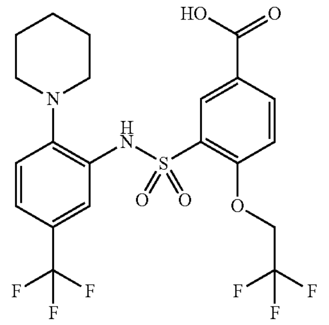 [SMILES: O=C(O)c1ccc(OCC(F)(F)F)c(S(=O)(=O)Nc2cc(C(F)(F)F)ccc2N2CCCCC2)c1]

Step 1: 3-(chlorosulfonyl)-4-(2,2,2-trifluoroethoxy)benzoic acid: 4-(2,2,2-trifluoroethoxy)benzoic acid (1 g, 4.54 mmol) in chlorosulfonic acid (5 ml, 74.7 mmol) was heated at 80° C. for 2 h. The mixture was cooled and carefully added to stirred ice-water (100 ml). The solid precipitated out was collected under filtration, washed with water (100 ml) and dried in vacuo to give the title compound (1.20 g, 3.58 mmol, 79% yield, 95% purity) as a cream solid. $^1$H NMR (500 MHz, DMSO-$d_6$) δ 8.34 (d, J=2.3 Hz, 1H), 7.89 (dd, J=8.5, 2.4 Hz, 1H), 7.16 (d, J=8.5 Hz, 1H), 4.82 (q, J=8.9 Hz, 2H). One exchangeable proton not observed.

Step 2: 3-(N-(2-(piperidin-1-yl)-5-(trifluoromethyl)phenyl)sulfamoyl)-4-(2,2,2-trifluoroethoxy)benzoic acid (2393-12): A solution of 2-(piperidin-1-yl)-5-(trifluoromethyl)aniline (0.100 g, 0.409 mmol) in DCM (5 ml) and pyridine (0.199 ml, 2.46 mmol) were added to a solution of the product from step 1 above (0.130 g, 0.409 mmol) in DCM (10 ml) and the solution was stirred at RT for 24 h. The solvent was removed in vacuo and the crude product was purified by chromatography on silica gel (40 g cartridge, 0-100% EtOAc/isohexane) to afford the title compound (42.8 mg, 0.077 mmol, 18.9% yield, 95% purity) as a cream waxy solid. UPLC-MS (Method 1) m/z 527.4 $(M+H)^+$, 525.1 $(M-H)^-$ at 1.82 min. $^1$H NMR (500 MHz, DMSO-$d_6$) δ 13.36 (br s, 1H), 8.50 (br s, 1H), 8.44 (d, J=2.2 Hz, 1H), 8.22 (dd, J=8.7, 2.2 Hz, 1H), 7.47 (d, J=8.8 Hz, 1H), 7.40-7.35 (m, 2H), 7.31 (d, J=8.6 Hz, 1H), 5.02 (q, J=8.6 Hz, 2H), 2.77 (t, J=5.2 Hz, 4H), 1.61 (p, J=5.7 Hz, 4H), 1.52 (p, J=6.2 Hz, 2H).

Example 228: 4-(2-hydroxypropan-2-yl)-3-(N-(2-(piperidin-1-yl)-5-(trifluoromethyl)phenyl)sulfamoyl)benzoic acid

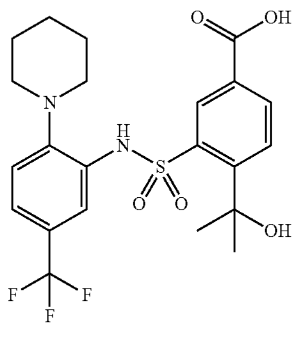 [SMILES: CC(C)(O)c1ccc(C(=O)O)cc1S(=O)(=O)Nc1cc(C(F)(F)F)ccc1N1CCCCC1]

Step 1: methyl 4-bromo-2-(N-(2-(piperidin-1-yl)-5-(trifluoromethyl)phenyl)sulfamoyl)benzoate: A solution of 2-(piperidin-1-yl)-5-(trifluoromethyl)aniline (0.200 g, 0.819 mmol) in DCM (1 ml) and pyridine (0.397 ml, 4.91 mmol) were added to a solution of methyl 4-bromo-2-(chlorosulfonyl)benzoate (0.257 g, 0.819 mmol) in DCM (10 ml) and the solution was stirred at RT for 24 h. The solvent was removed in vacuo and the crude product was purified by chromatography on silica gel (40 g cartridge, 0-50% EtOAc/isohexane) to afford the title compound (0.33 g, 0.601 mmol, 73.4% yield, 95% purity) as a cream waxy solid. UPLC-MS (Method 1) m/z 521.2 $(M+H)^+$, 518.7 $(M-H)^-$ at 2.07 min. $^1$H NMR (500 MHz, DMSO-$d_6$) δ 9.43 (s, 1H), 8.06 (d, J=2.0 Hz, 1H), 8.01 (dd, J=8.2, 2.0 Hz, 1H), 7.74 (d, J=8.2 Hz, 1H), 7.54 (d, J=2.1 Hz, 1H), 7.50-7.45 (m, 1H), 7.33 (d, J=8.4 Hz, 1H), 3.81 (s, 3H), 2.69 (t, J=5.2 Hz, 4H), 1.56 (p, J=5.5 Hz, 4H), 1.51-1.42 (m, 2H).

Step 2: 5-bromo-2-(2-hydroxypropan-2-yl)-N-(2-(piperidin-1-yl)-5-(trifluoromethyl)phenyl)benzenesulfonamide: A solution of the product from step 1 above (0.150 g, 0.288 mmol) in dry THF (10 ml) was treated with 3.0 M methylmagnesium bromide in $Et_2O$ (0.384 ml, 1.15 mmol) and the solution was stirred at RT for 16 h. The solvent was removed in vacuo and the crude product was purified by chromatography on silica gel (40 g cartridge, 0-50% EtOAc/isohexane) to afford the title compound (91 mg, 0.150 mmol, 52.2% yield, 87% purity) as a colourless waxy solid. UPLC-MS (Method 1) m/z 521.2 $(M+H)^+$, 519.1 $(M-H)^-$ at 2.11 min. $^1$H NMR (500 MHz, DMSO-$d_6$) δ 9.76 (br s, 1H), 8.15 (d, J=2.2 Hz, 1H), 7.79 (dd, J=8.5, 2.2 Hz, 1H), 7.74 (d, J=2.0 Hz, 1H), 7.53 (d, J=8.6 Hz, 1H), 7.38-7.23 (m, 2H), 6.15 (s, 1H), 2.71 (t, J=5.3 Hz, 4H), 1.67 (p, J=5.3 Hz, 4H), 1.58 (s, 6H), 1.54-1.49 (m, 2H).

Step 3: methyl 4-(2-hydroxypropan-2-yl)-3-(N-(2-(piperidin-1-yl)-5-(trifluoromethyl)phenyl)sulfamoyl)benzoate: A solution of the product from step 2 above (0.091 g, 0.175 mmol), $Et_3N$ (0.049 ml, 0.349 mmol) and PdCl2 (dppf) ·DCM (0.029 g, 0.035 mmol) in MeOH (10 ml) was stirred under a CO atmosphere (4 bar) overnight at 100° C. After 24 h, the reaction was cooled, filtered through Celite® and concentrated in vacuo. The crude product was purified by chromatography on silica gel (24 g cartridge, 0-50% EtOAc/isohexane) to afford the title compound (0.090 g, 0.171 mmol, 98% yield, 95% purity) as a blue oil. UPLC-MS (Method 1) m/z 501.4 $(M+H)^+$, 499.3 $(M-H)^-$ at 1.97 min.

Step 4: 4-(2-hydroxypropan-2-yl)-3-(N-(2-(piperidin-1-yl)-5-(trifluoromethyl)phenyl)sulfamoyl)benzoic acid: 1 M LiOH (aq) (0.013 g, 0.539 mmol) was added to a solution of the product from step 3 above (0.090 g, 0.180 mmol) in THF (5 ml) and the solution was stirred at RT overnight. The reaction mixture was concentrated in vacuo and the resultant aqueous phase was adjusted to pH 6 with 1M HCl. The precipitate was filtered and washed with water (10 ml) and isohexane (20 ml) to give the title compound (54.3 mg, 0.106 mmol, 59.0% yield, 95% purity) as a light grey solid. UPLC-MS (Method 1) m/z 487.3 $(M+H)^+$, 485.3 $(M-H)^-$ at 1.82 min. $^1$H NMR (500 MHz, DMSO-$d_6$) δ 13.38 (br s, 1H), 9.74 (br s, 1H), 8.66 (d, J=1.9 Hz, 1H), 8.06 (dd, J=8.3, 1.9 Hz, 1H), 7.78 (s, 1H), 7.71 (d, J=8.3 Hz, 1H), 7.33-7.28 (m, 2H), 6.20 (br s, 1H), 2.70 (t, J=5.3 Hz, 4H), 1.67 (p, J=5.2 Hz, 4H), 1.62 (s, 6H), 1.55-1.48 (m, 2H).

Example 229:4-(hydroxymethyl)-3-(N-(2-(piperidin-1-yl)-5-(trifluoromethyl)phenyl) sulfamoyl)benzoic acid

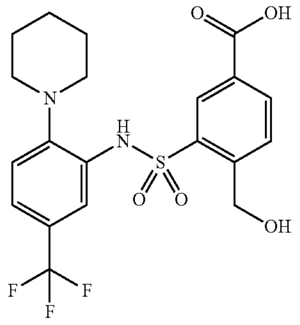 [SMILES: O=C(O)c1ccc(CO)c(S(=O)(=O)Nc2cc(C(F)(F)F)ccc2N2CCCCC2)c1]

Step 1: 5-bromo-2-(hydroxymethyl)-N-(2-(piperidin-1-yl)-5-(trifluoromethyl)phenyl)benzenesulfonamide: A solution of the product from Example 228 step 1 (0.285 g, 0.547 mmol) in THF (5 ml) was cooled to 0° C., then treated with 2.0 M $LiBH_4$ in THF (0.273 ml, 0.547 mmol). The mixture was stirred at RT for 16 h and then the mixture was diluted with water (100 ml), extracted with EtOAc (100 ml), dried ($MgSO_4$) and concentrated in vacuo. The crude product was purified by chromatography on silica gel (24 g cartridge, 0-50% EtOAc/isohexane) to afford the title compound (0.212 g, 0.408 mmol, 74.7% yield, 95% purity) as a colourless solid. UPLC-MS (Method 1) m/z 493.2 $(M+H)^+$, 491.1 $(M-H)^-$ at 1.86 min. 1H NMR (500 MHz, DMSO-$d_6$) δ 9.53 (br s, 1H), 7.87 (dd, J=8.3, 2.1 Hz, 1H), 7.83 (d, J=2.1 Hz, 1H), 7.71 (d, J=8.3 Hz, 1H), 7.45 (dd, J=8.5, 2.2 Hz, 1H), 7.38 (d, J=2.2 Hz, 1H), 7.26 (d, J=8.4 Hz, 1H), 5.67 (br s, 1H), 4.82 (s, 2H), 2.71 (t, J=5.3 Hz, 4H), 1.58-1.54 (m, 4H), 1.48-1.45 (m, 2H).

Step 2: methyl 4-(hydroxymethyl)-3-(N-(2-(piperidin-1-yl)-5-(trifluoromethyl)phenyl)sulfamoyl)benzoate: A solution of the product from step 1 above (0.210 g, 0.426 mmol), $Et_3N$ (0.119 ml, 0.851 mmol) and $PdCl_2$ (dppf)· DCM (0.070 g, 0.085 mmol) in MeOH (10 ml) was stirred under a CO atmosphere (4 bar) overnight at 100° C. After 24 h, the reaction was cooled, filtered through Celite® and concentrated in vacuo. The crude product was purified by chromatography on silica gel (24 g cartridge, 0-50% EtOAc/isohexane) to afford the title compound (0.180 g, 0.376 mmol, 88% yield, 99% purity) as a cream waxy solid. UPLC-MS (Method 1) m/z 473.3 $(M+H)^+$, 471.3 $(M-H)^-$ at 1.73 min.

Step 3: 4-(hydroxymethyl)-3-(N-(2-(piperidin-1-yl)-5-(trifluoromethyl)phenyl)sulfamoyl)benzoic acid: 1 M LiOH (aq) (0.027 g, 1.14 mmol) was added to a solution of the product from step 2 above (0.180 g, 0.381 mmol) in THF (5 ml) and the solution was stirred at RT overnight. The reaction mixture was concentrated in vacuo and the resultant aqueous phase was extracted with EtOAc (50 ml). The aqueous phase was then adjusted to pH 6 with 1 M HCl(aq) to form a precipitate which was filtered and washed with water (10 ml) and isohexane (20 ml) to afford the title compound (134 mg, 0.277 mmol, 72.8% yield, 95% purity) as a white solid. UPLC-MS (Method 1) m/z 459.3 $(M+H)^+$, 457.3 $(M-H)^-$ at 1.58 min. $^1$H NMR (500 MHz, DMSO-$d_6$) δ 13.33 (br s, 1H), 9.49 (br s, 1H), 8.30 (d, J=1.8 Hz, 1H), 8.17 (dd, J=8.0, 1.8 Hz, 1H), 7.90 (d, J=8.1 Hz, 1H), 7.42 (dd, J=8.4, 2.2 Hz, 1H), 7.37 (d, J=2.2 Hz, 1H), 7.24 (d, J=8.4 Hz, 1H), 5.74-5.30 (m, 1H), 4.94 (s, 2H), 2.69 (t, J=5.2 Hz, 4H), 1.55 (p, J=5.4 Hz, 4H), 1.46 (p, J=6.0 Hz, 2H).

Example 230:4-ethyl-3-(N-(2-(piperidin-1-yl)-4-(trifluoromethyl)phenyl)sulfamoyl)benzoic acid

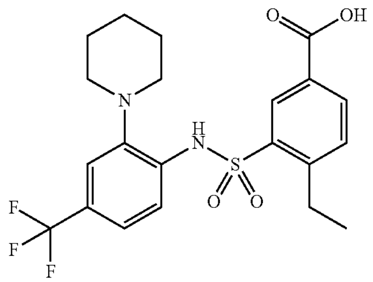

Step 1: 1-(2-nitro-5-(trifluoromethyl)phenyl)piperidine: 2-fluoro-1-nitro-4-(trifluoromethyl)benzene (1.1 g, 5.26 mmol) was dissolved in DMSO (10 ml) and treated with $K_2CO_3$ (0.872 g, 6.31 mmol) followed by piperidine (0.779 ml, 7.89 mmol) and the mixture was heated at 100° C. for 2 h. The reaction mixture was added to ice water (100 ml) and extracted with EtOAc (100 ml). The organic phase was washed with water (100 ml), dried over $MgSO_4$, filtered and concentrated in vacuo. The crude product was purified by chromatography on silica gel (40 g cartridge, 0-50% EtOAc/isohexane) to afford the title compound (1.32 g, 4.81 mmol, 91% yield, 95% purity) as a red oil. UPLC-MS (Method 1) m/z 275.2 $(M+H)^+$ at 1.82 min. $^1$H NMR (500 MHz, DMSO-$d_6$) δ 7.97 (d, J=8.4 Hz, 1H), 7.53 (d, J=1.8 Hz, 1H), 7.36 (dd, J=8.5, 1.8 Hz, 1H), 3.05-3.03 (m, 4H), 1.62-1.52 (m, 6H).

Step 2: 2-(piperidin-1-yl)-4-(trifluoromethyl)aniline: The product from step 1 above (1.32 g, 4.81 mmol) was added to a suspension of 10% Pd/C (0.051 g, 0.481 mmol) in EtOH (40 ml, 685 mmol) and the mixture was stirred at RT under $H_2$ (3 bar pressure) for 2 h. The reaction mixture was filtered through Celite® and the filtrate was concentrated in vacuo to afford the title compound (1.15 g, 4.61 mmol, 96% yield, 99% purity) as a light brown oil. UPLC-MS (Method 1) m/z 245.3 $(M+H)^+$ at 1.69 min.

Step 3: methyl 4-ethyl-3-(N-(2-(piperidin-1-yl)-4-(trifluoromethyl)phenyl)sulfamoyl)benzoate: A solution of the product from step 2 above (0.100 g, 0.409 mmol) in DCM (1 ml) and pyridine (0.199 ml, 2.46 mmol) were added to a solution of the product from Example 203 step 2 (0.108 g, 0.409 mmol) in DCM (10 ml) and the resultant mixture stirred at RT for 24 h. The solvent was removed in vacuo and the crude product was purified by chromatography on silica gel (24 g cartridge, 0-100% EtOAc/isohexane) to afford the title compound (86 mg, 0.174 mmol, 42.4% yield, 96% purity) as a pale yellow oil, which cystallised upon standing. UPLC-MS (Method 2) m/z 471.4 $(M+H)^+$, 469.2 $(M-H)^-$ at 2.02 min.

Step 4: 4-ethyl-3-(N-(2-(piperidin-1-yl)-4-(trifluoromethyl)phenyl)sulfamoyl)benzoic acid: 1 M LiOH (aq) (0.555 ml, 0.555 mmol) was added to a solution of the product from step 3 above (0.087 g, 0.185 mmol) in THF (5 ml, 61.0 mmol) and the solution was stirred at RT overnight. The reaction mixture was concentrated in vacuo and the resultant aqueous solution acidified to pH 6 using 1 M HCl(aq). The precipitate was filtered and washed with water (10 ml) and isohexane (20 ml) to afford the title compound (17.1 mg, 0.036 mmol, 19.3% yield, 95% purity) as a white solid. UPLC-MS (Method 1) m/z 457.4 $(M+H)^+$, 455.2 $(M-H)^-$ at 1.91 min. $^1H$ NMR (500 MHz, DMSO-$d_6$) δ 13.34 (br s, 1H), 9.38 (br s, 1H), 8.40 (d, J=1.8 Hz, 1H), 8.10 (dd, J=8.0, 1.8 Hz, 1H), 7.63 (d, J=8.0 Hz, 1H), 7.43 (s, 1H), 7.40 (d, J=8.6 Hz, 1H), 7.32 (d, J=8.6 Hz, 1H), 3.07 (q, J=7.4 Hz, 2H), 2.70 (t, J=5.2 Hz, 4H), 1.62 (p, J=5.7 Hz, 4H), 1.49 (p, J=5.6 Hz, 2H), 1.23 (t, J=7.4 Hz, 3H).

Example 231: 4-methoxy-3-(N-(2-(piperidin-1-yl)-4-(trifluoromethyl)phenyl) sulfamoyl)benzoic acid

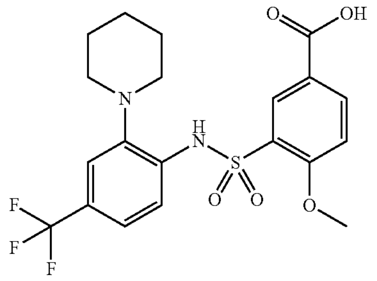

Step 1: methyl 4-methoxy-3-(N-(2-(piperidin-1-yl)-4-(trifluoromethyl)phenyl)sulfamoyl)benzoate: A solution of the product from Example 230 step 2 above (0.100 g, 0.409 mmol) in DCM (1 ml) and pyridine (0.199 ml, 2.46 mmol) was added to a solution of methyl 3-(chlorosulfonyl)-4-methoxybenzoate (0.108 g, 0.409 mmol) in DCM (10 ml) and the resultant solution was stirred at RT for 24 h. The solvent was removed in vacuo and the crude product was purified by chromatography on silica gel (24 g cartridge, 0-100% EtOAc/isohexane) to afford the title compound (0.150 g, 0.317 mmol, 78% yield, 100% purity) as a pale yellow slowly cystallising oil. UPLC-MS (Method 2) m/z 473.4 $(M+H)^+$, 471.2 $(M-H)^-$ at 1.85 min.

Step 2: 4-methoxy-3-(N-(2-(piperidin-1-yl)-4-(trifluoromethyl)phenyl)sulfamoyl)benzoic acid: 1 M LiOH (aq) (0.952 ml, 0.952 mmol) was added to a solution of the product from step 1 above (0.150 g, 0.317 mmol) in THF (5 ml) and the resultant solution was stirred at RT overnight. The reaction mixture was concentrated in vacuo and the resultant aqueous solution acidified to pH 6 using 1 M HCl(aq). The precipitate was filtered and washed with water (10 ml) and isohexane (20 ml) to afford the title compound (41.4 mg, 0.086 mmol, 27.0% yield, 95% purity) as a white solid. UPLC-MS (Method 1) m/z 459.4 $(M+H)^+$, 457.0 $(M-H)^-$ at 1.73 min. $^1H$ NMR (500 MHz, DMSO-$d_6$) δ 13.20 (br s, 1H), 8.81 (br s, 1H), 8.43 (d, J=2.2 Hz, 1H), 8.17 (dd, J=8.7, 2.2 Hz, 1H), 7.52 (d, J=1.9 Hz, 1H), 7.47-7.39 (m, 2H), 7.33 (d, J=8.8 Hz, 1H), 3.97 (s, 3H), 2.75 (t, J=5.3 Hz, 4H), 1.71 (p, J=5.2 Hz, 4H), 1.57 (p, J=5.4 Hz, 2H).

Example 232:4-(methylthio)-3-(N-(2-(piperidin-1-yl)-5-(trifluoromethyl)phenyl) sulfamoyl)benzoic acid

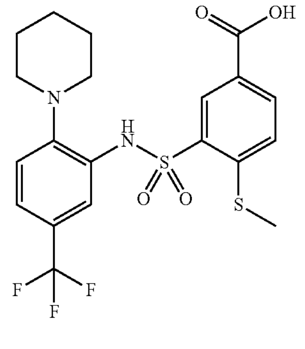

The aqueous phase from the reaction in Example 225 step 2 was acidified with conc. HCl and extracted with DCM (3×15 ml). The organic phases were combined and extracted with 0.5 M NaOH solution (3×20 ml). The aqueous extracts were combined, acidified with conc. HCl and extracted with TBME (3×30 ml). All of the organic phases were then combined, dried by passage through a phase separator and the solvent was removed in vacuo to afford the title compound (0.075 g, 0.156 mmol, 39.4% yield, 99% purity) as an off-white solid. UPLC-MS (Method 1) m/z 475.3 $(M+H)^+$, 472.9 $(M-H)^-$ at 1.79 min. $^1H$ NMR (500 MHz, DMSO-$d_6$) δ 13.31 (s, 1H), 9.26 (s, 1H), 8.39 (d, J=1.9 Hz, 1H), 8.04 (dd, J=8.3, 1.9 Hz, 1H), 7.60 (d, J=8.5 Hz, 1H), 7.46 (d, J=2.0 Hz, 1H), 7.39-7.32 (m, 2H), 2.72 (t, J=5.2 Hz, 4H), 2.57 (s, 3H), 1.64 (p, J=5.5 Hz, 4H), 1.54-1.51 (m, 2H).

Example 233:3-(N-(5-cyano-2-(3,3-difluoropiperidin-1-yl)phenyl)sulfamoyl)-4-methoxybenzoic acid

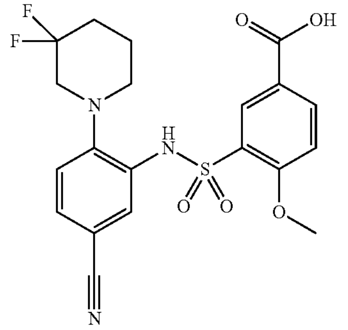 [SMILES: COc1ccc(C(=O)O)cc1S(=O)(=O)Nc1cc(C#N)ccc1N1CCCC(F)(F)C1]

Step 1: 4-(3,3-difluoropiperidin-1-yl)-3-nitrobenzonitrile: A mixture of 4-fluoro-3-nitrobenzonitrile (500 mg, 3.01 mmol), 3,3-difluoropiperidine hydrochloride (569 mg, 3.61 mmol) and $Et_3N$ (1.6 ml, 11.5 mmol) in DMF (5 ml) was stirred at 90° C. over the weekend. The mixture was diluted with water (20 ml) and extracted with EtOAc (3×35 ml). The organic extracts were combined, washed with brine (2×30 ml), dried by passage through a phase separator and the solvent was removed in vacuo. The residue was loaded onto silica and purified by chromatography on silica gel (24 g cartridge, 0-100% DCM/isohexane) to afford the title compound (635 mg, 2.35 mmol, 78% yield, 99% purity) as a bright yellow solid. UPLC-MS (Method 2) m/z no ionisation at 1.34 min. $^1$H NMR (500 MHz, DMSO-$d_6$) δ 8.36 (d, J=2.1 Hz, 1H), 7.93 (dd, J=8.8, 2.1 Hz, 1H), 7.42 (d, J=8.8 Hz, 1H), 3.55 (t, J=11.7 Hz, 2H), 3.18 (t, J=5.4 Hz, 2H), 2.15-2.03 (m, 2H), 1.81-1.72 (m, 2H).

Step 2: 3-amino-4-(3,3-difluoropiperidin-1-yl)benzonitrile: A mixture of the product from step 1 above (635 mg, 2.35 mmol), iron powder (2.6 g, 46.6 mmol), ammonium chloride (151 mg, 2.82 mmol), IPA (18 ml) and water (9 ml) was stirred at 90° C. overnight. The mixture was filtered through Celite®, rinsing with MeOH and the filtrate was concentrated in vacuo. The residue was diluted with DCM (20 ml), dried by passage through a phase separator and concentrated onto silica. The crude product was purified by chromatography on silica gel (24 g cartridge, 0-100% DCM/isohexane) to afford the title compound (334 mg, 1.41 mmol, 60% yield) as a light orange solid. UPLC-MS (Method 2) m/z no ionisation at 1.34 min. $^1$H NMR (500 MHz, DMSO-$d_6$) δ 7.05-6.96 (m, 3H), 5.13-5.01 (m, 2H), 3.14 (t, J=11.3 Hz, 2H), 2.88 (t, J=5.4 Hz, 2H), 2.09-1.97 (m, 2H), 1.88-1.81 (m, 2H).

Step 3: methyl 3-(N-(5-cyano-2-(3,3-difluoropiperidin-1-yl)phenyl)sulfamoyl)-4-methoxybenzoate: A mixture of the product from step 2 above (80 mg, 0.337 mmol), methyl 3-(chlorosulfonyl)-4-methoxybenzoate (100 mg, 0.378 mmol), pyridine (0.1 ml, 1.24 mmol) and DCM (2.2 ml) was stirred at RT for 4 h and then at 35° C. for 5 days. The mixture was concentrated onto silica and purified by chromatography on silica gel (4 g cartridge, 0-100% EtOAc/isohexane) to afford the title compound (105 mg, 0.219 mmol, 64.9% yield, 97% purity) as a white solid. UPLC-MS (Method 1) m/z 466.2 $(M+H)^+$, 464.1 $(M-H)^-$ at 1.53 min. $^1$H NMR (500 MHz, DMSO-$d_6$) δ 8.85 (s, 1H), 8.32 (d, J=2.2 Hz, 1H), 8.21 (dd, J=8.8, 2.2 Hz, 1H), 7.56-7.51 (m, 1H), 7.39 (d, J=8.8 Hz, 1H), 7.34-7.28 (m, 2H), 3.93 (s, 3H), 3.86 (s, 3H), 3.26 (t, J=11.2 Hz, 2H), 3.04-3.01 (m, 2H), 2.09-1.99 (m, 2H), 1.84-1.77 (m, 2H).

Step 4: 3-(N-(5-cyano-2-(3,3-difluoropiperidin-1-yl)phenyl)sulfamoyl)-4-methoxybenzoic acid: A mixture of the product from step 3 above (105 mg, 0.219 mmol) and LiOH (21.0 mg, 0.875 mmol) in THF/water/MeOH (4:1:1, 2.7 ml) was stirred at 40° C. overnight. The mixture was diluted with water (5 ml) and acidified to ~pH 4 using 1 M HCl(aq). The mixture was extracted with EtOAc (3×20 ml) and the combined organic extracts were washed with brine (10 ml) dried by passage through a phase separator and the solvent was removed in vacuo. The residue was loaded onto silica and purified by chromatography on silica gel (4 g cartridge, 0-100% EtOAc/isohexane) to afford the title compound (36.1 mg, 0.078 mmol, 36% yield, 98% purity) as a white solid after trituration with TBME. UPLC-MS (Method 1) m/z 452.2 $(M+H)^+$, 450.1 $(M-H)^-$ at 1.37 min. $^1$H NMR (500 MHz, DMSO-$d_6$) δ 13.19 (s, 1H), 8.79 (s, 1H), 8.32 (d, J=2.2 Hz, 1H), 8.18 (dd, J=8.7, 2.2 Hz, 1H), 7.52 (dd, J=8.3, 2.0 Hz, 1H), 7.38-7.28 (m, 3H), 3.92 (s, 3H), 3.25 (t, J=11.3 Hz, 2H), 3.02 (t, J=5.5 Hz, 2H), 2.11-2.00 (m, 2H), 1.86-1.77 (m, 2H).

Example 234: 3-(N-(5-cyano-2-(3,3-difluoropiperidin-1-yl)phenyl)sulfamoyl)-4-ethylbenzoic acid

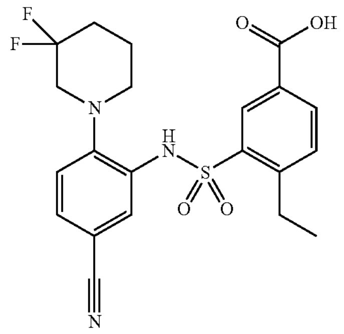 [SMILES: CCc1ccc(C(=O)O)cc1S(=O)(=O)Nc1cc(C#N)ccc1N1CCCC(F)(F)C1]

Step 1: methyl 3-(N-(5-cyano-2-(3,3-difluoropiperidin-1-yl)phenyl)sulfamoyl)-4-ethylbenzoate: A mixture of the product from Example 233 step 2 (80 mg, 0.337 mmol), the product from Example 203 step 2 (99 mg, 0.378 mmol), pyridine (0.1 ml, 1.24 mmol) and DCM (2.2 ml) was stirred at RT for 4 h and then at 35° C. for 5 days. The mixture was concentrated onto silica and purified by chromatography on silica gel (4 g cartridge, 0-100% EtOAc/isohexane) to afford the title compound (59 mg, 0.120 mmol, 36% yield, 94% purity) as a light brown solid. UPLC-MS (Method 1) m/z 464.2 $(M+H)^+$, 462.2 $(M-H)^-$ at 1.68 min. $^1$H NMR (500 MHz, DMSO-$d_6$) δ 9.59 (s, 1H), 8.29 (d, J=1.9 Hz, 1H), 8.14 (dd, J=8.0, 1.9 Hz, 1H), 7.66 (d, J=8.0 Hz, 1H), 7.59 (dd, J=8.5, 2.1 Hz, 1H), 7.23 (d, J=8.5 Hz, 1H), 7.13 (d, J=2.1 Hz, 1H), 3.86 (s, 3H), 3.28-3.24 (m, 2H), 3.05-2.95 (m, 4H), 2.04-1.95 (m, 2H), 1.77-1.69 (m, 2H), 1.20 (t, J=7.4 Hz, 3H).

Step 2: 3-(N-(5-cyano-2-(3,3-difluoropiperidin-1-yl)phenyl)sulfamoyl)-4-ethylbenzoic acid: A mixture of the product from step 1 above (59 mg, 0.120 mmol) and LiOH (21.0 mg, 0.875 mmol) in THF/water/MeOH (4:1:1, 2.7 ml) was stirred at 40° C. overnight. The mixture was diluted with water (5 ml) and acidified to ~pH 4 using 1 M HCl(aq). The mixture was extracted with EtOAc (3×20 ml) and the combined organic extracts were washed with brine (10 ml), dried by passage through a phase separator and the solvent was removed in vacuo. The residue was loaded onto silica and purified by chromatography on silica gel (4 g cartridge, 0-100% EtOAc/isohexane) to afford the title compound (12.4 mg, 0.028 mmol, 22% yield) as a white solid after trituration with TBME. UPLC-MS (Method 1) m/z 450.2 $(M+H)^+$, 448.1 $(M-H)^-$ at 1.53 min. $^1$H NMR (500 MHz, DMSO-$d_6$) δ 13.31 (s, 1H), 9.53 (s, 1H), 8.30 (s, 1H), 8.11 (d, J=8.6 Hz, 1H), 7.65-7.54 (m, 2H), 7.29-7.19 (m, 1H), 7.13 (s, 1H), 3.29-3.23 (m, 2H), 3.05-2.96 (m, 4H), 2.05-1.95 (m, 2H), 1.78-1.72 (m, 2H), 1.20 (t, J=7.4 Hz, 3H).

Example 235: I-4-methoxy-3-(N-(2-(2-methylpiperidin-1-yl)-5-(trifluoromethyl)phenyl) sulfamoyl)benzoic acid

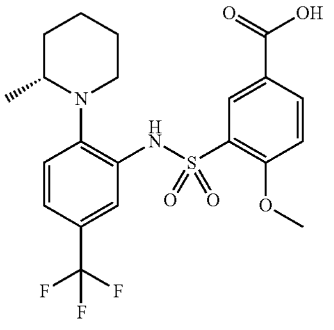 [SMILES: COc1ccc(C(=O)O)cc1S(=O)(=O)Nc1cc(C(F)(F)F)ccc1N1CCCC[C@H]1C]

Step 1: I-2-methyl-1-(2-nitro-4-(trifluoromethyl)phenyl) piperidine: A mixture of 1-fluoro-2-nitro-4-(trifluoromethyl) benzene (220 μl, 1.57 mmol), I-2-methylpiperidine (220 μl, 1.87 mmol) and $Et_3N$ (0.6 ml, 4.30 mmol) in DCM (8 ml) was stirred at RT for 2 h and then at 35° C. overnight. The mixture was washed with 1 M HCl(aq) (10 ml), dried by passage through a phase separator and concentrated onto silica. The crude product was purified by chromatography on silica gel (12 g cartridge, 0-100% DCM/isohexane) to afford the title compound (439 mg, 1.48 mmol, 94% yield, 97% purity) as an orange oil. UPLC-MS (Method 1) m/z 289.2 $(M+H)^+$ at 1.87 min. $^1H$ NMR (500 MHz, DMSO-$d_6$) δ 8.14 (d, J=2.3 Hz, 1H), 7.85 (dd, J=8.8, 2.3 Hz, 1H), 7.54 (d, J=8.8 Hz, 1H), 3.58-3.51 (m, 1H), 3.16 (ddd, J=12.5, 8.5, 4.0 Hz, 1H), 2.81 (dt, J=12.5, 4.6 Hz, 1H), 1.80-1.63 (m, 2H), 1.62-1.47 (m, 3H), 1.45-1.37 (m, 1H), 0.99 (d, J=6.5 Hz, 3H).

Step 2: I-2-(2-methylpiperidin-1-yl)-5-(trifluoromethyl) aniline: A solution of the product from step 1 above (438 mg, 1.47 mmol) in EtOH (35 ml) was hydrogenated in a ThalesNano H-cube® flow reactor (10% Pd/C, 30×4 mm cartridge, full hydrogen mode, RT, 1 ml/min flow rate, 1 pass). The resultant solution was concentrated in vacuo to give the title compound (361 mg, 1.34 mmol, 91% yield, 96% purity) as pale yellow oil. UPLC-MS (Method 2) m/z 259.2 $(M+H)^+$ at 1.88 min. $^1H$ NMR (500 MHz, DMSO-$d_6$) δ 7.09 (d, J=8.1 Hz, 1H), 6.95 (d, J=2.2 Hz, 1H), 6.81 (dd, J=8.1, 2.2 Hz, 1H), 5.24 (s, 2H), 3.09-2.96 (m, 1H), 2.91-2.84 (m, 1H), 2.44-2.35 (m, 1H), 1.81-1.69 (m, 2H), 1.66-1.57 (m, 2H), 1.49-1.28 (m, 2H), 0.78 (d, J=6.1 Hz, 3H).

Step 3: I-methyl 4-methoxy-3-(N-(2-(2-methylpiperidin-1-yl)-5-(trifluoromethyl)phenyl)sulfamoyl)benzoate: A mixture of the product from step 3 above (100 mg, 0.372 mmol), methyl 3-(chlorosulfonyl)-4-methoxybenzoate (113 mg, 0.427 mmol) and pyridine (0.1 ml, 1.24 mmol) in DCM (2.5 ml) was stirred at 35° C. over the weekend. The mixture was concentrated onto silica and purified by chromatography on silica gel (4 g cartridge, 0-50% EtOAc/isohexane) to afford the title compound (181 mg, 0.337 mmol, 91% yield, 91% purity) as a pale yellow oil. UPLC-MS (Method 1) m/z 487.3 $(M+H)^+$, 485.2 $(M-H)^-$ at 1.89 min. $^1H$ NMR (500 MHz, DMSO-$d_6$) δ 8.92 (s, 1H), 8.39 (d, J=2.3 Hz, 1H), 8.19 (dd, J=8.8, 2.3 Hz, 1H), 7.65 (d, J=2.1 Hz, 1H), 7.48 (d, J=8.3 Hz, 1H), 7.41-7.34 (m, 2H), 3.96 (s, 3H), 3.85 (s, 3H), 3.01-2.93 (m, 1H), 2.63-2.52 (m, 2H), 1.79-1.74 (m, 2H), 1.69-1.55 (m, 2H), 1.45-1.33 (m, 2H), 0.59 (d, J=6.1 Hz, 3H).

Step 4: I-4-methoxy-3-(N-(2-(2-methylpiperidin-1-yl)-5-(trifluoromethyl)phenyl)sulfamoyl)benzoic acid: A mixture of the product from step 3 above (181 mg, 0.337 mmol) and LiOH (32.3 mg, 1.35 mmol) in THF/MeOH/water (4:1:1, 4.5 ml) was stirred at 40° C. overnight. The mixture was diluted with water (5 ml) and acidified to ~pH 4 using 1 M HCl(aq). The mixture was extracted with EtOAc (3×20 ml) and the combined organic extracts were washed with brine (10 ml), dried by passage through a phase separator and the solvent was removed in vacuo. The residue was loaded onto silica and purified by chromatography on silica gel (4 g cartridge, 0-100% EtOAc/isohexane) to afford the title compound (15.9 mg, 0.033 mmol, 10% yield, 99% purity) as a white solid. UPLC-MS (Method 1) m/z 473.3 $(M+H)^+$, 471.2 $(M-H)^-$ at 1.74 min. $^1H$ NMR (500 MHz, DMSO-$d_6$)· 13.20 (s, 1H), 8.89 (s, 1H), 8.39 (d, J=2.2 Hz, 1H), 8.16 (dd, J=8.7, 2.2 Hz, 1H), 7.64 (d, J=2.1 Hz, 1H), 7.48 (d, J=8.3 Hz, 1H), 7.37 (dd, J=8.3, 2.1 Hz, 1H), 7.34 (d, J=8.7 Hz, 1H), 3.95 (s, 3H), 3.00-2.93 (m, 1H), 2.63-2.57 (m, 1H), 2.55-2.51 (m, 1H), 1.80-1.74 (m, 2H), 1.70-1.56 (m, 2H), 1.48-1.34 (m, 2H), 0.60 (d, J=6.1 Hz, 3H).

Example 236: I-4-ethyl-3-(N-(2-(2-methylpiperidin-1-yl)-5-(trifluoromethyl)phenyl) sulfamoyl)benzoic acid

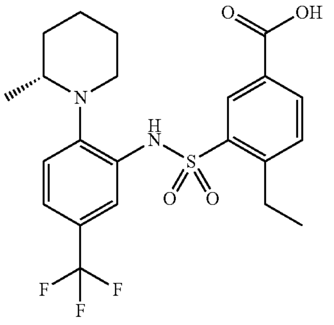 [SMILES: CCc1ccc(C(=O)O)cc1S(=O)(=O)Nc1cc(C(F)(F)F)ccc1N1CCCC[C@H]1C]

Step 1: I-methyl 4-ethyl-3-(N-(2-(2-methylpiperidin-1-yl)-5-(trifluoromethyl)phenyl)sulfamoyl)benzoate: A mixture of the product from Example 235 step 2 (100 mg, 0.372 mmol), the product from Example 203 step 2 (112 mg, 0.427 mmol) and pyridine (0.1 ml, 1.24 mmol) in DCM (2.5 ml) was stirred at 35° C. over the weekend. The mixture was concentrated onto silica and purified by chromatography on silica gel (4 g cartridge, 0-50% EtOAc/isohexane) to afford the title compound (120 mg, 0.238 mmol, 64% yield, 96% purity) as a pale yellow oil. UPLC-MS (Method 1) m/z 485.3 $(M+H)^+$, 483.2 $(M-H)^-$ at 2.06 min. $^1H$ NMR (500 MHz, DMSO-$d_6$) δ 9.42 (s, 1H), 8.38 (d, J=1.9 Hz, 1H), 8.10 (dd, J=8.0, 1.9 Hz, 1H), 7.63 (d, J=8.0 Hz, 1H), 7.57 (br s, 1H), 7.42 (br s, 2H), 3.84 (s, 3H), 3.16-2.99 (m, 2H), 2.98-2.91 (m, 1H), 2.46-2.38 (m, 2H), 1.72-1.65 (m, 2H), 1.63-1.48 (m, 2H), 1.41-1.32 (m, 2H), 1.23 (t, J=7.4 Hz, 3H), 0.57 (d, J=6.1 Hz, 3H).

Step 2: I-4-ethyl-3-(N-(2-(2-methylpiperidin-1-yl)-5-(trifluoromethyl)phenyl)sulfamoyl)benzoic acid: A mixture of the product from step 1 above (120 mg, 0.238 mmol) and LiOH (32.3 mg, 1.35 mmol) in THF/MeOH/water (4:1:1, 4.5 ml) was stirred at 40° C. overnight. The mixture was diluted with water (5 ml) and acidified to ~pH 4 using 1 M HCl(aq). The mixture was extracted with EtOAc (3×20 ml), the combined organic extracts were washed with brine (10 ml), dried by passage through a phase separator and the solvent was removed in vacuo. The residue was loaded onto silica and purified by chromatography on silica gel (4 g cartridge, 0-100% EtOAc/isohexane) to afford the title compound (28.6 mg, 0.060 mmol, 27% yield, 99% purity) as a white solid. UPLC-MS (Method 1) m/z 471.2 $(M+H)^+$, 469.2 $(M-H)^-$ at 1.91 min. 1H NMR (500 MHz, DMSO-$d_6$) δ 13.31 (s, 1H), 9.36 (s, 1H), 8.39 (d, J=1.9 Hz, 1H), 8.08 (dd, J=8.0, 1.9 Hz, 1H), 7.60 (d, J=8.0 Hz, 1H), 7.55 (s, 1H), 7.45-7.38 (m, 2H), 3.15-2.99 (m, 2H), 2.97-2.91 (m, 1H), 2.47-2.38 (m, 2H), 1.73-1.66 (m, 2H), 1.63-1.48 (m, 2H), 1.43-1.33 (m, 2H), 1.22 (t, J=7.4 Hz, 3H), 0.58 (d, J=6.2 Hz, 3H).

Example 237:3-(N-(2-(4-cyanopiperidin-1-yl)-5-(trifluoromethyl)phenyl)sulfamoyl)-4-methoxybenzoic acid

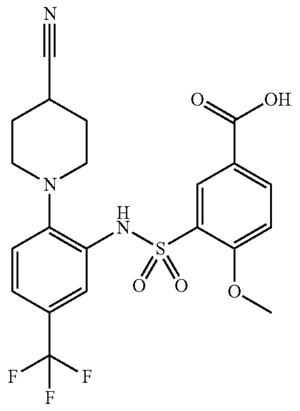 [SMILES: COc1ccc(C(=O)O)cc1S(=O)(=O)Nc1cc(C(F)(F)F)ccc1N1CCC(C#N)CC1]

Step 1: 1-(2-nitro-4-(trifluoromethyl)phenyl)piperidine-4-carbonitrile: A solution of 1-fluoro-2-nitro-4-(trifluoromethyl)benzene (200 μl, 1.43 mmol), piperidine-4-carbonitrile (250 μl, 2.24 mmol) and $Et_3N$ (500 μl, 3.59 mmol) in DCM (6 ml) was allowed to stand at RT for 4 h. The reaction mixture was washed with 1 M HCl(aq) (2×2 ml), dried over $MgSO_4$, filtered and concentrated in vacuo to afford the title compound (470 mg, 1.54 mmol, quant. Yield, 98% purity) as a bright yellow solid. UPLC-MS (Method 1) m/z 299.7 $(M+H)^+$ at 1.54 min. $^1H$ NMR (500 MHz, DMSO-$d_6$) δ 8.17 (d, J=2.2 Hz, 1H), 7.87 (dd, J=8.9, 2.3 Hz, 1H), 7.47 (d, J=8.8 Hz, 1H), 3.29-3.20 (m, 2H), 3.20-3.02 (m, 3H), 2.05-1.94 (m, 2H), 1.91-1.75 (m, 2H).

Step 2: 1-(2-amino-4-(trifluoromethyl)phenyl)piperidine-4-carbonitrile: The product from step 1 above (465 mg, 1.52 mmol) was dissolved in EtOH (40 ml) and hydrogenated in a ThalesNano H-cube® flow reactor (10% Pd/C, 30×4 mm cartridge, full hydrogen mode, RT, 1 ml/min flow rate, 1 pass). The resultant colourless solution was concentrated in vacuo to afford the title compound (407 mg, 1.50 mmol, 98% yield, 99% purity) as an off-white solid. UPLC-MS (Method 1) m/z 270.4 $(M+H)^+$ at 1.48 min.

Step 3: methyl 3-(N-(2-(4-cyanopiperidin-1-yl)-5-(trifluoromethyl)phenyl)sulfamoyl)-4-methoxybenzoate: The product from step 2 above (100 mg, 0.371 mmol) was dissolved in a mixture of DCM (1 ml) and pyridine (0.1 ml, 1.24 mmol) and treated with methyl 3-(chlorosulfonyl)-4-methoxybenzoate (140 mg, 0.529 mmol). The resultant solution was allowed to stand at RT for 18 h. The mixture was concentrated in vacuo and the residue was dissolved in EtOAc (4 ml) and sequentially washed with saturated $NaHCO_3$(aq) (3 ml) and brine (2 ml), dried over $MgSO_4$, filtered and concentrated in vacuo. The crude product was purified by chromatography on silica gel (4 g cartridge, 0-100% EtOAc/isohexane) to afford the title compound (157 mg, 0.309 mmol, 83% yield, 98% purity) as a white solid. UPLC-MS (Method 1) m/z 498.3 $(M+H)^+$, 496.2 $(M-H)^-$ at 1.64 min.

Step 4: 3-(N-(2-(4-cyanopiperidin-1-yl)-5-(trifluoromethyl)phenyl)sulfamoyl)-4-methoxybenzoic acid: The product from step 3 above (50 mg, 0.098 mmol) was dissolved in THF (2 ml) and treated with 1 M LiOH (aq) (400 μl, 0.400 mmol). MeOH was added to give a clear solution and the resultant mixture was stirred at RT for 3 days. The solution was diluted with water (4 ml) and concentrated in vacuo at 22° C. The resultant aqueous solution was acidified using 1 M HCl(aq). The precipitate was collected by filtration, washing with water, and dried in vacuo to afford the title compound (40 mg, 0.079 mmol, 80% yield, 98% purity) as a white powder. UPLC-MS (Method 2) m/z 484.3 $(M+H)^+$, 482.3 $(M-H)^-$ at 0.98 min. $^1H$ NMR (500 MHz, DMSO-$d_6$) δ 13.16 (br s, 1H), 9.06 (s, 1H), 8.36 (d, J=2.2 Hz, 1H), 8.17 (dd, J=8.7, 2.3 Hz, 1H), 7.46 (d, J=2.2 Hz, 1H), 7.39 (dd, J=8.6, 2.2 Hz, 1H), 7.35-7.29 (m, 2H), 3.90 (s, 3H), 3.02 (tt, J=8.4, 4.1 Hz, 1H), 2.94-2.86 (m, 2H), 2.82-2.71 (m, 2H), 2.08-1.95 (m, 2H), 1.95-1.80 (m, 2H).

Example 238:3-(N-(2-(4-cyanopiperidin-1-yl)-5-(trifluoromethyl)phenyl)sulfamoyl)-4-ethylbenzoic acid

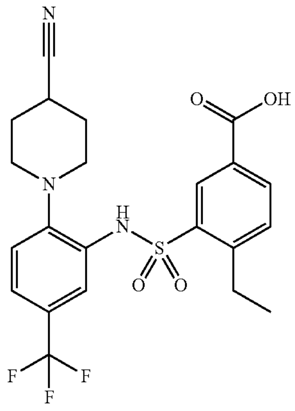 [SMILES: CCc1ccc(C(=O)O)cc1S(=O)(=O)Nc1cc(C(F)(F)F)ccc1N1CCC(C#N)CC1]

Step 1: methyl 3-(N-(2-(4-cyanopiperidin-1-yl)-5-(trifluoromethyl)phenyl)sulfamoyl)-4-ethylbenzoate: The product from Example 237 step 2 (100 mg, 0.371 mmol) was dissolved in a mixture of DCM (1 ml) and pyridine (0.1 ml, 1.24 mmol) and treated with the product from Example 203 step 2 (140 mg, 0.533 mmol). The resultant solution was allowed to stand at RT for 18 h. The mixture was concentrated in vacuo, the residue was dissolved in EtOAc (4 ml) and sequentially washed with saturated $NaHCO_3$(aq) (3 ml) and brine (2 ml), dried over $MgSO_4$, filtered and concentrated in vacuo. The crude product was purified by chromatography on silica gel (4 g cartridge, 0-100% EtOAc/isohexane) to afford the title compound (105 mg, 0.208 mmol, 56% yield, 98% purity) as a white solid. UPLC-MS (Method 1) m/z 496.3 $(M+H)^+$, 494.3 $(M-H)^-$ at 1.78 min.

Step 2: 3-(N-(2-(4-cyanopiperidin-1-yl)-5-(trifluoromethyl)phenyl)sulfamoyl)-4-ethylbenzoic acid: The product from step 1 above (50 mg, 0.099 mmol) was dissolved in THF (2 ml) and treated with 1 M LiOH (aq) (400 µl, 0.400 mmol). MeOH was added to give a clear solution and the resultant mixture stirred at RT for 3 days. The solution was diluted with water (4 ml) and concentrated in vacuo at 22° C. The resultant aqueous solution was acidified using 1 M HCl(aq). The precipitate was collected by filtration, washing with water, and dried in vacuo to afford the title compound (44 mg, 0.090 mmol, 91% yield, 98% purity) as a white powder. UPLC-MS (Method 2) m/z 482.3 $(M+H)^+$, 480.2 $(M-H)^-$ at 1.09 min. $^1$H NMR (500 MHz, DMSO-$d_6$) δ 13.30 (br s, 1H), 9.70 (br s, 1H), 8.35 (d, J=1.8 Hz, 1H), 8.10 (dd, J=8.0, 1.9 Hz, 1H), 7.62 (d, J=8.1 Hz, 1H), 7.44 (dd, J=8.5, 2.2 Hz, 1H), 7.32 (d, J=2.2 Hz, 1H), 7.28 (d, J=8.4 Hz, 1H), 3.04 (q, J=7.4 Hz, 2H), 2.96 (tt, J=8.7, 4.2 Hz, 1H), 2.89-2.78 (m, 2H), 2.74-2.64 (m, 2H), 1.99-1.88 (m, 2H), 1.88-1.76 (m, 2H), 1.20 (t, J=7.4 Hz, 3H).

Example 239: (S)-4-methoxy-3-(N-(2-(2-methylpiperidin-1-yl)-5-(trifluoromethyl)phenyl) sulfamoyl) benzoic acid

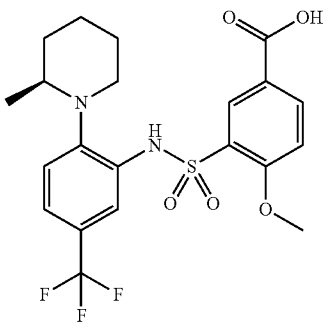 [SMILES: COc1ccc(C(=O)O)cc1S(=O)(=O)Nc1cc(C(F)(F)F)ccc1N1CCCC[C@@H]1C]

Step 1: (S)-2-methyl-1-(2-nitro-4-(trifluoromethyl)phenyl)piperidine: A mixture of 1-fluoro-2-nitro-4-(trifluoromethyl)benzene (250 µl, 1.79 mmol), (S)-2-methylpiperidine (250 µl, 2.13 mmol) and $Et_3N$ (0.6 ml, 4.30 mmol) in DCM (8 ml) was stirred at RT for 2 h and then at 35° C. overnight. The mixture was washed with 1 M HCl(aq) (10 ml), dried by passage through a phase separator and concentrated onto silica. The crude product was purified by chromatography on silica gel (12 g cartridge, 0-50% DCM/isohexane) to afford the title compound (503 mg, 1.68 mmol, 94% yield, 96% purity) as an orange oil. UPLC-MS (Method 1) m/z 289.2 $(M+H)^+$ at 1.87 min. $^1$H NMR (500 MHz, DMSO-$d_6$) δ 8.14 (d, J=2.3 Hz, 1H), 7.85 (dd, J=8.8, 2.3 Hz, 1H), 7.54 (d, J=8.8 Hz, 1H), 3.58-3.50 (m, 1H), 3.16 (ddd, J=12.5, 8.5, 4.0 Hz, 1H), 2.82 (dt, J=12.5, 4.6 Hz, 1H), 1.80-1.63 (m, 2H), 1.63-1.46 (m, 3H), 1.45-1.37 (m, 1H), 0.99 (d, J=6.5 Hz, 3H).

Step 2: (S)-2-(2-methylpiperidin-1-yl)-5-(trifluoromethyl)aniline: A solution of the product from step 1 above (503 mg, 1.68 mmol) in EtOH (35 ml) was hydrogenated in a ThalesNano H-cube® flow reactor (10% Pd/C, 30×4 mm cartridge, full hydrogen mode, RT, 1 ml/min flow rate, 1 pass). The solvent was evaporated to give the title compound (410 mg, 1.38 mmol, 82% yield, 87% purity) as a pale yellow oil. UPLC-MS (Method 2) m/z 259.2 $(M+H)^+$, 257.0 $(M-H)^-$ at 1.86 min. $^1$H NMR (500 MHz, DMSO-$d_6$) δ 7.10 (d, J=8.2 Hz, 1H), 6.96 (d, J=2.2 Hz, 1H), 6.82 (dd, J=8.2, 2.2 Hz, 1H), 5.25 (s, 2H), 3.09-2.98 (m, 1H), 2.91-2.85 (m, 1H), 2.45-2.36 (m, 1H), 1.84-1.70 (m, 2H), 1.67-1.58 (m, 2H), 1.50-1.29 (m, 2H), 0.79 (d, J=6.2 Hz, 3H).

Step 3: (S)-methyl 4-methoxy-3-(N-(2-(2-methylpiperidin-1-yl)-5-(trifluoromethyl)phenyl)sulfamoyl)benzoate: A mixture of the product from step 2 above (100 mg, 0.337 mmol), methyl 3-(chlorosulfonyl)-4-methoxybenzoate (103 mg, 0.387 mmol) and pyridine (0.1 ml, 1.24 mmol) in DCM (2.5 ml) was stirred at 35° C. for 4 days. The mixture was concentrated onto silica and purified by chromatography on silica gel (4 g cartridge, 0-50% EtOAc/isohexane) to afford the title compound (159 mg, 0.321 mmol, 95% yield, 98% purity) as a light brown oil. UPLC-MS (Method 1) m/z 487.2 $(M+H)^+$, 485.1 $(M-H)^-$ at 1.90 min. 1H NMR (500 MHz, DMSO-$d_6$) δ 8.92 (s, 1H), 8.39 (d, J=2.3 Hz, 1H), 8.19 (dd, J=8.8, 2.3 Hz, 1H), 7.65 (d, J=2.1 Hz, 1H), 7.48 (d, J=8.2 Hz, 1H), 7.41-7.34 (m, 2H), 3.96 (s, 3H), 3.85 (s, 3H), 2.98-2.95 (m, 1H), 2.62-2.51 (m, 2H), 1.76 (br d, J=10.8 Hz, 2H), 1.70-1.55 (m, 2H), 1.45-1.33 (m, 2H), 0.59 (d, J=6.1 Hz, 3H).

Step 4: (S)-4-methoxy-3-(N-(2-(2-methylpiperidin-1-yl)-5-(trifluoromethyl)phenyl)sulfamoyl)benzoic acid: A mixture of the product from step 3 above (159 mg, 0.321 mmol) and LiOH·$H_2O$ (55 mg, 1.31 mmol) in THF/MeOH/water (4:1:1, 4.5 ml) was stirred at 40° C. overnight. The mixture was diluted with water (5 ml) and acidified to ~pH 4 using 1 M HCl(aq). The mixture was extracted with EtOAc (3×20 ml) and the combined organic extracts were washed with brine (10 ml), dried by passage through a phase separator and the solvent was removed in vacuo. The residue was loaded onto silica and purified by chromatography on silica gel (4 g cartridge, 0-100% EtOAc/isohexane) to afford the product (29.6 mg, 0.062 mmol, 19% yield, 99% purity) as a white solid after trituration with TBME. UPLC-MS (Method 1) m/z 473.2 $(M+H)^+$, 471.1 $(M-H)^-$ at 1.76 min. $^1$H NMR (500 MHz, DMSO-$d_6$) δ 13.20 (s, 1H), 8.89 (s, 1H), 8.39 (d, J=2.2 Hz, 1H), 8.16 (dd, J=8.7, 2.2 Hz, 1H), 7.64 (d, J=2.1 Hz, 1H), 7.48 (d, J=8.2 Hz, 1H), 7.37 (dd, J=8.2, 2.1 Hz, 1H), 7.34 (d, J=8.7 Hz, 1H), 3.95 (s, 3H), 3.01-2.92 (m, 1H), 2.63-2.51 (m, 2H), 1.80-1.74 (m, 2H), 1.70-1.58 (m, 2H), 1.48-1.31 (m, 2H), 0.60 (d, J=6.1 Hz, 3H).

Example 240: (S)-4-ethyl-3-(N-(2-(2-methylpiperidin-1-yl)-5-(trifluoromethyl)phenyl) sulfamoyl)benzoic acid

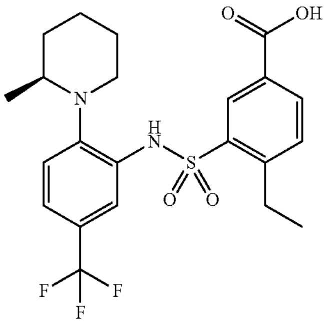 [SMILES: CCc1ccc(C(=O)O)cc1S(=O)(=O)Nc1cc(C(F)(F)F)ccc1N1CCCC[C@@H]1C]

Step 1: (S)-methyl 4-ethyl-3-(N-(2-(2-methylpiperidin-1-yl)-5-(trifluoromethyl)phenyl)sulfamoyl)benzoate: A mixture of the product from Example 239 step 2 (100 mg, 0.337 mmol), the product from Example 203 step 2 (102 mg, 0.387 mmol) and pyridine (0.1 ml, 1.24 mmol) in DCM (2.5 ml) was stirred at 35° C. for 4 days. The mixture was concentrated onto silica and purified by chromatography on silica gel (4 g cartridge, 0-50% EtOAc/isohexane) to afford the title compound (159 mg, 0.320 mmol, 95% yield, 97% purity) as a white solid. UPLC-MS (Method 1) m/z 485.3 $(M+H)^+$, 483.1 $(M-H)^-$ at 2.06 min. $^1H$ NMR (500 MHz, DMSO-$d_6$) δ 9.42 (s, 1H), 8.38 (d, J=1.9 Hz, 1H), 8.10 (dd, J=8.1, 1.9 Hz, 1H), 7.63 (d, J=8.1 Hz, 1H), 7.59-7.55 (m, 1H), 7.43-7.40 (m, 2H), 3.84 (s, 3H), 3.15-2.99 (m, 2H), 2.98-2.91 (m, 1H), 2.45-2.38 (m, 2H), 1.72-1.66 (m, 2H), 1.63-1.47 (m, 2H), 1.41-1.32 (m, 2H), 1.23 (t, J=7.4 Hz, 3H), 0.57 (d, J=6.2 Hz, 3H).

Step 2: (S)-4-ethyl-3-(N-(2-(2-methylpiperidin-1-yl)-5-(trifluoromethyl)phenyl)sulfamoyl)benzoic acid: A mixture of the product from step 1 above (159 mg, 0.320 mmol) and $LiOH \cdot H_2O$ (55 mg, 1.31 mmol) in THF/MeOH/water (4:1:1, 4.5 ml) was stirred at 40° C. overnight. The mixture was diluted with water (5 ml) and acidified to ~pH 4 using 1 M HCl(aq). The mixture was extracted with EtOAc (3×20 ml) and the combined organic extracts were washed with brine (10 ml), dried by passage through a phase separator and the solvent was removed in vacuo. The residue was loaded onto silica and purified by chromatography on silica gel (4 g cartridge, 0-100% EtOAc/isohexane) to afford the title compound (26.1 mg, 0.055 mmol, 17% yield, 99% purity) as a white solid after trituration with TBME. UPLC-MS (Method 1) m/z 471.3 $(M+H)^+$, 469.1 $(M-H)^-$ at 1.94 min. $^1H$ NMR (500 MHz, DMSO-$d_6$) δ 13.30 (s, 1H), 9.36 (s, 1H), 8.39 (d, J=1.8 Hz, 1H), 8.08 (dd, J=8.0, 1.8 Hz, 1H), 7.60 (d, J=8.0 Hz, 1H), 7.55 (s, 1H), 7.45-7.38 (m, 2H), 3.15-2.99 (m, 2H), 2.99-2.91 (m, 1H), 2.48-2.38 (m, 2H), 1.73-1.64 (m, 2H), 1.62-1.48 (m, 2H), 1.42-1.32 (m, 2H), 1.22 (t, J=7.4 Hz, 3H), 0.58 (d, J=6.2 Hz, 3H).

Example 241:4-ethyl-3-(N-(5-(methylsulfonyl)-2-(piperidin-1-yl)phenyl)sulfamoyl)benzoic acid

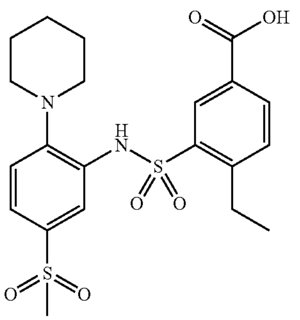 [SMILES: CCc1ccc(C(=O)O)cc1S(=O)(=O)Nc1cc(S(C)(=O)=O)ccc1N1CCCCC1]

Step 1: methyl 4-ethyl-3-(N-(5-(methylsulfonyl)-2-(piperidin-1-yl)phenyl)sulfamoyl)benzoate: A solution of the product from Example 207 step 2 (0.120 g, 0.472 mmol) and the product from Example 203 step 2 (0.124 g, 0.472 mmol) in DCM (10 ml) was treated with pyridine (0.229 ml, 2.83 mmol) and the solution was stirred at RT for 24 h and then at reflux for 20 h. The reaction mixture was concentrated in vacuo and the crude product was purified by chromatography on silica gel (24 g cartridge, 0-70% EtOAc/isohexane) to afford the title compound (0.180 g, 0.375 mmol, 79% yield, 100% purity) as a white solid. UPLC-MS (Method 1) m/z 481.3 $(M+H)^+$, 479.3 $(M-H)^-$ at 1.66 min.

Step 2: 4-ethyl-3-(N-(5-(methylsulfonyl)-2-(piperidin-1-yl)phenyl)sulfamoyl)benzoic acid: 1 M LiOH (aq) (1.12 ml, 1.12 mmol) was added to a solution of the product from step 1 above (0.180 g, 0.375 mmol) in THF (5 ml) and the solution was stirred at RT overnight. The solvent was removed in vacuo and the resultant aqueous solution was washed with EtOAc (50 ml). The aqueous phase was adjusted to pH 6 using 1M HCl(aq) to form a precipitate which was filtered and washed with water (10 ml) and isohexane (20 ml) to provide the title compound (142 mg, 0.289 mmol, 77% yield, 95% purity) as a white solid. UPLC-MS (Method 1) m/z 467.3 $(M+H)^+$, 465.3 $(M-H)^-$ at 1.52 min. $^1H$ NMR (500 MHz, DMSO-$d_6$)· 13.23 (br s, 1H), 9.58 (br s, 1H), 8.36 (d, J=1.8 Hz, 1H), 8.06 (d, J=7.9 Hz, 1H), 7.58-7.51 (m, 3H), 7.20 (s, 1H), 3.06 (q, J=7.4 Hz, 2H), 3.02 (s, 3H), 2.81-2.80 (m, 4H), 1.58-1.54 (m, 4H), 1.49-1.48 (m, 2H), 1.21 (t, J=7.4 Hz, 3H).

Example 242:4-ethyl-3-(N-(2-(piperidin-1-yl)-5-(tetrazol-1-yl)phenyl)sulfamoyl)benzoic acid

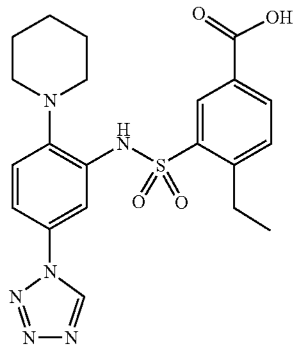 [SMILES: CCc1ccc(C(=O)O)cc1S(=O)(=O)Nc1cc(-n2cnnn2)ccc1N1CCCCC1]

Step 1: methyl 4-ethyl-3-(N-(2-(piperidin-1-yl)-5-(tetrazol-1-yl)phenyl)sulfamoyl)benzoate: Pyridine (0.099 ml, 1.23 mmol) was added to a solution of the product from Example 214 step 3 (100 mg, 0.409 mmol) and the product from Example 203 step 2 (129 mg, 0.491 mmol) in DCM (10 ml) and the solution was stirred at RT for 18 h. The solution was concentrated in vacuo and the crude product was purified by chromatography on silica gel (12 g cartridge, 0-100% EtOAc/isohexane) to afford the title compound (0.120 g, 0.245 mmol, 60% yield, 96% purity) as a white solid. UPLC-MS (Method 1) m/z 471.3 $(M+H)^+$, 469.4 $(M-H)^-$ at 1.72 min.

Step 2: 4-ethyl-3-(N-(2-(piperidin-1-yl)-5-(tetrazol-1-yl)phenyl)sulfamoyl)benzoic acid: 1 M LiOH (aq) (1.5 ml, 1.50 mmol) was added to a solution of the product from step 1 above (0.120 g, 0.245 mmol) in THF (6 ml) and methanol (1.5 ml) and the solution was stirred at RT overnight. The solvent was removed in vacuo and the residue was dissolved in water (5 ml) and washed with TBME (3×5 ml). The aqueous phase was acidified to ~pH 2 using conc. HCl and the product was extracted with TBME (3×10 ml). The organic phases were combined, dried by passage through a phase separator and the solvent was removed in vacuo to give the title compound (0.103 g, 0.220 mmol, 90% yield, 98% purity). UPLC-MS (Method 1) m/z 457.3 $(M+H)^+$, 455.3 $(M-H)^-$ at 1.58 min. $^1H$ NMR (500 MHz, DMSO-$d_6$) δ 13.27 (s, 1H), 9.97 (s, 1H), 9.44 (s, 1H), 8.38 (d, J=1.8 Hz, 1H), 8.08 (dd, J=8.0, 1.9 Hz, 1H), 7.70 (d, J=2.5 Hz, 1H), 7.66-7.57 (m, 2H), 7.37 (d, J=8.6 Hz, 1H), 3.07 (q, J=7.4 Hz, 2H), 2.71-2.58 (m, 4H), 1.62-1.49 (m, 4H), 1.49-1.40 (m, 2H), 1.22 (t, J=7.4 Hz, 3H).

Example 243: I-3-(N-(2-(3-hydroxypiperidin-1-yl)-5-(trifluoromethyl)phenyl)sulfamoyl)-4-methoxybenzoic acid

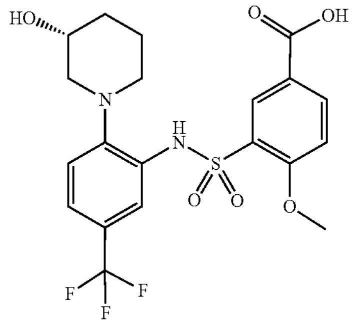

Step 1: I-1-(2-nitro-4-(trifluoromethyl)phenyl)piperidin-3-ol: $Et_3N$ (720 μl, 5.17 mmol) was added to a solution of 1-fluoro-2-nitro-4-(trifluoromethyl)benzene (201 μl, 1.44 mmol) and I-piperidin-3-ol hydrochloride (257 mg, 1.87 mmol) in DCM (6 ml) and the resultant solution was stirred at RT for 20 h. 1 M HCl(aq) (2 ml) was added and the organic phase was dried by passage through a phase separator and concentrated in vacuo to afford the title compound (421 mg, 1.44 mmol, 100% yield, 99% purity) as a dark yellow solid. UPLC-MS (Method 2) m/z 291.2 $(M+H)^+$ at 1.35 min.

Step 2: I-1-(2-amino-4-(trifluoromethyl)phenyl)piperidin-3-ol: 5% Pd/C (50% w/w water) Type 87L (107 mg, 0.025 mmol) in EtOH (1 ml) was added to a solution of the product from step 1 above (416 mg, 1.44 mmol) in EtOH (6.4 ml) at RT. The reaction mixture was stirred at RT under $H_2$ (4 bar pressure) for 19 h. The catalyst was removed by filtration through Celite® and washed with MeOH (20 ml). The filtrate was concentrated in vacuo and the residue was dissolved in EtOAc (10 ml). The organic phase was washed with water (5 ml), dried over $MgSO_4$, filtered and concentrated in vacuo to afford the title compound (384 mg, 1.48 mmol, quant. Yield) as a cream solid. UPLC-MS (Method 2) m/z 261.1 $(M+H)^+$, 259.1 $(M-H)^-$ at 1.28 min.

Step 3: I-methyl 3-(N-(2-(3-hydroxypiperidin-1-yl)-5-(trifluoromethyl)phenyl)sulfamoyl)-4-methoxybenzoate: The product from step 3 above (65.6 mg, 0.252 mmol) was dissolved in a mixture of DCM (1 ml) and pyridine (81 μl, 1.01 mmol) and treated with a solution of methyl 3-(chlorosulfonyl)-4-methoxybenzoate (80 mg, 0.302 mmol) in DCM (1 ml). The resultant solution was stirred at RT for 3 days. The crude product was purified directly by chromatography on silica gel (12 g cartridge, 0-100% EtOAc/isohexane) to afford the title compound (102 mg, 0.207 mmol, 82% yield, 99% purity) as a white solid. UPLC-MS (Method 2) m/z 489.2 $(M+H)^+$, 487.1 $(M-H)^-$ at 1.54 min.

Step 4: I-3-(N-(2-(3-hydroxypiperidin-1-yl)-5-(trifluoromethyl)phenyl)sulfamoyl)-4-methoxybenzoic acid: The product from step 3 above (100 mg, 0.205 mmol) was dissolved in THF (2 ml) and treated with 1.1 M LiOH (aq) (744 μl, 0.819 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (47.8 mg, 0.096 mmol, 47% yield, 95% purity) as a white solid. UPLC-MS (Method 1) m/z 475.3 $(M+H)^+$, 473.2 $(M-H)^-$ at 0.93 min. $^1H$ NMR (500 MHz, DMSO-$d_6$) δ 13.16 (br s, 1H), 9.16 (s, 1H), 8.40 (d, J=2.2 Hz, 1H), 8.15 (dd, J=8.7, 2.2 Hz, 1H), 7.47 (d, J=2.1 Hz, 1H), 7.38-7.16 (m, 3H), 5.11 (s, 1H), 3.90 (s, 3H), 3.82-3.70 (m, 1H), 2.89-2.78 (m, 2H), 2.77-2.55 (m, 2H), 1.96-1.85 (m, 1H), 1.79-1.68 (m, 1H), 1.63-1.37 (m, 2H).

Example 244: (S)-3-(N-(2-(3-hydroxypiperidin-1-yl)-5-(trifluoromethyl)phenyl)sulfamoyl)-4-methoxybenzoic acid

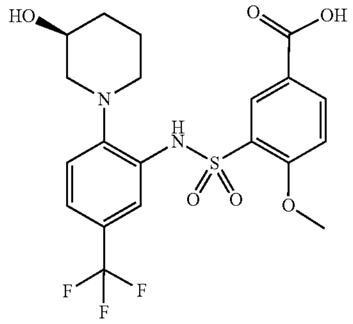 [SMILES: COc1ccc(C(=O)O)cc1S(=O)(=O)Nc1cc(C(F)(F)F)ccc1N1CCC[C@H](O)C1]

Step 1: (S)-1-(2-nitro-4-(trifluoromethyl)phenyl)piperidin-3-ol: $Et_3N$ (720 μl, 5.17 mmol) was added to a solution of 1-fluoro-2-nitro-4-(trifluoromethyl)benzene (201 μl, 1.44 mmol) and(S)-piperidin-3-ol hydrochloride (257 mg, 1.87 mmol) in DCM (6 ml) and the resultant solution was stirred at RT for 20 h. 1 M HCl(aq) (2 ml) was added and the organic phase was dried by passage through a phase separator. The filtrate was concentrated in vacuo to afford the title compound (416 mg, 1.44 mmol, 100% yield) as a dark yellow solid. UPLC-MS (Method 2) m/z 291.3 $(M+H)^+$, 289.1 $(M-H)^-$ at 1.35 min.

Step 2: (S)-1-(2-amino-4-(trifluoromethyl)phenyl)piperidin-3-ol: 5% Pd/C (50% w/w water) Type 87L (107 mg, 0.025 mmol) in EtOH (1 ml) was added to a solution of the product from step 1 above (416 mg, 1.44 mmol) in EtOH (6.4 ml) at RT. The reaction mixture was stirred at RT under $H_2$ (4 bar pressure) for 19 h. The catalyst was removed by filtration through Celite® and washed with MeOH (20 ml). The filtrate was concentrated in vacuo and the residue was dissolved in EtOAc (10 ml). The organic phase was washed with water (5 ml), dried over $MgSO_4$, filtered and concentrated in vacuo to afford the title compound (376 mg, 1.43 mmol, 100% yield, 99% purity) as a light yellow viscous oil. UPLC-MS (Method 2) m/z 261.1 $(M+H)^+$, 259.0 $(M-H)^-$ at 1.28 min.

Step 3: (S)-methyl 3-(N-(2-(3-hydroxypiperidin-1-yl)-5-(trifluoromethyl)phenyl)sulfamoyl)-4-methoxybenzoate: The product from step 2 above (65.6 mg, 0.252 mmol) was dissolved in a mixture of DCM (1 ml) and pyridine (81 μl, 1.01 mmol) and treated with a solution of methyl 3-(chlorosulfonyl)-4-methoxybenzoate (80 mg, 0.302 mmol) in DCM (1 ml). The resultant solution was stirred at RT for 3 days. The crude product was purified directly by chromatography on silica gel (12 g cartridge, 0-100% EtOAc/ isohexane) to afford the title compound (93.1 mg, 0.191 mmol, 76% yield) as a light yellow sticky solid. UPLC-MS (Method 2) m/z 489.3 $(M+H)^+$, 487.1 $(M-H)^-$ at 1.55 min.

Step 4: (S)-3-(N-(2-(3-hydroxypiperidin-1-yl)-5-(trifluoromethyl)phenyl)sulfamoyl)-4-methoxybenzoic acid: The product from step 3 above (91 mg, 0.186 mmol) was dissolved in THF (2 ml) and treated with 1.1 M LiOH (aq) (677 µl, 0.745 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration and washed with water (2×2 ml). The solid was suspended in MeCN (4 ml), concentrated in vacuo and dried at 45° C. to afford the title compound (79.7 mg, 0.163 mmol, 87% yield, 97% purity) as a white solid. UPLC-MS (Method 1) m/z 475.3 $(M+H)^+$, 473.2 $(M-H)^-$ at 0.94 min. $^1H$ NMR (500 MHz, DMSO-$d_6$) δ 13.16 (br s, 1H), 9.15 (s, 1H), 8.39 (d, J=2.2 Hz, 1H), 8.15 (dd, J=8.7, 2.2 Hz, 1H), 7.47 (d, J=2.1 Hz, 1H), 7.38-7.10 (m, 3H), 5.10 (s, 1H), 3.90 (s, 3H), 3.80-3.74 (m, 1H), 2.90-2.78 (m, 2H), 2.76-2.58 (m, 2H), 1.96-1.84 (m, 1H), 1.80-1.69 (m, 1H), 1.65-1.37 (m, 2H).

Example 245: I-3-(N-(2-(3-hydroxypiperidin-1-yl)-5-(methylsulfonyl)phenyl)sulfamoyl)-4-methoxybenzoic acid

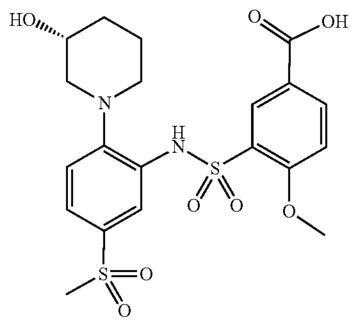

Step 1: I-1-(4-(methylsulfonyl)-2-nitrophenyl)piperidin-3-ol: $Et_3N$ (687 µl, 4.93 mmol) was added to a solution of 1-fluoro-4-(methylsulfonyl)-2-nitrobenzene (300 mg, 1.37 mmol) and I-piperidin-3-ol hydrochloride (245 mg, 1.78 mmol) in DCM (6 ml) and the resultant solution was stirred at RT for 20 h. 1 M HCl(aq) (2 ml) was added and the organic phase was dried by passage through a phase separator. The filtrate was concentrated in vacuo to afford the title compound (411 mg, 1.37 mmol, 100% yield) as a dark yellow solid. UPLC-MS (Method 2) m/z 301.2 $(M+H)^+$, 299.1 $(M-H)^-$ at 0.87 min.

Step 2: I-1-(2-amino-4-(methylsulfonyl)phenyl)piperidin-3-ol: 5% Pd/C (50% w/w water) Type 87L (107 mg, 0.025 mmol) in EtOH (1 ml) was added to a solution of the product from step 1 above (411 mg, 1.37 mmol) in EtOH (15 ml) at RT. The reaction mixture was stirred at RT under H2 (4 bar pressure) for 19 h. The catalyst was removed by filtration through Celite® and washed with MeOH (20 ml). The filtrate was concentrated in vacuo and the residue was dissolved in EtOAc (10 ml). The organic phase was washed with water (5 ml), dried over $MgSO_4$, filtered and concentrated in vacuo to afford the title compound (368 mg, 1.36 mmol, 99% yield) as a light yellow viscous oil. UPLC-MS (Method 2) m/z 271.1 $(M+H)^+$, 269.2 $(M-H)^-$ at 0.78 min.

Step 3: I-methyl 3-(N-(2-(3-hydroxypiperidin-1-yl)-5-(methylsulfonyl)phenyl)sulfamoyl)-4-methoxybenzoate: The product from step 2 above (68.1 mg, 0.252 mmol) was dissolved in a mixture of DCM (1 ml) and pyridine (81 µl, 1.01 mmol) and treated with a solution of methyl 3-(chlorosulfonyl)-4-methoxybenzoate (80 mg, 0.302 mmol) in DCM (1 ml). The resultant solution was stirred at RT for 3 days. The crude product was purified directly by chromatography on silica gel (12 g cartridge, 0-100% EtOAc/isohexane) to afford the title compound (96 mg, 0.189 mmol, 75% yield, 98% purity) as a cream solid. UPLC-MS (Method 1) m/z 499.3 $(M+H)^+$, 497.2 $(M-H)^-$ at 1.16 min.

Step 4: I-3-(N-(2-(3-hydroxypiperidin-1-yl)-5-(methylsulfonyl)phenyl)sulfamoyl)-4-methoxybenzoic acid: The product from step 3 above (94 mg, 0.185 mmol, 98% purity) was dissolved in THF (2 ml) and treated with 1.1 M LiOH (aq) (686 µl, 0.754 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2× 5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (32.4 mg, 0.062 mmol, 34% yield, 93% purity) as a white solid. UPLC-MS (Method 1) m/z 485.2 $(M+H)^+$, 483.2 $(M-H)^-$ at 0.68 min. $^1H$ NMR (500 MHz, DMSO-$d_6$) δ 13.19 (br s, 1H), 9.19 (br s, 1H), 8.38 (d, J=2.2 Hz, 1H), 8.14 (dd, J=8.7, 2.2 Hz, 1H), 7.69 (d, J=2.2 Hz, 1H), 7.50 (dd, J=8.4, 2.2 Hz, 1H), 7.29 (d, J=8.8 Hz, 1H), 7.27 (d, J=8.5 Hz, 1H), 5.55-4.80 (m, 1H), 3.91 (s, 3H), 3.80-3.74 (m, 1H), 2.98 (s, 3H), 2.94-2.86 (m, 2H), 2.82-2.61 (m, 2H), 1.95-1.83 (m, 1H), 1.79-1.68 (m, 1H), 1.63-1.38 (m, 2H).

Example 246: (S)-3-(N-(2-(3-hydroxypiperidin-1-yl)-5-(methylsulfonyl)phenyl)sulfamoyl)-4-methoxybenzoic acid

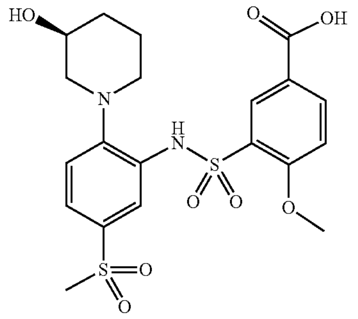 [SMILES: COc1ccc(C(=O)O)cc1S(=O)(=O)Nc1cc(S(C)(=O)=O)ccc1N1CCC[C@H](O)C1]

Step 1: (S)-1-(4-(methylsulfonyl)-2-nitrophenyl)piperidin-3-ol: $Et_3N$ (687 μl, 4.93 mmol) was added to a solution of 1-fluoro-4-(methylsulfonyl)-2-nitrobenzene (300 mg, 1.37 mmol) and (S)-piperidin-3-ol hydrochloride (245 mg, 1.78 mmol) in DCM (6 ml) and the solution was stirred at RT for 20 h. 1 M HCl(aq) (2 ml) was added and the filtrate was dried by passage through a phase separator. The organic phase was concentrated in vacuo to afford the title compound (415 mg, 1.37 mmol, 100% yield, 99% purity) as a dark yellow solid. UPLC-MS (Method 2) m/z 301.1 $(M+H)^+$, 299.1 $(M-H)^-$ at 0.88 min.

Step 2: (S)-1-(2-amino-4-(methylsulfonyl)phenyl)piperidin-3-ol: 5% Pd/C (50% w/w water) Type 87L (107 mg, 0.025 mmol) in EtOH (1 ml) was added to a solution of the product from step 1 above (415 mg, 1.37 mmol) in EtOH (6.4 ml) at RT. The reaction mixture was stirred at RT under $H_2$ (4 bar pressure) for 3 days. The catalyst was removed by filtration through Celite® and washed with MeOH (20 ml). The filtrate was concentrated in vacuo and the residue was dissolved in EtOAc (10 ml). The organic phase was washed with water (5 ml), dried over $MgSO_4$, filtered and concentrated in vacuo to afford the title compound (375 mg, 1.37 mmol, 100% yield, 99% purity) as a pale brown solid. UPLC-MS (Method 2) m/z 269.0 $(M-H)^-$ at 0.76 min.

Step 3: (S)-methyl 3-(N-(2-(3-hydroxypiperidin-1-yl)-5-(methylsulfonyl)phenyl)sulfamoyl)-4-methoxybenzoate: The product from step 3 above (68.1 mg, 0.252 mmol) was dissolved in a mixture of DCM (1 ml) and pyridine (81 μl, 1.01 mmol) and treated with a solution of methyl 3-(chlorosulfonyl)-4-methoxybenzoate (80 mg, 0.302 mmol) in DCM (1 ml). The resultant solution was stirred at RT for 20 h. The crude product was purified directly by chromatography on silica gel (12 g cartridge, 0-100% EtOAc/isohexane) to afford the title compound (68.4 mg, 0.136 mmol, 54% yield, 99% purity) as a cream solid. UPLC-MS (Method 1) m/z 499.3 $(M+H)^+$, 497.2 $(M-H)^-$ at 1.16 min.

Step 4: (S)-3-(N-(2-(3-hydroxypiperidin-1-yl)-5-(methylsulfonyl)phenyl)sulfamoyl)-4-methoxybenzoic acid: The product from step 3 above (66 mg, 0.132 mmol) was dissolved in THF (5 ml) and treated with 1.1 M LiOH(aq) (481 μl, 0.530 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (31.3 mg, 0.063 mmol, 48% yield, 98% purity) as a white solid. UPLC-MS (Method 1) m/z 485.3 $(M+H)^+$, 483.2 $(M-H)^-$ at 0.69 min. $^1H$ NMR (500 MHz, DMSO-$d_6$) δ 13.16 (s, 1H), 9.21 (s, 1H), 8.38 (d, J=2.2 Hz, 1H), 8.15 (dd, J=8.7, 2.2 Hz, 1H), 7.69 (d, J=2.2 Hz, 1H), 7.51 (dd, J=8.4, 2.2 Hz, 1H), 7.31 (d, J=8.7 Hz, 1H), 7.27 (d, J=8.4 Hz, 1H), 5.11 (s, 1H), 3.91 (s, 3H), 3.80-3.73 (m, 1H), 2.98 (s, 3H), 2.95-2.82 (m, 2H), 2.82-2.63 (m, 2H), 1.98-1.82 (m, 1H), 1.79-1.69 (m, 1H), 1.64-1.41 (m, 2H).

Example 247: (S)-4-ethyl-3-(N-(2-(3-hydroxypiperidin-1-yl)-5-(methylsulfonyl)phenyl) sulfamoyl)benzoic acid

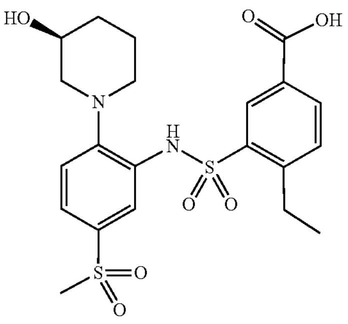

Step 1: (S)-methyl 4-ethyl-3-(N-(2-(3-hydroxypiperidin-1-yl)-5-(methylsulfonyl)phenyl)sulfamoyl)benzoate: The product from Example 246 step 2 (68.6 mg, 0.254 mmol) was dissolved in a mixture of DCM (1 ml) and pyridine (82 μl, 1.02 mmol) and treated with a solution of the product from Example 203 step 2 (80 mg, 0.305 mmol) in DCM (1 ml). The resultant solution was stirred at RT for 20 h. The crude product was purified directly by chromatography on silica gel (12 g cartridge, 0-100% EtOAc/isohexane) to afford the title compound (41.9 mg, 0.084 mmol, 33% yield, 100% purity) as a white solid. UPLC-MS (Method 1) m/z 497.3 $(M+H)^+$, 495.3 $(M-H)^-$ at 1.34 min.

Step 2: (S)-4-ethyl-3-(N-(2-(3-hydroxypiperidin-1-yl)-5-(methylsulfonyl)phenyl)sulfamoyl)benzoic acid: The product from step 1 above (40 mg, 0.081 mmol) was dissolved in THF (2 ml) and treated with 1.1 M LiOH(aq) (293 μl, 0.322 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (30.5 mg, 0.058 mmol, 72% yield, 92% purity) as a white solid. UPLC-MS (Method 1) m/z 483.3 $(M+H)^+$, 481.2 $(M-H)^-$ at 0.77 min. $^1H$ NMR (500 MHz, DMSO-$d_6$)· 13.33 (br s, 1H), 9.76 (br s, 1H), 8.40 (d, J=1.8 Hz, 1H), 8.08 (dd, J=8.0, 1.8 Hz, 1H), 7.63-7.58 (m, 2H), 7.54 (dd, J=8.4, 2.2 Hz, 1H), 7.23 (d, J=8.4 Hz, 1H), 5.21 (s, 1H), 3.87-3.69 (m, 1H), 2.98-3.15 (m, 7H), 2.77-2.59 (m, 2H), 1.90-1.79 (m, 1H), 1.73-1.64 (m, 1H), 1.56-1.45 (m, 2H), 1.21 (t, J=7.4 Hz, 3H).

Example 248: I-3-(N-(2-(3-hydroxypiperidin-1-yl)-5-(tetrazol-1-yl)phenyl)sulfamoyl)-4-methoxybenzoic acid

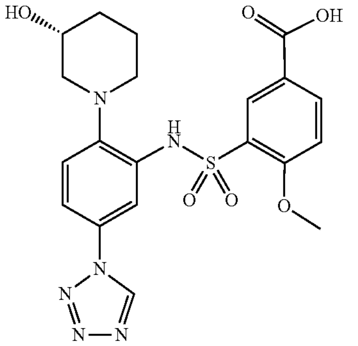 [SMILES: COc1ccc(C(=O)O)cc1S(=O)(=O)Nc1cc(-n2cnnn2)ccc1N1CCC[C@@H](O)C1]

Step 1: I-1-(2-nitro-4-(tetrazol-1-yl)phenyl)piperidin-3-ol: $Et_3N$ (720 μl, 5.16 mmol) was added to a solution of the product from Example 214 step 1 (300 mg, 1.43 mmol) and I-piperidin-3-ol hydrochloride (257 mg, 1.87 mmol) in DCM (6 ml) and the solution was stirred at RT for 20 h. 1 M HCl(aq) (2 ml) was added and the organic phase was dried by passage through a phase separator and concentrated in vacuo to afford the title compound (421 mg, 1.43 mmol, 100% yield, 99% purity) as a dark red viscous oil. UPLC-MS (Method 2) m/z no ionisation at 0.92 min.

Step 2: I-1-(2-amino-4-(tetrazol-1-yl)phenyl)piperidin-3-ol: 5% Pd/C (50% w/w water) Type 87L (107 mg, 0.025 mmol) in EtOH (1 ml) was added to a solution of the product from step 1 above (421 mg, 1.43 mmol, 99% purity) in EtOH (6.4 ml) at RT. The reaction mixture was stirred at RT under $H_2$ (4 bar pressure) for 3 days. The catalyst was removed by filtration through Celite® and washed with MeOH (20 ml). The filtrate was concentrated in vacuo and the residue was dissolved in EtOAc (10 ml). The organic phase was washed with water (5 ml), dried over $MgSO_4$, filtered and concentrated in vacuo to afford the title compound (369 mg, 1.42 mmol, 99% yield, 100% purity) as a cream solid. UPLC-MS (Method 2) m/z 259.1 $(M-H)^-$ at 0.82 min.

Step 3: I-methyl 3-(N-(2-(3-hydroxypiperidin-1-yl)-5-(tetrazol-1-yl)phenyl)sulfamoyl)-4-methoxybenzoate: The product from step 2 above (65.6 mg, 0.252 mmol) was dissolved in a mixture of DCM (1 ml) and pyridine (81 μl, 1.01 mmol) and treated with a solution of methyl 3-(chlorosulfonyl)-4-methoxybenzoate (80 mg, 0.302 mmol) in DCM (1 ml). The resultant solution was stirred at RT for 20 h. The crude product was purified directly by chromatography on silica gel (12 g cartridge, 0-100% EtOAc/isohexane) to afford the title compound (83.9 mg, 0.170 mmol, 68% yield, 99% purity) as a white solid. UPLC-MS (Method 1) m/z 489.3 $(M+H)^+$, 487.3 $(M-H)^-$ at 1.20 min.

Step 4: I-3-(N-(2-(3-hydroxypiperidin-1-yl)-5-(tetrazol-1-yl)phenyl)sulfamoyl)-4-methoxybenzoic acid: The product from step 3 above (81 mg, 0.166 mmol) was dissolved in THF (2 ml) and treated with 1.1 M LiOH(aq) (603 μl, 0.663 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (30.2 mg, 0.059 mmol, 35% yield, 92% purity) as a white solid. UPLC-MS (Method 1) m/z 475.3 $(M+H)^+$, 473.2 $(M-H)^-$ at 0.73 min. $^1H$ NMR (500 MHz, DMSO-$d_6$) δ 13.15 (br s, 1H), 9.94 (s, 1H), 9.18 (s, 1H), 8.44 (d, J=2.2 Hz, 1H), 8.14 (dd, J=8.7, 2.2 Hz, 1H), 7.80 (d, J=2.5 Hz, 1H), 7.50 (dd, J=8.5, 2.5 Hz, 1H), 7.38 (d, J=8.7 Hz, 1H), 7.31 (d, J=8.6 Hz, 1H), 5.06 (s, 1H), 3.93 (s, 3H), 3.82-3.73 (m, 1H), 2.92-2.56 (m, 4H), 1.99-1.80 (m, 1H), 1.82-1.70 (m, 1H), 1.65-1.51 (m, 1H), 1.52-1.41 (m, 1H).

Example 249: I-4-ethyl-3-(N-(2-(3-hydroxypiperidin-1-yl)-5-(trifluoromethyl)phenyl) sulfamoyl)benzoic acid

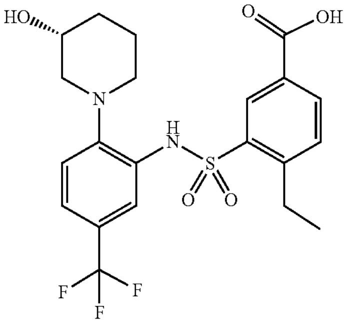

Step 1: I-methyl 4-ethyl-3-(N-(2-(3-hydroxypiperidin-1-yl)-5-(trifluoromethyl)phenyl)sulfamoyl)benzoate: The product from Example 243 step 2 (66.0 mg, 0.254 mmol) was dissolved in a mixture of DCM (1 ml) and pyridine (82 μl, 1.02 mmol) and treated with a solution of the product from Example 203 step 2 (80 mg, 0.305 mmol) in DCM (1 ml). The resultant solution was stirred at RT for 3 days. The crude product was purified directly by chromatography on silica gel (12 g cartridge, 0-100% EtOAc/isohexane) to afford the title compound (93.1 mg, 0.180 mmol, 71% yield, 94% purity) as a dark yellow sticky solid. UPLC-MS (Method 1) m/z 487.3 $(M+H)^+$ at 1.72 min.

Step 2: I-4-ethyl-3-(N-(2-(3-hydroxypiperidin-1-yl)-5-(trifluoromethyl)phenyl)sulfamoyl)benzoic acid: The product from step 1 above (91 mg, 0.187 mmol) was dissolved in THF (2 ml) and treated with 1.1 M LiOH(aq) (680 μl, 0.748 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension, which was concentrated in vacuo to ~2 ml. The precipitate was collected by filtration, washing with water (2×2 ml). The solid was suspended in MeCN (4 ml), concentrated in vacuo and dried at 45° C. to afford the title compound (30.2 mg, 0.062 mmol, 33% yield, 97% purity) as a white solid. UPLC-MS (Method 1) m/z 473.4 $(M+H)^+$, 471.2 $(M-H)^-$ at 1.06 min. $^1H$ NMR (500 MHz, DMSO-$d_6$) δ 13.22 (br s, 1H), 9.71 (br s, 1H), 8.42 (d, J=1.8 Hz, 1H), 8.08 (dd, J=8.0, 1.8 Hz, 1H), 7.59 (d, J=8.1

Hz, 1H), 7.47-7.27 (m, 2H), 7.20 (d, J=8.2 Hz, 1H), 5.31 (s, 1H), 3.84-3.71 (m, 1H), 3.15-3.00 (m, 2H), 2.95-2.75 (m, 2H), 2.71-2.63 (m, 2H), 1.95-1.77 (m, 1H), 1.77-1.59 (m, 1H), 1.57-1.45 (m, 2H), 1.20 (t, J=7.4 Hz, 3H).

Example 250: (S)-4-ethyl-3-(N-(2-(3-hydroxypiperidin-1-yl)-5-(trifluoromethyl)phenyl) sulfamoyl)benzoic acid

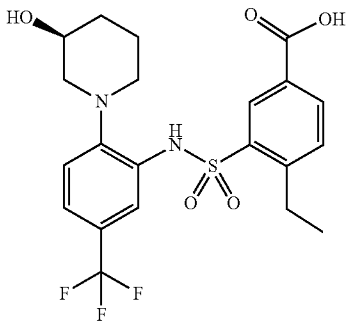

Step 1: (S)-methyl 4-ethyl-3-(N-(2-(3-hydroxypiperidin-1-yl)-5-(trifluoromethyl)phenyl)sulfamoyl)benzoate: The product from Example 244 step 2 (66.0 mg, 0.254 mmol) was dissolved in a mixture of DCM (1 ml) and pyridine (82 µl, 1.02 mmol) and treated with a solution of the product from Example 203 step 2 (80 mg, 0.305 mmol) in DCM (1 ml). The resultant solution was stirred at RT for 3 days. The crude product was purified directly by chromatography on silica gel (12 g cartridge, 0-100% EtOAc/isohexane) to afford the title compound (86.6 mg, 0.174 mmol, 69% yield, 98% purity) as a sticky cream solid. UPLC-MS (Method 1) m/z 485.2 $(M-H)^-$ at 1.71 min.

Step 2: (S)-4-ethyl-3-(N-(2-(3-hydroxypiperidin-1-yl)-5-(trifluoromethyl)phenyl)sulfamoyl)benzoic acid: The product from step 1 above (84 mg, 0.173 mmol) was dissolved in THF (2 ml) and treated with 1.1 M LiOH(aq) (628 µl, 0.691 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (66.6 mg, 0.133 mmol, 77% yield, 94% purity) as a cream solid. UPLC-MS (Method 1) m/z 473.3 $(M+H)^+$, 471.2 $(M-H)^-$ at 1.05 min. $^1H$ NMR (500 MHz, DMSO-$d_6$)· 13.31 (br s, 1H), 9.71 (br s, 1H), 8.41 (d, J=1.8 Hz, 1H), 8.09 (dd, J=8.0, 1.8 Hz, 1H), 7.60 (d, J=8.0 Hz, 1H), 7.42-7.27 (m, 2H), 7.21 (d, J=8.1 Hz, 1H), 5.20 (s, 1H), 3.84-3.68 (m, 1H), 3.15-2.99 (m, 2H), 2.94-2.75 (m, 2H), 2.72-2.61 (m, 2H), 1.94-1.74 (m, 1H), 1.73-1.61 (m, 1H), 1.58-1.41 (m, 2H), 1.20 (t, J=7.4 Hz, 3H).

Example 251: I-4-ethyl-3-(N-(2-(3-hydroxypiperidin-1-yl)-5-(methylsulfonyl)phenyl) sulfamoyl)benzoic acid

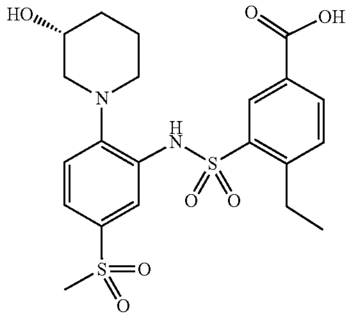 [SMILES: CCc1ccc(C(=O)O)cc1S(=O)(=O)Nc1cc(S(C)(=O)=O)ccc1N1CCC[C@@H](O)C1]

Step 1: I-methyl 4-ethyl-3-(N-(2-(3-hydroxypiperidin-1-yl)-5-(methylsulfonyl)phenyl)sulfamoyl)benzoate: The product from Example 245 step 2 (68.6 mg, 0.254 mmol) was dissolved in a mixture of DCM (1 ml) and pyridine (82 µl, 1.02 mmol) and treated with a solution of the product from Example 203 step 2 (80 mg, 0.305 mmol) in DCM (1 ml). The resultant solution was stirred at RT for 3 days. The crude product was purified directly by chromatography on silica gel (12 g cartridge, 0-100% EtOAc/isohexane) to afford the title compound (75.4 mg, 0.152 mmol, 60% yield) as a cream solid. UPLC-MS (Method 1) m/z 497.3 $(M+H)^+$, 495.2 $(M-H)^-$ at 1.32 min.

Step 2: I-4-ethyl-3-(N-(2-(3-hydroxypiperidin-1-yl)-5-(methylsulfonyl)phenyl)sulfamoyl)benzoic acid: The product from step 1 above (73 mg, 0.147 mmol) was dissolved in THF (2 ml) and treated with 1.1 M LiOH(aq) (535 µl, 0.588 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (28.4 mg, 0.056 mmol, 38% yield, 95% purity) as a white solid. UPLC-MS (Method 1) m/z 483.3 $(M+H)^+$, 481.2 $(M-H)^-$ at 0.78 min. $^1H$ NMR (500 MHz, DMSO-$d_6$) δ 13.33 (br s, 1H), 9.77 (s, 1H), 8.41 (d, J=1.8 Hz, 1H), 8.09 (dd, J=8.0, 1.9 Hz, 1H), 7.65-7.58 (m, 2H), 7.55 (dd, J=8.4, 2.2 Hz, 1H), 7.23 (d, J=8.4 Hz, 1H), 5.23 (s, 1H), 3.84-3.69 (m, 1H), 3.17-2.96 (m, 5H), 2.96-2.82 (m, 2H), 2.76-2.65 (m, 2H), 1.97-1.78 (m, 1H), 1.73-1.62 (m, 1H), 1.54-1.47 (m, 2H), 1.21 (t, J=7.4 Hz, 3H).

Example 252: I-4-ethyl-3-(N-(2-(3-hydroxypiperidin-1-yl)-5-(tetrazol-1-yl)phenyl)sulfamoyl)benzoic acid

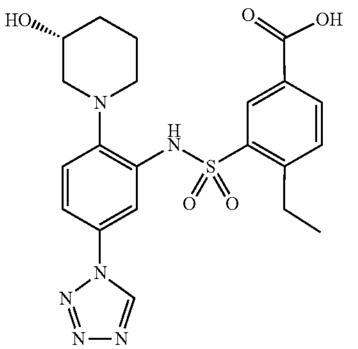 [SMILES: CCc1ccc(C(=O)O)cc1S(=O)(=O)Nc1cc(-n2cnnn2)ccc1N1CCC[C@@H](O)C1]

Step 1: I-methyl 4-ethyl-3-(N-(2-(3-hydroxypiperidin-1-yl)-5-(tetrazol-1-yl)phenyl)sulfamoyl)benzoate: The product from Example 248 step 2 (66.1 mg, 0.254 mmol) was dissolved in a mixture of DCM (1 ml) and pyridine (82 µl, 1.02 mmol) and treated with a solution of the product from Example 203 step 2 (80 mg, 0.305 mmol) in DCM (1 ml). The resultant solution was stirred at RT for 20 h. The crude product was purified directly by chromatography on silica gel (12 g cartridge, 0-100% EtOAc/isohexane) to afford the title compound (96.0 mg, 0.195 mmol, 77% yield, 99% purity) as a cream solid. UPLC-MS (Method 1) m/z 487.3 $(M+H)^+$, 485.3 $(M-H)^-$ at 1.38 min.

Step 2: I-4-ethyl-3-(N-(2-(3-hydroxypiperidin-1-yl)-5-(tetrazol-1-yl)phenyl)sulfamoyl)benzoic acid: The product from step 1 above (94 mg, 0.193 mmol) was dissolved in THF (2 ml) and treated with 1.1 M LiOH(aq) (703 µl, 0.773 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (58.4 mg, 0.120 mmol, 62% yield, 97% purity) as a white solid. UPLC-MS (Method 1) m/z 473.3 $(M+H)^+$, 471.3 $(M-H)^-$ at 0.82 min. $^1H$ NMR (500 MHz, DMSO-$d_6$) δ 13.29 (br s, 1H), 9.93 (s, 1H), 9.71 (br s, 1H), 8.44 (d, J=1.8 Hz, 1H), 8.08 (dd, J=8.0, 1.8 Hz, 1H), 7.73 (d, J=2.5 Hz, 1H), 7.60 (d, J=8.1 Hz, 1H), 7.54 (dd, J=8.6, 2.5 Hz, 1H), 7.32 (d, J=8.6 Hz, 1H), 5.17 (s, 1H), 3.87-3.66 (m, 1H), 3.18-3.03 (m, 2H), 2.80-2.72 (m, 1H), 2.69-2.59 (m, 1H), 2.68-2.60 (m, 2H), 1.92-1.80 (m, 1H), 1.74-1.62 (m, 1H), 1.59-1.38 (m, 2H), 1.22 (t, J=7.4 Hz, 3H).

Example 253: (S)-3-(N-(2-(3-hydroxypiperidin-1-yl)-5-(tetrazol-1-yl)phenyl)sulfamoyl)-4-methoxybenzoic acid

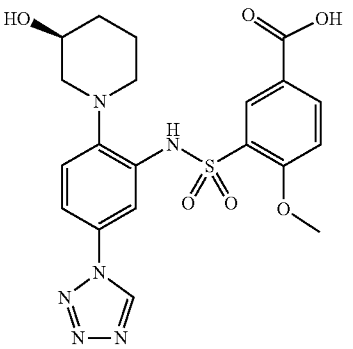 [SMILES: COc1ccc(C(=O)O)cc1S(=O)(=O)Nc1cc(-n2cnnn2)ccc1N1CCC[C@H](O)C1]

Step 1: (S)-1-(2-nitro-4-(tetrazol-1-yl)phenyl)piperidin-3-ol: $Et_3N$ (720 µl, 5.16 mmol) was added to a solution of the product from Example 214 step 1 (300 mg, 1.43 mmol) and(S)-piperidin-3-ol hydrochloride (257 mg, 1.87 mmol) in DCM (6 ml) and the resultant solution was stirred at RT for 20 h. 1 M HCl(aq) (2 ml) was added and the organic phase was dried by passage through a phase separator. The filtrate was concentrated in vacuo to afford the title compound (416 mg, 1.43 mmol, 100% yield) as a dark red viscous oil. UPLC-MS (Method 2) m/z no ionisation at 0.92 min.

Step 2: (S)-1-(2-amino-4-(tetrazol-1-yl)phenyl)piperidin-3-ol: 5% Pd/C (50% w/w water) Type 87L (107 mg, 0.025 mmol) in EtOH (1 ml) was added to a filtered solution of the product from step 1 above (416 mg, 1.43 mmol) in EtOH (6.4 ml) at RT. The reaction mixture was stirred at RT under $H_2$ (4 bar pressure) for 19 h. The catalyst was removed by filtration through Celite® and washed with MeOH (20 ml). The filtrate was concentrated in vacuo and the residue was dissolved in EtOAc (10 ml). The organic phase was washed with water (5 ml), dried over $MgSO_4$, filtered and concentrated in vacuo to afford the title compound (275 mg, 1.05 mmol, 73% yield, 99% purity) as a cream solid. UPLC-MS (Method 2) m/z 258.8 $(M-H)^-$ at 0.82 min.

Step 3: (S)-methyl 3-(N-(2-(3-hydroxypiperidin-1-yl)-5-(tetrazol-1-yl)phenyl)sulfamoyl)-4-methoxybenzoate: The product from step 2 above (65.6 mg, 0.252 mmol) was dissolved in a mixture of DCM (1 ml) and pyridine (81 µl, 1.01 mmol) and treated with a solution of methyl 3-(chlorosulfonyl)-4-methoxybenzoate (80 mg, 0.302 mmol) in DCM (1 ml). The resultant solution was stirred at RT for 20 h. The crude product was purified directly by chromatography on silica gel (12 g cartridge, 0-100% EtOAc/isohexane) to afford the title compound (57.8 mg, 0.115 mmol, 46% yield, 97% purity) as a cream solid. UPLC-MS (Method 1) m/z 489.3 $(M+H)^+$, 487.2 $(M-H)^-$ at 1.20 min.

Step 4: (S)-3-(N-(2-(3-hydroxypiperidin-1-yl)-5-(tetrazol-1-yl)phenyl)sulfamoyl)-4-methoxybenzoic acid: The product from step 1 above (56 mg, 0.115 mmol) was dissolved in THF (5 ml) and treated with 1.1 M LiOH(aq) (417 µl, 0.459 mmol). MeOH was added dropwise until the mixture was a solution and the reaction was stirred at 30° C. for 20 h. Additional 1.1 M LiOH(aq) (417 µl, 0.459 mmol) was added and the reaction mixture was heated at 40° C. for 4 h. The reaction mixture was diluted with water (3 ml), concentrated in vacuo and the resultant aqueous solution diluted with water (to ~5 ml). The aqueous phase was washed with EtOAc (2× 5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (27.3 mg, 0.052 mmol, 45% yield, 90% purity) as a white solid. UPLC-MS (Method 1) m/z 475.3 $(M+H)^+$, 473.3 $(M-H)^-$ at 0.72 min. $^1H$ NMR (500 MHz, DMSO-$d_6$) δ 13.14 (br s, 1H), 9.94 (s, 1H), 9.18 (br s, 1H), 8.43 (d, J=2.2 Hz, 1H), 8.14 (dd, J=8.7, 2.2 Hz, 1H), 7.80 (d, J=2.5 Hz, 1H), 7.50 (dd, J=8.5, 2.5 Hz, 1H), 7.38 (d, J=8.7 Hz, 1H), 7.31 (d, J=8.7 Hz, 1H), 5.08 (s, 1H), 3.93 (s, 3H), 3.83-3.73 (m, 1H), 2.95-2.56 (m, 4H), 1.96-1.85 (m, 1H), 1.82-1.71 (m, 1H), 1.66-1.37 (m, 2H).

Example 254: (S)-4-ethyl-3-(N-(2-(3-hydroxypiperidin-1-yl)-5-(tetrazol-1-yl)phenyl) sulfamoyl)benzoic acid

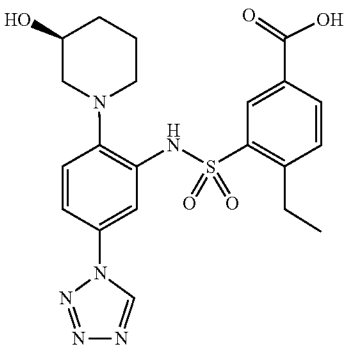

Step 1: (S)-methyl 4-ethyl-3-(N-(2-(3-hydroxypiperidin-1-yl)-5-(tetrazol-1-yl)phenyl)sulfamoyl)benzoate: The product from Example 253 step 2 (66.1 mg, 0.254 mmol) was dissolved in a mixture of DCM (1 ml) and pyridine (82 μl, 1.02 mmol) and treated with a solution of the product from Example 203 step 2 (80 mg, 0.305 mmol) in DCM (1 ml). The resultant solution was stirred at RT for 20 h. The crude product was purified directly by chromatography on silica gel (12 g cartridge, 0-100% EtOAc/isohexane) to afford the title compound (99.6 mg, 0.205 mmol, 81% yield) as a white solid. UPLC-MS (Method 1) m/z 487.3 $(M+H)^+$, 485.3 $(M-H)^-$ at 1.37 min.

Step 2: (S)-4-ethyl-3-(N-(2-(3-hydroxypiperidin-1-yl)-5-(tetrazol-1-yl)phenyl)sulfamoyl)benzoic acid: The product from step 1 above (97 mg, 0.199 mmol) was dissolved in THF (2 ml) and treated with 1.1 M LiOH(aq) (725 μl, 0.797 mmol). MeOH was added dropwise until the mixture was a solution and the reaction was stirred at 30° C. for 24 h. Additional 1.1 M LiOH(aq) (725 μl, 0.797 mmol) was added and the reaction was stirred at 40° C. for 24 h. The reaction mixture was diluted with water (3 ml), concentrated in vacuo and the resultant aqueous solution diluted with water (to ~5 ml). The aqueous phase was washed with EtOAc (2× 5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (39.9 mg, 0.080 mmol, 40% yield, 95% purity) as a white solid. UPLC-MS (Method 1) m/z 473.4 $(M+H)^+$, 471.3 $(M-H)^-$ at 0.83 min. $^1H$ NMR (500 MHz, DMSO-$d_6$)· 13.22 (br s, 1H), 9.93 (s, 1H), 9.71 (br s, 1H), 8.44 (d, J=1.8 Hz, 1H), 8.07 (dd, J=7.9, 1.8 Hz, 1H), 7.72 (d, J=2.5 Hz, 1H), 7.59 (d, J=8.0 Hz, 1H), 7.52 (dd, J=8.6, 2.5 Hz, 1H), 7.31 (d, J=8.6 Hz, 1H), 5.17 (s, 1H), 3.82-3.68 (m, 1H), 3.18-3.04 (m, 2H), 2.86 (dd, J=11.5, 2.7 Hz, 1H), 2.81-2.69 (m, 1H), 2.69-2.56 (m, 2H), 1.91-1.80 (m, 1H), 1.73-1.62 (m, 1H), 1.56-1.43 (m, 2H), 1.22 (t, J=7.4 Hz, 3H).

Example 255: 4-ethyl-3-(N-(2-(3-hydroxy-3-methylazetidin-1-yl)-5-(methylsulfonyl)phenyl) sulfamoyl) benzoic acid

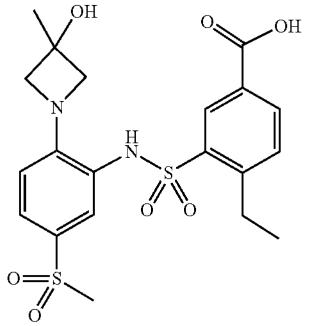 [SMILES: CCc1ccc(C(=O)O)cc1S(=O)(=O)Nc1cc(S(C)(=O)=O)ccc1N1CC(C)(O)C1]

Step 1: 3-methyl-1-(4-(methylsulfonyl)-2-nitrophenyl) azetidin-3-ol: $Et_3N$ (687 μl, 4.93 mmol) was added to a solution of 1-fluoro-4-(methylsulfonyl)-2-nitrobenzene (300 mg, 1.37 mmol) and 3-methylazetidin-3-ol hydrochloride (220 mg, 1.78 mmol) in DCM (6 ml) and the resultant solution was stirred at RT for 20 h. 1 M HCl(aq) (2 ml) was added and the organic phase was dried by passage through a phase separator. The filtrate was concentrated in vacuo to afford the title compound (392 mg, 1.37 mmol, 100% yield) as a light yellow solid. UPLC-MS (Method 2) m/z no ionisation at 0.83 min.

Step 2: 1-(2-amino-4-(methylsulfonyl)phenyl)-3-methylazetidin-3-ol: 5% Pd/C (50% w/w water) Type 87L (107 mg, 0.025 mmol) in EtOH (1 ml) was added to a fine suspension of the product from step 1 above (392 mg, 1.37 mmol) in EtOH (6.4 ml) at RT. The reaction mixture was stirred at RT under $H_2$ (4 bar pressure) for 19 h. The catalyst was removed by filtration through Celite® and washed with MeOH (20 ml). The filtrate was concentrated in vacuo and the residue was dissolved in EtOAc (10 ml). The organic phase was washed with water (5 ml), dried over $MgSO_4$, filtered and concentrated in vacuo to afford a dark brown oil. The crude product was purified by chromatography on silica gel (24 g cartridge, 0-100% EtOAc/isohexane) to afford the title compound (270 mg, 1.03 mmol, 74% yield, 98% purity) as a dark pink solid. UPLC-MS (Method 2) m/z 257.2 $(M+H)^+$ at 0.61 min.

Step 3: methyl 4-ethyl-3-(N-(2-(3-hydroxy-3-methylazetidin-1-yl)-5-(methylsulfonyl)phenyl)sulfamoyl)benzoate: The product from step 2 above (65.0 mg, 0.254 mmol) was dissolved in a mixture of DCM (1 ml) and pyridine (82 μl, 1.02 mmol) and treated with a solution of the product from Example 203 step 2 (80 mg, 0.305 mmol) in DCM (1 ml). The resultant solution was stirred at RT for 20 h. The crude product was purified directly by chromatography on silica gel (12 g cartridge, 0-100% EtOAc/isohexane) to afford the title compound (74.7 mg, 0.155 mmol, 61% yield, 100% purity) as a white solid. UPLC-MS (Method 1) m/z 483.2 $(M+H)^+$, 481.1 $(M-H)^-$ at 1.16 min.

Step 4: 4-ethyl-3-(N-(2-(3-hydroxy-3-methylazetidin-1-yl)-5-(methylsulfonyl)phenyl)sulfamoyl)benzoic acid: The product from step 1 above (72 mg, 0.149 mmol) was dissolved in THF (2 ml) and treated with 1.1 M LiOH(aq) (543 µl, 0.597 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 45° C. to afford the title compound (66.2 mg, 0.137 mmol, 92% yield, 97% purity) as a white solid. UPLC-MS (Method 1) m/z 467.1 $(M-H)^-$ at 1.02 min. $^1H$ NMR (500 MHz, DMSO-$d_6$) δ 13.29 (br s, 1H), 9.60 (br s, 1H), 8.25 (d, J=1.8 Hz, 1H), 8.12 (dd, J=8.0, 1.9 Hz, 1H), 7.65 (d, J=8.0 Hz, 1H), 7.51 (dd, J=8.7, 2.2 Hz, 1H), 6.58-6.50 (m, 2H), 5.58 (s, 1H), 4.07 (d, J=8.5 Hz, 2H), 3.98 (d, J=8.5 Hz, 2H), 2.95 (q, J=7.4 Hz, 2H), 2.80 (s, 3H), 1.43 (s, 3H), 1.20 (t, J=7.4 Hz, 3H).

Example 257: 4-ethyl-3-(N-(2-(3-hydroxy-3-methyl-azetidin-1-yl)-5-(tetrazol-1-yl)phenyl)sulfamoyl) benzoic acid

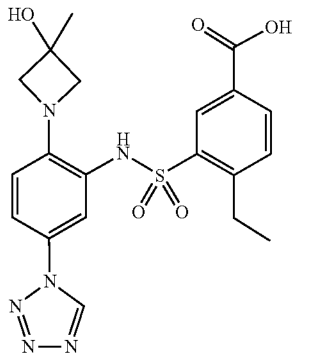 [SMILES: CCc1ccc(C(=O)O)cc1S(=O)(=O)Nc1cc(-n2cnnn2)ccc1N1CC(C)(O)C1]

Step 1: 3-methyl-1-(2-nitro-4-(tetrazol-1-yl)phenyl) azetidin-3-ol: $Et_3N$ (720 µl, 5.16 mmol) was added to a solution of the product from Example 214 step 1 (300 mg, 1.43 mmol) and 3-methylazetidin-3-ol hydrochloride (230 mg, 1.87 mmol) in DCM (6 ml) and the resultant solution was stirred at RT for 20 h. 1 M HCl(aq) (2 ml) was added, followed by 10% MeOH in DCM (200 ml) and the organic phase was dried by passage through a phase separator. The filtrate was concentrated in vacuo to afford the title compound (413 mg, 1.43 mmol, 100% yield) as a dark orange solid. UPLC-MS (Method 2) m/z no ionisation at 0.87 min.

Step 2: 1-(2-amino-4-(tetrazol-1-yl)phenyl)-3-methylazetidin-3-ol: 5% Pd/C (50% w/w water) Type 87L (214 mg, 0.050 mmol) in EtOH (1 ml) was added to a filtered solution of the product from step 1 above (396 mg, 1.44 mmol) in EtOH (150 ml) at RT. The reaction mixture was stirred at RT under $H_2$ (4 bar pressure) for 19 h. The catalyst was removed by filtration through Celite® and washed with MeOH (20 ml). The filtrate was concentrated in vacuo and the crude product was purified by chromatography on silica gel (24 g cartridge, 0-100% EtOAc/isohexane) to afford the title compound (117 mg, 0.474 mmol, 33% yield, 100% purity) as a light purple solid. UPLC-MS (Method 2) m/z no ionisation at 0.65 min.

Step 3: methyl 4-ethyl-3-(N-(2-(3-hydroxy-3-methylazetidin-1-yl)-5-(tetrazol-1-yl)phenyl)sulfamoyl)benzoate: The product from step 2 above (62.5 mg, 0.254 mmol) was dissolved in a mixture of DCM (1 ml) and pyridine (82 µl, 1.02 mmol) and treated with a solution of the product from Example 203 step 2 (80 mg, 0.305 mmol) in DCM (1 ml). The resultant solution was stirred at RT for 3 days. The crude product was purified directly by chromatography on silica gel (12 g cartridge, 0-100% EtOAc/isohexane) to afford the title compound (31.0 mg, 0.064 mmol, 25% yield, 98% purity) as a very pale pink solid. UPLC-MS (Method 1) m/z 473.4 $(M+H)^+$, 471.3 $(M-H)^-$ at 1.20 min.

Step 4: 4-ethyl-3-(N-(2-(3-hydroxy-3-methylazetidin-1-yl)-5-(tetrazol-1-yl)phenyl)sulfamoyl)benzoic acid: The product from step 3 above (29 mg, 0.061 mmol) was dissolved in THF (2 ml) and treated with 1 M LiOH(aq) (245 µl, 0.245 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (27.5 mg, 0.058 mmol, 94% yield, 96% purity) as a light pink solid. UPLC-MS (Method 1) m/z 459.2 $(M+H)^+$, 457.2 $(M-H)^-$ at 1.05 min. $^1H$ NMR (500 MHz, DMSO-$d_6$) δ 13.23 (br s, 1H), 9.74 (s, 1H), 9.70 (br s, 1H), 8.32 (d, J=1.9 Hz, 1H), 8.10 (dd, J=7.9, 1.9 Hz, 1H), 7.62 (d, J=8.0 Hz, 1H), 7.59-7.52 (m, 1H), 6.82 (d, J=2.6 Hz, 1H), 6.62 (d, J=8.8 Hz, 1H), 5.48 (s, 1H), 3.92 (d, J=8.0 Hz, 2H), 3.83 (d, J=7.9 Hz, 2H), 2.96 (q, J=7.4 Hz, 2H), 1.38 (s, 3H), 1.18 (t, J=7.4 Hz, 3H).

Example 258: I-3-(N-(5-cyano-2-(3-hydroxypiperidin-1-yl)phenyl)sulfamoyl)-4-methoxybenzoic acid

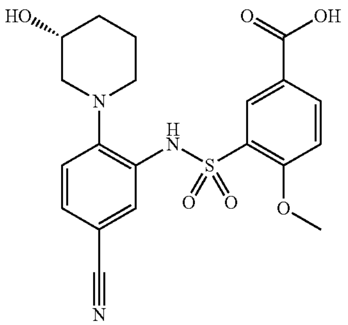 [SMILES: COc1ccc(C(=O)O)cc1S(=O)(=O)Nc1cc(C#N)ccc1N1CCC[C@@H](O)C1]

Step 1: I-4-(3-hydroxypiperidin-1-yl)-3-nitrobenzonitrile: $Et_3N$ (0.252 ml, 1.81 mmol) was added to a solution of 4-fluoro-3-nitrobenzonitrile (300 mg, 1.81 mmol), and I-piperidin-3-ol hydrochloride (249 mg, 1.81 mmol) in DCM (20 ml) and the resultant solution was stirred at RT overnight. 1 M HCl(aq) (10 ml) was added and the organic phase was dried by passage through a phase separator. The filtrate was concentrated in vacuo to afford the title compound (447 mg, 1.81 mmol, 100% yield) as a dark orange viscous oil. UPLC-MS (Method 2) m/z 248.3 $(M+H)^+$, 246.2 $(M-H)^-$ at 1.01 min.

Step 2: I-3-amino-4-(3-hydroxypiperidin-1-yl)benzonitrile: A mixture of the product from step 1 above (447 mg, 1.81 mmol), iron powder (2.48 g, 44.4 mmol), ammonium chloride (116 mg, 2.17 mmol), IPA (15 ml) and water (7.6 ml) was heated at 90° C. for 20 h. The reaction mixture was filtered through Celite®, washing with MeOH (25 ml), and the filtrate was concentrated in vacuo. The residue was diluted with DCM (20 ml), dried by passage through a phase separator and the crude product was purified directly by chromatography on silica gel (24 g cartridge, 0-100% EtOAc/isohexane) to afford the title compound (191 mg, 0.870 mmol, 48% yield, 99% purity) as a cream solid. UPLC-MS (Method 2) m/z 218.3 $(M+H)^+$ at 0.95 min.

Step 3: I-methyl 3-(N-(5-cyano-2-(3-hydroxypiperidin-1-yl)phenyl)sulfamoyl)-4-methoxybenzoate: The product from step 2 above (54.7 mg, 0.252 mmol) was dissolved in a mixture of DCM (1 ml) and pyridine (81 μl, 1.01 mmol) and treated with a solution of methyl 3-(chlorosulfonyl)-4-methoxybenzoate (80 mg, 0.302 mmol) in DCM (1 ml). The resultant solution was stirred at RT for 20 h. The crude product was purified directly by chromatography on silica gel (12 g cartridge, 0-100% EtOAc/isohexane) to afford the title compound (89.5 mg, 0.201 mmol, 80% yield) as a white solid. UPLC-MS (Method 1) m/z 446.3 $(M+H)^+$, 444.3 $(M-H)^-$ at 1.32 min.

Step 4: I-3-(N-(5-cyano-2-(3-hydroxypiperidin-1-yl)phenyl)sulfamoyl)-4-methoxybenzoic acid: The product from step 3 above (87 mg, 0.195 mmol) was dissolved in THF (2 ml) and treated with 1 M LiOH(aq) (781 μl, 0.781 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (74 mg, 0.166 mmol, 85% yield, 97% purity) as a white solid. UPLC-MS (Method 1) m/z 432.2 $(M+H)^+$, 430.3 $(M-H)^-$ at 1.15 min. $^1H$ NMR (500 MHz, DMSO-$d_6$) δ 13.20 (br s, 1H), 9.25 (br s, 1H), 8.37 (d, J=2.2 Hz, 1H), 8.17 (dd, J=8.7, 2.2 Hz, 1H), 7.45 (dd, J=8.3, 2.0 Hz, 1H), 7.42 (d, J=1.9 Hz, 1H), 7.32 (d, J=8.8 Hz, 1H), 7.19 (d, J=8.3 Hz, 1H), 5.11 (br s, 1H), 3.90 (s, 3H), 3.77-3.70 (m, 1H), 2.95-2.86 (m, 2H), 2.79-2.72 (m, 1H), 2.71-2.63 (m, 1H), 1.91-1.80 (m, 1H), 1.77-1.67 (m, 1H), 1.58-1.41 (m, 2H).

Example 259: 4-methoxy-3-(N-(2-(piperidin-1-yl)-5-(tetrazol-5-yl)phenyl)sulfamoyl)benzoic acid

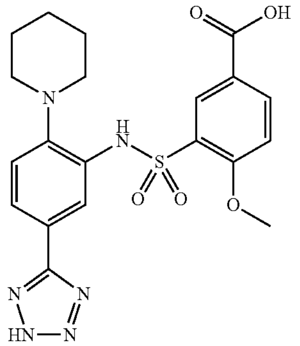

Step 1: 1-(2-nitro-4-(tetrazol-5-yl)phenyl)piperidine: $Et_3N$ (720 μl, 5.16 mmol) was added to a solution of 5-(4-fluoro-3-nitrophenyl)tetrazole (300 mg, 1.43 mmol) and piperidine (185 μl, 1.87 mmol) in DCM (6 ml) and the resultant solution was stirred at RT for 20 h. 1 M HCl(aq) (2 ml) was added and the organic phase was dried by passage through a phase separator. The filtrate was concentrated in vacuo to afford the title compound (406 mg, 1.43 mmol, 100% yield, 97% purity) as a dark orange viscous oil. UPLC-MS (Method 2) m/z 275.2 $(M+H)^+$, 273.1 $(M-H)^-$ at 0.92 min.

Step 2: 2-(piperidin-1-yl)-5-(tetrazol-5-yl)aniline: 5% Pd/C (50% w/w water) Type 87L (107 mg, 0.025 mmol) in EtOH (1 ml) was added to a filtered solution of the product from step 1 above (394 mg, 1.44 mmol) in EtOH (6.4 ml) at RT. The reaction mixture was stirred at RT under $H_2$ (4 bar pressure) for 19 h. The catalyst was removed by filtration through Celite® and washed with MeOH (20 ml). The filtrate was concentrated in vacuo and the residue was dissolved in DCM (5 ml) and dried by passage through a phase separator. The crude product was purified by chromatography on silica gel (24 g cartridge, 0-100% EtOAc/isohexane) to afford the title compound (206 mg, 0.801 mmol, 56% yield, 95% purity) as a cream solid. UPLC-MS (Method 2) m/z 243.1 $(M-H)^-$ at 0.78 min.

Step 3: methyl 4-methoxy-3-(N-(2-(piperidin-1-yl)-5-(tetrazol-5-yl)phenyl)sulfamoyl)benzoate: The product from step 2 above (61.5 mg, 0.252 mmol) was dissolved in a mixture of DCM (1 ml) and pyridine (81 μl, 1.01 mmol) and treated with a solution of methyl 3-(chlorosulfonyl)-4-methoxybenzoate (80 mg, 0.302 mmol) in DCM (1 ml). The resultant solution was stirred at RT for 3 days. The crude product was purified directly by chromatography on silica gel (12 g cartridge, 0-100% EtOAc/isohexane) to afford the title compound (37.4 mg, 0.078 mmol, 31% yield, 99% purity) as a sticky cream solid. UPLC-MS (Method 1) m/z 473.4 $(M+H)^+$, 471.3 $(M-H)^-$ at 1.45 min.

Step 4: 4-methoxy-3-(N-(2-(piperidin-1-yl)-5-(tetrazol-5-yl)phenyl)sulfamoyl)benzoic acid: The product from step 3 above (35 mg, 0.074 mmol) was dissolved in THF (2 ml) and treated with 1 M LiOH(aq) (296 μl, 0.296 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (29.1 mg, 0.060 mmol, 81% yield, 95% purity) as a pale yellow solid. UPLC-MS (Method 1) m/z 459.2 $(M+H)^+$, 457.2 $(M-H)^-$ at 1.31 min. $^1H$ NMR (500 MHz, DMSO-$d_6$) δ 16.79 (br s, 1H), 13.10 (br s, 1H), 8.74 (s, 1H), 8.42 (d, J=2.2 Hz, 1H), 8.12 (dd, J=8.7, 2.2 Hz, 1H), 7.98 (d, J=2.0 Hz, 1H), 7.67 (dd, J=8.3, 2.0 Hz, 1H), 7.37 (d, J=8.3 Hz, 1H), 7.32 (d, J=8.8 Hz, 1H), 3.95 (s, 3H), 2.83-2.71 (m, 4H), 1.71-1.63 (m, 4H), 1.58-1.50 (m, 2H).

Example 260: I-3-(N-(5-cyano-2-(3-hydroxypiperidin-1-yl)phenyl)sulfamoyl)-4-ethylbenzoic acid

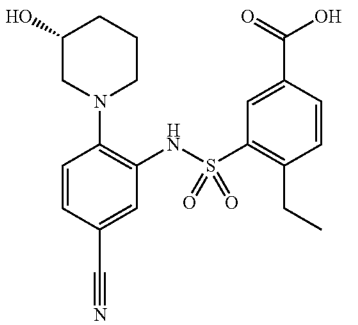 [SMILES: CCc1ccc(C(=O)O)cc1S(=O)(=O)Nc1cc(C#N)ccc1N1CCC[C@@H](O)C1]

Step 1: I-methyl 3-(N-(5-cyano-2-(3-hydroxypiperidin-1-yl)phenyl)sulfamoyl)-4-ethylbenzoate: The product from Example 258 step 2 (55.1 mg, 0.254 mmol) was dissolved in a mixture of DCM (1 ml) and pyridine (82 μl, 1.02 mmol) and treated with a solution of the product from Example 203 step 2 (80 mg, 0.305 mmol) in DCM (1 ml). The resultant solution was stirred at RT for 20 h. The crude product was purified directly by chromatography on silica gel (12 g cartridge, 0-100% EtOAc/isohexane) to afford the title compound (62.7 mg, 0.141 mmol, 56% yield, 100% purity) as a white solid. UPLC-MS (Method 1) m/z 444.4 $(M+H)^+$, 442.3 $(M-H)^-$ at 1.50 min.

Step 2: I-3-(N-(5-cyano-2-(3-hydroxypiperidin-1-yl)phenyl)sulfamoyl)-4-ethylbenzoic acid: The product from step 1 above (60 mg, 0.135 mmol) was dissolved in THF (2 ml) and treated with 1 M LiOH(aq) (541 μl, 0.541 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (57.8 mg, 0.125 mmol, 93% yield, 93% purity) as a white solid. UPLC-MS (Method 1) m/z 430.2 $(M+H)^+$, 428.2 $(M-H)^-$ at 1.33 min. $^1H$ NMR (500 MHz, DMSO-$d_6$) δ 13.34 (br s, 1H), 9.77 (br s, 1H), 8.36 (d, J=1.8 Hz, 1H), 8.10 (dd, J=8.0, 1.8 Hz, 1H), 7.62 (d, J=8.1 Hz, 1H), 7.48 (br d, J=8.2 Hz, 1H), 7.32 (d, J=2.0 Hz, 1H), 7.15 (d, J=8.3 Hz, 1H), 5.16 (br s, 1H), 3.71 (br s, 1H), 3.15-2.85 (m, 4H), 2.72-2.62 (m, 2H), 1.86-1.76 (m, 1H), 1.73-1.63 (m, 1H), 1.51-1.41 (m, 2H), 1.21 (t, J=7.4 Hz, 3H).

Example 261: 4-ethyl-3-(N-(2-(piperidin-1-yl)-5-(tetrazol-5-yl)phenyl)sulfamoyl)benzoic acid

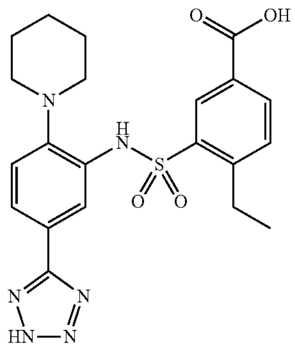

Step 1: methyl 4-ethyl-3-(N-(2-(piperidin-1-yl)-5-(tetrazol-5-yl)phenyl)sulfamoyl)benzoate: The product from Example 259 step 2 (62.0 mg, 0.254 mmol) was dissolved in a mixture of DCM (1 ml) and pyridine (82 μl, 1.02 mmol) and treated with a solution of the product from Example 203 step 2 (80 mg, 0.305 mmol) in DCM (1 ml). The resultant solution was stirred at RT for 3 days. The crude product was purified directly by chromatography on silica gel (12 g cartridge, 0-100% EtOAc/isohexane) to afford the title compound (37.6 mg, 0.076 mmol, 30% yield, 95% purity) as a light yellow solid. UPLC-MS (Method 1) m/z 471.3 $(M+H)^+$, 469.3 $(M-H)^-$ at 1.65 min.

Step 2: 4-ethyl-3-(N-(2-(piperidin-1-yl)-5-(tetrazol-5-yl)phenyl)sulfamoyl)benzoic acid: The product from step 1 above (35 mg, 0.074 mmol) was dissolved in THF (2 ml) and treated with 1 M LiOH(aq) (298 μl, 0.298 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (30.9 mg, 0.068 mmol, 91% yield, 95% purity) as a pale brown solid. UPLC-MS (Method 1) m/z 457.3 $(M+H)^+$, 455.2 $(M-H)^-$ at 1.51 min. $^1H$ NMR (500 MHz, DMSO-$d_6$) δ 16.75 (br s, 1H), 13.22 (br s, 1H), 9.33 (br s, 1H), 8.36 (d, J=1.9 Hz, 1H), 8.07 (dd, J=8.0, 1.9 Hz, 1H), 7.86 (d, J=2.1 Hz, 1H), 7.75 (dd, J=8.4, 2.1 Hz, 1H), 7.60 (d, J=8.0 Hz, 1H), 7.29 (d, J=8.4 Hz, 1H), 3.05 (q, J=7.4 Hz, 2H), 2.77-2.67 (m, 4H), 1.56-1.49 (m, 4H), 1.48-1.41 (m, 2H), 1.21 (t, J=7.4 Hz, 3H).

Example 262: I-4-ethyl-3-(N-(2-(3-fluoropiperidin-1-yl)-5-(methylsulfonyl)phenyl) sulfamoyl)benzoic acid

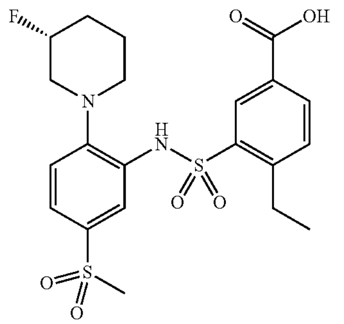 [SMILES: CCc1ccc(C(=O)O)cc1S(=O)(=O)Nc1cc(S(C)(=O)=O)ccc1N1CCC[C@@H](F)C1]

Step 1: I-3-fluoro-1-(4-(methylsulfonyl)-2-nitrophenyl) piperidine: $Et_3N$ (449 µl, 3.22 mmol) was added to a solution of 1-fluoro-4-(methylsulfonyl)-2-nitrobenzene (196 mg, 0.895 mmol) and I-3-fluoropiperidine hydrochloride (125 mg, 0.895 mmol) in DCM (6 ml) and the resultant solution was stirred at RT for 20 h. 1 M HCl(aq) (2 ml) was added and the organic phase was dried by passage through a phase separator. The filtrate was concentrated in vacuo to afford the title compound (273 mg, 0.895 mmol, 100% yield, 99% purity) as a dark yellow solid. UPLC-MS (Method 2) m/z no ionisation at 1.15 min.

Step 2: I-2-(3-fluoropiperidin-1-yl)-5-(methylsulfonyl) aniline: 5% Pd/C (50% w/w water) Type 87L (107 mg, 0.025 mmol) in EtOH (1 ml) was added to a suspension of the product from step 1 above (273 mg, 0.895 mmol, 99% purity) in EtOH (19 ml) at RT. The reaction mixture was stirred at RT under $H_2$ (4 bar pressure) for 3 days. The catalyst was removed by filtration through Celite® and washed with MeOH (20 ml). The filtrate was concentrated in vacuo to afford the title compound (239 mg, 0.867 mmol, 96% yield, 99% purity) as a cream solid. UPLC-MS (Method 2) m/z 273.1 $(M+H)^+$ at 1.37 min.

Step 3: I-methyl 4-ethyl-3-(N-(2-(3-fluoropiperidin-1-yl)-5-(methylsulfonyl)phenyl)sulfamoyl)benzoate: The product from step 2 above (69.1 mg, 0.254 mmol) was dissolved in a mixture of DCM (1 ml) and pyridine (82 µl, 1.02 mmol) and treated with a solution of the product from Example 203 step 2 (80 mg, 0.305 mmol) in DCM (1 ml). The resultant solution was stirred at RT for 2 days. The crude product was purified directly by chromatography on silica gel (12 g cartridge, 0-100% EtOAc/isohexane) to afford the title compound (55.7 mg, 0.112 mmol, 44% yield) as a white solid. UPLC-MS (Method 1) m/z 499.3 $(M+H)^+$, 497.2 $(M-H)^-$ at 1.54 min.

Step 4: I-4-ethyl-3-(N-(2-(3-fluoropiperidin-1-yl)-5-(methylsulfonyl)phenyl)sulfamoyl)benzoic acid: The product from step 3 above (53 mg, 0.106 mmol) was dissolved in THF (5 ml) and treated with 1 M LiOH(aq) (425 µl, 0.425 mmol). MeOH was added dropwise until the mixture was a solution and the reaction was stirred at 30° C. for 20 h. More 1 M LiOH(aq) (425 µl, 0.425 mmol) was added and the reaction mixture was stirred at 40° C. for 1 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (21.3 mg, 0.043 mmol, 40% yield, 97% purity) as a white solid. UPLC-MS (Method 1) m/z 485.3 $(M+H)^+$, 483.1 $(M-H)^-$ at 1.39 min. $^1H$ NMR (500 MHz, DMSO-$d_6$) δ13.32 (br s, 1H), 9.45 (br s, 1H), 8.35 (d, J=1.8 Hz, 1H), 8.09 (dd, J=8.0, 1.9 Hz, 1H), 7.64-7.57 (m, 2H), 7.49 (d, J=2.2 Hz, 1H), 7.31 (d, J=8.5 Hz, 1H), 4.86-4.64 (m, 1H), 3.21-3.11 (m, 1H), 3.07-2.98 (m, 5H), 2.95-2.85 (m, 2H), 2.81-2.74 (m, 1H), 2.00-1.86 (m, 1H), 1.82-1.72 (m, 1H), 1.71-1.53 (m, 2H), 1.20 (t, J=7.4 Hz, 3H).

Example 263: (S)-3-(N-(5-cyano-2-(3-hydroxypiperidin-1-yl)phenyl)sulfamoyl)-4-ethylbenzoic acid

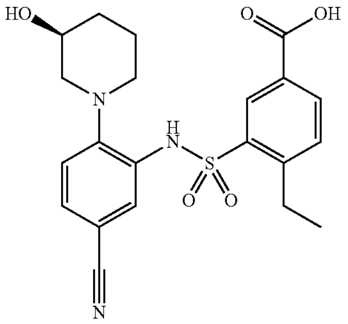 [SMILES: CCc1ccc(C(=O)O)cc1S(=O)(=O)Nc1cc(C#N)ccc1N1CCC[C@H](O)C1]

Step 1: (S)-4-(3-hydroxypiperidin-1-yl)-3-nitrobenzonitrile: $Et_3N$ (906 µl, 6.50 mmol) was added to a solution of 4-fluoro-3-nitrobenzonitrile (300 mg, 1.81 mmol) and(S)-piperidin-3-ol hydrochloride (249 mg, 1.81 mmol) in DCM (20 ml) and the resultant solution was stirred at RT overnight. 1 M HCl(aq) (2 ml) was added and the organic phase was concentrated in vacuo to afford the title compound (465 mg, 1.81 mmol, 100% yield, 96% purity) as a dark orange viscous oil. UPLC-MS (Method 2) m/z 248.3 $(M+H)^+$, 246.2 $(M-H)^-$ at 1.02 min.

Step 2: (S)-3-amino-4-(3-hydroxypiperidin-1-yl)benzonitrile: A mixture of the product from step 1 above (447 mg, 1.81 mmol), iron powder (2.48 g, 44.4 mmol), ammonium chloride (116 mg, 2.17 mmol), IPA (15 ml) and water (7.6 ml) was stirred at 90° C. for 20 h. The mixture was filtered through Celite®, rinsing with MeOH (25 ml) and the filtrate was concentrated in vacuo. The residue was diluted with DCM (20 ml), dried by passage through a phase separator and the crude product was purified by chromatography on silica gel (24 g cartridge, 0-100% EtOAc/isohexane) to afford the title compound (190 mg, 0.875 mmol, 48% yield, 100% purity) as a dark orange solid. UPLC-MS (Method 2) m/z 218.3 $(M+H)^+$ at 0.95 min.

Step 3: (S)-methyl 3-(N-(5-cyano-2-(3-hydroxypiperidin-1-yl)phenyl)sulfamoyl)-4-ethylbenzoate: The product from step 2 above (55.1 mg, 0.254 mmol) was dissolved in a mixture of DCM (1 ml) and pyridine (82 µl, 1.02 mmol) and treated with a solution of the product from Example 203 step 2 (80 mg, 0.305 mmol) in DCM (1 ml). The resultant solution was stirred at RT for 20 h. The crude product was purified directly by chromatography on silica gel (12 g cartridge, 0-100% EtOAc/isohexane) to afford the title compound (42.7 mg, 0.094 mmol, 37% yield, 98% purity) as a white solid. UPLC-MS (Method 1) m/z 444.4 $(M+H)^+$, 442.3 $(M-H)^-$ at 1.50 min.

Step 4: (S)-3-(N-(5-cyano-2-(3-hydroxypiperidin-1-yl)phenyl)sulfamoyl)-4-ethylbenzoic acid: The product from step 3 above (40 mg, 0.090 mmol) was dissolved in THF (2 ml) and treated with 1 M LiOH(aq) (361 μl, 0.361 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (34.7 mg, 0.078 mmol, 87% yield, 97% purity) as a white solid. UPLC-MS (Method 1) m/z 430.3 $(M+H)^+$, 428.2 $(M-H)^-$ at 1.33 min. $^1H$ NMR (500 MHz, DMSO-$d_6$) δ13.34 (br s, 1H), 9.76 (br s, 1H), 8.35 (d, J=1.8 Hz, 1H), 8.10 (dd, J=8.0, 1.8 Hz, 1H), 7.61 (d, J=8.0 Hz, 1H), 7.48 (dd, J=8.3, 1.9 Hz, 1H), 7.31 (d, J=1.9 Hz, 1H), 7.15 (d, J=8.3 Hz, 1H), 5.16 (s, 1H), 3.70 (br s, 1H), 3.13-2.82 (m, 4H), 2.71-2.61 (m, 2H), 1.85-1.75 (m, 1H), 1.73-1.62 (m, 1H), 1.51-1.41 (m, 2H), 1.20 (t, J=7.4 Hz, 3H).

Example 264: (S)-3-(N-(5-cyano-2-(3-hydroxypiperidin-1-yl)phenyl)sulfamoyl)-4-methoxybenzoic acid

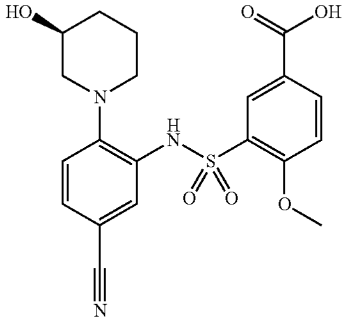 [SMILES: COc1ccc(C(=O)O)cc1S(=O)(=O)Nc1cc(C#N)ccc1N1CCC[C@H](O)C1]

Step 1: (S)-methyl 3-(N-(5-cyano-2-(3-hydroxypiperidin-1-yl)phenyl)sulfamoyl)-4-methoxybenzoate: The product from Example 263 step 2 (54.7 mg, 0.252 mmol) was suspended in a mixture of DCM (1 ml) and pyridine (81 μl, 1.01 mmol) and treated with a solution of methyl 3-(chlorosulfonyl)-4-methoxybenzoate (80 mg, 0.302 mmol) in DCM (1 ml). The resultant solution was stirred at RT for 20 h. The crude product was purified directly by chromatography on silica gel (12 g cartridge, 0-100% EtOAc/isohexane) to afford the title compound (91.9 mg, 0.206 mmol, 82% yield, 100% purity) as a cream solid. UPLC-MS (Method 1) m/z 446.3 $(M+H)^+$, 444.3 $(M-H)^-$ at 1.31 min.

Step 2: (S)-3-(N-(5-cyano-2-(3-hydroxypiperidin-1-yl)phenyl)sulfamoyl)-4-methoxybenzoic acid: The product from step 2 above (89 mg, 0.200 mmol) was dissolved in THF (5 ml) and treated with 1 M LiOH(aq) (799 μl, 0.799 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (79.6 mg, 0.179 mmol, 90% yield, 97% purity) as a cream solid. UPLC-MS (Method 1) m/z 432.2 $(M+H)^+$, 430.1 $(M-H)^-$ at 1.14 min. $^1H$ NMR (500 MHz, DMSO-$d_6$) δ 13.19 (br s, 1H), 9.24 (br s, 1H), 8.36 (d, J=2.2 Hz, 1H), 8.16 (dd, J=8.7, 2.2 Hz, 1H), 7.45 (dd, J=8.3, 1.9 Hz, 1H), 7.41 (d, J=1.9 Hz, 1H), 7.32 (d, J=8.8 Hz, 1H), 7.19 (d, J=8.3 Hz, 1H), 5.10 (s, 1H), 3.89 (s, 3H), 3.77-3.69 (m, 1H), 2.95-2.85 (m, 2H), 2.79-2.71 (m, 1H), 2.70-2.62 (m, 1H), 1.90-1.81 (m, 1H), 1.76-1.67 (m, 1H), 1.58-1.37 (m, 2H).

Example 265: I-3-(N-(2-(3-fluoropiperidin-1-yl)-5-(tetrazol-1-yl)phenyl)sulfamoyl)-4-methoxybenzoic acid

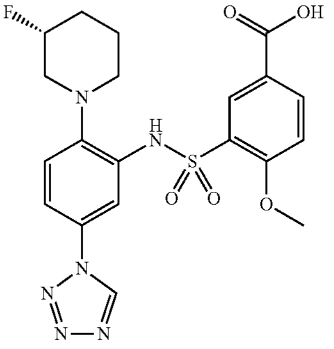 [SMILES: COc1ccc(C(=O)O)cc1S(=O)(=O)Nc1cc(-n2cnnn2)ccc1N1CCC[C@@H](F)C1]

Step 1: I-3-fluoro-1-(2-nitro-4-(tetrazol-1-yl)phenyl)piperidine: $Et_3N$ (449 μl, 3.22 mmol) was added to a solution of the product from Example 214 step 1 (187 mg, 0.895 mmol) and I-3-fluoropiperidine hydrochloride (125 mg, 0.895 mmol) in DCM (6 ml) and the resultant solution was stirred at RT for 20 h. 1 M HCl(aq) (2 ml) was added and the organic phase was dried by passage through a phase separator and concentrated in vacuo to afford the title compound (281 mg, 0.895 mmol, 100% yield, 93% purity) as a dark orange viscous oil. UPLC-MS (Method 2) m/z no ionisation at 1.20 min.

Step 2: I-2-(3-fluoropiperidin-1-yl)-5-(tetrazol-1-yl)aniline: 5% Pd/C (50% w/w water) Type 87L (107 mg, 0.025 mmol) in EtOH (1 ml) was added to a suspension of the product from step 1 above (281 mg, 0.895 mmol, 93% purity) in EtOH (19 ml) at RT. The reaction mixture was stirred at RT under $H_2$ (4 bar pressure) for 3 days. The catalyst was removed by filtration through Celite® and washed with MeOH (20 ml). The filtrate was concentrated in vacuo to afford the title compound (241 mg, 0.863 mmol, 96% yield, 96% purity) as a light yellow viscous oil. UPLC-MS (Method 2) m/z no ionisation at 1.14 min.

Step 3: I-methyl 3-(N-(2-(3-fluoropiperidin-1-yl)-5-(tetrazol-1-yl)phenyl)sulfamoyl)-4-methoxybenzoate: The product from step 2 above (66.1 mg, 0.237 mmol, 96% purity) was dissolved in a mixture of DCM (1 ml) and pyridine (81 μl, 1.01 mmol) and treated with a solution of methyl 3-(chlorosulfonyl)-4-methoxybenzoate (80 mg, 0.302 mmol) in DCM (1 ml). The resultant solution was stirred at RT for 20 h. The crude product was purified directly by chromatography on silica gel (12 g cartridge, 0-100% EtOAc/isohexane) to afford the title compound (73.0 mg, 0.144 mmol, 61% yield, 97% purity) as a white solid. UPLC-MS (Method 1) m/z 491.3 $(M+H)^+$, 489.2 $(M-H)^-$ at 1.31 min.

Step 4: I-3-(N-(2-(3-fluoropiperidin-1-yl)-5-(tetrazol-1-yl)phenyl)sulfamoyl)-4-methoxybenzoic acid: The product from step 3 above (71 mg, 0.141 mmol, 97% purity) was dissolved in THF (2 ml) and treated with 1 M LiOH(aq) (579 μl, 0.579 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (55.8 mg, 0.111 mmol, 77% yield, 95% purity) as a cream solid. UPLC-MS (Method 1) m/z 477.2 $(M+H)^+$, 475.2 $(M-H)^-$ at 1.25 min. $^1H$ NMR (500 MHz, DMSO-$d_6$) δ 13.16 (br s, 1H), 9.95 (s, 1H), 8.81 (br s, 1H), 8.42 (d, J=2.2 Hz, 1H), 8.14 (dd, J=8.7, 2.2 Hz, 1H), 7.79 (d, J=2.4 Hz, 1H), 7.54 (dd, J=8.6, 2.5 Hz, 1H), 7.47 (d, J=8.6 Hz, 1H), 7.32 (d, J=8.8 Hz, 1H), 4.95-4.79 (m, 1H), 3.93 (s, 3H), 3.07-2.70 (m, 4H), 1.97-1.74 (m, 3H), 1.74-1.64 (m, 1H).

Example 266: I-4-ethyl-3-(N-(2-(3-fluoropiperidin-1-yl)-5-(tetrazol-1-yl)phenyl) sulfamoyl)benzoic acid

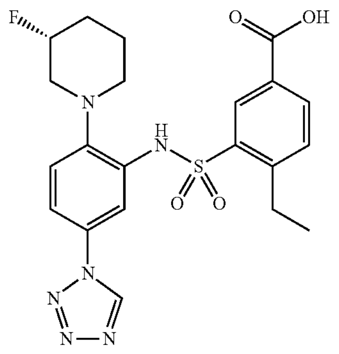 [SMILES: CCc1ccc(C(=O)O)cc1S(=O)(=O)Nc1cc(-n2cnnn2)ccc1N1CCC[C@@H](F)C1]

Step 1: I-methyl 4-ethyl-3-(N-(2-(3-fluoropiperidin-1-yl)-5-(tetrazol-1-yl)phenyl)sulfamoyl)benzoate: The product from Example 265 step 2 (66.6 mg, 0.254 mmol) was dissolved in a mixture of DCM (1 ml) and pyridine (82 μl, 1.02 mmol) and treated with a solution of the product from Example 203 step 2 (80 mg, 0.302 mmol) in DCM (1 ml). The resultant solution was stirred at RT for 20 h. The crude product was purified directly by chromatography on silica gel (12 g cartridge, 0-100% EtOAc/isohexane) to afford the title compound (35.6 mg, 0.071 mmol, 28% yield, 97% purity) as a sticky cream solid. UPLC-MS (Method 1) m/z 489.3 $(M+H)^+$, 487.3 $(M-H)^-$ at 1.58 min.

Step 2: I-4-ethyl-3-(N-(2-(3-fluoropiperidin-1-yl)-5-(tetrazol-1-yl)phenyl)sulfamoyl)benzoic acid: The product from step 2 above (33 mg, 0.068 mmol) was dissolved in THF (2 ml) and treated with 1 M LiOH(aq) (270 μl, 0.270 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (29.4 mg, 0.061 mmol, 90% yield, 98% purity) as a cream solid. UPLC-MS (Method 1) m/z 473.2 $(M-H)^-$ at 1.43 min. $^1H$ NMR (500 MHz, DMSO-$d_6$) δ 13.31 (br s, 1H), 9.97 (s, 1H), 9.38 (br s, 1H), 8.41 (d, J=1.8 Hz, 1H), 8.09 (dd, J=8.0, 1.8 Hz, 1H), 7.72 (d, J=2.5 Hz, 1H), 7.62 (app. D, J=8.0 Hz, 2H), 7.44 (d, J=8.6 Hz, 1H), 4.84-4.67 (m, 1H), 3.13-2.94 (m, 3H), 2.83-2.74 (m, 2H), 2.69-2.61 (m, 1H), 2.00-1.85 (m, 1H), 1.82-1.70 (m, 1H), 1.70-1.55 (m, 2H), 1.22 (t, J=7.4 Hz, 3H).

Example 267:4-cyclopropyl-3-(N-(2-(piperidin-1-yl)-5-(trifluoromethyl)phenyl)sulfamoyl)benzoic acid

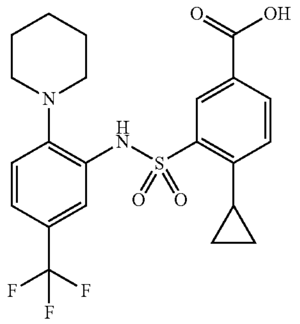 [SMILES: O=C(O)c1ccc(C2CC2)c(S(=O)(=O)Nc2cc(C(F)(F)F)ccc2N2CCCCC2)c1]

Step 1: methyl 4-bromo-3-(chlorosulfonyl)benzoate: A mixture of 4-bromo-3-(chlorosulfonyl)benzoic acid (500 mg, 1.67 mmol) and $SOCl_2$ (5 ml) was heated under reflux for 4 h. Upon cooling to RT mixture was concentrated in vacuo and the residue was added slowly to MeOH (10 ml) at 0° C. The mixture was concentrated in vacuo to provide the title compound (758 mg, 1.45 mmol, 87% yield, 60% purity), contaminated with 4-bromo-3-(chlorosulfonyl)benzoic acid, as a beige solid. $^1H$ NMR (500 MHz, DMSO-$d_6$) δ 8.50-8.46 (m, 1H), 7.78-7.68 (m, 2H), 3.86 (s, 3H).

Step 2: methyl 4-bromo-3-(N-(2-(piperidin-1-yl)-5-(trifluoromethyl)phenyl)sulfamoyl)benzoate: A mixture of 2-(piperidin-1-yl)-5-(trifluoromethyl)aniline (240 mg, 0.653 mmol, 60% purity), the product from step 1 above (341 mg, 1.09 mmol) and pyridine (0.25 ml, 3.09 mmol) in DCM (6.5 ml) was stirred at RT for 2 days. The mixture was concentrated onto silica and purified by chromatography on silica gel (12 g cartridge, 0-30% EtOAc/isohexane) to afford the title compound (325 mg, 0.605 mmol, 93% yield, 97% purity) as a beige solid. UPLC-MS (Method 1) m/z 521.1 $(M+H)^+$, 519.0 $(M-H)^-$ at 2.00 min. $^1H$ NMR (500 MHz, DMSO-$d_6$)· 9.49 (s, 1H), 8.46 (br s, 1H), 8.04 (br s, 2H), 7.47-7.41 (m, 1H), 7.38-7.34 (m, 1H), 7.34-7.28 (m, 1H), 3.88 (s, 3H), 2.77 (t, J=5.2 Hz, 4H), 1.62-1.54 (m, 4H), 1.51-1.44 (m, 2H).

Step 3: methyl 4-bromo-3-(N-(2-(piperidin-1-yl)-5-(trifluoromethyl)phenyl)-N-((2-(trimethylsilyl) ethoxy)methyl) sulfamoyl)benzoate: A suspension of NaH (36 mg, 0.900 mmol, 60% w/w in mineral oil) in THF (5 ml) was cooled to 0° C. and slowly treated with the product from step 2 above (325 mg, 0.605 mmol) in THF (5 ml). The mixture was warmed to RT and stirred for 1 h, then treated with SEM-CI (0.150 ml, 0.847 mmol). The resultant mixture was stirred at RT overnight. The mixture was carefully quenched with water (15 ml) and extracted with EtOAc (3×40 ml). The combined organic phases were washed with brine (15 ml), dried by passage through a phase separator and the solvent was removed in vacuo. The residue was loaded onto silica and purified by chromatography on silica gel (24 g cartridge, 0-20% EtOAc/isohexane) to afford the title compound (275 mg, 0.418 mmol, 69% yield, 99% purity) as a clear colourless oil. UPLC-MS (Method 1) m/z 651.7 $(M+H)^+$ at 2.30 min. $^1H$ NMR (500 MHz, DMSO-$d_6$) δ 8.44-8.40 (m, 1H), 8.11-8.04 (m, 2H), 7.69-7.63 (m, 1H), 7.34-7.28 (m, 2H), 5.45 (br s, 1H), 5.00 (br s, 1H), 3.86 (s, 3H), 3.38 (br s, 2H), 2.90-2.79 (m, 4H), 1.55 (br s, 4H), 1.53-1.48 (m, 2H), 0.67 (t, J=8.0 Hz, 2H), −0.16 (s, 9H).

Step 4: methyl 4-cyclopropyl-3-(N-(2-(piperidin-1-yl)-5-(trifluoromethyl)phenyl)sulfamoyl)benzoate: Two reactions were set up. A mixture of the product from step 3 above (20 mg, 0.030 mmol) and tributyl(cyclopropyl) stannane (20 mg, 0.060 mmol) in dioxane (0.5 ml) was purged with $N_2$ for 10 min before $^t$BuXPhos Pd G3 (2.5 mg, 3.15 μmol) was added. The mixture was purged with $N_2$ for 5 min and then heated to reflux and stirred overnight. The same reaction was set up using the product from step 3 above (80 mg, 0.122 mmol). The two reaction mixtures were combined, concentrated onto silica and purified by chromatography on silica gel (4 g cartridge, 0-50% EtOAc/isohexane) to provide the title compound (80 mg, 0.078 mmol, 51% yield, 47% purity) as a mixture with methyl 4-butyl-3-(N-(2-(piperidin-1-yl)-5-(trifluoromethyl)phenyl)sulfamoyl)benzoate (29% impurity). UPLC-MS (Method 1) m/z 483.3 $(M+H)^+$, 481.3 $(M-H)^-$ at 2.03 min.

Step 5: 4-cyclopropyl-3-(N-(2-(piperidin-1-yl)-5-(trifluoromethyl)phenyl)sulfamoyl)benzoic acid: A mixture of the product from step 4 above (80 mg, 0.078 mmol, 47% purity) and LiOH (30 mg, 0.702 mmol) in THF/MeOH/water (4:1:1, 2.4 ml) was stirred at 40° C. overnight. The mixture was diluted with water (5 ml) and the pH was adjusted to ~pH 4 using 1 M HCl(aq). The aqueous phase was extracted with EtOAc (3×20 ml). The combined organic phases were washed with brine (10 ml), dried by passage through a phase separator and the solvent was removed in vacuo. The crude product was purified by preparative HPLC (Waters, Acidic (0.1% Formic acid), Acidic, Waters X-Select Prep-C18, 5 μm, 19×50 mm column, 60-90% MeCN in Water) to afford the title compound (17.4 mg, 0.037 mmol, 47% yield, 99% purity) as a white solid. UPLC-MS (Method 1) m/z 469.3 $(M+H)^+$, 467.2 $(M-H)^-$ at 1.88 min. $^1H$ NMR (500 MHz, DMSO-$d_6$) δ8.44 (d, J=1.9 Hz, 1H), 7.98 (d, J=7.8 Hz, 1H), 7.35-7.26 (m, 2H), 7.25-7.17 (m, 1H), 7.12 (d, J=8.2 Hz, 1H), 2.88-2.77 (m, 5H), 1.63-1.55 (m, 4H), 1.52-1.45 (m, 2H), 1.11-1.04 (m, 2H), 0.86-0.79 (m, 2H). Two exchangeable protons not observed.

Example 268: 4-butyl-3-(N-(2-(piperidin-1-yl)-5-(trifluoromethyl)phenyl)sulfamoyl)benzoic acid

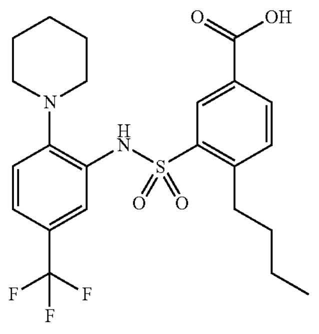 [SMILES: CCCCc1ccc(C(=O)O)cc1S(=O)(=O)Nc1cc(C(F)(F)F)ccc1N1CCCCC1]

The title compound (11.7 mg, 0.023 mmol, 53% yield, 95% purity) was obtained as a white solid by preparative HPLC (Waters, Acidic (0.1% Formic acid), Acidic, Waters X-Select Prep-C18, 5 μm, 19×50 mm column, 60-90% MeCN in Water) as a by-product from the reaction in Example 267 step 5. UPLC-MS (Method 1) m/z 485.3 $(M+H)^+$, 483.2 $(M-H)^-$ at 2.05 min. 1H NMR (500 MHz, DMSO-$d_6$) δ 8.39 (d, J=1.8 Hz, 1H), 8.03 (d, J=7.5 Hz, 1H), 7.53 (d, J=7.9 Hz, 1H), 7.43-7.28 (m, 2H), 7.26-7.15 (m, 1H), 2.92 (t, J=7.9 Hz, 2H), 2.81-2.66 (m, 4H), 1.61-1.41 (m, 8H), 1.39-1.29 (m, 2H), 0.87 (t, J=7.3 Hz, 3H). Two exchangeable protons not observed.

Example 269: I-3-(N-(2-(3-fluoropiperidin-1-yl)-5-(methylsulfonyl)phenyl)sulfamoyl)-4-methoxybenzoic acid

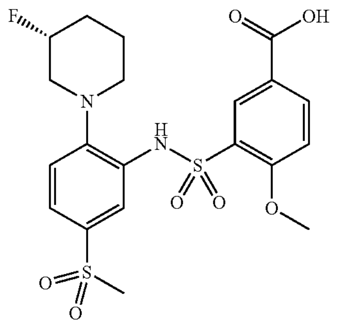 [SMILES: COc1ccc(C(=O)O)cc1S(=O)(=O)Nc1cc(S(C)(=O)=O)ccc1N1CCC[C@@H](F)C1]

Step 1: I-methyl 3-(N-(2-(3-fluoropiperidin-1-yl)-5-(methylsulfonyl)phenyl)sulfamoyl)-4-methoxybenzoate: The product from Example 262 step 2 (68.6 mg, 0.252 mmol) was dissolved in a mixture of DCM (1 ml) and pyridine (81 μl, 1.01 mmol) and treated with a solution of methyl 3-(chlorosulfonyl)-4-methoxybenzoate (80 mg, 0.302 mmol) in DCM (1 ml). The resultant solution was stirred at RT for 2 days. The crude product was purified directly by chromatography on silica gel (12 g cartridge, 0-100% EtOAc/isohexane) to afford the title compound (95.6 mg, 0.191 mmol, 76% yield) as a white solid. UPLC-MS (Method 1) m/z 501.3 $(M+H)^+$, 499.2 $(M-H)^-$ at 1.37 min.

Step 2: I-3-(N-(2-(3-fluoropiperidin-1-yl)-5-(methylsulfonyl)phenyl)sulfamoyl)-4-methoxybenzoic acid: The product from step 2 above (93 mg, 0.186 mmol) was dissolved in THF (5 ml) and treated with 1 M LiOH(aq) (743 μl, 0.743 mmol). MeOH was added dropwise until the mixture was a solution and the reaction was stirred at 30° C. for 20 h. Additional 1 M LiOH(aq) (743 μl, 0.743 mmol) was added and the reaction was stirred at 40° C. for a further 3 days. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. to afford the title compound (69.4 mg, 0.134 mmol, 72% yield, 94% purity) as a white solid. UPLC-MS (Method 1) m/z 487.2 $(M+H)^+$, 485.1 $(M-H)^-$ at 1.22 min. $^1H$ NMR (500 MHz, DMSO-$d_6$) δ 13.18 (br s, 1H), 8.82 (br s, 1H), 8.36 (d, J=2.2 Hz, 1H), 8.15 (dd, J=8.7, 2.2 Hz, 1H), 7.65 (d, J=2.2 Hz, 1H), 7.54 (dd, J=8.4, 2.2 Hz, 1H), 7.41-7.27 (m, 2H), 4.94-4.78 (m, 1H), 3.92 (s, 3H), 3.15-2.91 (m, 3H), 2.89-2.81 (m, 1H), 1.98-1.74 (m, 3H), 1.73-1.61 (m, 1H). Three protons obscured by solvent.

Example 270: 4-ethyl-3-(N-(2-(3-hydroxy-3-methyl-azetidin-1-yl)-5-(trifluoromethyl)phenyl) sulfamoyl) benzoic acid

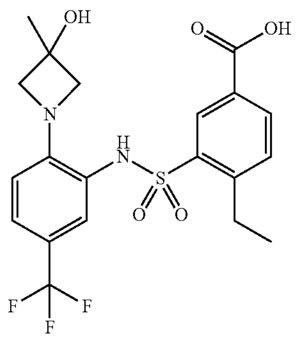 [SMILES: CCc1ccc(C(=O)O)cc1S(=O)(=O)Nc1cc(C(F)(F)F)ccc1N1CC(C)(O)C1]

Step 1: 3-methyl-1-(2-nitro-4-(trifluoromethyl)phenyl) azetidin-3-ol: $Et_3N$ (720 μl, 5.18 mmol) was added to a solution of 1-fluoro-2-nitro-4-(trifluoromethyl)benzene (201 μl, 1.44 mmol) and 3-methylazetidin-3-ol hydrochloride (230 mg, 1.87 mmol) in DCM (6 ml) and the resultant solution was stirred at RT for 20 h. 1 M HCl(aq) (2 ml) was added and the organic phase was dried by passage through a phase separator and concentrated in vacuo to afford the title compound (396 mg, 1.44 mmol, 100% yield) as a light orange viscous oil. UPLC-MS (Method 2) m/z no ionisation at 1.34 min.

Step 2: 1-(2-amino-4-(trifluoromethyl)phenyl)-3-methyl-azetidin-3-ol: 5% Pd/C (50% w/w water) Type 87L (107 mg, 0.025 mmol) in EtOH (1 ml) was added to a suspension of the product from step 1 above (396 mg, 1.44 mmol) in EtOH (6.4 ml) at RT. The reaction mixture was stirred at RT under $H_2$ (4 bar pressure) for 19 h. The catalyst was removed by filtration through Celite® and washed with MeOH (20 ml). The filtrate was concentrated in vacuo and the residue was suspended in DCM (5 ml) and dried by passage through a phase separator. The crude product was purified directly by chromatography on silica gel (24 g cartridge, 0-100% EtOAc/isohexane) to afford the title compound (326 mg, 1.32 mmol, 92% yield) as a light orange solid. UPLC-MS (Method 2) m/z 247.3 $(M+H)^+$ at 1.11 min.

Step 3: methyl 4-ethyl-3-(N-(2-(3-hydroxy-3-methylazetidin-1-yl)-5-(trifluoromethyl)phenyl)sulfamoyl)benzoate: The product from step 2 above (62.5 mg, 0.254 mmol) was dissolved in a mixture of DCM (1 ml) and pyridine (82 μl, 1.02 mmol) and treated with a solution of the product from Example 203 step 2 (80 mg, 0.305 mmol) in DCM (1 ml). The resultant solution was stirred at RT for 20 h. The crude product was purified directly by chromatography on silica gel (12 g cartridge, 0-100% EtOAc/isohexane) to afford the title compound (12.7 mg, 0.026 mmol, 10% yield, 95% purity) as a light pink viscous oil. UPLC-MS (Method 1) m/z 473.4 $(M+H)^+$, 471.3 $(M-H)^-$ at 1.52 min.

Step 4: 4-ethyl-3-(N-(2-(3-hydroxy-3-methylazetidin-1-yl)-5-(trifluoromethyl)phenyl)sulfamoyl)benzoic acid: The product from step 3 above (12.7 mg, 0.027 mmol) was dissolved in THF (2 ml) and treated with 1 M LiOH(aq) (108 μl, 0.108 mmol). MeOH was added dropwise until the mixture was a solution and the reaction was stirred at 30° C. for 2 days. Additional 1 M LiOH(aq) (108 μl, 0.108 mmol) was added and the reaction was stirred at 40° C. for 5 h. Additional 1 M LiOH(aq) (108 μl, 0.108 mmol) was added and the reaction was stirred at 40° C. for 3 days. Additional 1 M LiOH(aq) (108 μl, 0.108 mmol) was added and the reaction was stirred at 40° C. for 24 h. Additional 1 M LiOH(aq) (500 μl, 0.500 mmol) was added and the reaction was stirred at 40° C. for 24 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy suspension which was concentrated in vacuo to ~2 ml. The precipitate was collected by filtration, washing with water (2×2 ml). The solid was suspended in MeCN (4 ml), concentrated in vacuo and dried at 50° C. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (4 mg, 8.46 μmol, 32% yield, 97% purity) as a white solid. UPLC-MS (Method 1) m/z 459.3 $(M+H)^+$, 457.2 $(M-H)^-$ at 1.37 min. $^1H$ NMR (500 MHz, DMSO-$d_6$) δ 13.03 (br s, 1H), 9.60 (br s, 1H), 8.26 (d, J=1.8 Hz, 1H), 8.09 (d, J=7.7 Hz, 1H), 7.60 (d, J=7.5 Hz, 1H), 7.28 (br s, 1H), 6.49 (d, J=8.6 Hz, 1H), 6.33 (br s, 1H), 5.50 (s, 1H), 4.00 (d, J=8.1 Hz, 2H), 3.89 (d, J=8.1 Hz, 2H), 2.94 (q, J=7.4 Hz, 2H), 1.42 (s, 3H), 1.17 (t, J=7.4 Hz, 3H).

Example 271: 3-(N-(2-(piperidin-1-yl)-5-(trifluoromethyl)phenyl)sulfamoyl)-4-(pyrazol-1-yl)benzoic acid

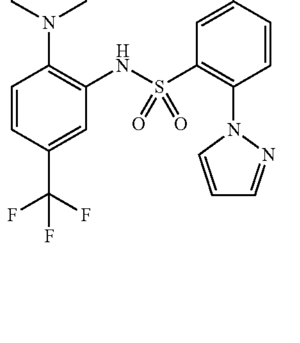

Step 1: methyl 3-(N-(2-(piperidin-1-yl)-5-(trifluoromethyl)phenyl)sulfamoyl)-4-(pyrazol-1-yl)benzoate: To a degassed solution of Example 267 Step 3 (100 mg, 0.152 mmol) in DMSO (0.75 ml) was added pyrazole (25.0 mg, 0.367 mmol), CuI (10 mg, 0.053 mmol), L-proline (8.0 mg, 0.069 mmol) and $K_2CO_3$ (75.0 mg, 0.543 mmol). The mixture was heated to 90° C. overnight. The mixture was diluted with water (10 ml) and EtOAc (10 ml) and the solid was removed by filtration. The filtrate was extracted with EtOAc (3×15 mL), the organic phases were then combined, washed with brine (10 ml) and dried by passage through a phase separator. The solvent was removed in vacuo and the crude product was purified by chromatography on silica gel (4 g cartridge, 0-100% EtOAc/isohexane) to afford the title compound (0.30 g, 0.047 mmol, 31% yield, 80% purity) as a pale yellow solid. UPLC-MS (Method 1) m/z 509.2 $(M+H)^+$, 507.2 $(M-H)^-$ at 1.98 min. $^1H$ NMR (500 MHz, DMSO-$d_6$) δ 13.68 (s, 1H), 10.00 (s, 1H), 8.51 (d, J=2.0 Hz, 1H), 8.45-8.35 (m, 1H), 8.31-8.25 (m, 1H), 8.02-7.96 (m, 1H), 7.85 (d, J=8.3 Hz, 1H), 7.81-7.77 (m, 1H), 7.46-7.40 (m, 1H), 7.38-7.33 (m, 1H), 6.69 (s, 1H), 2.74-2.66 (m, 4H), 1.63-1.55 (m, 4H), 1.52-1.46 (m, 2H).

Step 2: 3-(N-(2-(piperidin-1-yl)-5-(trifluoromethyl)phenyl)sulfamoyl)-4-(pyrazol-1-yl)benzoic acid: A mixture of the product from step 1 above (30 mg, 0.047 mmol) and LiOH (5.6 mg, 0.23 mmol) in THF/MeOH/water (4:1:1, 1 ml) was stirred at 40° C. overnight. The mixture was diluted with water (5 ml), acidified to ~pH 4 using 1 M HCl(aq) and extracted with EtOAc (3×20 ml). The combined organic extracts were washed with brine (10 ml), dried by passage through a phase separator and the solvent was removed in vacuo. The residue was loaded onto silica and purified by chromatography on silica gel (4 g cartridge, 0-100% EtOAc/isohexane) to afford the title compound (9.0 mg, 0.018 mmol, 37% yield, 97% purity) as a white solid. UPLC-MS (Method 1) m/z 495.2 $(M+H)^+$, 493.1 $(M-H)^-$ at 1.33 min. $^1H$ NMR (500 MHz, DMSO-$d_6$) δ13.68 (s, 1H), 10.00 (s, 1H), 8.51 (d, J=2.0 Hz, 1H), 8.45-8.35 (m, 1H), 8.31-8.25 (m, 1H), 8.02-7.96 (m, 1H), 7.85 (d, J=8.3 Hz, 1H), 7.81-7.77 (m, 1H), 7.46-7.40 (m, 1H), 7.38-7.33 (m, 1H), 6.69 (s, 1H), 2.74-2.66 (m, 4H), 1.63-1.55 (m, 4H), 1.52-1.46 (m, 2H).

Example 272: 4-(oxetan-2-yl)-3-(N-(2-(piperidin-1-yl)-5-(trifluoromethyl)phenyl) sulfamoyl)benzoic acid

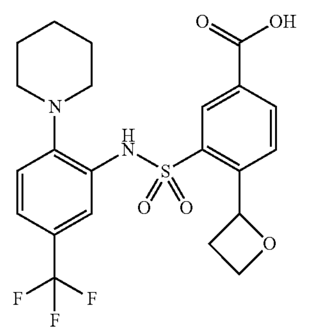 [SMILES: O=C(O)c1ccc(C2CCO2)c(S(=O)(=O)Nc2cc(C(F)(F)F)ccc2N2CCCCC2)c1]

Step 1: methyl 4-bromo-2-(N-(2-(piperidin-1-yl)-5-(trifluoromethyl)phenyl)-N-((2-(trimethylsilyl) ethoxy)methyl) sulfamoyl)benzoate: A solution of the product from Example 228 Step 1 (1.20 g, 2.30 mmol) in THF (10 ml, 122 mmol) was cooled to 0° C., then treated with sodium hydride (0.138 g, 3.45 mmol, 60% w/w in mineral oil). The mixture was warmed to RT and stirred for 1 h, then treated with SEM-CI (0.572 ml, 3.22 mmol). The resultant mixture was stirred at RT overnight, then diluted with water (50 ml) and extracted with EtOAc (50 ml). The organic phase was dried ($MgSO_4$), filtered and concentrated in vacuo. The residue was purified by chromatography on silica gel (40 g cartridge, 0-50% TBME/isohexane) to afford the title compound (1.33 g, 1.8 mmol, 80% yield, 90% purity) as a colourless oil. UPLC-MS (Method 1) m/z 651.3 $(M+H)^+$ at 2.30 min. $^1H$ NMR (500 MHz, DMSO-$d_6$) δ 8.11 (d, J=1.9 Hz, 1H), 8.04 (dd, J=8.2, 1.9 Hz, 1H), 7.71-7.64 (m, 1H), 7.62 (dd, J=8.3, 1.8 Hz, 1H), 7.30 (d, J=8.6 Hz, 1H), 7.27-7.21 (m, 1H), 5.76 (s, 2H), 3.61 (s, 3H), 3.52-3.42 (m, 2H), 3.00-2.75 (m, 4H), 1.54-1.48 (m, 6H), 0.84-0.76 (m, 2H), −0.13 (s, 9H).

Step 2: 5-bromo-2-(hydroxymethyl)-N-(2-(piperidin-1-yl)-5-(trifluoromethyl)phenyl)-N-((2-(trimethylsilyl) ethoxy)methyl)benzenesulfonamide: A solution of the product from Step 1 above (1.20 g, 1.66 mmol, 90% purity) in THF (20 ml, 244 mmol) was cooled to 0° C., then treated with 2.0 M $LiAlH_4$ in THF (0.921 ml, 1.8 mmol, 90% purity). The mixture was stirred at 0° C. for 1 h. The mixture was carefully quenched with water (20 ml) and extracted with EtOAc (100 ml). The organic phase was dried ($MgSO_4$), filtered and concentrated in vacuo. The residue was purified by chromatography on silica gel (40 g cartridge, 0-20% TBME/isohexane) to afford the title compound (0.685 g, 1.00 mmol, 60% yield, 90% purity) as a colourless oil. UPLC-MS (Method 1) m/z 622.9 $(M+H)^+$ at 2.25 min. $^1H$ NMR (500 MHz, DMSO-$d_6$)· 7.98-7.88 (m, 2H), 7.80 (d, J=8.3 Hz, 1H), 7.70-7.61 (m, 1H), 7.29 (d, J=8.6 Hz, 1H), 7.19 (d, J=2.3 Hz, 1H), 5.48 (t, J=5.3 Hz, 1H), 4.64 (d, J=45.8 Hz, 2H), 3.32 (s, 2H), 2.97-2.92 (m, 4H), 1.62-1.45 (m, 6H), 0.90-0.80 (m, 2H), 0.77-0.68 (m, 2H), −0.15 (s, 9H).

Step 3: 5-bromo-2-formyl-N-(2-(piperidin-1-yl)-5-(trifluoromethyl)phenyl)-N-((2-(trimethylsilyl) ethoxy)methyl) benzenesulfonamide: The product from Step 2 above (0.685 g, 1.00 mmol, 90% purity) in DCM (20 ml, 311 mmol) was treated with MnO2 (0.955 g, 10.9 mmol). The mixture was stirred at RT for 2 h, then filtered through Celite®, and concentrated in vacuo. The residue was purified by chromatography on silica gel (40 g cartridge, 0-20% TBME/isohexane) to afford the title compound (0.410 g, 0.60 mmol, 61% yield, 92% purity) as a colourless oil. UPLC-MS (Method 1) m/z 621.3 $(M+H)^+$ at 2.35 min. $^1H$ NMR (500 MHz, DMSO-$d_6$) δ 10.10 (d, J=0.8 Hz, 1H), 8.23-8.07 (m, 1H), 8.02 (d, J=2.0 Hz, 1H), 7.90 (d, J=8.3 Hz, 1H), 7.65 (dd, J=8.8, 2.3 Hz, 1H), 7.28 (d, J=8.6 Hz, 1H), 7.08 (d, J=2.3 Hz, 1H), 5.48 (d, J=10.7 Hz, 1H), 4.87 (d, J=10.8 Hz, 1H), 3.08-3.02 (br m, 4H), 1.65-1.52 (m, 6H), 0.93-0.78 (m, 2H), 0.73-0.62 (m, 2H), −0.15 (s, 9H).

Step 4: 5-bromo-2-(oxetan-2-yl)-N-(2-(piperidin-1-yl)-5-(trifluoromethyl)phenyl)-N-((2-(trimethylsilyl) ethoxy) methyl)benzenesulfonamide: Trimethylsulphoxonium iodide (0.581 g, 2.64 mmol) in tert-butanol (10 ml, 105 mmol) was treated with KOtBu (0.296 g, 2.64 mmol). The mixture was stirred at 50° C. for 30 min, then treated with the product from Step 3 above (0.410 g, 0.607 mmol, 92% purity). The resultant mixture was stirred at 50° C. overnight, then filtered and concentrated in vacuo. The residue was purified by chromatography on silica gel (40 g cartridge, 0-20% TBME/isohexane) to afford the title compound (0.165 g, 0.24 mmol, 40% yield, 95% purity) as a colourless oil. UPLC-MS (Method 1) m/z 649.3 at 2.40 min.

Step 5: methyl 4-(oxetan-2-yl)-3-(N-(2-(piperidin-1-yl)-5-(trifluoromethyl)phenyl)-N-((2-(trimethylsilyl) ethoxy)methyl)sulfamoyl)benzoate: A solution of the product from Step 4 above (0.160 g, 0.234 mmol), triethylamine (0.069 ml, 0.494 mmol) and PdCl2 (dppf)· DCM (0.040 g, 0.049 mmol) in MeOH (10 ml) was stirred at 100° C. under a CO atmosphere (4 bar). After 24 h, the reaction was cooled, filtered through Celite® and concentrated in vacuo. The residue was purified by chromatography on silica gel (24 g cartridge, 0-20% EtOAc/isohexane) to afford the title compound (0.085 g, 0.134 mmol, 57% yield, 99% purity) as a colourless oil. UPLC-MS (Method 1) m/z 629.4 $(M+H)^+$ at 2.28 min.

Step 6: 4-(oxetan-2-yl)-3-(N-(2-(piperidin-1-yl)-5-(trifluoromethyl)phenyl)sulfamoyl)benzoic acid: A solution of the product from Step 5 above (0.085 g, 0.134 mmol, 99% purity) in THF (5 ml, 0.13 mmol) was treated with 1.0 M TBAF in THF (0.135 ml, 0.135 mmol) and stirred at RT for 16 h. Additional 1.0 M TBAF in THF (0.135 ml, 0.135 mmol) added and the resultant mixture heated at 40° C. for 80 h. The mixture was then treated with a solution of LiOH (9.71 mg, 0.40 mmol) in water (2 ml) and stirred at RT for 3 h. The mixture was acidified using 1.0 M citric acid (aq) and extracted with EtOAc (50 ml). The organic phase was dried ($MgSO_4$), filtered and concentrated in vacuo. The residue was purified by chromatography on silica gel (24 g cartridge, 0-100% EtOAc/isohexane, followed by 0-10% MeOH/EtOAc) to afford the title compound (10.3 mg, 0.020 mmol, 15% yield, 98% purity) as a colourless solid. UPLC-MS (Method 1) m/z 485.3 $(M+H)^+$ at 1.73 min. $^1H$ NMR (500 MHz, DMSO-$d_6$) δ 13.37 (s, 1H), 9.61 (s, 1H), 8.31-8.21 (m, 2H), 8.16 (d, J=8.0 Hz, 1H), 7.45 (d, J=8.5 Hz, 1H), 7.31 (d, J=2.2 Hz, 1H), 7.21 (d, J=8.4 Hz, 1H), 6.34 (t, J=7.5 Hz, 1H), 4.69 (td, J=7.9, 5.9 Hz, 1H), 4.57 (dt, J=9.1, 6.1 Hz, 1H), 3.19-3.09 (m, 1H), 2.79-2.67 (m, 2H), 2.60-2.53 (m, 2H), 2.42-2.32 (m, 1H), 1.54-1.46 (m, 4H), 1.45-1.38 (m, 2H).

Example 273: 4-ethyl-3-(N-(5-(1-methyl-1,2,3-triazol-4-yl)-2-(piperidin-1-yl)phenyl) sulfamoyl)benzoic acid

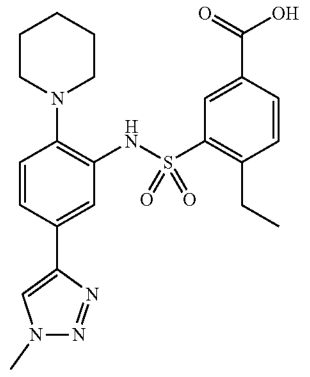 [SMILES: CCc1ccc(C(=O)O)cc1S(=O)(=O)Nc1cc(-c2cn(C)nn2)ccc1N1CCCCC1]

Step 1: 1-(4-bromo-2-nitrophenyl)piperidine: Piperidine (9.88 ml, 45.5 mmol) was added to a solution of 4-bromo-1-fluoro-2-nitrobenzene (5.60 ml, 45.5 mmol) in MeCN (50 ml) and then the resulting solution was stirred at RT for 2 h. The solution was concentrated in vacuo. The residue was purified by chromatography on silica gel (220 g cartridge, 0-50% EtOAc/isohexane) to afford the title compound (13.4 g, 44.7 mmol, 97% yield, 94% purity) as a red oil. UPLC-MS (Method 1) m/z 285.1 $(M+H)^+$ at 1.82 min. $^1H$ NMR (500 MHz, DMSO-$d_6$) 7.99 (d, J=2.4 Hz, 1H), 7.71 (dd, J=8.9, 2.5 Hz, 1H), 7.24 (d, J=8.9 Hz, 1H), 3.01-2.86 (m, 4H), 1.63-1.55 (m, 4H), 1.55-1.49 (m, 2H).

Step 2: 1-(2-nitro-4-(4,4,5,5-tetramethyl-1,3,2-dioxaborolan-2-yl)phenyl)piperidine: A mixture of the product from Step 1 above (12.30 g, 43.1 mmol, 94% purity), Bis(pinacolato)diboron (13.2 g, 51.8 mmol), KOAc (12.7 g, 129 mmol) and $PdCl_2$ (dppf)· DCM (3.16 g, 4.31 mmol) in dioxane (10 ml) was degassed with $N_2$ for 15 min and then heated at 80° C. for 16 h. The mixture was diluted with water (250 ml) and extracted with EtOAc (250 ml). The organic phase was dried ($MgSO_4$), filtered and concentrated in vacuo. The residue was purified by chromatography on silica gel (220 g cartridge, 0-50% EtOAc/isohexane) to afford the title compound (15.6 g, 44.7 mmol, 97% yield, 85% purity) as a brown oil. UPLC-MS (Method 1) m/z 333.3 $(M+H)^+$ at 1.99 min.

$^1H$ NMR (500 MHz, DMSO-$d_6$) δ 7.95 (d, J=1.6 Hz, 1H), 7.73 (dd, J=8.4, 1.6 Hz, 1H), 7.23 (d, J=8.4 Hz, 1H), 3.10-2.99 (m, 4H), 1.67-1.49 (m, 6H), 1.29 (s, 12H).

Step 3: 2-(piperidin-1-yl)-5-(4,4,5,5-tetramethyl-1,3,2-dioxaborolan-2-yl)aniline: A solution of the product from Step 2 above (15.6 g, 35.2 mmol, 85% purity) in MeOH (20 ml, 494 mmol) was treated with 10% Pd/C (3.75 g, 3.52 mmol). The resultant mixture was hydrogenated (2 bar) for 16 h, and then filtered through Celite® and concentrated in vacuo. The residue was purified by chromatography on silica gel (220 g cartridge, 0-50% EtOAc/isohexane) to afford the title compound (5.20 g, 12.0 mmol, 41% yield, 95% purity) as a brown solid. UPLC-MS (Method 1) m/z 303.3 $(M+H)^+$ at 1.41 min. $^1H$ NMR (500 MHz, DMSO-$d_6$) δ 7.04 (d, J=1.4 Hz, 1H), 6.90 (dd, J=7.7, 1.5 Hz, 1H), 6.84 (d, J=7.7 Hz, 1H), 4.63 (s, 2H), 2.80-2.70 (m, 4H), 1.65 (p, J=5.6 Hz, 4H), 1.55-1.49 (m, 2H), 1.26 (s, 12H).

Step 4: methyl 4-ethyl-3-(N-(2-(piperidin-1-yl)-5-(4,4,5,5-tetramethyl-1,3,2-dioxaborolan-2-yl)phenyl)sulfamoyl) benzoate: A solution of product from Step 3 above (3.53 g, 11.1 mmol, 95% purity), methyl 3-(chlorosulfonyl)-4-ethylbenzoate (3.20 g, 12.18 mmol) and pyridine (3.60 ml, 44.5 mmol) in DCM (20 ml) was vigorously stirred at RT for 41 h. The reaction mixture was loaded onto Celite® and purified by chromatography on silica gel (80 g cartridge, 0-100% EtOAc/isohexane) to afford the title compound (4.89 g, 9.16 mmol, 83% yield, 99% purity) as an off-white solid. UPLC-MS (Method 1) m/z 529.4 $(M+H)^+$ at 2.12 min. $^1H$ NMR (500 MHz, DMSO-$d_6$) δ 9.04 (br s, 1H), 8.38 (d, J=1.9 Hz, 1H), 8.11 (dd, J=8.0, 1.9 Hz, 1H), 7.62 (d, J=8.1 Hz, 1H), 7.34 (dd, J=7.9, 1.5 Hz, 1H), 7.31 (d, J=1.4 Hz, 1H), 7.07 (d, J=7.9 Hz, 1H), 3.85 (s, 3H), 3.05 (q, J=7.4 Hz, 2H), 2.68 (app. T, J=5.2 Hz, 4H), 1.59-1.49 (m, 4H), 1.49-1.41 (m, 2H), 1.24-1.18 (m, 15H).

Step 5: methyl 4-ethyl-3-(N-(5-(1-methyl-1,2,3-triazol-4-yl)-2-(piperidin-1-yl)phenyl)sulfamoyl)benzoate: To the reaction vessel containing product from Step 4 above (0.150 g, 0.28 mmol, 99% purity), 4-bromo-1-methyl-1,2,3-triazole (0.055 g, 0.34 mmol), $K_3PO_4$ (0.078 g, 0.37 mmol) in dioxane (5 ml, 0.28 mmol) and water (1 ml) was added Xphos Pd G3 (0.024 g, 0.03 mmol). The resultant mixture was degassed with $N_2$ for 15 min and then heated at 80° C. for 2 h. The reaction mixture was allowed to cool to RT and then concentrated in vacuo. The residue was purified by chromatography on silica gel (24 g cartridge, 0-100% EtOAc/isohexane) to afford the title compound (0.106 g, 0.22 mmol, 77% yield) as a white solid. UPLC-MS (Method 1) m/z 484.4 $(M+H)^+$ at 1.67 min.

Step 6: 4-ethyl-3-(N-(5-(1-methyl-1,2,3-triazol-4-yl)-2-(piperidin-1-yl)phenyl)sulfamoyl)benzoic acid: 1 M LiOH (aq) (0.658 ml, 0.658 mmol) was added to a solution of the product from Step 5 above (0.106 g, 0.219 mmol) in THF (5 ml, 61.0 mmol) and stirred at RT overnight. The mixture was then acidified to pH 6 using 10% w/v citric acid (aq) and the resultant precipitate was collected by filtration to afford the title compound (67.2 mg, 0.136 mmol, 65% yield, 99% purity) as a white solid. UPLC-MS (Method 1) m/z 470.4 $(M+H)^+$ at 1.58 min. $^1H$ NMR (500 MHz, DMSO-$d_6$) δ13.37 (br s, 1H), 9.26 (br s, 1H), 8.38 (d, J=1.9 Hz, 1H), 8.09 (dd, J=8.0, 1.9 Hz, 1H), 7.71 (s, 1H), 7.61 (d, J=8.1 Hz, 1H), 7.32 (dd, J=8.2, 2.1 Hz, 1H), 7.29-7.24 (m, 2H), 3.95 (s, 3H), 3.07 (q, J=7.4 Hz, 2H), 2.66 (t, J=5.3 Hz, 4H), 1.62-1.55 (m, 4H), 1.51-1.44 (m, 2H), 1.23 (t, J=7.4 Hz, 3H).

Example 274:4-ethyl-3-(N-(5-(1-methyl-1,2,3-triazol-5-yl)-2-(piperidin-1-yl)phenyl) sulfamoyl)benzoic acid

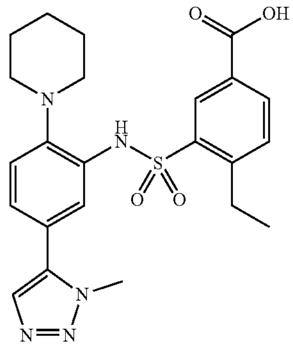 [SMILES: CCc1ccc(C(=O)O)cc1S(=O)(=O)Nc1cc(-c2cnnn2C)ccc1N1CCCCC1]

Step 1: methyl 4-ethyl-3-(N-(5-(1-methyl-1,2,3-triazol-5-yl)-2-(piperidin-1-yl)phenyl)sulfamoyl)benzoate: To the reaction vessel containing the product from Example 273 Step 4 (0.150 g, 0.28 mmol, 99% purity), 5-bromo-1-methyl-1,2,3-triazole (0.055 g, 0.34 mmol), $K_3PO_4$ (0.078 g, 0.36 mmol) in dioxane (5 ml, 0.28 mmol) and water (1 ml) was added Xphos Pd G3 (0.024 g, 0.03 mmol). The resultant mixture was degassed with $N_2$ for 15 min and then heated at 80° C. for 2 h. The reaction mixture was allowed to cool to RT and then concentrated in vacuo. The residue was purified by chromatography on silica gel (24 g cartridge, 0-100% EtOAc/isohexane) to afford the title compound (0.115 g, 0.238 mmol, 85% yield) as a light brown oil. UPLC-MS (Method 1) m/z 484.4 $(M+H)^+$ at 1.65 min.

Step 2: 4-ethyl-3-(N-(5-(1-methyl-1,2,3-triazol-5-yl)-2-(piperidin-1-yl)phenyl)sulfamoyl)benzoic acid: 1 M LiOH (aq) (0.713 ml, 0.71 mmol) was added to a solution of the product from Step 1 above (0.115 g, 0.238 mmol) in THF (5 ml) and stirred at RT overnight. The mixture was then acidified to pH 6 using 10% w/v citric acid (aq) and the resultant precipitate was collected by filtration to afford the title compound (76.1 mg, 0.154 mmol, 67% yield, 99% purity) as a white solid. UPLC-MS (Method 1) m/z 470.4 $(M+H)^+$ at 1.55 min. $^1H$ NMR (500 MHz, DMSO-$d_6$) δ 8.99 (br s, 1H), 8.42 (d, J=1.8 Hz, 1H), 8.36 (s, 1H), 8.05 (dd, J=7.9, 1.8 Hz, 1H), 7.70 (d, J=2.0 Hz, 1H), 7.56 (d, J=8.0 Hz, 1H), 7.49 (dd, J=8.2, 2.0 Hz, 1H), 7.21 (d, J=8.3 Hz, 1H), 4.06 (s, 3H), 3.06 (q, J=7.4 Hz, 2H), 2.61 (t, J=5.2 Hz, 4H), 1.57 (p, J=5.4 Hz, 4H), 1.50-1.45 (m, 2H), 1.21 (t, J=7.4 Hz, 3H).

Example 275:4-ethyl-3-(N-(2-(piperidin-1-yl)-5-(thiazol-5-yl)phenyl)sulfamoyl)benzoic acid

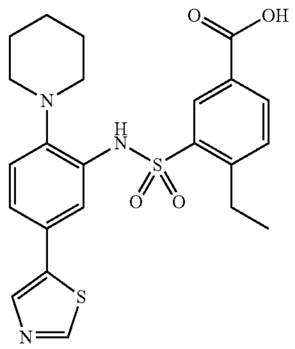 [SMILES: CCc1ccc(C(=O)O)cc1S(=O)(=O)Nc1cc(-c2cncs2)ccc1N1CCCCC1]

Step 1: methyl 4-ethyl-3-(N-(2-(piperidin-1-yl)-5-(thiazol-5-yl)phenyl)sulfamoyl)benzoate: To the reaction vessel containing the product from Example 273 Step 4 (0.150 g, 0.28 mmol, 99% purity), 5-bromothiazole (0.056 g, 0.34 mmol), $K_3PO_4$ (0.078 g, 0.37 mmol) in dioxane (5 ml) and water (1 ml) was added Xphos Pd G3 (0.024 g, 0.03 mmol). The resultant mixture was degassed with $N_2$ for 15 min and then heated at 80° C. for 6 h. The reaction mixture was allowed to cool to RT and then concentrated in vacuo. The residue was purified by chromatography on silica gel (24 g cartridge, 0-100% EtOAc/isohexane) to afford the title compound (0.100 g, 0.19 mmol, 69% yield, 95% purity) as a brown oil. UPLC-MS (Method 1) m/z 486.3 $(M+H)^+$ at 1.80 min.

Step 2: 4-ethyl-3-(N-(2-(piperidin-1-yl)-5-(thiazol-5-yl)phenyl)sulfamoyl)benzoic acid: 1.0 M LiOH(aq) (0.587 ml, 0.587 mmol) was added to a solution of the product from Step 1 above (0.100 g, 0.196 mmol, 95% purity) in THF (5 ml) and stirred at RT overnight. The mixture was then acidified to pH 6 with 10% w/v citric acid (aq) and the resultant precipitate was collected by filtration to afford the title compound (71.2 mg, 0.143 mmol, 75% yield, 97% purity) as a white solid. UPLC-MS (Method 1) m/z 472.3 $(M+H)^+$ at 1.75 min. $^1H$ NMR (500 MHz, DMSO-$d_6$) δ 13.36 (br s, 1H), 9.16 (br s, 1H), 9.03 (s, 1H), 8.44 (d, J=1.8 Hz, 1H), 8.10 (dd, J=8.0, 1.8 Hz, 1H), 8.05 (s, 1H), 7.62 (d, J=8.0 Hz, 1H), 7.42 (dd, J=8.3, 2.2 Hz, 1H), 7.28 (d, J=2.2 Hz, 1H), 7.19 (d, J=8.3 Hz, 1H), 3.07 (q, J=7.4 Hz, 2H), 2.67 (t, J=5.2 Hz, 4H), 1.59 (p, J=5.7 Hz, 4H), 1.48 (m, 2H), 1.22 (t, J=7.4 Hz, 3H).

Example 276: 4-ethyl-3-(N-(2-(piperidin-1-yl)-5-(pyrazol-3-yl)phenyl)sulfamoyl)benzoic acid

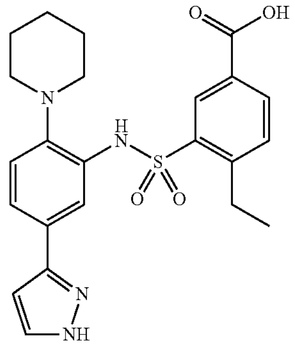 [SMILES: CCc1ccc(C(=O)O)cc1S(=O)(=O)Nc1cc(-c2cc[nH]n2)ccc1N1CCCCC1]

To the reaction vessel containing the product from Example 273 Step 4 (0.150 g, 0.28 mmol, 99% purity), 3-bromopyrazole (0.050 g, 0.34 mmol), $K_3PO_4$ (0.078 g, 0.37 mmol) in dioxane (5 ml) and water (1 ml) was added Xphos Pd G3 (0.024 g, 0.03 mmol). The resultant mixture was degassed with $N_2$ for 15 min and then heated at 80° C. for 10 h. The mixture was treated with 1 M NaOH (aq) (2 ml) and stirred for 1 h at RT and then extracted with TBME (50 ml). The aqueous phase was neutralised with saturated $NH_4Cl$ (aq) (1 ml) and extracted with EtOAc (20 ml). The organic phase was dried ($MgSO_4$), filtered and concentrated in vacuo. The crude product was purified by preparative HPLC (Waters, Acidic (0.1% Formic acid), Acidic, Waters X-Select Prep-C18, 5 μm, 19×50 mm column, 10-80% MeCN in Water) to afford the title compound to afford the title compound (18.2 mg, 0.04 mmol, 14% yield, 99% purity) as a brown solid. UPLC-MS (Method 1) m/z 455.4 $(M+H)^+$ at 1.54 min. $^1H$ NMR (500 MHz, DMSO-$d_6$) δ 13.13 (br s, 1H), 8.99 (s, 1H), 8.42 (d, J=1.8 Hz, 1H), 8.07 (dd, J=8.0, 1.8 Hz, 1H), 7.67 (s, 1H), 7.62-7.52 (m, 2H), 7.48 (dd, J=8.2, 2.0 Hz, 1H), 7.18 (d, J=8.3 Hz, 1H), 6.43 (d, J=2.2 Hz, 1H), 3.07 (q, J=7.4 Hz, 2H), 2.68-2.58 (m, 4H), 1.57 (p, J=5.4 Hz, 4H), 1.50-1.44 (m, 2H), 1.22 (t, J=7.4 Hz, 3H).

Example 277:4-ethyl-3-(N-(5-(1-methylpyrazol-4-yl)-2-(piperidin-1-yl)phenyl)sulfamoyl)benzoic acid

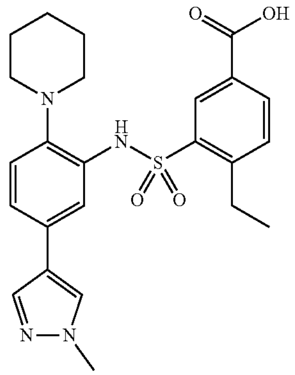 [SMILES: CCc1ccc(C(=O)O)cc1S(=O)(=O)Nc1cc(-c2cnn(C)c2)ccc1N1CCCCC1]

Step 1: methyl 4-ethyl-3-(N-(5-(1-methylpyrazol-4-yl)-2-(piperidin-1-yl)phenyl)sulfamoyl)benzoate: To the reaction vessel containing the product from Example 273 Step 4 (0.150 g, 0.28 mmol, 99% purity), 4-bromo-1-methylpyrazole (0.054 g, 0.34 mmol), $K_3PO_4$ (0.078 g, 0.37 mmol) in dioxane (5 ml) and water (1 ml) was added Xphos Pd G3 (0.024 g, 0.03 mmol). The resultant mixture was degassed with $N_2$ for 15 min and then heated at 80° C. for 2 h. The reaction mixture was allowed to cool to RT and then concentrated in vacuo. The residue was purified by chromatography on silica gel (24 g cartridge, 0-60% EtOAc/isohexane) to afford the title compound (0.105 g, 0.214 mmol, 76% yield, 98% purity) as a light brown oil. UPLC-MS (Method 1) m/z 483.4 $(M+H)^+$ at 1.76 min.

Step 2: 4-ethyl-3-(N-(5-(1-methylpyrazol-4-yl)-2-(piperidin-1-yl)phenyl)sulfamoyl)benzoic acid: 1.0 M LiOH(aq) (0.640 ml, 0.640 mmol) was added to a solution of the product from Step 1 above (0.105 g, 0.21 mmol, 98% purity) in THF (5 ml) and the resultant mixture stirred at RT overnight. The mixture was then acidified to pH 6 with 10% w/v citric acid (aq) and the resultant precipitate was collected by filtration to afford the title compound (41.9 mg, 0.085 mmol, 41% yield, 98% purity) as a tan solid. UPLC-MS (Method 1) m/z 469.4 $(M+H)^+$ at 1.64 min. $^1H$ NMR (500 MHz, DMSO-$d_6$) δ 13.40 (s, 1H), 8.92 (s, 1H), 8.48 (d, J=1.8 Hz, 1H), 8.08 (dd, J=8.0, 1.8 Hz, 1H), 7.91 (s, 1H), 7.59 (d, J=8.1 Hz, 1H), 7.58 (d, J=0.8 Hz, 1H), 7.28 (d, J=2.0 Hz, 1H), 7.21 (dd, J=8.2, 2.1 Hz, 1H), 7.14 (d, J=8.3 Hz, 1H), 3.84 (s, 3H), 3.06 (q, J=7.4 Hz, 2H), 2.59 (t, J=5.2 Hz, 4H), 1.59 (p, J=5.5 Hz, 4H), 1.52-1.45 (m, 2H), 1.22 (t, J=7.4 Hz, 3H).

Example 278: 4-ethyl-3-(N-(2-(piperidin-1-yl)-5-(1,3,4-thiadiazol-2-yl)phenyl)sulfamoyl)benzoic acid

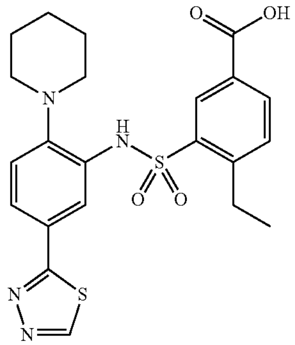

Step 1: methyl 4-ethyl-3-(N-(2-(piperidin-1-yl)-5-(1,3,4-thiadiazol-2-yl)phenyl)sulfamoyl)benzoate: To the reaction vessel containing the product from Example 273 Step 4 (0.150 g, 0.28 mmol, 99% purity), 2-bromo-1,3,4-thiadiazole (0.056 g, 0.34 mmol), $K_3PO_4$ (0.078 g, 0.36 mmol) in dioxane (4 ml, 0.28 mmol) and water (1 ml) was added Xphos Pd G3 (0.024 g, 0.03 mmol). The resultant mixture was degassed with $N_2$ for 15 min and then heated at 80° C. for 16 h. The reaction mixture was allowed to cool to RT and then concentrated in vacuo. The residue was purified by chromatography on silica gel (24 g cartridge, 0-50% EtOAc/isohexane) to afford the title compound (0.021 g, 0.04 mmol, 13% yield, 86% purity) as colourless oil. UPLC-MS (Method 1) m/z 487.3 $(M+H)^+$ at 1.78 min.

Step 2: 4-ethyl-3-(N-(2-(piperidin-1-yl)-5-(1,3,4-thiadiazol-2-yl)phenyl)sulfamoyl)benzoic acid: 1 M LiOH(aq) (0.111 ml, 0.11 mmol) was added to a solution of the product from Step 1 above (0.021 g, 0.04 mmol, 86% purity) in THF (5 ml) and the resultant mixture stirred at RT overnight. The mixture was then acidified to pH 6 using 10% w/v citric acid (aq) and the resultant precipitate was collected by filtration to afford the title compound (1.8 mg, 3.62 μmol, 10% yield, 95% purity) as a white solid. UPLC-MS (Method 1) m/z 473.3 $(M+H)^+$ at 1.63 min. $^1H$ NMR (500 MHz, DMSO-$d_6$) δ 9.55 (br s, 1H), 8.40 (d, J=1.8 Hz, 1H), 8.07 (d, J=8.1 Hz, 1H), 7.66 (d, J=2.0 Hz, 2H), 7.59 (d, J=8.0 Hz, 1H), 7.21 (d, J=8.1 Hz, 1H), 3.08 (q, J=7.4 Hz, 2H), 2.77 (t, J=5.8 Hz, 4H), 1.60-1.54 (m, 4H), 1.51-1.45 (m, 2H), 1.20 (t, J=7.4 Hz, 3H).

Example 279: 4-ethyl-3-(N-(5-(5-methylisoxazol-4-yl)-2-(piperidin-1-yl)phenyl)sulfamoyl)benzoic acid

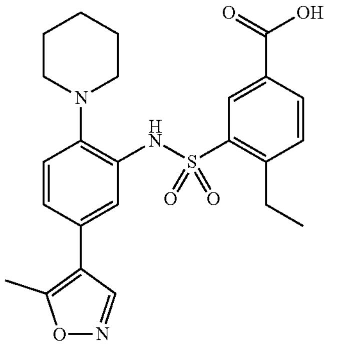 [SMILES: CCc1ccc(C(=O)O)cc1S(=O)(=O)Nc1cc(-c2cnoc2C)ccc1N1CCCCC1]

Step 1: methyl 4-ethyl-3-(N-(5-(5-methylisoxazol-4-yl)-2-(piperidin-1-yl)phenyl)sulfamoyl)benzoate: To the reaction vessel containing the product from Example 273 Step 4 (0.150 g, 0.28 mmol, 99% purity), 4-bromo-5-methylisoxazole (0.055 g, 0.34 mmol), $K_3PO_4$ (0.078 g, 0.36 mmol) in dioxane (4 ml, 0.28 mmol) and water (1 ml) was added Xphos Pd G3 (0.024 g, 0.03 mmol). The resultant mixture was degassed with $N_2$ for 15 min and then heated at 80° C. for 16 h. The reaction mixture was allowed to cool to RT and then concentrated in vacuo. The residue was purified by chromatography on silica gel (24 g cartridge, 0-30% EtOAc/isohexane) to afford the title compound (0.110 g, 0.22 mmol, 76% yield, 95% purity) as yellow oil. UPLC-MS (Method 1) m/z 484.4 $(M+H)^+$ at 1.90 min.

Step 2: 4-ethyl-3-(N-(5-(5-methylisoxazol-4-yl)-2-(piperidin-1-yl)phenyl)sulfamoyl)benzoic acid: 1 M LiOH(aq) (0.682 ml, 0.682 mmol) was added to a solution of the product from Step 1 above (0.110 g, 0.23 mmol, 95% purity) in THF (5 ml) and stirred at RT overnight. The mixture was then acidified to pH 6 using 10% w/v citric acid (aq) and the resultant precipitate was collected by filtration to afford crude mixture of products. The crude product was purified by preparative HPLC (Waters, Acidic (0.1% Formic acid), Acidic, Waters X-Select Prep-C18, 5 μm, 19×50 mm column, 10-80% MeCN in Water) to afford the title compound (13.3 mg, 0.03 mmol, 12% yield, 96% purity) as a white solid. UPLC-MS (Method 1) m/z 470.4 $(M+H)^+$ at 1.79 min. $^1H$ NMR (500 MHz, DMSO-$d_6$) δ 8.69 (s, 1H), 8.43 (d, J=1.8 Hz, 1H), 8.08 (dd, J=7.9, 1.8 Hz, 1H), 7.64 (dd, J=7.8 Hz, 1H), 7.34-7.13 (m, 3H), 3.07 (q, J=7.4 Hz, 2H), 2.63 (t, J=5.2 Hz, 4H), 2.42 (s, 3H), 1.59 (p, J=5.4 Hz, 4H), 1.48 (m, 2H), 1.22 (t, J=7.4 Hz, 3H).

Example 280:4-ethyl-3-(N-(5-(1-methylpyrazol-3-yl)-2-(piperidin-1-yl)phenyl)sulfamoyl)benzoic acid

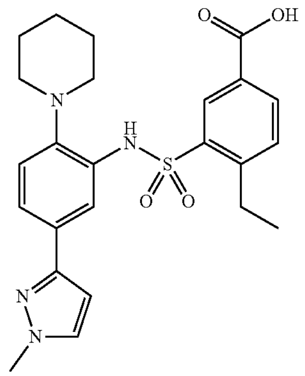 [SMILES: CCc1ccc(C(=O)O)cc1S(=O)(=O)Nc1cc(-c2ccn(C)n2)ccc1N1CCCCC1]

Step 1: methyl 4-ethyl-3-(N-(5-(1-methylpyrazol-3-yl)-2-(piperidin-1-yl)phenyl)sulfamoyl)benzoate: To the reaction vessel containing the product from Example 273 Step 4 (0.150 g, 0.28 mmol, 99% purity), 3-bromo-1-methylpyrazole (0.035 ml, 0.34 mmol), $K_3PO_4$ (0.078 g, 0.34 mmol) in dioxane (5 ml) and water (1 ml) was added Xphos Pd G3 (0.024 g, 0.04 mmol). The resultant mixture was degassed with $N_2$ for 15 min and then heated at 80° C. for 2 h. The reaction mixture was allowed to cool to RT, filtered and then concentrated in vacuo. The residue was purified by chromatography on silica gel (12 g cartridge, 0-100% EtOAc/isohexane) to afford the title compound (0.085 g, 0.16 mmol, 57% yield) as a pale brown solid. UPLC-MS (Method 1) m/z 483.3 $(M+H)^+$ at 1.82 min.

Step 2: 4-ethyl-3-(N-(5-(1-methylpyrazol-3-yl)-2-(piperidin-1-yl)phenyl)sulfamoyl)benzoic acid: 1 M LiOH(aq) (2.82 ml, 0.582 mmol) was added to a solution of the product from Step 1 above (0.085 g, 0.176 mmol, 92% purity) in THF (3.5 ml) and the resultant mixture stirred at RT for 72 h. The mixture was then acidified to pH 6 using 1 M citric acid (aq) and the resultant precipitate was collected by filtration to afford the title compound (44 mg, 0.089 mmol, 51% yield) as a white solid. UPLC-MS (Method 1) m/z 469.2 $(M+H)^+$ at 1.66 min. $^1H$ NMR (500 MHz, DMSO-$d_6$) δ 13.4 (s br, 1H), 8.91 (s, 1H), 8.45 (d, J=1.8 Hz, 1H), 8.07 (dd, J=8.0, 1.8 Hz, 1H), 7.66 (d, J=2.2 Hz, 1H), 7.60-7.53 (m, 2H), 7.43 (dd, J=8.2, 2.0 Hz, 1H), 7.15 (d, J=8.3 Hz, 1H), 6.43 (d, J=2.2 Hz, 1H), 3.84 (s, 3H), 3.06 (q, J=7.4 Hz, 2H), 2.63 (t, J=5.2 Hz, 4H), 1.63-1.55 (m, 4H), 1.51-1.44 (m, 2H), 1.21 (t, J=7.4 Hz, 3H).

Example 281: 4-ethyl-3-(N-(5-(1-methylpyrazol-5-yl)-2-(piperidin-1-yl)phenyl

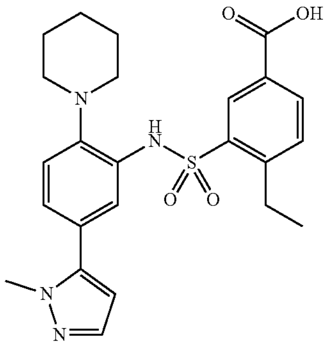 [SMILES: CCc1ccc(C(=O)O)cc1S(=O)(=O)Nc1cc(-c2ccnn2C)ccc1N1CCCCC1]

Step 1: methyl 4-ethyl-3-(N-(5-(1-methylpyrazol-5-yl)-2-(piperidin-1-yl)phenyl)sulfamoyl)benzoate: To the reaction vessel containing the product from Example 273 Step 4 (0.140 g, 0.26 mmol, 99% purity), 5-bromo-1-methylpyrazole (51.2 mg, 0.32 mmol), $K_3PO_4$ (0.073 g, 0.34 mmol) in dioxane (5 ml) and water (1 ml) was added Xphos Pd G3 (0.022 g, 0.03 mmol). The resultant mixture was degassed with $N_2$ for 15 min and then heated at 80° C. for 2 h. The reaction mixture was allowed to cool to RT, filtered and then concentrated in vacuo. The residue was purified by chromatography on silica gel (12 g cartridge, 0-100% EtOAc/isohexane) to afford the title compound (0.105 g, 0.22 mmol, 82% yield) as a brown oil. UPLC-MS (Method 1) m/z 483.6 $(M+H)^+$ at 1.79 min.

Step 2: 4-ethyl-3-(N-(5-(1-methylpyrazol-3-yl)-2-(piperidin-1-yl)phenyl)sulfamoyl)benzoic acid: 1 M LiOH(aq) (3.45 ml, 3.49 mmol) was added to a solution of the product from Step 1 above (0.105 g, 0.22 mmol) in THF (4 ml) and stirred at RT overnight. The mixture was then acidified to pH 6 using 1 M citric acid (aq) and the resultant precipitate was collected by filtration to afford the title compound (71 mg, 0.144 mmol, 66% yield) as a pale brown solid. UPLC-MS (Method 1) m/z 469.6 $(M+H)^+$ at 1.60 min. $^1H$ NMR (500 MHz, DMSO-$d_6$) δ 13.37 (br s, 1H), 9.18 (s, 1H), 8.40 (d, J=1.8 Hz, 1H), 8.09 (dd, J=8.0, 1.8 Hz, 1H), 7.61 (d, J=8.1 Hz, 1H), 7.42 (d, J=1.9 Hz, 1H), 7.26-7.19 (m, 3H), 6.22 (d, J=1.9 Hz, 1H), 3.71 (s, 3H), 3.07 (q, J=7.4 Hz, 2H), 2.66 (t, J=5.3 Hz, 4H), 1.65-1.55 (m, 4H), 1.53-1.44 (m, 2H), 1.23 (t, J=7.4 Hz, 3H).

Example 282: 4-ethyl-3-(N-(5-(2-methylthiazol-5-yl)-2-(piperidin-1-yl)phenyl)sulfamoyl)benzoic acid

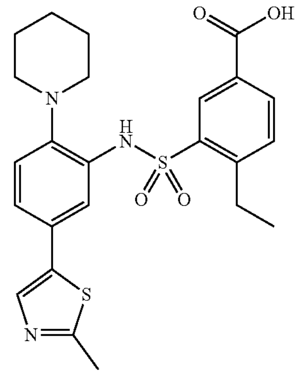 [SMILES: CCc1ccc(C(=O)O)cc1S(=O)(=O)Nc1cc(-c2cnc(C)s2)ccc1N1CCCCC1]

Step 1: methyl 4-ethyl-3-(N-(5-(2-methylthiazol-5-yl)-2-(piperidin-1-yl)phenyl)sulfamoyl)benzoate: To the reaction vessel containing the product from Example 273 Step 4 (0.140 g, 0.27 mmol, 99% purity), 5-bromo-2-methylthiazole (56.6 mg, 0.318 mmol), $K_3PO_4$ (0.073 g, 0.36 mmol) in dioxane (5 ml) and water (1 ml) was added Xphos Pd G3 (0.023 g, 0.03 mmol). The resultant mixture was degassed with $N_2$ for 15 min and then heated at 80° C. for 3 h. The reaction mixture was allowed to cool to RT, filtered and then concentrated in vacuo. The residue was purified by chromatography on silica gel (12 g cartridge, 0-100% EtOAc/isohexane) to afford the title compound (0.096 g, 0.19 mmol, 71% yield) as a brown oil. UPLC-MS (Method 1) m/z 500.2 $(M+H)^+$ at 1.92 min.

Step 2: 4-ethyl-3-(N-(5-(2-methylthiazol-5-yl)-2-(piperidin-1-yl)phenyl)sulfamoyl)benzoic acid: 1 M LiOH(aq) (2.88 ml, 2.88 mmol) was added to a solution of the product from Step 1 above (0.096 g, 0.19 mmol) in THF (4 ml) and stirred at RT overnight. The mixture was then acidified to pH 6 using 1 M citric acid (aq) and the resultant precipitate was collected by filtration to give material which was azeotroped with MeCN (5 ml) to afford the title compound (68 mg, 0.133 mmol, 69% yield) as a pale brown solid. UPLC-MS (Method 1) m/z 486.5 $(M+H)^+$ at 1.82 min. $^1H$ NMR (500 MHz, DMSO-$d_6$) δ 13.37 (br s, 1H), $^1H$ NMR (500 MHz, DMSO-$d_6$) δ 13.36 (s br, 1H), 9.12 (s, 1H), 8.45 (d, J=1.8 Hz, 1H), 8.10 (dd, J=7.9, 1.9 Hz, 1H), 7.75 (s, 1H), 7.61 (d, J=8.0 Hz, 1H), 7.34 (dd, J=8.3, 2.2 Hz, 1H), 7.21 (d, J=2.2 Hz, 1H), 7.17 (d, J=8.3 Hz, 1H), 3.07 (q, J=7.4 Hz, 2H), 2.69-2.62 (m, 7H), 1.64-1.55 (m, 4H), 1.51-1.44 (m, 2H), 1.22 (t, J=7.4 Hz, 3H).

Example 283:4-ethyl-3-(N-(2-(3-hydroxyazetidin-1-yl)-5-(tetrazol-1-yl)phenyl)sulfamoyl)benzoic acid

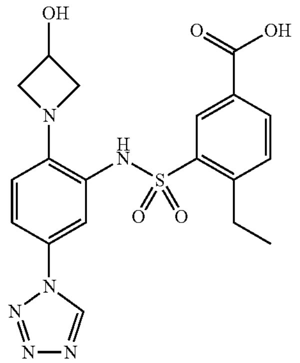 [SMILES: CCc1ccc(C(=O)O)cc1S(=O)(=O)Nc1cc(-n2cnnn2)ccc1N1CC(O)C1]

Step 1: 1-(2-nitro-4-(tetrazol-1-yl)phenyl) azetidin-3-ol: $Et_3N$ (720 µl, 5.16 mmol) was added to a solution of the product from Example 214 Step 1 (300 mg, 1.434 mmol) and azetidin-3-ol hydrochloride (204 mg, 1.86 mmol) in DCM (6 ml) and the resultant solution was stirred at RT for 3 days. The reaction mixture was concentrated in vacuo and the residue triturated with water (10 ml), filtered and washed with water (2×10 ml). The solid was dried at 50° C. for 4 h to afford the title compound (368 mg, 1.40 mmol, 98% yield) as a dark orange solid. UPLC-MS (Method 2) m/z no ionisation at 0.77 min.

Step 2: 1-(2-amino-4-(tetrazol-1-yl)phenyl) azetidin-3-ol: The product from step 1 above (368 mg, 1.40 mmol) was dissolved in MeOH (500 ml) and divided into three portions. To each portion was added 5% Pd/C (50% w/w water) Type 87L (140 mg, 0.033 mmol) in MeOH (1 ml). Each reaction mixture was hydrogenated at 4 bar at 40° C. for 6-20 h. The reaction mixtures were combined, filtered through Celite® and concentrated in vacuo to afford the title compound (316 mg, 1.32 mmol, 94% yield, 97% purity) as a light brown solid. UPLC-MS (Method 2) m/z 233.3 $(M+H)^+$ at 0.56 min.

Step 3: methyl 4-ethyl-3-(N-(2-(3-hydroxyazetidin-1-yl)-5-(tetrazol-1-yl)phenyl)sulfamoyl)benzoate: The product from step 2 above (58.9 mg, 0.246 mmol, 97% purity) was suspended in a mixture of DCM (1 ml) and pyridine (82 µl, 1.02 mmol) then treated with a solution of the product from Example 183 Step 1 (80 mg, 0.305 mmol) in DCM (1 ml). The resultant solution was stirred at RT for 4 days. The reaction mixture was purified directly by chromatography on silica gel (12 g cartridge, 0-100% EtOAc/isohexane) to afford the title compound (37 mg, 0.081 mmol, 33% yield) as an off-white solid.

Step 4: 4-ethyl-3-(N-(2-(3-hydroxyazetidin-1-yl)-5-(tetrazol-1-yl)phenyl)sulfamoyl)benzoic acid: The product from step 3 above (37 mg, 0.081 mmol) was dissolved in THF (2 ml) and treated with 1 M LiOH(aq) (323 µl, 0.323 mmol). MeOH was added dropwise until the mixture was a solution. The reaction mixture was stirred at 30° C. for 20 h. The mixture was diluted with water (3 ml), concentrated in vacuo and the resultant aqueous solution diluted with water (to ~5 ml). The aqueous phase was washed with EtOAc (2×5 ml) and then neutralised to ~pH 6 using 10% w/v citric acid (aq). The resultant precipitate was filtered and washed with water (2×2 ml), then dried in vacuo at 50° C. to afford the title compound (7.1 mg, 0.015 mmol, 19% yield, 97% purity) as a light brown solid. UPLC-MS (Method 1) m/z 443.2 $(M-H)^-$ at 0.98 min. 1H NMR (500 MHz, DMSO-$d_6$) δ 13.18 (br s, 1H), 9.72 (s, 1H), 8.32 (d, J=1.8 Hz, 1H), 8.10 (dd, J=8.0, 1.9 Hz, 1H), 7.62 (d, J=8.0 Hz, 1H), 7.59-7.49 (m, 1H), 6.76 (d, J=2.5 Hz, 1H), 6.63 (d, J=8.9 Hz, 1H), 5.61 (d, J=6.0 Hz, 1H), 4.53-4.46 (m, 1H), 4.33-4.28 (m, 2H), 3.75 (dd, J=8.6, 5.0 Hz, 2H), 2.98 (q, J=7.4 Hz, 2H), 1.19 (t, J=7.4 Hz, 3H). One exchangeable proton not observed.

Example 286: 4-ethyl-3-(N-(5-(isothiazol-5-yl)-2-(piperidin-1-yl)phenyl)sulfamoyl)benzoic acid

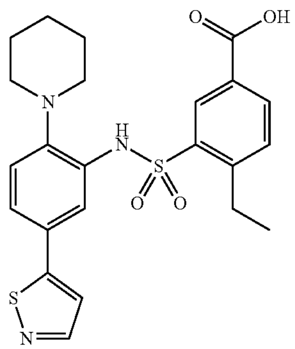 [SMILES: CCc1ccc(C(=O)O)cc1S(=O)(=O)Nc1cc(-c2ccns2)ccc1N1CCCCC1]

Step 1: Methyl 4-ethyl-3-(N-(5-(isothiazol-5-yl)-2-(piperidin-1-yl)phenyl)sulfamoyl)benzoate: A mixture of the product from Example 273 Step 4 (140 mg, 0.265 mmol), 5-bromoisothiazole (52.1 mg, 0.318 mmol) and $K_3PO_4$ (73.1 mg, 0.344 mmol) in dioxane (5 ml) and water (1 ml) was treated with Xphos Pd G3 (22.4 mg, 0.026 mmol). The reaction mixture was degassed with $N_2$ for 15 min, then heated at 80° C. for 3 h. The mixture was allowed to cool to RT, then was filtered and concentrated in vacuo. The residue was purified by chromatography on silica gel (12 g cartridge, 0-50% EtOAc/isohexane) to afford the title compound (121 mg, 0.239 mmol, 90% yield, 96% purity) as a brown oil. UPLC-MS (Method 2) m/z 486.3 $(M+H)^+$ at 1.94 min.

Step 2: 4-ethyl-3-(N-(5-(isothiazol-5-yl)-2-(piperidin-1-yl)phenyl)sulfamoyl)benzoic acid: 1 M LiOH(aq) (2.5 ml, 2.50 mmol) was added to a solution of the product from Step 1 above (121 mg, 0.239 mmol, 96% purity) in THF (5 ml) and the solution was stirred at RT overnight. Additional 1 M LiOH(aq) (1.75 ml, 1.75 mmol) was added and the solution was stirred overnight. The mixture was adjusted to pH 6 using 1 M citric acid (aq), the precipitate was collected by filtration and dried in vacuo to afford the title compound (37.8 mg, 0.076 mmol, 32% yield, 95% purity) as a pale brown solid. UPLC-MS (Method 1) m/z 472.5 $(M+H)^+$, 470.2 $(M-H)^-$ at 1.85 min. $^1H$ NMR (500 MHz, DMSO-$d_6$) 13.3 (br s, 1H), 9.26 (br s, 1H), 8.53 (d, J=1.8 Hz, 1H), 8.45 (d, J=1.8 Hz, 1H), 8.11 (dd, J=8.0, 1.8 Hz, 1H), 7.63 (d, J=8.0 Hz, 1H), 7.55 (d, J=1.8 Hz, 1H), 7.48 (dd, J=8.3, 2.2 Hz, 1H), 7.29 (d, J=2.2 Hz, 1H), 7.21 (d, J=8.3 Hz, 1H), 3.08 (q, J=7.4 Hz, 2H), 2.71 (t, J=5.3 Hz, 4H), 1.64-1.55 (m, 4H), 1.53-1.44 (m, 2H), 1.22 (t, J=7.4 Hz, 3H).

Example 287:4-ethyl-3-(N-(5-(1-methylimidazol-5-yl)-2-(piperidin-1-yl)phenyl) sulfamoyl)benzoic acid

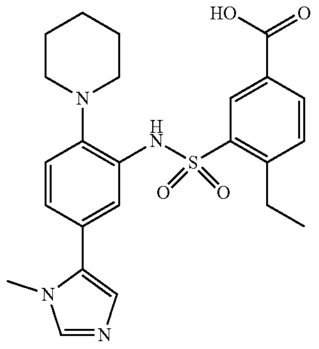 [SMILES: CCc1ccc(C(=O)O)cc1S(=O)(=O)Nc1cc(-c2cncn2C)ccc1N1CCCCC1]

Step 1: 1-(4-bromo-2-nitrophenyl)piperidine: Piperidine (9.88 ml, 100 mmol) was added to a solution of 4-bromo-1-fluoro-2-nitrobenzene (5.60 ml, 45.5 mmol) in MeCN (50 ml) and the resultant solution was stirred at RT for 2 h. The reaction mixture was concentrated in vacuo. The crude product was purified by chromatography on silica gel (220 g cartridge, 0-50% EtOAc/isohexane) to afford the title compound (13.4 g, 44.2 mmol, 97% yield, 94% purity) as a red oil. UPLC-MS (Method 1): m/z 285.1 $(M+H)^+$, at 1.82 min. $^1H$ NMR (500 MHz, DMSO-$d_6$) δ 7.99 (d, J=2.4 Hz, 1H), 7.71 (dd, J=8.9, 2.5 Hz, 1H), 7.24 (d, J=8.9 Hz, 1H), 3.01-2.86 (m, 4H), 1.63-1.55 (m, 4H), 1.55-1.49 (m, 2H).

Step 2: 1-(2-nitro-4-(4,4,5,5-tetramethyl-1,3,2-dioxaborolan-2-yl)phenyl)piperidine: A mixture of the product from Step 1 above (1 g, 3.33 mmol, 94% purity), bis (pinacolato)diboron (1.27 g, 5.00 mmol), KOAc (0.981 g, 10.0 mmol), $PdCl_2$ (dppf) (0.244 g, 0.333 mmol) in dioxane (10 ml) was degassed with $N_2$ for 5 min. The reaction was heated at 80° C. for 12 h. The mixture was then diluted with water (50 ml) and extracted with EtOAc (50 ml). The organic phase was dried ($MgSO_4$), filtered and concentrated in vacuo. The crude product was purified by chromatography on silica gel (40 g cartridge, 0-50% EtOAc/isohexane) to afford the title compound (1.40 g, 3.16 mmol, 95% yield, 75% purity) as a brown oil. UPLC-MS (Method 1): m/z 333.3 $(M+H)^+$, at 1.99 min. $^1H$ NMR (500 MHz, DMSO-$d_6$) δ 7.95 (d, J=1.6 Hz, 1H), 7.73 (dd, J=8.4, 1.6 Hz, 1H), 7.23 (d, J=8.4 Hz, 1H), 3.04 (t, J=5.1 Hz, 4H), 1.67-1.52 (m, 6H), 1.29 (s, 12H).

Step 3: 2-(piperidin-1-yl)-5-(4,4,5,5-tetramethyl-1,3,2-dioxaborolan-2-yl)aniline: A solution of the product from Step 2 above (15.6 g, 39.9 mmol, 75% purity) in MeOH (20 ml, 494 mmol) was treated with 10% Pd/C (4.25 g, 3.99 mmol). The solution was hydrogenated at a pressure of 2 bar for 16 h. The mixture was filtered through Celite® and the filtrate was concentrated in vacuo. The crude product was purified by chromatography on silica gel (220 g cartridge, 0-50% EtOAc/isohexane) to afford the title compound (5.20 g, 16.4 mmol, 41% yield, 95% purity) as a brown solid. UPLC-MS (Method 1): m/z 303.3 $(M+H)^+$, at 1.41 min, 95% purity (254 nm). $^1H$ NMR (500 MHz, DMSO-$d_6$) δ 7.04 (d, J=1.4 Hz, 1H), 6.90 (dd, J=7.7, 1.5 Hz, 1H), 6.84 (d, J=7.7 Hz, 1H), 4.63 (s, 2H), 2.80-2.70 (m, 4H), 1.65 (p, J=5.6 Hz, 4H), 1.55-1.49 (m, 2H), 1.26 (s, 12H).

Step 4: Methyl 4-ethyl-3-(N-(2-(piperidin-1-yl)-5-(4,4,5,5-tetramethyl-1,3,2-dioxaborolan-2-yl)phenyl)sulfamoyl) benzoate: A solution of the product from Step 3 above (3.53 g, 11.1 mmol, 95% purity), the product from Example 203 Step 2 (3.20 g, 12.2 mmol) and pyridine (3.60 ml, 44.5 mmol) in DCM (20 ml) was vigorously stirred at RT for 41 h. The reaction mixture was concentrated in vacuo onto Celite®. The crude product was purified by chromatography on silica gel (80 g cartridge, 0-30% then 100% EtOAc/isohexane) to afford the title compound (4.89 g, 9.16 mmol, 83% yield, 99% purity) as an off-white solid. UPLC-MS (Method 2): m/z 529.4 $(M+H)^+$, 527.3 $(M-H)^-$ at 2.12 min. $^1H$ NMR (500 MHz, DMSO-$d_6$) δ 9.04 (br s, 1H), 8.38 (d, J=1.9 Hz, 1H), 8.11 (dd, J=8.0, 1.9 Hz, 1H), 7.62 (d, J=8.1 Hz, 1H), 7.34 (dd, J=7.9, 1.5 Hz, 1H), 7.31 (d, J=1.4 Hz, 1H), 7.07 (d, J=7.9 Hz, 1H), 3.85 (s, 3H), 3.05 (q, J=7.4 Hz, 2H), 2.68 (t, J=5.2 Hz, 4H), 1.59-1.49 (m, 4H), 1.49-1.41 (m, 2H), 1.24-1.18 (m, 15H).

Step 5: methyl 4-ethyl-3-(N-(5-(1-methylimidazol-5-yl)-2-(piperidin-1-yl)phenyl)sulfamoyl)benzoate: To the reaction vessel containing the product from Step 4 above (0.150 g, 0.284 mmol, 99% purity), 5-bromo-1-methylimidazole (0.055 g, 0.341 mmol), $K_3PO_4$ (0.078 g, 0.369 mmol) and dioxane (5 ml, 0.284 mmol) and water (1 ml) was added Xphos Pd G3 (0.024 g, 0.028 mmol). The resultant reaction mixture was degassed with $N_2$ for 15 min and then heated to 80° C. for 6 h. The reaction mixture was allowed to cool to RT, filtered and then concentrated in vacuo. The crude product was purified by chromatography on silica gel (24 g cartridge, 0-100% 10% (MeOH/DCM) in DCM) to afford the title compound (0.100 g, 0.204 mmol, 72% yield, 99% purity) as a yellow oil. UPLC-MS (Method 1): m/z 483.4 $(M+H)^+$, 481.3 $(M-H)^-$ at 1.15 min.

Step 6: 4-ethyl-3-(N-(5-(1-methylimidazol-5-yl)-2-(piperidin-1-yl)phenyl)sulfamoyl)benzoic acid: 1 M LiOH(aq) (0.622 ml, 0.622 mmol) was added to a solution the product from Step 5 above (0.100 g, 0.207 mmol, 99% purity) in THF (5 ml, 61.0 mmol) and the solution was stirred at RT overnight. The mixture was then adjusted to pH 6 with citric acid to form a precipitate which was filtered under suction to afford the crude product. The crude product was purified by preparative HPLC (Waters, Basic (0.1% Ammonium Bicarbonate), Basic, Waters X-Bridge Prep-C18, 5 μm, 19×50 mm column, 20-50% MeCN in Water) to afford the title compound (4.4 mg, 9.30 μmol, 5% yield, 99% purity) as a white solid. UPLC-MS (Method 1): m/z 469.4 $(M+H)^+$, 467.3 $(M-H)^-$ at 1.08 min. $^1H$ NMR (500 MHz, DMSO-$d_6$) δ 9.08 (br s, 1H), 8.41 (d, J=1.8 Hz, 1H), 8.08 (dd, J=8.0, 1.8 Hz, 1H), 7.65 (s, 1H), 7.59 (d, J=8.0 Hz, 1H), 7.26-7.13 (m, 3H), 6.86 (s, 1H), 3.54 (s, 3H), 3.06 (q, J=7.4 Hz, 2H), 2.71-2.59 (m, 4H), 1.60 (p, J=5.6 Hz, 4H), 1.52-1.45 (m, 2H), 1.23 (t, J=7.4 Hz, 3H). 1 exchangeable proton not observed.

Example 288: 4-ethyl-3-(N-(5-(1-methyl-1,2,4-triazol-5-yl)-2-(piperidin-1-yl)phenyl) sulfamoyl)benzoic acid

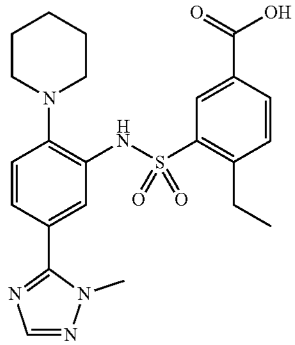 [SMILES: CCc1ccc(C(=O)O)cc1S(=O)(=O)Nc1cc(-c2ncnn2C)ccc1N1CCCCC1]

Step 1: 1-(4-bromo-2-nitrophenyl)piperidine: Piperidine (4.95 ml, 50.0 mmol) was added to a solution of 4-bromo-1-fluoro-2-nitrobenzene (2.79 ml, 22.7 mmol) in MeCN (25 ml) and the resultant solution was stirred at RT overnight. The reaction mixture was concentrated in vacuo. The crude product was purified by chromatography on silica gel (120 g cartridge, 0-50% EtOAc/isohexane) to afford the title compound (6.8 g, 22.7 mmol, 100% yield, >95% purity) as a red liquid. UPLC-MS (Method 2): m/z 285.1 $(M+H)^+$, at 1.82 min. $^1$H NMR (500 MHz, DMSO-$d_6$) δ 8.00 (d, J=2.5 Hz, 1H), 7.71 (dd, J=8.9, 2.5 Hz, 1H), 7.25 (d, J=8.8 Hz, 1H), 2.98-2.92 (m, 4H), 1.63-1.50 (m, 6H).

Step 2: 1-(2-nitro-4-(4,4,5,5-tetramethyl-1,3,2-dioxaborolan-2-yl)phenyl)piperidine: A mixture of the product from Step 1 above (6.8 g, 22.7 mmol, >95% purity), bis(pinacolato)diboron (9.08 g, 35.8 mmol), KOAc (7.02 g, 71.5 mmol), Pd (dppf) Cl2·DCM (1.95 g, 2.39 mmol) in 1dioxane (70 ml) was degassed with nitrogen for 15 min. The reaction was heated at 80° C. for 12 h. The mixture was diluted with brine (350 ml) and extracted with EtOAc (350 ml). The organic phase was dried ($MgSO_4$), filtered and concentrated in vacuo. The crude product was purified by chromatography on silica gel (220 g cartridge, 0-50% EtOAc/isohexane) to afford the title compound (7.7 g, 16.2 mmol, 72% yield, 70% purity) as an orange oil. UPLC-MS (Method 2): m/z 333.6 $(M+H)^+$, at 1.98 min.

Step 3: 1-(4-(1-methyl-1,2,4-triazol-5-yl)-2-nitrophenyl) piperidine: To the reaction vessel containing 5-bromo-1-methyl-1,2,4-triazole (0.102 g, 0.632 mmol), the product from Step 2 above (0.250 g, 0.527 mmol, 70% purity), $K_3PO_4$ (0.145 g, 0.685 mmol) and 5:1 dioxane: water (12 ml) was added Xphos Pd G3 (0.045 g, 0.053 mmol). The resultant reaction mixture was degassed with $N_2$ for 15 min and then heated to 80° C. for 2 h. The mixture was diluted with EtOAc (50 ml) and washed with water (50 ml). The organic phase was dried ($MgSO_4$), filtered and concentrated in vacuo. The crude product was purified by chromatography on silica gel (24 g cartridge, 0-100% EtOAc/isohexane) to afford the title compound (0.150 g, 0.517 mmol, 98% yield, 99% purity) as an orange solid. UPLC-MS (Method 1): m/z 288.2 $(M+H)^+$, at 1.29 min.

Step 4: 5-(1-methyl-1,2,4-triazol-5-yl)-2-(piperidin-1-yl) aniline: The product from Step 3 above (0.150 g, 0.522 mmol) was dissolved in MeOH (10 ml) and 10% Pd/C (50% w/w water) Type 39 (0.013 g, 6.11 μmol) was added and the reaction was placed under hydrogen (2 bar) and stirred at room temperature for 16 h. The mixture was filtered through Celite®, washed with MeOH (20 ml) and the filtrate concentrated in vacuo to afford the title compound (0.121 g, 0.353 mmol, 68% yield, 75% purity) as a brown oil. UPLC-MS (Method 1): m/z 258.3 $(M+H)^+$ at 0.88 min.

Step 5: Methyl 4-ethyl-3-(N-(5-(1-methyl-1,2,4-triazol-5-yl)-2-(piperidin-1-yl)phenyl)sulfamoyl)benzoate: A solution of the product from Step 4 above (0.121 g, 0.353 mmol, 75% purity) in DCM (3 ml) and pyridine (0.171 ml, 2.12 mmol) were added to a solution of the product from Example 203 Step 2 (0.093 g, 0.353 mmol) in DCM (3 ml) and the solution was stirred at RT for 48 h. The mixture was concentrated in vacuo. The crude product was purified by chromatography on silica gel (24 g cartridge, 0-50% EtOAc/isohexane) to afford the title compound (0.095 g, 0.187 mmol, 53% yield, 95% purity) as a white solid. UPLC-MS (Method 1): m/z 484.4 $(M+H)^+$, 482.3 $(M-H)^-$ at 1.64 min.

Step 6: 4-ethyl-3-(N-(5-(1-methyl-1,2,4-triazol-5-yl)-2-(piperidin-1-yl)phenyl)sulfamoyl)benzoic acid: 1 M LiOH (aq) (0.560 ml, 0.560 mmol) was added to a solution of the product from Step 5 above (0.095 g, 0.187 mmol, 95% purity) in THF (5 ml, 61.0 mmol) and the solution was stirred at RT for 16 h. The mixture was then adjusted to pH 6 with citric acid to form a precipitate which was filtered under suction to afford the title compound (46.8 mg, 0.098 mmol, 52% yield, 98% purity) as a white solid. UPLC-MS (Method 1): m/z 470.3 $(M+H)^+$, 468.3 $(M-H)^-$ at 1.49 min. $^1$H NMR (500 MHz, DMSO-$d_6$) δ 8.37 (d, J=1.8 Hz, 1H), 8.06 (dd, J=8.0, 1.8 Hz, 1H), 7.92 (s, 1H), 7.57 (d, J=8.0 Hz, 1H), 7.53-7.43 (m, 2H), 7.24 (d, J=8.2 Hz, 1H), 3.84 (s, 3H), 3.07 (q, J=7.4 Hz, 2H), 2.71 (t, J=5.2 Hz, 4H), 1.58 (p, J=5.5 Hz, 4H), 1.52-1.45 (m, 2H), 1.22 (t, J=7.4 Hz, 3H). 2 exchangeable protons not observed.

Example 289: 4-ethyl-3-(N-(5-(oxazol-2-yl)-2-(piperidin-1-yl)phenyl)sulfamoyl)benzoic acid

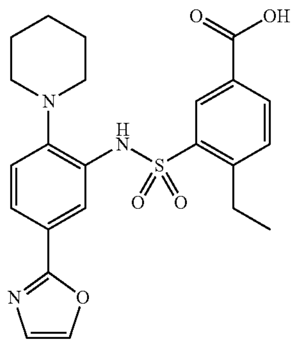 [SMILES: CCc1ccc(C(=O)O)cc1S(=O)(=O)Nc1cc(-c2ncco2)ccc1N1CCCCC1]

Step 1: 2-(3-nitro-4-(piperidin-1-yl)phenyl) oxazole: To the reaction vessel containing 2-bromooxazole (0.094 g, 0.632 mmol), the product from Example 287 Step 2 (0.250 g, 0.527 mmol), $K_3PO_4$ (0.145 g, 0.685 mmol) and 5:1 dioxane:water (12 ml) was added Xphos Pd G3 (0.045 g, 0.053 mmol). The resultant reaction mixture was degassed with $N_2$ for 15 min and then heated to 80° C. for 2 h. The mixture was diluted with EtOAc (50 ml) and washed with water (50 ml). The organic phase was dried ($MgSO_4$), filtered and concentrated in vacuo. The crude product was purified by chromatography on silica gel (24 g cartridge, 0-50% EtOAc/isohexane) to afford the title compound (0.137 g, 0.481 mmol, 91% yield, 96% purity) as an orange oil. UPLC-MS (Method 1): m/z 274.2 $(M+H)^+$, at 1.60 min.

Step 2: 5-(oxazol-2-yl)-2-(piperidin-1-yl)aniline: The product from Step 1 above (0.137 g, 0.501 mmol) was dissolved in MeOH (10 ml), 10% Pd/C (50% w/w water) Type 39 (0.013 g, 5.64 μmol) was added and the reaction was stirred under hydrogen (2 bar) at room temperature for 16 h. The mixture was filtered through Celite®, washed with MeOH (20 ml) and concentrated in vacuo to afford the title compound (0.119 g, 0.489 mmol, 98% yield) as a brown oil. UPLC-MS (Method 1): m/z 244.3 $(M+H)^+$ at 1.18 min.

Step 3: Methyl 4-ethyl-3-(N-(5-(oxazol-2-yl)-2-(piperidin-1-yl)phenyl)sulfamoyl)benzoate: A solution of the product from Step 2 above (0.119 g, 0.489 mmol) in DCM (3 ml) and pyridine (0.237 ml, 2.93 mmol) was added to a solution of the product from Example 203 Step 2 (0.128 g, 0.489 mmol) in DCM (3 ml, 46.6 mmol) and the resultant solution was stirred at RT for 48 h. The mixture was concentrated in vacuo. The crude product was purified by chromatography on silica gel (24 g cartridge, 0-50% EtOAc/isohexane) to afford the title compound (0.140 g, 0.298 mmol, 61% yield) as a brown oil. UPLC-MS (Method 1): m/z 470.4 $(M+H)^+$, 468.3 $(M-H)^-$ at 1.86 min.

Step 4: 4-ethyl-3-(N-(5-(oxazol-2-yl)-2-(piperidin-1-yl)phenyl)sulfamoyl)benzoic acid: 1 M LiOH(aq) (0.894 ml, 0.894 mmol) was added to a solution of the product from Step 3 above (0.140 g, 0.298 mmol) in THF (5 ml) and the solution was stirred at RT for 16 h. The mixture was then adjusted to pH 6 with citric acid to form a precipitate which was filtered under suction to afford the title compound (95 mg, 0.207 mmol, 70% yield, 99% purity) as an off-white solid. UPLC-MS (Method 1): m/z 456.4 $(M+H)^+$, 454.3 $(M-H)^-$ at 1.72 min. $^1$H NMR (500 MHz, DMSO-$d_6$) δ 13.28 (br s, 1H), 9.27 (br s, 1H), 8.38 (d, J=1.8 Hz, 1H), 8.13 (s, 1H), 8.08 (dd, J=8.0, 1.8 Hz, 1H), 7.75 (d, J=2.0 Hz, 1H), 7.69 (dd, J=8.3, 2.1 Hz, 1H), 7.61 (d, J=8.0 Hz, 1H), 7.31 (s, 1H), 7.23 (d, J=8.4 Hz, 1H), 3.07 (q, J=7.4 Hz, 2H), 2.70 (t, J=5.2 Hz, 4H), 1.56 (p, J=5.6 Hz, 4H), 1.50-1.44 (m, 2H), 1.22 (t, J=7.4 Hz, 3H).

Example 290:4-ethyl-3-(N-(2-(piperidin-1-yl)-5-(pyrazin-2-yl)phenyl)sulfamoyl)benzoic acid

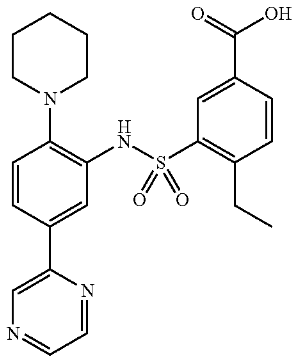 [SMILES: CCc1ccc(C(=O)O)cc1S(=O)(=O)Nc1cc(-c2cnccn2)ccc1N1CCCCC1]

Step 1: 2-(3-nitro-4-(piperidin-1-yl)phenyl) pyrazine: To the reaction vessel the product from Example 287 Step 2 (0.250 g, 0.527 mmol), 2-bromopyrazine (0.084 g, 0.527 mmol), $K_3PO_4$ (0.145 g, 0.685 mmol) and 5:1 dioxane:water (12 ml) was added Xphos Pd G3 (0.045 g, 0.053 mmol). The resultant reaction mixture was degassed with $N_2$ for 15 min and then heated to 80° C. for 16 h. The mixture was diluted with EtOAc (50 ml) and washed with water (50 ml). The organic phase was dried ($MgSO_4$), filtered and concentrated in vacuo. The crude product was purified by chromatography on silica gel (24 g cartridge, 0-100% EtOAc/isohexane) to afford the title compound (0.145 g, 0.500 mmol, 95% yield, 98% purity) as an orange oil. UPLC-MS (Method 1): m/z 285.2 $(M+H)^+$, at 1.57 min.

Step 2: 2-(piperidin-1-yl)-5-(pyrazin-2-yl)aniline: The product from Step 1 above (0.145 g, 0.510 mmol, 98% purity) was dissolved in MeOH (10 ml) and 10% Pd/C (50% w/w water) Type 39 (0.013 g, 6.11 μmol) was added and the reaction was stirred under hydrogen (3 bar) at room temperature for 1 h. The mixture was filtered through Celite®, washed with MeOH (20 ml) and concentrated in vacuo to afford the crude product. The crude product was purified by chromatography on silica gel (24 g cartridge, 0-50% EtOAc/isohexane) to afford the title compound (0.051 g, 0.201 mmol, 39% yield) as a yellow oil. UPLC-MS (Method 1): m/z 255.3 $(M+H)^+$ at 0.95 min.

Step 3: Methyl 4-ethyl-3-(N-(2-(piperidin-1-yl)-5-(pyrazin-2-yl)phenyl)sulfamoyl)benzoate: A solution of the product from Step 2 above (0.051 g, 0.201 mmol) in DCM (3 ml) and pyridine (0.097 ml, 1.20 mmol) was added to a solution of the product from Example 203 Step 2 (0.063 g, 0.241 mmol) in DCM (3 ml) and the resultant solution was stirred at RT for 72 h. The mixture was concentrated in vacuo. The crude product was purified by chromatography on silica gel (24 g cartridge, 0-50% EtOAc/isohexane) to afford the title compound (0.090 g, 0.176 mmol, 88% yield, 94% purity) as a white solid. UPLC-MS (Method 1): m/z 481.4 $(M+H)^+$, 479.3 $(M-H)^-$ at 1.86 min.

Step 4: 4-ethyl-3-(N-(2-(piperidin-1-yl)-5-(pyrazin-2-yl)phenyl)sulfamoyl)benzoic acid: 1 M LiOH(aq) (0.562 ml, 0.562 mmol) was added to a solution of the product from Step 3 above (0.090 g, 0.187 mmol, 94% purity) in THF (5 ml) and the solution was stirred at RT for 16 h. The mixture was then adjusted to pH 6 with citric acid to form a precipitate which was filtered under suction and washed with water (10 ml) to afford the title compound (67 mg, 0.141 mmol, 75% yield, 98% purity) as a pale yellow solid. UPLC-MS (Method 1): m/z 467.3 $(M+H)^+$, 465.3 $(M-H)^-$ at 1.70 min. $^1$H NMR (500 MHz, DMSO-$d_6$) δ 13.28 (br s, 1H), 9.18 (br s, 1H), 9.04 (d, J=1.5 Hz, 1H), 8.62 (dd, J=2.5, 1.5 Hz, 1H), 8.55 (d, J=2.5 Hz, 1H), 8.44 (d, J=1.8 Hz, 1H), 8.08 (dd, J=8.0, 1.8 Hz, 1H), 7.91 (d, J=2.1 Hz, 1H), 7.85 (dd, J=8.4, 2.1 Hz, 1H), 7.60 (d, J=8.0 Hz, 1H), 7.24 (d, J=8.4 Hz, 1H), 3.08 (q, J=7.4 Hz, 2H), 2.71 (t, J=5.2 Hz, 4H), 1.58 (q, J=5.6 Hz, 4H), 1.52-1.44 (m, 2H), 1.22 (t, J=7.4 Hz, 3H).

Example 291:3-(N-(5-(3,5-dimethylisoxazol-4-yl)-2-(piperidin-1-yl)phenyl)sulfamoyl)-4-ethylbenzoic acid

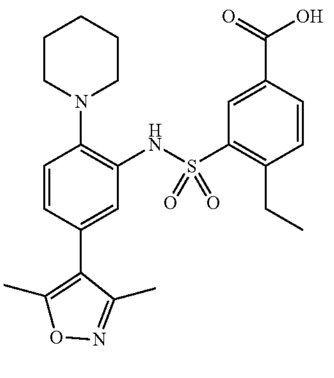 [SMILES: CCc1ccc(C(=O)O)cc1S(=O)(=O)Nc1cc(-c2c(C)noc2C)ccc1N1CCCCC1]

Step 1: 1-(4-bromo-2-nitrophenyl)piperidine: Piperidine (9.88 ml, 100 mmol) was added to a solution of 4-bromo-1-fluoro-2-nitrobenzene (5.60 ml, 45.5 mmol) in MeCN (50 ml) and the resultant solution was stirred at RT for 2 h. The reaction mixture was concentrated in vacuo. The crude product was purified by chromatography on silica gel (220 g cartridge, 0-50% EtOAc/isohexane) to afford the title compound (13.4 g, 44.2 mmol, 97% yield, 94% purity) as a red oil. UPLC-MS (Method 1): m/z 285.1 $(M+H)^+$, at 1.82 min. $^1H$ NMR (500 MHz, DMSO-$d_6$) δ 7.99 (d, J=2.4 Hz, 1H), 7.71 (dd, J=8.9, 2.5 Hz, 1H), 7.24 (d, J=8.9 Hz, 1H), 3.01-2.86 (m, 4H), 1.63-1.55 (m, 4H), 1.55-1.49 (m, 2H).

Step 2: 1-(2-nitro-4-(4,4,5,5-tetramethyl-1,3,2-dioxaborolan-2-yl)phenyl)piperidine: A mixture of the product from Step 1 above (1 g, 3.33 mmol, 94% purity), bis (pinacolato)diboron (1.27 g, 5.00 mmol), KOAc (0.981 g, 10.0 mmol), and $PdCl_2$ (dppf) (0.244 g, 0.333 mmol) in dioxane (10 ml) was degassed with $N_2$ for 5 min. The reaction was heated at 80° C. for 12 h. The mixture was diluted with water (50 ml) and extracted with EtOAc (50 ml). The organic phase was dried ($MgSO_4$), filtered and concentrated in vacuo. The crude product was purified by chromatography on silica gel (40 g cartridge, 0-50% EtOAc/isohexane) to afford the title compound (1.40 g, 3.16 mmol, 95% yield, 75% purity) as a brown oil. UPLC-MS (Method 1): m/z 333.3 $(M+H)^+$ at 1.99 min. $^1H$ NMR (500 MHz, DMSO-$d_6$) δ 7.95 (d, J=1.6 Hz, 1H), 7.73 (dd, J=8.4, 1.6 Hz, 1H), 7.23 (d, J=8.4 Hz, 1H), 3.04 (t, J=5.1 Hz, 4H), 1.67-1.52 (m, 6H), 1.29 (s, 12H).

Step 3: 2-(piperidin-1-yl)-5-(4,4,5,5-tetramethyl-1,3,2-dioxaborolan-2-yl)aniline: A solution of the product from Step 2 above (1.40 g, 3.16 mmol, 75% purity) in MeOH (20 ml) was treated with 10% Pd/C (0.336 g, 0.316 mmol). The solution was hydrogenated (2 bar) for 2 h. The mixture was filtered through Celite® and the filtrate was concentrated in vacuo. The crude product was purified by chromatography on silica gel (80 g cartridge, 0-50% EtOAc/isohexane) to afford the title compound (0.695 g, 2.21 mmol, 70% yield, 96% purity) as a waxy white solid. UPLC-MS (Method 1): m/z 303.3 $(M+H)^+$, at 1.41 min. $^1H$ NMR (500 MHz, DMSO-$d_6$) δ 7.04 (d, J=1.4 Hz, 1H), 6.90 (dd, J=7.7, 1.5 Hz, 1H), 6.84 (d, J=7.7 Hz, 1H), 4.63 (s, 2H), 2.80-2.70 (m, 4H), 1.55-1.49 (m, 2H), 1.55-1.49 (m, 2H), 1.26 (s, 12H).

Step 4: 5-(3,5-dimethylisoxazol-4-yl)-2-(piperidin-1-yl) aniline: A mixture of the product from Step 3 above (0.150 g, 0.496 mmol, 96% purity), 4-bromo-3,5-dimethylisoxazole (0.105 g, 0.596 mmol) and $K_3PO_4$ (0.137 g, 0.645 mmol) in dioxane (5 ml) and water (1 ml) was treated with Xphos Pd G3 (0.042 g, 0.050 mmol). The resultant mixture was degassed with $N_2$ for 15 min and then heated to 80° C. for 2 h. The reaction mixture was allowed to cool to RT and then concentrated in vacuo. The crude product was purified by chromatography on silica gel (24 g cartridge, 0-50% EtOAc/isohexane) to afford the title compound (0.100 g, 0.276 mmol, 56% yield, 75% purity) as a brown oil. UPLC-MS (Method 1): m/z 272.3 $(M+H)^+$, at 1.11 min.

Step 5: Methyl 3-(N-(5-(3,5-dimethylisoxazol-4-yl)-2-(piperidin-1-yl)phenyl)sulfamoyl)-4-ethylbenzoate: A solution of the product from Step 4 above (0.10 g, 0.276 mmol, 75% purity) in DCM (3 ml) and pyridine (0.134 ml, 1.66 mmol) was added to a solution of the product from Example 203 Step 2 (0.087 g, 0.332 mmol) in DCM (3 ml) and the resultant solution was stirred at RT for 72 h. The mixture was concentrated in vacuo. The crude product was purified by chromatography on silica gel (24 g cartridge, 0-40% EtOAc/isohexane) to afford the title compound (0.110 g, 0.206 mmol, 74% yield, 93% purity) as a white solid. UPLC-MS (Method 1): m/z 498.4 $(M+H)^+$, 496.3 $(M-H)^-$ at 1.94 min.

Step 6: 3-(N-(5-(3,5-dimethylisoxazol-4-yl)-2-(piperidin-1-yl)phenyl)sulfamoyl)-4-ethylbenzoic acid: 4 M HCl(aq) (0.276 ml, 1.11 mmol) was added to a solution of the product from Step 5 above (0.110 g, 0.221 mmol, 93%) in dioxane (5 ml) and the solution was stirred at 60° C. for 16 h. Conc. HCl(aq) (2 ml) was added and the mixture heated to 70° C. for 16 h. The mixture was concentrated in vacuo to afford crude product. The crude product was purified by purified by chromatography (40 g reverse phase C18 cartridge, 15-70% MeCN/0.1% formic acid (aq)) to afford the title compound (23 mg, 0.045 mmol, 20% yield, 97% purity) as a cream solid. UPLC-MS (Method 1): m/z 484.4 $(M+H)^+$, 482.3 $(M-H)^-$ at 1.80 min. $^1H$ NMR (500 MHz, DMSO-$d_6$) δ 8.39 (d, J=1.8 Hz, 1H), 8.09 (dd, J=7.9, 1.9 Hz, 1H), 7.60 (d, J=8.0 Hz, 1H), 7.23 (d, J=8.1 Hz, 1H), 7.09 (dd, J=8.1, 2.1 Hz, 1H), 7.06 (d, J=2.0 Hz, 1H), 3.10-3.02 (q, J=7.4 Hz, 2H), 2.64 (t, J=5.1 Hz, 4H), 2.27 (s, 3H), 2.09 (s, 3H), 1.60 (p, J=5.4 Hz, 4H), 1.53-1.44 (m, 2H), 1.22 (t, J=7.4 Hz, 3H). 2 exchangeable protons not observed.

Example 292:4-ethyl-3-(N-(5-(5-methyl-1,3,4-oxadiazol-2-yl)-2-(piperidin-1-yl)phenyl) sulfamoyl) benzoic acid

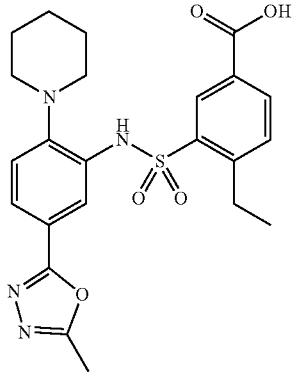 [SMILES: CCc1ccc(C(=O)O)cc1S(=O)(=O)Nc1cc(-c2nnc(C)o2)ccc1N1CCCCC1]

Step 1: 1-(4-bromo-2-nitrophenyl)piperidine: Piperidine (4.95 ml, 50 mmol) was added to a solution of 4-bromo-1-fluoro-2-nitrobenzene (2.79 ml, 22.7 mmol) in MeCN (25 ml). The reaction mixture was stirred at RT overnight then concentrated in vacuo. The residue was purified by chromatography on silica gel (120 g cartridge, 0-50% EtOAc/isohexane) to afford the title compound (6.8 g, 22.7 mmol, 100% yield, 95% purity) as a red liquid. UPLC-MS (Method 2) m/z 285.1 $(M+H)^+$ at 1.82 min.

Step 2: 1-(2-nitro-4-(4,4,5,5-tetramethyl-1,3,2-dioxaborolan-2-yl)phenyl)piperidine: A mixture of the product from Step 1 above (6.8 g, 22.7 mmol, 95% purity), bis (pinacolato)diboron (9.08 g, 35.8 mmol), KOAc (7.02 g, 71.5 mmol) and $PdCl_2$ (dppf)· DCM (1.95 g, 2.39 mmol) in dioxane (70 ml) was degassed using $N_2$ for 15 min. The resultant mixture was heated at 80° C. for 12 h. The mixture was allowed to cool to RT and was then diluted with brine (350 ml) and extracted with EtOAc (350 ml). The phases were separated and the organic phase dried over $MgSO_4$, filtered and concentrated in vacuo. The residue was purified by chromatography on silica gel (220 g cartridge, 0-50% EtOAc/isohexane) to afford the title compound (7.7 g, 16.2 mmol, 72% yield, 70% purity) as an orange oil. UPLC-MS (Method 2) m/z 333.6 $(M+H)^+$ at 1.98 min.

Step 3: 2-methyl-5-(3-nitro-4-(piperidin-1-yl)phenyl)-1,3,4-oxadiazole: A mixture of the product from Step 2 above (360 mg, 0.759 mmol, 70% purity), 2-bromo-5-methyl-1,3,4-oxadiazole (212 mg, 1.3 mmol), and $K_3PO_4$ (299 mg, 1.41 mmol) in dioxane (10 ml) and water (2 ml) was treated with Xphos Pd G3 (92 mg, 0.108 mmol). The resultant mixture was degassed with $N_2$ for 15 min, then heated at 80° C. for 2 h. The mixture was allowed to cool to RT, then was filtered and concentrated in vacuo. The residue was purified by chromatography on silica gel (40 g cartridge, 0-50% EtOAc/isohexane) to afford the title compound (115 mg, 0.279 mmol, 37% yield, 70% purity) as a brown oil. UPLC-MS (Method 2) m/z 289.5 $(M+H)^+$ at 1.39 min.

Step 4: 5-(5-methyl-1,3,4-oxadiazol-2-yl)-2-(piperidin-1-yl)aniline: A solution of the product from Step 3 above (115 mg, 0.279 mmol, 70% purity) in EtOH (3 ml) was treated with 5% Pd/C (50% w/w water) Type 87L (42.4 mg, 0.029 mmol). The resultant mixture was hydrogenated (1 bar) for 1 h, filtered through Celite® and the filtrate concentrated in vacuo to afford the crude product (75 mg). UPLC-MS (Method 2) m/z 259.6 $(M+H)^+$ at 1.33 min.

Step 5: methyl 4-ethyl-3-(N-(5-(5-methyl-1,3,4-oxadiazol-2-yl)-2-(piperidin-1-yl)phenyl)sulfamoyl)benzoate: A solution of the product from Step 4 above (75 mg) in DCM (1 ml) and pyridine (73.3 µl, 0.906 mmol) was added to a solution of the product from Example 203 Step 2 (43.6 mg, 0.166 mmol, 95% purity) in DCM (1 ml) and the resultant solution was stirred at RT for 2 days. The solvent was removed in vacuo and the residue was purified by chromatography on silica gel (40 g cartridge, 0-50% EtOAc/isohexane) to afford the title compound (20 mg, 0.039 mmol, 14% yield over two steps, 95% purity) as a colourless oil. UPLC-MS (Method 2) m/z 485.3 $(M+H)^+$ at 1.69 min.

Step 6: 4-ethyl-3-(N-(5-(5-methyl-1,3,4-oxadiazol-2-yl)-2-(piperidin-1-yl)phenyl)sulfamoyl)benzoic acid: 1 M LiOH(aq) (413 µl, 0.413 mmol) was added to a solution of the product from Step 5 above (20 mg, 0.039 mmol, 95% purity) in THF (1 ml) and the resultant mixture was stirred at RT overnight. The reaction mixture was concentrated in vacuo to remove THE, acidified to ~pH 6 using 1 M citric acid (aq) and the resultant precipitate was collected by filtration and dried in vacuo to afford the title compound (6 mg, 0.012 mmol, 31% yield, 95% purity) as a pale brown solid. UPLC-MS (Method 1) m/z 471.4 $(M+H)^+$, 469.3 $(M-H)^-$ at 1.61 min. $^1H$ NMR (500 MHz, DMSO-$d_6$) δ 13.3 (br s, 1H), 9.37 (br s, 1H), 8.40 (d, J=1.8 Hz, 1H), 8.10 (dd, J=8.0, 1.8 Hz, 1H), 7.68 (dd, J=8.4, 2.1 Hz, 1H), 7.64-7.61 (m, 2H), 7.26 (d, J=8.4 Hz, 1H), 3.07 (q, J=7.4 Hz, 2H), 2.75 (t, J=5.2 Hz, 4H), 2.53 (s, 3H), 1.57 (m, J=6.5 Hz, 4H), 1.52-1.43 (m, 2H), 1.22 (t, J=7.4 Hz, 3H).

Example 293: 4-ethyl-3-(N-(2-(piperidin-1-yl)-5-(pyridazin-3-yl)phenyl)sulfamoyl)benzoic

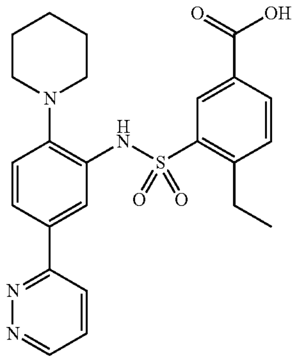 [SMILES: CCc1ccc(C(=O)O)cc1S(=O)(=O)Nc1cc(-c2cccnn2)ccc1N1CCCCC1]

Step 1: 3-(3-nitro-4-(piperidin-1-yl)phenyl)pyridazine: A mixture of the product from Example 287 Step 2 (360 mg, 0.759 mmol, 70% purity), 3-bromopyridazine (258 mg, 1.63 mmol) and $K_3PO_4$ (299 mg, 1.41 mmol) in dioxane (10 ml) and water (2 ml) was treated with Xphos Pd G3 (92 mg, 0.108 mmol). The reaction mixture was degassed with $N_2$ for 15 min and then heated at 80° C. overnight. Additional 3-bromopyridazine (129 mg, 0.813 mmol), Xphos Pd G3 (56 mg, 0.054 mmol) and $K_3PO_4$ (150 mg, 0.75 mmol) was added and the mixture heated at 80° C. for 4 days. The mixture was allowed to cool to RT, then was filtered through Celite® and concentrated in vacuo. The residue was purified by chromatography on silica gel (40 g cartridge, 0-100% EtOAc/isohexane) to afford the title compound (53 mg, 0.186 mmol, 19% yield, 80% purity) as a brown oil. UPLC-MS (Method 2) m/z 285.2 $(M+H)^+$ at 1.33 min. Two batches of product were combined to afford the title compound (95 mg, 0.294 mmol, 19% yield, 88% purity).

Step 2: 2-(piperidin-1-yl)-5-(pyridazin-3-yl)aniline: A solution of the product from Step 1 above (95 mg, 0.294 mmol, 88% purity) in EtOH (3 ml) was treated with 10% Pd/C (50% w/w water) Type 87L (35.6 mg, 0.023 mmol). The resultant mixture was hydrogenated (1 bar) for 1.5 h, filtered through Celite® and the filtrate removed in vacuo to afford the crude product (83 mg). UPLC-MS (Method 2) m/z 255.6 $(M+H)^+$ at 1.21 min.

Step 3: methyl 4-ethyl-3-(N-(2-(piperidin-1-yl)-5-(pyridazin-3-yl)phenyl)sulfamoyl)benzoate: A solution of the product from Step 2 above (83 mg) in DCM (1 ml) and pyridine (60.2 µl, 0.744 mmol) was added to a solution of the product from Example 203 Step 2 (35.8 mg, 0.129 mmol, 95% purity) in DCM (1 ml) and the resultant solution was stirred at RT for 72 h. The reaction mixture was concentrated in vacuo. The residue was purified by chromatography on silica gel (4 g cartridge, 0-50% EtOAc/isohexane) to afford the title compound (22 mg, 0.043 mmol, 15% yield over two steps, 95% purity) as a colourless oil. UPLC-MS (Method 2) m/z 481.1 $(M+H)^+$ at 2.59 min.

Step 4: 4-ethyl-3-(N-(2-(piperidin-1-yl)-5-(pyridazin-3-yl)phenyl)sulfamoyl)benzoic acid: 1 M LiOH(aq) (458 µl, 0.458 mmol) was added to a solution of the product from Step 3 above (22 mg, 0.043 mmol, 95% purity) in THF (1 ml) and the resultant mixture was stirred at RT overnight. The reaction mixture was concentrated in vacuo to remove THE, acidified to ~pH 6 using 1 M citric acid (aq) and the precipitate collected by filtration and dried in vacuo to afford the title compound (11 mg, 0.022 mmol, 52% yield, 95% purity) as a pale yellow solid. UPLC-MS (Method 1) m/z 467.3 $(M+H)^+$, 465.3 $(M-H)^-$ at 1.56 min. $^1$H NMR (500 MHz, DMSO-$d_6$) 13.3 (br s, 1H), 9.16 (dd, J=4.9, 1.5 Hz, 2H), 8.40 (d, J=1.8 Hz, 1H), 8.07 (dd, J=8.0, 1.8 Hz, 1H), 8.03-7.98 (m, 2H), 7.85 (dd, J=8.4, 2.2 Hz, 1H), 7.72 (dd, J=8.7, 4.9 Hz, 1H), 7.60 (d, J=8.0 Hz, 1H), 7.27 (d, J=8.4 Hz, 1H), 3.08 (q, J=7.5 Hz, 2H), 2.70 (t, J=5.2 Hz, 4H), 1.60-1.53 (m, 4H), 1.51-1.44 (m, 2H), 1.22 (t, J=7.4 Hz, 3H).

Example 294: 3-(N-(4-bromo-2-(piperidin-1-yl)-5-(trifluoromethyl)phenyl)sulfamoyl)-4-ethylbenzoic acid

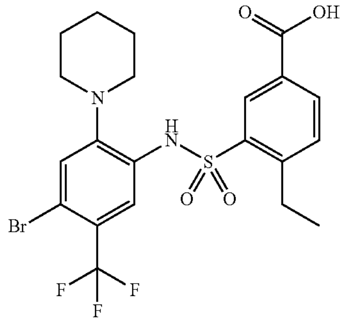

Step 1: 1-(5-bromo-2-nitro-4-(trifluoromethyl)phenyl)piperidine: A solution of 1-bromo-5-fluoro-4-nitro-2-(trifluoromethyl)benzene (300 mg, 1.04 mmol) and piperidine (250 µl, 2.53 mmol) in DCM (6 ml) was allowed to stand at RT for 1 h. The reaction mixture was washed with 1 M HCl(aq) (2×2 ml), dried over $MgSO_4$, filtered and concentrated in vacuo, azeotroping with toluene (3 ml), to afford the title compound (353 mg, 1.00 mmol, 96% yield) as a bright orange oil, which crystallised upon standing. UPLC-MS (Method 1) m/z 352.9 $(M+H)^+$ at 1.96 min.

Step 2: 4-bromo-2-(piperidin-1-yl)-5-(trifluoromethyl) aniline: The product from Step 1 above (353 mg, 1.00 mmol) was combined with zinc dust (500 mg, 7.65 mmol) and $NH_4Cl$(s) (410 mg, 7.66 mmol) in THF (9 ml) and water (3 ml). The resultant mixture was stirred at RT for 4 days, then allowed to stand for 1 day. The mixture was filtered through Celite®, washing with EtOAc (3×5 ml). The phases were separated, the organic phase dried over $MgSO_4$, filtered and concentrated in vacuo to afford the title compound (315 mg, 0.799 mmol, 80% yield, 82% purity) as a dark orange oil. UPLC-MS (Method 1) m/z 323.2 $(M+H)^+$ at 1.96 min.

Step 3: Methyl 3-(N-(4-bromo-2-(piperidin-1-yl)-5-(trifluoromethyl)phenyl)sulfamoyl)-4-ethylbenzoate: The product from Step 2 above (315 mg, 0.799 mmol, 82% purity) was dissolved in a mixture of DCM (1 ml) and pyridine (150 µl, 1.86 mmol) and treated with the product from Example 203 Step 2 (250 mg, 0.952 mmol). The resultant solution was allowed to stand at RT for 18 h, then heated at 35° C. for 4 days. The mixture was concentrated in vacuo and the residue dissolved in EtOAc (4 ml) and sequentially washed with water (3 ml), saturated $NaHCO_3$(aq) (3 ml) and brine (2 ml), dried over $MgSO_4$, filtered and concentrated in vacuo. The crude product was purified by chromatography on silica gel (12 g cartridge, 0-50% EtOAc/isohexane) to afford the title compound (363 mg, 0.614 mmol, 77% yield, 93% purity) as a brown oil. UPLC-MS (Method 1): m/z 549.2 $(M+H)^+$, 547.1 $(M-H)^-$ at 2.13 min.

Step 4: 3-(N-(4-bromo-2-(piperidin-1-yl)-5-(trifluoromethyl)phenyl)sulfamoyl)-4-ethylbenzoic acid: The product from Step 3 above (63 mg, 0.107 mmol, 93% purity) was dissolved in THF (1 ml) and treated with 1 M LiOH(aq) (427 µl, 0.427 mmol). The resultant solution was allowed to stand at RT for 18 h. The mixture was diluted with water (2 ml) and concentrated in vacuo. The resultant aqueous solution was diluted with water (1 ml) and acidified to PH ~5 using 1 M HCl(aq). The resultant precipitate was filtered, washing with water (3×1 ml) and dried in vacuo to afford a tan solid (50 mg). The crude product was purified by preparative HPLC (Waters, Acidic (0.1% Formic acid), Acidic, Waters X-Select Prep-C18, 5 µm, 19×50 mm column, 50-80% MeCN in Water) to afford the title compound (32 mg, 0.057 mmol, 53% yield, 95% purity) as a tan solid. UPLC-MS (Method 2): m/z 535.2 $(M+H)^+$, 533.1 $(M-H)^-$ at 1.34 min. $^1$H NMR (500 MHz, DMSO-$d_6$) δ 13.27 (br s, 1H), 9.68 (br s, 1H), 8.32 (d, J=1.8 Hz, 1H), 8.10 (dd, J=8.0, 1.8 Hz, 1H), 7.62 (d, J=8.0 Hz, 1H), 7.36 (s, 1H), 7.24 (s, 1H), 3.04 (q, J=7.4 Hz, 2H), 2.88-2.77 (m, 4H), 1.59-1.40 (m, 6H), 1.21 (t, J=7.4 Hz, 3H).

Example 295:3-(N-(5-cyano-2-(piperidin-1-yl)phenyl)sulfamoyl)-4-cyclopropylbenzoic acid

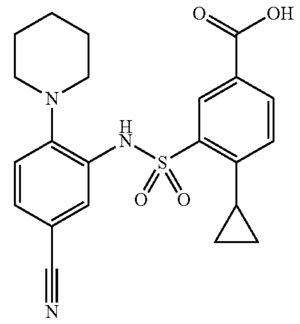 [SMILES: N#Cc1ccc(N2CCCCC2)c(NS(=O)(=O)c2cc(C(=O)O)ccc2C2CC2)c1]

Step 1: Methyl 4-bromo-3-(N-(5-cyano-2-(piperidin-1-yl) phenyl)sulfamoyl)benzoate: A mixture of the product from Example 182 Step 2 (250 mg, 1.24 mmol), the product from Example 316 Step 1 (433 mg, 1.37 mmol) and pyridine (300 µl, 3.71 mmol) in DCM (7 ml) was stirred at 35° C. for 3 days. The mixture was concentrated in vacuo onto silica and purified by chromatography on silica gel (12 g cartridge, 0-50% EtOAc/isohexane) to afford the title compound (403 mg, 0.834 mmol, 67% yield, 99% purity) as a white solid. UPLC-MS (Method 1) m/z 478.2 $(M+H)^+$, 476.0 $(M-H)^-$ at 1.79 min. $^1$H NMR (500 MHz, DMSO-$d_6$) δ 9.65 (s, 1H), 8.45-8.41 (m, 1H), 8.07-8.01 (m, 2H), 7.57 (dd, J=8.4, 2.0 Hz, 1H), 7.37 (d, J=2.0 Hz, 1H), 7.22 (d, J=8.4 Hz, 1H), 3.88 (s, 3H), 2.85-2.79 (m, 4H), 1.54-1.47 (m, 4H), 1.47-1.42 (m, 2H).

Step 2: Methyl 3-(N-(5-cyano-2-(piperidin-1-yl)phenyl) sulfamoyl)-4-cyclopropylbenzoate: The product from Step 1 above (403 mg, 0.834 mmol, 99% purity) and Pd-174 (61 mg, 85.0 µmol) in THF (17 ml) was treated with cyclopropylzinc (II) bromide (0.5 M in THF) (6.7 ml, 3.35 mmol) and the mixture was stirred at RT for 2 h and then at 55° C. for 3 h. Upon cooling to RT the mixture was quenched with MeOH (5 ml). The mixture was concentrated in vacuo onto silica and purified by chromatography on silica gel (12 g cartridge, 0-50% EtOAc/isohexane to afford the title compound (267 mg, 0.565 mmol, 67% yield, 93% purity) as a pale yellow solid. UPLC-MS (Method 1) m/z 440.3 $(M+H)^+$, 438.2 $(M-H)^-$ at 1.81 min. $^1H$ NMR (500 MHz, DMSO-$d_6$) δ 9.53 (s, 1H), 8.37 (d, J=1.9 Hz, 1H), 8.04 (dd, J=8.3, 1.9 Hz, 1H), 7.54 (d, J=8.2 Hz, 1H), 7.24 (d, J=2.0 Hz, 1H), 7.19 (d, J=8.3 Hz, 1H), 7.17 (d, J=8.5 Hz, 1H), 3.86 (s, 3H), 2.86-2.81 (m, 4H), 2.75-2.70 (m, 1H), 1.53-1.48 (m, 4H), 1.47-1.42 (m, 2H), 1.13-1.06 (m, 2H), 0.92-0.85 (m, 2H).

Step 3: 3-(N-(5-cyano-2-(piperidin-1-yl)phenyl)sulfamoyl)-4-cyclopropylbenzoic acid: A mixture of the product from Step 2 above (267 mg, 0.565 mmol, 93% purity) and LiOH (97 mg, 2.26 mmol) in THF/MeOH/water (4:1:1, 10.8 ml) was stirred at 40° C. for 4 days. The mixture was diluted with water (10 ml), acidified to ~pH 4 using 1 M HCl(aq) and extracted with EtOAc (3×20 ml). The combined organic extracts were washed with brine (20 ml), dried by passage through a phase separator and the solvent removed in vacuo. The residue was dissolved in DCM, concentrated in vacuo onto silica and purified by chromatography on silica gel (12 g cartridge, 0-10% MeOH/DCM). The residue was triturated with TBME to afford the title compound (138 mg, 0.311 mmol, 55% yield, 96% purity) as a white solid. UPLC-MS (Method 1) m/z 426.3 $(M+H)^+$, 424.3 $(M-H)^-$ at 1.65 min. $^1H$ NMR (500 MHz, DMSO-$d_6$) δ 13.27 (s, 1H), 9.48 (s, 1H), 8.37 (d, J=1.9 Hz, 1H), 8.02 (dd, J=8.2, 1.9 Hz, 1H), 7.54 (dd, J=8.4, 2.0 Hz, 1H), 7.24 (d, J=2.0 Hz, 1H), 7.17 (dd, J=8.4, 1.9 Hz, 2H), 2.86-2.80 (m, 4H), 2.77-2.68 (m, 1H), 1.55-1.41 (m, 6H), 1.12-1.05 (m, 2H), 0.90-0.82 (m, 2H).

Example 296: 4-cyclopropyl-3-(N-(5-(methylsulfonyl)-2-(piperidin-1-yl)phenyl)sulfamoyl)benzoic acid

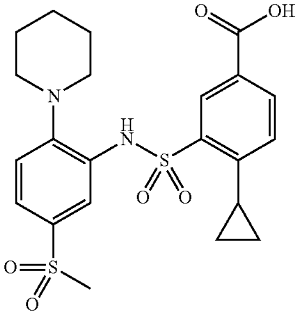 [SMILES: CS(=O)(=O)c1ccc(N2CCCCC2)c(NS(=O)(=O)c2cc(C(=O)O)ccc2C2CC2)c1]

Step 1: Methyl 4-bromo-3-(N-(5-(methylsulfonyl)-2-(piperidin-1-yl)phenyl)sulfamoyl)benzoate: A mixture of the product from Example 207 Step 2 (250 mg, 0.983 mmol), the product of Example 316 Step 1 (342 mg, 1.08 mmol) and pyridine (240 μl, 2.97 mmol) in DCM (6 ml) was stirred at 35° C. for 4 days. The mixture was concentrated in vacuo onto silica and purified by chromatography on silica gel (12 g cartridge, 0-100% EtOAc/isohexane) to afford the title compound (326 mg, 0.583 mmol, 59% yield, 95% purity) as a light tan solid. UPLC-MS (Method 1) m/z 531.1 $(M+H)^+$, 529.0 $(M-H)^-$ at 1.63 min. $^1H$ NMR (500 MHz, DMSO-$d_6$) δ 9.57 (s, 1H), 8.48-8.44 (m, 1H), 8.08-8.01 (m, 2H), 7.62 (dd, J=8.6, 2.2 Hz, 1H), 7.53 (d, J=2.2 Hz, 1H), 7.32 (d, J=8.6 Hz, 1H), 3.87 (s, 3H), 3.04 (s, 3H), 2.86-2.81 (m, 4H), 1.60-1.53 (m, 4H), 1.51-1.46 (m, 2H).

Step 2: Methyl 4-cyclopropyl-3-(N-(5-(methylsulfonyl)-2-(piperidin-1-yl)phenyl)sulfamoyl)benzoate: The product from Step 1 above (326 mg, 0.583 mmol, 95% purity) and Pd-174 (42 mg, 58.0 μmol) in THF (12 ml) was treated with cyclopropylzinc (II) bromide (0.5 M in THF) (4.7 ml, 2.35 mmol) and the mixture was stirred at RT for 2 h and then at 55° C. for 3 h. Upon cooling to RT, the mixture was quenched with MeOH (5 ml). The mixture was concentrated in vacuo onto silica and purified by chromatography on silica gel (12 g cartridge, 0-5% MeOH/DCM) to afford the title compound (284 mg, 0.461 mmol, 79% yield, 80% purity) as a yellow solid. UPLC-MS (Method 1) m/z 493.3 $(M+H)^+$, 491.2 $(M-H)^-$ at 1.66 min. $^1H$ NMR (500 MHz, DMSO-$d_6$) δ 9.46 (s, 1H), 8.39 (d, J=1.9 Hz, 1H), 8.03 (dd, J=8.3, 1.9 Hz, 1H), 7.62-7.57 (m, 1H), 7.46 (d, J=2.2 Hz, 1H), 7.26 (d, J=8.5 Hz, 1H), 7.20 (d, J=8.3 Hz, 1H), 3.85 (s, 3H), 3.00 (s, 3H), 2.87-2.82 (m, 4H), 2.80-2.72 (m, 1H), 1.58-1.52 (m, 4H), 1.50-1.45 (m, 2H), 1.12-1.08 (m, 2H), 0.91-0.85 (m, 2H).

Step 3: 4-cyclopropyl-3-(N-(5-(methylsulfonyl)-2-(piperidin-1-yl)phenyl)sulfamoyl)benzoic acid: A mixture of the product from Step 2 above (284 mg, 0.461 mmol, 80% purity) and LiOH (79 mg, 1.85 mmol) in THF/MeOH/water (4:1:1, 9 ml) was stirred at 40° C. for 4 days. The mixture was diluted with water (10 ml), acidified to ~pH 4 using 1 M HCl(aq) and extracted with EtOAc (3×20 ml). The combined organic extracts were washed with brine (20 ml), dried by passage through a phase separator and the solvent removed in vacuo. The residue was loaded onto silica and purified by chromatography on silica gel (12 g cartridge, 0-10% MeOH/DCM) to afford the title compound (121 mg, 0.245 mmol, 53% yield, 97% purity) as a white solid after trituration with TBME. UPLC-MS (Method 1) m/z 479.2 $(M+H)^+$, 477.2 $(M-H)^-$ at 1.50 min. 1H NMR (500 MHz, DMSO-$d_6$) δ 13.26 (s, 1H), 9.41 (s, 1H), 8.39 (d, J=1.9 Hz, 1H), 8.01 (dd, J=8.3, 1.9 Hz, 1H), 7.59 (dd, J=8.4, 2.2 Hz, 1H), 7.47 (d, J=2.2 Hz, 1H), 7.27 (d, J=8.4 Hz, 1H), 7.17 (d, J=8.3 Hz, 1H), 2.99 (s, 3H), 2.88-2.81 (m, 4H), 2.79-2.71 (m, 1H), 1.60-1.52 (m, 4H), 1.50-1.44 (m, 2H), 1.14-1.06 (m, 2H), 0.90-0.83 (m, 2H).

Example 297:4-ethyl-3-(N-(5-(isoxazol-4-yl)-2-(piperidin-1-yl)phenyl)sulfamoyl)benzoic acid

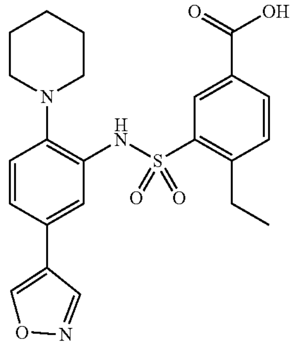 [SMILES: CCc1ccc(C(=O)O)cc1S(=O)(=O)Nc1cc(-c2cnoc2)ccc1N1CCCCC1]

Step 1: 5-(isoxazol-4-yl)-2-(piperidin-1-yl)aniline: A mixture of the product from Example 273 Step 3 (250 mg, 0.827 mmol), 4-bromoisoxazole (147 mg, 0.993 mmol), $K_3PO_4$ (228 mg, 1.08 mmol) in dioxane (10 ml) and water (2 ml) was treated with Xphos Pd G3 (70 mg, 0.083 mmol). The reaction mixture was degassed with $N_2$ for 15 min, then heated at 80° C. overnight. Additional 4-bromoisoxazole (74 mg, 0.50 mmol), $K_3PO_4$ (114 mg, 0.540 mmol) and Xphos Pd G3 (35 mg, 0.042 mmol) was added. The mixture was heated at 80° C. overnight. The mixture was allowed to cool to RT, then was filtered and concentrated in vacuo. The residue was purified by chromatography on silica gel (24 g cartridge, 0-50% EtOAc/isohexane) to afford the title compound (90 mg, 0.277 mmol, 34% yield, 75% purity) as a brown oil. UPLC-MS (Method 2) m/z 244.2 $(M+H)^+$ at 1.51 min.

Step 2: Methyl 4-ethyl-3-(N-(5-(isoxazol-4-yl)-2-(piperidin-1-yl)phenyl)sulfamoyl)benzoate: A solution of the product from Step 1 above (90 mg, 0.277 mmol, 75% purity) in DCM (1 ml) and pyridine (180 μl, 2.22 mmol) was added to a solution of the product from Example 203 Step 2 (107 mg, 0.407 mmol, 95% purity) in DCM (1 ml) and the resultant solution was stirred at RT for 2 days. The mixture was concentrated in vacuo and the residue was purified by chromatography on silica gel (4 g cartridge, 0-100% EtOAc/isohexane) to afford the title compound (139 mg, 0.237 mmol, 85% yield, 80% purity) as a light brown solid. UPLC-MS (Method 2) m/z 470.6 $(M+H)^+$ at 1.85 min.

Step 3: 4-ethyl-3-(N-(5-(isoxazol-4-yl)-2-(piperidin-1-yl)phenyl)sulfamoyl)benzoic acid: 4 M HCl in dioxane (370 μl, 1.48 mmol) was added to a solution of the product from Step 2 above (139 mg, 0.237 mmol, 80% purity) in dioxane (3 ml) and the resultant solution was stirred at 60° C. overnight. Water (1 ml) was added and the solution was heated at 60° C. overnight. Additional 4 M HCl in dioxane (370 μL, 1.48 mmol) and water (1 ml) was added and the solution was heated at 60° C. for 2 days. The reaction mixture was concentrated in vacuo and purified by chromatography (13 g reverse phase C18 cartridge, 5-90% MeCN/0.1% formic acid (aq)) to afford the title compound (33 mg, 0.069 mmol, 29% yield, 95% purity) as an off white solid. UPLC-MS (Method 1) m/z 456.3 $(M+H)^+$, 454.2 $(M-H)^-$ at 1.76 min. $^1H$ NMR (500 MHz, DMSO-d6) δ 13.3 (br s, 1H), 9.27 (s, 1H), 9.08 (br s, 1H), 8.93 (s, 1H), 8.41 (d, J=1.8 Hz, 1H), 8.06 (dd, J=8.0, 1.9 Hz, 1H), 7.58 (d, J=8.0 Hz, 1H), 7.44 (d, J=2.1 Hz, 1H), 7.39 (dd, J=8.2, 2.1 Hz, 1H), 7.20 (d, J=8.3 Hz, 1H), 3.05 (q, J=7.4 Hz, 2H), 2.57 (t, J=5.2 Hz, 4H), 1.57-1.49 (m, 4H), 1.48-1.40 (m, 2H), 1.21 (t, J=7.4 Hz, 3H).

Example 298:4-ethyl-3-(N-(2-(piperidin-1-yl)-5-(1,2,3-triazol-4-yl)phenyl)sulfamoyl)benzoic acid

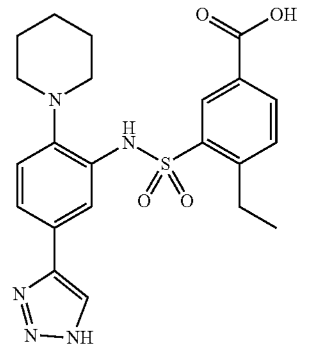 [SMILES: CCc1ccc(C(=O)O)cc1S(=O)(=O)Nc1cc(-c2c[nH]nn2)ccc1N1CCCCC1]

Step 1: 1-(2-nitro-4-((trimethylsilyl) ethynyl)phenyl)piperidine: The product from Example 273 Step 1 (0.680 g, 2.39 mmol) in dry THF (5 ml) was treated with $Et_3N$ (0.499 ml, 3.58 mmol), $Pd(PPh_3)_4$ (0.055 g, 0.048 mmol) and CuI(s) (0.018 g, 0.095 mmol) followed by ethynyltrimethylsilane (0.219 ml, 3.10 mmol). The resultant dark mixture was stirred at RT for 16 h, then heated at 70° C. for 16 h and then at 100° C. for 16 h. The mixture was cooled, diluted with water (50 ml) and extracted with DCM (2×50 ml). The organic phases were combined and dried over $MgSO_4$, filtered and concentrated in vacuo. The residue was purified by chromatography on silica gel (40 g cartridge, 0-10% TBME in isohexane) to afford the title compound (0.520 g, 1.31 mmol, 55% yield, 76% purity) as a brown oil. UPLC-MS (Method 1): m/z 303.3 $(M+H)^+$, at 2.17 min.

Step 2: 1-(4-ethynyl-2-nitrophenyl)piperidine: The product from Step 1 above (0.520 g, 1.31 mmol, 76% purity) in dry THF (5 ml) was treated with 1.0 M TBAF (1.57 ml, 1.57 mmol). The resultant mixture was stirred at RT for 16 h, then concentrated in vacuo. The residue was purified by chromatography on silica gel (40 g cartridge, 0-50% EtOAc/isohexane) to afford the title compound (0.240 g, 0.907 mmol, 69% yield, 87% purity) as a brown oil. UPLC-MS (Method 1): m/z 231.3 $(M+H)^+$ at 1.72 min.

Step 3: 1-(2-nitro-4-(1,2,3-triazol-4-yl)phenyl)piperidine: The product from Step 2 above (0.240 g, 0.907 mmol, 87% purity) in dry MeOH (1 ml) and DMF (9 ml) was treated with CuI(s) (8.6 mg, 0.045 mmol) followed by trimethylsilylazide (0.169 ml, 1.27 mmol). The resultant mixture was heated at 100° C. for 16 h, then concentrated in vacuo. The residue was purified by chromatography on silica gel (40 g cartridge, 0-50% EtOAc/isohexane) to afford the title compound (0.090 g, 0.319 mmol, 35% yield, 97% purity) as a red oil. UPLC-MS (Method 1): m/z 274.3 $(M+H)^+$, 272.2 $(M-H)^-$, at 1.39 min.

Step 4: 2-(piperidin-1-yl)-5-(1,2,3-triazol-4-yl)aniline: The product from Step 3 above (0.090 g, 0.319 mmol, 97% purity) was dissolved in MeOH (10 ml) and treated with 10% Pd/C (50% w/w water) Type 39 (8.1 mg, 3.80 μmol). The resultant mixture was hydrogenated (2 bar) at RT for 16 h. The mixture was filtered through Celite®, washing with MeOH (20 ml). The filtrate was concentrated in vacuo to afford the title compound (70 mg, 0.282 mmol, 88% yield, 98% purity) as a colourless oil. UPLC-MS (Method 1): m/z 244.3 $(M+H)^+$ at 0.72 min.

Step 5: methyl 4-ethyl-3-(N-(2-(piperidin-1-yl)-5-(1,2,3-triazol-4-yl)phenyl)sulfamoyl)benzoate: A solution of the product from Step 4 above (70 mg, 0.282 mmol, 98% purity) in DCM (3 ml) and pyridine (0.047 ml, 0.575 mmol) was added to a solution of the product from Example 203 Step 2 (0.076 g, 0.288 mmol) in DCM (3 ml) and the resultant solution was stirred at RT for 16 h, then concentrated in vacuo. The residue was purified by chromatography on silica gel (24 g cartridge, 0-50% EtOAc/isohexane) to afford the title compound (75 mg, 0.152 mmol, 54% yield, 95% purity) as a white solid. UPLC-MS (Method 1): m/z 470.4 $(M+H)^+$, 468.3 $(M-H)^-$, at 1.69 min. $^1H$ NMR (500 MHz, DMSO-$d_6$) δ 9.12 (br s, 1H), 8.41 (d, J=1.9 Hz, 1H), 8.09 (dd, J=8.0, 1.9 Hz, 1H), 7.75-7.58 (m, 2H), 7.54 (d, J=8.1 Hz, 1H), 7.20 (d, J=8.3 Hz, 1H), 3.83 (s, 3H), 3.13-2.97 (q, J=7.4 Hz, 2H), 2.66-2.58 (m, 4H), 1.60-1.53 (m, 4H), 1.50-1.43 (m, 2H), 1.22 (t, J=7.4 Hz, 3H). Two exchangeable protons not observed.

Step 6: 4-ethyl-3-(N-(2-(piperidin-1-yl)-5-(1,2,3-triazol-4-yl)phenyl)sulfamoyl)benzoic acid: A solution of the product from Step 5 above (75 mg, 0.152 mmol, 95% purity) in THF (5 ml) was treated with 1 M LiOH(aq) (0.479 ml, 0.479 mmol) and the resultant mixture stirred at RT over the weekend. The mixture was then acidified to pH 7 using 10% w/v citric acid (aq) and then concentrated in vacuo. The residue was purified by chromatography (12 g reverse phase C18 cartridge, 10-45% MeCN/0.1% formic acid (aq)) to afford the title compound (40.2 mg, 0.086 mmol, 57% yield, 98% purity) as a pale yellow solid. UPLC-MS (Method 1): m/z 456.4 $(M+H)^+$, 454.3 $(M-H)^-$ at 1.54 min. $^1H$ NMR (500 MHz, DMSO-$d_6$) δ 9.02 (br s, 1H), 8.42 (d, J=1.8 Hz, 1H), 8.12 (br s, 1H), 8.05 (dd, J=7.9, 1.8 Hz, 1H), 7.67 (s, 1H), 7.56 (d, J=8.0 Hz, 1H), 7.53 (dd, J=8.3, 2.0 Hz, 1H), 7.21 (d, J=8.3 Hz, 1H), 3.06 (q, J=7.4 Hz, 2H), 2.66-2.60 (m, 4H), 1.60-1.53 (m, 4H), 1.50-1.43 (m, 2H), 1.22 (t, J=7.4 Hz, 3H).

Example 299:3-(N-(5-(1,3,4-oxadiazol-2-yl)-2-(piperidin-1-yl)phenylsulfamoyl)-4-ethylbenzoic acid

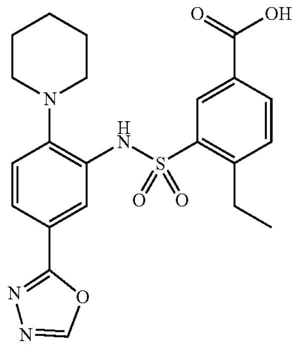 [SMILES: CCc1ccc(C(=O)O)cc1S(=O)(=O)Nc1cc(-c2nnco2)ccc1N1CCCCC1]

Step 1: methyl 3-nitro-4-(piperidin-1-yl)benzoate: methyl 4-fluoro-3-nitrobenzoate (500 mg, 2.51 mmol) in dry DMF (5 ml) was treated with piperidine (744 µl, 7.53 mmol) and stirred at RT for 2 h. The mixture was diluted with water (50 ml) and extracted with EtOAc (100 ml). The organic phase was washed with brine (50 ml), dried ($MgSO_4$), filtered and concentrated in vacuo to afford the title compound (650 mg, 2.31 mmol, 92% yield, 94% purity) as a red oil. UPLC-MS (Method 1) m/z 265.2 $(M+H)^+$ at 1.62 min.

Step 2: 3-nitro-4-(piperid-1-yl)benzohydrazide: The product from Step 1 above (650 mg, 2.31 mmol, 94% purity) in dry EtOH (5 ml) was treated with hydrazine hydrate (1.04 ml, 11.5 mmol) and heated at 80° C. for 16 h. The mixture was allowed to cool to RT and then concentrated in vacuo. The residue was purified by chromatography on silica gel (40 g cartridge, 0-5% MeOH/DCM) to afford the title compound (530 mg, 2.00 mmol, 86% yield, 99% purity) as an orange oil. UPLC-MS (Method 1) m/z 265.2 $(M+H)^+$ at 0.99 min.

Step 3: 2-(3-nitro-4-(piperidin-1-yl)phenyl)-1,3,4-oxadiazole: The product from Step 2 above (530 mg, 2.00 mmol, 99% purity) was treated with triethyl orthoformate (5 ml) and the mixture was heated at 100° C. for 16 h. The mixture was allowed to cool to RT and was then concentrated in vacuo. The residue was purified by chromatography on silica gel (40 g cartridge, 0-5% MeOH/DCM) to afford the title compound (486 mg, 1.75 mmol, 87% yield, 99% purity) as a red solid. UPLC-MS (Method 1) m/z 275.3 $(M+H)^+$ at 1.38 min.

Step 4: 5-(1,3,4-oxadiazol-2-yl)-2-(piperidin-1-yl)aniline: The product from Step 3 above (486 mg, 1.75 mmol, 99% purity) in MeOH (10 ml) was treated with 10% Pd/C (50% w/w water) Type 39 (45.0 mg, 0.180 mmol). The reaction mixture was hydrogenated (2 bar) at RT for 16 h. The mixture was filtered through Celite®, washing with MeOH (20 ml) and then concentrated in vacuo to afford the title compound (302 mg, 1.17 mmol, 66% yield, 95% purity) as a red oil. UPLC-MS (Method 1) m/z 245.3 $(M+H)^+$ at 1.15 min.

Step 5: methyl 3-(N-(5-(1,3,4-oxadiazol-2-yl)-2-(piperidin-1-yl)phenyl)sulfamoyl)-4-ethylbenzoate: A solution of the product from Step 4 above (100 mg, 0.409 mmol, 95% purity) in DCM (3 ml) and pyridine (199 µl, 2.45 mmol) were added to a solution of the product from Example 203 Step 2 (108 mg, 0.409 mmol) in DCM (1 ml) and the solution was stirred at RT for 4 days. The reaction mixture was concentrated in vacuo. The residue was purified by chromatography on silica gel (40 g cartridge, 0-50% EtOAc/isohexane) to afford the title compound (133 mg, 0.257 mmol, 63% yield, 91% purity) as a white solid. UPLC-MS (Method 1) m/z 471.4 $(M+H)^+$, 469.3 $(M-H)^-$ at 1.72 min.

Step 6: 3-(N-(5-(1,3,4-oxadiazol-2-yl)-2-(piperidin-1-yl)phenylsulfamoyl)-4-ethylbenzoic acid: 1 M LiOH(aq) (772 µl, 0.772 mmol) was added to a solution of the product from Step 5 above (133 mg, 0.257 mmol, 91% purity) in THF (5 ml) and the mixture was stirred at RT overnight. The mixture was acidified to pH 6 using 10% w/v citric acid (aq) and the resultant mixture was concentrated in vacuo. The residue was purified by chromatography (12 g reverse phase C18 cartridge, 10-45% MeCN/0.1% formic acid (aq)) to afford the title compound (55.8 mg, 0.12 mmol, 47% yield, 98% purity) as a white solid. UPLC-MS (Method 1) m/z 457.3 $(M+H)^+$, 455.3 $(M-H)^-$ at 1.58 min. $^1H$ NMR (500 MHz, DMSO-$d_6$) δ 13.24 (br s, 1H), 9.43 (br s, 1H), 9.24 (s, 1H), 8.37 (d, J=1.8 Hz, 1H), 8.09 (dd, J=8.0, 1.9 Hz, 1H), 7.80-7.68 (m, 2H), 7.62 (d, J=8.0 Hz, 1H), 7.27 (d, J=8.3 Hz, 1H), 3.07 (q, J=7.4 Hz, 2H), 2.76 (t, J=5.2 Hz, 4H), 1.58-1.52 (m, 4H), 1.47 (m, 2H), 1.23 (t, J=7.4 Hz, 3H).

Example 300:4-ethyl-3-(N-(5-(isoxazol-5-yl)-2-(piperidin-1-yl)phenyl)sulfamoyl)benzoic acid

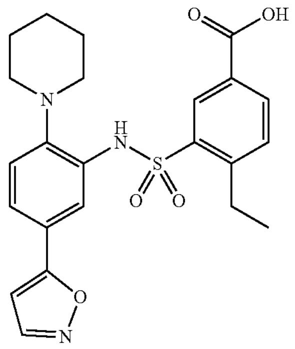 [SMILES: CCc1ccc(C(=O)O)cc1S(=O)(=O)Nc1cc(-c2ccno2)ccc1N1CCCCC1]

Step 1: 1-(3-nitro-4-(piperidin-1-yl)phenyl) ethanone: Piperidine (539 µl, 5.46 mmol) was added to a solution of 1-(4-fluoro-3-nitrophenyl) ethanone (1 g, 5.46 mmol) and $Et_3N$ (2.28 ml, 16.4 mmol) in MeCN (10 ml) and the resultant solution was stirred at RT overnight. The reaction mixture was concentrated in vacuo to afford the title compound (1.2 g, 4.64 mmol, 85% yield, 96% purity) as a red oil. UPLC-MS (Method 1) m/z 249.3 $(M+H)^+$ at 1.48 min.

Step 2: I-3-(dimethylamino)-1-(3-nitro-4-(piperidin-1-yl) phenyl) prop-2-en-1-one: The product from Step 1 above (1.2 g, 4.64 mmol, 96% purity) was treated with N,N-dimethylformamide dimethyl acetal (10.0 ml, 4.64 mmol) and the mixture was heated at 120° C. for 16 h. The mixture was allowed to cool to RT and then concentrated in vacuo to afford the title compound (1.3 g, 4.07 mmol, 88% yield, 95% purity) as a red oil. UPLC-MS (Method 1) m/z 304.3 $(M+H)^+$ at 1.39 min.

Step 3: 5-(3-nitro-4-(piperidin-1-yl)phenyl) isoxazole: The product from Step 2 above (1.3 g, 4.07 mmol, 95% purity) was combined with hydroxylamine hydrochloride (339 mg, 4.89 mmol) in MeOH (10 ml) and the mixture was heated at 70° C. for 3 h. The reaction mixture was concentrated in vacuo. The residue was purified by chromatography on silica gel (40 g cartridge, 0-50% EtOAc/isohexane) to afford the title compound (937 mg, 3.26 mmol, 80% yield, 95% purity) as a red oil. UPLC-MS (Method 1) m/z 274.2 $(M+H)^+$ at 1.62 min.

Step 4: 5-(isoxazol-5-yl)-2-(piperidin-1-yl)aniline: A mixture of the product from Step 3 above (200 mg, 0.730 mmol, 95% purity) in THF (9 ml) and water (3 ml) was treated with zinc dust (287 mg, 4.39 mmol) and $NH_4Cl(s)$ (235 mg, 4.39 mmol). The resultant mixture was stirred at RT for 1 h. The mixture was filtered through Celite®, washing with EtOAc, and then concentrated in vacuo. The residue was purified by chromatography on silica gel (24 g cartridge, 0-50% TBME/isohexane) to afford the title compound (102 mg, 0.419 mmol, 57% yield) as a cream solid. UPLC-MS (Method 1) m/z 244.3 $(M+H)^+$ at 1.27 min.

Step 5: methyl 4-ethyl-3-(N-(5-(isoxazol-5-yl)-2-(piperidin-1-yl)phenyl)sulfamoyl)benzoate: A solution of the product from Step 4 above (102 mg, 0.419 mmol) in DCM (3 ml) and pyridine (203 μl, 2.52 mmol) were added to a solution of the product from Example 203 Step 2 (110 mg, 0.419 mmol) in DCM (5 ml) and the solution was stirred at RT for 2 days. The reaction mixture was concentrated in vacuo. The residue was purified by chromatography on silica gel (40 g cartridge, 0-50% EtOAc/isohexane) to afford the title compound (150 mg, 0.319 mmol, 76% yield) as a white solid. UPLC-MS (Method 1) m/z 470.4 $(M+H)^+$, 468.3 $(M-H)^-$ at 1.85 min.

Step 6: 4-ethyl-3-(N-(5-(isoxazol-5-yl)-2-(piperidin-1-yl) phenyl)sulfamoyl)benzoic acid: 4 M HCl in dioxane (399 μl, 1.59 mmol) was added to a solution of the product from Step 5 above (150 mg, 0.319 mmol) in dioxane (5 ml) and the mixture was heated at 60° C. for 16 h. Concentrated HCl(aq) (2 ml) was added and the mixture was heated at 70° C. for a further 16 h. The mixture was concentrated in vacuo and the solid slurried with TBME (20 ml) for 30 min. The solid was collected to afford the title compound (145 mg, 0.309 mmol, 97% yield, 97% purity) as a cream solid. UPLC-MS (Method 1) m/z 456.4 $(M+H)^+$, 454.3 $(M-H)^-$ at 1.74 min. $^1H$ NMR (500 MHz, DMSO-$d_6$) δ 9.32 (br s, 1H), 8.59 (d, J=1.9 Hz, 1H), 8.39 (d, J=1.8 Hz, 1H), 8.09 (dd, J=8.0, 1.8 Hz, 1H), 7.61 (dd, J=8.2, 1.9 Hz, 2H), 7.54 (d, J=2.1 Hz, 1H), 7.25 (d, J=8.4 Hz, 1H), 6.79 (d, J=1.9 Hz, 1H), 3.06 (q, J=7.4 Hz, 2H), 2.75-2.68 (m, 4H), 1.60-1.53 (m, 4H), 1.50-1.43 (m, 2H), 1.22 (t, J=7.4 Hz, 3H). One exchangeable proton not observed.

Example 301: 4-ethyl-3-(N-(2-(piperidin-1-yl)-5-(pyrazol-4-yl)phenyl)sulfamoyl)benzoic acid

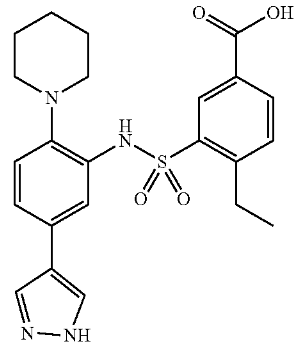 [SMILES: CCc1ccc(C(=O)O)cc1S(=O)(=O)Nc1cc(-c2cn[nH]c2)ccc1N1CCCCC1]

Step 1: tert-butyl 4-(3-nitro-4-(piperidin-1-yl)phenyl)-pyrazole-1-carboxylate: A mixture of the product from Example 287 Step 2 (291 mg, 0.714 mmol, 70% purity), tert-butyl 4-(4,4,5,5-tetramethyl-1,3,2-dioxaborolan-2-yl)-pyrazole-1-carboxylate (250 mg, 0.85 mmol) and $K_3PO_4$ (235 mg, 1.11 mmol) in dioxane (10 ml) and water (2 ml) was treated with Xphos Pd G3 (71.9 mg, 0.085 mmol). The reaction mixture was degassed with $N_2$ for 15 min and then heated at 80° C. for 1 h. The mixture was allowed to cool to RT, then was filtered and concentrated in vacuo. The residue was purified by chromatography on silica gel (12 g cartridge, 0-100% EtOAc/isohexane) to afford the title compound (201 mg, 0.497 mmol, 83% yield, 92% purity) as a red oil. UPLC-MS (Method 2) m/z 373.3 $(M+H)^+$ at 1.85 min.

Step 2: tert-butyl 4-(3-amino-4-(piperidin-1-yl)phenyl)-pyrazole-1-carboxylate: A solution of the product from Step 1 above (201 mg, 0.497 mmol, 92% purity) in MeOH (10 ml) was treated with 10% Pd/C (57.4 mg, 0.027 mmol). The solution was hydrogenated at a pressure of 1 bar for 1 h. The reaction mixture was filtered through Celite® and the filtrate was concentrated in vacuo to afford the title compound (160 mg, 0.439 mmol, 88% yield, 94% purity) as a clear oil. UPLC-MS (Method 2) m/z 343.3 $(M+H)^+$ at 1.77 min.

Step 3: tert-butyl 4-(3-(2-ethyl-5-(methoxycarbonyl)phenylsulfonamido)-4-(piperidin-1-yl)phenyl)-pyrazole-1-carboxylate: A solution of the product from Step 2 above (160 mg, 0.439 mmol, 94% purity) in DCM (5 ml) and pyridine (227 μl, 2.80 mmol) was treated with the product from Example 203 Step 2 (135 mg, 0.488 mmol, 95% purity) and the solution was stirred at RT for 2 days. The solvent was removed in vacuo and the residue was purified by chromatography on silica gel (40 g cartridge, 0-100% EtOAc/isohexane) to afford the title compound (112 mg, 0.158 mmol, 36% yield, 80% purity) as a yellow solid. UPLC-MS (Method 2) m/z 569.4 $(M+H)^+$ at 2.06 min.

Step 4: 4-ethyl-3-(N-(2-(piperidin-1-yl)-5-(pyrazol-4-yl) phenyl)sulfamoyl)benzoic acid: The product from Step 3 above (112 mg, 0.158 mmol, 80% purity) was treated with 4 M HCl in dioxane (59.8 μl, 1.97 mmol) and water (0.5 ml). The solution was heated at 60° C. for 6 h. Concentrated HCl(aq) (1 ml) and water (1 ml) was added and reaction mixture heated at 60° C. overnight. The reaction mixture was concentrated in vacuo and the residue was purified by chromatography using a (13 g reverse phase C18 cartridge, 15-80% MeCN/0.1% formic acid (aq)) to afford the title compound (35.5 mg, 0.074 mmol, 47% yield, 95% purity) as a pale yellow solid. UPLC-MS (Method 1) m/z 455.4

(M+H)$^+$, 453.3 (M−H)$^-$ at 1.54 min. $^1$H NMR (500 MHz, DMSO-d$_6$) δ 13.1 (br s, 1H), 8.94 (br s, 1H), 8.47 (d, J=1.8 Hz, 1H), 8.08 (dd, J=8.0, 1.9 Hz, 1H), 7.79 (s, 2H), 7.59 (d, J=8.0 Hz, 1H), 7.33-7.22 (m, 2H), 7.14 (d, J=8.2 Hz, 1H), 3.06 (q, J=7.4 Hz, 2H), 2.59 (t, J=5.2 Hz, 4H), 1.62-1.54 (m, 4H), 1.51-1.43 (m, 2H), 1.22 (t, J=7.4 Hz, 3H). One exchangeable proton not observed.

Example 302: 4-ethyl-3-(N-(2-(piperidin-1-yl)-5-(pyridazin-4-yl)phenyl)sulfamoyl)benzoic acid

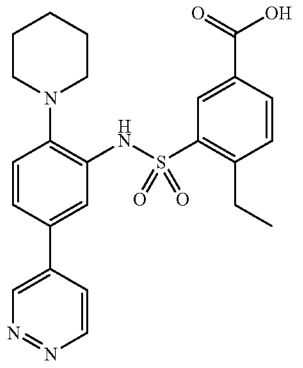 [SMILES: CCc1ccc(C(=O)O)cc1S(=O)(=O)Nc1cc(-c2ccnnc2)ccc1N1CCCCC1]

Step 1: methyl 4-ethyl-3-(N-(2-(piperidin-1-yl)-5-(pyridazin-4-yl)phenyl)sulfamoyl)benzoate: A mixture of the product from Example 273 Step 4 (150 mg, 0.281 mmol, 99% purity), 4-chloropyridazine hydrochloride (51.4 mg, 0.341 mmol) and $K_3PO_4$ (139 mg, 0.653 mmol) in dioxane (5 ml) and water (1 ml) was treated with Xphos Pd G3 (24 mg, 0.028 mmol). The reaction mixture was degassed with $N_2$ for 15 min, then heated at 80° C. for 2 h. The mixture was allowed to cool to RT and was then diluted with water (50 ml) and extracted with EtOAc (2× 50 ml). The combined organic extracts were dried over $MgSO_4$, filtered and concentrated in vacuo. The residue was purified by chromatography on silica gel (12 g cartridge, 0-100% EtOAc/isohexane) to afford the title compound (82 mg, 0.171 mmol, 61% yield) as a yellow oil. UPLC-MS (Method 2) m/z 481.4 (M+H)$^+$ at 1.64 min.

Step 2: 4-ethyl-3-(N-(2-(piperidin-1-yl)-5-(pyridazin-4-yl)phenyl)sulfamoyl)benzoic acid: 1 M LiOH(aq) (1.71 ml, 1.71 mmol) was added to a solution of the product from Step 1 above (82 mg, 0.171 mmol) in THF (2 ml) and the solution was stirred at RT overnight. The reaction mixture was concentrated in vacuo to remove THE, acidified to ~pH 6 using 1 M HCl(aq) and the resultant precipitate collected by filtration and dried in vacuo to afford the title compound (60 mg, 0.122 mmol, 72% yield, 95% purity) as a yellow solid. UPLC-MS (Method 1) m/z 467.4 (M+H)$^+$, 465.3 (M−H)$^-$ at 1.56 min. $^1$H NMR (500 MHz, DMSO-d$_6$) δ 13.4 (br s, 1H), 9.38 (dd, J=2.5, 1.2 Hz, 1H), 9.30 (br s, 1H), 9.21 (dd, J=5.5, 1.2 Hz, 1H), 8.43 (d, J=1.8 Hz, 1H), 8.09 (dd, J=8.0, 1.9 Hz, 1H), 7.74 (dd, J=5.5, 2.6 Hz, 1H), 7.65 (dd, J=8.3, 2.2 Hz, 1H), 7.61 (d, J=8.0 Hz, 1H), 7.53 (d, J=2.2 Hz, 1H), 7.27 (d, J=8.4 Hz, 1H), 3.07 (q, J=7.4 Hz, 2H), 2.70 (t, J=5.2 Hz, 4H), 1.63-1.53 (m, 4H), 1.51-1.42 (m, 2H), 1.22 (t, J=7.4 Hz, 3H).

Example 303: 4-ethyl-3-(N-(4-methyl-5-(5-methylisoxazol-4-yl)-2-(piperidin-1-yl)phenyl) sulfamoyl) benzoic acid

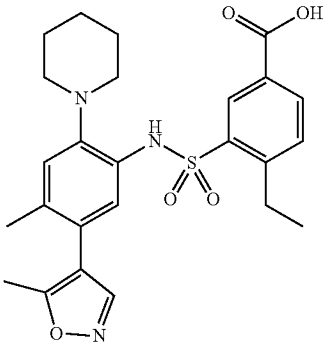 [SMILES: CCc1ccc(C(=O)O)cc1S(=O)(=O)Nc1cc(-c2cnoc2C)c(C)cc1N1CCCCC1]

Step 1: 1-(4-bromo-5-methyl-2-nitrophenyl)piperidine: 1-bromo-4-fluoro-2-methyl-5-nitrobenzene (1.1 g, 4.70 mmol) in dry DMF (5 ml) was treated with piperidine (1.39 ml, 14.1 mmol) and the resultant mixture stirred at RT for 72 h. The mixture was diluted with water (50 ml) and extracted with EtOAc (100 ml). The organic phase was washed with brine (50 ml), dried over $MgSO_4$, filtered, and concentrated in vacuo to afford the title compound (1.4 g, 4.63 mmol, 99% yield, 99% purity) as a red oil. UPLC-MS (Method 1) m/z 299.1 (M+H)$^+$ at 1.95 min.

Step 2: 1-(5-methyl-2-nitro-4-(4,4,5,5-tetramethyl-1,3,2-dioxaborolan-2-yl)phenyl)piperidine: A mixture of the product from Step 1 above (1.4 g, 4.63 mmol, 99% purity), bis(pinacolato)diboron (1.76 g, 6.95 mmol), KOAc (1.36 g, 13.9 mmol) and $PdCl_2$ (dppf)·DCM (339 mg, 0.463 mmol) in dioxane (10 ml) was degassed with $N_2$ for 15 min and then heated at 80° C. for 16 h. The mixture was diluted with water (50 ml) and extracted with EtOAc (50 ml). The organic phase was dried over $MgSO_4$, filtered, and concentrated in vacuo. The residue was purified by chromatography on silica gel (40 g cartridge, 0-50% EtOAc/isohexane) to afford the title compound (1.6 g, 3.23 mmol, 70% yield, 70% purity) as an orange solid. UPLC-MS (Method 1) m/z 347.4 (M+H)$^+$ at 2.15 min.

$^1$H NMR (500 MHz, DMSO-d$_6$) δ 8.01 (s, 1H), 7.02 (s, 1H), 3.02 (t, J=5.1 Hz, 4H), 2.48 (s, 3H), 1.67-1.50 (m, 6H), 1.29 (s, 12H).

Step 3: 4-methyl-2-(piperidin-1-yl)-5-(4,4,5,5-tetramethyl-1,3,2-dioxaborolan-2-yl)aniline: The product from Step 2 above (500 mg, 1.01 mmol, 70% purity) in MeOH (5 ml) was treated with 10% Pd/C (108 mg, 0.101 mmol). The reaction mixture was hydrogenated (2 bar) at RT for 2 h. The mixture was filtered through Celite®, washing with MeOH (20 ml), and then concentrated in vacuo to afford the title compound (340 mg, 1.00 mmol, 99% yield, 93% purity) as a light brown solid. UPLC-MS (Method 1) m/z 317.7 (M+H)$^+$ at 1.44 min.

Step 4: 4-methyl-5-(5-methylisoxazol-4-yl)-2-(piperidin-1-yl)aniline: A mixture of the product from Step 3 above (200 mg, 0.588 mmol, 93% purity), 4-iodo-5-methylisoxazole (135 mg, 0.647 mmol), $K_3PO_4$ (162 mg, 0.765 mmol), dioxane (4 ml) and water (1 ml) was treated with Xphos Pd G3 (50 mg, 0.059 mmol). The resultant mixture was degassed with $N_2$ for 15 min and then heated at 80° C. for 2 h. The mixture was allowed to cool to RT and then concentrated in vacuo. The residue was purified by chromatography on silica gel (24 g cartridge, 0-30% EtOAc/isohexane) to afford the title compound (150 mg, 0.531 mmol, 90% yield, 96% purity) as a waxy tan solid. UPLC-MS (Method 1) m/z 272.3 $(M+H)^+$ at 1.07 min. 1H NMR (500 MHz, DMSO-$d_6$) δ 8.53 (s, 1H), 6.79 (s, 1H), 6.52 (s, 1H), 4.58 (s, 2H), 2.82-2.70 (m, 4H), 2.33 (s, 3H), 2.04 (s, 3H), 1.70-1.63 (m, 4H), 1.57-1.47 (m, 2H).

Step 5: methyl 4-ethyl-3-(N-(4-methyl-5-(5-methylisoxazol-4-yl)-2-(piperidin-1-yl)phenyl)sulfamoyl)benzoate: A solution of the product from Step 4 above (150 mg, 0.531 mmol, 96% purity) in DCM (3 ml) and pyridine (258 μl, 3.18 mmol) was added to a solution of the product from Example 203 Step 2 (139 mg, 0.531 mmol) in DCM (3 ml) and the resultant solution was stirred at RT for 2 days. The reaction mixture was concentrated in vacuo. The residue was purified by chromatography on silica gel (40 g cartridge, 0-40% EtOAc/isohexane) to afford the title compound (220 mg, 0.438 mmol, 82% yield, 99% purity) as a light brown oil. UPLC-MS (Method 1) m/z 498.4 $(M+H)^+$, 496.2 $(M-H)^-$ at 1.95 min.

Step 6: 4-ethyl-3-(N-(4-methyl-5-(5-methylisoxazol-4-yl)-2-(piperidin-1-yl)phenyl)sulfamoyl)benzoic acid: 4 M HCl in dioxane (553 μl, 2.21 mmol) was added to a solution of the product from Step 5 above (220 mg, 0.438 mmol, 99% purity) in dioxane (5 ml) and the mixture was heated at 60° C. for 16 h. The mixture was concentrated in vacuo and the solid slurried with MeCN (5 ml) for 30 min. The solid was collected by filtration to afford the title compound (195 mg, 0.390 mmol, 89% yield, 98% purity) as a cream solid. UPLC-MS (Method 1) m/z 484.4 $(M+H)^+$, 482.3 $(M-H)^-$ at 1.80 min. $^1$H NMR (500 MHz, DMSO-$d_6$) δ 8.89 (br s, 1H), 8.57 (s, 1H), 8.35 (d, J=1.8 Hz, 1H), 8.08 (dd, J=7.9, 1.8 Hz, 1H), 7.61 (d, J=8.0 Hz, 1H), 7.13 (br s, 1H), 6.92 (br s, 1H), 3.06 (q, J=7.4 Hz, 2H), 2.82-2.55 (m, 4H), 2.20 (s, 3H), 2.12 (s, 3H), 1.73-1.55 (m, 4H), 1.54-1.40 (m, 2H), 1.22 (t, J=7.4 Hz, 3H). One exchangeable proton not observed.

Example 304: 4-ethyl-3-(N-(4-fluoro-5-(5-methylisoxazol-4-yl)-2-(piperidin-1-yl)phenyl) sulfamoyl) benzoic acid

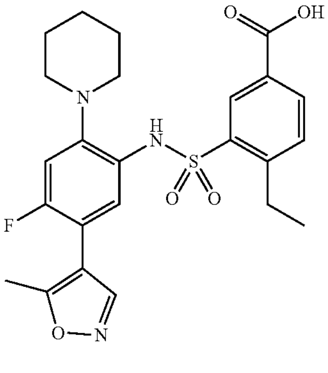

Step 1: 1-(4-bromo-5-fluoro-2-nitrophenyl)piperidine: 1-bromo-2,4-difluoro-2-methyl-5-nitrobenzene (1 g, 4.20 mmol) in dry DMF (5 ml) was treated with $Et_3N$ (586 μl, 4.20 mmol) followed by piperidine (415 μl, 4.20 mmol) and the mixture was stirred at RT for 3 days. The mixture was diluted with water (50 ml) and extracted with EtOAc (100 ml). The organic phase was washed with brine (50 ml), dried over $MgSO_4$, filtered, and concentrated in vacuo to afford the title compound (1.27 g, 3.02 mmol, 72% yield, 72% purity) as a red oil. UPLC-MS (Method 1) m/z 303.2 $(M+H)^+$ at 1.84 min.

Step 2: 1-(5-fluoro-2-nitro-4-(4,4,5,5-tetramethyl-1,3,2-dioxaborolan-2-yl)phenyl)piperidine: A mixture of the product from Step 1 above (1.27 g, 3.02 mmol, 72% purity), bis(pinacolato)diboron (1.15 g, 4.52 mmol), KOAc (888 mg, 9.05 mmol) and $PdCl_2$ (dppf)·DCM (221 mg, 0.302 mmol) in dioxane (10 ml) was degassed with $N_2$ for 15 min and then heated at 80° C. for 16 h. The mixture was diluted with water (50 ml) and extracted with EtOAc (50 ml). The organic phase was dried over $MgSO_4$, filtered, and concentrated in vacuo. The residue was purified by chromatography on silica gel (40 g cartridge, 0-100% TBME/isohexane) to afford the title compound (1.05 g, 1.80 mmol, 59% yield, 60% purity) as an orange solid. UPLC-MS (Method 1) m/z 347.4 $(M+H)^+$ at 2.15 min. $^1$H NMR (500 MHz, DMSO-$d_6$) δ 8.03 (d, J=6.4 Hz, 1H), 6.97 (d, J=12.1 Hz, 1H), 3.07 (t, J=5.0 Hz, 4H), 1.68-1.49 (m, 6H), 1.29 (s, 12H).

Step 3: 4-fluoro-2-(piperidin-1-yl)-5-(4,4,5,5-tetramethyl-1,3,2-dioxaborolan-2-yl)aniline: The product from Step 2 above (500 mg, 0.857 mmol, 60% purity) in MeOH (5 ml) was treated with 10% Pd/C (50% w/w water) Type 39 (91 mg, 0.086 mmol). The reaction mixture was hydrogenated at 2 bar at RT for 2 h. The mixture was filtered through Celite®, washing with MeOH (20 ml), and then concentrated in vacuo to afford the title compound (373 mg, 0.559 mmol, 65% yield, 48% purity) as a dark blue oil. UPLC-MS (Method 1) m/z 321.4 $(M+H)^+$ at 1.62 min.

Step 4: 4-fluoro-5-(5-methylisoxazol-4-yl)-2-(piperidin-1-yl)aniline: A mixture of the product from Step 3 above (373 mg, 0.559 mmol, 48% purity), 4-iodo-5-methylisoxazole (128 mg, 0.610 mmol), $K_3PO_4$ (153 mg, 0.721 mmol), dioxane (4 ml) and water (1 ml) was treated with Xphos Pd G3 (47 mg, 0.060 mmol). The resultant mixture was degassed with $N_2$ for 15 min and then heated at 80° C. for 2 h. The mixture was allowed to cool to RT and then concentrated in vacuo. The residue was purified by chromatography on silica gel (24 g cartridge, 0-30% EtOAc/isohexane) to afford the title compound (180 mg, 0.458 mmol, 83% yield, 70% purity) as a dark brown solid. UPLC-MS (Method 1) m/z 276.3 $(M+H)^+$ at 1.50 min. $^1$H NMR (500 MHz, DMSO-$d_6$) δ 8.60 (d, J=1.6 Hz, 1H), 6.81 (d, J=12.0 Hz, 1H), 6.72 (d, J=7.8 Hz, 1H), 4.66 (br s, 2H), 2.82-2.75 (m, 4H), 2.46 (s, 3H), 1.70-1.57 (m, 6H).

Step 5: methyl 4-ethyl-3-(N-(4-fluoro-5-(5-methylisoxazol-4-yl)-2-(piperidin-1-yl)phenyl)sulfamoyl)benzoate: A solution of the product from Step 4 above (180 mg, 0.458 mmol, 70% purity) in DCM (3 ml) and pyridine (222 μl, 2.75 mmol) was added to a solution of the product from Example 203 Step 2 (120 mg, 0.458 mmol) in DCM (3 ml) and the resultant solution stirred at RT for 72 h. The reaction mixture was concentrated in vacuo. The residue was purified by chromatography on silica gel (24 g cartridge, 0-30% EtOAc/isohexane) to afford the title compound (120 mg, 0.167 mmol, 37% yield, 70% purity) as a white solid. UPLC-MS (Method 1) m/z 502.4 $(M+H)^+$, 500.3 $(M-H)^-$ at 1.96 min.

Step 6: 4-ethyl-3-(N-(4-fluoro-5-(5-methylisoxazol-4-yl)-2-(piperidin-1-yl)phenyl)sulfamoyl)benzoic acid: 4 M HCl in dioxane (210 μl, 0.840 mmol) was added to a solution of the product from Step 5 above (120 mg, 0.167 mmol, 70% purity) in dioxane (5 ml) and the mixture was heated at 60° C. for 16 h. The mixture was concentrated in vacuo. The residue was purified by chromatography (12 g reverse phase C18 cartridge, 15-85% MeCN/0.1% formic acid (aq)) to afford the title compound (30.5 mg, 0.061 mmol, 36% yield, 98% purity) as an off-white solid. UPLC-MS (Method 1)

m/z 488.3 $(M+H)^+$, 486.2 $(M-H)^-$ at 1.83 min. $^1$H NMR (500 MHz, DMSO-$d_6$) δ13.30 (br s, 1H), 9.48-9.07 (s, 1H), 8.59 (d, J=1.8 Hz, 1H), 8.32 (d, J=1.8 Hz, 1H), 8.08 (dd, J=8.0, 1.8 Hz, 1H), 7.60 (d, J=8.0 Hz, 1H), 7.12 (d, J=8.0 Hz, 1H), 7.06 (d, J=12.0 Hz, 1H), 3.04 (q, J=7.4 Hz, 2H), 2.64 (t, J=5.1 Hz, 4H), 2.35 (s, 3H), 1.48 (d, J=9.7 Hz, 4H), 1.43 (d, J=8.6 Hz, 2H), 1.22 (t, J=7.4 Hz, 3H).

Example 305: 4-ethyl-3-(N-(2-fluoro-3-(5-methylisoxazol-4-yl)-6-(piperidin-1-yl)phenyl)sulfamoyl)benzoic acid

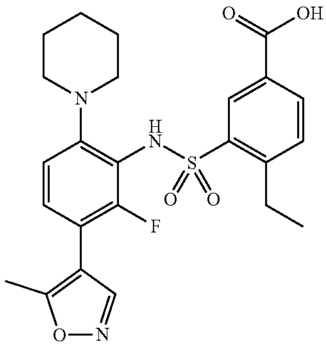 [SMILES: CCc1ccc(C(=O)O)cc1S(=O)(=O)Nc1c(N2CCCCC2)ccc(-c2cnoc2C)c1F]

Step 1: 1-(4-bromo-3-fluoro-2-nitrophenyl)piperidine: 1-bromo-2,4-fluoro-3-nitrobenzene (1 g, 4.20 mmol) in dry DMF (5 ml) was cooled to 0° C. $Et_3N$ (1.17 ml, 8.40 mmol) followed by piperidine (415 μl, 4.20 mmol) were added and the mixture was stirred at RT for 24 h. The mixture was diluted with water (50 ml) and extracted with EtOAc (100 ml). The organic phase was washed with brine (50 ml), dried over $MgSO_4$, filtered, and concentrated in vacuo to afford the title compound (1.2 g, 3.76 mmol, 90% yield, 95% purity) as a red oil. UPLC-MS (Method 1) m/z 303.4 $(M+H)^+$ at 1.88 min. $^1$H NMR (500 MHz, DMSO-$d_6$) δ 7.82 (t, J=8.5 Hz, 1H), 7.13 (dd, J=9.1 Hz, 1H), 2.97 (t, J=5.1 Hz, 4H), 1.62-1.48 (m, 6H).

Step 2: 3-bromo-2-fluoro-6-(piperidin-1-yl)aniline: A solution of the product from Step 1 above (500 mg, 1.56 mmol, 95% purity) in THF (9 ml) and water (3 ml) was treated with zinc dust (615 mg, 9.40 mmol) and $NH_4Cl$(s) (503 mg, 9.40 mmol). The resultant mixture was stirred at RT for 2 h. The mixture was filtered through Celite®, washing with EtOAc (3×5 ml), and then concentrated in vacuo. The residue was purified by chromatography on silica gel (24 g cartridge, 0-20% EtOAc/isohexane) to afford the title compound (320 mg, 1.14 mmol, 72% yield, 97% purity) as a light brown oil. UPLC-MS (Method 1) m/z 273.1 $(M+H)^+$ at 1.79 min.

Step 3: 2-fluoro-6-(piperidin-1-yl)-3-(4,4,5,5-tetramethyl-1,3,2-dioxaborolan-2-yl)aniline: A mixture of the product from Step 2 above (320 mg, 1.14 mmol, 97% purity), bis(pinacolato)diboron (433 mg, 1.70 mmol), KOAc (335 mg, 3.41 mmol) and $PdCl_2$ (dppf)· DCM (83 mg, 0.114 mmol) in dioxane (10 ml) was degassed with $N_2$ for 15 min and then heated at 80° C. for 16 h. The mixture was diluted with water (50 ml) and extracted with EtOAc (50 ml). The organic phase was dried over $MgSO_4$, filtered, and concentrated in vacuo. The residue was purified by chromatography on silica gel (40 g cartridge, 0-50% EtOAc/isohexane) to afford the title compound (379 mg, 1.11 mmol, 98% yield, 94% purity) as a light green solid. UPLC-MS (Method 1) m/z 321.4 $(M+H)^+$ at 1.83 min. $^1$H NMR (500 MHz, DMSO-$d_6$) δ 8.01 (s, 1H), 7.02 (s, 1H), 3.02 (t, J=5.1 Hz, 4H), 2.48 (s, 3H), 1.67-1.50 (m, 6H), 1.29 (s, 12H).

Step 4: 2-fluoro-3-(5-methylisoxazol-4-yl)-6-(piperidin-1-yl)aniline: A mixture of the product from Step 3 above (200 mg, 0.587 mmol, 94% purity), 4-iodo-5-methylisoxazole (135 mg, 0.646 mmol), $K_3PO_4$ (162 mg, 0.763 mmol), dioxane (4 ml) and water (1 ml) was treated with Xphos Pd G3 (50.0 mg, 0.059 mmol). The resultant mixture was degassed with $N_2$ for 15 min and then heated at 80° C. for 2 h. The mixture was allowed to cool to RT and then concentrated in vacuo. The residue was purified by chromatography on silica gel (24 g cartridge, 0-50% EtOAc/isohexane) to afford the title compound (140 mg, 0.386 mmol, 66% yield, 76% purity) as waxy tan solid. UPLC-MS (Method 1) m/z 276.3 $(M+H)^+$ at 1.58 min.

Step 5: Methyl 4-ethyl-3-(N-(2-fluoro-3-(5-methylisoxazol-4-yl)-6-(piperidin-1-yl)phenyl)sulfamoyl)benzoate: A solution of the product from Step 4 above (140 mg, 0.386 mmol, 76% purity) in DCM (3 ml) and pyridine (188 μl, 2.32 mmol) was added to a solution of the product from Example 203 Step 2 (102 mg, 0.386 mmol) in DCM (3 ml) and the resultant solution was stirred at RT for 48 h. The reaction mixture was concentrated in vacuo. The residue was purified by chromatography on silica gel (40 g cartridge, 0-40% EtOAc/isohexane) to afford the title compound (64 mg, 0.089 mmol, 23% yield, 70% purity) as a light brown oil. UPLC-MS (Method 1) m/z 502.4 $(M+H)^+$, 500.3 $(M-H)^-$ at 1.81 min.

Step 6: 4-ethyl-3-(N-(2-fluoro-3-(5-methylisoxazol-4-yl)-6-(piperidin-1-yl)phenyl)sulfamoyl)benzoic acid: 4 M HCl in dioxane (110 μl, 0.440 mmol) was added to a solution of the product from Step 5 above (64 mg, 0.089 mmol, 70% purity) in dioxane (5 ml) and the mixture was heated at 60° C. for 72 h. The mixture was concentrated in vacuo. The residue was purified by preparative HPLC (Waters, Acidic (0.1% Formic acid), Acidic, Waters X-Select Prep-C18, 5 μm, 19×50 mm column, 50-80% MeCN in Water) to afford the title compound (4 mg, 7.88 μmol, 9% yield, 96% purity) as a white solid. UPLC-MS (Method 1) m/z 488.4 $(M+H)^+$, 486.3 $(M-H)^-$ at 1.68 min. $^1$H NMR (500 MHz, DMSO-$d_6$) δ 13.21 (br s, 1H), 9.52 (s, 1H), 8.58 (s, 1H), 8.30 (d, J=1.8 Hz, 1H), 8.08 (dd, J=8.0, 1.9 Hz, 1H), 7.60 (d, J=8.0 Hz, 1H), 7.32 (t, J=8.4 Hz, 1H), 6.90 (d, J=8.6 Hz, 1H), 3.08 (d, J=7.1 Hz, 2H), 2.80-2.69 (m, 4H), 2.38 (s, 3H), 1.35-1.18 (m, 9H).

Example 306: 4-ethyl-3-(N-(4-Chloro-5-(5-methylisoxazol-4-yl)-2-(piperidin-1-yl)phenyl)sulfamoyl)benzoic acid

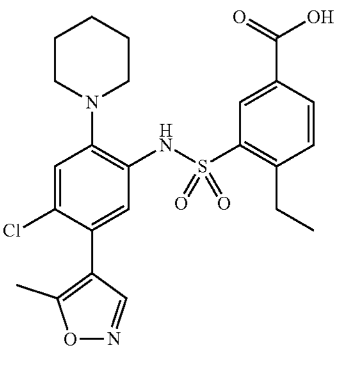 [SMILES: CCc1ccc(C(=O)O)cc1S(=O)(=O)Nc1cc(-c2cnoc2C)c(Cl)cc1N1CCCCC1]

Step 1: 1-(4-bromo-5-chloro-2-nitrophenyl)piperidine: 1-bromo-2-chloro-4-fluoro-5-nitrobenzene (1 g, 3.93 mmol) in dry DMF (5 ml) was cooled to 0° C. $Et_3N$ (1.09 ml, 7.86 mmol) and piperidine (388 μl, 3.93 mmol) were sequentially added and the mixture was stirred at RT for 24 h. The mixture was diluted with water (50 ml) and extracted with EtOAc (100 ml). The organic phase was washed with brine (50 ml), dried over $MgSO_4$, filtered, and concentrated in vacuo to afford the title compound (1.2 g, 3.68 mmol, 94% yield, 98% purity) as a red oil. UPLC-MS (Method 1) m/z 319.2 $(M+H)^+$ at 1.97 min.

Step 2: 5-bromo-4-chloro-2-(piperidin-1-yl)aniline: A solution of the product from Step 1 above (1.20 g, 3.68 mmol, 98% purity) in THF (9 ml) and water (3 ml) was treated with zinc dust (1.44 g, 22.1 mmol) and $NH_4Cl$(s) (1.18 g, 22.1 mmol). The resultant mixture was stirred at RT for 2 h. The mixture was filtered through Celite®, washing with EtOAc (3×5 ml), and then concentrated in vacuo. The residue was purified by chromatography on silica gel (24 g cartridge, 0-20% EtOAc/isohexane) to afford the title compound (880 mg, 2.92 mmol, 79% yield, 96% purity) as a light brown oil. UPLC-MS (Method 1) m/z 289.1 $(M+H)^+$ at 1.87 min.

Step 3: 4-chloro-2-(piperidin-1-yl)-5-(4,4,5,5-tetramethyl-1,3,2-dioxaborolan-2-yl)aniline: A mixture of the product from Step 2 above (880 mg, 2.92 mmol, 96% purity), bis(pinacolato)diboron (1.11 g, 4.38 mmol), KOAc (859 mg, 8.75 mmol) and $PdCl_2$ (dppf)· DCM (213 mg, 0.292 mmol) in dioxane (10 ml) was degassed with $N_2$ for 15 min and then heated at 80° C. for 16 h. The mixture was diluted with water (50 ml) and extracted with EtOAc (50 ml). The organic phase was dried over $MgSO_4$, filtered, and concentrated in vacuo. The residue was purified by chromatography on silica gel (40 g cartridge, 0-50% EtOAc/isohexane) to afford the title compound (980 mg, 2.38 mmol, 82% yield, 82% purity) as a brown oil. UPLC-MS (Method 1) m/z 337.3 $(M+H)^+$ at 1.89 min.

Step 4: 4-chloro-5-(5-methylisoxazol-4-yl)-2-(piperidin-1-yl)aniline: A mixture of the product from Step 3 above (300 mg, 0.731 mmol, 82% purity), 4-iodo-5-methylisoxazole (168 mg, 0.804 mmol), $K_3PO_4$ (202 mg, 0.950 mmol), dioxane (4 ml) and water (1 ml) was treated with Xphos Pd G3 (62.0 mg, 0.073 mmol). The resultant mixture was degassed with $N_2$ for 15 min and then heated at 80° C. for 2 h. The mixture was allowed to cool to RT and then concentrated in vacuo. The residue was purified by chromatography on silica gel (24 g cartridge, 0-50% EtOAc/isohexane) to afford the title compound (225 mg, 0.717 mmol, 98% yield, 93% purity) as waxy tan solid. UPLC-MS (Method 1) m/z 292.2 $(M+H)^+$ at 1.69 min.

Step 5: methyl 3-(N-(4-chloro-5-(5-methylisoxazol-4-yl)-2-(piperidin-1-yl)phenyl)sulfamoyl)-4-ethylbenzoate: A solution of the product from Step 4 above (225 mg, 0.717 mmol, 93% purity) in DCM (3 ml) and pyridine (348 μl, 4.30 mmol) was added to a solution of the product from Example 203 Step 2 (188 mg, 0.717 mmol) in DCM (3 ml) and the resultant solution was stirred at RT for 3 days. The reaction mixture was concentrated in vacuo. The residue was purified by chromatography on silica gel (40 g cartridge, 0-40% EtOAc/isohexane) to afford the title compound (320 mg, 0.525 mmol, 73% yield, 85% purity) as a light brown oil. UPLC-MS (Method 1) m/z 518.3 $(M+H)^+$, 516.1 $(M-H)^-$ at 2.02 min.

Step 6: 3-(N-(4-chloro-5-(5-methylisoxazol-4-yl)-2-(piperidin-1-yl)phenyl)sulfamoyl)-4-ethylbenzoic acid: 4 M HCl in dioxane (656 μl, 2.63 mmol) was added to a solution of the product from Step 5 above (320 mg, 0.525 mmol, 85% purity) in dioxane (5 ml) and the mixture was heated at 60° C. for 24 h. The mixture was concentrated in vacuo. The residue was purified by preparative HPLC (Waters, Acidic (0.1% Formic acid), Acidic, Waters X-Select Prep-C18, 5 μm, 19×50 mm column, 50-80% MeCN in Water) to afford the title compound (42.6 mg, 0.083 mmol, 16% yield, 98% purity) as a white solid. UPLC-MS (Method 1) m/z 504.3 $(M+H)^+$, 502.2 $(M-H)^-$ at 1.90 min. $^1H$ NMR (500 MHz, DMSO-$d_6$) 8.59 (br s, 1H), 8.35 (d, J=1.8 Hz, 1H), 8.08 (dd, J=7.9, 1.8 Hz, 1H), 7.59 (d, J=8.0 Hz, 1H), 7.24 (s, 1H), 7.09 (s, 1H), 3.12-2.97 (m, 2H), 2.67 (t, J=7.4 Hz, 4H), 2.26 (s, 3H), 1.55 (q, J=5.6 Hz, 4H), 1.45 (q, J=5.8 Hz, 2H), 1.22 (t, J=7.4 Hz, 3H). Two exchangeable protons not observed.

Example 308: 3-(N-(2-(4,4-difluoropiperidin-1-yl)-5-(methylsulfonyl)phenyl)sulfamoyl)-4-ethylbenzoic acid

288

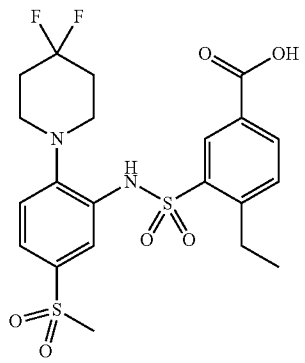

Step 1: 4,4-difluoro-1-(4-(methylsulfonyl)-2-nitrophenyl)piperidine: A mixture of 1-fluoro-4-(methylsulfonyl)-2-nitrobenzene (500 mg, 2.28 mmol) and 4,4-difluoropiperidine (276 mg, 2.28 mmol) and $Et_3N$ (400 μl, 2.87 mmol) was sonicated in DCM (6 ml) until a clear solution was formed. The resultant solution was allowed to stand at RT for 2 h. The reaction mixture was sequentially washed with 1 M HCl(aq) (4 ml), water (4 ml) and brine (2 ml), dried over $MgSO_4$, filtered and concentrated in vacuo to afford the title compound (717 mg, 1.90 mmol, 83% yield, 85% purity) as a bright yellow solid. UPLC-MS (Method 1) m/z 321.3 $(M+H)^+$ at 1.28 min.

Step 2: 2-(4,4-difluoropiperidin-1-yl)-5-(methylsulfonyl)aniline: The product from Step 1 above (717 mg, 2.24 mmol, 85% purity) was dissolved in 1:1 EtOH/THF (100 ml) and hydrogenated in a ThalesNano H-cube® flow reactor (10% Pd/C, 30×4 mm, full hydrogen mode, RT, 1 ml/min, then 20 bar, 40° C., recirculating for 2 h, then 40 bar, 50° C. recirculating for 2 h, then 40 bar, 50° C.). The mixture was concentrated in vacuo. The residue was dissolved in a mixture of AcOH (50 ml), THF (50 ml) and water (10 ml) and filtered. The filtrate was concentrated in vacuo and dissolved in AcOH (50 ml) and hydrogenated in a ThaleSNano H-cube® flow reactor (10% Pd/C, 30×4 mm, Full hydrogen, RT, 1 ml/min, recirculating for 1.5 h). The mixture was concentrated in vacuo, azeotroping with toluene (50 ml). The crude product was purified by chromatography on silica gel (12 g cartridge, 0-100% EtOAc/isohexane) to afford the title compound (162 mg, 0.469 mmol, 21% yield, 84% purity) as a pale yellow foam. UPLC-MS (Method 1) m/z 291.2 $(M+H)^+$ at 1.18 min.

Step 3: Methyl 3-(N-(2-(4,4-difluoropiperidin-1-yl)-5-(methylsulfonyl)phenyl)sulfamoyl)-4-ethylbenzoate: The product from Step 2 above (62 mg, 0.179 mmol, 84% purity) was dissolved in a mixture of DCM (1 ml) and pyridine (50 μl, 0.618 mmol) and treated with the product from Example 203 Step 2 (50 mg, 0.188 mmol). The resultant solution was allowed to stand at RT for 3 days. Additional product from Example 203 Step 2 (53 mg, 0.200 mmol) was added and the resultant solution allowed to stand at RT for 4 days. The mixture was concentrated in vacuo onto silica and purified by chromatography on silica gel (12 g cartridge, 0-100% EtOAc/isohexane) to afford the title compound (104 mg, 0.167 mmol, 93% yield, 83% purity) as a light beige foam. UPLC-MS (Method 1) m/z 517.2 $(M+H)^+$, 515.3 $(M-H)^-$ at 1.55 min.

Step 4: 3-(N-(2-(4,4-difluoropiperidin-1-yl)-5-(methylsulfonyl)phenyl)sulfamoyl)-4-ethylbenzoic acid: A mixture of the product from Step 3 above (104 mg, 0.167 mmol, 83% purity) and LiOH (28 mg, 0.655 mmol) in THF/MeOH/water (4:1:1, 6 ml) was stirred at 40° C. for 18 h. The mixture was diluted with water (5 ml), acidified to ~pH 4 using 1 M HCl(aq) and extracted with EtOAc (3×10 ml). The organic extracts were combined and washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (36.3 mg, 72 μmol, 42% yield, 99% purity) as a white solid. UPLC-MS (Method 1) m/z 503.2 $(M+H)^+$, 501.1 $(M-H)^-$ at 1.41 min. $^1H$ NMR (500 MHz, DMSO-$d_6$) δ 13.33 (s, 1H), 9.89 (s, 1H), 8.36 (d, J=1.8 Hz, 1H), 8.10 (dd, J=8.0, 1.8 Hz, 1H), 7.65-7.59 (m, 2H), 7.55 (d, J=2.2 Hz, 1H), 7.35 (d, J=8.5 Hz, 1H), 3.05 (s, 3H), 3.02 (q, J=7.4 Hz, 2H), 2.94-2.88 (m, 4H), 2.12-2.01 (m, 4H), 1.20 (t, J=7.4 Hz, 3H).

Example 309:4-cyclopropyl-3-(N-(2-(4,4-difluoropiperidin-1-yl)-5-(methylsulfonyl)phenyl) sulfamoyl) benzoic acid

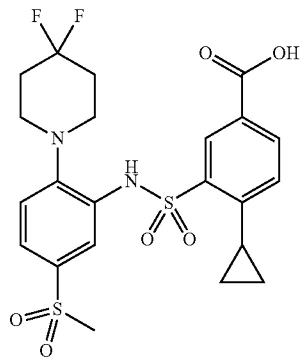 [SMILES: CS(=O)(=O)c1ccc(N2CCC(F)(F)CC2)c(NS(=O)(=O)c2cc(C(=O)O)ccc2C2CC2)c1]

Step 1: Methyl 4-bromo-3-(N-(2-(4,4-difluoropiperidin-1-yl)-5-(methylsulfonyl)phenyl)sulfamoyl)benzoate: The product from Example 308 Step 2 (102 mg, 0.313 mmol, 84% purity) was dissolved in a mixture of DCM (1 ml) and pyridine (50 μl, 0.618 mmol) and treated with the product from Example 316 Step 1 (103 mg, 0.325 mmol). The resultant suspension was sonicated, and then diluted with DCM (1 ml) to afford a clear solution. The mixture was allowed to stand at RT for 4 days. The mixture was concentrated in vacuo onto silica and purified by chromatography on silica gel (12 g cartridge, 0-100% EtOAc/isohexane) to afford the title compound (108 mg, 0.101 mmol, 32% yield, 53% purity) as a beige foam. UPLC-MS (Method 1) m/z 567.2 $(M+H)^+$, 565.0 $(M-H)^-$ at 1.52 min.

Step 2: Methyl 4-bromo-3-(N-(2-(4,4-difluoropiperidin-1-yl)-5-(methylsulfonyl)phenyl)sulfamoyl)benzoate: A degassed mixture of the product from Step 1 above (108 mg, 0.101 mmol, 53% purity) and Pd-174 (7.00 mg, 9.71 μmol) in THF (2 ml) was treated with cyclopropylzinc (II) bromide (0.5 M in THF) (800 μl, 0.400 mmol). The mixture was heated at 60° C. for 18 h. Upon cooling to RT the mixture was concentrated onto silica and purified by chromatography on silica gel (12 g cartridge, 0-100% EtOAc/isohexane) to afford the title compound (54 mg, 62.0 μmol, 61% yield, 61% purity) as a light brown oil. UPLC-MS (Method 1) m/z 529.2 $(M+H)^+$, 527.1 $(M-H)^-$ at 1.55 min.

Step 3: 4-cyclopropyl-3-(N-(2-(4,4-difluoropiperidin-1-yl)-5-(methylsulfonyl)phenyl)sulfamoyl)benzoic acid: A mixture of the product from Step 2 above (54 mg, 62.0 μmol, 61% purity) and LiOH (11 mg, 0.257 mmol) in THF/MeOH/water (4:1:1, 2.4 ml) was stirred at 40° C. for 18 h. The mixture was diluted with water (5 ml), acidified to ~pH 4 with 1 M HCl(aq) and extracted with EtOAc (3×10 ml). The organic extracts were combined and washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (13.8 mg, 27.0 μmol, 42% yield, 99% purity) as a white solid. UPLC-MS (Method 1) m/z 515.2 $(M+H)^+$, 513.0 $(M-H)^-$ at 1.40 min. $^1H$ NMR (500 MHz, DMSO-$d_6$) δ 13.27 (s, 1H), 9.80 (s, 1H), 8.40 (d, J=1.8 Hz, 1H), 8.01 (dd, J=8.2, 1.8 Hz, 1H), 7.65-7.58 (m, 1H), 7.55 (d, J=2.2 Hz, 1H), 7.36 (d, J=8.4 Hz, 1H), 7.15 (d, J=8.2 Hz, 1H), 3.02 (s, 3H), 2.98-2.93 (m, 4H), 2.84-2.75 (m, 1H), 2.10-2.01 (m, 4H), 1.11-1.03 (m, 2H), 0.90-0.83 (m, 2H).

Example 310: 3-(N-(5-cyano-2-(4,4-difluoropiperidin-1-yl)phenyl)sulfamoyl)-4-cyclopropylbenzoic acid

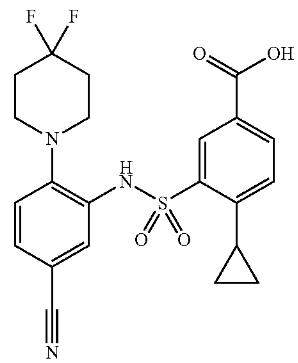 [SMILES: N#Cc1ccc(N2CCC(F)(F)CC2)c(NS(=O)(=O)c2cc(C(=O)O)ccc2C2CC2)c1]

Step 1: methyl 4-bromo-3-(N-(5-cyano-2-(4,4-difluoropiperidin-1-yl)phenyl)sulfamoyl)benzoate: The product from Example 221 Step 2 (100 mg, 0.400 mmol) was dissolved in a mixture of DCM (1 ml) and pyridine (100 μl, 1.23 mmol) and treated with the product from Example 316 Step 1 (130 mg, 0.410 mmol). The resultant solution was allowed to stand at RT for 4 days. The mixture was concentrated in vacuo onto silica and purified by chromatography on silica gel (12 g cartridge, 0-100% EtOAc/isohexane) to afford the title compound (123 mg, 0.234 mmol, 58% yield, 98% purity) as a light orange solid. UPLC-MS (Method 1) m/z 514.2 $(M+H)^+$, 512.0 $(M-H)^-$ at 1.65 min.

Step 2: methyl 4-bromo-3-(N-(5-cyano-2-(4,4-difluoropiperidin-1-yl)phenyl)sulfamoyl)benzoate: A degassed mixture of the product from Step 1 above (123 mg, 0.234 mmol, 98% purity) and Pd-174 (17 mg, 24 μmol) in THF (4.5 ml) was treated with cyclopropylzinc (II) bromide (0.5 M in THF) (1.8 ml, 0.900 mmol). The mixture was heated at 60° C. for 18 h. Upon cooling to RT the mixture was concentrated in vacuo onto silica and purified by chromatography on silica gel (12 g cartridge, 0-100% EtOAc/isohexane) to afford the title compound (99.4 mg, 0.192 mmol, 82% yield, 92% purity) as a yellow solid. UPLC-MS (Method 1) m/z 476.3 $(M+H)^+$, 474.2 $(M-H)^-$ at 1.69 min.

Step 3: 3-(N-(5-cyano-2-(4,4-difluoropiperidin-1-yl)phenyl)sulfamoyl)-4-cyclopropylbenzoic acid: A mixture of the product from Step 2 above (99.4 mg, 0.192 mmol, 92% purity) and LiOH (33 mg, 0.772 mmol) in THF/MeOH/water (4:1:1, 6.6 ml) was stirred at 40° C. for 18 h. The mixture was diluted with water (10 ml), acidified to ~pH 4 using 1 M HCl(aq) and extracted with EtOAc (3×20 ml). The combined organic extracts were washed with brine (20 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (55.8 mg, 0.120 mmol, 62% yield, 99% purity) as a white solid. UPLC-MS (Method 1) m/z 462.2 $(M+H)^+$, 460.2 $(M-H)^-$ at 1.54 min. $^1H$ NMR (500 MHz, DMSO-$d_6$) δ 13.29 (s, 1H), 9.81 (s, 1H), 8.37 (d, J=1.8 Hz, 1H), 8.02 (dd, J=8.2, 2.0 Hz, 1H), 7.56 (dd, J=8.4, 1.8 Hz, 1H), 7.33 (d, J=2.0 Hz, 1H), 7.27 (d, J=8.4 Hz, 1H), 7.16 (d, J=8.2 Hz, 1H), 2.97-2.91 (m, 4H), 2.80-2.71 (m, 1H), 2.07-1.95 (m, 4H), 1.10-1.03 (m, 2H), 0.90-0.83 (m, 2H).

Example 311: I-3-(N-(5-cyano-2-(3-fluoropiperidin-1-yl)phenyl)sulfamoyl)-4-ethylbenzoic

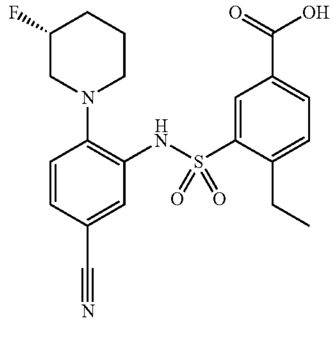 [SMILES: CCc1ccc(C(=O)O)cc1S(=O)(=O)Nc1cc(C#N)ccc1N1CCC[C@@H](F)C1]

Step 1: I-4-(3-fluoropiperidin-1-yl)-3-nitrobenzonitrile: A mixture of 4-fluoro-3-nitrobenzonitrile (400 mg, 2.41 mmol) and I-3-fluoropiperidine hydrochloride (336 mg, 2.41 mmol) and $Et_3N$ (700 μl, 5.02 mmol) was sonicated in DCM (6 ml) for 5 min. The resultant suspension was stirred at RT for 18 h. The reaction mixture was sequentially washed with 1 M HCl(aq) (4 ml), water (4 ml) and brine (2 ml), dried over $MgSO_4$, filtered and concentrated in vacuo to afford the title compound (596 mg, 2.37 mmol, 98% yield, 99% purity) as a bright yellow solid. UPLC-MS (Method 1): m/z 250.3 $(M+H)^+$ at 1.35 min.

Step 2: I-3-amino-4-(3-fluoropiperidin-1-yl)benzonitrile: The product from Step 1 above (596 mg, 2.37 mmol, 99% purity) was combined with iron powder (2.5 g, 44.8 mmol) and $NH_4Cl(s)$ (150 mg, 2.80 mmol) in IPA (20 ml) and water (10 ml), then heated at 80° C. and stirred overnight. The mixture was cooled and allowed to stand for 24 h. The mixture was filtered through Celite®, rinsing with EtOAc (2×10 ml) and the filtrate was concentrated in vacuo. The residue was purified by chromatography on silica gel (12 g cartridge, 0-50% EtOAc/isohexane) to afford the title compound (304 mg, 1.36 mmol, 62% yield, 98% purity). UPLC-MS (Method 1): m/z 220.3 $(M+H)^+$ at 1.32 min.

Step 3: I-methyl 3-(N-(5-cyano-2-(3-fluoropiperidin-1-yl)phenyl)sulfamoyl)-4-ethylbenzoate: The product from Example 203 Step 2 (300 mg, 1.13 mmol) was added to a solution of pyridine (0.1 ml, 1.24 mmol) and the product from Step 2 above (152 mg, 0.679 mmol, 98% purity) in DCM (1 ml). The resultant solution was allowed to stand at RT for 3 days. The mixture was treated with PhMe (1 ml) and concentrated in vacuo. The residue was purified by chromatography on silica gel (12 g cartridge, 0-50% EtOAc/isohexane) to afford the title compound (254 mg, 0.570 mmol, 84% yield) as a white foamy solid. UPLC-MS (Method 1): m/z 446.4 $(M+H)^+$, 444.3 $(M-H)^-$, at 1.70 min.

Step 4: I-3-(N-(5-cyano-2-(3-fluoropiperidin-1-yl)phenyl)sulfamoyl)-4-ethylbenzoic acid: The product from Step 3 above (254 mg, 0.570 mmol) was dissolved in THF (10 ml) and treated with 1 M LiOH(aq) (2 ml, 2.00 mmol). MeOH was added to afford a clear solution. The resultant solution was allowed to stand at RT for 1 week. The mixture was diluted with water (4 ml) and concentrated in vacuo. The resultant aqueous solution was diluted with water (2 ml) and washed with TBME (8 ml), then concentrated in vacuo to remove residual TBME. The solution was diluted with water (4 ml) and acidified with 1 M HCl(aq) to ~pH 4 and the resultant white precipitate collected by filtration, washing with water (2×4 ml). The resultant solid was dried in vacuo to afford the title compound (214 mg, 0.471 mmol, 83% yield, 95% purity) as a white solid. UPLC-MS (Method 2): m/z 432.4 $(M+H)^+$, 430.3 $(M-H)^-$ at 0.99 min. 1H NMR (500 MHz, DMSO-$d_6$) δ 13.33 (s, 1H), 9.52 (s, 1H), 8.32 (d, J=1.8 Hz, 1H), 8.11 (dd, J=8.0, 1.8 Hz, 1H), 7.63 (d, J=8.0 Hz, 1H), 7.55 (d, J=8.4 Hz, 1H), 7.31-7.14 (m, 2H), 4.69 (dtt, J=48.2, 7.3, 3.6 Hz, 1H), 3.25-3.09 (m, 1H), 3.02 (q, J=7.4 Hz, 2H), 2.95-2.84 (m, 2H), 2.83-2.70 (m, 1H), 2.05-1.84 (m, 1H), 1.82-1.69 (m, 1H), 1.69-1.45 (m, 2H), 1.21 (t, J=7.4 Hz, 3H).

Example 312: I-3-(N-(5-cyano-2-(3-fluoropiperidin-1-yl)phenyl)sulfamoyl)-4-cyclopropylbenzoic acid

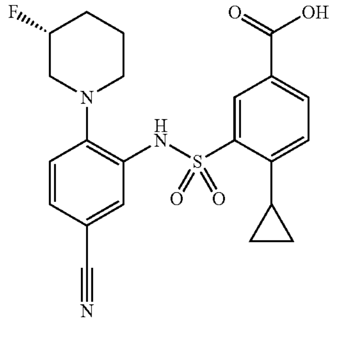 [SMILES: N#Cc1ccc(N2CCC[C@@H](F)C2)c(NS(=O)(=O)c2cc(C(=O)O)ccc2C2CC2)c1]

Step 1: I-methyl 4-bromo-3-(N-(5-cyano-2-(3-fluoropiperidin-1-yl)phenyl)sulfamoyl)benzoate: The product from Example 316 Step 1 (350 mg, 1.11 mmol) was added to a solution of pyridine (100 μl, 1.24 mmol) and the product from Example 311 Step 2 (152 mg, 0.679 mmol, 98% purity) in DCM (1 ml). The resultant solution was allowed to stand at RT for 3 days. The mixture was treated with PhMe (1 ml) and concentrated in vacuo. The residue was purified by chromatography on silica gel (12 g cartridge, 0-50% EtOAc/isohexane) to afford the title compound (313 mg, 0.618 mmol, 91% yield, 98% purity) as a white foamy solid. UPLC-MS (Method 1): m/z 496.2 $(M+H)^+$, 494.1 $(M-H)^-$, at 1.66 min.

Step 2: I-methyl 3-(N-(5-cyano-2-(3-fluoropiperidin-1-yl)phenyl)sulfamoyl)-4-cyclopropylbenzoate: A mixture of the product from Step 1 above (313 mg, 0.618 mmol, 98% purity) and Pd-174 (45 mg, 0.062 mmol) in THF (10 ml) was treated with cyclopropylzinc (II) bromide (0.5 M in THF) (5 ml, 2.50 mmol) and then heated at 60° C. for 45 min. The mixture was cooled in an ice bath, quenched with saturated $NH_4Cl$ (aq) (1 ml) and the THF removed in vacuo. The residue was extracted with DCM (4 ml, then 2×1 ml). The combined organic extracts were directly purified by chromatography on silica gel (12 g cartridge, 0-50% EtOAc/isohexane) to afford two batches of the title compound:

Batch 1 (50 mg, 0.105 mmol, 17% yield, 96% purity) as a clear colourless oil, which partially crystallised on standing. UPLC-MS (Method 1): m/z 458.4 $(M+H)^+$, 456.3 $(M-H)^-$, at 1.70 min. Batch 2 (192 mg, 0.386 mmol, 63% yield, 92% purity) as a clear colourless oil, which partially crystallised on standing.

Step 3: I-3-(N-(5-cyano-2-(3-fluoropiperidin-1-yl)phenyl)sulfamoyl)-4-cyclopropylbenzoic acid: The products from Step 2 above: Batch 1 (50 mg, 0.105 mmol, 17% yield, 96% purity) and Batch 2 (192 mg, 0.386 mmol, 63% yield, 92% purity) were each dissolved in THF (2 ml or 8 ml respectively) and treated with 1 M LiOH(aq) (400 μl, 0.400 mmol; or 1.6 ml, 1.60 mmol respectively). MeOH was added to the reaction mixtures to form clear solutions, which were allowed to stand at RT for 30 h. The mixtures were neutralised with AcOH and concentrated in vacuo. The residues were combined and purified by preparative HPLC (Waters, Acidic (0.1% Formic acid), Acidic, Waters X-Select Prep-C18, 5 μm, 19×50 mm column, 50-85% MeCN in Water) to afford the title compound (127 mg, 0.281 mmol, 57% yield, 98% purity) as a white solid. UPLC-MS (Method 2): m/z 444.4 $(M+H)^+$, 442.3 $(M-H)^-$, at 1.01 min. $^1H$ NMR (500 MHz, DMSO-$d_6$) δ 13.30 (s, 1H), 9.43 (s, 1H), 8.38 (d, J=1.8 Hz, 1H), 8.03 (dd, J=8.2, 1.9 Hz, 1H), 7.54 (d, J=8.3 Hz, 1H), 7.32-7.09 (m, 3H), 4.71 (dtt, J=48.0, 7.3, 3.5 Hz, 1H), 3.26-3.13 (m, 1H), 3.01-2.88 (m, 2H), 2.86-2.77 (m, 1H), 2.76-2.66 (m, 1H), 1.97-1.84 (m, 1H), 1.79-1.70 (m, 1H), 1.69-1.50 (m, 2H), 1.21-1.03 (m, 2H), 0.97-0.73 (m, 2H).

Example 313: 3-(N-(2-(3,3-difluoropiperidin-1-yl)-5-(methylsulfonyl)phenyl)sulfamoyl)-4-ethylbenzoic acid

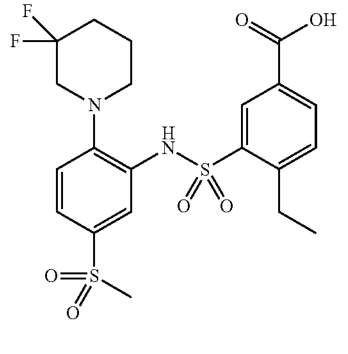 [SMILES: CCc1ccc(C(=O)O)cc1S(=O)(=O)Nc1cc(S(C)(=O)=O)ccc1N1CCCC(F)(F)C1]

Step 1: 3,3-difluoro-1-(4-(methylsulfonyl)-2-nitrophenyl)piperidine: A mixture of 1-fluoro-4-(methylsulfonyl)-2-nitrobenzene (500 mg, 2.28 mmol) and 3,3-difluoropiperidine hydrochloride (359 mg, 2.28 mmol) and triethylamine (700 μl, 5.02 mmol) was sonicated in DCM (6 ml) for 5 min. The resultant suspension was stirred at RT for 18 h. The reaction mixture was sequentially washed with 1 M HCl (4 ml), water (4 ml) and brine (2 ml), diluted with EtOAc (175 ml), washed with brine (10 ml), dried over $MgSO_4$, filtered and concentrated in vacuo to afford the title compound (709 mg, 2.19 mmol, 96% yield, 99% purity) as a bright yellow solid. UPLC-MS (Method 1): m/z 321.1 $(M+H)^+$, at 1.24 min.

Step 2: 2-(3,3-difluoropiperidin-1-yl)-5-(methylsulfonyl)aniline: The product from Step 1 above (709 mg, 2.19 mmol, 99% purity) was combined with iron powder (2.5 g, 44.8 mmol) and $NH_4Cl$(s) (150 mg, 2.80 mmol) in IPA (20 ml) and water (10 ml), heated at 80° C. and stirred overnight. The mixture was cooled and allowed to stand for 24 h. The mixture was filtered through Celite®, rinsing with EtOAc (2×10 ml) and the filtrate was concentrated in vacuo. The residue was purified by chromatography on silica gel (12 g cartridge, 0-50% EtOAc/isohexane) to afford the title compound (505 mg, 1.74 mmol, 79% yield) as a white solid. UPLC-MS (Method 1): m/z 291.1 $(M+H)^+$ at 1.16 min.

Step 3: methyl 3-(N-(2-(3,3-difluoropiperidin-1-yl)-5-(methylsulfonyl)phenyl)sulfamoyl)-4-ethylbenzoate: The product from Example 203 Step 2 (300 mg, 1.13 mmol) was added to a solution of pyridine (100 μl, 1.24 mmol) and the product from Step 2 above (252 mg, 0.868 mmol) in DCM (2 ml). The resultant solution was allowed to stand at RT for 11 days. The mixture was treated with PhMe (1 ml) and concentrated in vacuo. The residue was purified by chromatography on silica gel (12 g cartridge, 0-60% EtOAc/isohexane) to afford the title compound (319 mg, 0.618 mmol, 71% yield) as a white foamy solid. UPLC-MS (Method 1): m/z 517.4 $(M+H)^+$, 515.2 $(M-H)^-$ at 1.57 min.

Step 4: 3-(N-(2-(3,3-difluoropiperidin-1-yl)-5-(methylsulfonyl)phenyl)sulfamoyl)-4-ethylbenzoic acid: The product from Step 3 above (319 mg, 0.618 mmol) was dissolved in THF (9 ml) and treated with 1 M LiOH(aq) (3 ml, 3.00 mmol). The resultant biphasic mixture was stirred at RT for 18 h. The mixture was concentrated in vacuo. The resultant aqueous solution was diluted with water (6 ml) and acidified with 1 M HCl(aq) to ~pH 4 and the resultant white precipitated collected by filtration, washing with water (2×4 ml). The resultant solid was suspended in MeCN (5 ml), the suspension concentrated and dried in vacuo to afford the title compound (292 mg, 0.569 mmol, 92% yield, 98% purity) as a white solid. UPLC-MS (Method 2): m/z 503.2 $(M+H)^+$, 501.2 $(M-H)^-$ at 0.99 min. $^1$H NMR (500 MHz, DMSO-$d_6$)· 12.81 (s, 1H), 8.60-8.35 (m, 1H), 7.96-7.74 (m, 1H), 7.73-7.51 (m, 1H), 7.42-7.20 (m, 1H), 7.12-6.51 (m, 2H), 3.54-3.41 (m, 2H), 3.24-3.11 (m, 4H), 2.84 (s, 3H), 2.05-1.92 (m, 2H), 1.82-1.71 (m, 2H), 1.15 (t, J=7.4 Hz, 3H).

Example 314: I-4-cyclopropyl-3-(N-(2-(3-hydroxypiperidin-1-yl)-5-(trifluoromethyl)phenyl) sulfamoyl)benzoic acid

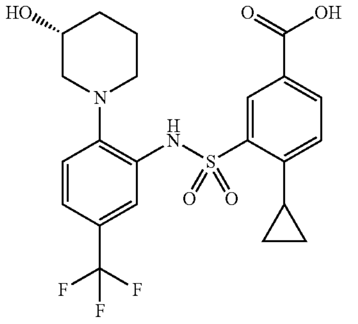 [SMILES: O=C(O)c1ccc(C2CC2)c(S(=O)(=O)Nc2cc(C(F)(F)F)ccc2N2CCC[C@@H](O)C2)c1]

Step 1: I-methyl 4-bromo-3-(N-(2-(3-hydroxypiperidin-1-yl)-5-(trifluoromethyl)phenyl)sulfamoyl)benzoate: The product from Example 316 Step 1 (300 mg, 0.947 mmol) was added to a solution of pyridine (0.1 ml, 1.24 mmol) and the product from Example 243 Step 2 (191 mg, 0.735 mmol) in DCM (2 ml). The resultant solution was allowed to stand at RT for 24 h. The mixture was treated with PhMe (1 ml) and concentrated in vacuo.

The residue was purified by chromatography on silica gel (12 g cartridge, 0-50% EtOAc/isohexane) to afford the title compound (379 mg, 0.698 mmol, 95% yield, 99% purity) as a white foamy solid. UPLC (Method 1): m/z 537.2 $(M+H)^+$, 535.1 $(M-H)^-$ at 1.67 min.

Step 2: I-methyl 4-cyclopropyl-3-(N-(2-(3-hydroxypiperidin-1-yl)-5-(trifluoromethyl)phenyl)sulfamoyl)benzoate: A mixture of the product from Step 1 above (379 mg, 0.698 mmol, 99% purity) and Pd-174 (50 mg, 0.069 mmol) in THF (10 ml) was treated with cyclopropylzinc (II) bromide (0.5 M in THF) (5 ml, 2.50 mmol) and then heated to 60° C. and stirred for 18 h. Additional cyclopropylzinc (II) bromide (0.5 M in THF) (1 ml, 0.500 mmol) was added and heating continued for 1 h. The mixture was neutralised using saturated $NH_4Cl$ (aq) (1 ml) and concentrated in vacuo. The residue was extracted with DCM (2×4 ml). The extracts were combined and concentrated in vacuo. The residue was partially purified by chromatography on silica gel (24 g cartridge, 0-50% EtOAc/isohexane) to afford the title compound (184 mg, 0.343 mmol, 49% yield, 93% purity) as a clear white foam. UPLC (Method 1): m/z 499.3 $(M+H)^+$, 497.3 $(M-H)^-$ at 1.73 min.

Step 3: I-4-cyclopropyl-3-(N-(2-(3-hydroxypiperidin-1-yl)-5-(trifluoromethyl)phenyl)sulfamoyl)benzoic acid: The product from Step 2 above (184 mg, 0.343 mmol, 93% purity) was dissolved in THF (5 ml) and treated with 1 M LiOH(aq) (2.5 ml, 2.50 mmol). The resultant biphasic mixture was stirred at RT for 3 days. The mixture was concentrated in vacuo to remove the THF, then diluted with water (5 ml) and acidified to ~pH 4 using 1 M HCl(aq). The resultant white precipitate was collected by filtration, washing with water, and dried in vacuo to afford a white solid. The solid was purified by preparative HPLC (Waters, Acidic (0.1% Formic acid), Acidic, Waters X-Select Prep-C18, 5 μm, 19×50 mm column, 35-65% MeCN in Water) to afford the title compound (106 mg, 0.214 mmol, 63% yield, 98% purity). UPLC (Method 2): m/z 485.3 $(M+H)^+$, 483.3 $(M-H)^-$ at 1.09 min. $^1$H NMR (500 MHz, DMSO-$d_6$) δ 13.29 (s, 1H), 9.61 (s, 1H), 8.49 (d, J=1.9 Hz, 1H), 8.02 (dd, J=8.2, 1.9 Hz, 1H), 7.38-7.29 (m, 2H), 7.22 (d, J=8.7 Hz, 1H), 7.17 (d, J=8.3 Hz, 1H), 5.42-4.92 (m, 1H), 3.84-3.71 (m, 1H), 3.37-3.22 (m, 1H), 2.94-2.82 (m, 2H), 2.82-2.65 (m, 2H), 1.91-1.74 (m, 1H), 1.74-1.61 (m, 1H), 1.61-1.40 (m, 2H), 1.23-1.03 (m, 2H), 0.92-0.83 (m, 1H), 0.83-0.73 (m, 1H).

Example 315: 3-(N-(2-(4-cyanopiperidin-1-yl)-5-(trifluoromethyl)phenyl)sulfamoyl)-4-cyclopropylbenzoic acid

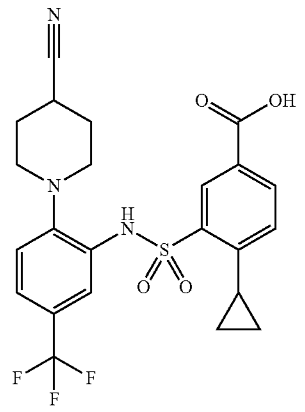 [SMILES: N#CC1CCN(c2ccc(C(F)(F)F)cc2NS(=O)(=O)c2cc(C(=O)O)ccc2C2CC2)CC1]

Step 1: Methyl 4-bromo-3-(N-(2-(4-cyanopiperidin-1-yl)-5-(trifluoromethyl)phenyl)sulfamoyl)benzoate: The product from Example 316 Step 1 (300 mg, 0.947 mmol) was added to a solution of pyridine (100 μl, 1.24 mmol) and the product from Example 237 Step 2 (200 mg, 0.735 mmol) in DCM (1 ml). The resultant solution was allowed to stand at RT for 24 h. The mixture was treated with PhMe (1 ml) and concentrated in vacuo. The residue was purified by chromatography on silica gel (12 g cartridge, 0-50% EtOAc/isohexane) to afford the title compound (388 mg, 0.710 mmol, 97% yield) as a pale yellow foamy solid. UPLC-MS (Method 1): m/z 546.2 $(M+H)^+$, 544.1 $(M-H)^-$ at 1.74 min.

Step 2: Methyl 3-(N-(2-(4-cyanopiperidin-1-yl)-5-(trifluoromethyl)phenyl)sulfamoyl)-4-cyclopropylbenzoate: A mixture of the product from Step 1 above (388 mg, 0.710 mmol) and Pd-174 (50 mg, 0.069 mmol) in THF (10 ml) was treated with cyclopropylzinc (II) bromide (0.5 M in THF) (5 ml, 2.50 mmol) and then heated at 60° C. for 1.5 h. The mixture was cooled and allowed to stand at RT overnight. The mixture was neutralised using saturated $NH_4Cl$ (aq) (1 ml) and concentrated in vacuo. The residue was extracted with DCM (2×4 ml). The extracts were combined and concentrated in vacuo. The residue was partially purified by chromatography on silica gel (24 g cartridge, 0-50% EtOAc/isohexane) to afford the title compound (263 mg, 0.430 mmol, 61% yield, 83% purity) as a white solid. UPLC-MS (Method 1): m/z 508.3 $(M+H)^+$, 506.2 $(M-H)^-$ at 1.77 min.

Step 3: 3-(N-(2-(4-cyanopiperidin-1-yl)-5-(trifluoromethyl)phenyl)sulfamoyl)-4-cyclopropylbenzoic acid: The product from Step 2 above (263 mg, 0.430 mmol, 83% purity) was dissolved in THF (5 ml) and treated with 1 M LiOH(aq) (2.5 ml, 2.50 mmol). The resultant biphasic mixture was stirred at RT for 3 days. The mixture was concentrated in vacuo to remove the THF. The resultant aqueous mixture was acidified using AcOH and concentrated in vacuo. The residue was purified by preparative HPLC (Waters, Acidic (0.1% Formic acid), Acidic, Waters X-Select Prep-C18, 5 μm, 19×50 mm column, 35-65% MeCN in Water) to afford the title compound (125 mg, 0.248 mmol, 58% yield, 98% purity). UPLC-MS (Method 2): m/z 494.3 $(M+H)^+$, 492.2 $(M-H)^-$ at 1.13 min. $^1H$ NMR (500 MHz, DMSO-$d_6$) δ 13.26 (s, 1H), 9.59 (s, 1H), 8.42 (d, J=1.9 Hz, 1H), 8.01 (dd, J=8.2, 1.9 Hz, 1H), 7.45-7.35 (m, 1H), 7.35-7.22 (m, 2H), 7.16 (d, J=8.3 Hz, 1H), 3.03-2.85 (m, 3H), 2.85-2.78 (m, 1H), 2.78-2.67 (m, 2H), 2.01-1.89 (m, 2H), 1.89-1.78 (m, 2H), 1.13-0.99 (m, 2H), 0.92-0.75 (m, 2H).

Example 316: 3-(N-(5-cyano-2-(3,3-difluoropiperidin-1-yl)phenyl)sulfamoyl)-4-cyclopropylbenzoic acid

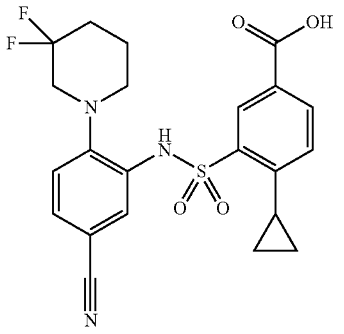 [SMILES: N#Cc1ccc(N2CCCC(F)(F)C2)c(NS(=O)(=O)c2cc(C(=O)O)ccc2C2CC2)c1]

Step 1: Methyl 4-bromo-3-(chlorosulfonyl)benzoate: A mixture of 4-bromo-3-(chlorosulfonyl)benzoic acid (23.9 g, 76 mmol) and $SOCl_2$ (160 ml) was heated under reflux for 4 h. Upon cooling to RT the volatiles were removed in vacuo and the residue was added slowly to MeOH (500 ml) at 0° C. The precipitate was collected and washed with small amounts of cold MeOH to afford the title compound (17.3 g, 54.7 mmol, 72% yield, 99% purity) as a white solid. $^1H$ NMR (500 MHz, DMSO-$d_6$) δ 8.47 (d, J=2.0 Hz, 1H), 7.78-7.71 (m, 2H), 3.86 (s, 3H).

Step 2: Methyl 4-bromo-3-(N-(5-cyano-2-(3,3-difluoropiperidin-1-yl)phenyl)sulfamoyl)benzoate: A mixture of the product from Example 233 Step 2 (150 mg, 0.632 mmol, 99% purity), the product from Step 1 above (218 mg, 0.695 mmol, 99% purity) and pyridine (153 μl, 1.9 mmol) in DCM (4 ml) was stirred at 35° C. for 6 days. The reaction mixture was concentrated in vacuo. The residue was purified by chromatography on silica gel (12 g cartridge, 0-100% EtOAc/isohexane) to afford the title compound (327 mg, 0.547 mmol, 86% yield, 86% purity) as a brown oil. UPLC-MS (Method 2) m/z 514.1 $(M+H)^+$ at 1.50 min.

Step 3: methyl 3-(N-(5-cyano-2-(3,3-difluoropiperidin-1-yl)phenyl)sulfamoyl)-4-cyclopropylbenzoate: A degassed mixture of the product from Step 2 above (180 mg, 0.301 mmol, 86% purity) and Pd-174 (25.2 mg, 0.035 mmol) in THF (4 ml) was treated with cyclopropylzinc (II) bromide (0.5 M in THF) (2.80 ml, 1.40 mmol). The reaction mixture was stirred at 40° C. for 1 h then concentrated in vacuo. The residue was purified by chromatography on silica gel (12 g cartridge, 0-100% EtOAc/isohexane) to afford the title compound (84 mg, 0.139 mmol, 46% yield, 79% purity) as a brown oil. UPLC-MS (Method 2) m/z 476.3 $(M+H)^+$ at 1.56 min.

Step 4: 3-(N-(5-cyano-2-(3,3-difluoropiperidin-1-yl)phenyl)sulfamoyl)-4-cyclopropylbenzoic acid: 1 M LiOH(aq) (1.39 ml, 1.39 mmol) was added to a solution of the product from Step 3 above (84 mg, 0.139 mmol, 79% purity) in THF (2 ml) and the resultant mixture was stirred at RT overnight. The reaction mixture was diluted with EtOAc (50 ml) and washed with water (2× 50 ml). The organic phase was dried by passage through a phase separator and concentrated in vacuo. The residue was purified by preparative HPLC (Waters, Acidic (0.1% Formic acid), Acidic, Waters X-Select Prep-C18, 5 μm, 19×50 mm column, 35-65% MeCN in Water) to afford the title compound (5 mg, 10.3 μmol, 7% yield, 95% purity) as a white solid. UPLC-MS (Method 1) m/z 462.1 $(M+H)^+$, 460.2 $(M-H)^-$ at 1.56 min. $^1H$ NMR (500 MHz, DMSO-$d_6$) δ 8.63 (d, J=1.8 Hz, 1H), 8.13 (dd, J=8.2, 1.9 Hz, 1H), 7.49 (d, J=1.9 Hz, 1H), 7.40 (dd, J=8.3, 1.9 Hz, 1H), 7.32 (d, J=8.3 Hz, 1H), 7.19 (d, J=8.2 Hz, 1H), 3.13 (t, J=10.9 Hz, 2H), 3.00 (t, J=5.4 Hz, 2H), 2.71 (tt, J=8.5, 5.2 Hz, 1H), 2.06 (tt, J=13.6, 6.4 Hz, 2H), 1.90 (h, J=6.0, 5.4 Hz, 2H), 1.19-1.14 (m, 2H), 0.87 (dt, J=6.8, 4.7 Hz, 2H). Two exchangeable protons not observed.

Example 317: 4-ethyl-3-(N-(2-(4-fluoropiperidin-1-yl)-5-(methylsulfonyl)phenyl) sulfamoyl)benzoic acid

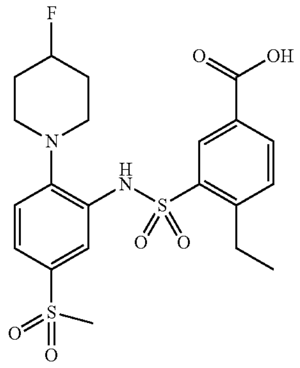 [SMILES: CCc1ccc(C(=O)O)cc1S(=O)(=O)Nc1cc(S(C)(=O)=O)ccc1N1CCC(F)CC1]

Step 1: 4-fluoro-1-(4-(methylsulfonyl)-2-nitrophenyl)piperidine: A mixture of 1-fluoro-4-(methylsulfonyl)-2-nitrobenzene (500 mg, 2.28 mmol), 4-fluoropiperidine hydrochloride (318 mg, 2.28 mmol) and triethylamine (699 μl, 5.02 mmol) was sonicated in DCM (6 ml) until a clear solution was formed. The reaction solution was stirred at RT for 2 h then diluted with DCM (10 ml) and sequentially washed with 1 M HCl(aq) (15 ml), water (15 ml) and brine (15 ml). The organic phase was dried by passage through a phase separator and concentrated in vacuo to afford the title compound (651 mg, 2.09 mmol, 92% yield, 97% purity) as a bright orange solid. UPLC-MS (Method 2) m/z 303.2 $(M+H)^+$ at 1.15 min.

Step 2: 2-(4-fluoropiperidin-1-yl)-5-(methylsulfonyl)aniline: The product from Step 1 above (651 mg, 2.09 mmol, 97% purity) was dissolved in acetic acid (20 ml) and 5% Pd/C (50% w/w water) Type 87L (130 mg, 2.09 mmol) was added. The solution was hydrogenated (5 bar) for 3 days. The reaction mixture was filtered through Celite® and concentrated in vacuo. The residue was purified by chromatography on silica gel (24 g cartridge, 0-100% EtOAc/isohexane) to afford the title compound (482 mg, 1.65 mmol, 79% yield, 93% purity) as a red oil which solidified on standing. UPLC-MS (Method 2) m/z 273.2 $(M+H)^+$ at 1.04 min.

Step 3: methyl 4-ethyl-3-(N-(2-(4-fluoropiperidin-1-yl)-5-(methylsulfonyl)phenyl)sulfamoyl)benzoate: The product from Example 203 Step 2 (159 mg, 0.575 mmol, 95% purity) was added to a solution of pyridine (134 μl, 1.65 mmol) and the product from Step 2 above (150 mg, 0.512 mmol, 93% purity) in DCM (1 ml). The resultant solution was stirred at RT overnight. The reaction mixture was concentrated in vacuo then partially purified by chromatography on silica gel (12 g cartridge, 0-100% EtOAc/isohexane) and then purified by chromatography (24 g reverse phase C18 cartridge, 15-65% MeCN/0.1% formic acid (aq)) to afford the title compound (175 mg, 0.351 mmol, 69% yield) as a white solid. UPLC-MS (Method 2) m/z 499.3 $(M+H)^+$ at 1.40 min.

Step 4: 4-ethyl-3-(N-(2-(4-fluoropiperidin-1-yl)-5-(methylsulfonyl)phenyl)sulfamoyl)benzoic acid: 1 M LiOH(aq) (1.4 ml, 1.4 mmol) was added to a solution of the product from Step 3 above (175 mg, 0.351 mmol) in THF (3 ml). The reaction mixture was stirred at RT overnight then concentrated in vacuo. The residue was dissolved in water (12 ml) and washed with EtOAc (12 ml). The aqueous phase was acidified using 1 M HCl until pH 4-5 and the product was extracted with EtOAc (2×12 ml). The combined organic extracts were dried over $MgSO_4$ and concentrated in vacuo to afford the title compound (106 mg, 0.208 mmol, 59% yield, 95% purity) as a white solid. UPLC-MS (Method 1) m/z 485.3 $(M+H)^+$, 483.3 $(M-H)^-$ at 1.39 min. 1H NMR (500 MHz, DMSO-$d_6$) δ 13.3 (br s, 1H), 9.77 (br s, 1H), 8.31 (d, J=1.8 Hz, 1H), 8.11 (dd, J=8.0, 1.9 Hz, 1H), 7.63 (d, J=8.0 Hz, 1H), 7.57 (d, J=8.3 Hz, 1H), 7.29 (d, J=2.0 Hz, 1H), 7.21 (d, J=8.4 Hz, 1H), 4.88-4.67 (m, 1H), 3.32 (s, 3H), 3.02 (q, J=7.4 Hz, 2H), 2.99-2.92 (m, 2H), 2.83-2.73 (m, 2H), 1.98-1.79 (m, 2H), 1.80-1.68 (m, 2H), 1.21 (t, J=7.4 Hz, 3H).

Example 318:3-(N-(5-cyano-2-(4-fluoropiperidin-1-yl)phenyl)sulfamoyl)-4-ethylbenzoic acid

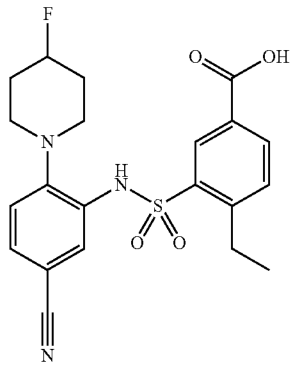 [SMILES: CCc1ccc(C(=O)O)cc1S(=O)(=O)Nc1cc(C#N)ccc1N1CCC(F)CC1]

Step 1: 4-(4-fluoropiperidin-1-yl)-3-nitrobenzonitrile: A mixture of 4-fluoro-3-nitrobenzonitrile (500 mg, 3.01 mmol), 4-fluoropiperidine hydrochloride (420 mg, 3.01 mmol) and triethylamine (923 μl, 6.62 mmol) was sonicated in DCM (6 ml) until a clear solution was formed. The reaction mixture was stirred at RT overnight, diluted with DCM (40 ml) and sequentially washed with water (50 ml) and brine (50 ml). The organic phase was dried by passage through a phase separator and concentrated in vacuo to afford the title compound (735 mg, 2.80 mmol, 93% yield, 95% purity) as a bright orange solid. UPLC-MS (Method 2) m/z 250.5 $(M+H)^+$ at 1.31 min.

Step 2: 3-amino-4-(4-fluoropiperidin-1-yl)benzonitrile: The product from Step 1 above (735 mg, 2.80 mmol, 95% purity) was combined with iron powder (3.29 g, 59 mmol) and $NH_4Cl$(s) (205 mg, 3.83 mmol) in 2:1 IPA/water (30 ml), heated at 70° C. overnight. The reaction mixture was allowed to cool then filtered through Celite®, rinsing with EtOAc (200 ml) and the filtrate was concentrated in vacuo. The residue was purified by chromatography on silica gel (24 g cartridge, 0-100% EtOAc/isohexane) to afford the title compound (350 mg, 1.56 mmol, 56% yield, 98% purity) as a red oil. UPLC-MS (Method 2) m/z 220.6 $(M+H)^+$ at 1.27 min.

Step 3: methyl 3-(N-(5-cyano-2-(4-fluoropiperidin-1-yl)phenyl)sulfamoyl)-4-ethylbenzoate: The product from Example 203 Step 2 (198 mg, 0.753 mmol) was added to a solution of pyridine (166 μl, 2.05 mmol) and the product from Step 3 above (150 mg, 0.670 mmol, 98% purity) in DCM (1 ml). The reaction mixture was stirred at RT for 4 days then concentrated in vacuo. The residue was purified by chromatography on silica gel (12 g cartridge, 0-100% EtOAc/isohexane) to afford the title compound (322 mg) as a red oil. UPLC-MS (Method 2) m/z 446.3 $(M+H)^+$ at 1.57 min.

Step 4: 3-(N-(5-cyano-2-(4-fluoropiperidin-1-yl)phenyl)sulfamoyl)-4-ethylbenzoic acid: 1 M LiOH(aq) (2.89 ml, 2.89 mmol) was added to a solution of the product from Step 3 above (322 mg) in THF (6 ml). The reaction mixture was stirred at RT overnight then concentrated in vacuo. The residue was dissolved in water (12 ml) and washed with EtOAc (12 ml). The aqueous phase was acidified using 1 M HCl until pH 4-5 and the product extracted with EtOAc (2×15 ml). The combined organic extracts were dried by passage through a phase separator and concentrated in vacuo to afford the title compound (234 mg, 0.515 mmol, 77% yield over 2 steps, 95% purity) as a white solid. UPLC-MS (Method 1) m/z 432.4 $(M+H)^+$, 430.3 $(M-H)^-$ at 1.53 min. $^1H$ NMR (500 MHz, DMSO-$d_6$) δ 13.3 (br s, 1H), 9.77 (br s, 1H), 8.31 (d, J=1.8 Hz, 1H), 8.11 (dd, J=8.0, 1.8 Hz, 1H), 7.63 (d, J=8.0 Hz, 1H), 7.57 (d, J=8.3 Hz, 1H), 7.29 (d, J=2.0 Hz, 1H), 7.21 (d, J=8.4 Hz, 1H), 4.77 (ddt, J=48.6, 7.0, 3.5 Hz, 1H), 3.02 (q, J=7.4 Hz, 2H), 2.96 (t, J=9.9 Hz, 2H), 2.83-2.71 (m, 2H), 1.95-1.83 (m, 2H), 1.80-1.67 (m, 2H), 1.21 (t, J=7.4 Hz, 3H).

Example 319: 4-cyclopropyl-3-(N-(2-(3,3-difluoropiperidin-1-yl)-5-(methylsulfonyl)phenyl) sulfamoyl)benzoic acid

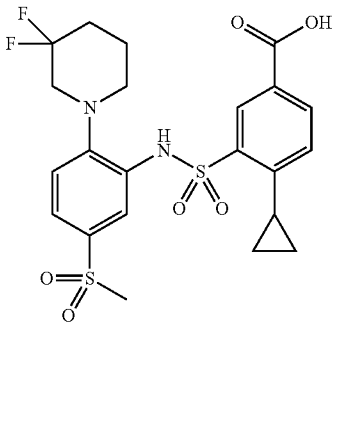 [SMILES: CS(=O)(=O)c1ccc(N2CCCC(F)(F)C2)c(NS(=O)(=O)c2cc(C(=O)O)ccc2C2CC2)c1]

Step 1: methyl 4-bromo-3-(N-(2-(3,3-difluoropiperidin-1-yl)-5-(methylsulfonyl)phenyl)sulfamoyl)benzoate: The product from Example 316 Step 1 (350 mg, 1.11 mmol) was added to a solution of pyridine (100 μl, 1.24 mmol) and the product from Example 313 Step 2 (252 mg, 0.868 mmol) in DCM (2 ml). The resultant solution was allowed to stand at RT for 11 days. The mixture was treated with PhMe (1 ml) and concentrated in vacuo. The residue was purified by chromatography on silica gel (12 g cartridge, 0-60% EtOAc/isohexane) to afford the title compound (276 mg, 0.482 mmol, 56% yield, 99% purity) as a white foamy solid. UPLC-MS (Method 1): m/z 567.3 $(M+H)^+$, 565.5 $(M-H)^-$ at 1.54 min.

Step 2: methyl 4-cyclopropyl-3-(N-(2-(3,3-difluoropiperidin-1-yl)-5-(methylsulfonyl)phenyl)sulfamoyl)benzoate: A mixture of the product from Step 1 above (276 mg, 0.482 mmol, 99% purity) and Pd-174 (50 mg, 0.069 mmol) in THF (10 ml) was treated with cyclopropylzinc (II) bromide (0.5 M in THF) (5 ml, 2.50 mmol) and then heated at 60° C. for 1.5 h. The mixture was cooled and allowed to stand at RT overnight. The mixture was neutralised using saturated $NH_4Cl$ (aq) (1 ml) and concentrated in vacuo. The residue was extracted with DCM (2×4 ml). The extracts were combined and concentrated in vacuo. The residue was partially purified by chromatography on silica gel (24 g cartridge, 0-50% EtOAc/DCM), then by chromatography on silica gel (24 g cartridge, 10-60% EtOAc/isohexane) to afford the title compound (160 mg, 0.275 mmol, 57% yield, 91% purity) as a white solid. UPLC-MS (Method 1): m/z 529.3 $(M+H)^+$, 527.3 $(M-H)^-$, at 1.58 min.

Step 3: 4-cyclopropyl-3-(N-(2-(3,3-difluoropiperidin-1-yl)-5-(methylsulfonyl)phenyl)sulfamoyl)benzoic acid: The product from Step 2 above (160 mg, 0.275 mmol, 91% purity) was dissolved in THF (5 ml) and treated with 1 M LiOH(aq) (2.5 ml, 2.50 mmol). The resultant biphasic mixture was stirred at RT for 3 days. The mixture was concentrated in vacuo to remove the THF. The resultant aqueous mixture was acidified using AcOH and concentrated in vacuo. The residue was purified by preparative HPLC (Waters, Acidic (0.1% Formic acid), Acidic, Waters X-Select Prep-C18, 5 μm, 19×50 mm column, 35-65% MeCN in Water) to afford the title compound (86 mg, 0.164 mmol, 60% yield, 98% purity). UPLC-MS (Method 2): m/z 515.3 $(M+H)^+$, 513.2 $(M-H)^-$ at 1.00 min. $^1H$ NMR (500 MHz, DMSO-$d_6$) δ 13.27 (s, 1H), 9.38 (s, 1H), 8.37 (d, J=1.8 Hz, 1H), 8.02 (d, J=8.2 Hz, 1H), 7.61 (s, 1H), 7.42-7.27 (m, 2H), 7.19 (d, J=8.2 Hz, 1H), 3.40-3.24 (m, 2H), 3.17-3.04 (m, 2H), 2.97 (s, 3H), 2.81-2.66 (m, 1H), 2.09-1.94 (m, 2H), 1.87-1.68 (m, 2H), 1.20-1.00 (m, 2H), 0.96-0.79 (m, 2H). Two protons partially obscured by water.

Example 320: 4-cyclopropyl-3-(N-(2-(4-fluoropiperidin-1-yl)-5-(methylsulfonyl)phenyl) sulfamoyl) benzoic acid

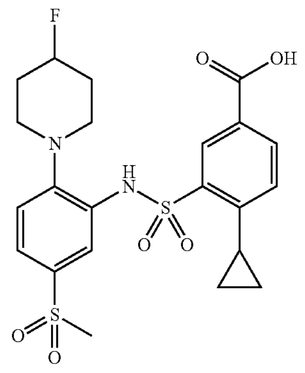 [SMILES: CS(=O)(=O)c1ccc(N2CCC(F)CC2)c(NS(=O)(=O)c2cc(C(=O)O)ccc2C2CC2)c1]

Step 1: Methyl 4-bromo-3-(N-(2-(4-fluoropiperidin-1-yl)-5-(methylsulfonyl)phenyl)sulfamoyl)benzoate: The product from Example 316 Step 1 (420 mg, 1.33 mmol, 99% purity) was added to a solution of pyridine (296 μl, 3.66 mmol) and the product from Example 317 Step 2 (332 mg, 1.13 mmol, 93% purity) in DCM (2 ml). The reaction mixture was stirred at RT for 6 days then concentrated in vacuo. The crude product was purified by chromatography on silica gel (24 g cartridge, 0-100% EtOAc/isohexane) to afford the title compound (395 mg, 0.623 mmol, 55% yield, 87% purity) as a pale red solid. UPLC-MS (Method 2) m/z 549.1 $(M+H)^+$ at 1.40 min.

Step 2: methyl 4-cyclopropyl-3-(N-(2-(4-fluoropiperidin-1-yl)-5-(methylsulfonyl)phenyl)sulfamoyl)benzoate: A degassed mixture of the product from Step 1 above (395 mg, 0.623 mmol, 87% purity) and Pd-174 (51.8 mg, 0.072 mmol) in THF (10 ml) was treated with cyclopropylzinc (II) bromide (0.5 M in THF) (5.75 ml, 2.88 mmol). The reaction mixture was heated at 70° C. for 1 h. Additional Pd-174 (51.8 mg, 0.072 mmol) and cyclopropylzinc (II) bromide (0.5 M in THF) (5.75 ml, 2.88 mmol) was added and the mixture was stirred at 70° C. for 3 h. The mixture was allowed to cool to RT and was concentrated in vacuo. The residue was partitioned between brine (75 ml) and DCM (75 ml) and the phases separated. The aqueous phase was extracted with DCM (75 ml) and the organic phases were combined and filtered through Celite®. The filtrate was dried over $MgSO_4$, filtered and concentrated in vacuo. The residue was purified by chromatography on silica gel (24 g cartridge, 0-100% EtOAc/isohexane) to afford the title compound (226 mg, 0.398 mmol, 64% yield, 90% purity) as a pale yellow solid. UPLC-MS (Method 2) m/z 511.3 $(M+H)^+$ at 1.48 min.

Step 3: 4-cyclopropyl-3-(N-(2-(4-fluoropiperidin-1-yl)-5-(methylsulfonyl)phenyl)sulfamoyl)benzoic acid: 1 M LiOH (aq) (1.77 ml, 1.77 mmol) was added to a solution of the product from Step 2 above (226 mg, 0.398 mmol, 90% purity) in THF (3.5 ml). The reaction mixture was stirred at RT overnight then concentrated in vacuo. The residue was dissolved in water (12 ml) and washed with EtOAc (12 ml). The aqueous phase was acidified to pH 4-5 using 1 M HCl(aq) and the precipitate was collected by filtration and dried in vacuo. The crude product was purified by chromatography on a 24 g reverse phase cartridge (0-100% MeCN/Water 0.1% Formic Acid) to afford the title compound (93 mg, 0.178 mmol, 45% yield, 95% purity) as a white solid.

UPLC-MS (Method 1) m/z 497.3 $(M+H)^+$, 495.2 $(M-H)^-$ at 1.38 min. $^1$H NMR (500 MHz, DMSO-$d_6$) δ 13.2 (br s, 1H), 9.65 (br s, 1H), 8.40 (d, J=1.9 Hz, 1H), 8.01 (d, J=8.1 Hz, 1H), 7.59 (s, 1H), 7.51 (d, J=2.2 Hz, 1H), 7.30 (d, J=8.6 Hz, 1H), 7.16 (d, J=8.2 Hz, 1H), 4.87-4.71 (m, 1H), 3.02-2.99 (m, 5H), 2.87-2.74 (m, 3H), 2.01-1.88 (m, 2H), 1.85-1.74 (m, 2H), 1.13-1.05 (m, 2H), 0.89-0.85 (m, 2H).

Example 321: I-4-cyclopropyl-3-(N-(2-(3-fluoropiperidin-1-yl)-5-(methylsulfonyl)phenyl) sulfamoyl) benzoic acid

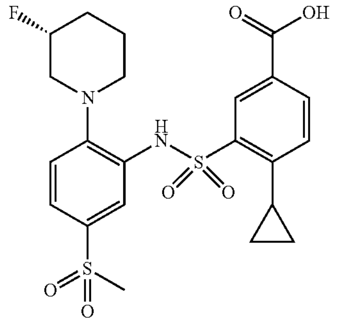 [SMILES: CS(=O)(=O)c1ccc(N2CCC[C@@H](F)C2)c(NS(=O)(=O)c2cc(C(=O)O)ccc2C2CC2)c1]

Step 1: ®-methyl 4-bromo-3-(N-(2-(3-fluoropiperidin-1-yl)-5-(methylsulfonyl)phenyl)sulfamoyl)benzoate: The product from Example 316 Step 1 (198 mg, 0.63 mmol, 99% purity) was added to a solution of the product from Example 262 Step 2 (156 mg, 0.567 mmol, 99% purity) and pyridine (139 μl, 1.72 mmol) in DCM (1 ml). The resultant solution was stirred at RT for 6 days. The reaction mixture was concentrated in vacuo and purified by chromatography on silica gel (12 g cartridge, 0-100% EtOAc/isohexane) to afford the title compound (207 mg, 0.377 mmol, 66% yield) as a pale yellow solid. UPLC-MS (Method 2) m/z 550.1 $(M+H)^+$ at 1.46 min.

Step 2: ®-methyl 4-cyclopropyl-3-(N-(2-(3-fluoropiperidin-1-yl)-5-(methylsulfonyl)phenyl)sulfamoyl)benzoate: A degassed mixture of the product from Step 1 above (207 mg, 0.377 mmol) and Pd-174 (27.2 mg, 0.038 mmol) in THF (6 ml) was treated with cyclopropylzinc (II) bromide (0.5 M in THF) (3.01 ml, 1.51 mmol). The resultant mixture was heated at 70° C. for 1 h. Additional Pd-174 (27.2 mg, 0.038 mmol) and cyclopropylzinc (II) bromide (0.5 M in THF) (3.01 ml, 1.51 mmol) was added and the reaction was stirred at 70° C. for 3 h. The mixture was allowed to cool to RT, then was filtered through Celite® and concentrated in vacuo. The residue was partitioned between brine (75 ml) and DCM (75 ml) and the phases separated. The organic phase was dried by passage through a phase separator and concentrated in vacuo. The residue was purified by chromatography on silica gel (12 g cartridge, 0-100% EtOAc/isohexane) to afford the title compound (128 mg, 0.248 mmol, 66% yield, 99% purity) as a pale yellow solid. UPLC-MS (Method 2) m/z 511.3 $(M+H)^+$ at 1.49 min.

Step 3: ®-4-cyclopropyl-3-(N-(2-(3-fluoropiperidin-1-yl)-5-(methylsulfonyl)phenyl)sulfamoyl)benzoic acid: 1 M LiOH(aq) (1 ml, 1.00 mmol) was added to a solution of the product from Step 2 above (128 mg, 0.248 mmol, 99% purity) in THF (2 ml). The resultant mixture was stirred at RT overnight. The reaction mixture was concentrated in vacuo, dissolved in water (12 ml) and washed with EtOAc (12 ml). The aqueous phase was acidified to pH 4-5 using 1 M HCl(aq) and extracted with EtOAc (2×12 ml). The product precipitated as a white solid in the organic phase and was dissolved in THF (20 ml). The organic phase was dried by passage through a phase separator and concentrated in vacuo. To remove residual THF, the residue was dissolved in 1 M LiOH(aq) (5 ml) and acidified using 1 M HCl(aq) until pH 4-5. The product precipitated as a white solid and was collected by filtration to afford the title compound (63 mg, 0.121 mmol, 49% yield, 95% purity) as a white solid. UPLC-MS (Method 1) m/z 497.6 $(M+H)^+$, 495.2 $(M-H)^-$ at 1.40 min. $^1$H NMR (500 MHz, DMSO-$d_6$) δ 13.3 (br s, 1H), 9.37 (br s, 1H), 8.41 (d, J=1.9 Hz, 1H), 8.01 (dd, J=8.2, 1.9 Hz, 1H), 7.58 (d, J=8.4 Hz, 1H), 7.49 (d, J=2.2 Hz, 1H), 7.32 (d, J=8.5 Hz, 1H), 7.18 (d, J=8.3 Hz, 1H), 4.84-4.68 (m, 1H), 3.26-3.13 (m, 1H), 3.02-2.88 (m, 5H), 2.89-2.79 (m, 1H), 2.79-2.67 (m, 1H), 2.01-1.85 (m, 1H), 1.77 (d, J=6.7 Hz, 1H), 1.71-1.51 (m, 2H), 1.14-1.04 (m, 2H), 0.95-0.88 (m, 1H), 0.87-0.80 (m, 1H).

Example 322: 3-(N-(5-cyano-2-(4-fluoropiperidin-1-yl)phenyl)sulfamoyl)-4-cyclopropylbenzoic acid

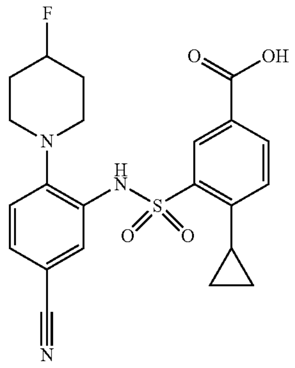 [SMILES: N#Cc1ccc(N2CCC(F)CC2)c(NS(=O)(=O)c2cc(C(=O)O)ccc2C2CC2)c1]

Step 1: Methyl 4-bromo-3-(N-(5-cyano-2-(4-fluoropiperidin-1-yl)phenyl)sulfamoyl)benzoate: The product from Example 316 Step 1 (393 mg, 1.24 mmol, 99% purity) was added to a solution of pyridine (277 μl, 3.42 mmol) and the product from Example 318 Step 2 (250 mg, 1.12 mmol, 98% purity) in DCM (2 ml). The resultant solution was stirred at RT for 6 days. The reaction mixture was concentrated in vacuo and purified by chromatography on silica gel (24 g cartridge, 0-100% EtOAc/isohexane) to afford the title compound (372 mg, 0.749 mmol, 67% yield) as a pink solid. UPLC-MS (Method 2) m/z 497.2 $(M+H)^+$ at 1.46 min.

Step 2: Methyl 3-(N-(5-cyano-2-(4-fluoropiperidin-1-yl) phenyl)sulfamoyl)-4-cyclopropylbenzoate: A degassed mixture of the product from Step 1 above (372 mg, 0.749 mmol) and Pd-174 (54.1 mg, 0.075 mmol) in THF (10 ml) was treated with cyclopropylzinc (II) bromide (0.5 M in THF) (6 ml, 3.00 mmol). The resultant mixture was heated at 70° C. for 1 h. The reaction mixture was concentrated in vacuo and purified by chromatography on silica gel (24 g cartridge, 0-100% EtOAc/isohexane) to afford the title compound (276 mg, 0.57 mmol, 76% yield, 95% purity) as a pale yellow solid. UPLC-MS (Method 2) m/z 458.4 $(M+H)^+$ at 1.53 min.

Step 3: 3-(N-(5-cyano-2-(4-fluoropiperidin-1-yl)phenyl) sulfamoyl)-4-cyclopropylbenzoic acid: 1 M LiOH(aq) (2.41 ml, 2.41 mmol) was added to a solution of the product from Step 2 above (276 mg, 0.573 mmol, 95% purity) in THF (5 ml). The reaction mixture was stirred at RT overnight then concentrated in vacuo. The reaction mixture was acidified to pH 4-5 using 1 M HCl(aq). The precipitate was collected by filtration and dried in vacuo. The crude product was purified by chromatography (24 g reverse phase C18 cartridge, 0-100% MeCN/0.1% formic acid (aq)) to afford the title compound (169 mg, 0.362 mmol, 63% yield, 95% purity) as a white solid. UPLC-MS (Method 1) m/z 444.3 $(M+H)^+$, 442.3 $(M-H)^-$ at 1.53 min. $^1$H NMR (500 MHz, DMSO-$d_6$) δ 13.3 (br s, 1H), 9.69 (br s, 1H), 8.37 (d, J=1.9 Hz, 1H), 8.03 (dd, J=8.2, 1.9 Hz, 1H), 7.55 (d, J=8.5 Hz, 1H), 7.28 (d, J=2.0 Hz, 1H), 7.22 (d, J=8.4 Hz, 1H), 7.17 (d, J=8.3 Hz, 1H), 4.86-4.69 (m, 1H), 3.04-2.96 (m, 2H), 2.87-2.71 (m, 3H), 1.97-1.83 (m, 2H), 1.82-1.69 (m, 2H), 1.13-1.04 (m, 2H), 0.91-0.84 (m, 2H).

Example 323: 4-cyclopropyl-3-(N-(2-(piperidin-1-yl)-5-(tetrazol-1-yl)phenyl)sulfamoyl)benzoic acid

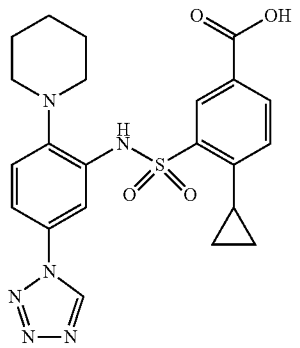 [SMILES: O=C(O)c1ccc(C2CC2)c(S(=O)(=O)Nc2cc(-n3cnnn3)ccc2N2CCCCC2)c1]

Step 1: Methyl 3-(benzylthio)-4-cyclopropylbenzoate: To a degassed mixture of methyl 3-bromo-4-cyclopropylbenzoate (850 mg, 3.33 mmol), DIPEA (1.2 ml, 6.87 mmol) and XantPhos Pd G3 (300 mg, 0.316 mmol) in dioxane (13 ml) was added phenylmethanethiol (425 μl, 3.62 mmol) and the mixture was stirred at 100° C. overnight. The mixture was cooled to RT, concentrated in vacuo onto silica and purified by chromatography on silica gel (40 g cartridge, 20-70% DCM/isohexane) to afford the title compound (600 mg, 1.91 mmol, 58% yield, 95% purity) as an orange oil. $^1$H NMR (500 MHz, DMSO-$d_6$) δ 7.86 (d, J=1.8 Hz, 1H), 7.67 (dd, J=8.1, 1.8 Hz, 1H), 7.40-7.35 (m, 2H), 7.35-7.29 (m, 2H), 7.28-7.22 (m, 1H), 7.04 (d, J=8.1 Hz, 1H), 4.27 (s, 2H), 3.83 (s, 3H), 2.21-2.12 (m, 1H), 1.06-0.99 (m, 2H), 0.75-0.68 (m, 2H).

Step 2: Methyl 3-(chlorosulfonyl)-4-cyclopropylbenzoate: A mixture of the product from Step 1 above (600 mg, 1.91 mmol, 95% purity), AcOH (110 μl, 1.92 mmol) and water (250 μl) in MeCN (9 ml) at −10° C. was treated with 1,3-dichloro-5,5-dimethylimidazolidine-2,4-dione (565 mg, 2.87 mmol). The mixture was stirred at −10° C. for 3 h. The mixture was diluted with water (50 ml) and extracted with DCM (2×50 ml). The organic phases were combined, dried over $MgSO_4$, filtered and concentrated in vacuo onto silica, then purified by chromatography on silica gel (40 g cartridge, 0-50% DCM/isohexane) to afford the title compound (440 mg, 1.52 mmol, 80% yield, 95% purity) as a pale yellow oil. $^1$H NMR (500 MHz, DMSO-$d_6$) δ 8.36 (d, J=2.0 Hz, 1H), 7.77 (dd, J=8.2, 2.1 Hz, 1H), 6.84 (d, J=8.2 Hz, 1H), 3.84 (s, 3H), 3.22-3.01 (m, 1H), 1.08-0.98 (m, 2H), 0.79-0.70 (m, 2H).

Step 3: Methyl 4-cyclopropyl-3-(N-(2-(piperidin-1-yl)-5-(tetrazol-1-yl)phenyl)sulfamoyl)benzoate: The product from Step 2 above (50 mg, 0.182 mmol) was added to a solution of pyridine (40 μl, 0.495 mmol) and the product from Example 214 Step 3 (40 mg, 0.164 mmol, 99% purity) in DCM (300 μl). The resultant solution was stirred at RT overnight. Additional pyridine (40 μl, 0.495 mmol) was added and the reaction was stirred for 3 days. The reaction mixture was concentrated in vacuo and purified by chromatography on silica gel (12 g cartridge, 0-100% EtOAc/isohexane) to afford the title compound (76 mg, 0.157 mmol, 96% yield) as a white solid. UPLC-MS (Method 2) m/z 483.4 $(M+H)^+$ at 1.66 min.

Step 4: 4-cyclopropyl-3-(N-(2-(piperidin-1-yl)-5-(tetrazol-1-yl)phenyl)sulfamoyl)benzoic acid: 1 M LiOH(aq) (630 μl, 0.63 mmol) was added to a solution of the product from Step 3 above (76 mg, 0.157 mmol) in THF (1.3 ml). The reaction mixture was stirred at RT overnight then concentrated in vacuo. The reaction mixture was adjusted to pH 6 with 1 M HCl(aq). The precipitate collected by filtration and dried in vacuo. The crude product was purified by chromatography on a 24 g reverse phase cartridge (0-100% MeCN/Water 0.1% Formic Acid) to afford the title compound (52 mg, 0.105 mmol, 67% yield, 95% purity) as a white solid.

UPLC-MS (Method 1) m/z 469.4 $(M+H)^+$, 467.3 $(M-H)^-$ at 1.57 min. $^1$H NMR (500 MHz, DMSO-$d_6$) δ 9.94 (s, 1H), 8.48 (d, J=1.9 Hz, 1H), 8.00 (dd, J=8.2, 1.9 Hz, 1H), 7.67 (d, J=2.5 Hz, 1H), 7.56 (d, J=8.6 Hz, 1H), 7.37 (d, J=8.6 Hz, 1H), 7.16 (d, J=8.2 Hz, 1H), 2.86-2.76 (m, 1H), 2.73 (t, J=5.2 Hz, 4H), 1.62-1.53 (m, 4H), 1.52-1.43 (m, 2H), 1.13-1.06 (m, 2H), 0.88-0.79 (m, 2H). Two exchangeable protons not observed.

Example 324: 3-(N-(5-cyano-4-fluoro-2-(piperidin-1-yl)phenyl)sulfamoyl)-4-cyclopropylbenzoic acid

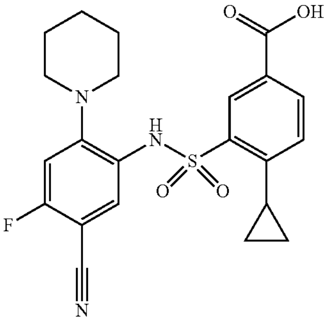 [SMILES: N#Cc1cc(NS(=O)(=O)c2cc(C(=O)O)ccc2C2CC2)c(N2CCCCC2)cc1F]

Step 1: 2-fluoro-5-nitro-4-(piperidin-1-yl)benzonitrile: Piperidine (269 μl, 2.72 mmol) was added to a suspension of 2,4-difluoro-5-nitrobenzonitrile (500 mg, 2.72 mmol) in DCM (5 ml) at 0° C. The resultant solution was allowed to warm to RT and stirred for 2 h. Additional DCM (50 ml) was added and the reaction mixture was washed with water (2×60 ml). The organic phase was dried by passage through a phase separator and concentrated in vacuo to afford the title compound (660 mg, 2.44 mmol, 90% yield, 92% purity) as a yellow solid. UPLC-MS (Method 2) m/z 250.6 $(M+H)^+$ at 1.50 min.

Step 2: 5-amino-2-fluoro-4-(piperidin-1-yl)benzonitrile: The product from Step 1 above (660 mg, 2.44 mmol, 92% purity) was combined with Zinc dust (1.04 g, 15.9 mmol) and $NH_4Cl(s)$ (850 mg, 15.9 mmol) in THF (11 ml) and water (4 ml). The resultant solution was stirred at RT overnight. The reaction mixture was filtered through Celite® and concentrated in vacuo. The residue was dissolved in EtOAc (60 ml) and washed with water (60 ml). The organic phase was dried by passage through a phase separator and concentrated in vacuo. The crude product was purified by chromatography on silica gel (24 g cartridge, 0-100% EtOAc/isohexane) to afford the title compound (533 mg, 2.19 mmol, 90% yield, 90% purity) as a dark brown solid. UPLC-MS (Method 2) m/z 220.3 $(M+H)^+$ at 1.51 min.

Step 3: methyl 4-bromo-3-(N-(5-cyano-4-fluoro-2-(piperidin-1-yl)phenyl)sulfamoyl)benzoate: The product from Example 316 Step 1 (393 mg, 1.21 mmol, 99% purity) was added to a solution of pyridine (277 μl, 3.42 mmol) and the product from Step 2 above (250 mg, 1.03 mmol, 90% purity) in DCM (2 ml). The resultant solution was stirred at RT for 5 days. The reaction mixture was concentrated in vacuo and purified by chromatography on silica gel (12 g cartridge, 0-100% EtOAc/isohexane) to afford the title compound (357 mg, 0.712 mmol, 69% yield, 99% purity) as a brown oil. UPLC-MS (Method 2) m/z 497.3 $(M+H)^+$ at 1.63 min.

Step 4: methyl 3-(N-(5-cyano-4-fluoro-2-(piperidin-1-yl)phenyl)sulfamoyl)-4-cyclopropylbenzoate: To a degassed mixture of the product from Step 3 above (357 mg, 0.712 mmol, 99% purity) and Pd-174 (52 mg, 0.072 mmol) in THF (10 ml) was added cyclopropylzinc (II) bromide (0.5 M in THF) (5.8 ml, 2.9 mmol). The resultant solution was heated at 70° C. for 1 h. The mixture was allowed to cool to RT, concentrated in vacuo and purified by chromatography on silica gel (24 g cartridge, 0-100% EtOAc/isohexane) to afford the title compound (273 mg, 0.489 mmol, 68% yield, 82% purity) as a brown oil. UPLC-MS (Method 2) m/z 458.4 $(M+H)^+$ at 1.69 min.

Step 5: 3-(N-(5-cyano-4-fluoro-2-(piperidin-1-yl)phenyl)sulfamoyl)-4-cyclopropylbenzoic acid: 1 M LiOH(aq) (2.4 ml, 2.4 mmol) was added to a solution of the product from Step 4 above (273 mg, 0.489 mmol, 82% purity) in THF (5 ml). The reaction mixture was stirred at RT overnight, concentrated in vacuo for the removal of THF and adjusted to pH 6 with 1 M HCl(aq). The precipitate was collected by filtration and dried in vacuo. The crude product was purified by chromatography on a 24 g reverse phase cartridge (0-100% MeCN/Water 0.1% Formic Acid) to afford the title compound (80 mg, 0.177 mmol, 36% yield, 98% purity) as a white solid. UPLC-MS (Method 1) m/z 444.4 $(M+H)^+$, 442.4 $(M-H)^-$ at 1.57 min. $^1H$ NMR (500 MHz, DMSO-$d_6$) δ 13.3 (br s, 1H), 9.65 (br s, 1H), 8.30 (d, J=1.9 Hz, 1H), 8.02 (dd, J=8.2, 1.9 Hz, 1H), 7.16 (d, J=8.2 Hz, 1H), 7.13 (d, J=7.2 Hz, 1H), 7.03 (d, J=12.0 Hz, 1H), 3.02-2.92 (m, 4H), 2.74-2.65 (m, 1H), 1.49-1.39 (m, 6H), 1.13-1.04 (m, 2H), 0.95-0.84 (m, 2H).

Example 325:4-cyclopropyl-3-(N-(2-(3-hydroxyazetidin-1-yl)-5-(tetrazol-1-yl)phenyl)sulfamoyl)benzoic acid

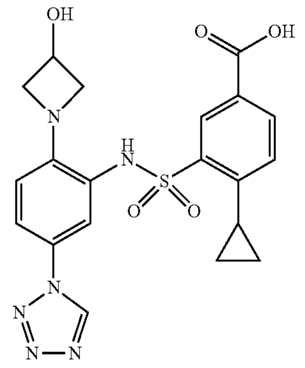 [SMILES: O=C(O)c1ccc(C2CC2)c(S(=O)(=O)Nc2cc(-n3cnnn3)ccc2N2CC(O)C2)c1]

The product from Example 323 Step 2 (42.9 mg, 0.148 mmol) was added to a solution of pyridine (34.5 μl, 0.426 mmol) and the product from Example 283 Step 2 (33 mg, 0.134 mmol) in DCM (0.2 ml). The resultant solution was stirred at RT for 3 days, then concentrated in vacuo. The residue was dissolved in THF (0.5 ml) and treated with 1 M LiOH(aq) (240 μl, 0.240 mmol). The resultant mixture was stirred at RT overnight. Additional 1 M LiOH(aq) (240 μl, 0.240 mmol) was added and the mixture was stirred for 24 h. The reaction mixture was concentrated in vacuo and the residue dissolved in water (12 ml) and washed with TBME (12 ml). The aqueous phase was acidified using 1 M HCl(aq) to pH 4-5 and the product was extracted into EtOAc (2×12 ml). The organic phases were combined and passed through a phase separator, then concentrated in vacuo. The residue was purified by chromatography (24 g reverse phase C18 cartridge, 15-40% MeCN/0.1% formic acid (aq)) to afford the title compound (6 mg, 0.013 mmol, 10% yield, 96% purity) as a white solid. UPLC-MS (Method 2): m/z 457.4 $(M+H)^+$, 455.3 $(M-H)^-$, at 0.61 min. $^1H$ NMR (500 MHz, Methanol-$d_4$) δ 9.33 (s, 1H), 8.51 (d, J=1.8 Hz, 1H), 8.35 (s, 1H), 8.11 (dd, J=8.2, 1.8 Hz, 1H), 7.50 (dd, J=8.8, 2.5 Hz, 1H), 7.11 (d, J=8.2 Hz, 1H), 6.97 (d, J=2.5 Hz, 1H), 6.68 (d, J=8.8 Hz, 1H), 4.69-4.60 (m, 1H), 4.47-4.41 (m, 2H), 3.87 (dd, J=8.6, 4.9 Hz, 2H), 2.86-2.77 (m, 1H), 1.18-1.10 (m, 2H), 0.96-0.89 (m, 2H).

Example 326: 3-(N-(5-cyano-2-(4-cyanopiperidin-1-yl)phenyl)sulfamoyl)-4-cyclopropylbenzoic acid

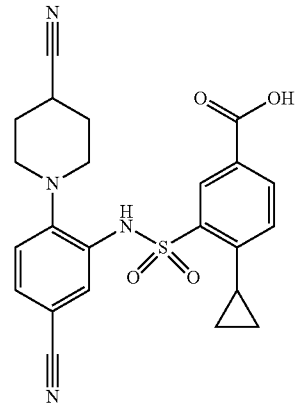 [SMILES: N#Cc1ccc(N2CCC(C#N)CC2)c(NS(=O)(=O)c2cc(C(=O)O)ccc2C2CC2)c1]

Step 1: 1-(4-cyano-2-nitrophenyl)piperidine-4-carbonitrile: A mixture of 4-fluoro-3-nitrobenzonitrile (300 mg, 1.81 mmol), piperidine-4-carbonitrile (220 μl, 1.97 mmol) and $Et_3N$ (800 μl, 5.74 mmol) in DCM (9 ml) was stirred at RT overnight. The mixture was diluted with DCM (15 ml), washed with saturated $NH_4Cl$ (aq) (15 ml), dried by passage through a phase separator, and the solvent was removed in vacuo to afford the title compound (449 mg, 1.73 mmol, 96% yield, 99% purity) as a yellow solid. $^1H$ NMR (500 MHz, DMSO-$d_6$) δ 8.33 (d, J=2.1 Hz, 1H), 7.90 (dd, J=8.8, 2.1 Hz, 1H), 7.40 (d, J=8.8 Hz, 1H), 3.31-3.23 (m, 2H), 3.18-3.09 (m, 3H), 2.03-1.93 (m, 2H), 1.86-1.76 (m, 2H).

Step 2: 1-(2-amino-4-cyanophenyl)piperidine-4-carbonitrile: A mixture the product from Step 1 above (449 mg, 1.73 mmol, 99% purity), iron powder (2 g, 35.8 mmol) and $NH_4Cl$(s) (111 mg, 2.08 mmol) in IPA (15 ml) and water (7.5 ml) was heated at 90° C. overnight. Upon cooling to RT, the mixture was filtered through Celite®, rinsing with EtOAc and then concentrated in vacuo. The residue was extracted with DCM (2×30 ml) and the combined organic phases were dried by passage through a phase separator, and the solvent was removed in vacuo. The residue was loaded onto silica and purified by chromatography on silica gel (24 g cartridge, 0-100% EtOAc/isohexane) to afford the title compound (196 mg, 0.840 mmol, 48% yield, 97% purity) as a light tan solid after trituration with TBME. $^1H$ NMR (500 MHz, DMSO-$d_6$) δ 7.00-6.92 (m, 3H), 5.19 (s, 2H), 3.07-2.92 (m, 3H), 2.80-2.70 (m, 2H), 2.07-1.97 (m, 2H), 1.97-1.86 (m, 2H).

Step 3: methyl 3-(N-(5-cyano-2-(4-cyanopiperidin-1-yl)phenyl)sulfamoyl)-4-cyclopropylbenzoate: A mixture of the product from Step 2 above (50 mg, 0.214 mmol, 97% purity), the product from Example 323 Step 2 (62 mg, 0.214 mmol,) and pyridine (52.0 μl, 0.643 mmol) in DCM (1 ml) was stirred at 35° C. for 3 days. The mixture was concentrated in vacuo onto silica and purified by chromatography on silica gel (12 g cartridge, 0-100% EtOAc/isohexane) to afford the title compound (77 mg, 0.157 mmol, 73% yield, 95% purity) as a light purple solid. UPLC-MS (Method 1) m/z 465.4 $(M+H)^+$, 463.3 $(M-H)^-$ at 1.57 min. $^1H$ NMR (500 MHz, DMSO-$d_6$) δ 9.72 (s, 1H), 8.37 (d, J=1.9 Hz, 1H), 8.04 (d, J=8.1 Hz, 1H), 7.62-7.52 (m, 1H), 7.31 (d, J=2.0 Hz, 1H), 7.23-7.16 (m, 2H), 3.86 (s, 3H), 2.99-2.89 (m, 3H), 2.79-2.71 (m, 3H), 1.90-1.84 (m, 2H), 1.76-1.66 (m, 2H), 1.11-1.04 (m, 2H), 0.91-0.84 (m, 2H).

Step 4: 3-(N-(5-cyano-2-(4-cyanopiperidin-1-yl)phenyl)sulfamoyl)-4-cyclopropylbenzoic acid: A mixture of the product from Step 3 above (77 mg, 0.157 mmol, 95% purity) and LiOH (27 mg, 0.631 mmol) in THF/MeOH/water (4:1:1, 2.7 ml) was stirred at 40° C. overnight. The mixture was diluted with water (5 ml), acidified to ~pH 4 using 1 M HCl(aq) and extracted with EtOAc (3×10 ml). The organic phases were combined and washed with brine (5 ml), dried by passage through a phase separator and the solvent was removed in vacuo. The residue was loaded onto silica and purified by chromatography on silica gel (12 g cartridge, 0-100% EtOAc/isohexane) to afford the title compound (12.1 mg, 0.026 mmol, 16% yield, 98% purity) as a white solid. UPLC-MS (Method 1) m/z 451.8 $(M+H)^+$, 449.3 $(M-H)^-$ at 1.39 min. $^1H$ NMR (500 MHz, DMSO-$d_6$) δ 13.28 (s, 1H), 9.68 (s, 1H), 8.36 (d, J=1.9 Hz, 1H), 8.02 (dd, J=8.2, 1.9 Hz, 1H), 7.55 (d, J=8.2 Hz, 1H), 7.30 (d, J=2.0 Hz, 1H), 7.21 (d, J=8.3 Hz, 1H), 7.17 (d, J=8.3 Hz, 1H), 3.01-2.89 (m, 3H), 2.81-2.71 (m, 3H), 1.93-1.85 (m, 2H), 1.80-1.70 (m, 2H), 1.12-1.04 (m, 2H), 0.91-0.84 (m, 2H).

Example 327: 3-(N-(4-chloro-5-cyano-2-(piperidin-1-yl)phenyl)sulfamoyl)-4-cyclopropylbenzoic acid

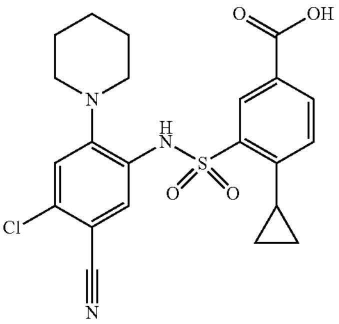 [SMILES: N#Cc1cc(NS(=O)(=O)c2cc(C(=O)O)ccc2C2CC2)c(N2CCCCC2)cc1Cl]

Step 1: 2-chloro-4-fluoro-5-nitrobenzonitrile: 2-chloro-4-fluoro-benzonitrile (1.00 g, 6.43 mmol) was dissolved in conc $H_2SO_4$ (aq) (6.85 ml, 129 mmol) and cooled to 0° C. before adding nitric acid (8.45 ml, 129 mmol). The mixture was kept at 0° C. for 30 min before stirring at RT overnight. The reaction mixture was diluted with water (50 ml) and extracted with DCM (50 ml). The organic phase was dried ($MgSO_4$), filtered and concentrated in vacuo. The crude product was purified by chromatography on silica gel (40 g cartridge, 0-50% TBME/isohexane) to afford the title compound (0.240 g, 1.15 mmol, 18% yield, 96% purity) as a white solid. UPLC-MS (Method 1) m/z no ionisation at 1.17 min. $^1H$ NMR (500 MHz, DMSO-$d_6$) δ 8.97 (d, J=7.7 Hz, 1H), 8.30 (d, J=10.9 Hz, 1H).

Step 2: 2-chloro-5-nitro-4-(piperidin-1-yl)benzonitrile: The product from Step 1 above (0.240 g, 1.15 mmol, 96% purity) in dry DCM (10 ml) was treated with triethylamine (0.160 ml, 1.15 mmol) and piperidine (0.113 ml, 1.15 mmol) and the mixture was stirred at RT for 24 h. The reaction mixture was diluted with water (50 ml) and extracted with EtOAc (100 ml). The organic phase was washed with brine (50 ml), dried ($MgSO_4$), filtered and concentrated in vacuo to afford the title compound (0.298 g, 1.10 mmol, 96% yield, 98% purity) as a bright orange solid. UPLC-MS (Method 1) m/z 266.5 $(M+H)^+$, at 1.63 min.

Step 3: 5-amino-2-chloro-4-(piperidin-1-yl)benzonitrile: The product from Step 2 above (0.298 g, 1.10 mmol, 98% purity) was combined with zinc dust (0.431 g, 6.59 mmol) and $NH_4Cl$(s) (0.353 g, 6.59 mmol) in THF (9 ml) and water (3 ml). The resultant mixture was stirred at RT for 16 h, filtered through Celite® and then concentrated in vacuo. The crude product was purified by chromatography on silica gel (24 g cartridge, 0-20% EtOAc/isohexane) to afford the title compound (0.243 g, 0.897 mmol, 82% yield, 87% purity) as a brown solid. UPLC-MS (Method 1) m/z 236.3 $(M+H)^+$, at 1.66 min.

Step 4: Methyl 3-(N-(4-chloro-5-cyano-2-(piperidin-1-yl)phenyl)sulfamoyl)-4-cyclopropylbenzoate: To a solution of the product from Step 3 above (0.050 g, 0.212 mmol, 87% purity) in DCM (3 ml) and pyridine (0.103 ml, 1.27 mmol) was added the product from Example 323 Step 2 (0.058 g, 0.212 mmol) and the reaction mixture was stirred at RT for 72 h and then concentrated in vacuo. The crude product was purified by chromatography on silica gel (24 g cartridge, 0-50% EtOAc/isohexane) to afford the title compound (0.039 g, 0.081 mmol, 38% yield, 98% purity) as a brown solid. UPLC-MS (Method 1) m/z 474.3 $(M+H)^+$, 472.2 $(M-H)^-$ at 1.91 min.

Step 5: 3-(N-(4-chloro-5-cyano-2-(piperidin-1-yl)phenyl)sulfamoyl)-4-cyclopropylbenzoic acid: 1 M LiOH(aq) (0.242 ml, 0.242 mmol) was added to a solution of the product from Step 4 above (39 mg, 0.081 mmol, 98% purity) in THF (5 ml) and the resultant solution was stirred at RT for 16 h. The reaction mixture was then adjusted to pH 6 with 10% w/v citric acid (aq) and the resultant precipitate was collected under suction and washed with water (5 ml) to afford the title compound (21.6 mg, 0.046 mmol, 57% yield, 98% purity) as a tan solid. UPLC-MS (Method 1): m/z 460.3 $(M+H)^+$, 458.3 $(M-H)^-$ at 1.77 min. $^1H$ NMR (500 MHz, DMSO-$d_6$) δ 13.20 (br s, 1H), 9.70 (br s, 1H), 8.35 (d, J=1.9 Hz, 1H), 8.00 (d, J=8.2 Hz, 1H), 7.24 (s, 1H), 7.13 (d, J=8.7 Hz, 2H), 3.00-2.87 (m, 4H), 2.85-2.70 (m, 1H), 1.55-1.40 (m, 6H), 1.07 (dd, J=8.2, 2.5 Hz, 2H), 0.87 (d, J=5.5 Hz, 2H).

Example 328: 3-(N-(5-cyano-2-(cis-3,5-dimethylpiperidin-1-yl)phenyl)sulfamoyl)-4-cyclopropylbenzoic acid

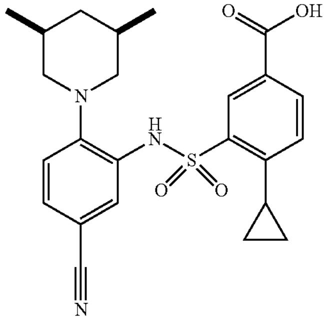 [SMILES: C[C@@H]1C[C@H](C)CN(c2ccc(C#N)cc2NS(=O)(=O)c2cc(C(=O)O)ccc2C2CC2)C1]

Step 1: 4-(cis-3,5-dimethylpiperidin-1-yl)-3-nitrobenzonitrile: Triethylamine (520 μl, 3.73 mmol) was added to a solution of 4-fluoro-3-nitrobenzonitrile (250 mg, 1.51 mmol) and cis-3,5-dimethylpiperidine (190 mg, 1.68 mmol) in DCM (2 ml) and the resultant solution was stirred at RT overnight. The reaction mixture was diluted with DCM (10 ml), washed with water (2×12 ml) and brine (12 ml). The organic phase was dried by passage through a phase separator and concentrated in vacuo to afford the title compound (370 mg, 1.41 mmol, 94% yield, 99% purity) as a bright yellow solid. UPLC-MS (Method 2): m/z 260.3 $(M+H)^+$ at 1.71 min.

Step 2: 3-amino-4-(cis-3,5-dimethylpiperidin-1-yl)benzonitrile: The product from Step 1 above (370 mg, 1.43 mmol) was combined with Zinc dust (560 mg, 8.56 mmol) and Ammonium chloride (458 mg, 8.56 mmol) in THF (6 ml) and water (2 ml). The resultant mixture was stirred at RT overnight. The reaction mixture was filtered through Celite® and concentrated in vacuo. The residue was dissolved in EtOAc (20 ml) and washed with water (20 ml). The organic phase was dried over $MgSO_4$, filtered and concentrated in vacuo. The crude product was purified by chromatography on silica gel (24 g cartridge, 0-50% EtOAc/isohexane) to afford the title compound (300 mg, 1.24 mmol, 87% yield, 95% purity) as a dark red solid. UPLC-MS (Method 2): m/z 230.4 $(M+H)^+$ at 1.72 min. $^1H$ NMR (500 MHz, DMSO-$d_6$) δ 6.99-6.93 (m, 3H), 5.07 (s, 2H), 3.11-3.05 (m, 2H), 2.03 (t, J=11.1 Hz, 2H), 1.88-1.75 (m, 3H), 0.87 (d, J=6.5 Hz, 6H), 0.66 (q, J=11.8 Hz, 1H).

Step 3: Methyl 3-(N-(5-cyano-2-(cis-3,5-dimethylpiperidin-1-yl)phenyl)sulfamoyl)-4-cyclopropylbenzoate: To a mixture the product from Step 2 above (70 mg, 0.290 mmol) and the product from Example 323 Step 2 (88 mg, 0.319 mmol) in DCM (600 μl) at RT was added pyridine (152 μl, 1.89 mmol). The resultant solution was stirred at RT for 72 h and then concentrated in vacuo. The crude product was purified by chromatography on silica gel (12 g cartridge, 0-60% EtOAc/isohexane) to afford the title compound (108 mg, 0.224 mmol, 77% yield, 97% purity) as a pale yellow solid. UPLC-MS (Method 2): m/z 468.5 $(M+H)^+$, at 1.94 min.

Step 4: 3-(N-(5-cyano-2-(cis-3,5-dimethylpiperidin-1-yl)phenyl)sulfamoyl)-4-cyclopropylbenzoic acid: A mixture of methyl of the product from Step 3 above (108 mg, 0.231 mmol) and 1 M LiOH(aq) (23 mg, 0.924 mmol) in THF/MeOH/water (4:1:1, 4 ml) was heated to 40° C. and stirred for 3 days. The reaction mixture was concentrated in vacuo and the residue was adjusted to ~pH 4 with 1 M HCl(aq). The resultant precipitate was filtered, washed with water and dried to afford the crude product. The crude product was purified by chromatography on silica gel (12 g cartridge, 0-10% MeOH/DCM) to afford the title compound (37 mg, 0.080 mmol, 35% yield, 98% purity) as a clear colourless oil. UPLC-MS (Method 1): m/z 454.4 $(M+H)^+$, 452.3 $(M-H)^-$ at 1.82 min. $^1H$ NMR (500 MHz, Methanol-$d_4$) δ 8.60 (d, J=1.9 Hz, 1H), 8.13 (dd, J=8.2, 1.8 Hz, 1H), 7.52 (d, J=1.9 Hz, 1H), 7.41 (dd, J=8.3, 1.9 Hz, 1H), 7.27 (d, J=8.3 Hz, 1H), 7.19 (d, J=8.2 Hz, 1H), 2.99-2.93 (m, 2H), 2.80-2.71 (m, 1H), 2.18 (t, J=11.2 Hz, 2H), 1.86-1.74 (m, 3H), 1.17-1.08 (m, 2H), 0.93-0.83 (m, 8H), 0.69 (q, J=12.2 Hz, 1H).

Example 329: 4-cyclopropyl-3-(N-(2-(piperidin-1-yl)-5-sulfamoylphenyl)sulfamoyl)benzoic acid

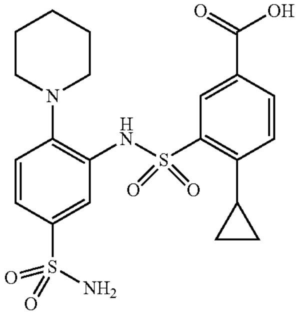 [SMILES: NS(=O)(=O)c1ccc(N2CCCCC2)c(NS(=O)(=O)c2cc(C(=O)O)ccc2C2CC2)c1]

Step 1: Methyl 4-cyclopropyl-3-(N-(2-(piperidin-1-yl)-5-sulfamoylphenyl)sulfamoyl)benzoate: A mixture of 3-amino-4-(piperidin-1-yl)benzenesulfonamide (100 mg, 0.392 mmol), the product from Example 323 Step 2 (129 mg, 0.470 mmol) and pyridine (100 µl, 1.24 mmol) in DCM (2 ml) was stirred at RT for 2 days. The mixture was concentrated in vacuo onto silica and purified by chromatography on silica gel (12 g cartridge, 0-10% MeOH/DCM) to afford the title compound (174 mg, 0.296 mmol, 76% yield, 84% purity) as a white solid. UPLC-MS (Method 1): m/z 494.4 $(M+H)^+$, 492.1 $(M-H)^-$ at 1.58 min.

Step 2: 4-cyclopropyl-3-(N-(2-(piperidin-1-yl)-5-sulfamoylphenyl)sulfamoyl)benzoic acid: A mixture of the product from Step 1 above (174 mg, 0.296 mmol, 84% purity) and LiOH (50 mg, 1.17 mmol) in THF/MeOH/water (4:1:1, 5.4 ml) was stirred at 40° C. overnight. The mixture was diluted with water (5 ml), acidified to ~pH 4 with 1 M HCl(aq) and extracted with EtOAc (3×20 ml). The combined organic phases were washed with brine (15 ml), dried by passage through a phase separator and then concentrated in vacuo. The crude product was purified by preparative HPLC (Waters, Acidic (0.1% Formic acid), Acidic, Waters X-Select Prep-C18, 5 µm, 19×50 mm column, 35-65% MeCN in Water) to afford the title compound (93.9 mg, 0.194 mmol, 66% yield, 99% purity) as a white solid. UPLC-MS (Method 1): m/z 480.4 $(M+H)^+$, 478.3 $(M-H)^-$ at 1.44 min. $^1$H NMR (500 MHz, DMSO-$d_6$) δ 13.22 (s, 1H), 9.23 (s, 1H), 8.44 (d, J=1.9 Hz, 1H), 8.00 (dd, J=8.2, 1.9 Hz, 1H), 7.59 (d, J=2.2 Hz, 1H), 7.52 (dd, J=8.4, 2.2 Hz, 1H), 7.29-7.23 (m, 3H), 7.15 (d, J=8.4 Hz, 1H), 2.77-2.67 (m, 5H), 1.54-1.46 (m, 4H), 1.46-1.38 (m, 2H), 1.10-1.02 (m, 2H), 0.86-0.79 (m, 2H).

Example 330: 3-(N-(5-cyano-2-(piperidin-1-yl)phenyl)sulfamoyl)-4-cyclobutylbenzoic acid

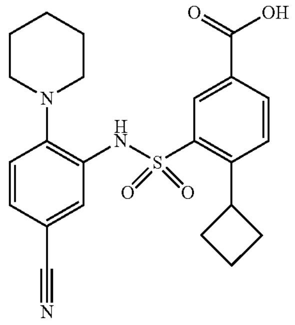 [SMILES: N#Cc1ccc(N2CCCCC2)c(NS(=O)(=O)c2cc(C(=O)O)ccc2C2CCC2)c1]

Step 1: Methyl 4-bromo-3-(N-(5-cyano-2-(piperidin-1-yl)phenyl)sulfamoyl)benzoate: A mixture of the product from Example 182 Step 2 (250 mg, 1.23 mmol), the product from Example 316 Step 1 (409 mg, 1.29 mmol) and pyridine (300 µl, 3.71 mmol) in DCM (6 ml) was stirred at RT for 5 days. The mixture was concentrated in vacuo onto silica and purified by chromatography on silica gel (24 g cartridge, 0-100% EtOAc/isohexane) to afford the title compound (360 mg, 0.753 mmol, 61% yield) as a light tan solid. UPLC-MS (Method 1): m/z 478.3 $(M+H)^+$, 476.1 $(M-H)^-$ at 1.80 min.

Step 2: Methyl 3-(N-(5-cyano-2-(piperidin-1-yl)phenyl)sulfamoyl)-4-cyclobutylbenzoate: To a flame-dried flask was added Mg turnings (137 mg, 5.64 mmol) and iodine (10 mg, 0.039 mmol). A small aliquot of bromocyclobutane (0.35 ml, 3.72 mmol) in THF (4 ml) was added and the mixture was heated to reflux with a heat gun. Once the brown colour disappeared the remaining solution was added at a rate that reflux was maintained. Upon complete addition the mixture was stirred at RT for 2 h. The mixture was slowly added to 2 M zinc chloride in 2-methyltetrahydrofuran (2.8 ml, 5.60 mmol) at 0° C. and then warmed to RT and stirred for 1 h. A solution of the product from Step 1 above (180 mg, 0.376 mmol) In THF (2 ml) and $PdCl_2$ (dppf). DCM (62 mg, 0.076 mmol) were added and the mixture was heated at 70° C. for 4 h and then stirred at RT overnight. The mixture was quenched with saturated $NH_4Cl$ (aq) (20 ml) and extracted with EtOAc (3×20 ml). The organic extracts were combined, washed with brine (20 ml), dried by passage through a phase separator and concentrated in vacuo. The residue was loaded onto silica and purified by chromatography on silica gel (12 g cartridge, 0-75% EtOAc/isohexane) to afford the title compound (118 mg, 0.250 mmol, 66% yield, 96% purity) as a light brown oil. UPLC-MS (Method 1): m/z 454.4 $(M+H)^+$, 452.4 $(M-H)^-$ at 1.95 min.

Step 3: 3-(N-(5-cyano-2-(piperidin-1-yl)phenyl)sulfamoyl)-4-cyclobutylbenzoic acid: A mixture of the product from Step 2 above (118 mg, 0.250 mmol, 96% purity) and LiOH (43 mg, 1.01 mmol) in THF/MeOH/water (4:1:1, 4 ml) was stirred at 40° C. overnight. The mixture was diluted with water (5 ml), acidified to ~pH 4 with 1 M HCl(aq) and extracted with EtOAc (3×20 ml). The combined organic phases were washed with brine (15 ml), dried by passage through a phase separator and concentrated in vacuo. The crude product was purified by preparative HPLC (Waters, Acidic (0.1% Formic acid), Acidic, Waters X-Select Prep-C18, 5 µm, 19×50 mm column, 50-80% MeCN in Water) to afford the title compound (60 mg, 0.134 mmol, 54% yield, 99% purity) as a white solid. UPLC-MS (Method1): m/z 440.4 $(M+H)^+$, 438.3 $(M-H)^-$ at 1.80 min. $^1H$ NMR (500 MHz, DMSO-$d_6$) δ 13.30 (s, 1H), 9.57 (s, 1H), 8.31 (d, J=2.0 Hz, 1H), 8.16 (d, J=8.2 Hz, 1H), 7.93 (d, J=8.2 Hz, 1H), 7.59-7.48 (m, 1H), 7.21 (d, J=2.0 Hz, 1H), 7.15 (d, J=8.6 Hz, 1H), 4.34-4.23 (m, 1H), 2.84-2.73 (m, 4H), 2.28-2.12 (m, 4H), 1.98-1.82 (m, 2H), 1.51-1.41 (m, 6H).

Example 331: 4-cyclopropyl-3-(N-(4-fluoro-5-(methylsulfonyl)-2-(piperidin-1-yl)phenyl)sulfamoyl)benzoic acid

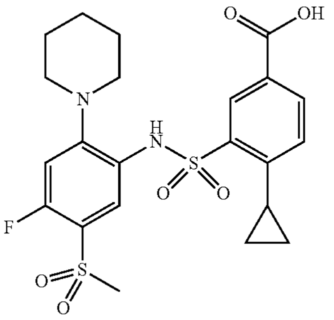 [SMILES: CS(=O)(=O)c1cc(NS(=O)(=O)c2cc(C(=O)O)ccc2C2CC2)c(N2CCCCC2)cc1F]

PART A; Preparation of INTERMEDIATE 1; 4-fluoro-5-(methylsulfonyl)-2-(pyridin-2-yl)aniline

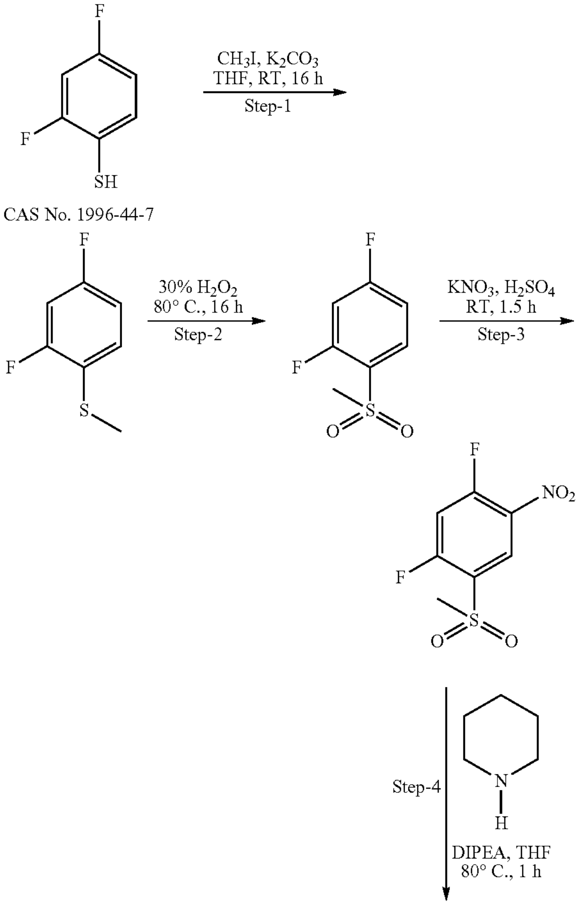

-continued

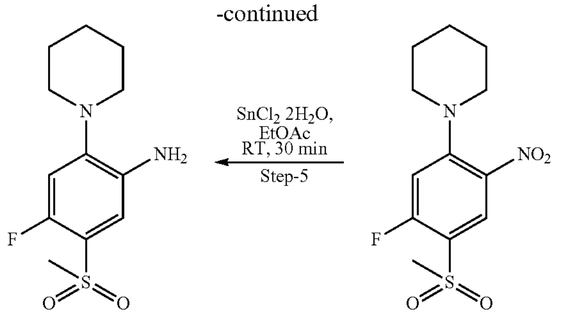

Step-1: Synthesis of (2,4-difluorophenyl)(methyl)sulfane

To a stirred solution of 2,4-difluorobenzenethiol (CAS No. 1996-44-7; 5 g, 0.03421 mol, 1 eq) in THF (50 ml, 10 Vol) was added $K_2CO_3$ (23.60 g, 0.17105 mol, 5 eq) at 0° C. followed by methyl iodide (14.5 g, 0.102 mol, 3 eq). The reaction mixture was stirred at room temperature for 16 hr, then poured into water (500 mL) and extracted with ethyl acetate (2×200 ml). The combined organic layer was washed with brine solution (200 ml), dried over anhydrous $Na_2SO_4$ and concentrated under reduced pressure to give title sulfane (4.3 g, 78.47%).

Step-2: Synthesis of 2,4-difluoro-1-(methylsulfonyl)benzene

A mixture of Step-1 sulfane (2.5 g, 0.0141 mole, 1 eq) in 30% $H_2O_2$ (1 g (3.5 mL), 0.0312 mole, 2.2 eq) was stirred at 80° C. for 16 h, cooled and diluted with water (250 mL) then extracted with EtOAc (2×200 ml). The organic layer was dried over anhydrous $Na_2SO_4$, concentrated under reduced pressure to get crude. The crude was purified by flash column chromatography (230-400 silica) using 13% EtOAc in hexane to give title methylsulphone as brown liquid (1.9 g, 63.35%). UPLC-MS (Method 1) m/z 193.1 $(M+H)^+$ at 1.54 min.

Step-3: Synthesis of 1,5-difluoro-2-(methylsulfonyl)-4-nitrobenzene

To a stirred solution of Step-2 methylsulphone (1.4 g, 0.00728 mole, 1 eq) in conc. $H_2SO_4$ (14 ml, 10 V) was added $KNO_3$ (2.2 g, 0.0218 mol, 3 eq) portion wise. After completion of reaction as indicated by TLC (30% EtOAc in hexane), the reaction mixture was poured into ice cold water (250 mL) and extracted with DCM (2×150 ml). The combined organic layer was washed with sat $NaHCO_3$ solution (250 ml), dried over anhydrous $Na_2SO_4$, concentrated under reduced pressure to give title nitrobenzene as yellow solid (1.5 g, 86.82%).

Step-4: Synthesis of 1-(5-fluoro-4-(methylsulfonyl)-2-nitrophenyl)piperidine To a stirred solution of Step-3 nitrobenzene (1.5 g, 0.00632 mole, 1 eq) in THF (30 mL) was added DIPEA (2.447 g, 0.01897 mole, 3 eq) and piperidine (0.538 g, 0.00632 mole, 1 eq). The reaction mixture was stirred at 80° C. for 1 h, cooled and diluted with water (250 mL) then extracted with EtOAc (2×100 ml). The combined organic layer was dried over anhydrous $Na_2SO_4$, concentrated under reduced pressure to give title piperidine as a yellow solid (1.2 g, 62.76%). UPLC-MS (Method 1) m/z 303.3 $(M+H)^+$ at 2.14 min. $^1H$ NMR (500 MHz, DMSO-$d_6$)· 8.17 (d, 1H), 7.34 (d, 1H), 3.34 (s, 3H), 3.10 (bs, 4H), 1.66 (m, 6H).

Step-5: Synthesis of 4-fluoro-5-(methylsulfonyl)-2-(piperidin-1-yl)aniline

To a solution of Step-4 piperidine (1.2 g, 0.00396 mol, 1 eq) in EtOAc (10 ml) was added $SnCl_2$ $2H_2O$ (4.48 g, 0.01984 mol, 5 eq). The reaction mixture was stirred at room temperature for 30 min, diluted with water (200 ml) and pH was set ~12 using 1 N NaOH solution. The aqueous layer was extracted with ethyl acetate (2×100 ml). The combined organic layer was dried over anhydrous $Na_2SO_4$ and concentrated under reduced pressure. The resulting crude was dissolved in DCM (10 mL) and followed by addition of n-pentane (20 mL). The precipitated solid was filtered to give title aniline as off white solid (0.9 g, 92.51%). UPLC-MS (Method 1) m/z 273.3 $(M+H)^+$ at 2.08 min. $^1H$ NMR (500 MHz, DMSO-$d_6$) δ 7.12 (d, 1H), 6.89 (d, 1H), 4.99 (s, 2H), 3.20 (s, 3H), 2.83 (bs, 4H), 1.67 (bs, 4H), 1.54 (bs, 2H).

PART B; Step 1: Methyl 4-cyclopropyl-3-(N-(4-fluoro-5-(methylsulfonyl)-2-(piperidin-1-yl)phenyl)sulfamoyl)benzoate: A solution of 4-fluoro-5-(methylsulfonyl)-2-(piperidin-1-yl)aniline (INTERMEDIATE 1) (0.10 g, 0.367 mmol) in pyridine (1.04 ml, 12.9 mmol) was treated with the product from Example 323 Step 2 (0.131 g, 0.477 mmol) and the resultant solution was stirred at RT for 24 h then at 50° C. for 96 h. The mixture was concentrated in vacuo and the residue purified by chromatography on silica gel (24 g cartridge, 0-60% EtOAc/isohexane) to afford the title compound (73 mg, 0.143 mmol, 39% yield) as a brown solid. UPLC-MS (Method 1): m/z 511.3 $(M+H)^+$, 509.2 $(M-H)^-$ at 1.64 min.

Step 2: 4-cyclopropyl-3-(N-(4-fluoro-5-(methylsulfonyl)-2-(piperidin-1-yl)phenyl)sulfamoyl)benzoic acid: LiOH (10.3 mg, 0.429 mmol) was added to a mixture of the product from Step 1 above (0.073 g, 0.143 mmol) in THF (3 ml) and water (1 ml) at RT. The resultant mixture was stirred at RT for 24 h. The reaction mixture was concentrated in vacuo. The residue was acidified with 10% w/v citric acid (aq) and the precipitate collected by filtration to afford the title compound (32 mg, 0.064 mmol, 45% yield, 99% purity) as a white solid. UPLC-MS (Method 1): m/z 497.3 $(M+H)^+$, 495.2 $(M-H)^-$ at 1.50 min. $^1H$ NMR (500 MHz, DMSO-$d_6$) δ 13.17 (br s, 1H), 9.60 (br s, 1H), 8.30 (d, J=1.9 Hz, 1H), 8.01 (d, J=8.2 Hz, 1H), 7.21 (d, J=7.7 Hz, 1H), 7.15 (d, J=8.3 Hz, 1H), 7.02 (d, J=12.6 Hz, 1H), 3.11 (s, 3H), 3.06-2.98 (m, 4H), 2.80-2.72 (m, 1H), 1.55-1.45 (m, 6H), 1.17-1.04 (m, 2H), 0.93-0.87 (m, 2H).

Example 332:3-(N-(4-chloro-5-(methylsulfonyl)-2-(piperidin-1-yl)phenyl)sulfamoyl)-4-cyclopropylbenzoic acid

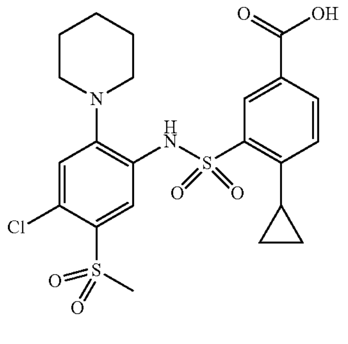 [SMILES: CS(=O)(=O)c1cc(NS(=O)(=O)c2cc(C(=O)O)ccc2C2CC2)c(N2CCCCC2)cc1Cl]

PART A; Preparation of INTERMEDIATE 4; 4-chloro-5-(methylsulfonyl)-2-(pyridin-2-yl)aniline

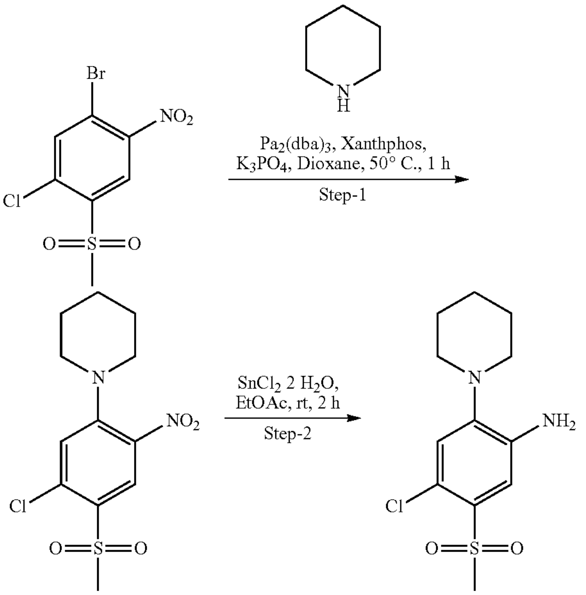

Step-1: Synthesis of 1-(5-chloro-4-(methylsulfonyl)-2-nitrophenyl)piperidine

To a mixture of 1-bromo-5-chloro-4-(methylsulfonyl)-2-nitrobenzene (1 g, 0.00319 mol, 1 eq) and piperidine (0.273 g, 0.00319 mole, 1 eq) in 1,4-dioxane (10 mL) was added $K_3PO_4$ (1.01 g, 0.00478 mol, 1.5 eq). The reaction mixture was purged with $N_2$ for 30 min at room temperature, then $Pd_2$ (dba) 3 (0.145 g, 0.00015 mole, 0.05 eq) and Xanthphos (0.184 g, 0.000319) were added. The resulting reaction mixture was stirred at 50° C. for 1 h, cooled, diluted with water (100 mL) and extracted with ethyl acetate (2×50 mL). The combined organic layer was dried over anhydrous $Na_2SO_4$ and reduced in vacuo to give title piperidine as a brown liquid (1 g, 73.78%). This crude material was used directly for the next step.

Step-2: Synthesis of 4-chloro-5-(methylsulfonyl)-2-(piperidin-1-yl)aniline

To a solution of Step-1 piperidine (1.5 g, 0.0047 mol, 1 eq) in EtOAc (50 ml) was added $SnCl_2$ $2H_2O$ (5.32 g, 0.0235 mol, 5 eq). The reaction mixture was stirred at room temperature for 2 h, diluted with water (100 ml) and pH was set ~12 using 1 N NaOH solution. The aqueous layer was extracted with ethyl acetate (2×100 ml). The combined organic layer was dried over anhydrous $Na_2SO_4$ and concentrated under reduced pressure. The resulting crude was purified by column chromatography using neutral alumina using 20% EtOAc in Hexane as eluent. The resulting material was dissolved in DCM (10 mL) and followed by addition of n-pentane (20 mL). The precipitated solid was filtered to give title aniline as off white solid (0.41 g, 30.18%). UPLC-MS (Method 1) m/z 289.2/291.2 $(M+H)^+$ at 2.27 min. $^1H$ NMR (500 MHz, DMSO-$d_6$) δ 7.37 (d, 1H), 6.99 (d, 1H), 5.31 (s, 2H), 3.24 (s, 3H), 2.82 (bs, 4H), 1.67 (bs, 4H), 1.52 (bs, 2H).

PART B; Step 1: Methyl 3-(N-(4-chloro-5-(methylsulfonyl)-2-(piperidin-1-yl)phenyl)sulfamoyl)-4-cyclopropylbenzoate: A solution of 4-chloro-5-(methylsulfonyl)-2-(piperidin-1-yl)aniline (0.10 g, 0.346 mmol) in pyridine (0.980 ml, 12.1 mmol) was treated with the product from Example 323 Step 2 (0.124 g, 0.450 mmol) and the resultant solution was stirred at RT for 24 h then at 50° C. for 96 h. The mixture was concentrated in vacuo and the residue purified by chromatography on silica gel (24 g cartridge, 0-10% EtOAc/DCM followed by 0-50% EtOAc/Isohexane) to afford the title compound (84 mg, 0.159 mmol, 46% yield, 100% purity) as a cream solid. UPLC-MS (Method 1): m/z 527.3 $(M+H)^+$, 525.1 $(M-H)^-$ at 1.72 min.

Step 2: 3-(N-(4-chloro-5-(methylsulfonyl)-2-(piperidin-1-yl)phenyl)sulfamoyl)-4-cyclopropylbenzoic acid: LiOH (0.011 g, 0.478 mmol) was added to a mixture of the product from Step 1 above (0.084 g, 0.159 mmol, 100% purity) in THF (3 ml) and water (1 ml) at RT. The resultant mixture was stirred at RT for 24 h. The reaction mixture was concentrated in vacuo. The residue was acidified with 10% w/v citric acid (aq) and the precipitate collected by filtration to afford the title compound (65 mg, 0.126 mmol, 79% yield, 99% purity) as a pale yellow solid. UPLC-MS (Method 1): m/z 513.3 $(M+H)^+$, 511.2 $(M-H)^-$ at 1.58 min. $^1H$ NMR (500 MHz, DMSO-$d_6$) δ 13.20 (br s, 1H), 9.50 (br s, 1H), 8.34 (d, J=1.9 Hz, 1H), 8.01 (d, J=8.1 Hz, 1H), 7.51 (s, 1H), 7.20 (s, 1H), 7.16 (d, J=8.3 Hz, 1H), 3.16 (s, 3H), 3.02-2.96 (m, 4H), 2.80-2.72 (m, 1H), 1.54-1.50 (m, 4H), 1.49-1.43 (m, 2H), 1.13-1.04 (m, 2H), 0.92-0.86 (m, 2H).

Example 333: 4-cyclopropyl-3-(N-(4-fluoro-2-(piperidin-1-yl)-5-(tetrazol-1-yl)phenyl) sulfamoyl)benzoic acid

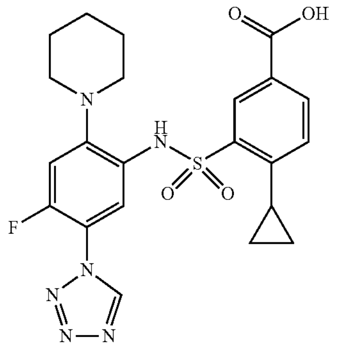 [SMILES: O=C(O)c1ccc(C2CC2)c(S(=O)(=O)Nc2cc(-n3cnnn3)c(F)cc2N2CCCCC2)c1]

PART A; Preparation of INTERMEDIATE 3; 4-fluoro-2-(piperidin-1-yl)-5-(1H-tetrazol-1-yl) aniline

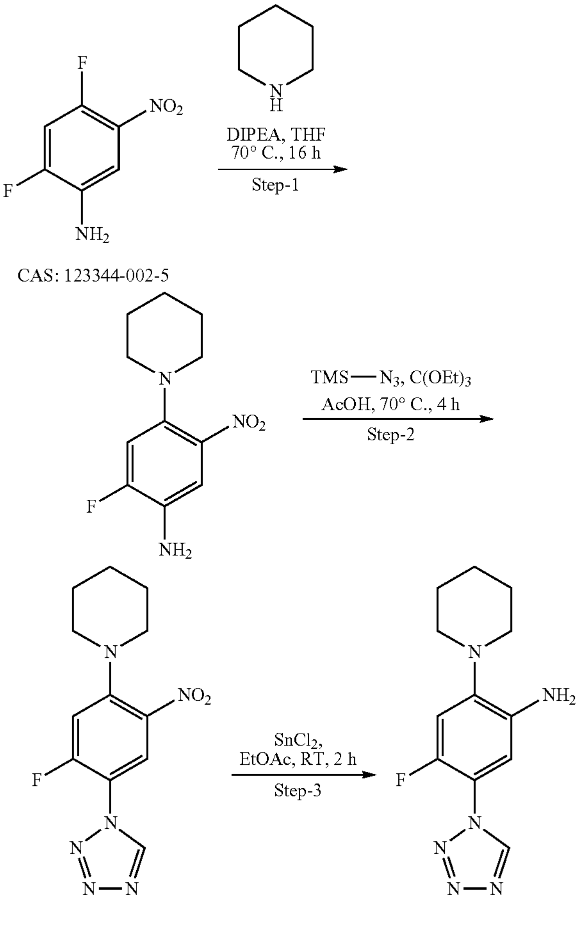

Step-1: Synthesis of 2-fluoro-5-nitro-4-(piperidin-1-yl)aniline

To a stirred solution of 2,4-difluoro-5-nitroaniline (7 g, 0.0287 mol, 1 eq) in THF (70 ml, 10 Vol) was added DIPEA (11.1 g, 0.0861 mol, 3 eq) at room temperature under $N_2$, followed by piperidine (2.44 g, 0.0287 mol, 1 eq) at 0° C. The reaction mixture was then stirred at 70° C. for 16 h, cooled and poured into water (500 mL) then extracted with ethyl acetate (3×250 mL). The combined organic layer was dried over sodium sulfate and concentrated under reduced pressure to give title aniline as a brown oil and a mixture of regioisomers (10 g, quantitative). UPLC-MS (Method 1) m/z 240.3 $(M+H)^+$ at 2.14 and 2.44 min. This material was used directly in the next step.

Step-2: Synthesis of 1-(5-fluoro-2-nitro-4-(1H-tetrazol-1-yl)phenyl)piperidine

A solution of Step-1 aniline (10 g, 0.042 mol, 1 eq) in acetic acid (200 ml, 20 Vol) was stirred for 5 min, then triethylorthoformate (31.08 g, 0.21 mol, 5 eq) was added followed by $TMS-N_3$ (24.15 g, 0.21 mol, 5 eq) at 0° C. The resulting reaction mixture was stirred at 70° C. for 4 h, cooled and poured into water (500 mL) then extracted with ethyl acetate (3×250 mL). The combined organic layer was washed with $NaHCO_3$ solution (50 ml), dried over sodium sulfate and concentrated under reduced pressure to give title tetrazole as a brown oil and a mixture of regioisomers (15 g, Quantitative). UPLC-MS (Method 1) m/z 293.3 $(M+H)^+$ at 2.19 and 2.24 min. This material was used directly in the next step.

Step-3: Synthesis of 4-fluoro-2-(piperidin-1-yl)-5-(1H-tetrazol-1-yl)aniline

To a stirred solution of Step-2 tetrazole (15 g, 0.051 mol, 1 eq) in ethyl acetate (100 ml) was added $SnCl_2$. $2H_2O$ (38.9 g, 0.205 mol, 4 eq). The reaction mixture was stirred at room temperature for 2 h then poured into water (700 mL) and ethyl acetate (250 mL). The precipitate of stannous hydroxide was filtered through a cellite bed and the organic layer was dried over sodium sulfate and concentrated under reduced pressure. The crude product was purified by flash chromatography using neutral alumina using 20-100% EtOAc in hexane eluent to give a mixture of regioisomers. The desired regioisomer was isolated by reverse phase column chromatography (A) 0.1% FA in water, (B) acetonitrile (40:60) and identified by $^1H$ NMR NOE experiments to give title aniline as pale yellow solid (0.560 g, 14.18%). UPLC-MS (Method 1) m/z 263.3 $(M+H)^+$ at 2.19 min. $^1H$ NMR (500 MHz, DMSO-$d_6$) δ 9.93 (s, 1H), 7.06 (d, 1H), 7.02 (d, 1H), 5.04 (s, 2H), 2.82 (bs, 4H), 1.69 (m, 4H), 1.54 (m, 2H).

PART B; Step 1: Methyl 4-cyclopropyl-3-(N-(4-fluoro-2-(piperidin-1-yl)-5-(tetrazol-1-yl)phenyl)sulfamoyl)benzoate: A solution of 4-fluoro-2-(piperidin-1-yl)-5-(tetrazol-1-yl)aniline (INTERMEDIATE 3) (0.30 g, 1.14 mmol) in pyridine (3.24 ml, 40.0 mmol) was treated with the product from Example 323 Step 2 (0.408 g, 1.49 mmol) and the resultant solution was stirred at RT for 24 h then at 50° C. for 96 h. The mixture was concentrated in vacuo and the residue purified by chromatography on silica gel (24 g cartridge, 0-50% EtOAc/isohexane followed by 0-10% EtOAc/DCM) to afford (0.277 g, 0.548 mmol, 48% yield, 99% purity) as a white solid. UPLC-MS (Method 1): m/z 523.4 $(M+Na)^+$, 499.2 $(M-H)^-$ at 1.72 min.

Step 2: 4-cyclopropyl-3-(N-(4-fluoro-2-(piperidin-1-yl)-5-(1H-tetrazol-1-yl)phenyl)sulfamoyl)benzoic acid: LiOH (0.039 g, 1.644 mmol) was added to a solution of the product from Step 1 above (0.277 g, 0.548 mmol, 99% purity) in THF (3 ml, 0.548 mmol) and water (1 ml) at RT. The resultant mixture was stirred at RT for 24 h. The reaction mixture was concentrated in vacuo. The residue was acidified with 10% w/v citric acid (aq) and the precipitate collected by filtration to give (220 mg, 0.447 mmol, 82% yield, 99% purity) as a cream solid. UPLC-MS (Method 1): m/z 509.3 (M+Na)+, 485.2 $(M-H)^-$ at 1.57 min. $^1H$ NMR (500 MHz, DMSO-$d_6$) δ 13.21 (br s, 1H), 9.80 (d, J=1.6 Hz, 1H), 9.55 (br s, 1H), 8.39 (d, J=1.9 Hz, 1H), 8.01 (dd, J=8.2, 1.9 Hz, 1H), 7.46 (d, J=7.8 Hz, 1H), 7.29 (d, J=12.3 Hz, 1H), 7.15 (d, J=8.3 Hz, 1H), 2.79 (m, 5H), 1.48 (d, J=6.4 Hz, 4H), 1.43 (q, J=9.4, 7.3 Hz, 2H), 1.13-1.04 (m, 2H), 0.90-0.81 (m, 2H).

Example 334: 3-(N-(4-chloro-2-(piperidin-1-yl)-5-(tetrazol-1-yl)phenyl)sulfamoyl)-4-cyclopropylbenzoic acid

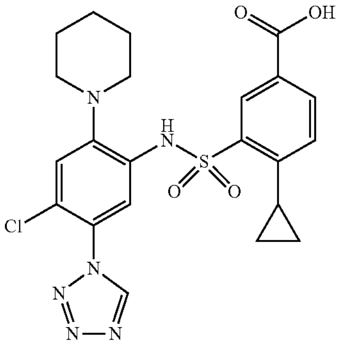 [SMILES: O=C(O)c1ccc(C2CC2)c(S(=O)(=O)Nc2cc(-n3cnnn3)c(Cl)cc2N2CCCCC2)c1]

PART A; Preparation of INTERMEDIATE 4; 4-chloro-2-(piperidin-1-yl)-5-(1H-tetrazol-1-yl) aniline

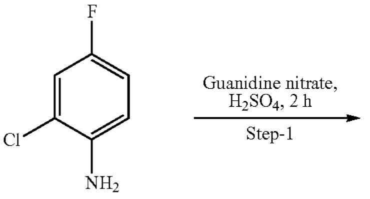

CAS No: 2106-02-7

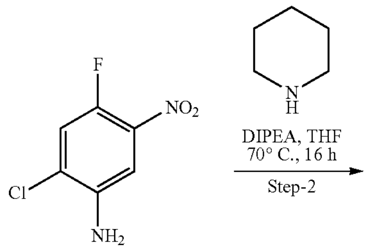

-continued

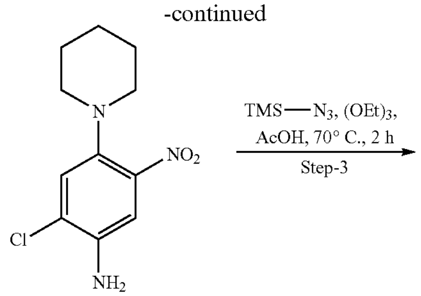

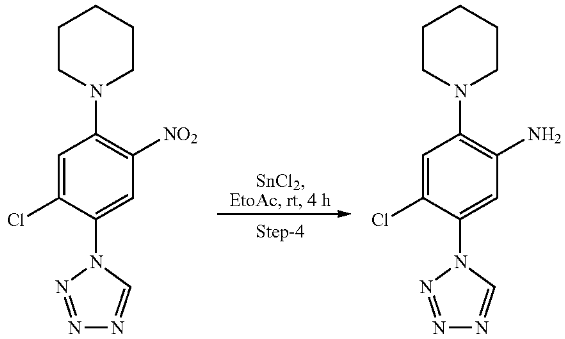

Step-1: Synthesis of 2-chloro-4-fluoro-5-nitroaniline

To a solution of 2-chloro-4-fluoroaniline (5.00 g, 0.0343 mole, 1 eq) in $H_2SO_4$ (15 mL) was added guanidine nitrite (4.19 g, 0.0343 mole, 1 eq) at 0° C. The reaction mixture was stirred for 2 h at room temperature, then basified using 20% NaOH solution (100 ml) and poured in cold water (500 mL). The precipitated solid was filtered and dried in vacuo to give title nitroaniline brown solid (3.7 g, 56.92%).

Step-2: Synthesis of 2-chloro-5-nitro-4-(piperidin-1-yl)aniline

To a solution of Step-1 nitroaniline (3.56 g, 0.0191 mole, 1 eq) and piperidine (3.56 g, 0.038 mole, 2 eq) in THF (35 mL) was added DIPEA (7.5 mL, 0.057 mole, 2 eq). The resulting reaction mixture was stirred at 70° C. for 16 h, cooled and diluted with water (100 mL) then extracted with ethyl acetate (3×100 mL). The combined organic layer was washed with brine (50 mL), dried over anhydrous $Na_2SO_4$ concentrated under reduced pressure to give title aniline as orange solid (4.20 g, 89.36%). UPLC-MS (Method 1) m/z 256.3/258.3 $(M+H)^+$ at 2.43 min. $^1H$ NMR (500 MHz, DMSO-$d_6$) δ 7.28 (s, 1H), 7.17 (s, 1H), 5.65 (s, 2H), 2.77 (m, 4H), 1.36 (m, 4H), 1.54 (m, 2H).

Step-3: Synthesis of 1-(5-chloro-2-nitro-4-(1H-tetrazol-1-yl)phenyl)piperidine

To a solution of Step-2 aniline (4.2 g, 0.0164 mol, 1 eq) in acetic acid (40 mL) was added triethyl orthoformate (12.15 g, 0.0821 mole, 5 eq) and TMS-azide (9.4 g, 0.0821 mole, 5 eq) at 0° C. The reaction mixture was stirred at 70° C. for 2 h, cooled and basified in sat $NaHCO_3$ solution (400 mL) and extracted with ethyl acetate (3×100 mL). The combined organic layer was washed with brine (100 mL), dried over anhydrous $Na_2SO_4$. The solvent was evaporated under reduced pressure and the resulting crude material was purified by trituration in pentane (50 mL) and (diethyl ether (20 mL) to give title piperidine as a brown solid (3.20 g, 63.11%). UPLC-MS (Method 1) m/z 309.3/311.3 $(M+H)^+$ at 2.31 min. $^1H$ NMR (500 MHz, DMSO-$d_6$) δ 9.84 (s, 1H), 8.39 (s, 1H), 7.63 (s, 1H), 3.14 (bs, 4H), 1.62 (bs, 6H).

Step-4: Synthesis of 4-chloro-2-(piperidin-1-yl)-5-(1H-tetrazol-1-yl)aniline

To a solution of Step-3 piperidine (1.0 g, 0.0032 mol, 1.0 eq) in EtOAC was stirred and $SnCl_2$ was added (3.06 g, 0.0161 mol, 3 eq.) The reaction mixture was stirred at room temperature for 4 h, filtered through a celite bed, diluted with water (100 mL) and extracted with ethyl acetate (3×100 mL). The combined organic layer was dried over anhydrous $Na_2SO_4$. The solvent was evaporated under reduced pressure and the crude product was purify by combi flash chromatography neutral silica using (5% ethyl acetate in hexane) to give title aniline as a light brown solid (0.587 g, 56.72%). UPLC-MS (Method 1) m/z 279.3/281.3 $(M+H)^+$ at 2.36 min. 1H NMR (500 MHz, DMSO-$d_6$) δ 9.84 (s, 1H), 7.11 (s, 1H), 6.91 (s, 1H), 5.33 (s, 2H), 2.82 (bs, 4H), 1.69 (m, 4H), 1.54 (m, 2H).

PART B; Step 1: Methyl 3-(N-(4-chloro-2-(piperidin-1-yl)-5-(tetrazol-1-yl)phenyl)sulfamoyl)-4-cyclopropylbenzoate: A solution of 4-chloro-2-(piperidin-1-yl)-5-(tetrazol-1-yl)aniline (INTERMEDIATE 4) (0.30 g, 1.08 mmol) in pyridine (3.05 ml, 37.7 mmol) was treated with the product from Example 323 Step 2 (0.384 g, 1.40 mmol) and the solution was stirred at RT for 24 h then at 70° C. for 96 h. The mixture was concentrated in vacuo and the residue was purified by chromatography on silica gel (24 g cartridge, 0-50% EtOAc/isohexane followed by 0-10% EtOAc/DCM) to afford the title compound (52 mg, 0.099 mmol, 9% yield, 99% purity) as a colourless solid. UPLC-MS (Method 1): m/z 539.3 (M+Na)+, 515.2 $(M-H)^-$ at 1.74 min.

Step 2: 3-(N-(4-chloro-2-(piperidin-1-yl)-5-(tetrazol-1-yl)phenyl)sulfamoyl)-4-cyclopropylbenzoic acid: LiOH (7.08 mg, 0.296 mmol) was added to a mixture of the product from Step 1 above (0.052 g, 0.099 mmol, 99% purity) in THF (3 ml) and water (1 ml) at RT. The resultant mixture was stirred at RT for 24 h. The reaction mixture was concentrated in vacuo and the residue acidified with 10% w/v citric acid (aq). The resultant precipitate was collected by filtration to afford the title compound (33 mg, 0.062 mmol, 63% yield, 95% purity) as a cream solid. UPLC-MS (Method 1): m/z 525.3 $(M+Na)^+$, 501.2 $(M-H)^-$ at 1.63 min. 1H NMR (500 MHz, DMSO-$d_6$) δ 13.20 (br s, 1H), 9.80 (s, 1H), 8.40 (d, J=1.9 Hz, 1H), 8.00 (dd, J=8.2, 1.8 Hz, 1H), 7.40 (d, J=7.2 Hz, 2H), 7.17-7.11 (m, 1H), 2.80 (t, J=5.2 Hz, 5H), 1.52 (q, J=5.6 Hz, 4H), 1.48-1.42 (m, 2H), 1.13-0.99 (m, 2H), 0.89-0.77 (m, 2H). 1 exchangeable proton not observed.

Example 335: 3-(N-(5-cyano-2-(piperidin-1-yl)phenyl)sulfamoyl)-4-(cyclopropyl-$d_5$)benzoic acid

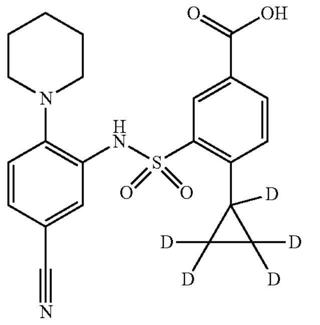 [SMILES: [2H]C1([2H])C([2H])([2H])C1([2H])c1ccc(C(=O)O)cc1S(=O)(=O)Nc1cc(C#N)ccc1N1CCCCC1]

Step 1: Methyl 4-bromo-3-(N-(5-cyano-2-(piperidin-1-yl)phenyl)sulfamoyl)benzoate: A mixture of the product from Example 182 step 2 (1.00 g, 4.92 mmol), the product from Example 316 Step 1 (1.64 g, 5.18 mmol) and pyridine (1.2 ml, 14.8 mmol) in DCM (25 ml) was stirred at RT overnight. The mixture was loaded onto silica and purified by chromatography on silica gel (40 g cartridge, 0-100% EtOAc/isohexane) and then triturated with TBME to afford the title compound (1.44 g, 3.01 mmol, 61% yield) as a white solid. UPLC-MS (Method 1): m/z 478.3 $(M+H)^+$, 476.3 $(M-H)^-$ at 1.80 min.

Step 2: Methyl 3-(N-(5-cyano-2-(piperidin-1-yl)phenyl)sulfamoyl)-4-(cyclopropyl-$d_5$)benzoate: A flame-dried flask was charged with Mg turnings (72 mg, 2.96 mmol) and iodine (5 mg, 0.020 mmol). A small portion (~0.25 ml) of a solution of cyclopropyl-$d_5$ bromide (250 mg, 1.98 mmol) in THF (2 ml) was added and the mixture was heated to reflux with a heat gun. Once the brown colour disappeared the remaining solution was added at a rate that reflux was maintained. Upon complete addition the mixture was stirred at RT for 30 min. The mixture was slowly added to 2 M ZnCl in 2-methyltetrahydrofuran (1.5 ml, 3.00 mmol) at 0° C. and then warmed to RT and stirred for 20 min. A solution of the product from Step 1 above (95 mg, 0.198 mmol) in THF (1 ml) and $PdCl_2$ (dppf)·DCM (30 mg, 0.037 mmol) were added and the mixture was heated to 70° C. for 2 h. The mixture was quenched with saturated $NH_4Cl$ (aq) (10 ml) and extracted with EtOAc (3×20 ml). The combined organic phase was washed with brine (10 ml), dried by passage through a phase separator and then concentrated in vacuo. The residue was loaded onto silica and purified by chromatography on silica gel (12 g cartridge, 0-100% EtOAc/isohexane) to afford the title compound (82 mg, 0.179 mmol, 90% yield, 97% purity) as a pale yellow oil. UPLC-MS (Method 1): m/z 445.5 $(M+H)^+$, 443.4 $(M-H)^-$ at 1.82 min.

Step 3: 3-(N-(5-cyano-2-(piperidin-1-yl)phenyl)sulfamoyl)-4-(cyclopropyl-$d_5$)benzoic acid: A mixture of the product from step 2 above (82 mg, 0.179 mmol, 97% purity) and $LiOH \cdot H_2O$ (30.0 mg, 0.716 mmol) in THF/MeOH/water (4:1:1, 3 ml) was stirred at 40° C. over the weekend. The mixture was diluted with water (5 ml), acidified to ~pH 4 using 1 M HCl(aq) and extracted with EtOAc (3×15 ml). The organic phases were combined and washed with brine (10 ml), dried by passage through a phase separator and concentrated in vacuo. The residue was loaded onto silica and purified by chromatography on silica gel (4 g cartridge, 0-100% EtOAc/isohexane) to afford the title compound (27 mg, 0.060 mmol, 33% yield, 96% purity) as a white solid.

UPLC-MS (Method 1): m/z 431.6 $(M+H)^+$, 429.4 $(M-H)^-$ at 1.66 min. $^1H$ NMR (500 MHz, DMSO-$d_6$) δ 13.25 (s, 1H), 9.48 (s, 1H), 8.37 (d, J=1.9 Hz, 1H), 8.02 (dd, J=8.3, 1.9 Hz, 1H), 7.54 (dd, J=8.4, 2.0 Hz, 1H), 7.24 (d, J=2.0 Hz, 1H), 7.20-7.14 (m, 2H), 2.87-2.80 (m, 4H), 1.53-1.47 (m, 4H), 1.47-1.43 (m, 2H).

Example 336:3-(N-(5-cyano-3-methyl-2-(piperidin-1-yl)phenyl)sulfamoyl)-4-cyclopropylbenzoic acid

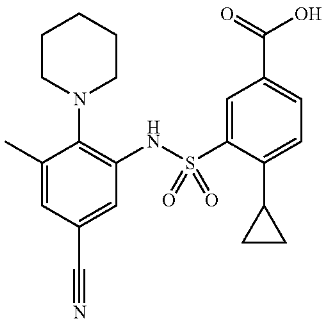 [SMILES: Cc1cc(C#N)cc(NS(=O)(=O)c2cc(C(=O)O)ccc2C2CC2)c1N1CCCCC1]

Step 1: 1-(4-bromo-2-methyl-6-nitrophenyl)piperidine: To a solution of 5-bromo-2-fluoro-1-methyl-3-nitrobenzene (1.01 g, 4.32 mmol) in DCM (10 ml) at RT was added piperidine (0.64 ml, 6.4 mmol) and then triethylamine (1.2 ml, 8.6 mmol). The resultant solution was stirred at RT for 17 h. Additional piperidine (1.3 ml, 13 mmol) was added and the mixture heated at 40° C. for 6 h. Additional piperidine (3.5 ml, 35 mmol) was added and the mixture heated at 40° C. for 17 h and then at 50° C. for 3 h. Additional piperidine (7.0 ml, 70 mmol) was added and the mixture was heated at 50° C. for 4 h. The reaction mixture was allowed to cool to RT and then washed with water (3×20 ml). The aqueous phase was extracted with DCM (10 ml) and the organic phase was dried by passage through a phase separator and concentrated in vacuo. The residue was diluted with DCM (100 ml) and washed with 0.5 M HCl(aq) (3×50 ml). The organic phase was dried over $MgSO_4$ and concentrated in vacuo to afford the title compound (1.17 g, 3.84 mmol, 89% yield, 98% purity) as an orange solid. $^1H$ NMR (500 MHz, DMSO-$d_6$) δ 7.80 (s, 1H), 7.71 (s, 1H), 2.90-2.77 (m, 4H), 2.33 (s, 3H), 1.61-1.51 (m, 6H).

Step 2: 3-methyl-5-nitro-4-(piperidin-1-yl)benzonitrile: A solution of the product from step 1 above (1.17 g, 3.84 mmol, 98% purity) and dicyanozinc (0.483 g, 4.12 mmol) in DMA (5 ml) was degassed with $N_2$ for 10 min, then $Pd(PPh_3)_4$ (0.453 g, 0.392 mmol) was added in 4 portions. The reaction mixture was heated to 100° C. under $N_2$ for 2 h. The reaction mixture was allowed to cool to RT and then filtered through Celite® with EtOAc (50 ml). The filtrate was washed with saturated $NaHCO_3$(aq) (2×20 ml), water (2×20 ml) and brine (2×20 ml). The organic phase was dried over $Na_2SO_4$, filtered and concentrated in vacuo. The crude product was purified by chromatography on silica gel (12 g column, 0-40% EtOAc/isohexane) to afford the title compound (720 mg, 2.88 mmol, 73% yield, 98% purity) as a bright yellow colourless solid. $^1H$ NMR (500 MHz, DMSO-$d_6$) δ 8.17 (d, J=2.0 Hz, 1H), 7.93 (d, J=2.1 Hz, 1H), 2.95-2.85 (m, 4H), 2.36 (s, 3H), 1.65-1.50 (m, 6H).

Step 3: 3-amino-5-methyl-4-(piperidin-1-yl)benzonitrile: To a mixture of the product from step 2 above (720 mg, 2.88 mmol, 98% purity) and $NH_4Cl$ (188 mg, 3.52 mmol) in IPA (10 ml) and water (3 mL) was added iron powder (1.64 g, 29.4 mmol) and the reaction mixture was heated at 90° C. for 4 h. The suspension was cooled to RT and filtered through Celite®, washing with MeOH (10 ml) and the solvent were removed in vacuo. 0.1 M HCl(aq) (100 ml) was added and the solution washed with EtOAc (50 ml). The aqueous solution was neutralised with sat. $NaHCO_3$(aq) (50 ml) and then extracted with ethyl acetate (5×50 ml). The combined organic phases were dried over $MgSO_4$, filtered and concentrated in vacuo to afford the title compound (220 mg) as a light brown oil and was used without further purification.

Step 4: Methyl 3-(N-(5-cyano-3-methyl-2-(piperidin-1-yl)phenyl)sulfamoyl)-4-cyclopropylbenzoate: To a solution of the product from step 3 above (110 mg) and pyridine (0.204 ml, 2.52 mmol) in DCM (5 ml) was added the product from Example 323 step 2 (177 mg, 0.613 mmol, 95% purity) at 0° C. and the mixture was stirred at RT for 19 h. The reaction mixture was diluted with DCM (50 ml) and sequentially washed with 0.5 M HCl(aq) (2×50 ml), water (50 ml) and brine (50 ml). The combined organic phases were dried over $MgSO_4$ and concentrated in vacuo. The residue was purified by chromatography on silica gel (12 g cartridge, 0-100% EtOAc/isohexane) to afford the title compound (104 mg, 0.225 mmol, 16% yield over 2 steps, 98% purity) as a cream solid. $^1$H NMR (500 MHz, DMSO-$d_6$) δ 9.52 (s, 1H), 8.33 (s, 1H), 8.06 (d, J=8.3 Hz, 1H), 7.45 (s, 1H), 7.21 (d, J=8.4 Hz, 1H), 6.88 (s, 1H), 3.86 (s, 3H), 3.07-2.96 (m, 4H), 2.77-2.66 (m, 1H), 2.29 (s, 3H), 1.65-1.52 (m, 6H), 1.16-1.10 (m, 2H), 0.98-0.87 (m, 2H).

Step 5: 3-(N-(5-cyano-3-methyl-2-(piperidin-1-yl)phenyl)sulfamoyl)-4-cyclopropylbenzoic acid: LiOH (16.5 mg, 0.688 mmol) was added to a solution of the product from step 4 above (104 mg, 0.225 mmol, 98% purity) in THF (1 ml) and water (0.5 ml) at RT. The resultant mixture was stirred at RT for 24 h. The reaction mixture was concentrated in vacuo and the residue was acidified with 10% w/v citric acid (aq). The resultant precipitate was collected under filtration and washed with water (50 ml) to afford the title compound (57.5 mg, 0.125 mmol, 55% yield, 96% purity) as a white solid. UPLC-MS (Method 2): m/z 440.7 $(M+H)^+$, 438.3 $(M-H)^-$ at 1.29 min. $^1$H NMR (500 MHz, DMSO-$d_6$) δ 13.30 (s, 1H), 9.46 (s, 1H), 8.33 (d, J=1.8 Hz, 1H), 8.04 (dd, J=8.2, 1.8 Hz, 1H), 7.44 (s, 1H), 7.18 (d, J=8.3 Hz, 1H), 6.90 (d, J=2.1 Hz, 1H), 3.03-2.95 (m, 4H), 2.75-2.67 (m, 1H), 2.29 (s, 3H), 1.66-1.49 (m, 6H), 1.14-1.09 (m, 2H), 0.94-0.89 (m, 2H).

Example 337:4-(tert-butyl)-3-(N-(5-cyano-2-(piperidin-1-yl)phenyl)sulfamoyl)benzoic acid

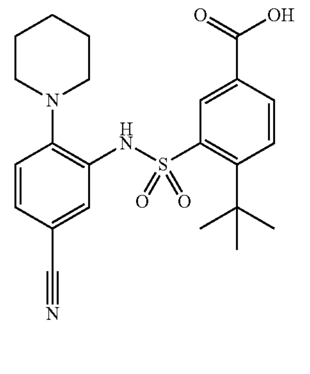 [SMILES: CC(C)(C)c1ccc(C(=O)O)cc1S(=O)(=O)Nc1cc(C#N)ccc1N1CCCCC1]

Step 1: 3-bromo-4-(tert-butyl)benzoic acid: To a mixture of 4-(tert-butyl)benzoic acid (10 g, 56.1 mmol), nitric acid (37 ml), water (28 ml), AcOH (170 ml) and $Br_2$ (5.20 ml, 101 mmol) was added silver nitrate (9.63 g, 56.7 mmol) in water (28.5 ml) via dropping funnel over 30 min. Upon complete addition the mixture was stirred at RT overnight. The mixture was poured onto ice/water and stirred until all the ice melted. The precipitate was collected by filtration, dissolved in EtOAc (600 ml) and sequentially washed with water (200 ml) and brine (200 ml). The organic phase was dried by passage through a phase separator and concentrated in vacuo to afford the title compound (13.4 g, 21.9 mmol, 39% yield, 42% purity) as a yellow solid and was used without further purification. UPLC-MS (Method 1): 255.1 $(M-H)^-$ at 1.73 min.

Step 2: Methyl 3-bromo-4-(tert-butyl)benzoate: A mixture of the product from step 1 above (13.4 g, 21.9 mmol, 42% purity), iodomethane (2.7 ml, 43.4 mmol) and $K_2CO_3$ (6.06 g, 43.8 mmol) in DMF (20 ml) was stirred at RT for 2 h. The mixture was filtered and the filtrate was concentrated in vacuo. The residue was dissolved in DCM (100 ml), washed with 1 M HCl(aq) (100 ml) and brine (3×100 ml). The organic phase was dried by passage through a phase separator and the solvent was concentrated in vacuo onto silica and partially purified by chromatography on silica gel (80 g cartridge, 0-10% EtOAc/isohexane) and then further purified by chromatography (40 g reverse phase C18 cartridge, 35-95% MeCN/0.1% formic acid (aq) to afford the title compound (4.19 g, 15.0 mmol, 68% yield, 97% purity) as a pale yellow oil. $^1$H NMR (500 MHz, DMSO-$d_6$) δ 8.09 (d, J=1.9 Hz, 1H), 7.88 (dd, J=8.3, 1.9 Hz, 1H), 7.63 (d, J=8.3 Hz, 1H), 3.85 (s, 3H), 1.48 (s, 9H).

Step 3: Methyl 3-(benzylthio)-4-(tert-butyl)benzoate: A mixture of the product from step 2 above (4.19 g, 15.0 mmol, 97% purity), DIPEA (5.50 ml, 31.5 mmol), $Pd_2$ (dba) 3 (1.38 g, 1.51 mmol) and Xantphos (1.30 g, 2.25 mmol) in dioxane (70 ml) was sparged with $N_2$ for 15 min. benzyl mercaptan (1.90 ml, 16.1 mmol) was added and the mixture was stirred at 100° C. for 18 h and then at RT for 3 days. Additional benzyl mercaptan (1.90 ml, 16.1 mmol) was added and the mixture was stirred at 100° C. for 5 h. Additional $Pd_2$ (dba) 3 (1.38 g, 1.51 mmol) and xantphos (1.30 g, 2.25 mmol) were added and stirring at 100° C. was continued overnight. Additional DIPEA (5.50 ml, 31.5 mmol) was added and stirring at 100° C. was continued overnight. Upon cooling to RT the mixture was filtered through Celite® and the filtrate was concentrated in vacuo. The residue was loaded onto silica and purified by chromatography on silica gel (120 g cartridge, 0-100% DCM/isohexane) to afford the title compound (1.18 g, 2.85 mmol, 19% yield, 76% purity) as a pale yellow oil. UPLC-MS (Method 1): m/z 315.2 $(M+H)^+$, 313.2 $(M-H)^-$ $(ES^-)$ at 2.06 min.

Step 4: Methyl 4-(tert-butyl)-3-(chlorosulfonyl)benzoate: To a solution of the product from step 3 above (1.18 g, 2.85 mmol, 76% purity) in AcOH (0.21 ml), water (1.5 ml), and MeCN (20 ml) at −10° C. was added 1,3-dichloro-5,5-dimethylimidazolidine-2,4-dione (843 mg, 4.28 mmol) and the mixture was stirred at −10° C. for 2 h. The mixture was concentrated in vacuo to ~5 ml, extracted with DCM (2×40 ml), and the combined organic phase was dried by passage through a phase separator and concentrated in vacuo. The residue was loaded onto silica and purified by chromatography on silica gel (40 g cartridge, 0-100% DCM/isohexane) to afford the title compound (697 mg, 2.28 mmol, 80% yield, 95% purity) as a white solid. $^1$H NMR (500 MHz, DMSO- $d_6$) δ 8.76 (d, J=2.2 Hz, 1H), 7.79 (dd, J=8.3, 2.2 Hz, 1H), 7.55 (d, J=8.3 Hz, 1H), 3.84 (s, 3H), 1.53 (s, 9H).

Step 5: Methyl 4-(tert-butyl)-3-(N-(5-cyano-2-(piperidin-1-yl)phenyl)sulfamoyl)benzoate: A mixture of the product from Example 182 step 2 (100 mg, 492 μmol, 93% purity), the product from step 4 above (226 mg, 738 μmol, 95% purity) and pyridine (0.12 ml, 1.52 mmol) in DCM (2 ml) was stirred at 35° C. for 3 days. The mixture was concentrated in vacuo onto silica and purified by chromatography on silica gel (12 g cartridge, 0-100% DCM/isohexane) to afford the title compound (111 mg, 135 μmol, 27% yield, 55% purity) as a light brown oil. UPLC-MS (Method 1): m/z 456.6 $(M+H)^+$, 454.3 $(M-H)^-$ at 1.98 min.

Step 6: 4-(tert-butyl)-3-(N-(5-cyano-2-(piperidin-1-yl) phenyl)sulfamoyl)benzoic acid: A mixture of the product from step 5 above (111 mg, 135 μmol, 55% purity) and $LiOH \cdot H_2O$ (23.0 mg, 548 μmol) THF/MeOH/water (4:1:1, 2.1 ml) was stirred at 40° C. overnight. The mixture was diluted with water (5 ml), acidified to ~pH 4 with 1 M HCl(aq) and extracted with EtOAc (3×15 ml). The combined organic extracts were washed with brine (10 ml), dried by passage through a phase separator and the solvent was removed in vacuo. The residue was loaded onto silica and purified by chromatography on silica gel (12 g cartridge, 0-100% EtOAc/isohexane) to afford the title compound as a white solid. UPLC-MS (Method 1): m/z 442.6 $(M+H)^+$, 440.3 $(M-H)^-$, at 1.98 min. $^1H$ NMR (500 MHz, DMSO-$d_6$) δ 8.09 (d, J=1.9 Hz, 1H), 7.88 (dd, J=8.3, 1.9 Hz, 1H), 7.63 (d, J=8.3 Hz, 1H), 3.85 (s, 3H), 1.48 (s, 9H).

Example 338: 3-(N-(5-cyano-2-(piperidin-1-yl)phenyl)sulfamoyl)-4-ethynylbenzoic acid

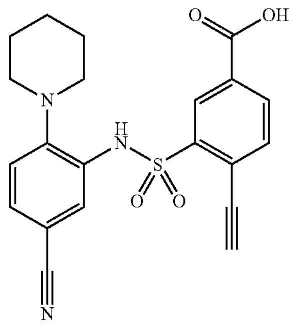 [SMILES: C#Cc1ccc(C(=O)O)cc1S(=O)(=O)Nc1cc(C#N)ccc1N1CCCCC1]

Step 1: methyl 3-bromo-4-((trimethylsilyl) ethynyl)benzoate: A mixture of methyl 3-bromo-4-iodobenzoate (1.00 g, 2.93 mmol), $PdCl_2(PPh_3)_2$ (51 mg, 0.073 mmol) and CuI(s) (14 mg, 0.073 mmol) in THF (10 ml) was prepared under a $N_2$ atmosphere. $Et_3N$ (2.04 ml, 14.7 mmol) and ethynyltrimethylsilane (488 μl, 3.52 mmol) were added and the mixture was stirred at RT overnight. The reaction mixture was filtered through Celite® and concentrated in vacuo. The crude product was purified by chromatography on silica gel (80 g cartridge, 0-20% EtOAc/isohexane) to afford the title compound (870 mg, 2.52 mmol, 86% yield, 90% purity) as a yellow liquid. $^1H$ NMR (500 MHz, DMSO-$d_6$) δ 8.17-8.14 (m, 1H), 7.94-7.90 (m, 1H), 7.70 (d, J=8.1 Hz, 1H), 3.87 (s, 3H), 0.27 (s, 9H).

Step 2: methyl 3-(benzylthio)-4-((trimethylsilyl) ethynyl) benzoate: A mixture of the product from step 1 above (870 mg, 2.52 mmol, 90% purity), $Pd_2$ (dba) 3 (140 mg, 0.598 mmol), DIPEA (780 μl, 4.47 mmol) and dioxane (6.5 ml) was sparged with $N_2$ for 15 min before benzyl mercaptan (280 μl, 2.37 mmol) was added. The mixture was heated to 100° C. and stirred overnight. Upon cooling to RT the mixture was filtered through Celite®. The filtrate was loaded onto silica and purified by chromatography on silica gel (330 g cartridge, 0-50% DCM/isohexane) to afford the title compound (880 mg, 2.36 mmol, 94% yield, 95% purity) as an orange solid. $^1H$ NMR (500 MHz, DMSO-$d_6$) δ 7.91-7.86 (m, 1H), 7.70-7.66 (m, 1H), 7.56 (d, J=8.0 Hz, 1H), 7.46-7.42 (m, 2H), 7.37-7.31 (m, 2H), 7.29-7.24 (m, 1H), 4.36 (s, 2H), 3.85 (s, 3H), 0.25 (s, 9H).

Step 3: methyl 3-(chlorosulfonyl)-4-((trimethylsilyl) ethynyl)benzoate: To a solution of the product from step 2 above (880 mg, 2.36 mmol, 95% purity), AcOH (150 μl, 2.62 mmol) and water (300 μl) in MeCN (12 ml) at −10° C. was added 1,3-dichloro-5,5-dimethylimidazolidine-2,4-dione (700 mg, 3.55 mmol) in 4 portions and the mixture was stirred at −10° C. for 2 h. The mixture was concentrated in vacuo, dissolved in water (30 ml) and extracted with DCM (3×30 ml). The combined organic phases were dried by passage through a phase separator and concentrated onto silica in vacuo. The crude product was purified by chromatography on silica gel (40 g cartridge, 0-100% DCM/isohexane) to afford the title compound (637 mg, 1.35 mmol, 57% yield, 70% purity) as a clear colourless oil. $^1H$ NMR (500 MHz, DMSO-$d_6$) δ 8.38 (d, J=1.9 Hz, 1H), 7.84 (dd, J=8.0, 1.9 Hz, 1H), 7.54 (d, J=8.0 Hz, 1H), 3.87 (s, 3H), 0.22 (s, 9H).

Step 4: methyl 3-(N-(5-cyano-2-(piperidin-1-yl)phenyl) sulfamoyl)-4-((trimethylsilyl) ethynyl)benzoate: The product from step 3 above (256 mg, 0.541 mmol, 70% purity) was added to a solution of pyridine (0.12 mL, 1.5 mmol) and the product from Example 182, step 2 (100 mg, 0.492 mmol, 93% purity) in DCM (1 mL). The resultant solution was stirred at RT for 3 days. The reaction mixture was concentrated in vacuo and purified by chromatography on silica gel (12 g cartridge, 0-100% EtOAc/isohexane) to the title compound (285 mg, 0.492 mmol, 100% yield, 85% purity) as a pale yellow oil. UPLC-MS (Method 1): m/z 496.3 $(M+H)^+$, 494.2 $(M-H)^-$, at 2.08 min.

Step 5: 3-(N-(5-cyano-2-(piperidin-1-yl)phenyl)sulfamoyl)-4-ethynylbenzoic acid: To a solution of the product from step 4 above (285 mg, 492 μmol, 85% purity) in THF (3 ml) was added 1 M LiOH(aq) (1.50 mL, 1.50 mmol). The reaction mixture was heated to 40° C. and stirred for 3 h. The reaction mixture was cooled to RT and concentrated in vacuo. The residue was acidified to ~pH 4 using 1 M HCl(aq). The precipitate was collected by filtration and purified by chromatography purified by chromatography (24 g reverse phase C18 cartridge, 15-80% MeCN/0.1% formic acid (aq)) to afford the title compound (100 mg, 0.230 mmol, 47% yield, 94% purity) as a white solid. UPLC-MS (Method 1): m/z 410.5 $(M+H)^+$, 408.3 $(M-H)^-$, at 1.66 min. $^1H$ NMR (500 MHz, DMSO-$d_6$) δ 13.75 (br s, 1H), 8.47 (s, 1H), 8.37-8.31 (m, 2H), 7.83 (dd, J=8.7, 2.1 Hz, 1H), 7.71 (d, J=2.1 Hz, 1H), 7.27 (d, J=8.7 Hz, 1H), 5.65 (d, J=2.9 Hz, 1H), 4.41 (d, J=2.9 Hz, 1H), 3.23-3.10 (m, 4H), 1.50-1.38 (m, 6H).

Biological Investigations

The following assays can be used to illustrate the commercial utilities of the compounds according to the present invention.

Biological Assay 1: ERAP1 Mediated Hydrolysis of an Amide Substrate Measured in a Biochemical System Materials and Solutions 1× Assay buffer (AB): 25 mM Bis-tris propane, 0.05% w/v Hydroxypropylmethylcellulose pH 7.75 made with Optima grade water Decapeptide WRVYEKC(Dnp)ALK-acid (where Dnp is Dinitrophenyl maleimide) (10-mer) L-Leucine 7-amido-4-methylcoumarin (L-AMC)

Purified ERAP1 (37-941)-10His (ERAP1)

Assay Procedure:

12.5 μL ERAP1 enzyme in 1×AB was combined with 250 nL test compound in DMSO. 12.5 μL of either 240 UM L-AMC in 1×AB or 100 UM 10-mer in 1×AB was added to the reaction and incubated at 23° C. for 1 h. For detection, plates were read at excitation 365 nm and emission 442 nm (L-AMC) or excitation 279 nm and emission 355 nm (10-mer). Compound $IC_{50}$ was determined using a 4 parameter equation. The results for selected compounds according to the invention are shown in Table 1.

OVA Antigen Presentation Assay

The cellular effect of representative compounds according to the invention on antigen presentation was measured by assessing their effect on the presentation of an ovalbumin-specific peptide (SIINFEKL) to T-cells, as previously described [Reeves et al, (2014) *Proc. Natl. Acad. Sci. USA* 111; 17594-17599]. Briefly, SiHa cells were transiently transfected with plasmids encoding mouse H2Kb and an ER-targeted N-terminally extended precursor peptide derived from ovalbumin (MRYMILGLLALAAVCSAAIVMKSIINFEHL) using Lipofectamine 3000. The cells were harvested 6 h post-transfection and transfected SiHa cells were plated compounds across a 12-point concentration response curve to quantify ERAP1 inhibitor $IC_{50}$. SiHa cells were cultured in the presence of compound for 48 h. Subsequently, B3Z cells [Karttunen et al, (1992) *Proc. Natl. Acad. Sci. USA* 89; 6020-6024] were added to the cell culture for 4 h; the B3Z T-cell hybridoma encodes a TCR recognizing specifically the SIINFEHL/H2Kb complex at the cell surface, which upon activation, triggers a signalling cascade leading to the transcription of the LacZ gene that is under the control of the IL-2 promoter. Intracellular β-galactosidase activity as a readout of T-cell activation was measured by quantifying the conversion of chlorophenored-β-D-galacto-pyrannoside (CPRG) to chlorophenol red by measuring absorbance at 570 nm.

Representative $IC_{50}$ curve for exemplar compounds according to the invention are shown in FIG. 1. Data was normalized to the signal obtained in the absence of compound (high) and absence of antigen (low) and presented as the mean±STD (n=2). FIG. 2 shows a summary of the $IC_{50}$ data generated for exemplar compounds according to the invention. The data is presented as the mean±SEM (n=6).

Immunopeptidomics

The effect of representative compounds according to the invention on global antigen processing was determined using an unbiased proteomics pipeline as described by Purcell and colleagues [Purcell et al, (2019) Nat Protoc. 14; 1687-1707]. Briefly, 500 million SiHa cells were treated with compound for 24 h or siRNA for 72 hours and then harvested, lysed and MHC-bound peptides isolated by immunoaffinity capture. The peptides were eluted using 10% (v/v) acetic acid and separated from the MHC-1 and B2-microglobulin proteins by HPLC before analysis by LC-MS/MS. Representative results are shown in FIG. 3, which demonstrates the comparable effects of ERAP1 siRNA and compound inhibition on the immunopeptidome (and hence antigen presentation) of SiHa cells. ERAP1 knockdown impacts the length of antigens presented on MHC Class I, reducing the total proportion of 8 and 9 amino acid peptides but increasing the number of 10, 11, 12 and 13 amino acid peptides. 10 μM of compound led to greater effects on antigen peptide length compared with 1 μM.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

Activity of selected compounds according to the invention

| | |
|---|---|
| 1 | High |
| 3 | High |
| 4 | High |
| 6 | High |
| 7 | Medium |
| 8 | Low |
| 9 | High |
| 10 | High |
| 11 | Medium |
| 12 | High |
| 13 | High |
| 14 | High |
| 15 | High |
| 16 | High |
| 17 | Low |
| 18 | Medium |
| 19 | Medium |
| 20 | Medium |
| 21 | Low |
| 22 | Low |
| 23 | Low |
| 24 | High |
| 25 | Medium |
| 26 | High |
| 27 | Medium |
| 28 | High |
| 29 | High |
| 30 | High |
| 31 | High |
| 32 | High |
| 33 | High |
| 34 | Low |
| 35 | High |
| 36 | Medium |
| 37 | Medium |
| 39 | Medium |
| 40 | Medium |
| 41 | High |
| 42 | Low |
| 43 | High |
| 46 | Medium |
| 49 | High |
| 51 | High |
| 52 | Medium |
| 54 | High |
| 55 | High |
| 59 | High |
| 61 | Low |
| 62 | High |
| 63 | Medium |
| 64 | High |
| 65 | High |
| 66 | High |
| 67 | High |
| 68 | High |

TABLE 1-continued

| Activity of selected compounds according to the invention | |
|---|---|
| 69 | High |
| 70 | Medium |
| 71 | High |
| 72 | High |
| 73 | High |
| 74 | High |
| 75 | Medium |
| 77 | Medium |
| 78 | Medium |
| 80 | Medium |
| 83 | Medium |
| 84 | Medium |
| 86 | High |
| 161 | High |
| 165 | Medium |
| 171 | Medium |
| 177 | High |
| 178 | Medium |
| 179 | High |
| 180 | High |
| 181 | High |
| 182 | High |
| 183 | Low |
| 184 | High |
| 185 | High |
| 186 | High |
| 187 | Medium |
| 188 | Medium |
| 189 | Low |
| 190 | Medium |
| 200 | Medium |
| 201 | High |
| 202 | High |
| 203 | High |
| 204 | High |
| 205 | High |
| 206 | High |
| 207 | High |
| 208 | High |
| 209 | High |
| 210 | High |
| 211 | High |
| 212 | High |
| 213 | High |
| 214 | High |
| 215 | High |
| 216 | High |
| 217 | High |
| 218 | High |
| 219 | High |
| 220 | High |
| 221 | High |
| 222 | High |
| 223 | High |
| 224 | High |
| 225 | Low |
| 227 | Medium |
| 228 | High |
| 229 | High |
| 230 | High |
| 231 | High |
| 232 | High |
| 233 | High |
| 234 | High |
| 235 | High |
| 236 | High |
| 237 | High |
| 238 | High |
| 239 | High |
| 240 | High |
| 241 | High |
| 242 | High |
| 243 | High |
| 244 | High |
| 245 | High |
| 246 | High |
| 247 | High |
| 248 | High |

TABLE 1-continued

| Activity of selected compounds according to the invention | |
|---|---|
| 249 | High |
| 250 | High |
| 251 | High |
| 252 | High |
| 253 | High |
| 254 | High |
| 255 | Medium |
| 257 | High |
| 258 | High |
| 259 | High |
| 260 | High |
| 261 | High |
| 262 | High |
| 263 | High |
| 264 | High |
| 265 | High |
| 266 | High |
| 267 | High |
| 268 | High |
| 269 | High |
| 270 | Medium |
| 271 | Medium |
| 272 | High |
| 273 | High |
| 274 | High |
| 275 | High |
| 276 | High |
| 277 | High |
| 278 | High |
| 279 | High |
| 280 | High |
| 281 | High |
| 282 | High |
| 283 | High |
| 286 | High |
| 287 | High |
| 288 | High |
| 289 | High |
| 290 | High |
| 291 | High |
| 292 | High |
| 293 | High |
| 294 | High |
| 295 | High |
| 296 | High |
| 297 | High |
| 298 | High |
| 299 | High |
| 300 | High |
| 301 | High |
| 302 | High |
| 303 | High |
| 304 | High |
| 305 | High |
| 306 | High |
| 308 | High |
| 309 | High |
| 310 | High |
| 311 | High |
| 312 | High |
| 313 | High |
| 314 | High |
| 315 | High |
| 316 | High |
| 317 | High |
| 318 | High |
| 319 | High |
| 320 | High |
| 321 | High |
| 322 | High |
| 323 | High |
| 324 | High |
| 325 | High |
| 326 | High |
| 327 | High |
| 328 | High |
| 329 | High |
| 330 | High |

TABLE 1-continued
| Activity of selected compounds according to the invention | |
|---|---|
| 331 | High |
| 332 | High |
| 333 | High |
| 334 | High |
| 335 | High |
| 336 | High |
| 337 | Medium |
| 338 | Low |
$IC_{50}$ vs Decapeptide WRVYEKC(Dnp)ALK-acid (where Dnp is Dinitrophenyl maleimide) (10-mer); High (<500 nM), Medium (<5 μM), Low (>5 μM).
TABLE 2
Structures of compounds according to the invention
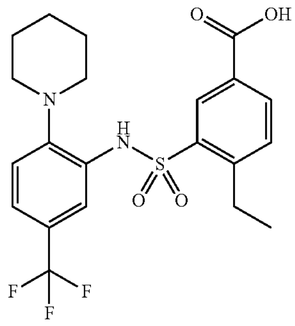
(1)
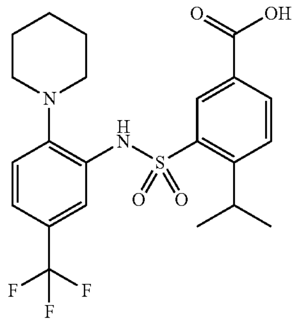
(3)
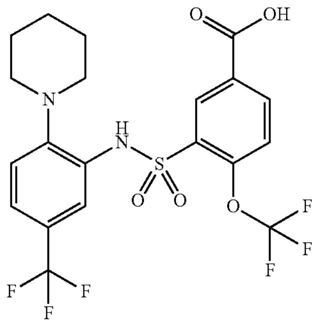 [SMILES: O=C(O)c1ccc(OC(F)(F)F)c(S(=O)(=O)Nc2cc(C(F)(F)F)ccc2N2CCCCC2)c1]
(4)
TABLE 2-continued
Structures of compounds according to the invention
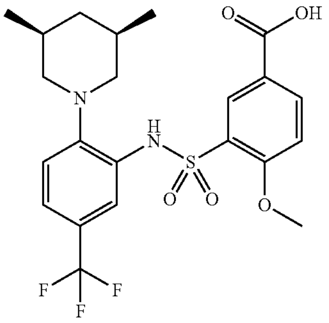
(6)
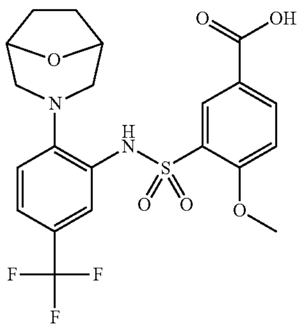 [SMILES: COc1ccc(C(=O)O)cc1S(=O)(=O)Nc1cc(C(F)(F)F)ccc1N1CC2CCC(C1)O2]
(7)
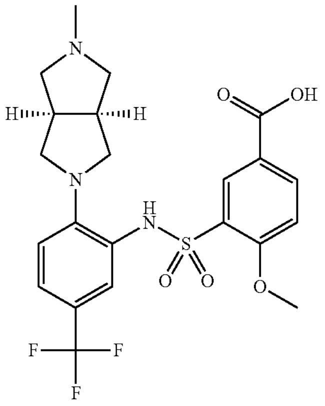 [SMILES: COc1ccc(C(=O)O)cc1S(=O)(=O)Nc1cc(C(F)(F)F)ccc1N1C[C@H]2CN(C)C[C@H]2C1]
(8)
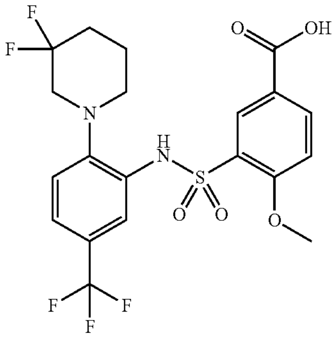 [SMILES: COc1ccc(C(=O)O)cc1S(=O)(=O)Nc1cc(C(F)(F)F)ccc1N1CCCC(F)(F)C1]
(9)

TABLE 2-continued
| Structures of compounds according to the invention |
|---|
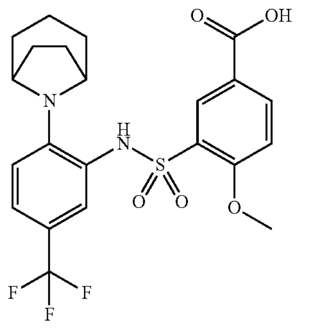
(10)
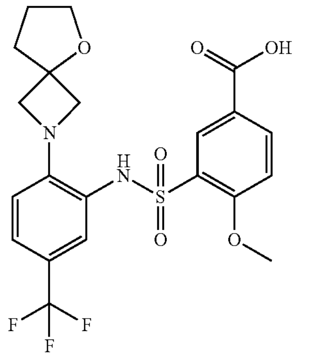
(11)
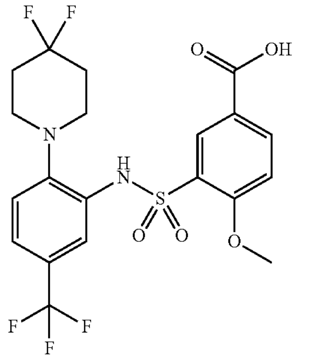
(12)
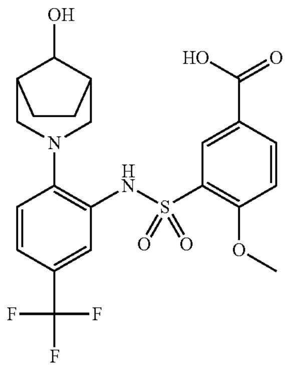 [SMILES: COc1ccc(C(=O)O)cc1S(=O)(=O)Nc1cc(C(F)(F)F)ccc1N1CC2CCC(C1)C2O]
(13)
TABLE 2-continued
| Structures of compounds according to the invention |
|---|
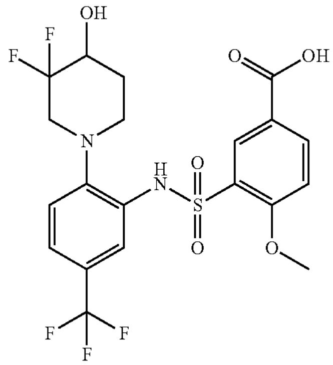
(14)
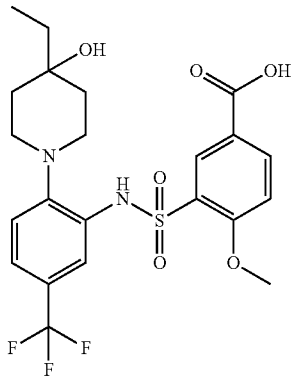
(15)
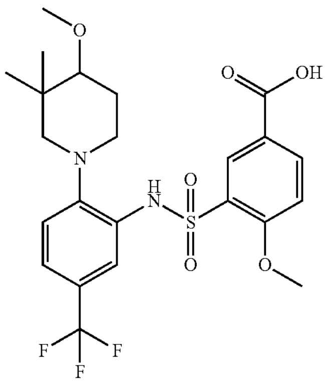
(16)
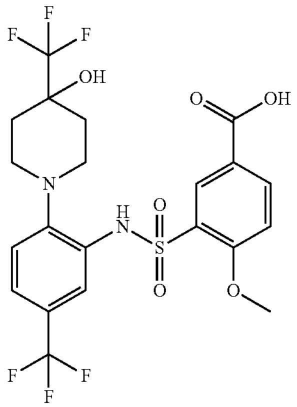 [SMILES: COc1ccc(C(=O)O)cc1S(=O)(=O)Nc1cc(C(F)(F)F)ccc1N1CCC(O)(C(F)(F)F)CC1]
(17)

TABLE 2-continued
Structures of compounds according to the invention
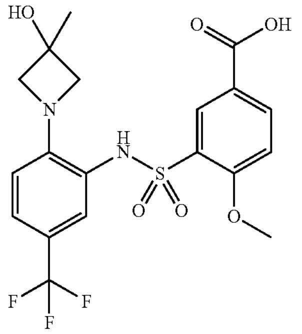 [SMILES: COc1ccc(C(=O)O)cc1S(=O)(=O)Nc1cc(C(F)(F)F)ccc1N1CC(C)(O)C1]
(18)
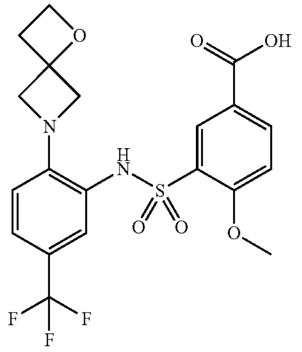
(19)
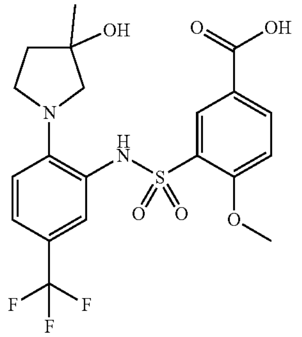 [SMILES: COc1ccc(C(=O)O)cc1S(=O)(=O)Nc1cc(C(F)(F)F)ccc1N1CCC(C)(O)C1]
(20)
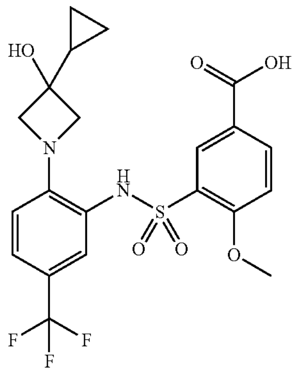 [SMILES: COc1ccc(C(=O)O)cc1S(=O)(=O)Nc1cc(C(F)(F)F)ccc1N1CC(O)(C2CC2)C1]
(21)
TABLE 2-continued
Structures of compounds according to the invention
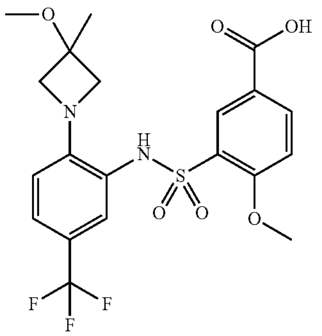
(22)
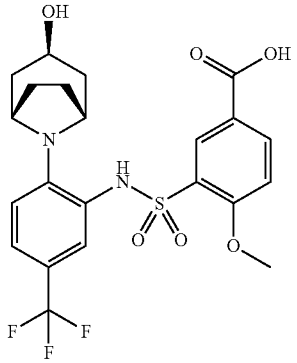 [SMILES: COc1ccc(C(=O)O)cc1S(=O)(=O)Nc1cc(C(F)(F)F)ccc1N1[C@@H]2CC[C@H]1C[C@@H](O)C2]
(23)
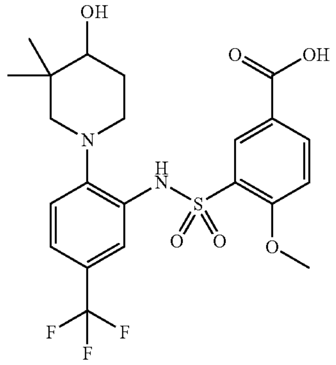 [SMILES: COc1ccc(C(=O)O)cc1S(=O)(=O)Nc1cc(C(F)(F)F)ccc1N1CCC(O)C(C)(C)C1]
(24)
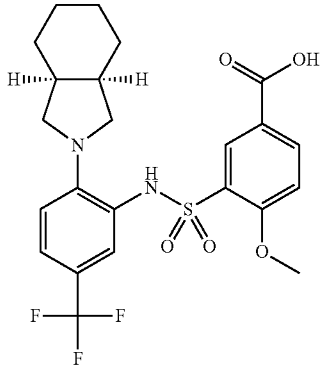 [SMILES: COc1ccc(C(=O)O)cc1S(=O)(=O)Nc1cc(C(F)(F)F)ccc1N1C[C@H]2CCCC[C@H]2C1]
(25)

TABLE 2-continued
| Structures of compounds according to the invention |
|---|
| 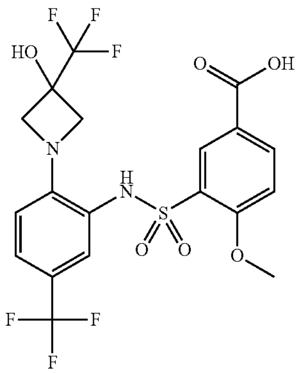 (26) |
| 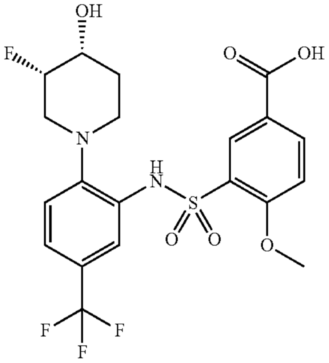 (27) |
| 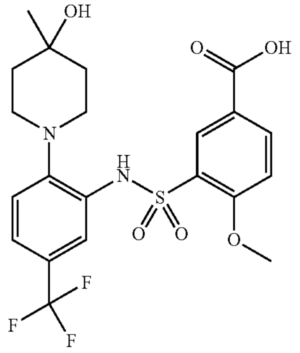 [SMILES: COc1ccc(C(=O)O)cc1S(=O)(=O)Nc1cc(C(F)(F)F)ccc1N1CCC(C)(O)CC1] (28) |
| 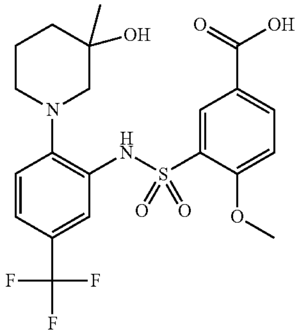 (29) |
TABLE 2-continued
| Structures of compounds according to the invention |
|---|
| 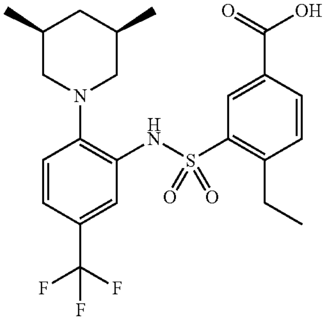 [SMILES: CCc1ccc(C(=O)O)cc1S(=O)(=O)Nc1cc(C(F)(F)F)ccc1N1C[C@H](C)C[C@H](C)C1] (30) |
| 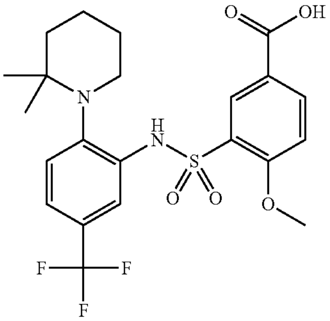 (31) |
| 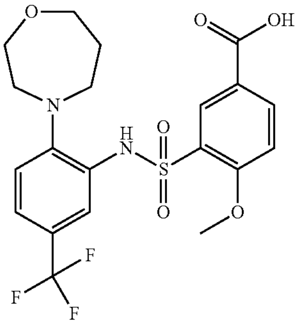 [SMILES: COc1ccc(C(=O)O)cc1S(=O)(=O)Nc1cc(C(F)(F)F)ccc1N1CCCOCC1] (32) |
| 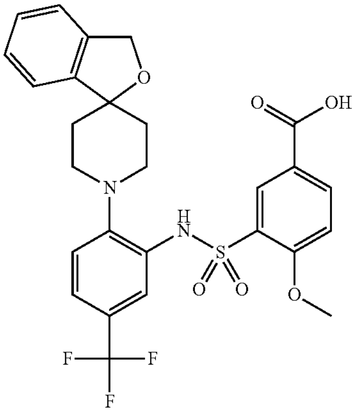 [SMILES: COc1ccc(C(=O)O)cc1S(=O)(=O)Nc1cc(C(F)(F)F)ccc1N1CCC2(CC1)OCc1ccccc12] (33) |

TABLE 2-continued
| Structures of compounds according to the invention |
| --- |
| 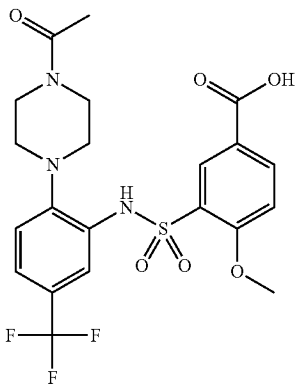 [SMILES: COc1ccc(C(=O)O)cc1S(=O)(=O)Nc1cc(C(F)(F)F)ccc1N1CCN(C(C)=O)CC1] (34) |
| 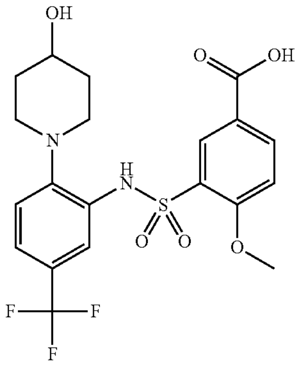 (35) |
| 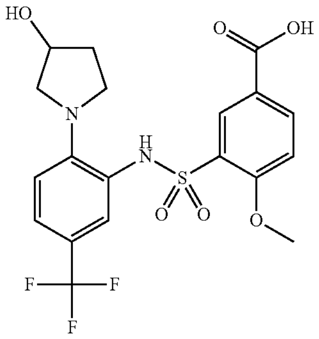 [SMILES: COc1ccc(C(=O)O)cc1S(=O)(=O)Nc1cc(C(F)(F)F)ccc1N1CCC(O)C1] (36) |
| 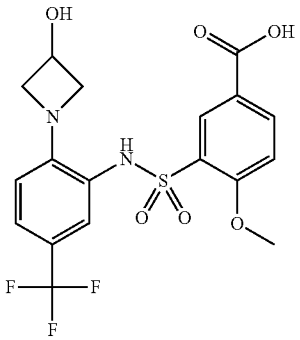 (37) |
TABLE 2-continued
| Structures of compounds according to the invention |
| --- |
| 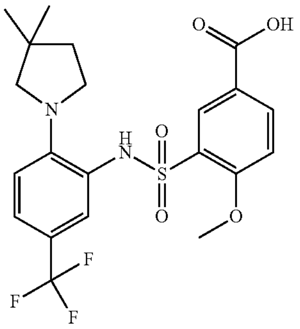 [SMILES: COc1ccc(C(=O)O)cc1S(=O)(=O)Nc1cc(C(F)(F)F)ccc1N1CCC(C)(C)C1] (39) |
| 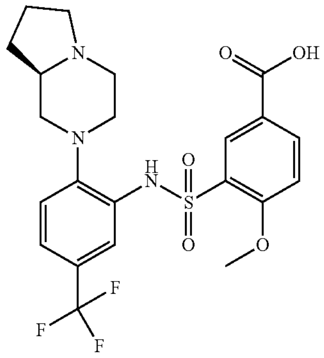 [SMILES: COc1ccc(C(=O)O)cc1S(=O)(=O)Nc1cc(C(F)(F)F)ccc1N1CCN2CCC[C@@H]2C1] (40) |
| 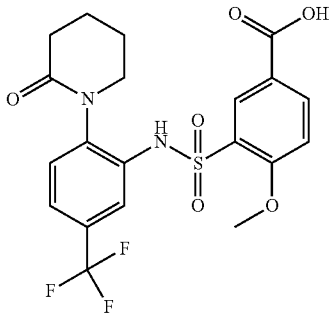 [SMILES: COc1ccc(C(=O)O)cc1S(=O)(=O)Nc1cc(C(F)(F)F)ccc1N1CCCCC1=O] (41) |
| 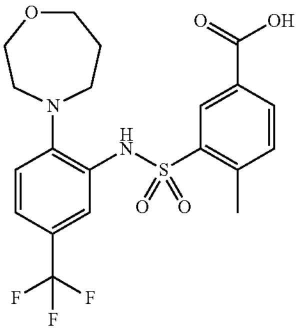 [SMILES: Cc1ccc(C(=O)O)cc1S(=O)(=O)Nc1cc(C(F)(F)F)ccc1N1CCCOCC1] (42) |

TABLE 2-continued
Structures of compounds according to the invention
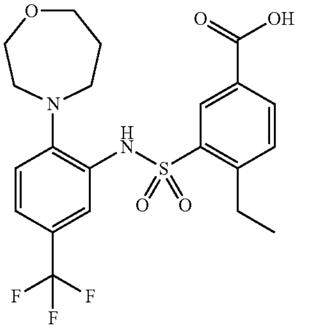
(43)
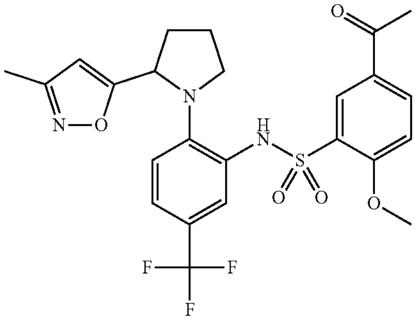
(46)
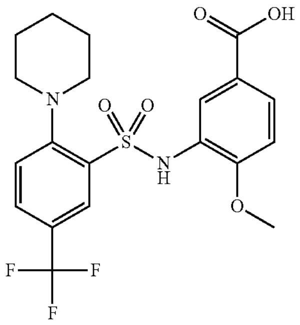
(49)
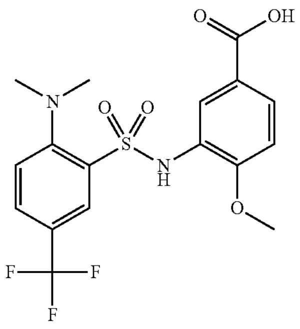
(51)
TABLE 2-continued
Structures of compounds according to the invention
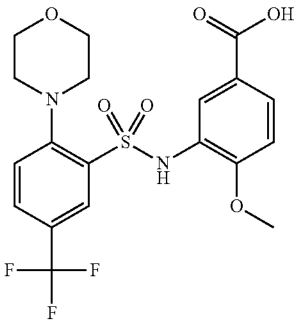
(52)
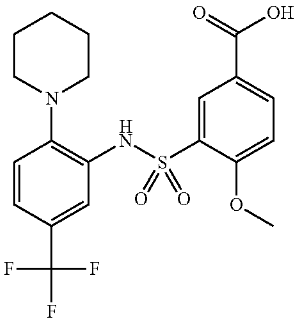 [SMILES: COc1ccc(C(=O)O)cc1S(=O)(=O)Nc1cc(C(F)(F)F)ccc1N1CCCCC1]
(54)
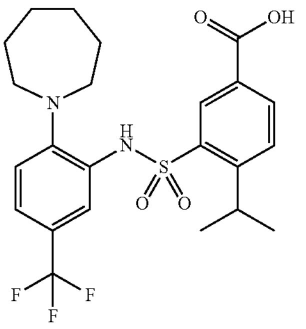 [SMILES: CC(C)c1ccc(C(=O)O)cc1S(=O)(=O)Nc1cc(C(F)(F)F)ccc1N1CCCCCC1]
(55)
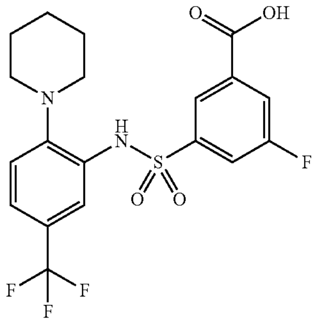 [SMILES: O=C(O)c1cc(F)cc(S(=O)(=O)Nc2cc(C(F)(F)F)ccc2N2CCCCC2)c1]
(59)

TABLE 2-continued
Structures of compounds according to the invention
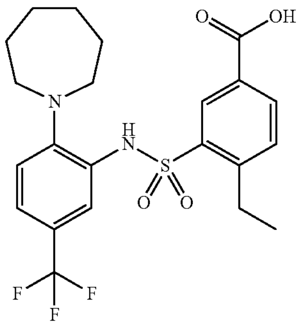 [SMILES: CCc1ccc(C(=O)O)cc1S(=O)(=O)Nc1cc(C(F)(F)F)ccc1N1CCCCCC1]
(61)
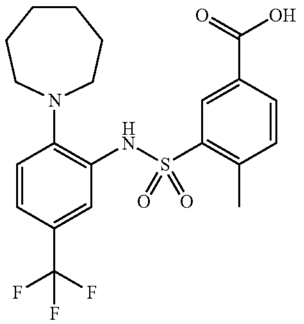 [SMILES: Cc1ccc(C(=O)O)cc1S(=O)(=O)Nc1cc(C(F)(F)F)ccc1N1CCCCCC1]
(62)
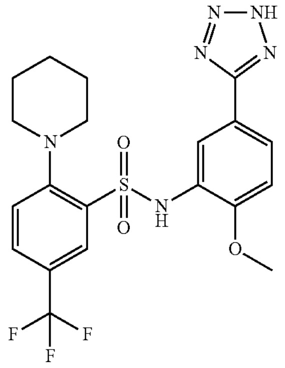 [SMILES: COc1ccc(-c2nn[nH]n2)cc1NS(=O)(=O)c1cc(C(F)(F)F)ccc1N1CCCCC1]
(63)
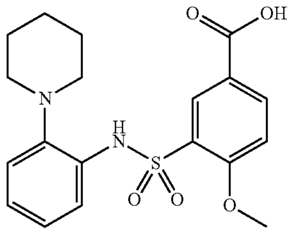 [SMILES: COc1ccc(C(=O)O)cc1S(=O)(=O)Nc1ccccc1N1CCCCC1]
(64)
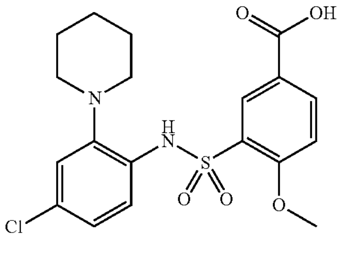 [SMILES: COc1ccc(C(=O)O)cc1S(=O)(=O)Nc1ccc(Cl)cc1N1CCCCC1]
(65)
TABLE 2-continued
Structures of compounds according to the invention
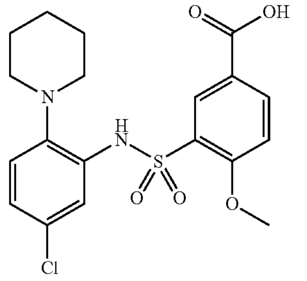 [SMILES: COc1ccc(C(=O)O)cc1S(=O)(=O)Nc1cc(Cl)ccc1N1CCCCC1]
(66)
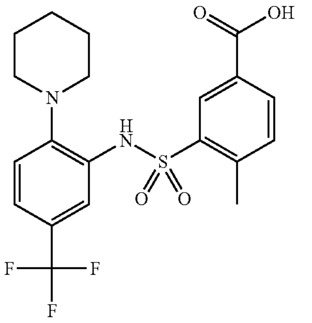
(67)
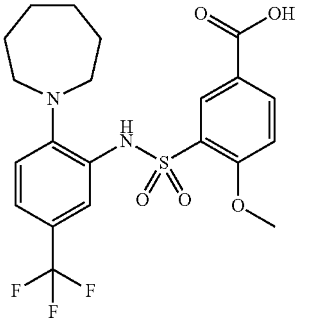 [SMILES: COc1ccc(C(=O)O)cc1S(=O)(=O)Nc1cc(C(F)(F)F)ccc1N1CCCCCC1]
(68)
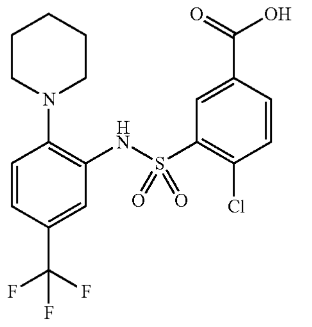
(69)
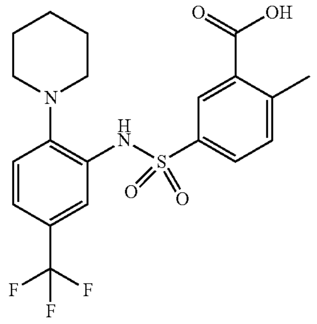 [SMILES: Cc1ccc(S(=O)(=O)Nc2cc(C(F)(F)F)ccc2N2CCCCC2)cc1C(=O)O]
(70)

TABLE 2-continued
| Structures of compounds according to the invention |
| --- |
| 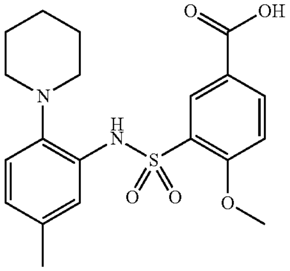 [SMILES: COc1ccc(C(=O)O)cc1S(=O)(=O)Nc1cc(C)ccc1N1CCCCC1] (71) |
| 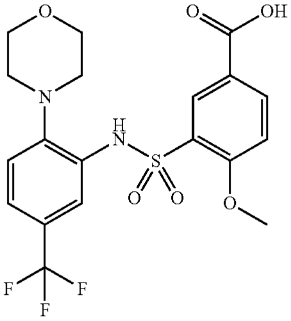 (72) |
| 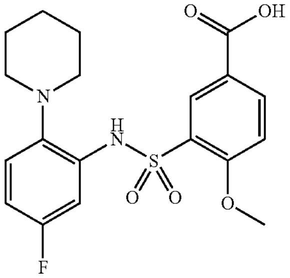 [SMILES: COc1ccc(C(=O)O)cc1S(=O)(=O)Nc1cc(F)ccc1N1CCCCC1] (73) |
| 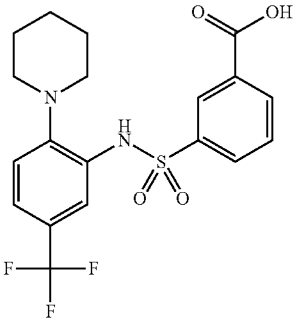 [SMILES: O=C(O)c1cccc(S(=O)(=O)Nc2cc(C(F)(F)F)ccc2N2CCCCC2)c1] (74) |
| 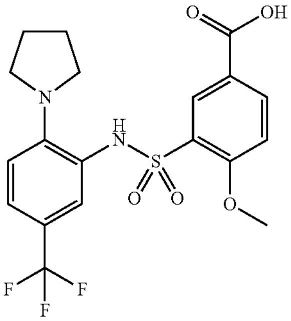 [SMILES: COc1ccc(C(=O)O)cc1S(=O)(=O)Nc1cc(C(F)(F)F)ccc1N1CCCC1] (75) |
TABLE 2-continued
| Structures of compounds according to the invention |
| --- |
| 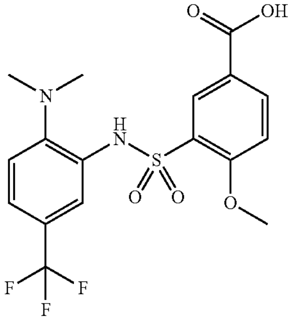 [SMILES: COc1ccc(C(=O)O)cc1S(=O)(=O)Nc1cc(C(F)(F)F)ccc1N(C)C] (77) |
| 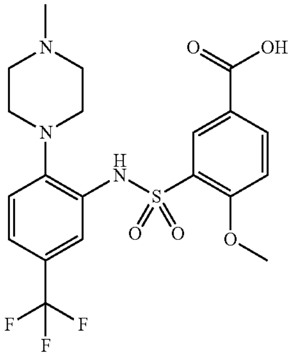 (78) |
| 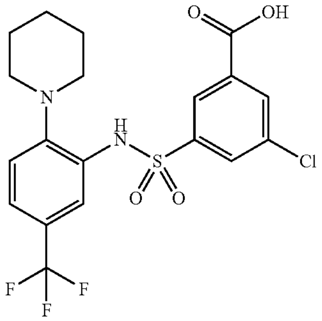 [SMILES: O=C(O)c1cc(Cl)cc(S(=O)(=O)Nc2cc(C(F)(F)F)ccc2N2CCCCC2)c1] (80) |
| 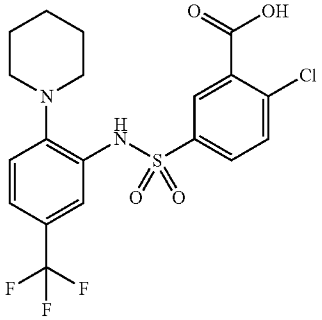 [SMILES: O=C(O)c1cc(S(=O)(=O)Nc2cc(C(F)(F)F)ccc2N2CCCCC2)ccc1Cl] (83) |

TABLE 2-continued
| Structures of compounds according to the invention |
|---|
| 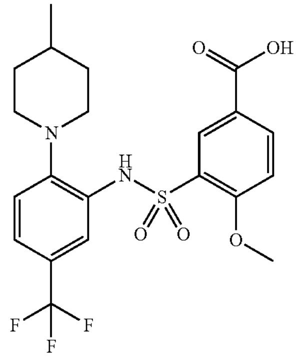 (84) |
| 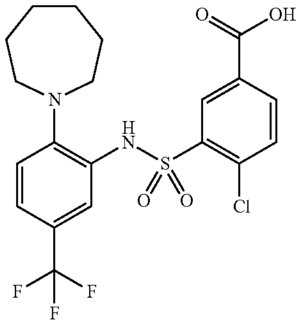 [SMILES: O=C(O)c1ccc(Cl)c(S(=O)(=O)Nc2cc(C(F)(F)F)ccc2N2CCCCCC2)c1] (86) |
| 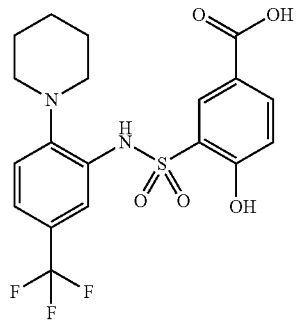 (161) |
| 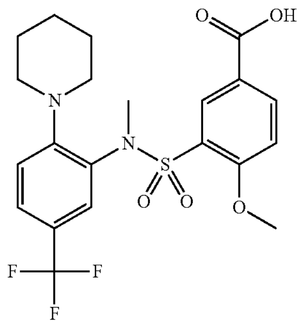 (165) |
TABLE 2-continued
| Structures of compounds according to the invention |
|---|
| 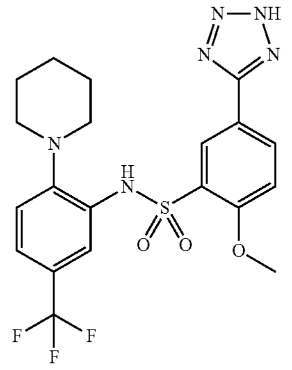 [SMILES: COc1ccc(-c2nn[nH]n2)cc1S(=O)(=O)Nc1cc(C(F)(F)F)ccc1N1CCCCC1] (171) |
| 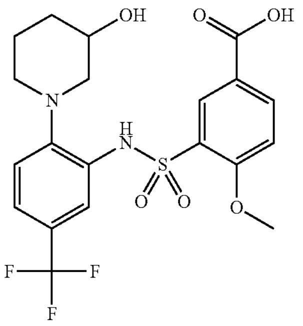 (177) |
| 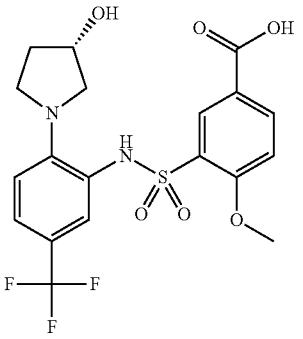 [SMILES: COc1ccc(C(=O)O)cc1S(=O)(=O)Nc1cc(C(F)(F)F)ccc1N1CC[C@H](O)C1] (178) |
| 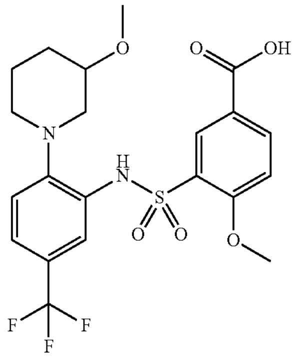 (179) |

TABLE 2-continued
| Structures of compounds according to the invention |
| --- |
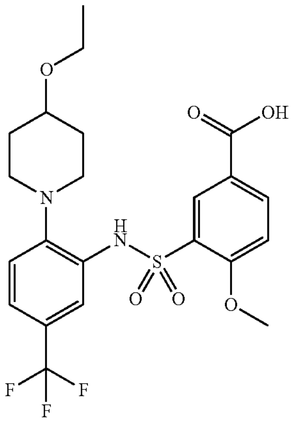
(180)
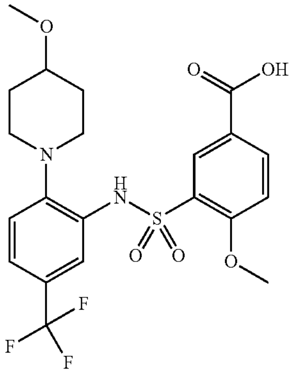
(181)
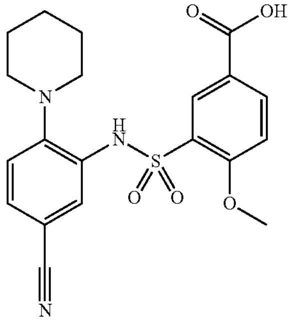
(182)
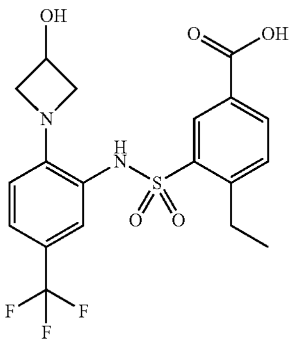
(183)
TABLE 2-continued
| Structures of compounds according to the invention |
| --- |
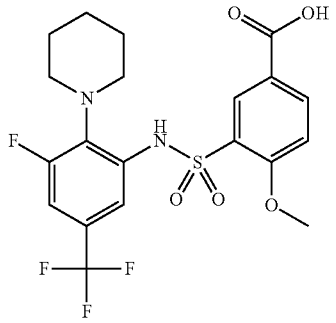 [SMILES: COc1ccc(C(=O)O)cc1S(=O)(=O)Nc1cc(C(F)(F)F)cc(F)c1N1CCCCC1]
(184)
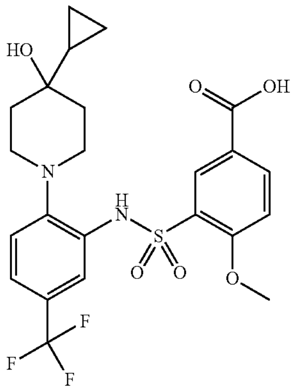 [SMILES: COc1ccc(C(=O)O)cc1S(=O)(=O)Nc1cc(C(F)(F)F)ccc1N1CCC(O)(C2CC2)CC1]
(185)
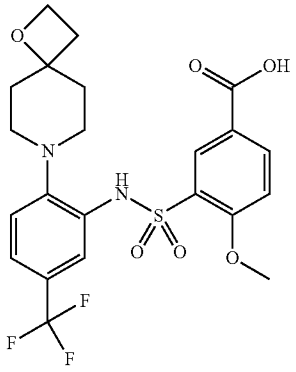
(186)
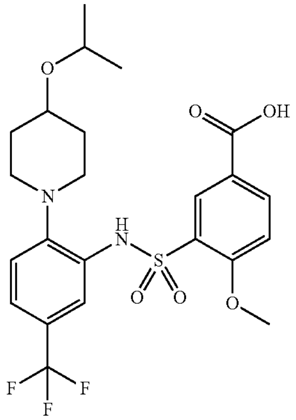
(187)

TABLE 2-continued
| Structures of compounds according to the invention |
|---|
| 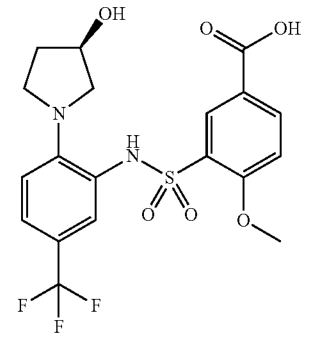 [SMILES: COc1ccc(C(=O)O)cc1S(=O)(=O)Nc1cc(C(F)(F)F)ccc1N1CC[C@@H](O)C1] (188) |
| 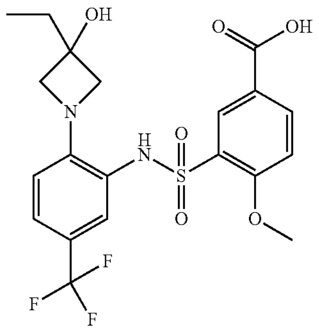 [SMILES: CCC1(O)CN(c2ccc(C(F)(F)F)cc2NS(=O)(=O)c2cc(C(=O)O)ccc2OC)C1] (189) |
| 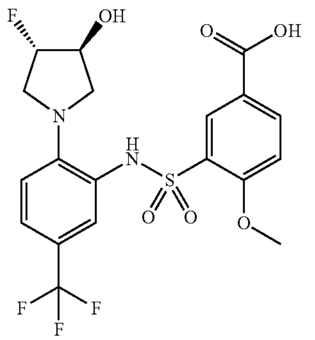 [SMILES: COc1ccc(C(=O)O)cc1S(=O)(=O)Nc1cc(C(F)(F)F)ccc1N1C[C@H](O)[C@@H](F)C1] (190) |
| 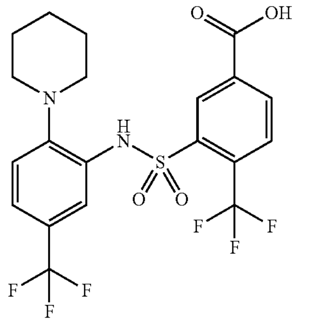 (200) |
TABLE 2-continued
| Structures of compounds according to the invention |
|---|
| 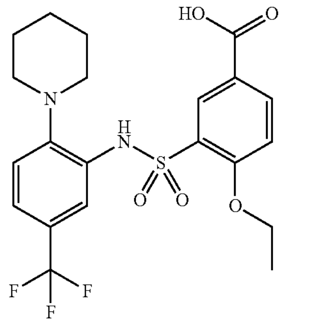 [SMILES: CCOc1ccc(C(=O)O)cc1S(=O)(=O)Nc1cc(C(F)(F)F)ccc1N1CCCCC1] (201) |
| 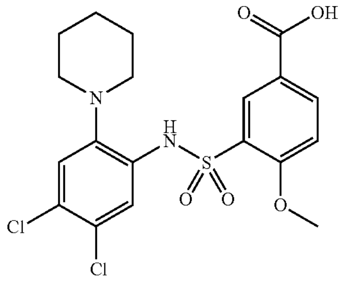 [SMILES: COc1ccc(C(=O)O)cc1S(=O)(=O)Nc1cc(Cl)c(Cl)cc1N1CCCCC1] (202) |
| 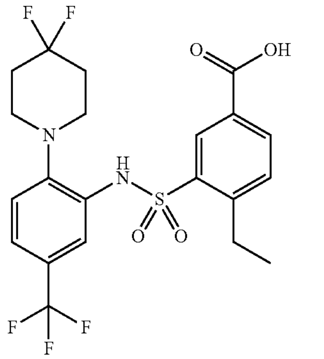 (203) |
| 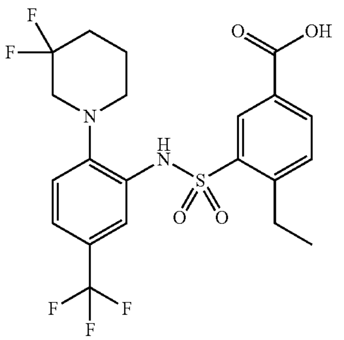 [SMILES: CCc1ccc(C(=O)O)cc1S(=O)(=O)Nc1cc(C(F)(F)F)ccc1N1CCCC(F)(F)C1] (204) |

TABLE 2-continued
| Structures of compounds according to the invention |
|---|
| 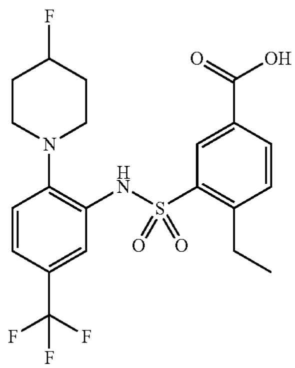 (205) |
| 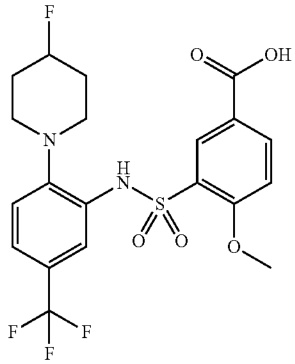 (206) |
| 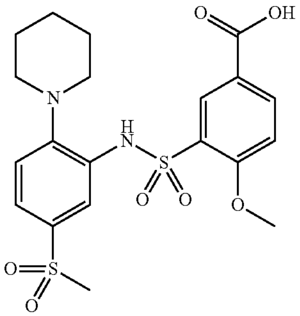 [SMILES: COc1ccc(C(=O)O)cc1S(=O)(=O)Nc1cc(S(C)(=O)=O)ccc1N1CCCCC1] (207) |
| 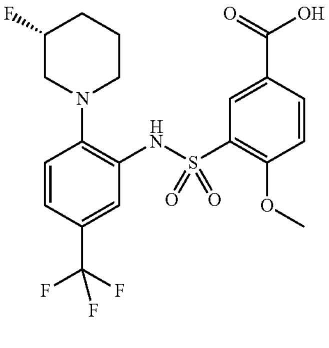 (208) |
TABLE 2-continued
| Structures of compounds according to the invention |
|---|
| 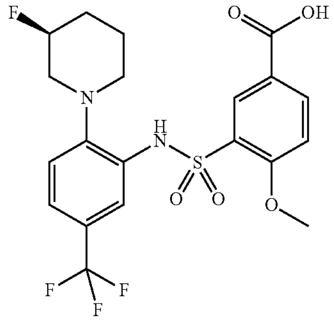 (209) |
| 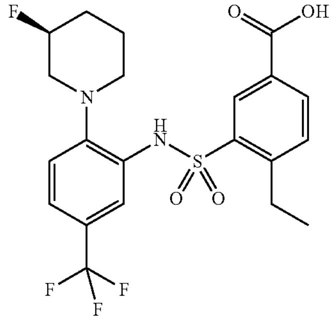 (210) |
| 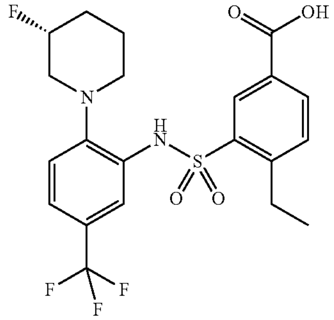 (211) |
| 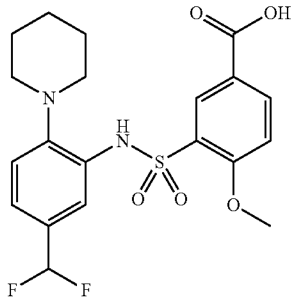 (212) |
| 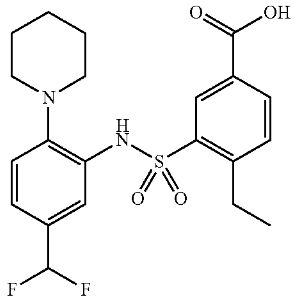 (213) |

TABLE 2-continued
| Structures of compounds according to the invention |
| --- |
| 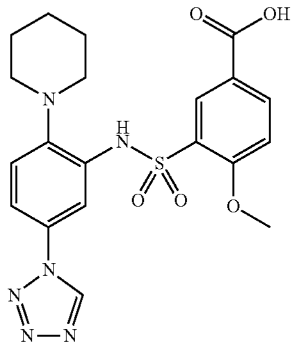 [SMILES: COc1ccc(C(=O)O)cc1S(=O)(=O)Nc1cc(-n2cnnn2)ccc1N1CCCCC1] (214) |
| 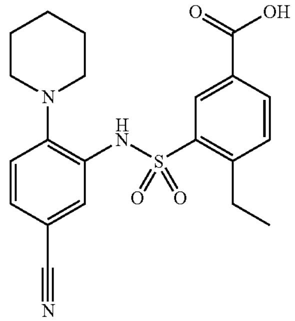 [SMILES: CCc1ccc(C(=O)O)cc1S(=O)(=O)Nc1cc(C#N)ccc1N1CCCCC1] (215) |
| 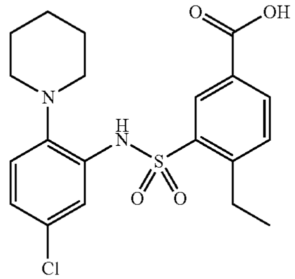 [SMILES: CCc1ccc(C(=O)O)cc1S(=O)(=O)Nc1cc(Cl)ccc1N1CCCCC1] (216) |
| 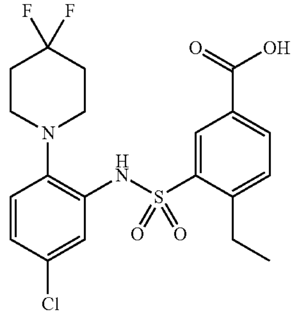 [SMILES: CCc1ccc(C(=O)O)cc1S(=O)(=O)Nc1cc(Cl)ccc1N1CCC(F)(F)CC1] (217) |
| 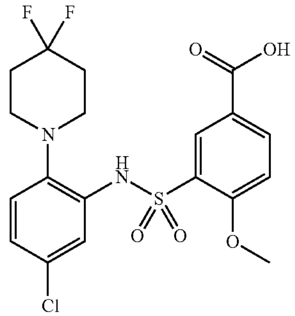 [SMILES: COc1ccc(C(=O)O)cc1S(=O)(=O)Nc1cc(Cl)ccc1N1CCC(F)(F)CC1] (218) |
TABLE 2-continued
| Structures of compounds according to the invention |
| --- |
| 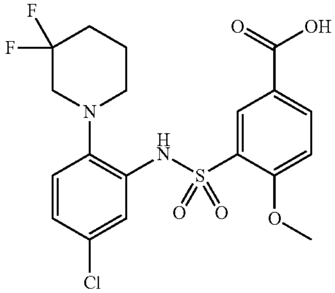 [SMILES: COc1ccc(C(=O)O)cc1S(=O)(=O)Nc1cc(Cl)ccc1N1CCCC(F)(F)C1] (219) |
| 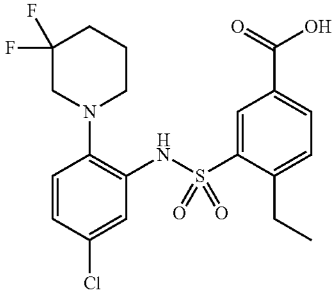 [SMILES: CCc1ccc(C(=O)O)cc1S(=O)(=O)Nc1cc(Cl)ccc1N1CCCC(F)(F)C1] (220) |
| 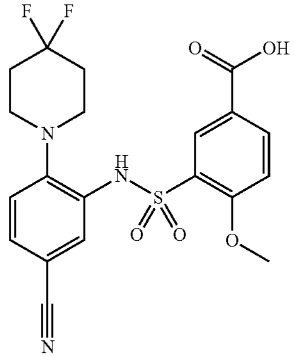 (221) |
| 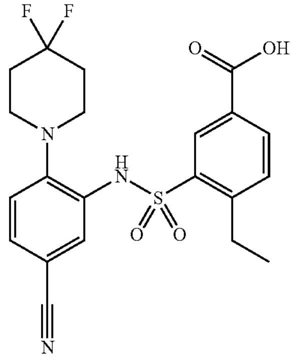 (222) |

TABLE 2-continued
| Structures of compounds according to the invention |
|---|
| 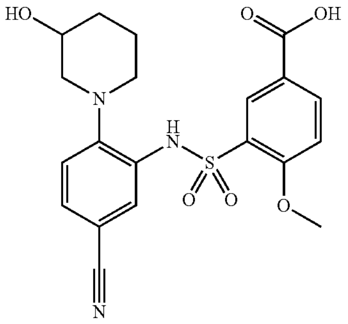 (223) |
| 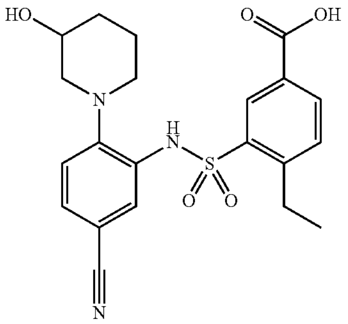 (224) |
| 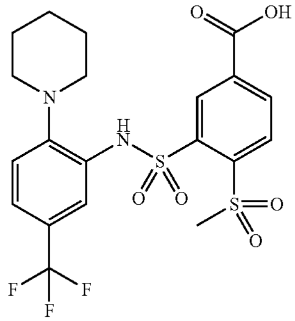 (225) |
| 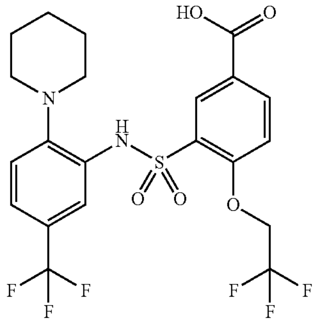 [SMILES: O=C(O)c1ccc(OCC(F)(F)F)c(S(=O)(=O)Nc2cc(C(F)(F)F)ccc2N2CCCCC2)c1] (227) |
TABLE 2-continued
| Structures of compounds according to the invention |
|---|
| 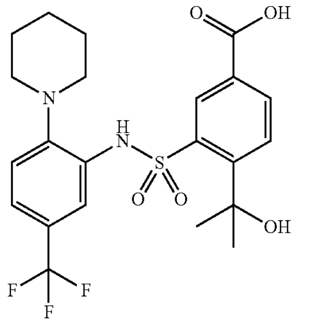 (228) |
| 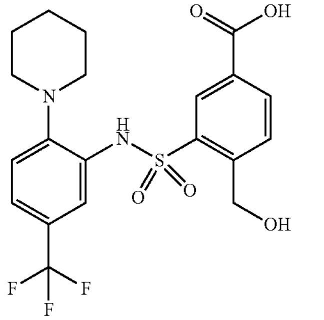 (229) |
| 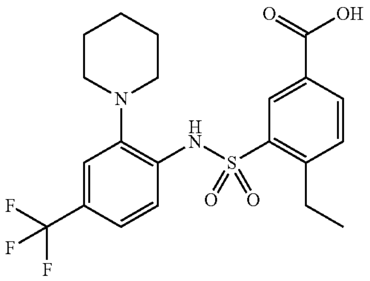 (230) |
| 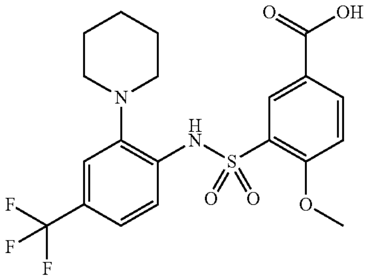 (231) |
| 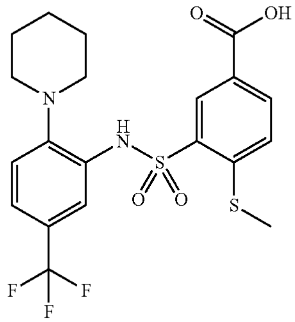 (232) |

TABLE 2-continued
| Structures of compounds according to the invention |
| --- |
| 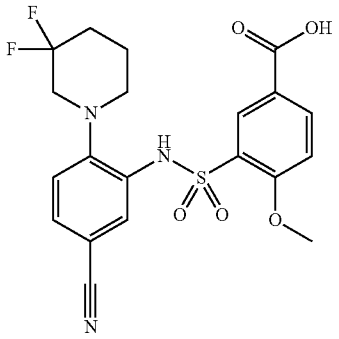 [SMILES: COc1ccc(C(=O)O)cc1S(=O)(=O)Nc1cc(C#N)ccc1N1CCCC(F)(F)C1] (233) |
| 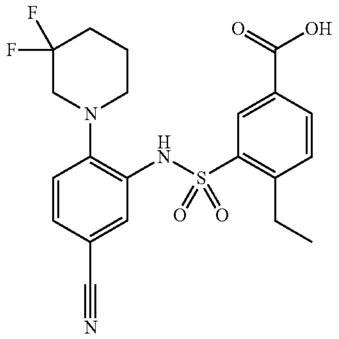 (234) |
| 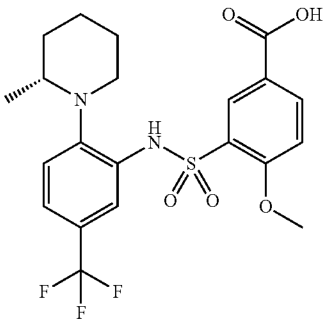 (235) |
| 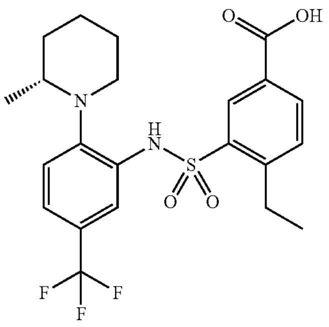 (236) |
TABLE 2-continued
| Structures of compounds according to the invention |
| --- |
| 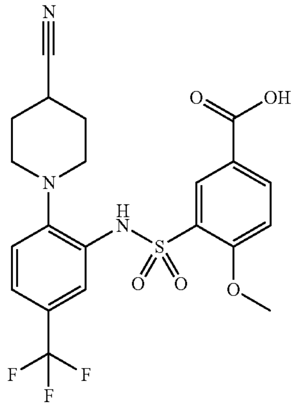 (237) |
| 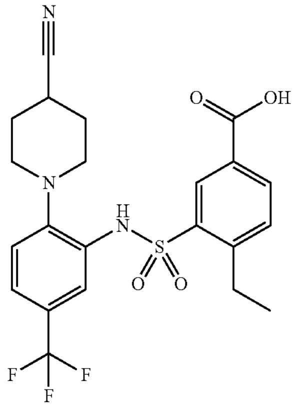 (238) |
| 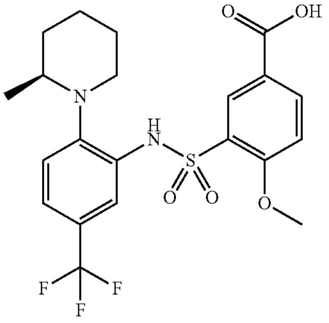 (239) |
| 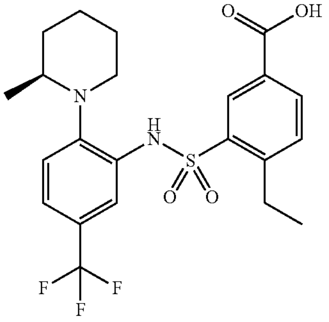 (240) |

TABLE 2-continued
| Structures of compounds according to the invention |
|---|
| 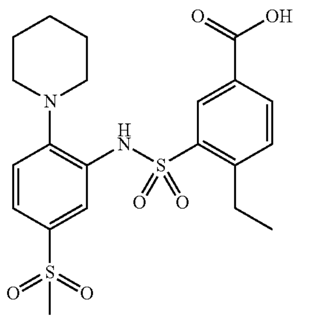 [SMILES: CCc1ccc(C(=O)O)cc1S(=O)(=O)Nc1cc(S(C)(=O)=O)ccc1N1CCCCC1] (241) |
| 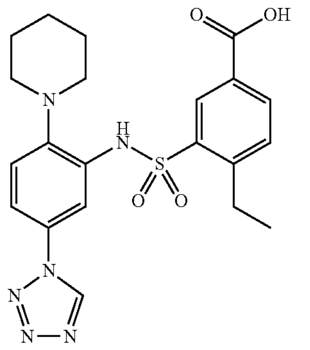 [SMILES: CCc1ccc(C(=O)O)cc1S(=O)(=O)Nc1cc(-n2cnnn2)ccc1N1CCCCC1] (242) |
| 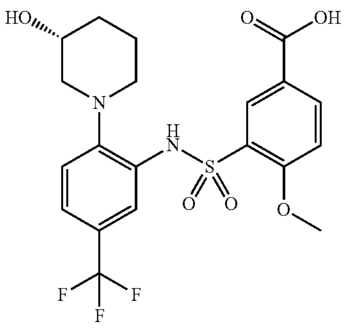 [SMILES: COc1ccc(C(=O)O)cc1S(=O)(=O)Nc1cc(C(F)(F)F)ccc1N1CCC[C@@H](O)C1] (243) |
| 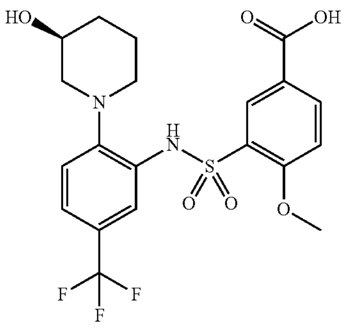 [SMILES: COc1ccc(C(=O)O)cc1S(=O)(=O)Nc1cc(C(F)(F)F)ccc1N1CCC[C@H](O)C1] (244) |
TABLE 2-continued
| Structures of compounds according to the invention |
|---|
| 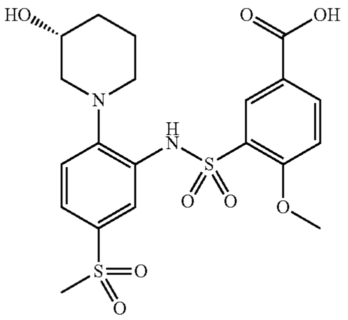 [SMILES: COc1ccc(C(=O)O)cc1S(=O)(=O)Nc1cc(S(C)(=O)=O)ccc1N1CCC[C@@H](O)C1] (245) |
| 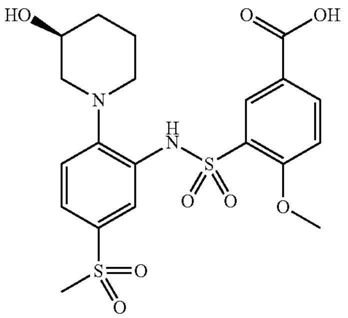 [SMILES: COc1ccc(C(=O)O)cc1S(=O)(=O)Nc1cc(S(C)(=O)=O)ccc1N1CCC[C@H](O)C1] (246) |
| 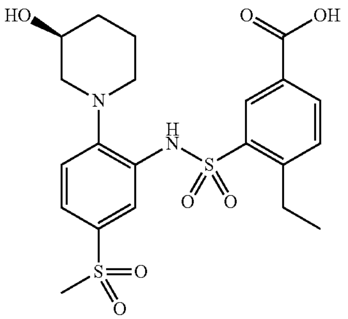 [SMILES: CCc1ccc(C(=O)O)cc1S(=O)(=O)Nc1cc(S(C)(=O)=O)ccc1N1CCC[C@H](O)C1] (247) |
| 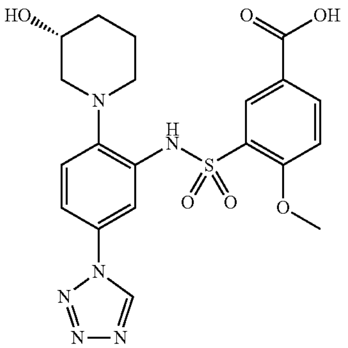 [SMILES: COc1ccc(C(=O)O)cc1S(=O)(=O)Nc1cc(-n2cnnn2)ccc1N1CCC[C@@H](O)C1] (248) |

TABLE 2-continued
Structures of compounds according to the invention
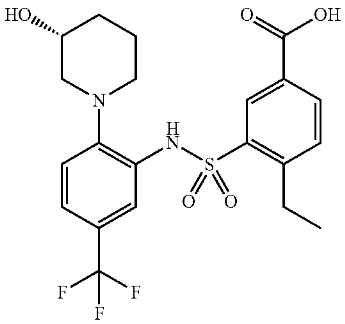 [SMILES: CCc1ccc(C(=O)O)cc1S(=O)(=O)Nc1cc(C(F)(F)F)ccc1N1CCC[C@@H](O)C1]
(249)
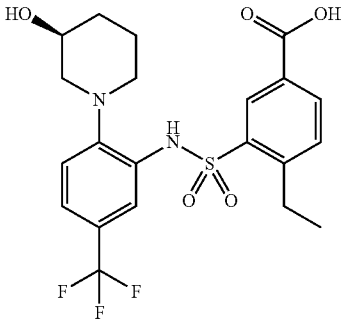 [SMILES: CCc1ccc(C(=O)O)cc1S(=O)(=O)Nc1cc(C(F)(F)F)ccc1N1CCC[C@H](O)C1]
(250)
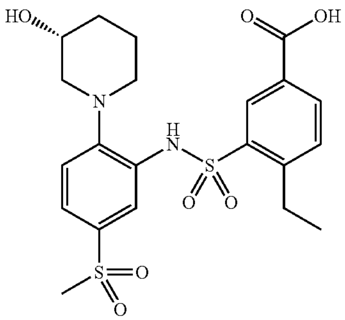 [SMILES: CCc1ccc(C(=O)O)cc1S(=O)(=O)Nc1cc(S(C)(=O)=O)ccc1N1CCC[C@@H](O)C1]
(251)
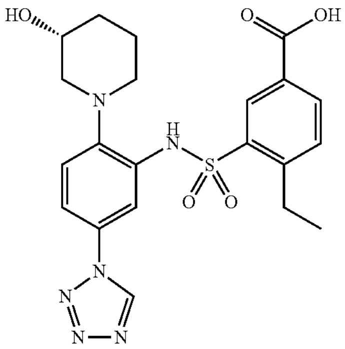 [SMILES: CCc1ccc(C(=O)O)cc1S(=O)(=O)Nc1cc(-n2cnnn2)ccc1N1CCC[C@@H](O)C1]
(252)
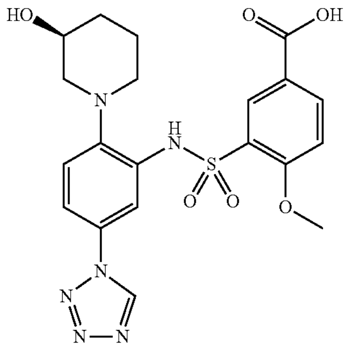 [SMILES: COc1ccc(C(=O)O)cc1S(=O)(=O)Nc1cc(-n2cnnn2)ccc1N1CCC[C@H](O)C1]
(253)
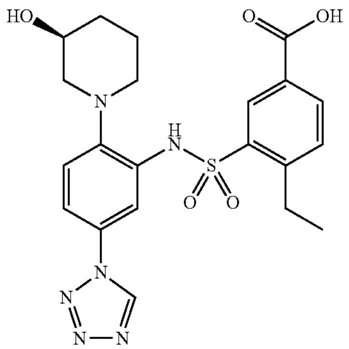 [SMILES: CCc1ccc(C(=O)O)cc1S(=O)(=O)Nc1cc(-n2cnnn2)ccc1N1CCC[C@H](O)C1]
(254)
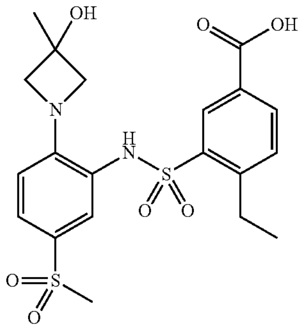 [SMILES: CCc1ccc(C(=O)O)cc1S(=O)(=O)Nc1cc(S(C)(=O)=O)ccc1N1CC(C)(O)C1]
(255)
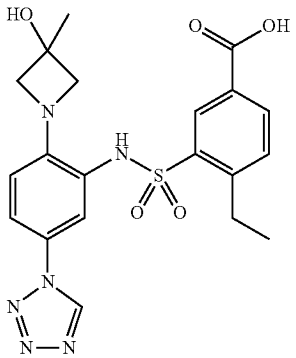
(257)

TABLE 2-continued
| Structures of compounds according to the invention | |
|---|---|
| 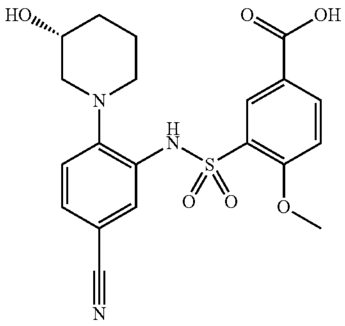 | (258) |
| 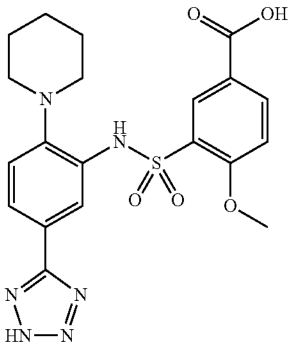 | (259) |
| 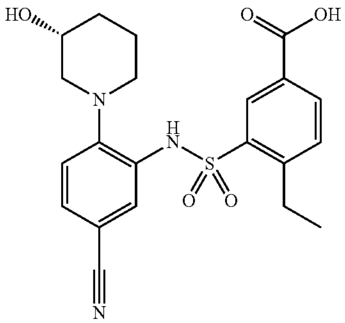 | (260) |
| 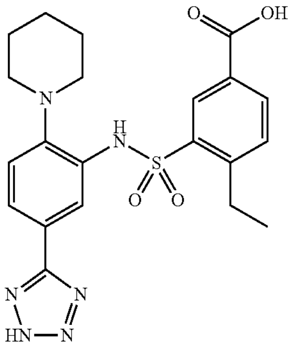 | (261) |
TABLE 2-continued
| Structures of compounds according to the invention | |
|---|---|
| 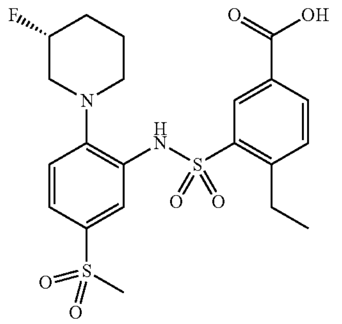 | (262) |
| 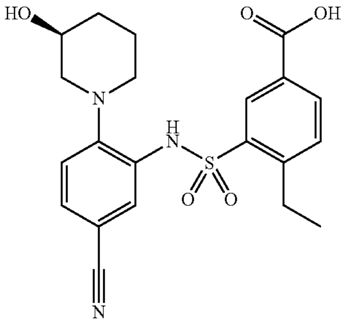 | (263) |
| 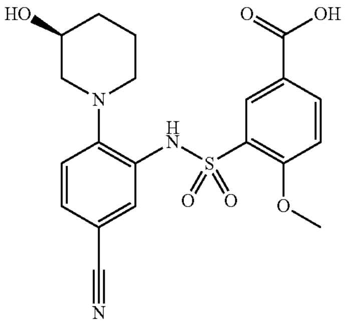 | (264) |
| 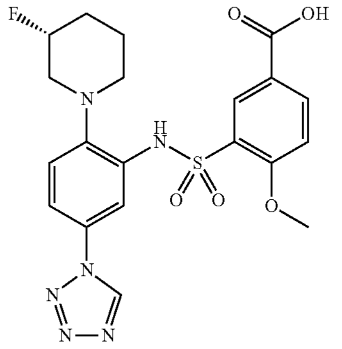 | (265) |

TABLE 2-continued
| Structures of compounds according to the invention |
|---|
| 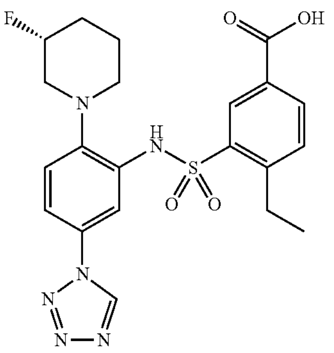 (266) |
| 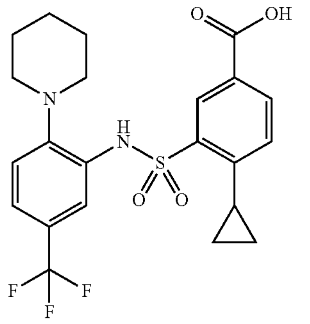 (267) |
| 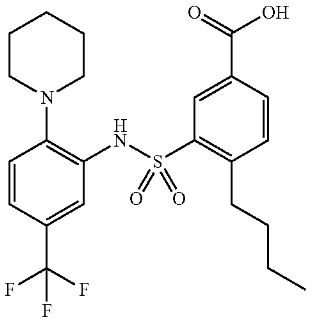 [SMILES: CCCCc1ccc(C(=O)O)cc1S(=O)(=O)Nc1cc(C(F)(F)F)ccc1N1CCCCC1] (268) |
| 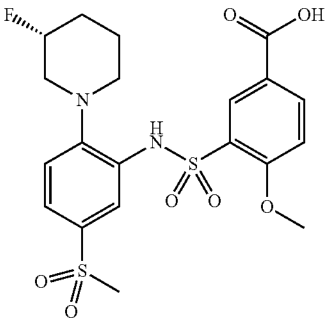 (269) |
TABLE 2-continued
| Structures of compounds according to the invention |
|---|
| 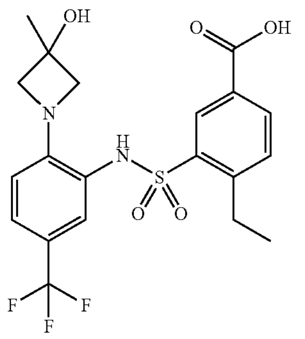 (270) |
| 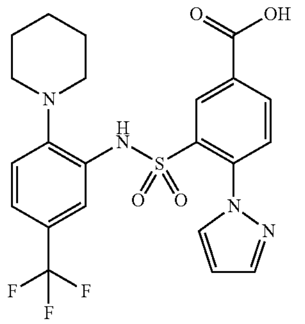 (271) |
| 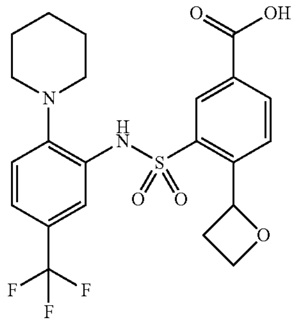 (272) |
| 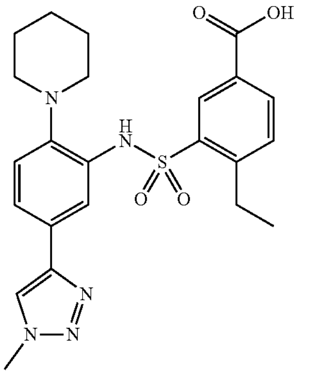 [SMILES: CCc1ccc(C(=O)O)cc1S(=O)(=O)Nc1cc(-c2cn(C)nn2)ccc1N1CCCCC1] (273) |

TABLE 2-continued
| Structures of compounds according to the invention |
| --- |
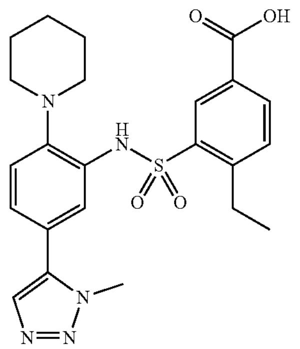 [SMILES: CCc1ccc(C(=O)O)cc1S(=O)(=O)Nc1cc(-c2cnnn2C)ccc1N1CCCCC1]
(274)
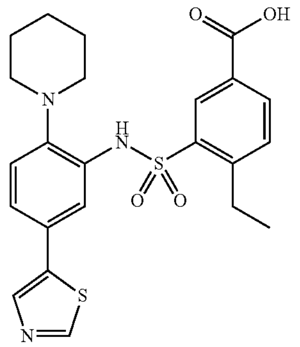 [SMILES: CCc1ccc(C(=O)O)cc1S(=O)(=O)Nc1cc(-c2cncs2)ccc1N1CCCCC1]
(275)
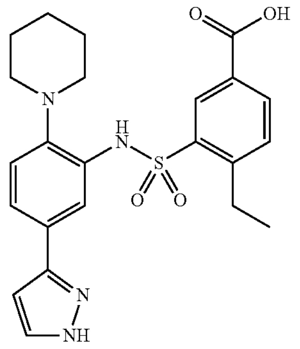 [SMILES: CCc1ccc(C(=O)O)cc1S(=O)(=O)Nc1cc(-c2cc[nH]n2)ccc1N1CCCCC1]
(276)
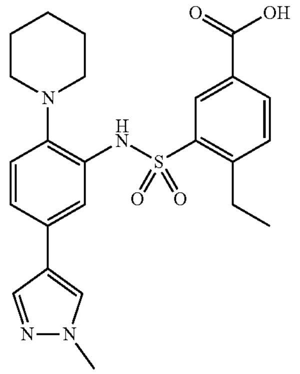 [SMILES: CCc1ccc(C(=O)O)cc1S(=O)(=O)Nc1cc(-c2cnn(C)c2)ccc1N1CCCCC1]
(277)
TABLE 2-continued
| Structures of compounds according to the invention |
| --- |
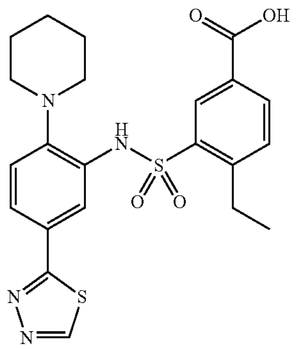 [SMILES: CCc1ccc(C(=O)O)cc1S(=O)(=O)Nc1cc(-c2nncs2)ccc1N1CCCCC1]
(278)
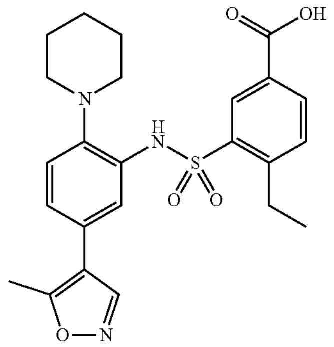 [SMILES: CCc1ccc(C(=O)O)cc1S(=O)(=O)Nc1cc(-c2cnoc2C)ccc1N1CCCCC1]
(279)
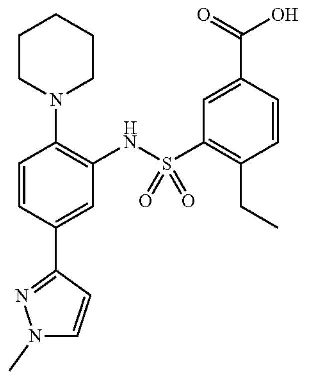 [SMILES: CCc1ccc(C(=O)O)cc1S(=O)(=O)Nc1cc(-c2ccn(C)n2)ccc1N1CCCCC1]
(280)
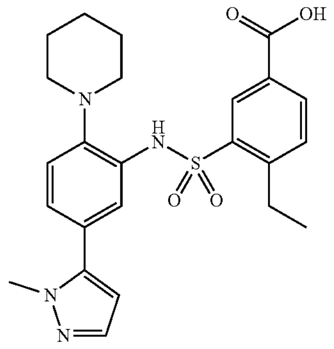 [SMILES: CCc1ccc(C(=O)O)cc1S(=O)(=O)Nc1cc(-c2ccnn2C)ccc1N1CCCCC1]
(281)

TABLE 2-continued
| Structures of compounds according to the invention |
|---|
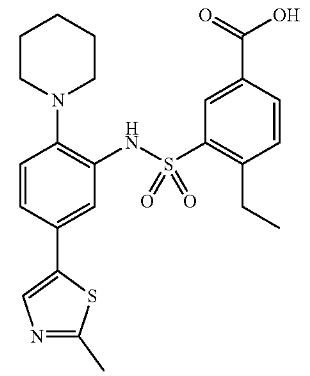 [SMILES: CCc1ccc(C(=O)O)cc1S(=O)(=O)Nc1cc(-c2cnc(C)s2)ccc1N1CCCCC1]
(282)
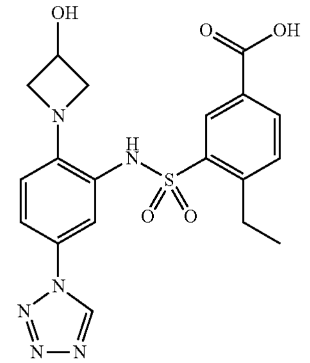 [SMILES: CCc1ccc(C(=O)O)cc1S(=O)(=O)Nc1cc(-n2cnnn2)ccc1N1CC(O)C1]
(283)
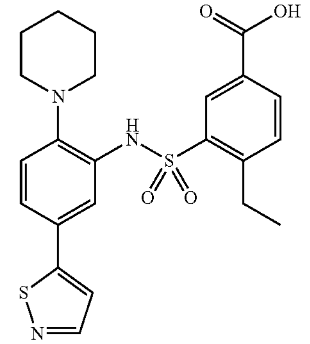 [SMILES: CCc1ccc(C(=O)O)cc1S(=O)(=O)Nc1cc(-c2ccns2)ccc1N1CCCCC1]
(286)
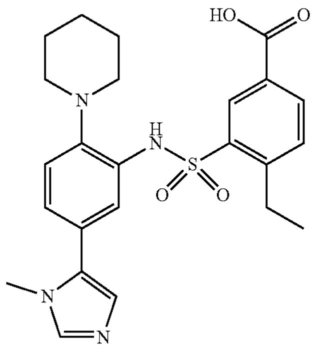 [SMILES: CCc1ccc(C(=O)O)cc1S(=O)(=O)Nc1cc(-c2cncn2C)ccc1N1CCCCC1]
(287)
TABLE 2-continued
| Structures of compounds according to the invention |
|---|
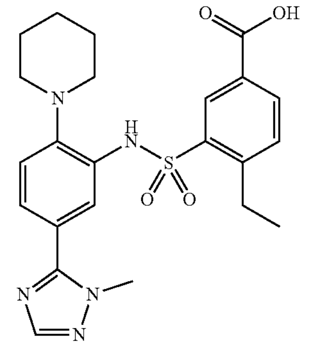 [SMILES: CCc1ccc(C(=O)O)cc1S(=O)(=O)Nc1cc(-c2ncnn2C)ccc1N1CCCCC1]
(288)
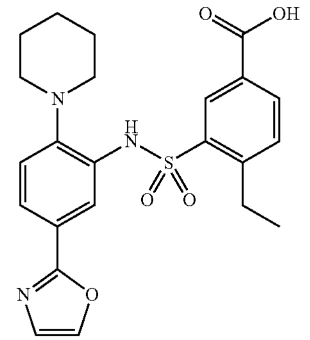 [SMILES: CCc1ccc(C(=O)O)cc1S(=O)(=O)Nc1cc(-c2ncco2)ccc1N1CCCCC1]
(289)
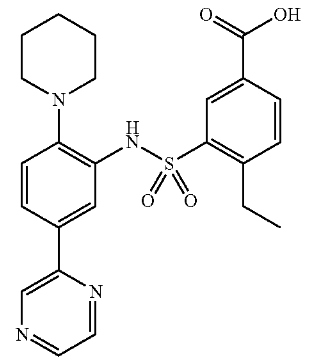
(290)
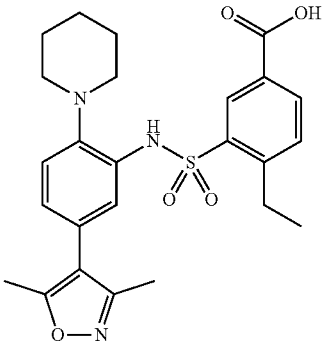 [SMILES: CCc1ccc(C(=O)O)cc1S(=O)(=O)Nc1cc(-c2c(C)noc2C)ccc1N1CCCCC1]
(291)

TABLE 2-continued
| Structures of compounds according to the invention |
|---|
| 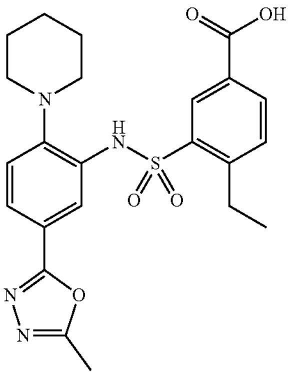 [SMILES: CCc1ccc(C(=O)O)cc1S(=O)(=O)Nc1cc(-c2nnc(C)o2)ccc1N1CCCCC1] (292) |
| 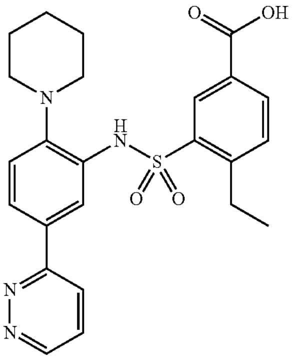 (293) |
| 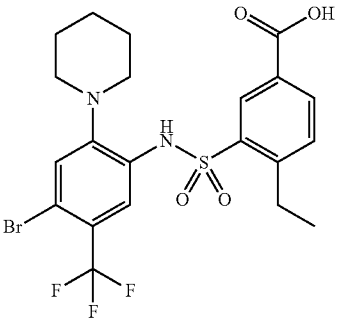 [SMILES: CCc1ccc(C(=O)O)cc1S(=O)(=O)Nc1cc(C(F)(F)F)c(Br)cc1N1CCCCC1] (294) |
| 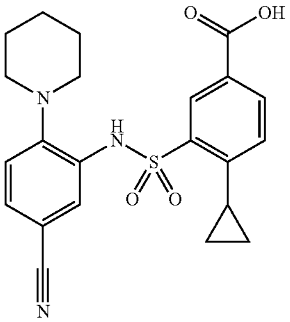 [SMILES: N#Cc1ccc(N2CCCCC2)c(NS(=O)(=O)c2cc(C(=O)O)ccc2C2CC2)c1] (295) |
TABLE 2-continued
| Structures of compounds according to the invention |
|---|
| 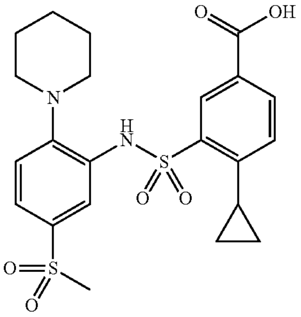 [SMILES: CS(=O)(=O)c1ccc(N2CCCCC2)c(NS(=O)(=O)c2cc(C(=O)O)ccc2C2CC2)c1] (296) |
| 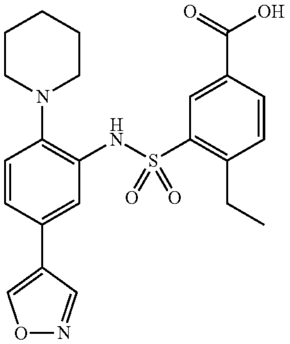 [SMILES: CCc1ccc(C(=O)O)cc1S(=O)(=O)Nc1cc(-c2cnoc2)ccc1N1CCCCC1] (297) |
| 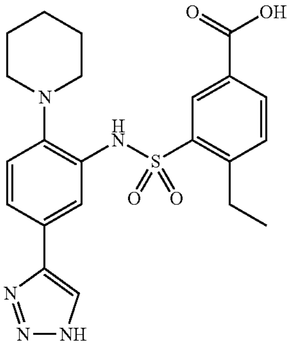 [SMILES: CCc1ccc(C(=O)O)cc1S(=O)(=O)Nc1cc(-c2c[nH]nn2)ccc1N1CCCCC1] (298) |
| 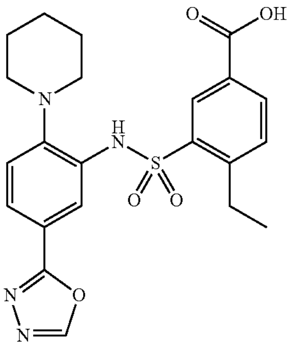 (299) |

TABLE 2-continued
| Structures of compounds according to the invention |
|---|
| 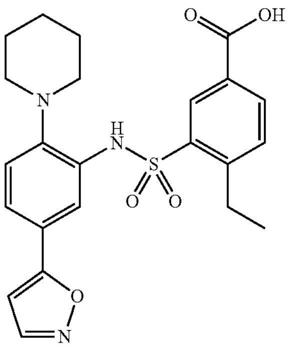 [SMILES: CCc1ccc(C(=O)O)cc1S(=O)(=O)Nc1cc(-c2ccno2)ccc1N1CCCCC1] (300) |
| 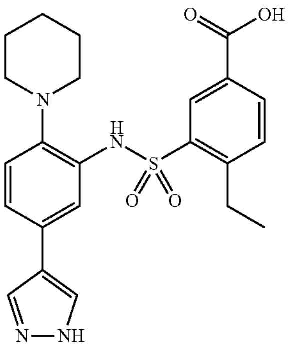 [SMILES: CCc1ccc(C(=O)O)cc1S(=O)(=O)Nc1cc(-c2cn[nH]c2)ccc1N1CCCCC1] (301) |
| 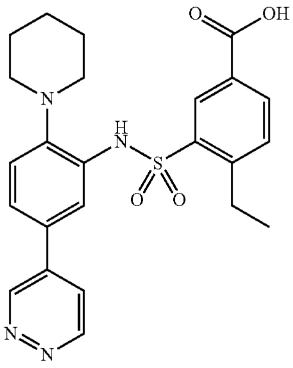 [SMILES: CCc1ccc(C(=O)O)cc1S(=O)(=O)Nc1cc(-c2ccnnc2)ccc1N1CCCCC1] (302) |
| 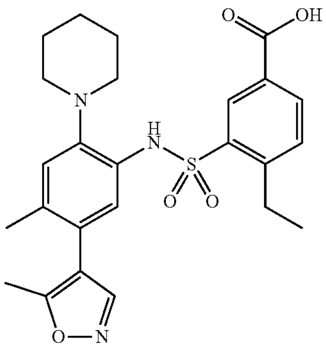 [SMILES: CCc1ccc(C(=O)O)cc1S(=O)(=O)Nc1cc(-c2cnoc2C)c(C)cc1N1CCCCC1] (303) |
TABLE 2-continued
| Structures of compounds according to the invention |
|---|
| 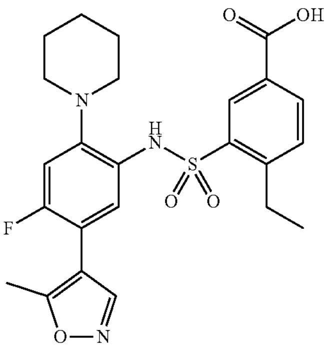 (304) |
| 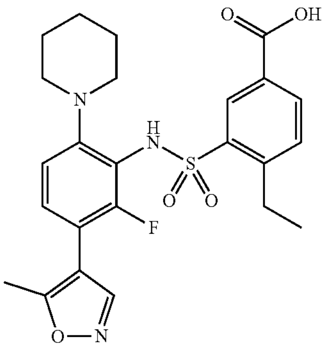 [SMILES: CCc1ccc(C(=O)O)cc1S(=O)(=O)Nc1c(N2CCCCC2)ccc(-c2cnoc2C)c1F] (305) |
| 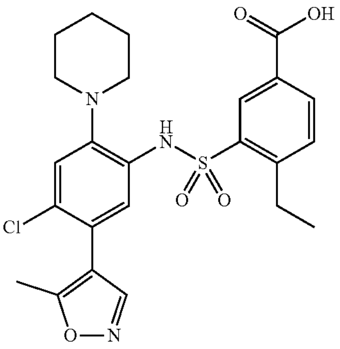 [SMILES: CCc1ccc(C(=O)O)cc1S(=O)(=O)Nc1cc(-c2cnoc2C)c(Cl)cc1N1CCCCC1] (306) |
| 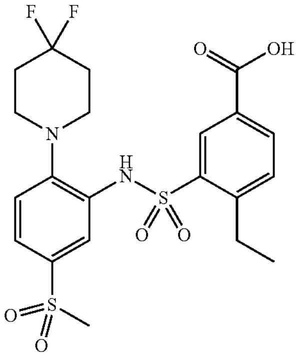 [SMILES: CCc1ccc(C(=O)O)cc1S(=O)(=O)Nc1cc(S(C)(=O)=O)ccc1N1CCC(F)(F)CC1] (308) |

TABLE 2-continued
| Structures of compounds according to the invention |
|---|
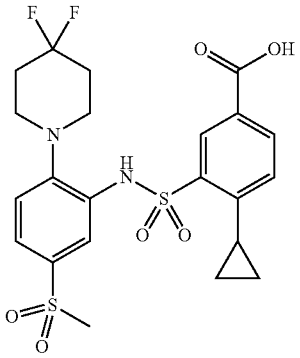 [SMILES: CS(=O)(=O)c1ccc(N2CCC(F)(F)CC2)c(NS(=O)(=O)c2cc(C(=O)O)ccc2C2CC2)c1]
(309)
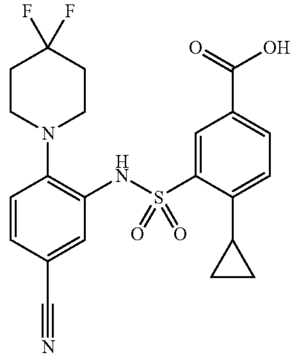 [SMILES: N#Cc1ccc(N2CCC(F)(F)CC2)c(NS(=O)(=O)c2cc(C(=O)O)ccc2C2CC2)c1]
(310)
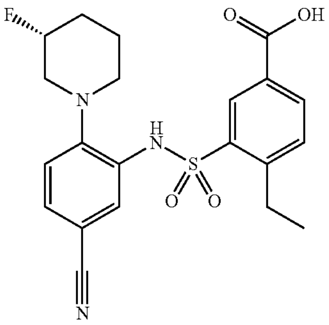
(311)
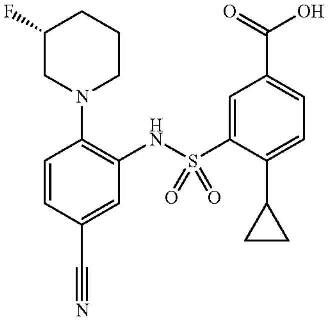
(312)
TABLE 2-continued
| Structures of compounds according to the invention |
|---|
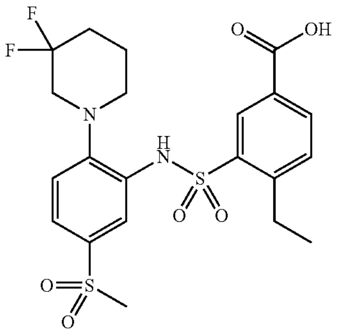 [SMILES: CCc1ccc(C(=O)O)cc1S(=O)(=O)Nc1cc(S(C)(=O)=O)ccc1N1CCCC(F)(F)C1]
(313)
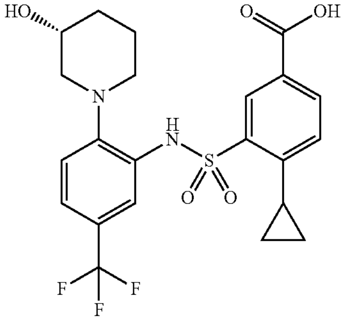 [SMILES: O=C(O)c1ccc(C2CC2)c(S(=O)(=O)Nc2cc(C(F)(F)F)ccc2N2CCC[C@@H](O)C2)c1]
(314)
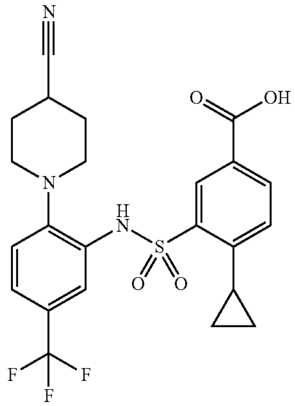
(315)
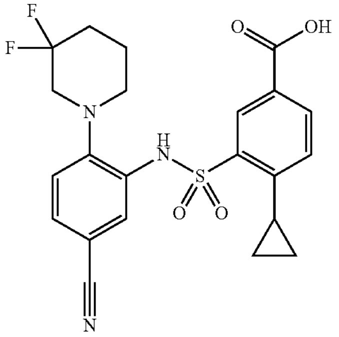 [SMILES: N#Cc1ccc(N2CCCC(F)(F)C2)c(NS(=O)(=O)c2cc(C(=O)O)ccc2C2CC2)c1]
(316)

TABLE 2-continued
| Structures of compounds according to the invention |
| --- |
| 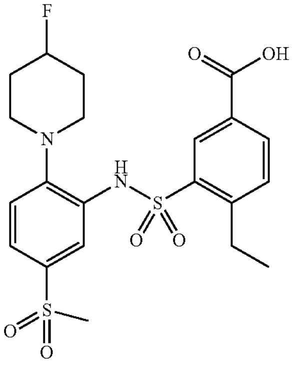 [SMILES: CCc1ccc(C(=O)O)cc1S(=O)(=O)Nc1cc(S(C)(=O)=O)ccc1N1CCC(F)CC1] (317) |
| 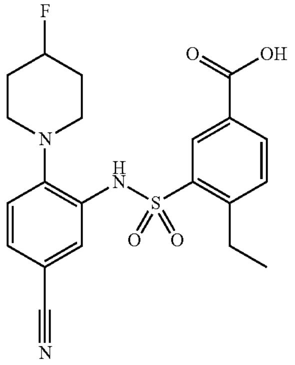 [SMILES: CCc1ccc(C(=O)O)cc1S(=O)(=O)Nc1cc(C#N)ccc1N1CCC(F)CC1] (318) |
| 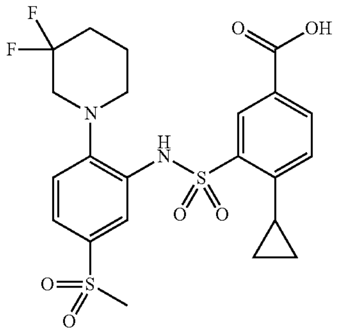 [SMILES: CS(=O)(=O)c1ccc(N2CCCC(F)(F)C2)c(NS(=O)(=O)c2cc(C(=O)O)ccc2C2CC2)c1] (319) |
| 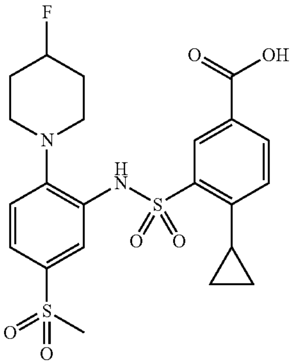 [SMILES: CS(=O)(=O)c1ccc(N2CCC(F)CC2)c(NS(=O)(=O)c2cc(C(=O)O)ccc2C2CC2)c1] (320) |
TABLE 2-continued
| Structures of compounds according to the invention |
| --- |
| 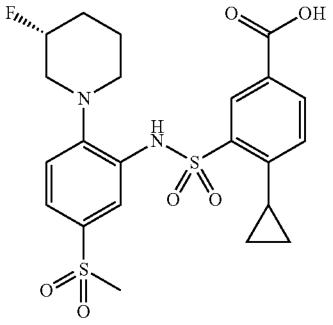 (321) |
| 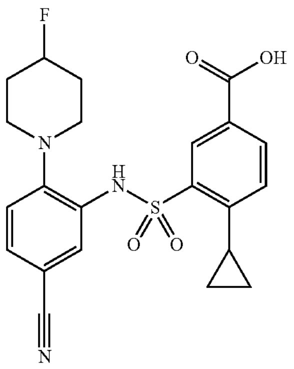 [SMILES: N#Cc1ccc(N2CCC(F)CC2)c(NS(=O)(=O)c2cc(C(=O)O)ccc2C2CC2)c1] (322) |
| 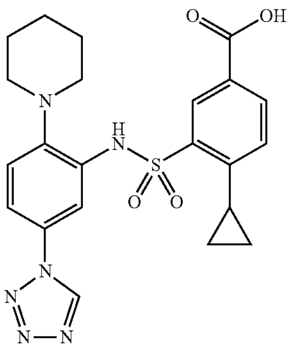 [SMILES: O=C(O)c1ccc(C2CC2)c(S(=O)(=O)Nc2cc(-n3cnnn3)ccc2N2CCCCC2)c1] (323) |
| 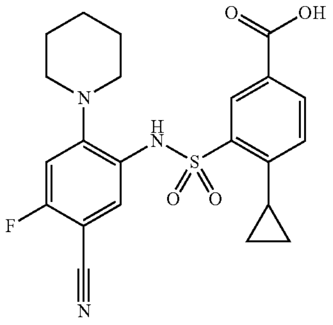 [SMILES: N#Cc1cc(NS(=O)(=O)c2cc(C(=O)O)ccc2C2CC2)c(N2CCCCC2)cc1F] (324) |

TABLE 2-continued
Structures of compounds according to the invention
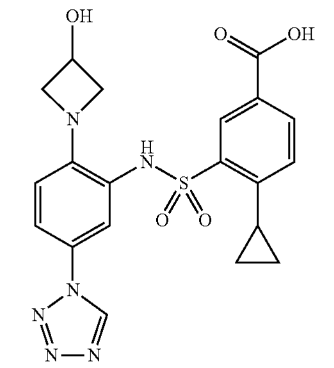 [SMILES: O=C(O)c1ccc(C2CC2)c(S(=O)(=O)Nc2cc(-n3cnnn3)ccc2N2CC(O)C2)c1]
(325)
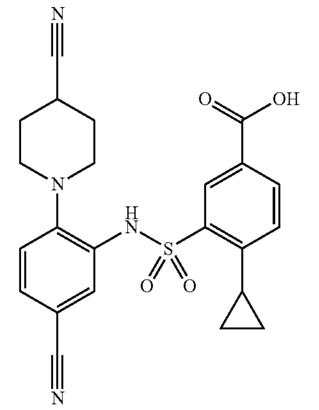 [SMILES: N#Cc1ccc(N2CCC(C#N)CC2)c(NS(=O)(=O)c2cc(C(=O)O)ccc2C2CC2)c1]
(326)
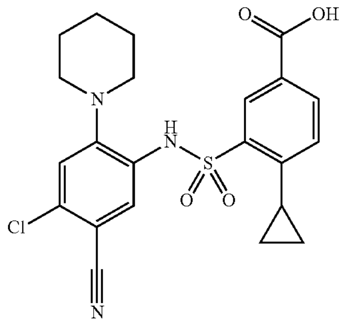 [SMILES: N#Cc1cc(NS(=O)(=O)c2cc(C(=O)O)ccc2C2CC2)c(N2CCCCC2)cc1Cl]
(327)
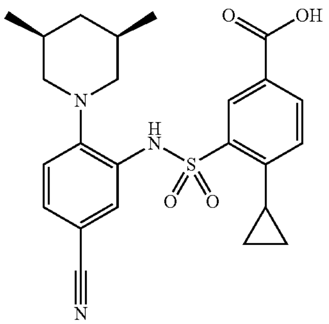 [SMILES: C[C@@H]1C[C@H](C)CN(c2ccc(C#N)cc2NS(=O)(=O)c2cc(C(=O)O)ccc2C2CC2)C1]
(328)
TABLE 2-continued
Structures of compounds according to the invention
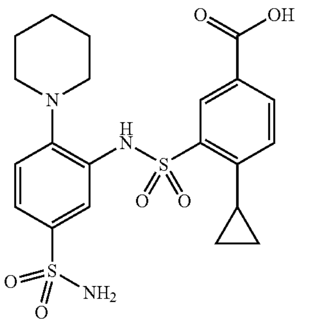 [SMILES: NS(=O)(=O)c1ccc(N2CCCCC2)c(NS(=O)(=O)c2cc(C(=O)O)ccc2C2CC2)c1]
(329)
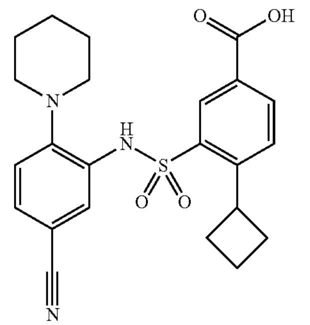 [SMILES: N#Cc1ccc(N2CCCCC2)c(NS(=O)(=O)c2cc(C(=O)O)ccc2C2CCC2)c1]
(330)
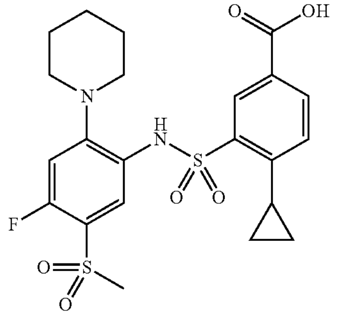 [SMILES: CS(=O)(=O)c1cc(NS(=O)(=O)c2cc(C(=O)O)ccc2C2CC2)c(N2CCCCC2)cc1F]
(331)
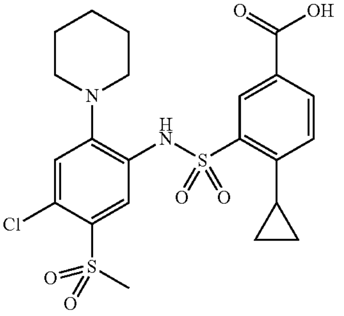 [SMILES: CS(=O)(=O)c1cc(NS(=O)(=O)c2cc(C(=O)O)ccc2C2CC2)c(N2CCCCC2)cc1Cl]
(332)

TABLE 2-continued

| Structures of compounds according to the invention | |
|---|---|
| 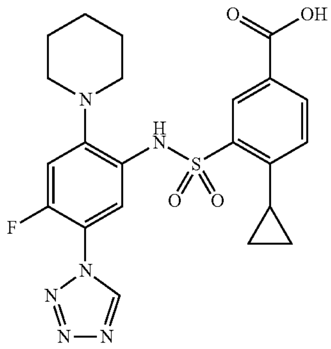 [SMILES: O=C(O)c1ccc(C2CC2)c(S(=O)(=O)Nc2cc(-n3cnnn3)c(F)cc2N2CCCCC2)c1] | (333) |
| 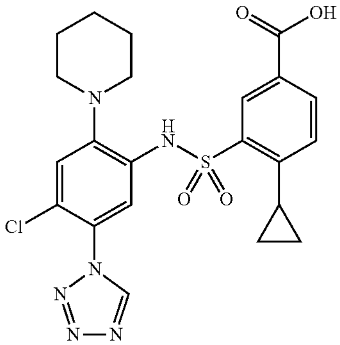 [SMILES: O=C(O)c1ccc(C2CC2)c(S(=O)(=O)Nc2cc(-n3cnnn3)c(Cl)cc2N2CCCCC2)c1] | (334) |
| 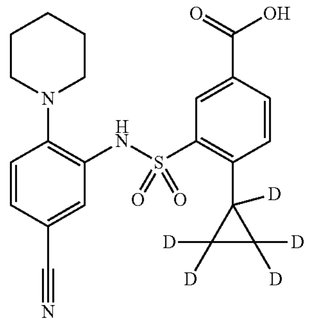 [SMILES: [2H]C1([2H])C([2H])([2H])C1([2H])c1ccc(C(=O)O)cc1S(=O)(=O)Nc1cc(C#N)ccc1N1CCCCC1] | (335) |
| 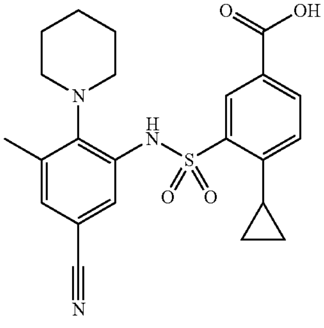 [SMILES: Cc1cc(C#N)cc(NS(=O)(=O)c2cc(C(=O)O)ccc2C2CC2)c1N1CCCCC1] | (336) |

TABLE 2-continued

| Structures of compounds according to the invention | |
|---|---|
| 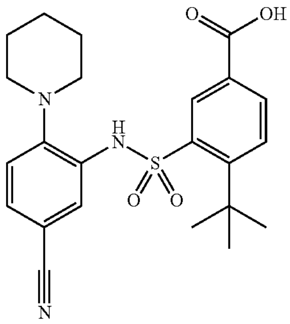 [SMILES: CC(C)(C)c1ccc(C(=O)O)cc1S(=O)(=O)Nc1cc(C#N)ccc1N1CCCCC1] | (337) |
| 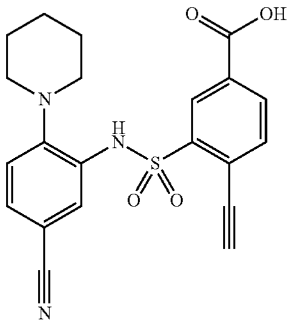 [SMILES: C#Cc1ccc(C(=O)O)cc1S(=O)(=O)Nc1cc(C#N)ccc1N1CCCCC1] | (338) |

REFERENCES

1. Serwold et al, (2002), ERAAP customizes peptides for MHC class I molecules in the endoplasmic reticulum; Nature: 419, p480.
2. Snyder et al, (2014), Genetic Basis for Clinical Response to CTLA-4 Blockade in Melanoma; NEJM: 371, p2189.
3. Van Allen et al, (2015), Genomic correlates of response to CTLA-4 blockade in metastatic melanoma; Science: 348, p124.
4. James et al, (2013), Induction of Protective Antitumor Immunity through Attenuation of ERAAP Function; J Immunol: 190, p5839.
5. Niranjana et al, (2016), ERAAP Shapes the Peptidome Associated with Classical and Nonclassical MHC Class I Molecules; J Immunol: 197, p1035.
6. Pepelyayeva et al, (2018), ERAP1 deficient mice have reduced Type 1 regulatory T cells and develop skeletal and intestinal features of Ankylosing Spondylitis; Sci. Reports: 8: p12464.
7. Cifaldi et al, (2015), ERAP1 Regulates Natural Killer Cell Function by Controlling the Engagement of Inhibitory Receptors, Cancer Res.: 75, p824.
8. Steinbach et al, (2017), ERAP1 overexpression in HPV-induced malignancies: A possible novel immune evasion mechanism, Oncoimmunol: 6, e1336594.
9. Kim et al, (2011), Human cytomegalovirus microRNA miR-US4-1 inhibits $CD8^+$ T cell responses by targeting the aminopeptidase ERAP1, Nat. Immunol.: 12, p984.
10. Tenzer et al, (2009), Antigen processing influences HIV-specific cytotoxic T lymphocyte immunodominance, Nat. Immunol.: 10, p636.
11. Reeves et al, (2018), The role of polymorphic ERAP1 in autoinflammatory disease, Biosci. Rep.: 29, p38.
12. Chen et al, (2014), Silencing or inhibition of endoplasmic reticulum aminopeptidase 1 (ERAP1) suppresses free heavy chain expression and Th17 responses in ankylosing spondylitis, Ann Rheum Dis: 75, p916.

13. Sheehan, N J (January 2004). "The ramifications of HLA-B27". *Journal of the Royal Society of Medicine.* 97 (1): 10-4.
14. Smith, J A (January 2015). "Update on ankylosing spondylitis: current concepts in pathogenesis". Current allergy and asthma reports. 15 (1): 489.
15. Kuiper J J W, Mutis T, de Jager W, de Groot-Mijnes J D, Rothova A (2011). "Intraocular interleukin-17 and proinflammatory cytokines in HLA-A29-associated birdshot chorioretinopathy". *Am J Ophthalmol.* 152 (2): 177-182
16. Kuiper J J W, Emmelot M E, Rothova A, Mutis T (2013). "Interleukin-17 production and T helper 17 cells in peripheral blood mononuclear cells in response to ocular lysate in patients with birdshot chorioretinopathy". *Mol Vis.* 19:2606-14
17. Kuiper J J W, van Setten J, Ripke S, Van't Slot R, Mulder F, Missotten T, Baarsma G S, Francioli L C, Pulit S L, de Kovel C G, Ten Dam-van Loon N, den Hollander A I, Huis In Het Veld P, Hoyng C B, Cordero-Coma M, Martin J, Llorenç V, Arya B, Thomas D, Bakker S C, Ophoff R A, Rothova A, de Bakker P I, Mutis T, Koeleman B P (2014). "A genome-wide association study identifies a functional ERAP2 haplotype associated with birdshot chorioretinopathy". *Hum Mol Genet.* 23 (22): 6081-6087
18. Evans et al (2011), Interaction between ERAP1 and HLA-B27 in ankylosing spondylitis implicates peptide handling in the mechanism for HLA-B27 in disease susceptibility. Nat Genet. 10; 43 (8): 761-7
19. Conde-Jaldon et al (2014), Epistatic interaction of ERAP1 and HLA-B in Behçet disease: a replication study in the Spanish population. PLOS One. 14; 9 (7)
20. Kuiper et al (2018), Functionally distinct ERAP1 and ERAP2 are a hallmark of HLA-A29-(Birdshot) Uveitis. Hum Mol Genet. doi: 10.1093/hmg/ddy319
21. Strange et al (2010), A genome-wide association study identifies new psoriasis susceptibility loci and an interaction between HLA-C and ERAP1. Nat Genet.; 42 (11): 985-90

The invention claimed is:

1. A compound of formula (Id), or a pharmaceutically acceptable salt or hydrate thereof, (Id)

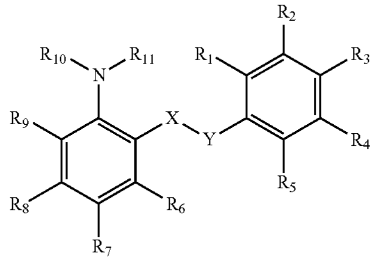

wherein:

the group X—Y is —$NHSO_2$— or —$SO_2NH$—;

$R_1$ is H or alkyl;

$R_2$ is selected from COOH and a tetrazolyl group;

$R_3$ is selected from H, Cl and alkyl;

$R_4$ is selected from H, Cl and F;

$R_5$ is selected from alkyl, alkenyl, alkynyl, haloalkyl, $SO_2$-alkyl, Cl, alkoxy, OH, CN, hydroxyalkyl, alkylthio, heteroaryl, cycloalkyl, heterocycloalkyl and haloalkoxy;

$R_6$ is H;

$R_7$ is CN, $SO_2$-alkyl, $SO_2NR_{13}R_{14}$ or a heteroaryl group, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is H, $C_1$-$C_3$-alkyl or halo;

$R_{10}$ and $R_{11}$, together with the nitrogen to which they are attached, form a 4, 5, 6 or 7-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl; or $R_{10}$ and $R_{11}$, together with the nitrogen to which they are attached, form an 8, 9 or 10-membered bicyclic heterocycloalkyl group, wherein one or two carbons in the bicyclic heterocycloalkyl ring are optionally replaced by a group selected from O, NH, S and CO, and said bicyclic heterocycloalkyl group is optionally substituted by one or more groups selected from alkyl, CN, cycloalkyl, OH, alkoxy, halo, haloalkyl and heteroaryl; or $R_{10}$ and $R_{11}$, together with the nitrogen to which they are attached, form a 6 to 12-membered bicyclic group containing a spirocyclic carbon atom, wherein one or two carbons in the bicyclic group are optionally replaced by a group selected from O, NH, S and CO, and said bicyclic group is optionally substituted by one or more groups selected from alkyl, CN, cycloalkyl, OH, alkoxy, halo, haloalkyl and heteroaryl, or said bicyclic group is optionally fused to a 5 or 6-membered aryl or heteroaryl group; and $R_{13}$ and $R_{14}$ are each H.

2. The compound according to claim 1, wherein $R_{10}$ and $R_{11}$, together with the nitrogen to which they are attached, form a 6-membered monocyclic heterocycloalkyl group, wherein one or two carbons in the monocyclic heterocycloalkyl group are optionally replaced by a group selected from O, NH, S and CO, and said monocyclic heterocycloalkyl group is optionally substituted by one or more groups selected from alkyl, CN, cycloalkyl, OH, alkoxy, halo, haloalkyl and heteroaryl, wherein said heteroaryl group is in turn optionally further substituted with one or more groups selected from halo and alkyl.

3. The compound of claim 1, wherein $R_{10}$ and $R_{11}$, together with the nitrogen to which they are attached, form a piperidinyl group which is optionally substituted by one or more groups selected from alkyl, CN, cycloalkyl, OH, alkoxy, halo, haloalkyl, and heteroaryl, wherein said heteroaryl group is in turn optionally further substituted with one or more groups selected from halo and alkyl.

4. The compound of claim 1, wherein $R_{10}$ and $R_{11}$, together with the nitrogen to which they are attached, form an unsubstituted piperidinyl group.

5. The compound according to claim 1, wherein $R_7$ is a heteroaryl group selected from imidazolyl, pyrazolyl, pyrazinyl, pyradizinyl, thiazolyl, isothiazolyl, oxazolyl, isoxazolyl, oxadiazolyl, tetrazolyl and triazolyl, each of which is optionally substituted by one or more substituents selected from alkyl, halo, alkoxy, CN, haloalkyl and OH.

6. The compound of claim 1, wherein $R_7$ is CN.

7. The compound of claim 1, wherein $R_8$ is selected from H, Me, $CF_3$, Cl, Br, and F.

8. The compound of claim 1, wherein $R_2$ is COOH.

9. The compound according to claim 1, wherein the compound of formula (Id) is selected from the following:

(182)

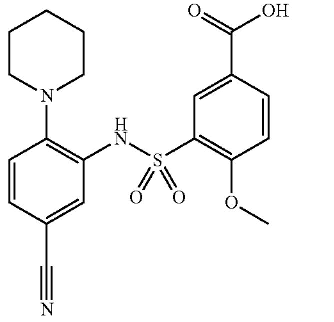

-continued
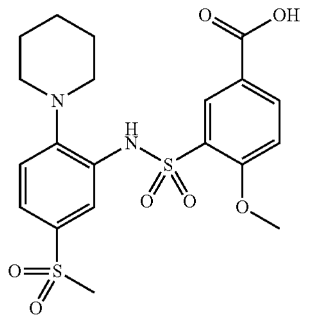 [SMILES: COc1ccc(C(=O)O)cc1S(=O)(=O)Nc1cc(S(C)(=O)=O)ccc1N1CCCCC1]
(207)
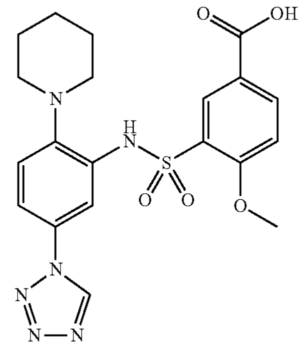 [SMILES: COc1ccc(C(=O)O)cc1S(=O)(=O)Nc1cc(-n2cnnn2)ccc1N1CCCCC1]
(214)
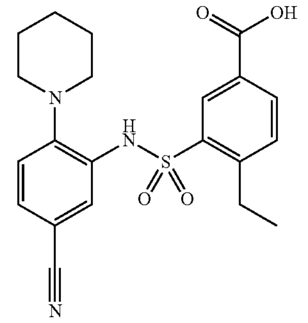
(215)
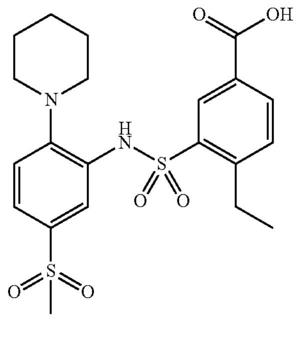 [SMILES: CCc1ccc(C(=O)O)cc1S(=O)(=O)Nc1cc(S(C)(=O)=O)ccc1N1CCCCC1]
(241)
-continued
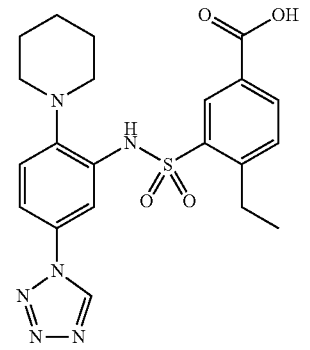 [SMILES: CCc1ccc(C(=O)O)cc1S(=O)(=O)Nc1cc(-n2cnnn2)ccc1N1CCCCC1]
(242)
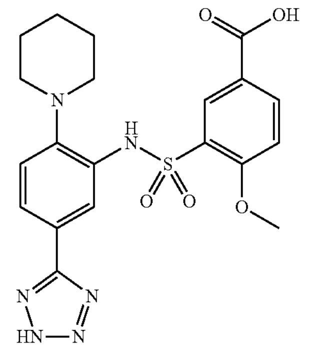 [SMILES: COc1ccc(C(=O)O)cc1S(=O)(=O)Nc1cc(-c2nn[nH]n2)ccc1N1CCCCC1]
(259)
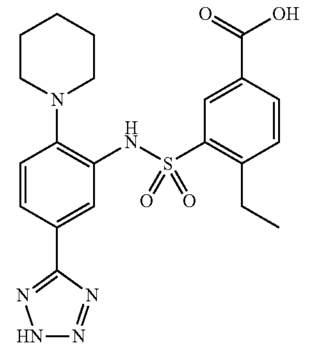 [SMILES: CCc1ccc(C(=O)O)cc1S(=O)(=O)Nc1cc(-c2nn[nH]n2)ccc1N1CCCCC1]
(261)
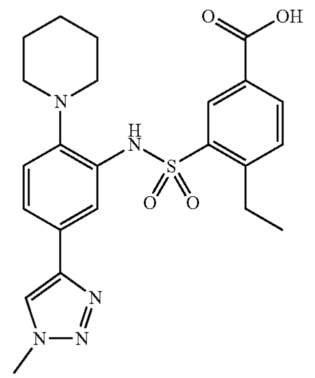 [SMILES: CCc1ccc(C(=O)O)cc1S(=O)(=O)Nc1cc(-c2cn(C)nn2)ccc1N1CCCCC1]
(273)

-continued
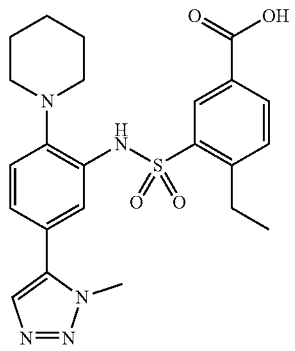 [SMILES: CCc1ccc(C(=O)O)cc1S(=O)(=O)Nc1cc(-c2cnnn2C)ccc1N1CCCCC1]
(274)
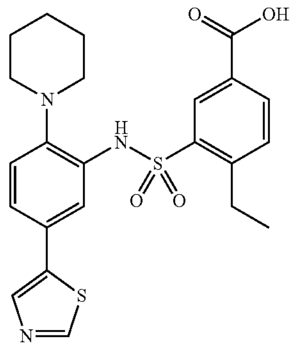 [SMILES: CCc1ccc(C(=O)O)cc1S(=O)(=O)Nc1cc(-c2cncs2)ccc1N1CCCCC1]
(275)
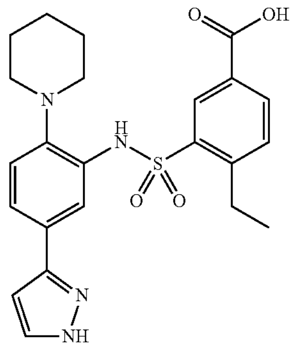 [SMILES: CCc1ccc(C(=O)O)cc1S(=O)(=O)Nc1cc(-c2cc[nH]n2)ccc1N1CCCCC1]
(276)
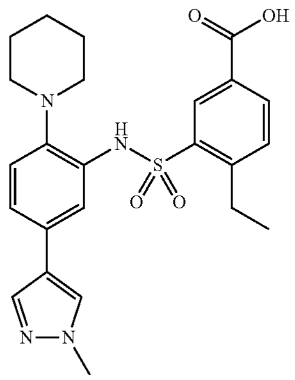 [SMILES: CCc1ccc(C(=O)O)cc1S(=O)(=O)Nc1cc(-c2cnn(C)c2)ccc1N1CCCCC1]
(277)
-continued
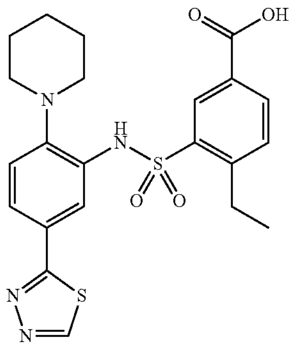 [SMILES: CCc1ccc(C(=O)O)cc1S(=O)(=O)Nc1cc(-c2nncs2)ccc1N1CCCCC1]
(278)
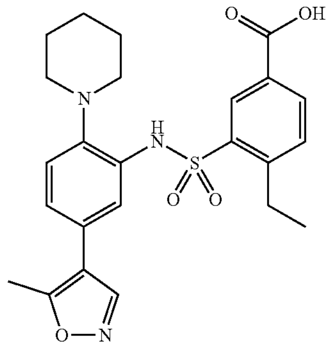 [SMILES: CCc1ccc(C(=O)O)cc1S(=O)(=O)Nc1cc(-c2cnoc2C)ccc1N1CCCCC1]
(279)
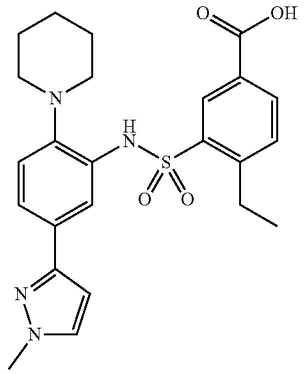 [SMILES: CCc1ccc(C(=O)O)cc1S(=O)(=O)Nc1cc(-c2ccn(C)n2)ccc1N1CCCCC1]
(280)
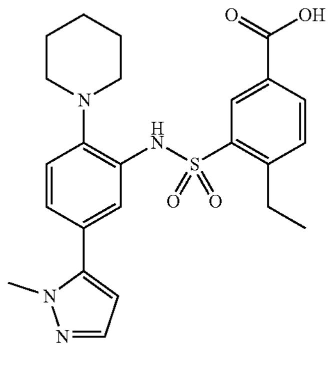 [SMILES: CCc1ccc(C(=O)O)cc1S(=O)(=O)Nc1cc(-c2ccnn2C)ccc1N1CCCCC1]
(281)

-continued
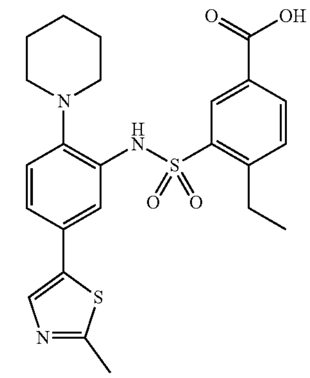 [SMILES: CCc1ccc(C(=O)O)cc1S(=O)(=O)Nc1cc(-c2cnc(C)s2)ccc1N1CCCCC1]
(282)
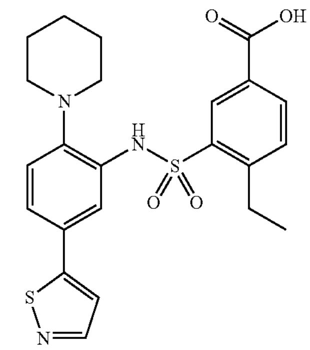 [SMILES: CCc1ccc(C(=O)O)cc1S(=O)(=O)Nc1cc(-c2ccns2)ccc1N1CCCCC1]
(286)
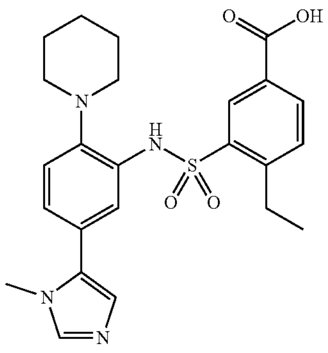 [SMILES: CCc1ccc(C(=O)O)cc1S(=O)(=O)Nc1cc(-c2cncn2C)ccc1N1CCCCC1]
(287)
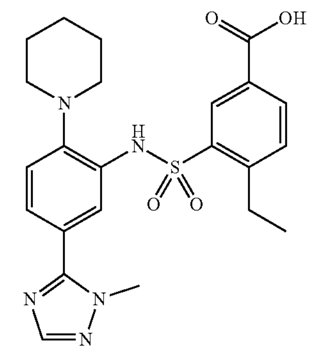 [SMILES: CCc1ccc(C(=O)O)cc1S(=O)(=O)Nc1cc(-c2ncnn2C)ccc1N1CCCCC1]
(288)
-continued
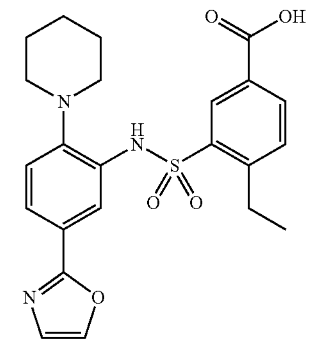 [SMILES: CCc1ccc(C(=O)O)cc1S(=O)(=O)Nc1cc(-c2ncco2)ccc1N1CCCCC1]
(289)
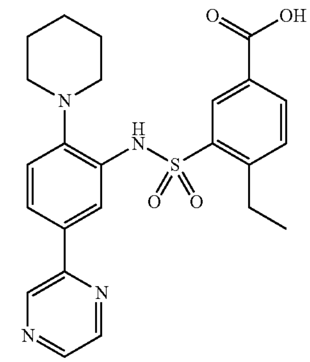
(290)
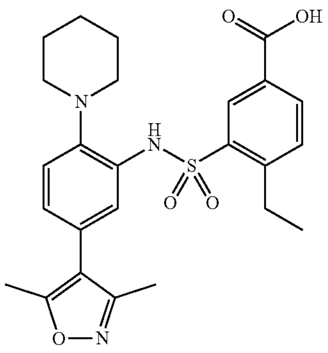 [SMILES: CCc1ccc(C(=O)O)cc1S(=O)(=O)Nc1cc(-c2c(C)noc2C)ccc1N1CCCCC1]
(291)
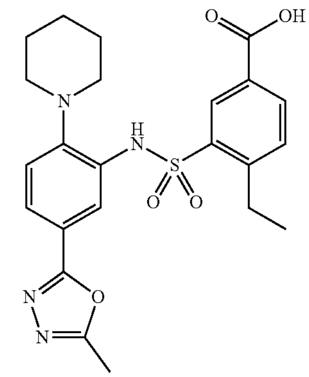 [SMILES: CCc1ccc(C(=O)O)cc1S(=O)(=O)Nc1cc(-c2nnc(C)o2)ccc1N1CCCCC1]
(292)

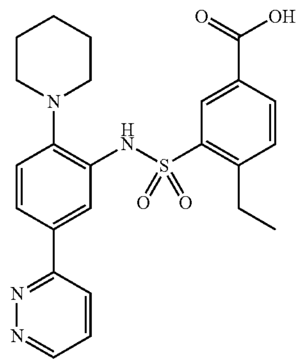
(293)
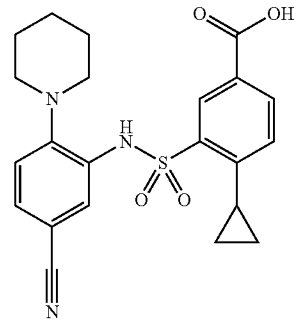 [SMILES: N#Cc1ccc(N2CCCCC2)c(NS(=O)(=O)c2cc(C(=O)O)ccc2C2CC2)c1]
(295)
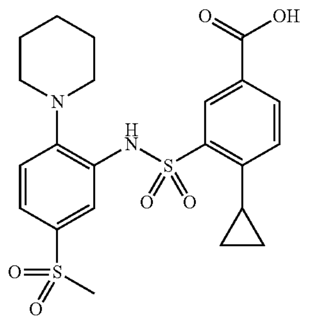
(296)
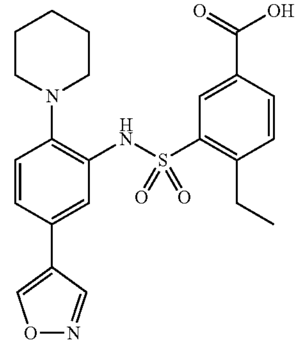 [SMILES: CCc1ccc(C(=O)O)cc1S(=O)(=O)Nc1cc(-c2cnoc2)ccc1N1CCCCC1]
(297)
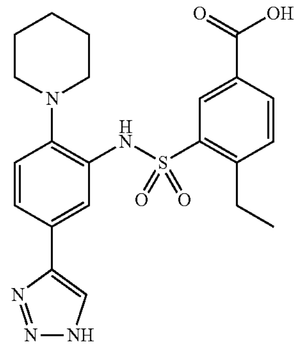 [SMILES: CCc1ccc(C(=O)O)cc1S(=O)(=O)Nc1cc(-c2c[nH]nn2)ccc1N1CCCCC1]
(298)
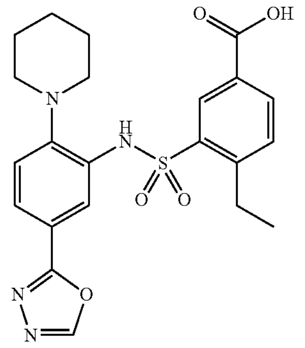 [SMILES: CCc1ccc(C(=O)O)cc1S(=O)(=O)Nc1cc(-c2nnco2)ccc1N1CCCCC1]
(299)
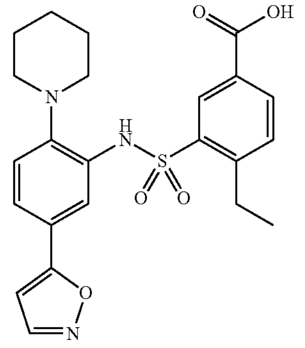 [SMILES: CCc1ccc(C(=O)O)cc1S(=O)(=O)Nc1cc(-c2ccno2)ccc1N1CCCCC1]
(300)
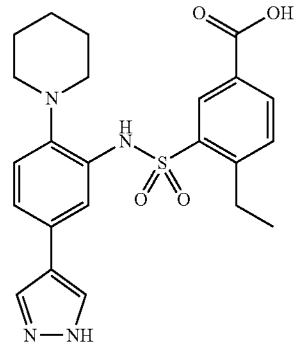 [SMILES: CCc1ccc(C(=O)O)cc1S(=O)(=O)Nc1cc(-c2cn[nH]c2)ccc1N1CCCCC1]
(301)

-continued
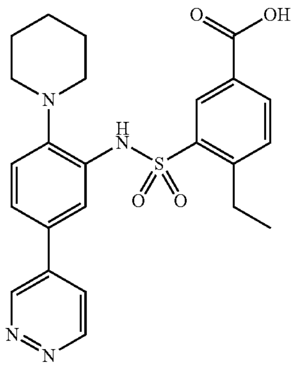 [SMILES: CCc1ccc(C(=O)O)cc1S(=O)(=O)Nc1cc(-c2ccnnc2)ccc1N1CCCCC1]
(302)
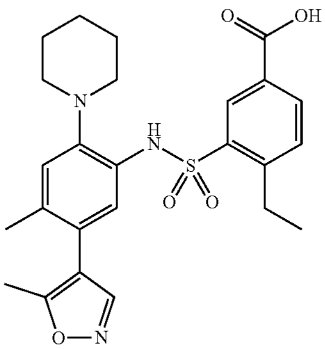 [SMILES: CCc1ccc(C(=O)O)cc1S(=O)(=O)Nc1cc(-c2cnoc2C)c(C)cc1N1CCCCC1]
(303)
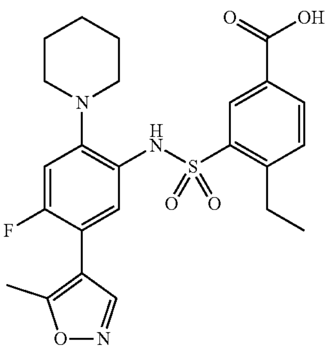
(304)
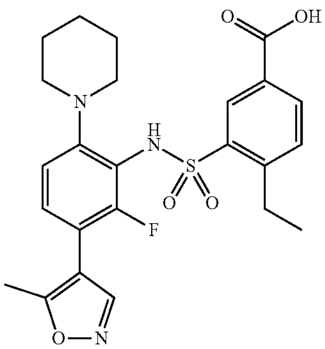 [SMILES: CCc1ccc(C(=O)O)cc1S(=O)(=O)Nc1c(N2CCCCC2)ccc(-c2cnoc2C)c1F]
(305)
-continued
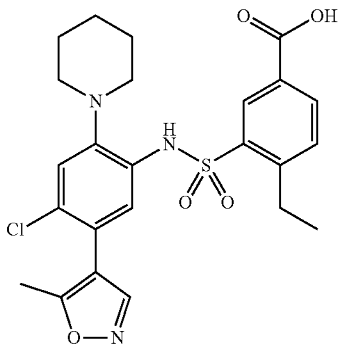 [SMILES: CCc1ccc(C(=O)O)cc1S(=O)(=O)Nc1cc(-c2cnoc2C)c(Cl)cc1N1CCCCC1]
(306)
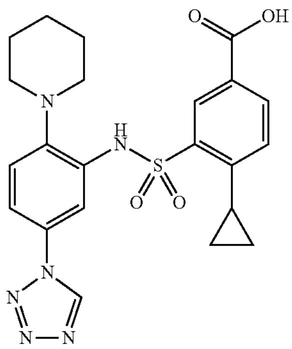 [SMILES: O=C(O)c1ccc(C2CC2)c(S(=O)(=O)Nc2cc(-n3cnnn3)ccc2N2CCCCC2)c1]
(323)
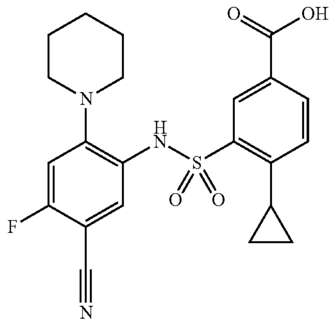 [SMILES: N#Cc1cc(NS(=O)(=O)c2cc(C(=O)O)ccc2C2CC2)c(N2CCCCC2)cc1F]
(324)
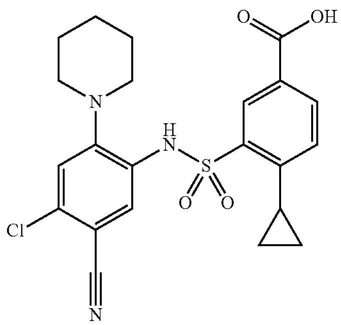 [SMILES: N#Cc1cc(NS(=O)(=O)c2cc(C(=O)O)ccc2C2CC2)c(N2CCCCC2)cc1Cl]
(327)

-continued
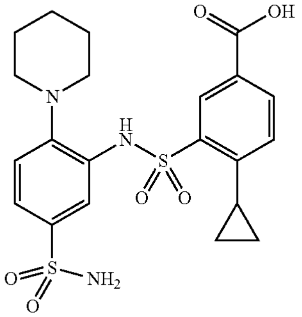 [SMILES: NS(=O)(=O)c1ccc(N2CCCCC2)c(NS(=O)(=O)c2cc(C(=O)O)ccc2C2CC2)c1]
(329)
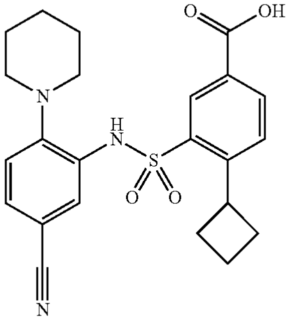 [SMILES: N#Cc1ccc(N2CCCCC2)c(NS(=O)(=O)c2cc(C(=O)O)ccc2C2CCC2)c1]
(330)
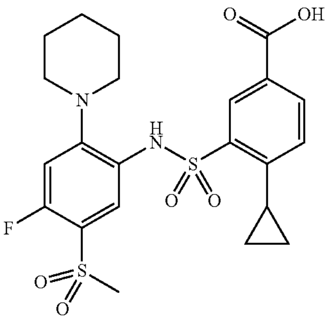 [SMILES: CS(=O)(=O)c1cc(NS(=O)(=O)c2cc(C(=O)O)ccc2C2CC2)c(N2CCCCC2)cc1F]
(331)
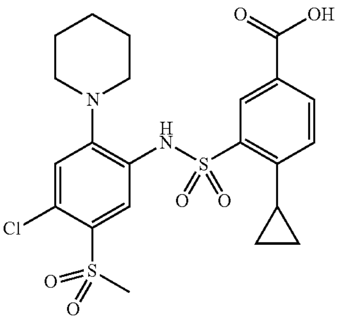 [SMILES: CS(=O)(=O)c1cc(NS(=O)(=O)c2cc(C(=O)O)ccc2C2CC2)c(N2CCCCC2)cc1Cl]
(332)
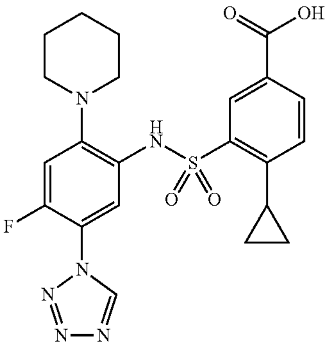 [SMILES: O=C(O)c1ccc(C2CC2)c(S(=O)(=O)Nc2cc(-n3cnnn3)c(F)cc2N2CCCCC2)c1]
(333)
-continued
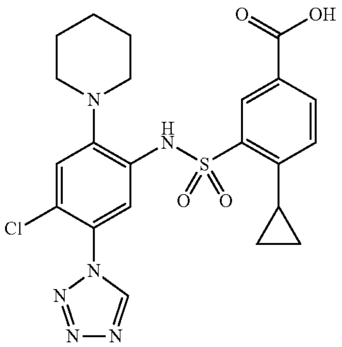 [SMILES: O=C(O)c1ccc(C2CC2)c(S(=O)(=O)Nc2cc(-n3cnnn3)c(Cl)cc2N2CCCCC2)c1]
(334)
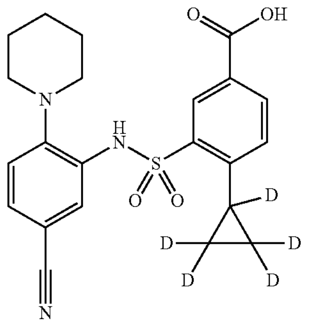 [SMILES: [2H]C1([2H])C([2H])([2H])C1([2H])c1ccc(C(=O)O)cc1S(=O)(=O)Nc1cc(C#N)ccc1N1CCCCC1]
(335)
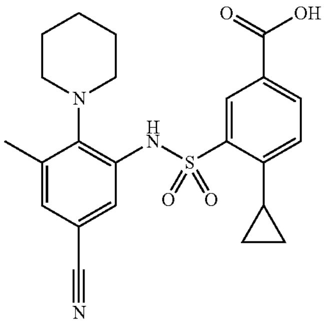 [SMILES: Cc1cc(C#N)cc(NS(=O)(=O)c2cc(C(=O)O)ccc2C2CC2)c1N1CCCCC1]
(336)
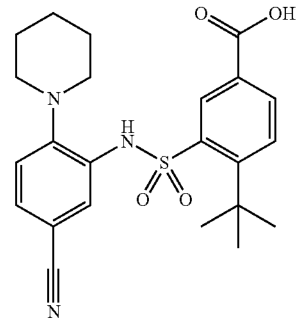 [SMILES: CC(C)(C)c1ccc(C(=O)O)cc1S(=O)(=O)Nc1cc(C#N)ccc1N1CCCCC1]
(337)
(338)
and pharmaceutically acceptable salts and hydrates thereof.

10. The compound of claim 1, having the following structure:
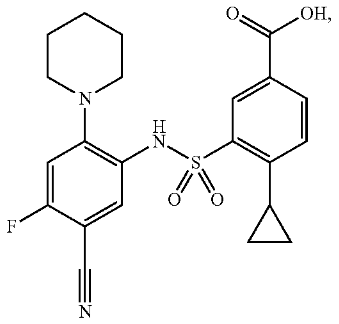 [SMILES: N#Cc1cc(NS(=O)(=O)c2cc(C(=O)O)ccc2C2CC2)c(N2CCCCC2)cc1F]
or a pharmaceutically acceptable salt or hydrate thereof.
11. A pharmaceutical composition comprising a compound according to claim 1 admixed with a pharmaceutically acceptable diluent, excipient or carrier.
* * * * *